United States Patent
Hertzberg et al.

(10) Patent No.: US 8,937,219 B2
(45) Date of Patent: Jan. 20, 2015

(54) WOODY PLANTS HAVING IMPROVED GROWTH CHARACTERISTICS AND METHOD FOR MAKING THE SAME USING TRANSCRIPTION FACTORS

(75) Inventors: Magnus Hertzberg, Umeå (SE); Rishikeshi Bhalerao, Umeå (SE); David Jonsén, Umeå (SE); Linus Möller, Umeå (SE); Pär Jonsson, Umeå (SE)

(73) Assignee: Sweetree Technologies AB, Umea (SE)

( * ) Notice: Subject to any disclaimer, the term of this patent is extended or adjusted under 35 U.S.C. 154(b) by 645 days.

(21) Appl. No.: 12/810,966

(22) PCT Filed: Dec. 18, 2008

(86) PCT No.: PCT/SE2008/051495
§ 371 (c)(1),
(2), (4) Date: Sep. 21, 2010

(87) PCT Pub. No.: WO2009/084999
PCT Pub. Date: Jul. 9, 2009

(65) Prior Publication Data
US 2011/0016550 A1 Jan. 20, 2011

Related U.S. Application Data

(60) Provisional application No. 61/018,679, filed on Jan. 3, 2008.

(30) Foreign Application Priority Data

Dec. 28, 2007 (SE) ..................................... 0702908

(51) Int. Cl.
*C12N 15/00* (2006.01)
*C12N 15/82* (2006.01)
*C12N 5/10* (2006.01)
*C07H 21/02* (2006.01)
*A01H 5/00* (2006.01)
*C12Q 1/68* (2006.01)

(52) U.S. Cl.
CPC .......... *C12Q 1/6895* (2013.01); *C12N 15/8261* (2013.01); *C12Q 2600/158* (2013.01)
USPC ........... 800/290; 800/298; 800/278; 435/419; 435/468; 435/320.1

(58) Field of Classification Search
None
See application file for complete search history.

(56) References Cited

U.S. PATENT DOCUMENTS

| | | | |
|---|---|---|---|
| 2005/0108791 A1* | 5/2005 | Edgerton | 800/284 |
| 2006/0135758 A1 | 6/2006 | Wu | |
| 2007/0039070 A1 | 2/2007 | Bloksberg et al. | |
| 2007/0061916 A1 | 3/2007 | Kovalic et al. | |
| 2007/0192889 A1 | 8/2007 | La Rosa et al. | |
| 2007/0192907 A1* | 8/2007 | Alexandrov et al. | 800/288 |
| 2007/0283460 A9 | 12/2007 | Liu et al. | |

FOREIGN PATENT DOCUMENTS

| | | |
|---|---|---|
| EP | 1 659 180 | 5/2006 |
| WO | WO 02/092823 | 11/2002 |
| WO | WO 2004/035798 | 4/2004 |
| WO | WO 2005/001050 | 1/2005 |
| WO | WO 2005/065339 | 7/2005 |
| WO | WO 2006/036741 | 4/2006 |
| WO | WO 2007/003409 | 1/2007 |

OTHER PUBLICATIONS

Ng et al., BBA 1769_316 (2007).*
Yu et al., Plant J 40:699-711 (2004).*
Seki et al., Plant J 31(3):279-92 (2002).*
Ralph et al., Mol Ecol 15:1275-97 (2006).*
DT488710—Aug. 29, 2005.*
Shen, Plant J 28(4):371-83 (2001)).*
Tuskan_B9GMX2_2006.*
Database EMBL [online], database accession No. cv242851, downloaded Oct. 18, 2012, 4 pages.
Database Uniprot [Online], database accession No. A7UGC9, downloaded Oct. 18, 2012, 3 pages.
Ralph, et al. "Genomics of Hybrid Poplar (*Populus trichocarpa x deltoides*) Interacting with Forest Tent Caterpillars (*Malacosoma disstria*): Normalized and Full-length cDNA Libraries, Expressed Sequence Tags, and a cDNA Microarray for the Study of Insect-induced defences in Poplar," *Molecular Ecology*, vol. 15, pp. 1275-1297, 2006.
Shen, Wen-Hui, "NtSET1, a Member of a Newly Identified Subgroup of Plant SET-domain-containing Proteins, is Chromatin-associated and its Ectopic Overexpression Inhibits Tobacco Plant Growth," *The Plant Journal*, vol. 28, No. 4, pp. 371-383, 2001.
Taylor, Gail. "*Populus:* Arabidopsis for Forestry. Do We Need a Model Tree?," *Annals of Botany*, vol. 90, pp. 681-689, 2002.
First Office action dated Sep. 29, 2011 issued by the Chinese Patent Office to related Chinese patent application 200880127543.2.
Second Office action dated Jul. 10, 2012 issued by the Chinese Patent Office to related Chinese patent application 200880127543.2.
Office action dated Apr. 17, 2012 issued by the European Patent Office to related European application 08 869 183.7.
First Examination Report dated Jul. 12, 2012 issued by the New Zealand Patent Office to related New Zealand application 601188.
First Examination Report dated Feb. 15, 2011 issued by the New Zealand Patent Office to related new Zealand application 586643.
Second Examination Report dated Jul. 31, 2012 issued by the New Zealand Patent Office to related New Zealand application 586643.
Supplementary European Search report dated Jul. 19, 2011 issued to related European application EP 08 86 9183.
Written Opinion dated May 8, 2009 issued to related international application No. PCT/SE2008/051495.
Aharoni, et al. "Identification of the *SATT* Gene Involved in Strawberry Flavor Biogenesis by Use of DNA Microarrays," *The Plant Cell*, vol. 12, pp. 647-661, May 2000.

(Continued)

*Primary Examiner* — Medina A Ibrahim
*Assistant Examiner* — Russell Boggs
(74) *Attorney, Agent, or Firm* — Knobbe, Martens, Olson & Bear LLP

(57) ABSTRACT

The present invention pertains to a novel and extensive analytical platform for selecting genes with a possible commercial phenotype from a large group of candidate genes identified using tools in bioinformatics, data from EST sequencing and DNA array. An aspect of the invention provides methods of producing a transgenic plant having an increased growth compared to its wild type. The method comprises altering in the plant the level of a gene product of at least one gene specifically expressed during different phases of wood formation. This may be done with transgenic methods or by specific crossing methods. Further aspects of the invention provide a plant cell or plant progeny and wood having modulated gene expression according to the invention. Other aspects pertain a DNA construct comprising a nucleotide sequence of the invention and a plant cell or plant progeny comprising the DNA construct.

10 Claims, 1 Drawing Sheet

(56) References Cited

OTHER PUBLICATIONS

*Antisense Technology a Practical Approach*, Edited by C. Lichtenstein and W. Nellen, Oxford University Press, Inc., New York, 1997. The title page, frontispiece and table of contents are provided in eight pages.
The *Arabidopsis* Genome Initiative, "Analysis of the Genome Sequence of the Flowering Plant *Arabidopsis thaliana*," *Nature*, vol. 408, pp. 796-815, Dec. 14, 2000.
Brady, et al. "Perspective Extreme Breeding: Leveraging Genomics for Crop Improvement," *Journal of the Science of Food and Agriculture*, vol. 87, pp. 925-929, 2007.
Burke, et al. "Crop Evolution: From Genetics to Genomics," *Current Opinion in Genetics & Development*, vol. 17, pp. 525-532, 2007.
*Cell Culture and Somatic Cell Genetics of Plants*, vols. 1-3, Edited by Indra K. Vasil, Academic Press, Inc., Orlando, Florida, 1984. Title pages, frontispieces and Table of Contents for each of the three volumes are included in 33 pages.
Chern, et al. "Evidence for a Disease-resistance Pathway in Rice Similar to the *NPR1*-mediated Signaling Pathway in *Arabidopsis*," *The Plant Journal*, vol. 27, No. 2, pp. 101-113, 2001.
Fan, et al. "In Vivo Interaction between NPR1 and Transcription Factor TGA2 Leads to Salicylic Acid-mediated Gene Activation in *Arabidopsis*," *The Plant Cell*, vol. 14, pp. 1377-1389, Jun. 2002.
Feng, et al. "Progressive Sequence Alignment as a Prerequisite to Correct Phylogenetic Trees," *Journal of Molecular Evolution*, vol. 25, pp. 351-360, 1987.
Gilmour, et al. "Low Temperature Regulation of the *Arabidopsis* CBF Family of AP2 Transcriptional Activators as an Early Step in Cold-induced *COR* Gene Expression," *The Plant Journal*, vol. 16, No. 4, pp. 433-442, 1998.
Henikoff, et al. "TILLING. Traditional Mutagenesis Meets Functional Genomics," *Plant Physiology*, vol. 135, pp. 630-636, Jun. 2004.
Hertzberg, et al. "A Transcriptional Roadmap to Wood Formation," *PNAS*, vol. 98, No. 25, pp. 14732-14737, Dec. 4, 2001.
Higgins, et al. "Using CLUSTAL for Multiple Sequence Alignments," *Methods Enzymol*, vol. 266, pp. 383-402, 1996.
Ichikawa, et al. "Identification and Role of Adenylyl Cyclase in Auxin Signalling in Higher Plants," *Nature*, vol. 390, pp. 698-701, Dec. 18/25, 1997 and *Nature*, vol. 396, p. 390, Nov. 26, 1998.
Jaglo, et al. "Components of the *Arabidopsis* C-Repeat/Dehydration-Responsive Element Binding Factor Cold-Response Pathway are Conserved in *Brassica napus* and Other Plant Species," *Plant Physiology*, vol. 127, pp. 910-917, Nov. 2001.
Jin, et al. "Multifunctionality and Diversity within the Plant *MYB*-gene Family," *Plant Molecular Biology*, vol. 41, pp. 577-585, 1999.
Journot-Catalino, et al. "The Transcription Factors WRKY11 and WRKY17 Act as Negative Regulators of Basal Resistance in *Arabidopsis thaliana*," *The Plant Cell*, vol. 18, pp. 3289-3302, Nov. 2006.
Kakimoto. "CKI1, A Histidine Kinase Homolog Implicated in Cytokinin Signal Transduction," *Science*, vol. 274, No. 5289, pp. 982-985, Nov. 8, 1996.
Karimi, et al. "Gateway™ Vectors for *Agrobacterium*-mediated Plant Transformation," *TRENDS in Plant Science*, vol. 7, No. 5, pp. 193-195, May 2002.
Katou, et al. "Involvement of PPS3 Phosphorylated by Elicitor-Responsive Mitogen-Activated Protein Kinases in the Regulation of Plant Cell Death," *Plant Physiology*, vol. 139, pp. 1914-1926, Dec. 2005.
Kosugi, et al. "E2F Sites that can Interact with E2F Proteins Cloned from Rice are Required for Meristematic Tissue-specific Expression of Rice and Tobacco Proliferating Cell Nuclear Antigen Promoters," *The Plant Journal*, vol. 29, No. 1, pp. 45-59, 2002.
Lee, et al. "Cross-Referencing Eukaryotic Genomes: TIGR Orthologous Gene Alignments (TOGA)," *Genome Research*, vol. 12, pp. 493-502, 2002.

Li, et al. "Genome-wide Analysis of Basic/Helix-Loop-Helix Transcription Factor Family in Rice and *Arabidopsis*," *Plant Physiology*, vol. 141, pp. 1167-1184, Aug. 2006.
Moyle, et al. "Environmental and Auxin Regulation of Wood Formation Involves Members of the *Aux/IAA* Gene Family in Hybrid Aspen," *The Plant Journal*, vol. 31, No. 6, pp. 675-685, 2002.
Neurath, et al. *The Proteins*, 1977-1982, 3$^{rd}$ Edition, Academic Press, Inc., New York. One page.
Ng, et al. "Plant SET Domain-containing Proteins: Structure, Function and Regulation," *Biochim Biophys Acta*, vol. 1769, Nos. 5-6, pp. 316-329, 2007.
Ratcliff, et al. Regulation of Flowering in *Arabidopsis* by an *FLC* Homologue, *Plant Physiology*, vol. 126, pp. 122-132, May 2001.
Remm, et al. "Automatic Clustering of Orthologs and In-paralogs from Pairwise Species Comparisons," *Journal of Molecular Biology*, vol. 314, pp. 1041-1052, 2001.
Riaño-Pachón, et al. "PInTFDB: An Integrative Plant Transcription Factor Database," *BMC Bioinformatics*, vol. 8, No. 42, 10 pages, 2007.
Riechmann, et al. "*Arabidopsis* Transcription Factors: Genome-wide Comparative Analysis Among Eukaryotes," *Science*, vol. 290, No. 5499, pp. 2105-2110, Dec. 15, 2000.
Rognes. "ParAlign A Parallel Sequence Alignment Algorithm for Rapid and Sensitive Database Searches," *Nucleic Acids Research*, vol. 29, No. 7, pp. 1647-1652, 2001.
Sambrook, et al. *Molecular Cloning a Laboratory Manual*, vol. 1, 3$^{rd}$ Edition, Cold Spring Harbor Laboratory Press, Cold Spring Harbor, New York, 2001. The title page and frontispiece are provided.
Schrader, et al. "A High-Resolution Transcript Profile Across the Wood-Forming Meristem of Poplar Identifies Potential Regulators of Cambial Stem Cell Identity," *The Plant Cell*, vol. 16, pp. 2278-2292, Sep. 2004.
Slade, et al. "TILLING Moves Beyond Functional Genomics into Crop Improvement," *Transgenic Research*, vol. 14, pp. 109-115, 2005.
Sterky, et al. "Gene Discovery in the Wood-forming Tissues of Poplar: Analysis of 6,692 Expressed Sequence Tags," *PNAS*, vol. 95, pp. 13330-13335, Oct. 1998.
Sterky, et al. "A *Populus* EST Resource for Plant Functional Genomics," *PNAS*, vol. 101, No. 38, pp. 13951-13956, Sep. 21, 2004.
Thompson, et al. "CLUSTAL W: Improving the Sensitivity of Progressive Multiple Sequence Alignment through Sequence Weighting, Position-specific Gap Penalties and Weight Matrix Choice," *Nucleic Acids Research*, vol. 22, No. 22, pp. 4673-4680, 1994.
Tuskan, et al. "The Genome of Black Cottonwood, *Populus trichocarpa* (Torr. & Gray)," *Science*, vol. 313, pp. 1596-1604, 2006.
Ülker et al. "WRKY Transcription Factors: from DNA Binding Towards Biological Function," *Current Opinion in Plant Biology*, vol. 7, pp. 491-498, 2004.
Varshney, et al. "Genomics-assisted Breeding for Crop Improvement," *TRENDS in Plant Science*, vol. 10, No. 12, pp. 621-630, Dec. 2005.
White, et al. Microarray Analysis of *Drosophila* Development During Metamorphosis, *Science*, vol. 286, pp. 2179-2184, Dec. 10, 1999.
Nilsson, et al. "Spatial Pattern of Cauliflower Mosaic Virus 35S Promoter-Luciferase Expression in Transgenic Hybrid Aspen Trees Monitored by Enzymatic Assay and Non-Destructive Imaging," *Transgenic Research*, vol. 1, pp. 209-220, 1992.
International Search Report mailed May 8, 2009 and issued to international application No. PCT/SE2008/051495.
Office Action issued in corresponding Japanese Patent Application No. 2010-540614, mailed on May 7, 2013. i.
Nanjo et al., "Characterization of Full-length Enriched Expressed Sequence Tags of Stress-treated Poplar Leaves," *Plant Cell Physiol.*, vol. 45(12), pp. 1738-1748 (2004).
Nanjo, BP2922672 full-length enriched poplar cDNA library Populus nigra cDNA clone PnFL1-010_G05.f5-, mRNA sequence, Genbank [online]; Feb. 2005, National Center for Biotechnology Information, Bethesda MD, USA, [retrieved on Apr. 30, 2013] Retrieved from the Internet: URL:http://www.ncbi.nlmnih.gov/nucest/BP922672, Accession No. BP922672, GenInfo Identifier No. 60204114.

(56) References Cited

OTHER PUBLICATIONS

Ralph et al., "Genomics of hybrid poplar (*Populus trichocarpa* x *deltoides*) interacting with forest tent caterpillars (*Malacosoma disstria*): normalized and full-length cDNA libraries, expressed sequence tags, and a cDNA microarray for the study of insect-induced defences in poplar," *Molecular Ecology*, vol. 15(5), pp. 1275-1297 (2006).

Sterky et al., "A *Populus* EST resource for plant functional genomics," PNAS, vol. 101(38), pp. 13951-13956 (Sep. 21, 2004).

Office Action issued in corresponding Japanese Patent Application No. 2010-540614, mailed on Feb. 10, 2014.

Bohlmann et al., WS02537.B21_D06 PT-MB-N-A-15 *Populus trichocarpa* cDNA clone WS02537_D06 3-, mRNA sequence, Genbank [online]; Aug. 2005, National Center for Biotechnology Information, Bethesda, MD, USA, [retrieved on Jan. 28, 2014] Retrieved from the Internet<URL:http://www.ncbi.nlm.nih.gov/nucest/Dt488710>, Accession No. DT488710, GenInfo Identifier No. 73885972.

\* cited by examiner

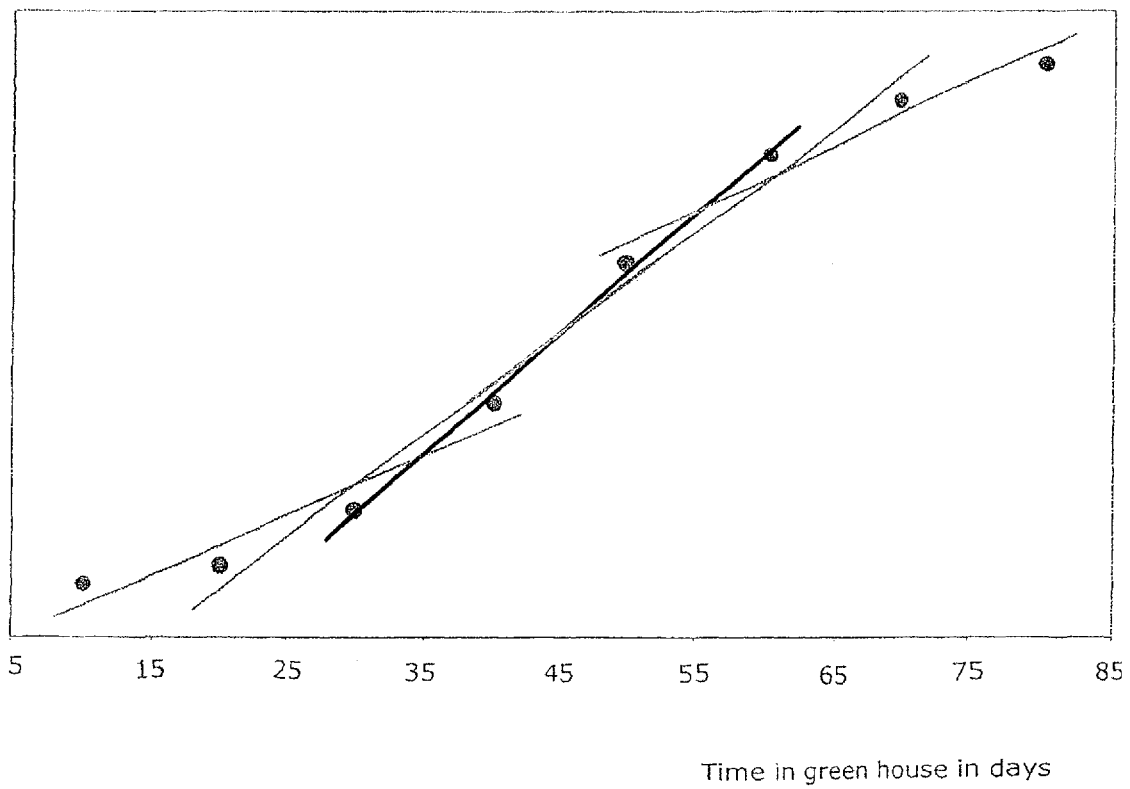
Time in green house in days

WOODY PLANTS HAVING IMPROVED GROWTH CHARACTERISTICS AND METHOD FOR MAKING THE SAME USING TRANSCRIPTION FACTORS

CROSS REFERENCE TO RELATED APPLICATIONS

This is a U.S. National Phase patent application of PCT/SE2008/051495, filed Dec. 18, 2008, which claims priority to Swedish patent application Serial No. SE 0702908-5, filed Dec. 28, 2007, and U.S. provisional patent application Serial No. 61/018,679, filed Jan. 3, 2008, all of which are hereby incorporated by reference in the present disclosure in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 616562004000SeqList.txt, date recorded: Jun. 23, 2010, size: 231 KB).

TECHNICAL FIELD OF THE INVENTION

The present invention relates generally to the field of molecular biology and relates to a method for improving plant growth characteristics. More specifically, the invention relates to methods for phenotypically modifying plants and transgenic plants and plants obtained by a specific crossing method having altered expression of a gene resulting in a modified growth phenotype. The invention also provides constructs useful in the method of the invention. Further, the invention relates to a plant cell or plant progeny of the plants and wood produced by the plants according to the invention.

BACKGROUND OF THE INVENTION

At present, the primary objectives of forest-tree engineering and molecular breeding are to improve wood quality and yield. The global demand for wood products is growing at around 1.7% annually, and this increase in wood consumption is occurring despite the fact that the maximum sustainable rate of harvesting from the worlds forests has already been reached or exceeded. Therefore, there is a need for increases in plantation wood production worldwide. Forestry plantations may also have advantages as a carbon sequestration crop in response to increasing atmospheric $CO_2$. Similarly, increased production of biomass from non-woody plants is desirable, for instance in order to meet the demand for raw material for energy production. Modification of specific processes during cell development in higher species is therefore of great commercial interest, not only when it comes to improving the properties of trees, but also other plants.

Plant growth by means of apical meristems results in the development of sets of primary tissues and in lengthening of the stem and roots. In addition to this primary growth, tree species undergo secondary growth and produce the secondary tissue "wood" from the cambium. The secondary growth increases the girth of stems and roots.

Perennial plants such as long-lived trees have a life style considerably different from annual plants such as *Arabidopsis* in that perennial plants such as trees has an indeterminate growth whereas plants like *Arabidopsis* have an terminate end of growth when the plant flowers. The final size of an *Arabidopsis* plant is in many ways dependent on the developmental program from germination to flowering and seed set. One example is that any change in the timing of these events can drastically change the size of the plant.

Perennial plants also cycle between periods of active growth and dormancy. During active growth leaves perform photosynthesis to capture energy which then used to drive various cellular processes. The fixed carbon which converted to sucrose is transferred to stem tissues and apical bud where it is stored during the dormant state initially as starch and later as sucrose. As growth reinitiates after release from dormancy, this sucrose is translocated to actively growing tissues since early stages of reactivation occur before photosynthesis starts. Similarly for nitrogen, amino acids are translocated also to stem and apical tissues and stored as storage proteins during dormancy and broken down as growth starts. Thus the life cycle of long lived trees differs significantly from annual crops which often translocate carbon and nitrogen to seeds.

Due to these differences between annual crops and perennial plants such as trees, determinants of yield and the ability to measure them are likely to considerably different. Actually, in many instances is a model system such as *Populus tremula× tremuloides* much better for reliably finding genes that can be used for increasing biomass production. For example for annual crops, seed size/yield has been proposed to be a measure of plant size and productivity but this is unlikely to be the case since perennial plants such as trees take several years to flower and thus seed yield, if at all, is only indicator of growth conditions that prevail during the year the plant flowered. Thus direct translation of research and findings from annual crops are unlikely to be useful in case of trees.

A very important part of the biomass of trees is present in stem tissues. This biomass accumulation is a result of leaf photosynthesis and nitrogen acquisition and redistribution of nutrients to various cellular processes. As such leaf size, leaf photosynthesis, ability to acquire nitrogen size of root system can all be important players in determination of plant productivity and biomass production. However none by themselves can account for the entire biomass production. For example, leaf size is not always related to biomass as significant variation can be found in leaf size. Moreover the ability to cope with stress is an important determinant of biomass production. Thus there are several factors that need to be altered in order to enhance biomass production in trees.

Furthermore, wood density is an important trait in increased biomass production, an increased wood density gives less volume that have to be transported and contain more energy content per volume. Therefore increased density is of interest even if the total biomass is not increased. Density is also a important in showing that an increased metrical growth in height and diameter is not coupled to an decrease in wood density.

One way to increase growth is to learn more about gene function and use that information to increase growth and biomass production. Such gene function knowledge and ways to use the knowledge is described in this patent.

Most genes have now been identified in a number of plants such as *Arabidopsis thaliana* (*Arabidopsis* Genome Initiative 2000) and *Populus tremula×tremuloides* (Sterky et al. 2004) and *Populus trichocarpa* (Tuskan et al. 2006).

Hertzberg et al. 2001, and Schrader et al. 2005 have used transcript profiling to reveal a transcriptional hierarchy for thousands of genes during xylem development as well as providing expression data. Such data can facilitate further elucidation of many genes with unknown function White et al. 1999; Aharoni et al. 2000.

One problem remaining is how to identify the potentially most important genes involved in regulation of cell division and other processes related to growth. In this present invention we examined a number of transcription factors for their use, which resulted in an unexpectedly increased growth when over expressed. The reason to select transcription factors for analysis is because they are known to be part regulators of many if not most processes in living organisms including plants. It is predictive that *Arabidopsis thaliana* contains 1500 different transcription factors that can be divided into ~30 subclasses based on sequence homologies (Riechmann et al. 2000). The function a certain transcription factor have within a plant is closely connected to which genes it regulates, e.g. although transcription factors within a transcription factor sub group as the MYB class are similar, they are known to regulate several different processes in plants. Transcription factors are proteins that regulate transcription of genes by either repressing or activating transcription initiation of specific genes or genomic regions containing different genes.

Specifically targeting transcription factors in plants in order to find genes that can be used to alter plant characteristics have been done before. In for example WO 02/15675, a large numbers of transcription factors have been analysed and the possible use for many of them been mentioned. US2007/0039070 describes and lists a large number of transcription factor genes from Eucalyptus and *Pinus radiata* and speculates in the use of such genes. Here we present specific transcription factors that have an industrially relevant effect in substantially increasing growth, which is supported with experimental data.

Although it is obvious that results from EST programs, genome sequencing and expression studies using DNA array technologies can verify where and when a gene is expressed it is rarely possible to clarify the biological and/or technical function of a gene only from these types of analytical tools. In order to analyze and verify the gene function a functional characterization must be performed, e.g. by gene inactivation and/or gene over-expression. However, in order to be able to identify genes with interesting and most often unexpected commercial features, candidate genes has to be evaluated based on functional analysis and measuring increased growth with multiple criteria.

MYB transcription factors. One of the genes presented here (SEQ ID:12) belongs to the MYB class of transcription factors. The MYB transcription factor family is predicted to have ~180 members in *Arabidopsis* (Riechmann et al 2000). Several different functions have been found for MYB genes in plants (Jin and Martin 1999). More specifically genes closely related to SEQ ID: 12 have not to our knowledge been shown to be involved in regulating growth rates and biomass production. The closely related genes AT2G01060 and AB192880 are implicated to be involved in biotic stress responses, US2003101481 and Katou et al 2005.

SET domain transcription factors (Ng et al. 2007). One of the genes presented here SEQ ID: 11 belongs to the SET domain class of transcription factors. SET domain proteins regulate transcription by modulating chromatin structure. The *Arabidopsis* genome is known to contain at least 29 active set domain proteins. Genes closely related to SEQ ID: 11 have not to our knowledge been shown to be involved in regulating growth rates and biomass production.

The bHLH class of transcriptional regulators is an large group of transcription factors in plants, for example is *Arabidopsis thaliana* predicted to contain ~139 members (Riechmann et al 2000). bHLH proteins have been implicated in many different processes se Xiaoxing et al 2006 for an overview in rice. One of the genes presented here SEQ ID: 10 belong to the bHLH class of transcription factors. Genes closely related to SEQ ID:10 have not to our knowledge been shown to be involved in regulating growth rates and biomass production.

The gene SEQ ID: 9 belong to the Homeobox class of genes. The closest *Arabidopsis thaliana* homolog to the gene over-expressed with construct TF0013 is predicted to be AT1G23380. Over-expression of a related *Solanum tuberosum* homolog to the gene over-expressed with construct TF0013 decreases growth, internode length and leaf size (U.S. Pat. No. 7265263). Over-expression of a related *Arabidopsis thaliana* homolog to the gene over-expressed with construct TF0013 alters leaf morphology (U.S. Pat. No. 7,265,263, US 20070022495, and WO01036444). The use to increase yield and biomass production by altering the expression level of the gene over-expressed with construct TF0013 is previously unknown.

The IAA/AUX group of transcription factors is a small group of transcription factors mainly found in plants (26 members predicted in *Arabidopsis* by Riechmann et al. 2000). The gene corresponding to SEQ ID: 13 belong to this group and is described in Moyle et al 2002. Genes closely related to SEQ ID: 13 have not to our knowledge been shown to be involved in regulating growth rates and biomass production.

The WRKY gene family group. The WRKY transcription factor family is a large family of genes in plants. Rice is predicted to have more than 90 members and *Arabidopsis* is predicted to have 74 members (Ülker and Somssich 2004). One of the functions that have been mostly associated with WRKY genes are wound and pathogen defense signalling, but also signalling coupled to abiotic stress, and resistance against both abiotic and biotic stress.

Eight of the genes presented here belong to the WRKY class of transcription factors.

SEQ ID:4 and SEQ ID:7 belongs to one sub group of WRKY genes. Genes closely related to SEQ ID:4 and SEQ ID:7 have not, to our knowledge, been shown to be involved in regulating growth rates and biomass production.

SEQ ID:1 belongs to another sub group of WRKY genes. A closely related *Arabidopsis thaliana* homolog (AT2G23320) to the gene SEQ ID:1 is believed to be involved in C/N sensing (US 20060272060), altering leaf size (U.S. Pat. No. 7,238,860, US 20030226173, US 20040019927, and WO02015675) and altering seed protein content (US 20030226173). AT2G23320 is also believed to be involved in the reaction and adaptation to peroxide stress according to Patent Application No. WO04087952. US 20040019927, U.S. Pat. No. 7,238,860, US 20030226173, WO02015675 mention the gene AT2G23320 in combination with increased leaf size and increased stature and speculate that over expression of this gene can be used to increase growth and biomass production. We have here shown that SEQ ID:1 can be used in trees to increase growth to an industrial significant degree.

SEQ ID:6 belongs to an sub group of WRKY genes that is related to the subgroup that SEQ ID:1 belongs to but clearly different from that group of genes. Genes closely related to this gene are known to be negative regulators of basal resistance in *Arabidopsis thaliana*. Journot-Catalino eta al 2006. The closely related gene AT4G31550 is believed to be related to seed prenyl lipid and seed lutein levels (US 20060195944 and US 20070022495, and WO01035727). Another predicted *Arabidopsis thaliana* homolog AT2G24570 to SEQ ID:6 is believed to be involved in C/N sensing (US 20070022495 and 20060272060). Genes closely related to SEQ ID:6 have not to our knowledge been shown to be involved in regulating growth rates and biomass production.

SEQ ID:2 belongs to another sub group of WRKY genes. Genes closely related to SEQ ID:2 have not to our knowledge been shown to be involved in regulating growth rates and biomass production.

SEQ ID:3 and SEQ ID:5 belongs to a large group of WRKY genes containing 2 WRKY domains. A number of related homologs to SEQ ID:3 and SEQ ID:5 containing two WRKY-domains are believed to be involved in altering seed yield and number of flowers in Oryza sativa according to Patent Application No. WO 2007003409. The use to increase growth and biomass production by altering the expression level is previously unknown.

SEQ ID:8 belongs to another sub group of WRKY genes. The closely related Arabidopsis thaliana gene AT4G23810 is known to reduce plant size and be involved in altering seed protein content (US 20030226173). Another related Arabidopsis thaliana homolog (AT5G24110) is known to be involved in altering seed protein content and inducing early flowering (US 20030226173). Genes closely related to SEQ ID:8 have not to our knowledge been shown to be involved in regulating growth rates and biomass production.

SUMMARY OF THE INVENTION

The present invention pertains to novel genes that can be used to increase growth. The genes are found by using a analytical platform that is concentrated on analysing growth behavior based on a combination of multiple criteria. The invention provides methods for producing a transgenic plant by changing the expression of one or more genes selected from a group of genes which fulfil said criteria. Thus, the invention relates to methods for phenotypically modifying plants and transgenic plants and plants obtained by a specific crossing method having altered expression of a gene resulting in a modified growth phenotype. The invention also provides constructs useful in the method of the invention. Further, the invention relates to a plant cell or plant progeny of the plants and wood produced with unexpectedly good properties by the plants according to the invention.

A number of genes analyzed using the analytical platform show interesting and most often unexpected commercial features. Thus, an aspect of the present invention provides a method of producing a plant having an unexpectedly high growth compared to its wild type, comprising altering (increasing) in the plant the level of a gene product of at least one gene belonging to one of the transcription factor sequences SEQ ID:1-13, 97-115.

The increase in growth can be observed when comparing a group of transgenic plants grown for 8 weeks in a greenhouse under a photoperiod of 18 hours, a temperature of 22° C./15° C. (day/night) and a weekly fertilization Weibulls Rika S NPK 7-1-5 diluted 1 to 100 with a group of wild-type plants grown under identical conditions;

Another aspect of the invention provides a plant cell or plant progeny of a transgenic plant or a plant with intentionally changed (increased) levels of one gene's SEQ ID: 1-13, 97-115 according to the invention and comprising a recombinant polynucleotide.

A further aspect of the invention provides biomass and products thereof produced by a intentionally plant having the characteristics described above.

Still another aspect of the invention provides a DNA construct comprising at least one sequence as described as described herein.

Finally, one aspect of the invention provides a plant cell or plant progeny comprising the DNA construct according to the invention.

DESCRIPTION OF THE FIGURES

FIG. 1 shows an example of a height growth curve with four different data point linear regression lines shown, the black regression line shows the maximum height growth rate;

DETAILED DESCRIPTION OF THE INVENTION

Definitions

Prior to discussing the present invention in further details, the following terms and conventions will first be defined:

The term "transgenic plant" refers to a plant that contains genetic material, not found in a wild type plant of the same species, variety or cultivar. The genetic material may include a transgene, an insertional mutagenesis event (such as by transposon or T-DNA insertional mutagenesis), an activation tagging sequence, a mutated sequence, a homologous recombination event or a sequence modified by chimeraplasty. Typically, the foreign genetic material has been introduced into the plant by human manipulation. The term also refers to plants in which genetic material has been inserted to function as a selection marker. Examples of such selectable markers include kanamycin, hygromycin, phosphoinotricin, chlorsulfron, methotrexate, gentamycin, spectinomycin, imidazolinones, d-aminoacids and glyphosate.

In the present context the term "growth" includes primary growth, including a lengthening of the stem and roots, as well as secondary growth of a plant, including production of secondary tissue, "wood", from the cambium and an increase in the girth of stems and roots. Thus, the expression "increased growth" relates in the present context to an increase growth of a transgenic plant relative to the wild-type plant from which the transgenic plant is derived, when grown under the same growth conditions. As described below, a transgenic plant is characterized to have an increased growth if the plant meets at least one of the "growth difference selection criteria" as defined in the below Examples.

The term "phenotype" refers in the present context to an individual plant's total physical appearance, such as growth. Examples of different growth phenotypes used in the present context are listed in the below table 1.2.

The term "gene" broadly refers to any segment of DNA associated with a biological function. Genes include coding sequences and/or regulatory sequences required for their expression. Genes also include non-expressed DNA nucleic acid segments that, e.g., form recognition sequences for other proteins (e.g., promoter, enhancer, or other regulatory regions). Genes can be obtained from a variety of sources, including cloning from a source of interest or synthesizing from known or predicted sequence information, and may include sequences designed to have desired parameters.

"Overexpression" refers to the expression of a polypeptide or protein encoded by a DNA of SEQ ID NO: 1-13, 97-115 or similar sequences introduced into a host cell, wherein said polypeptide or protein is either not normally present in the host cell, or wherein said polypeptide or protein is present in said host cell at a higher level than that normally expressed from the endogenous gene encoding said polypeptide or protein.

Overexpression of the proteins of the instant invention may be accomplished by first constructing a chimeric gene in which the coding region is operably linked to a promoter capable of directing expression of a gene in the desired tissues at the desired stage of development. The chimeric gene may comprise promoter sequences and translation leader sequences derived from the same genes. 3' Non-coding sequences encoding transcription termination signals may also be provided. The instant chimeric gene may also comprise one or more introns in order to facilitate gene expression. A suitable promoter may be the CaMV 35 S promoter which may be used with *Agrobacterium* as a vector.

The term "RNA interference" or "RNAi" refers generally to a process in which a double-stranded RNA molecule or a short hairpin RNA changes the expression of a nucleic acid sequence with which they share substantial or total homology.

The term "RNAi down-regulation" refers to the reduction in the expression of a nucleic acid sequence mediated by one or more RNAi species. The term "RNAi species" refers to a distinct RNA sequence that elicits RNAi.

The term "photoperiod" refers to the daily cycle of light and darkness.

The terms "nucleic acid construct", "DNA construct" and "vector" refer to a genetic sequence used to transform plants or other organisms. The nucleic acid construct or DNA construct may be able to direct, in a transformed plant the expression of a protein or a nucleic acid sequence, such as for example an antisense RNA. Typically, such a nucleic acid construct or DNA construct comprises at least a coding region for a desired gene product or a desired nucleic acid product operably linked to 5' and 3' transcriptional regulatory elements. In some embodiments, such nucleic acid constructs or DNA constructs are chimeric, i.e. consisting of a mixture of sequences from different sources. However, non-chimeric nucleic acid constructs or DNA constructs may also be used in the present invention.

The term "recombinant" when used with reference, e.g., to a cell, nucleotide, vector, protein, or polypeptide typically indicates that the cell, nucleotide, or vector has been modified by the introduction of a heterologous (or foreign) nucleic acid or the alteration of a native nucleic acid, or that the protein or polypeptide has been modified by the introduction of a heterologous amino acid, or that the cell is derived from a cell so modified. Recombinant cells express nucleic acid sequences (e.g., genes) that are not found in the native (non-recombinant) form of the cell or express native nucleic acid sequences (e.g. genes) that would be abnormally expressed under-expressed, or not expressed at all. The term "recombinant" when used with reference to a cell indicates that the cell replicates a heterologous nucleic acid, or expresses a peptide or protein encoded by a heterologous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques.

The term "nucleic acid sequence" refers to a polymer of deoxyribonucleotides or ribonucleotides in either single- or double-stranded form. Unless specifically limited, the term encompasses nucleic acid sequences containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated.

A "polynucleotide" is a nucleic acid sequence comprising a plurality of polymerized nucleotide residues, e.g., at least about 15 consecutive polymerized nucleotide residues, optionally at least about 30 consecutive nucleotides, at least about 50 consecutive nucleotides. In many instances, a polynucleotide comprises a nucleotide sequence encoding a polypeptide (or protein) or a domain or fragment thereof. Additionally, the polynucleotide may comprise a promoter, an intron, an enhancer region, a polyadenylation site, a translation initiation site, 5' or 3' untranslated regions, a reporter gene, a selectable marker, or the like. The polynucleotide can be single stranded or double stranded DNA or RNA. The polynucleotide optionally comprises modified bases or a modified backbone. The polynucleotide can be e.g. genomic DNA or RNA, a transcript (such as an mRNA), a cDNA, a PCR product, a cloned DNA, a synthetic DNA or RNA, or the like. The polynucleotide can comprise a sequence in either sense or antisense orientation.

The term "polypeptide" is used broadly to define linear chains of amino acid residues, including occurring in nature and synthetic analogues thereof.

In the context of the present invention "complementary" refers to the capacity for precise pairing between two nucleotides sequences with one another. For example, if a nucleotide at a certain position of an oligonucleotide is capable of hydrogen bonding with a nucleotide at the corresponding position of a DNA or RNA molecule, then the oligonucleotide and the DNA or RNA are considered to be complementary to each other at that position. The DNA or RNA strand are considered complementary to each other when a sufficient number of nucleotides in the oligonucleotide can form hydrogen bonds with corresponding nucleotides in the target DNA or RNA to enable the formation of a stable complex.

In the present context the expressions "complementary sequence" or "complement" therefore also refer to nucleotide sequences which will anneal to a nucleic acid molecule of the invention under stringent conditions.

The term "stringent conditions" refers to general conditions of high, weak or low stringency.

The term "stringency" is well known in the art and is used in reference to the conditions (temperature, ionic strength and the presence of other compounds such as organic solvents) under which nucleic acid hybridisations are conducted. With "high stringency" conditions, nucleic acid base pairing will occur only between nucleic acid fragments that have a high frequency of complementary base sequences, as compared to conditions of "weak" or "low" stringency. Suitable conditions for testing hybridization involve pre-soaking in 5×SSC and pre-hybridizing for 1 hour at ~40° C. in a solution of 20% formamide, 5×Denhardt's solution, 50 mM sodium phosphate, pH 6.8, and 50 mg of denatured sonicated calf thymus DNA, followed by hybridization in the same solution supplemented with 100 mM ATP for 18 hours at ~40° C., followed by three times washing of the filter in 2×SSC, 0.2% SDS at 40° C. for 30 minutes (low stringency), preferred at 50° C. (medium stringency), more preferably at 65° C. (high stringency), even more preferably at ~75° C. (very high stringency). More details about the hybridization method can be found in Sambrook et al., Molecular Cloning: A Laboratory Manual, 2nd Ed., Cold Spring Harbor, 1989.

The terms "hybridization" and "hybridize" are used broadly to designate the association between complementary or partly complementary nucleic acid sequences, such as in a reversal of the process of denaturation by which they were separated. Hybridization occurs by hydrogen bonding, which may be Watson-Crick, Hoogsteen, reversed Hoogsteen hydrogen bonding, etc., between complementary nucleoside or nucleotide bases. The four nucleobases commonly found in DNA are G, A, T and C of which G pairs with C, and A pairs with T. In RNA T is replaced with uracil (U), which then pairs with A. The chemical groups in the nucleobases that participate in standard duplex formation constitute the Watson-Crick face. Hoogsteen showed a couple of years later that the purine nucleobases (G and A) in addition to their Watson-Crick face have a Hoogsteen face that can be recognised from the outside of a duplex, and used to bind pyrimidine oligonucleotides via hydrogen bonding, thereby forming a triple helix structure.

A "subsequence" or a "fragment" is any portion of an entire sequence. Thus, a fragment or subsequence refers to a sequence of amino acids or nucleic acids that comprises a part of a longer sequence of amino acids (e.g. polypeptide) or nucleic acids (e.g. polynucleotide), respectively.

In the present context, the term "homology" indicates similarities between two amino acid sequences or between two nucleotide sequences is described by the parameter "sequence identity".

The term "sequence identity" indicates a quantitative measure of the degree of homology between two amino acid sequences or between two nucleic acid sequences of equal length. If the two sequences to be compared are not of equal length, they must be aligned to give the best possible fit, allowing the insertion of gaps or, alternatively, truncation at the ends of the polypeptide sequences or nucleotide sequences. The sequence identity can be calculated as $$\frac{(N_{ref} - N_{dif})100}{N_{ref}},$$

wherein $N_{dif}$ is the total number of non-identical residues in the two sequences when aligned and wherein $N_{ref}$ is the number of residues in one of the sequences. Hence, the DNA sequence AGTCAGTC will have a sequence identity of 75% with the sequence AATCAATC ($N_{dif}=2$ and $N_{ref}=8$). A gap is counted as non-identity of the specific residue(s), i.e. the DNA sequence AGTGTC will have a sequence identity of 75% with the DNA sequence AGTCAGTC ($N_{dif}=2$ and $N_{ref}=8$).

With respect to all embodiments of the invention relating to nucleotide sequences, the percentage of sequence identity between one or more sequences may also be based on alignments using the clustalW software with default settings. For nucleotide sequence alignments these settings are:
Alignment=3Dfull, Gap Open 10.00, Gap Ext. 0.20, Gap separation Dist. 4, DNA weight matrix: identity (IUB). Alternatively, the sequences may be analysed using the program DNASIS Max. This service is based on the two comparison algorithms called Smith-Waterman (SW) and ParAlign. The first algorithm was published by Smith and Waterman (1981) and is a well established method that finds the optimal local alignment of two sequences The other algorithm, ParAlign, is a heuristic method for sequence alignment; details on the method is published in Rognes (2001). Default settings for score matrix and Gap penalties as well as E-values were used.

The phrase "substantially identical" or "substantial identity" in the context of two nucleic acids or polypeptides, refers to two or more sequences or sub-sequences that have at least about 60%, 70%, 75%, preferably 80% or 85%, more preferably 90%, 91%, 92%, 93%, 94%, 95%, 96%, 97%, 98%, 99%, 99.5%, or greater nucleotide or amino acid residue percent identity, respectively, when compared and aligned for maximum correspondence, as measured using one of the following sequence comparison algorithms or by visual inspection. In certain aspects, the substantial identity exists over a region of amino acid sequences of at least about 50 residues in length, such as, at least about 100, 110, 120, 125, 130, 135, 140, 145, 150, 155, 160, or 165 amino acid residues. In certain aspects, substantial identity exists over a region of nucleic acid sequences of at least about 150 nucleic acid residues, such as at least about 200, 250, 300, 330, 360, 375, 400, 425, 450, 460, 480, 500, 600, 700, 800 such as at least about 900 nucleotides or such as at least about 1 kb, 1.1 kb, 1.2 kb, 1.3 kb, 1.4 kb, 1.5 kb, 1.6 kb, 1.7 kb, 1.8 kb, 1.9 kb, 2 kb, 2.1 kb, 2.2 kb, 2.3 kb, 2.4 kb, 2.5 kb, 2.6 kb, 2.7 kb, 2.8 kb, 2.9 kb or such as at least about 3 kb. In some aspects, the amino acid or nucleic acid sequences are substantially identical over the entire length of the polypeptide sequence or the corresponding coding region.

The term "Conservative substitutions" are within the group of basic amino acids (arginine, lysine and histidine), acidic amino acids (glutamic acid and aspartic acid), polar amino acids (glutamine and asparagine), hydrophobic amino acids (leucine, isoleucine, valine and methionine), aromatic amino acids (phenylalanine, tryptophan and tyrosine), and small amino acids (glycine, alanine, serine and threonine). Amino acid substitutions which do not generally alter the specific activity are known in the art and are described, for example, by Neurath and Hill, 1979. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

The term "conservatively substituted variant" as used herein refers to a variant of a nucleotide sequence comprising one or more conservative substitutions.

Generally and in the present context, the term "silent substitution" refers to a base substitution which does not affect the sense of a codon and thus has no effect on polypeptide structure. As the skilled person will know silent substitutions are possible because of the degeneracy of the genetic code.

The term "conserved domain" refers to a sequence of amino acids in a polypeptide or a sequence of nucleotides in DNA or RNA that is similar across multiple species. A known set of conserved sequences is represented by a consensus sequence. Amino acid motifs are often composed of conserved sequences. Additionally, the term "conserved sequence" refers to a base sequence in a nucleic acid sequence molecule or an amino acid sequence in a protein that has remained essentially unchanged throughout evolution. A "consensus sequence" is defined in terms of an idealized sequence that represents the base most often present at each position in a nucleic acid sequence or the amino acid most often present at each position in a protein. A "consensus sequence" is identified by aligning all known examples of a nucleic acid sequence or a protein so as to maximise their sequence identity. For a sequence to be accepted as a consensus sequence each particular base or amino acid must be reasonably predominant at its position and most of the sequences must be related to the consensus by only few substitutions, such as 1 or 2.

A homologue may also be in the form of an "insertional variant" of a protein, i.e. where one or more amino acid residues are introduced into a predetermined site in a protein. Insertions may comprise N-terminal and/or C-terminal fusions as well as intra-sequence insertions of single or multiple amino acids. Generally, insertions within the amino acid sequence will be smaller than N- or C-terminal fusions, of the order of about 1 to 10 residues. Examples of N- or C-terminal fusion proteins or peptides include the binding domain or activation domain of a transcriptional activator as used in the yeast two-hybrid system, phage coat proteins, (histidine)-6-tag, glutathione S-transferase-tag, protein A, maltose-binding protein, dihydrofolate reductase, Tag-100 epitope, c-myc epitope, FLAG®-epitope, lacZ, CMP (calmodulin-binding peptide), HA epitope, protein C epitope and VSV epitope.

Homologues in the form of "deletion variants" of a protein are characterised by the removal of one or more amino acids from a protein.

Homologues in the form of "addition variants" of a protein are characterised by the addition of one or more amino acids from a protein, whereby the addition may be at the end of the sequence.

Amino acid variants of a protein may readily be made using peptide synthetic techniques well known in the art, such as solid phase peptide synthesis and the like, or by recombinant DNA manipulations. Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gen in vitro mutagenesis (USB, Cleveland, Ohio), QuickChange Site-Directed mutagenesis (Stratagene, San Diego, Calif.), PCR-mediated site-directed mutagenesis or other site-directed mutagenesis protocols.

The terms "Orthologs" and "Paralogs"-sequences are also a type of homologous sequences as described above. Several different methods are known by those of skill in the art for identifying and defining these functionally homologous sequences. Three general methods for defining orthologs and paralogs are described; an ortholog, paralog or homolog may be identified by one or more of the methods described below.

Orthologs and paralogs are evolutionarily related genes that have similar sequence and similar functions. Orthologs are structurally related genes in different species that are derived by a speciation event. Paralogs are structurally related genes within a single species that are derived by a duplication event.

Within a single plant species, gene duplication may cause two copies of a particular gene, giving rise to two or more genes with similar sequence and often similar function known as paralogs. A paralog is therefore a similar gene formed by duplication within the same species. Paralogs typically cluster together or in the same clade (a group of similar genes) when a gene family phylogeny is analyzed using programs such as CLUSTAL (Thompson et al.; Higgins et al. Groups of similar genes can also be identified with pair-wise BLAST analysis (Feng and Doolittle. For example, a clade of very similar MADS domain transcription factors from *Arabidopsis* all share a common function in flowering time (Ratcliffe et al.), and a group of very similar AP2 domain transcription factors from *Arabidopsis* are involved in tolerance of plants to freezing (Gilmour et al.). Analysis of groups of similar genes with similar function that fall within one clade can yield sub-sequences that are particular to the clade. These sub-sequences, known as consensus sequences, can not only be used to define the sequences within each clade, but define the functions of these genes; genes within a clade may contain paralogous sequences, or orthologous sequences that share the same function (see also, for example, Mount (2001), in Bioinformatics: Sequence and Genome Analysis Cold Spring Harbor Laboratory Press, Cold Spring Harbor, N.Y., page 543.)

Speciation, the production of new species from a parental species, can also give rise to two or more genes with similar sequence and similar function. These genes, termed orthologs, often have an identical function within their host plants and are often interchangeable between species without losing function. Because plants have common ancestors, many genes in any plant species will have a corresponding orthologous gene in another plant species. Once a phylogenic tree for a gene family of one species has been constructed using a program such as CLUSTAL potential orthologous sequences can be placed into the phylogenetic tree and their relationship to genes from the species of interest can be determined. Orthologous sequences can also be identified by a reciprocal BLAST strategy. Once an orthologous sequence has been identified, the function of the ortholog can be deduced from the identified function of the reference sequence.

Orthologous genes from different organisms have highly conserved functions, and very often essentially identical functions (Lee et al. and Remm et al.). Paralogous genes, which have diverged through gene duplication, may retain similar functions of the encoded proteins. In such cases, paralogs can be used interchangeably with respect to certain embodiments of the instant invention (for example, transgenic expression of a coding sequence). An example of such highly related paralogs is the CBF family, with three well-defined members in *Arabidopsis* and at least one ortholog in *Brassica napus*, all of which control pathways involved in both freezing and drought stress (Gilmour et al. and Jaglo et al.)

The following references represent a small sampling of the many studies that demonstrate that conserved transcription factor genes from diverse species are likely to function similarly (i.e., regulate similar target sequences and control the same traits), and that transcription factors may be transformed into diverse species to confer or improve traits.

(1) The *Arabidopsis* NPR1 gene regulates systemic acquired resistance (SAR); over-expression of NPR1 leads to enhanced resistance in *Arabidopsis*. When either *Arabidopsis* NPR1 or the rice NPR1 ortholog was overexpressed in rice (which, as a monocot, is diverse from *Arabidopsis*), challenge with the rice bacterial blight pathogen *Xanthomonas oryzae* pv. *Oryzae*, the transgenic plants displayed enhanced resistance (Chern et al.). NPR1 acts through activation of expression of transcription factor genes, such as TGA2 (Fan and Dong).

(2) E2F genes are involved in transcription of plant genes for proliferating cell nuclear antigen (PCNA). Plant E2Fs share a high degree of similarity in amino acid sequence between monocots and dicots, and are even similar to the conserved domains of the animal E2Fs. Such conservation indicates a functional similarity between plant and animal E2Fs. E2F transcription factors that regulate meristem development act through common cis-elements, and regulate related (PCNA) genes (Kosugi and Ohashi).

The term "closely related" genes is used for genes that are orthologous or paralogous.

The term "promoter," as used herein, refers to a region of sequence determinants located upstream from the start of transcription of a gene and which are involved in recognition and binding of RNA polymerase and other proteins to initiate and modulate transcription. Promoters useful in plants need not be of plant origin. A "basal promoter" is the minimal sequence necessary for assembly of a transcription complex required for transcription initiation. Basal promoters frequently include a TATA box" element usually located between 15 and 35 nucleotides upstream from the site of initiation of transcription. Basal promoters also sometimes include a CCAAT box" element (typically a sequence CCAAT) and/or a GGGCG sequence, usually located between 40 and 200 nucleotides, preferably 60 to 120 nucleotides, upstream from the start site of transcription.

Promoters referred to herein as "constitutive promoters" actively promote transcription under most, but not necessarily all, environmental conditions and states of development or cell differentiation. Examples of constitutive promoters include the cauliflower mosaic virus (CaMV) 35S transcript initiation region and the 1' or 2' promoter derived from T-DNA of *Agrobacterium tumefaciens*, and other transcription initiation regions from various plant genes, such as the maize ubiquitin-1 promoter, known to those of skill. Organ-specific promoters may be, for example, a promoter from storage sink tissues such as seeds, potato tubers, and fruits, or from metabolic sink tissues such as meristems, a seed specific promoter such as the glutelin, prolamin, globulin, or albumin promoter from rice, a *Vicia faba* promoter from the legumin B4 and the unknown seed protein gene from *Vicia faba*, a promoter from a seed oil body protein, the storage protein napA promoter from *Brassica napus*, or any other seed specific promoter known in the art, e.g., as described in WO 91/14772. Furthermore, the promoter may be a leaf specific promoter such as the rbcs promoter from rice or tomato, the *chlorella* virus adenine methyltransferase gene promoter, or the aldP gene promoter from rice, or a wound inducible promoter such as the potato pin2 promoter.

An "inducible promoter" in the context of the present invention refers to a promoter which is regulated under certain conditions, such as light, chemical concentration, protein concentration, conditions in an organism, cell, or organelle, etc. An example of an inducible promoter is the HSP promoter and the PARSK1, the promoter from the *Arabidopsis* gene encoding a serine-threonine kinase enzyme and which is induced by dehydration, abscissic acid and sodium chloride. In essence, expression under the control of an inducible promoter is "switched on" or increased in response to an applied stimulus. The nature of the stimulus varies between promoters and may include the above environmental factors. Whatever the level of expression is in the absence of the stimulus, expression from any inducible promoter is increased in the presence of the correct stimulus.

As used herein, the term "tissue specific" refers to a characteristic of a particular tissue that is not generally found in all tissues, or may be exclusive found in a tissue of interest. In the present application, "tissue specific" is used in reference to a gene regulatory element (promoter or promoter plus enhancer and/or silencer), the gene it encodes, or the polypeptide product of such a gene. In the context of a gene regulatory element or a "tissue specific promoter", the term means that the promoter (and also other regulatory elements such as enhancer and/or silencer elements) directs the transcription of a linked sequence in a cell of a particular lineage, tissue, or cell type, but is substantially inactive in cells or tissues not of that lineage, tissue, or cell type. A tissue specific promoter useful according to the invention is at least 5-fold, 10-fold, 25-fold, 50fold, 100-fold, 500-fold or even 1,000 times more active in terms of transcript production in the particular tissue than it is in cells of other tissues or in transformed or malignant cells of the same lineage. In the context of a gene or the polypeptide product of a gene, the term tissue specific means that the polypeptide product of the gene is detectable in cells of that particular tissue or cell type, but not substantially detectable in certain other cell types. Particularly relevant tissue specific promoters include promoter sequences specifically expressed or active in the xylem forming tissue in a plant. Examples of such promoters are the Lmp1, Lmx2, Lmx3, Lmx4 and Lmx5 promoters, described in WO2004097024.

A "terminator sequence" refers to a section of genetic sequence that marks the end of gene or operon on genomic DNA for transcription. Terminator sequences are recognized by protein factors that co-transcriptionally cleave the nascent RNA at a polyadenylation signal, halting further elongation of the transcript by RNA polymerase. A nucleic acid is "operably linked" when it is placed into a functional relationship with another nucleic acid sequence. For instance, a promoter or enhancer is operably linked to a coding sequence if it increases the transcription of the coding sequence. Operably linked means that the DNA sequences being linked are typically contiguous and, where necessary to join two protein coding regions, contiguous and in reading frame. However, since enhancers generally function when separated from the promoter by several kilobases and intronic sequences may be of variable lengths, some polynucleotide elements may be operably linked but not contiguous.

In the context of the present invention the terms "transformation" and "transforming" are used interchangeably and as synonyms to "transfecting" and "transfection", respectively, to refer to the process of introducing DNA into a cell. The DNA constructs, including at least a portion of the gene or promoter of interest, can be introduced into host cells, which as stated previously, can be individual cells, cells in culture, cells as part of a host organism, a fertilized oocyte orgametophyte or an embryonic cell. By the term "introduction" when used in reference to a host cell is meant to refer to standard procedures known in the art for introducing recombinant vector DNA into the target host cell. Such procedures include, but are not limited to, transfection, infection, transformation, natural uptake, electroporation, biolistics and *Agrobacterium*.

By "regenerable cell" is meant a plant cell from which a whole plant can be regenerated. It will be understood that the regenerable cell is a cell that has maintained its genetic potential, also known in the art as "totipotency". It will further be understood that the regenerable cells, when grown in culture, may need the appropriate stimuli to express the total genetic potential of the parent plant.

Method of Producing a Transgenic Plant

In specific embodiments of the invention advantageous plant phenotypes are generated by modifying, relative to the corresponding wild-type plant, the expression level of candidate genes that have been evaluated and selected according to the above criteria. According to these aspects a method is provided which comprises altering in the plant the level of a gene product of at least one gene comprising a nucleotide sequence selected from the group consisting of:
 a) a nucleotide sequence from SEQ ID NO: 1-13, 97-115;
 b) a nucleotide sequence being at least 60% identical to a nucleotide sequence from SEQ ID NO 1-13, 97-115;
 c) a subsequence or fragment of a nucleotide sequence of a) or b).

This may be done by following technically modified crossing method comprising
i) selecting plant species expressing at least one of the nucleotide sequences selected from the group consisting of
 a) a nucleotide sequence from SEQ ID NO 1-13, 97-115;
 b) a nucleotide sequence being at least 60% identical to a nucleotide sequence from SEQ ID NO 1-13, 97-115;
 c) a subsequence or fragment of a nucleotide sequence of a) or b,
ii) crossing a plant species selected in i) with the same or another plant species selected in i), iii) selecting plants with modulated expression of at least one of the nucleotide sequences selected from the group consisting of
  a) a nucleotide sequence from SEQ ID NO 1-13, 97-115;
  b) a nucleotide sequence being at least 60% identical to a nucleotide sequence from SEQ ID NO 1-13, 97-115;
  c) a subsequence or fragment of a nucleotide sequence of a) or b, compared to the plant species selected under i)
iv) optionally backcrossing one or more times the plants obtained in iii) and selecting plants with modulated expression of at least one of the nucleotide sequences selected from the group consisting of
  a) a nucleotide sequence from SEQ ID NO 1-13, 97-115;
  b) a nucleotide sequence being at least 60% identical to a nucleotide sequence from SEQ ID NO 1-13, 97-115;
  c) a subsequence or fragment of a nucleotide sequence of a) or b) compared to any of the plant species used in i) and/or plants obtained in iii).

According to one aspect of the invention a method is provided comprising the following steps:
(i) providing an expression vector comprising a nucleotide sequence selected from the group consisting of
  a) a nucleotide sequence from SEQ ID NO 1-13, 97-115; or
  b) a nucleotide sequence being at least 60% identical to a nucleotide sequence from SEQ ID NO 1-13, 97-115; or
  c) a subsequence or fragment of a nucleotide sequence of a) or b) and
  d) at least one regulatory element operably linked to the polynucleotide sequence, wherein said at least one regulatory element controls expression of the polynucleotide sequence in a target plant;
(ii) introducing the expression vector into at least one plant; and
(iii) selecting at least one transgenic plant that has a modulated growth and/or biomass compared to its wild type.

The sequences specified by sequence ID numbers 1-13, 97-115; represent sequences of the candidate genes as predicted from *Populus trichocarpa* and seq ID numbers 73-95 as cloned from hybrid aspen. As the skilled person will understand, additional sequence from these genes 5' as well as 3' to the sequence described in SEQ ID NOs: 73-95 is readily achievable using conventional cloning techniques, such as those described in Sambrook et al.

According to one embodiment the modulated expression is effected by introducing a genetic modification preferably in the locus of a gene encoding a polypeptide comprising SEQ ID NO: 1-13, 97-115 or a homologue of such polypeptide.

The modification may be effected by one of: T-DNA activation, TILLING, homologous recombination, site-directed mutagenesis or directed breeding using one or more of SEQ ID NO: 1-13, 97-115 as markers in any step of the process.

The effect of the modulation may be increased yield in growth and/or in biomass.

Nucleic Acid Constructs

According to more particular embodiments of the invention, the method comprises the step of providing a nucleic acid construct, such as a recombinant DNA construct, comprising a nucleotide sequence selected from the group consisting of:
  a) a nucleotide sequence comprising a sequence selected from SEQ ID NO: 1-13, 97-115;
  b) a complementary nucleotide sequence of a nucleotide sequence of a);
  c) a sub-sequence or fragment of a nucleotide sequence of b) or c);
  d) a nucleic acid sequence being at least 60% identical to any one of the sequences in a), b) and c); and
  e) a nucleotide sequence which hybridizes under stringent conditions to a nucleotide sequence of a), b) or c).

In further embodiments of the invention the nucleic acid sequence in c) or g) is at least 65% identical to any one of the sequences in a), c), d), e) or f), such as at least 70% identical, at least 75% identical, at least 80% identical, at least 85% identical, at least 87% identical, at least 90% identical, at least 95% identical, at least 97% identical, at least 98% identical, at least 99% identical, or at least 99.5% identical to any one of the sequences in a), c), d), e) or f).

In preferred embodiments of this aspect of the invention the nucleotide sequence of a) is selected from the group consisting of SEQ ID NOs: 1, 4, 6, 7, 9, 10, 101, 102, 104, 106 and 107.

A variety of methods exist in the art for producing the nucleic acid sequences and nucleic acid/DNA constructs of the invention. Procedures for identifying and isolating DNA clones are well known to those of skill in the art, and are described in, e.g. Sambrook et al., Molecular Cloning-A Laboratory Manual (2nd Ed.), Vol. 1-3, Cold Spring Harbor Laboratory, Cold Spring Harbor, N.Y., 1989. Alternatively, the nucleic acid sequences of the invention can be produced by a variety of in vitro amplification methods adapted to the present invention by appropriate selection of specific or degenerate primers. Examples of protocols sufficient to direct persons of skill through in vitro amplification methods, including the polymerase chain reaction (PCR) the ligase chain reaction (LCR), Qbeta-replicase amplification and other RNA polymerase mediated techniques (e.g., NASBA), e.g., for the production of the homologous nucleic acids of the invention are found in Sambrook, supra.

Alternatively, nucleic acid constructs of the invention can be assembled from fragments produced by solid-phase synthesis methods. Typically, fragments of up to approximately 100 bases are individually synthesized and then enzymatically or chemically ligated to produce a desired sequence, e.g., a polynucletotide encoding all or part of a transcription factor. For example, chemical synthesis using the phosphoramidite method is well known to the skilled person. According to such methods, oligonucleotides are synthesized, purified, annealed to their complementary strand, ligated and then optionally cloned into suitable vectors. The invention also relates to vectors comprising the DNA constructs.

As mentioned, the above described sequences are from hybrid aspen and *Populus trichocarpa*. As the skilled person will understand, homologues of the described sequences may be isolated from other species, non-limiting examples of which include acacia, eucalyptus, hornbeam, beech, mahogany, walnut, oak, ash, hickory, birch, chestnut, alder, maple, sycamore, ginkgo, palm tree, sweet gum, cypress, Douglas fir, fir, sequoia, hemlock, cedar, juniper, larch, pine, redwood, spruce and yew, apple, plum, pear, banana, orange, kiwi, lemon, cherry, grapevine, fig, cotton, bamboo, switch grass, red canary grass and rubber plants. Useful homologues of the described sequences may also be isolated from hardwood plants from the Salicaceae family, e.g. from the *salix* and *populus* genus. Members of this genus are known by their common names: willow, poplar and aspen.

Examples of other suitable plants for use in accordance with any aspect of the invention described herein include monocotyledons, dicotelydons, gymnosperms and algae, ferns and mosses. Of particular interest are transgenic higher plants, especially agricultural crops, for example cereals, and flowers, which have been engineered to carry a heterologous nucleic acid as described above, including tobacco, cucurbits, carrot, vegetable *brassica*, melons, capsicums, grape vines, lettuce, strawberry, oilseed *brassica*, sugar beet, wheat, barley, maize, rice, sugar cane, soybeans, peas, sorghum, sunflower, tomato, potato, pepper, chrysanthemum, carnation, linseed, hemp and rye.

In some preferred embodiments, the plant is a perennial plant, for example a woody perennial plant. A woody perennial plant is a plant which has a life cycle which takes longer than 2 years and involves a long juvenile period in which only vegetative growth occurs. This is contrasted with an annual or herbaceous plant such as *Arabidopsis thaliana* or *Lycopersicon esculentum* (tomato), which have a life cycle which is completed in one year.

In particular, the method according to the present invention may comprise a step of providing a nucleic acid construct, such as a recombinant DNA construct, comprising a nucleotide sequence which relative to the particular sequences described, comprises conservative variations altering only one, or a few amino acids in the encoded polypeptide may also be provided and used according to the present invention. Accordingly, it is within the scope of the invention to provide and use a recombinant DNA construct comprising a nucleotide sequence which encodes a polypeptide comprising a conservatively substituted variant of a polypeptide of a).

Sequence alterations that do not change the amino acid sequence encoded by the polynucleotide are termed "silent" substitutions. With the exception of the codons ATG and TGG, encoding methionine and tryptophan, respectively, any of the possible codons for the same amino acid can be substituted by a variety of techniques, e.g., site-directed mutagenesis, available in the art. Accordingly, the present invention may also provide a recombinant nucleic acid construct, wherein the nucleotide sequence comprises a silent substitution in a nucleotide sequence.

In certain further embodiments of the invention, the subsequences or fragments have at least 65% sequence identity to a conserved domain of a nucleotide sequence as described above under item a) or d), such as at least 70% identical, at least 75% identical, at least 80% identical, at least 85% identical, at least 87% identical, at least 90% identical, at least 95% identical, at least 97% identical, at least 98% identical, at least 99% identical, or at least 99.5% identical to a conserved domain of a nucleotide sequence as described above under item a) or d).

Thus, there are methods for identifying a sequence similar or paralogous or orthologous or homologous to one or more polynucleotides as noted herein, or one or more target polypeptides encoded by the polynucleotides, or otherwise noted herein and may include linking or associating a given plant phenotype or gene function with a sequence. In the methods, a sequence database is provided (locally or across an internet or intranet) and a query is made against the sequence database using the relevant sequences herein and associated plant phenotypes or gene functions.

Approaches to Obtaining Altering the Level of a Gene Product

This invention is used by increasing the expression of certain genes, non limiting examples how this can be done are presented here. The nucleic acid construct or recombinant DNA construct as described above may be used for the identification of plants having altered growth characteristics as compared to the wild-type. Such plants may for instance be naturally occurring variants or plants that have been modified genetically to exhibit altered growth properties. For such purposes the nucleic acid construct or recombinant DNA construct according to the invention may be used e.g. as a probe in conventional hybridization assays or as a primer for specific amplification of nucleic acid fragments.

Although the main part of this invention is how an up regulation of the gene products gives the desired effect. It also shows that changing the expression of the genes presented here can be used to modify the desired properties, this is another way to look at the data, and an effect of this view is that also decreasing the gene products within the plant is a way to modify the desired trait. There are different ways to increase the levels of a gene product, these are described below in parallel with the ways to up-regulate a gene product.

One of the genes SEQ ID NO:1-13, 97-115; could also be used as targets for marker assisted breeding because changes in the gene regulatory sequences can give changes in the expression patterns and changes in the coding sequences can give changes in the gene function, and we have shown that manipulating these genes gives changes in the desired traits. This is usually referred to that the genes SEQ ID No 1-13, 97-115; can be used as candidate genes Brady and Provart 2007, and Varshney et al 2005

One particular way to use this invention is to measure the expression of one or more of the genes SEQ ID NO:1-13, 97-115; using for example quantitative RT-PCR in natural populations and select for unusual high expression of the measured gene and use such plants as parents in a breeding program, this could be repeated for each breeding cycle. Methods to quantify gene expression, including real time PCR, are described in Sambrook et al.

The genes presented here can also be used in candidate gene-based association studies, the result from such studies can then be used in marker assisted breeding. Burke et al 2007.

Up regulation or over expression of a gene can be achieved by placing the full open reading frame of the gene behind a suitable promoter, which are described elsewhere, and usually placing terminator and poly-adenylation signal sequence 3' of the gene to be over expressed.

In addition, the nucleic acid construct or recombinant DNA construct according to the invention may be used for the purpose of gene replacement in order to modify the plant growth phenotype.

Suppression of endogenous gene expression can for instance be achieved using a ribozyme. Ribozymes are RNA molecules that possess highly specific endoribonuclease activity. The production and use of ribozymes are disclosed in U.S. Pat. Nos. 4,987,071 and 5,543,508. While antisense techniques are discussed below, it should be mentioned that synthetic ribozyme sequences including antisense RNAs can be used to confer RNA cleaving activity on the antisense RNA, such that endogenous mRNA molecules that hybridize to the antisense RNA are cleaved, which in turn leads to an enhanced antisense inhibition of endogenous gene expression.

Vectors in which RNA encoded by a relevant gene homologue is over-expressed can also be used to obtain co-suppression of a corresponding endogenous gene, e.g., in the manner described in U.S. Pat. No. 5,231,020 to Jorgensen. Such co-suppression (also termed sense suppression) does not require that the entire gene sequence be introduced into the plant cells, nor does it require that the introduced sequence be exactly identical to the endogenous sequence of interest. However, the suppressive efficiency will be enhanced as specificity of hybridization is increased, e.g., as the introduced sequence is lengthened, and/or as the sequence similarity between the introduced sequence and the endogenous transcription factor gene is increased.

Vectors expressing an untranslatable form of gene, e.g., sequences comprising one or more stop codons, or nonsense mutation, can also be used to suppress expression of an endogenous transcription factor, thereby reducing or eliminating it's activity and modifying one or more traits. Methods for producing such constructs are described in U.S. Pat. No. 5,583,021. In particular, such constructs can be made by introducing a premature stop codon into the gene.

One way of performing targeted DNA insertion is by use of the retrovirus DNA integration machinery as described in WO2006078431. This technology is based on the possibility of altering the integration site specificity of retroviruses and retrotransposons integrase by operatively coupling the integrase to a DNA-binding protein (tethering protein). Engineering of the integrase is preferably carried out on the nucleic acid level, via modification of the wild type coding sequence of the integrase by PCR. The integrase complex may thus be directed to a desired portion or be directed away from an undesired portion of genomic DNA thereby producing a desired integration site characteristic.

Another technology that can be used to alter and preferably, in this invention, increase gene expression is the "Targeting Induced Local Lesions in Genomes", which is a non-transgenic way to alter gene function in a targeted way. This approach involves mutating a plant with foe example ethyl methanesulfonate (EMS) and later locating the individuals in which a particular desired gene has been modified. The technology is described for instance in Slade and Knauf, 2005 and Henikoff, et al.

A method for abolishing the expression of a gene is by insertion mutagenesis using the T-DNA of *Agrobacterium tumefaciens*. After generating the insertion mutants, the mutants can be screened to identify those containing the insertion in an appropriate gene. Plants containing a single transgene insertion event at the desired gene can be crossed to generate homozygous plants for the mutation.

As will be apparent to the skilled person, a plant trait can also be modified by using the cre-lox system. A plant genome can be modified to include first and second lox sites that are then contacted with a Cre recombinase. Provided that the lox sites are in the same orientation, the intervening DNA sequence between the two sites will be excised. If the lox sites are in the opposite orientation, the intervening sequence is inverted.

The polynucleotides and polypeptides of this invention can also be expressed in a plant in the absence of an expression cassette by manipulating the activity or expression level of the endogenous gene by other means, for example, by ectopically expressing a gene by T-DNA activation tagging, Ichikawa et al. (1997); Kakimoto et al. (1996). This method entails transforming a plant with a gene tag containing multiple transcriptional enhancers and once the tag has inserted into the genome, expression of a flanking gene coding sequence becomes deregulated. In another example, the transcriptional machinery in a plant can be modified so as to increase transcription levels of a polynucleotide of the invention (See, e.g., PCT Publications WO 96/06166 and WO 98/53057 which describe the modification of the DNA binding specificity of zinc finger proteins by changing particular amino acids in the DNA binding motif).

Antisense Suppression of Expression

However, the recombinant DNA construct, comprising a nucleotide sequence as described above is particularly useful for sense and anti-sense suppression of expression, e.g., to down-regulate expression of a particular gene, in order to obtain a plant phenotype with increased growth. That is, the nucleotide sequence of the invention, or sub-sequences or anti-sense sequences thereof, can be used to block expression of naturally occurring homologous nucleic acids. Varieties of traditional sense and antisense technologies are known in the art, e.g., as set forth in Lichtenstein and Nellen (1997). The objective of the antisense approach is to use a sequence complementary to the target gene to block its expression and create a mutant cell line or organism in which the level of a single chosen protein is selectively reduced or abolished.

For more elaborate descriptions of anti-sense regulation of gene expression as applied in plant cells reference is made to U.S. Pat. No. 5,107,065, the content of which is incorporated herein in its entirety.

RNA Interference

Gene silencing that is induced by double-stranded RNA is commonly called RNA interference or RNAi. RNA interference is a molecular mechanism in which fragments of double-stranded ribonucleic acid (dsRNA) interfere with the expression of a particular gene that shares a homologous sequence with the dsRNA. The process that is mediated by the same cellular machinery that processes microRNA, known as the RNA-induced silencing complex (RISC). The process is initiated by the ribonuclease protein Dicer, which binds and cleaves exogenous double-stranded RNA molecules to produce double-stranded fragments of 20-25 base pairs with a few unpaired overhang bases on each end. The short double-stranded fragments produced by Dicer, called small interfering RNAs (siRNAs), are separated and integrated into the active RISC complex. If one part of an RNA transcript is targeted by an RNAi molecule or construct, the whole transcript is down-regulated.

For more elaborate descriptions of RNAi gene suppression in plants by transcription of a dsRNA reference is made to U.S. Pat. No. 6,506,559, US 2002/0168707, and WO 98/53083, WO 99/53050 and WO 99/61631, all of which are incorporated herein by reference in their entirety.

Construction of Vectors

In general, those skilled in the art are well able to construct vectors of the present invention and design protocols for recombinant gene expression. For further details on general protocols for preparation of vectors reference is made to: Molecular Cloning: a Laboratory Manual: 2nd edition, Sambrook et al, 1989, Cold Spring Harbor Laboratory Press. The promoter used for the gene may influence the level, timing, tissue, specificity, or inducibility of the over expression.

Generally, over expression of a gene can be achieved using a recombinant DNA construct having a promoter operably linked to a DNA element comprising a sense element of a segment of genomic DNA or cDNA of the gene, e.g., the segment should contain enough of the open reading frame to produce a functional protein and preferably the full open reading frame.

In pertinent embodiments of the invention the nucleic acid construct, or recombinant DNA construct, further comprising a constitutive, inducible, or tissue specific promoter operably linked to said nucleotide sequence.

In a presently preferred embodiment of the invention, the nucleic acid construct, or recombinant DNA construct, comprises the sequence of SEQ ID NO: 96 the vector.

The presently preferred nucleic acid construct for over expression, is a vector termed pK2GW7. The vector is described in: Gateway vectors for *Agrobacterium*-mediated plants transformation, Karimi, 2002.

Transformation of Plant Cells

In accordance with the present invention, the method comprise the further step of transforming regenerable cells of a plant with said nucleic acid construct or recombinant DNA construct and regenerating a transgenic plant from said transformed cell. When introducing the above DNA construct or vector into a plant cell, certain considerations must be taken into account, well known to those skilled in the art. The nucleic acid to be inserted should be assembled within a construct that contains effective regulatory elements that will drive transcription, as described above. There must be available a method of transporting the construct into the cell. Once the construct is within the cell, integration into the endogenous chromosomal material either will or will not occur.

Transformation techniques, well known to those skilled in the art, may be used to introduce the DNA constructs and vectors into plant cells to produce transgenic plants, in particular transgenic trees, with improved plant growth.

A person of skills in the art will realise that a wide variety of host cells may be employed as recipients for the DNA constructs and vectors according to the invention. Non-limiting examples of host cells include cells in embryonic tissue, callus tissue type I, II, and III, hypocotyls, meristem, root tissue, tissues for expression in phloem.

As listed above, *Agrobacterium* transformation is one method widely used by those skilled in the art to transform tree species, in particular hardwood species such as poplar. Production of stable, fertile transgenic plants is now a routine in the art. Other methods, such as microprojectile or particle bombardment, electroporation, microinjection, direct DNA uptake, liposome mediated DNA uptake, or the vortexing method may be used where *Agrobacterium* transformation is inefficient or ineffective, for example in some gymnosperm species.

Alternatively, a combination of different techniques may be employed to enhance the efficiency of the transformation process, e.g. bombardment with *Agrobacterium* coated microparticles or microprojectile bombardment to induce wounding followed by co-cultivation with *Agrobacterium*.

It will be understood, that the particular choice of a transformation technology will be determined by its efficiency to transform certain plant species as well as the experience and preference of the person practising the invention with a particular methodology of choice. It will be apparent to the skilled person that the particular choice of a transformation system to introduce nucleic acid into plant cells is not essential to or a limitation of the invention, nor is the choice of technique for plant regeneration.

Following transformation, transgenic plants are preferably selected using a dominant selectable marker incorporated into the transformation vector. Typically, such a marker will confer antibiotic or herbicide resistance on the transformed plants and selection of transformants can be accomplished by exposing the plants to appropriate concentrations of the antibiotic or herbicide. A novel selection marker using the D-form of amino acids and based on the fact that plants can only tolerate the L-form offers a fast, efficient and environmentally friendly selection system. An interesting feature of this selection system is that it enables both selection and counter-selection.

Subsequently, a plant may be regenerated, e.g. from single cells, callus tissue or leaf discs, as is standard in the art. Almost any plant can be entirely regenerated from cells, tissues and organs of the plant. Available techniques are reviewed in Vasil et al. 1984.

After transformed plants are selected and grown to maturity, those plants showing an increase growth phenotype are identified. Additionally, to confirm that the phenotype is due to changes in expression levels or activity of the polypeptide or polynucleotide disclosed herein can be determined by analyzing mRNA expression using Northern blots, RT-PCR or microarrays, or protein expression using immunoblots or Western blots or gel shift assays.

Plant Species

In accordance with the invention, the present method produces a transgenic plant having an increased growth compared to its wild type plant from which it is derived. In an embodiment of the present method, the transgenic plant is a perennial plant, i.e. a plant that lives for more than two years. In a specific embodiment, the perennial plant is a woody plant which may be defined as a vascular plant that has a stem (or more than one stem) which is lignified to a high degree.

In a preferred embodiment, the woody plant is a hardwood plant, i.e. broad-leaved or angiosperm trees, which may be selected from the group consisting of acacia, eucalyptus, hornbeam, beech, mahogany, walnut, oak, ash, willow, hickory, birch, chestnut, poplar, alder, maple, sycamore, ginkgo, palm tree and sweet gum. Hardwood plants from the Salicaceae family, such as willow, poplar and aspen, including variants thereof, are of particular interest, as these two groups include fast-growing species of tree or woody shrub which are grown specifically to provide timber and bio-fuel for heating. Cellulosic grasses used for bioenergy like Switch grass and Red Canary Grass are also interesting.

In further embodiments, the woody plant is softwood or a conifer which may be selected from the group consisting of cypress, Douglas fir, fir, sequoia, hemlock, cedar, juniper, larch, pine, redwood, spruce and yew.

In useful embodiments, the woody plant is a fruit bearing plant which may be selected from the group consisting of apple, plum, pear, banana, orange, kiwi, lemon, cherry, grapevine and FIG.

Other woody plants which may be useful in the present method may also be selected from the group consisting of cotton, bamboo and rubber plants.

DNA Construct

According to a second main aspect of the invention a DNA construct, such as a recombinant DNA construct, is provided comprising at least one sequence as described above. In particular, the recombinant DNA construct may comprise a nucleotide sequence selected from the group consisting of:
 a) a nucleotide sequence comprising a sequence selected from SEQ ID NO: 1-13, 97-115;
 b) a complementary nucleotide sequence of a nucleotide sequence of a);
 c) a sub-sequence or fragment of a nucleotide sequence of a) or b);
 d) a nucleic acid sequence being at least 60% identical to any one of the sequences in a), b) and c); and
 e) a nucleotide sequence which hybridizes under stringent conditions to a nucleotide sequence of a), b) or c).

In selected embodiments of the invention the nucleic acid sequence in d) is at least 65% identical to any one of the sequences in a), b) and c), such as at least 70% identical, at least 75% identical, at least 80% identical, at least 85% identical, at least 87% identical, at least 90% identical, at least 95% identical, at least 97% identical, at least 98% identical, at least 99% identical, or at least 99.5% identical to any one of the sequences in a), b) and c).

Also, in accordance with the discussion above, the nucleotide sequence encodes a polypeptide comprising a conservatively substituted variant of a polypeptide of (a). Further, the nucleotide sequence comprises a silent substitution in a nucleotide sequence.

In additional embodiments of the pertaining to this aspect of the invention, the sub-sequences or fragments have at least 65% sequence identity to a conserved domain of a nucleotide sequence as described above under item a), such as at least 70% identical, at least 75% identical, at least 80% identical, at least 85% identical, at least 87% identical, at least 90% identical, at least 95% identical, at least 97% identical, at least 98% identical, at least 99% identical, or at least 99.5% identical to a conserved domain of a nucleotide sequence as described above under item a).

In further embodiments and in accordance with the description above, the recombinant DNA construct further comprising a constitutive, inducible, or tissue specific promoter operably linked to said nucleotide sequence. In particular, the recombinant DNA construct may further comprise a strong constitutive promoter in front of a transcribed cassette consisting of the full open reading frame of the gene followed by an terminator sequence. Such a cassette may comprise a nucleotide sequence as defined in claim 7 and on page 21 and the paragraph bridging pages 21 and 22.

In the presently exemplified embodiments of the invention the recombinant DNA construct comprises the sequence of SEQ ID NO: 96.

Transgenic Plants

A third aspect of the invention provides a transgenic plant comprising a recombinant polynucleotide (DNA construct) comprising a nucleotide sequence capable of altering in the plant the level of a gene product of at least one of the genes SEQ ID 1-13, 97-115. Giving increased growth when comparing said group of transgenic plants grown for 8 weeks in a greenhouse under a photoperiod of 18 hours, a temperature of 22° C./15° C. (day/night) and a weekly fertilization with N 84 g/l, Pl 2 g/l, K 56 g/l, with a group of wild-type plants grown under identical conditions;

According to particular embodiments of the invention the level of a gene product of at least one gene comprising a nucleotide sequence selected from the group consisting of:

a) a nucleotide sequence from SEQ ID NO: 1-13, 97-115;

b) a nucleotide sequence being at least 60% identical to a nucleotide sequence from SEQ ID NO 1-13, 97-115;

c) a subsequence or fragment of a nucleotide sequence of a) or b) has been altered relative to the level found in the respective corresponding wild-type plant.

According to yet another embodiment of the invention, the transgenic plant comprises a recombinant polynucleotide (DNA construct) comprising a nucleotide sequence selected from the group consisting of:

a) a nucleotide sequence comprising a sequence selected from SEQ ID NO: 1-13, 97-115;

b) a complementary nucleotide sequence of a nucleotide sequence of a);

c) a sub-sequence or fragment of a nucleotide sequence of a) or b);

d) a nucleic acid sequence being at least 60% identical to any one of the sequences in a), b) and c); and e) a nucleotide sequence which hybridizes under stringent conditions to a nucleotide sequence of a), b) or c).

In further embodiments of this aspect of the invention the nucleic acid sequence in c) or g) is at least 65% identical to any one of the sequences in a), b), c), d) or e), such as at least 70% identical, at least 75% identical, at least 80% identical, at least 85% identical, at least 87% identical, at least 90% identical, at least 95% identical, at least 97% identical, at least 98% identical, at least 99% identical, or at least 99.5% identical to any one of the sequences in a), b), c), d) or e). The transgenic plant may also comprise a nucleotide sequence encoding a polypeptide comprising a conservatively substituted variant of a polypeptide of a) or b). The nucleotide sequence may comprise a silent substitution in a nucleotide sequence. Further, sub-sequences or fragments may have at least 65% sequence identity to a conserved domain.

As mentioned above the skilled person will realize that a variety of methods exist in the art for producing the nucleic acid sequences and polynucleotide constructs of the invention, e.g. by cloning techniques, assembly of fragments generated by solid phase synthesis. Again, the skilled person will understand, homologues of the described sequences may be isolated from other species, non-limiting examples of which include acacia, eucalyptus, hornbeam, beech, mahogany, walnut, oak, ash, hickory, birch, chestnut, alder, maple, sycamore, ginkgo, palm tree, sweet gum, cypress, Douglas fir, fir, sequoia, hemlock, cedar, juniper, larch, pine, redwood, spruce and yew, apple, plum, pear, banana, orange, kiwi, lemon, cherry, grapevine, fig, cotton, bamboo, switchgrass, red canary grass and rubber plants. Useful homologues of the described sequences may also be isolated from hardwood plants from the Salicaceae family, such as from willow, poplar or aspen.

In particular, the transgenic plant according to the present invention may comprise a recombinant DNA construct comprising a nucleotide sequence which relative to the particular sequences described, comprises conservative variations altering only one, or a few amino acids in the encoded polypeptide may also be provided and used according to the present invention. Accordingly, it is within the scope of the invention to provide a transgenic plant comprising a recombinant DNA construct comprising a nucleotide sequence which encodes a polypeptide comprising a conservatively substituted variant of a polypeptide of a) or d).

Accordingly, the present invention may also provide a recombinant DNA construct, wherein the nucleotide sequence comprises a silent substitution in a nucleotide sequence, that is, the recombinant DNA construct may comprise a sequence alteration that does not change the amino acid sequence encoded by the polynucleotide.

In certain further embodiments of the invention, the sub-sequences or fragments have at least 65% sequence identity to a conserved domain of a nucleotide sequence as described above under item a) or d), such as at least 70% identical, at least 75% identical, at least 80% identical, at least 85% identical, at least 87% identical, at least 90% identical, at least 95% identical, at least 97% identical, at least 98% identical, at least 99% identical, or at least 99.5% identical to a conserved domain of a nucleotide sequence as described above under item a) or d).

In the particular embodiments by which the present invention is exemplified the sub-sequences or fragments in c) comprise the sequences of SEQ ID NOs: 18-34.

In further embodiments the transgenic plant provided according to the invention comprises a recombinant polynucleotide construct which further comprises a constitutive, inducible, or tissue specific promoter operably linked to said nucleotide sequence.

In still further embodiments the recombinant polynucleotide construct further comprises a strong constitutive promoter in front of a transcribed cassette. The cassette may comprise a nucleotide sequence, wherein modulated expression is effected by introducing a genetic modification preferably in the locus of a gene encoding a polypeptide comprising SEQ ID NO: 1-13, 97-115 or a homologue of such polypeptide followed by a plant functional intron followed by a nucleotide sequence encoding a polypeptide comprising a conservatively substituted variant of a polypeptide of a) or d), in reverse orientation.

In a presently preferred embodiment of the invention, the transgenic plant according to the invention comprises a recombinant DNA construct comprising the sequence of SEQ ID NO: 96

Plant Species

In accordance with the present invention, the transgenic plant may be a perennial plant which preferable is a woody plant or a woody species. In a useful embodiment, the woody plant is a hardwood plant which may be selected from the group consisting of acacia, eucalyptus, hornbeam, beech, mahogany, walnut, oak, ash, willow, hickory, birch, chestnut, poplar, alder, maple, sycamore, ginkgo, a palm tree and sweet gum. Hardwood plants from the Salicaceae family, such as willow, poplar and aspen including variants thereof, are of particular interest, as these two groups include fast-growing species of tree or woody shrub which are grown specifically to provide timber and bio-fuel for heating.

In further embodiments, the woody plant is a conifer which may be selected from the group consisting of cypress, Douglas fir, fir, sequoia, hemlock, cedar, juniper, larch, pine, redwood, spruce and yew.

In useful embodiments, the woody plant is a fruit bearing plant which may be selected from the group consisting of apple, plum, pear, banana, orange, kiwi, lemon, cherry, grapevine and FIG.

Other woody plants which may be useful in the present method may also be selected from the group consisting of cotton, bamboo and rubber plants.

The present invention extends to any plant cell of the above transgenic plants obtained by the methods described herein, and to all plant parts, including harvestable parts of a plant, seeds and propagules thereof, and plant explant or plant tissue. The present invention also encompasses a plant, a part thereof, a plant cell or a plant progeny comprising a DNA construct according to the invention. The present invention extends further to encompass the progeny of a primary transformed or transfected cell, tissue, organ or whole plant that has been produced by any of the aforementioned methods, the only requirement being that progeny exhibit the same genotypic and/or phenotypic characteristic(s) as those produced in the parent by the methods according to the invention.

It should be noted that embodiments and features described in the context of one of the aspects of the present invention also apply to the other aspects of the invention. Thus, definitions of one embodiment regard mutatis mutandis to all other embodiments comprising or relating to the one embodiment. When for example definitions are made regarding DNA constructs or sequences, such definitions also regard e.g. methods for producing a plant, vectors, plant cells, plants, biomass and wood comprising the DNA construct and vice versa. A DNA construct described in relation to a plant also regards all other embodiments.

All patent and non-patent references cited in the present application, are hereby incorporated by reference in their entirety.

The invention will now be described in further details in the following non-limiting examples.

EXAMPLES

Introduction

In order to find and elucidate the function of genes involved in growth, an extensive gene mining program was performed, resulting in the identification of genes useful in increasing growth which are of industrial application.

Materials and Methods

Gene Selection

The first step in this gene mining program was to select a number of genes from a large gene pool in order to narrow the genes to be tested for their function.

We decided to test transcription factors. The reason to select transcription factors for analysis is because they are long known to be part regulators of many if not most processes in living organisms plants.

Although the selection of the genes, for which functions are to be analysed, is an important part of the discovery of genes with functions interesting for forest biotechnology in an economic efficient way, it is the actual testing of the gene function of the selected genes which is the crucial step for finding their use in industrial applications.

The Transcription Factor genes were identified by BLAST analysis of the genes present in Populus DB, Sterky et al. 2004, against plant genes annotated as transcription factors present in databases described in Riano-Pachon et al 2007. In some instances were genes also selected based on having an differential expression pattern during wood formation (the genes corresponding to the constructs TFSTT 019, 035, 047 and 051).

Cloning of the Selected Genes

The corresponding gene models for the selected genes were extracted from data derived from the genome sequencing of Populus trichocarpa, Tuskan et al. 2006 using BLAST analysis. The gene models were compared to, and in some instances corrected based on, information published for homologous genes in Arabidopsis thaliana and other plant species. This was done using publically available databases. Selected genes were subsequently cloned into an over-expression vector under the control of the CaMV 35S promoter. For isolation of cDNA, total RNA was isolated from stem, leaf and bark tissue sampled from hybrid aspen clone T89 plants and reverse transcribed to cDNA using Superscript III First Strand Synthesis System (Invitrogen). cDNA were then amplified by PCR with gene specific forward and reverse primers using Phusion high fidelity DNA polymerase (Finnzymes). PCR primers were selected as follows, the 5'-primer was placed at the start codon and the 3' reverse primer was placed 3' of the translational stop site. Forward primers were modified by the introduction of a Kozak sequence (5"-AGAACC-3") upstream and next to the start codon of each target gene. The amplified cDNAs were inserted into a Gateway entry vector pENTR/D-TOPO (Invitrogen), followed by transfer of the genes into the expression vector pK2GW7 (SEQ ID NO:96) using the Gateway LR recombination reaction (Invitrogen). The cloned genes were control sequenced and compared to the selected genes using standard techniques before sub cloning into the plant vector pK2GW7.

The sequences of the genes, the polypeptide sequences and PCR primers for the genes presented here are listed in Table A to C.

TABLE A

| | | | | | |
|---|---|---|---|---|---|
| | \multicolumn{5}{c|}{PCR cloning primers} |
| Construct | Forward cloning primer | Reverse cloning primer | Construct | Forward cloning primer | Reverse cloning primer |
| TF0002 | SEQ ID NO: 27 | SEQ ID NO: 40 | TF0003 | SEQ ID NO: 135 | SEQ ID NO: 154 |
| TF0052 | SEQ ID NO: 28 | SEQ ID NO: 41 | TF0011 | SEQ ID NO: 136 | SEQ ID NO: 155 |
| TF0065 | SEQ ID NO: 29 | SEQ ID NO: 42 | TF0045 | SEQ ID NO: 137 | SEQ ID NO: 156 |
| TF0076 | SEQ ID NO: 30 | SEQ ID NO: 43 | TF0058 | SEQ ID NO: 138 | SEQ ID NO: 157 |
| TF0089 | SEQ ID NO: 31 | SEQ ID NO: 44 | TF0096 | SEQ ID NO: 139 | SEQ ID NO: 158 |
| TF0109 | SEQ ID NO: 32 | SEQ ID NO: 45 | TF0104 | SEQ ID NO: 140 | SEQ ID NO: 159 |
| TF0132 | SEQ ID NO: 33 | SEQ ID NO: 46 | TF0116 | SEQ ID NO: 141 | SEQ ID NO: 160 |
| TFSTT051 | SEQ ID NO: 34 | SEQ ID NO: 47 | TF0146 | SEQ ID NO: 142 | SEQ ID NO: 161 |
| TF0013 | SEQ ID NO: 35 | SEQ ID NO: 48 | TF0173 | SEQ ID NO: 143 | SEQ ID NO: 162 |
| TF0097 | SEQ ID NO: 36 | SEQ ID NO: 49 | TF0247 | SEQ ID NO: 144 | SEQ ID NO: 163 |
| TFSTT019 | SEQ ID NO: 37 | SEQ ID NO: 50 | TF0405 | SEQ ID NO: 145 | SEQ ID NO: 164 |
| TFSTT035 | SEQ ID NO: 38 | SEQ ID NO: 51 | TFSTT001 | SEQ ID NO: 146 | SEQ ID NO: 165 |
| TFSTT047 | SEQ ID NO: 39 | SEQ ID NO: 52 | TFSTT004 | SEQ ID NO: 147 | SEQ ID NO: 166 |
| | | | TFSTT013 | SEQ ID NO: 148 | SEQ ID NO: 167 |
| | | | TFSTT016 | SEQ ID NO: 149 | SEQ ID NO: 168 |
| | | | TFSTT017 | SEQ ID NO: 150 | SEQ ID NO: 169 |
| | | | TFSTT036 | SEQ ID NO: 151 | SEQ ID NO: 170 |
| | | | TFSTT038 | SEQ ID NO: 152 | SEQ ID NO: 171 |
| | | | TFSTT045 | SEQ ID NO: 153 | SEQ ID NO: 172 |

Binary destination vector: pK2GW7 SEQ ID NO: 96

TABLE B

| | Over-expressed gene cDNA and polypeptide sequences | | |
|---|---|---|---|
| Construct | Gene model for the over-expressed gene cDNA sequence | Predicted sequence of over-expressed protein | Species |
| TF0002 | SEQ ID NO: 1 | SEQ ID NO: 14 | *Populus trichocarpa* |
| TF0052 | SEQ ID NO: 2 | SEQ ID NO: 15 | *Populus trichocarpa* |
| TF0065 | SEQ ID NO: 3 | SEQ ID NO: 16 | *Populus trichocarpa* |
| TF0076 | SEQ ID NO: 4 | SEQ ID NO: 17 | *Populus trichocarpa* |
| TF0089 | SEQ ID NO: 5 | SEQ ID NO: 18 | *Populus trichocarpa* |
| TF0109 | SEQ ID NO: 6 | SEQ ID NO: 19 | *Populus trichocarpa* |
| TF0132 | SEQ ID NO: 7 | SEQ ID NO: 20 | *Populus trichocarpa* |
| TFSTT051 | SEQ ID NO: 8 | SEQ ID NO: 21 | *Populus trichocarpa* |
| TF0013 | SEQ ID NO: 9 | SEQ ID NO: 22 | *Populus trichocarpa* |
| TF0097 | SEQ ID NO: 10 | SEQ ID NO: 23 | *Populus trichocarpa* |
| TFSTT019 | SEQ ID NO: 11 | SEQ ID NO: 24 | *Populus trichocarpa* |
| TFSTT035 | SEQ ID NO: 12 | SEQ ID NO: 25 | *Populus trichocarpa* |
| TFSTT047 | SEQ ID NO: 13 | SEQ ID NO: 26 | *Populus trichocarpa* |
| TF0003 | SEQ ID NO: 97 | SEQ ID NO: 116 | *Populus trichocarpa* |
| TF0011 | SEQ ID NO: 98 | SEQ ID NO: 117 | *Populus trichocarpa* |
| TF0045 | SEQ ID NO: 99 | SEQ ID NO: 118 | *Populus trichocarpa* |
| TF0058 | SEQ ID NO: 100 | SEQ ID NO: 119 | *Populus trichocarpa* |
| TF0096 | SEQ ID NO: 101 | SEQ ID NO: 120 | *Populus trichocarpa* |
| TF0104 | SEQ ID NO: 102 | SEQ ID NO: 121 | *Populus trichocarpa* |
| TF0116 | SEQ ID NO: 103 | SEQ ID NO: 122 | *Populus trichocarpa* |
| TF0146 | SEQ ID NO: 104 | SEQ ID NO: 123 | *Populus trichocarpa* |
| TF0173 | SEQ ID NO: 105 | SEQ ID NO: 124 | *Populus trichocarpa* |
| TF0247 | SEQ ID NO: 106 | SEQ ID NO: 125 | *Populus trichocarpa* |
| TF0405 | SEQ ID NO: 107 | SEQ ID NO: 126 | *Populus trichocarpa* |
| TFSTT001 | SEQ ID NO: 108 | SEQ ID NO: 127 | *Populus trichocarpa* |
| TFSTT004 | SEQ ID NO: 109 | SEQ ID NO: 128 | *Populus trichocarpa* |
| TFSTT013 | SEQ ID NO: 110 | SEQ ID NO: 129 | *Populus trichocarpa* |
| TFSTT016 | SEQ ID NO: 111 | SEQ ID NO: 130 | *Populus trichocarpa* |
| TFSTT017 | SEQ ID NO: 112 | SEQ ID NO: 131 | *Populus trichocarpa* |
| TFSTT036 | SEQ ID NO: 113 | SEQ ID NO: 132 | *Populus trichocarpa* |
| TFSTT038 | SEQ ID NO: 114 | SEQ ID NO: 133 | *Populus trichocarpa* |
| TFSTT045 | SEQ ID NO: 115 | SEQ ID NO: 134 | *Populus trichocarpa* |

TABLE C

Control sequences of cloned cDNA

| Construct | Full control sequence of cloned cDNA | 5' control sequence of cloned cDNA | 3' control sequence of cloned cDNA | Species |
|---|---|---|---|---|
| TF0002 | SEQ ID NO: 73 | | | Populus tremula × tremuloides |
| TF0052 | SEQ ID NO: 74 | | | Populus tremula × tremuloides |
| TF0065 | | SEQ ID NO: 76 | SEQ ID NO: 86 | Populus tremula × tremuloides |
| TF0076 | | SEQ ID NO: 77 | SEQ ID NO: 87 | Populus tremula × tremuloides |
| TF0089 | | SEQ ID NO: 78 | SEQ ID NO: 88 | Populus tremula × tremuloides |
| TF0109 | SEQ ID NO: 75 | | | Populus tremula × tremuloides |
| TF0132 | | SEQ ID NO: 79 | SEQ ID NO: 89 | Populus tremula × tremuloides |
| TFSTT051 | | SEQ ID NO: 80 | SEQ ID NO: 90 | Populus tremula × tremuloides |
| TF0013 | | SEQ ID NO: 81 | SEQ ID NO: 91 | Populus tremula × tremuloides |
| TF0097 | | SEQ ID NO: 82 | SEQ ID NO: 92 | Populus tremula × tremuloides |
| TFSTT019 | | SEQ ID NO: 83 | SEQ ID NO: 93 | Populus tremula × tremuloides |
| TFSTT035 | | SEQ ID NO: 84 | SEQ ID NO: 94 | Populus tremula × tremuloides |
| TFSTT047 | | SEQ ID NO: 85 | SEQ ID NO: 95 | Populus tremula × tremuloides |
| TF0003 | SEQ ID NO: 173 | | | Populus tremula × tremuloides |
| TF0011 | SEQ ID NO: 174 | | | Populus tremula × tremuloides |
| TF0045 | | SEQ ID NO: 180 | SEQ ID NO: 192 | Populus tremula × tremuloides |
| TF0058 | SEQ ID NO: 175 | | | Populus tremula × tremuloides |
| TF0096 | | SEQ ID NO: 181 | SEQ ID NO: 193 | Populus tremula × tremuloides |
| TF0104 | | SEQ ID NO: 182 | SEQ ID NO: 194 | Populus tremula × tremuloides |
| TF0116 | | SEQ ID NO: 183 | SEQ ID NO: 195 | Populus tremula × tremuloides |
| TF0146 | | SEQ ID NO: 184 | SEQ ID NO: 196 | Populus tremula × tremuloides |
| TF0173 | SEQ ID NO: 176 | | | Populus tremula × tremuloides |
| TF0247 | SEQ ID NO: 177 | | | Populus tremula × tremuloides |
| TF0405 | | SEQ ID NO: 185 | SEQ ID NO: 197 | Populus tremula × tremuloides |
| TFSTT001 | | SEQ ID NO: 186 | SEQ ID NO: 198 | Populus tremula × tremuloides |
| TFSTT004 | | SEQ ID NO: 187 | SEQ ID NO: 199 | Populus tremula × tremuloides |
| TFSTT013 | SEQ ID NO: 178 | | | Populus tremula × tremuloides |
| TFSTT016 | | SEQ ID NO: 188 | SEQ ID NO: 200 | Populus tremula × tremuloides |
| TFSTT017 | | SEQ ID NO: 189 | SEQ ID NO: 201 | Populus tremula × tremuloides |
| TFSTT036 | | SEQ ID NO: 190 | SEQ ID NO: 202 | Populus tremula × tremuloides |
| TFSTT038 | | SEQ ID NO: 191 | SEQ ID NO: 203 | Populus tremula × tremuloides |
| TFSTT045 | SEQ ID NO: 179 | | | Populus tremula × tremuloides |

Plant Transformation

CaMV 35S: over-expression DNA constructs were transformed into *Agrobacterium* and subsequently into Hybrid aspen, where *Populus tremula* L.x*P. tremuloides* Minch clone T89, hereafter called "poplar", was transformed and regenerated essentially as described in Nilsson et al. (1992). Approximately 3-8 independent lines were generated for each construct. One such group of transgenic trees produced using one construct is hereafter called a "construction group", e.g. different transgenic trees emanating from one construct. Each transgenic line within each construction group, e.g. TF0555-2B, TF0555-3A, and so on, are different transformation events and therefore most probably have the recombinant DNA inserted into different locations in the plant genome. This makes the different lines within one construction group partly different. For example it is known that different transformation events will produce plants with different levels of gene over-expression. Construction groups named for example TF0555RP with individuals such as TF055RP-2B, are the same as the one without the RP part. RP means that this is a re-planting of the same construction group as the one without the rp part. RP2 means the second re-planting, RP3 the third re-planting and so on.

Plant Growth

The transgenic poplar lines were grown together with their wildtype control (wt) trees, in a greenhouse under a photoperiod of 18 h and a temperature of 22° C./15° C. (day/night). The plants were fertilized weekly with Weibulls Rika S NPK 7-1-5 diluted 1 to 100 (final concentrations $NO_3$, 55 g/l; $NH_4$, 29 g/l; P, 12 g/l; K, 56 g/l; Mg 7.2 g/l; S, 7.2 g/l; B, 0.18 g/l; Cu, 0.02 g/l; Fe, 0.84 g/l; Mn, 0.42 g/l; Mo, 0.03 g/l; Zn, 0.13 g/L). The plants were grown for 8-9 weeks before harvest. During this time their height and diameter was measured one to two times per week. In a growth group a number of wildtype trees (typically 35-45 trees) and a number of transgenic trees comprising several construction groups (typically 6-20 construction groups) were grown in parallel in the greenhouse under the same above conditions. All comparisons between the wildtype trees and construction groups are made within each growth group.

Sampling

Two principal types of harvests and samplings were performed. One general type was designed for example chemical analysis, wood morphology analysis, gene expression analysis, wood density analysis and metabolomics analysis. The second type was designed for dry weight measurements of bark, wood, leafs and roots.

Selection of Construction Groups

In the first round of growth for each group of trees with a specific gene over-expressed, i.e. a construction group, a number of the following analyses were performed: Growth measurements and in many cases wood density. These data were analysed in order to single out the construction groups that showed a phenotypic variation, e.g. increased growth compared to wild type control trees.

Replant and Regrowth

Based on growth data in the first round of greenhouse growth, groups of trees, with a specific gene over-expressed, i.e. a construction group, were selected, replanted and regrown under the same conditions as in the first round of growth. Selected transgenic poplar lines within each construction group were regrown in triplicates. Replant round number and plant line individual replicate numbers were added to the names of the construction group lines to keep them unique, e.g TF0555rp1-2B-1, TF0555rp1-2B-2, TF0555rp1-2B-3, where rp1 means first round of replanting of construction group TF0555 line 2B and -1, -2, -3 denotes plant line individual replicates. Similarly rp2 means second round of replanting. In cases where new construction group lines, not included in the first round of greenhouse growth, are planted, a suffix (0.2nd) is added to construction group name to illustrate this.

Based on growth data a number of analyses and growth rate factors were performed and calculated in order to select the construction groups and thereby the genes which are possible to use for altering growth characteristics. Selection criteria and methods were as described below.

Example 1

Growth Analysis

Maximum Height Growth Rate

A height growth rate measure (here named "Maximum height growth rate") was defined as the slope of a linear function fitted over four consecutive height data points. A height growth rate value was calculated for data point 1-4, data point 2-5 etc. in a step-wise manner, se FIG. 1 for an example. A maximum height growth rate defined as the maximum value produced from step-wise linear regression analysis for each plant was computed. The primary data for high Maximum height growth rate values from individual transformants in a construction group were checked so they were not based on bad values. From FIG. 1, showing an example of a height growth curve, it can be seen that the height growth rate increases during the first part of growth then the plants reach their maximum height growth rate and then the growth rate declines as the plants become larger. Because these phases have different timing in different plants and there are some noise added measuring the plants our above described Maximum height growth using rate method is very useful in calculating the maximum growth speed in these conditions for the different individual trees.

Diameter Growth Rate

Under the above defined growth conditions, stem width exhibit a comparatively linear increase over time described by the formula $d(t)=c*t+d_0$ where $d_0$ is the initial width and c is the rate of diameter growth (slope). Linear regression on diameter data was used for estimating diameter growth rate.

Final Height and Diameter

The final heights and diameters were also used to select construction groups with altered growth characteristics. These values take into account both the trees growth capacity and the trees ability to start growing when transferred from tissue culture into soil and placed in a greenhouse.

Selection Parameters

Construction groups that showed a significant or pronounced increase compared to the wild type population in the above mentioned growth parameters, i.e. diameter growth rate, maximum height growth rate, final height and final diameter, were identified as construction groups that have altered growth properties. Therefore, the corresponding genes can be used to alter these properties. The selection criteria's are stated below. Two different selection criteria levels were used, one basic level and one for constructs giving growth phenotypes of extra interest.

Growth Difference Selection Criteria

Table 1.2 lists the abbreviations used for the different growth parameters when used to describe construction group phenotypes.

TABLE 1.2

| | Abbreviations used for the different phenotypes |
|---|---|
| AFH | Average final height of the wild type population and each construction group population |
| AFD | Average final diameter of the wild type population and each construction group population |
| AMHGR | Average Maximum height growth rate of the wild type population and each construction group population |
| ADGR | Average diameter growth rate of the wild type population and each construction group population |
| MFH | Maximum final height of the wild type population and each construction group population |
| MFD | Maximum final diameter of the wild type population and each construction group population |
| MMHGR | Maximum of Maximum height growth rate of the wild type population and each construction group population |
| MDC | Maximum diameter growth rate of the wild type population and each construction group population |

The growth difference selection criteria are as follows:
1. If construction group AFH, MFH, AMHGR and MMHGR are at least 5% (or 8% in a second more stringent level) greater than corresponding wild type group AFH, MFH, AMHGR and MMHGR, or
2. If construction group AFD, MFD, ADGR and MDC are at least 5% (or 8% in a second more stringent level) greater than corresponding wild type group AFD, MFD, ADGR and MDC, or
3. If construction group AFH, AFD, AMHGR or ADGR is at least 18% (or 22% in the second more stringent level) greater than corresponding wild type group AFH, AFD, AMHGR or ADGR, or
4. If construction group MFH, MFD, MMHGR or MDC is at least 18% (or 22% in the second more stringent level) greater than corresponding wild type group MFH, MFD, MMHGR or MDC Running a large scale functional genomics program produces a certain amount of variation and uncertainty in the data produced. In this setup variation is originating from sources such as: the different lines within an construction group have different levels of over-expression resulting in that one to all tested lines within an construction group can show the phenotype; the variation in growth that occur during the experimental procedure due to small variations in plant status when transferring the plants from tissue culture to the greenhouse and variations based on different positions in the greenhouse during different time points during the growth cycle. These variations have to be dealt with when analysing the data.

Based on this we used two different thresholds of increase 5% and 18% for selecting construction groups with increased growth. The selection criteria 1 and 2 uses an 5% increase, however this increase have to be present in all the phenotypes AFH, MFH, AMHGR and MMHGR corresponding to height growth or all the phenotypes AFD, MFD, ADGR and MDC corresponding to diameter growth. In the cases that the phenotype only can be seen in some or one of the plants and only in one phenotype class, an higher 18% increase were used to select positive construction groups in order not to select construction groups based on random variations (selection criteria's 3 and 4 selecting on average values and maximum individual values respectively).

Construction groups meeting one or more of these criteria were selected.

Over-expression Level Analysis

Real-time RT PCR was used to compare construct gene expression levels of the recombinant over-expression construction group with corresponding wild type group. The expression level of 26S proteasome regulatory subunit S2 was used as a reference to which construct gene expression was normalized. The comparative CT method was used for calculation of relative construct gene expression levels, where the ratio between construction and reference gene expression levels is described by $(1+E_{target})^{-CTtarget}/(1+E_{reference})^{-CTreference}$ where $E_{target}$ and $E_{reference}$ are the efficiencies of construct and reference gene PCR amplification respectively and $CT_{target}$ and $CT_{reference}$ are the threshold cycles as calculated for construct and reference gene amplification respectively. The ratios between construct and reference gene expression levels were subsequently normalized to the average of wild type group ratios.

For total RNA extraction, stem samples (approx. 50 mg) were harvested from greenhouse grown plants and flash frozen in liquid nitrogen. Frozen samples were ground in a bead mill (Retsch MM301). Total RNA was extracted using E-Z 96 Plant RNA kit according to manufacturer's recommendations (Omega Bio-Tek). cDNA synthesis was performed using iScript cDNA synthesis kit according to manufacturer's recommendations (Bio-Rad). RNA concentrations were measured and equal amounts were used for cDNA synthesis to ensure equal amounts of cDNA for PCR reactions. The cDNA was diluted 12.5× prior to real-time PCR.

Real-time PCR primers were designed using Beacon Designer 6 (PREMIER Biosoft International) using included tool to minimize interference of template secondary structure at primer annealing sites.

For real-time PCR, cDNA template was mixed with corresponding construct gene specific primers (SEQ ID NO: 53-61 and SEQ ID NO: 63-71), internal reference gene specific primers (SEQ ID NO: 62 and 72) and SYBR Green Supermix (Bio-Rad). Real-time PCR reactions were run on a MyiQ PCR thermocycler (Bio-Rad) and analysed using included software iQ5. Reactions were set up in triplicates, three times using construct gene specific primers and three times using reference gene specific primers for each sample, and the average threshold cycle for each triplicate was subsequently used for calculation of relative construct gene expression levels.

The 96 well plate was covered with microfilm and set in the thermocycler to start the reaction cycle. By way of illustration, the reaction cycle may include the following steps: Initial denaturation at 95° C. for 3 minutes 30 seconds followed by 40 rounds of amplification comprising the following steps 95° C. for 10 seconds, 55° C. for 30 seconds and 72° C. for 40 seconds.

TABLE 1.3

Real-time RT-PCR primers

| Construct | Forward real-time RT-PCR primer | Reverse real-time RT-PCR primer |
|---|---|---|
| TF0002 | SEQ ID NO: 53 | SEQ ID NO: 63 |
| TF0052 | SEQ ID NO: 54 | SEQ ID NO: 64 |
| TF0065 | SEQ ID NO: 55 | SEQ ID NO: 65 |
| TF0076 | SEQ ID NO: 56 | SEQ ID NO: 66 |
| TF0089 | SEQ ID NO: 57 | SEQ ID NO: 67 |
| TF0109 | SEQ ID NO: 58 | SEQ ID NO: 68 |
| TFSTT051 | SEQ ID NO: 59 | SEQ ID NO: 69 |
| TF0013 | SEQ ID NO: 60 | SEQ ID NO: 70 |
| TF0097 | SEQ ID NO: 61 | SEQ ID NO: 71 |
| Real-time RT PCR reference gene: 26S proteasome regulatory subunit S2 | SEQ ID NO: 62 | SEQ ID NO: 72 |

Results

Growth raw data for the specified construction group and the corresponding wild type group are shown in tables 1.4 to 1.16. Table rows contain height and diameter measurements of individuals of specified construction group (named "TF") and corresponding wild type group (named "T89"). Time of measurement as number of days in greenhouse is shown in table headers.

Real-time RT-PCR was used to confirm over-expression of constructs. Real-time RT-PCR data tables contain gene expression levels of construct gene relative to reference gene expression. All ratios between construct and reference gene expression levels shown are normalized to the average of wild type group ratios.

Construction Group TF0002

This construct induces increased growth. The final height is 12% higher comparing the average of the construction group and wild type control group. The maximum height growth rate is 31% higher comparing the average of the construction group and wild type control group. The TF0002 construction group meets the more stringent level of growth difference selection criterion (3) as shown in table 1.4d.

Tables 1.4a and 1.4b contain growth data for specified construction group and corresponding wild type group. Table rows contain height and diameter measurements of individuals of specified construction group and corresponding wild type group. Time of measurement as number of days in greenhouse is shown in table headers.

TABLE 1.4a

Height growth data for TF0002

| | Height (cm) Days in greenhouse | | | | | | | |
|---|---|---|---|---|---|---|---|---|
| | 18 | 22 | 25 | 29 | 32 | 39 | 46 | 50 | 53 |
| TF0002-1B | 12 | 18 | 23 | 35 | 49 | 82 | 115 | 134 | 150 |
| TF0002-2A | 15 | 21 | 27 | 40 | 55 | 87 | 122 | 142 | 157 |
| TF0002-2B | 9 | 12 | 15 | 23 | 36 | 64 | 95 | 113 | 129 |
| TF0002-3A | 17 | 22 | 29 | 42 | 57 | 92 | 129 | 150 | 166 |
| TF0002-3B | 16 | 21 | 24 | 39 | 52 | 83 | 117 | 136 | 154 |
| TF0002-4B | 14 | 19 | 25 | 38 | 52 | 85 | 121 | 141 | 159 |
| T89-01 | 25 | 29 | 34 | 45 | 54 | 79 | 104 | 119 | 132 |
| T89-02 | 28 | 33 | 41 | 54 | 64 | 83 | 109 | 125 | 136 |
| T89-03 | 26 | 34 | 41 | 51 | 61 | 90 | 125 | 143 | 155 |
| T89-04 | 29 | 36 | 42 | 58 | 72 | 98 | 127 | 146 | 159 |
| T89-05 | 21 | 25 | 29 | 37 | 45 | 68 | 93 | 108 | 120 |
| T89-06 | 25 | 31 | 39 | 49 | 60 | 83 | 109 | 125 | 137 |
| T89-07 | 24 | 29 | 34 | 45 | 58 | 83 | 109 | 125 | 138 |
| T89-08 | 24 | 32 | 41 | 53 | 67 | 94 | 121 | 138 | 150 |
| T89-09 | 24 | 32 | 41 | 54 | 66 | 94 | 120 | 135 | 145 |

TABLE 1.4a-continued

Height growth data for TF0002

| | Height (cm) Days in greenhouse | | | | | | | | |
|---|---|---|---|---|---|---|---|---|---|
| | 18 | 22 | 25 | 29 | 32 | 39 | 46 | 50 | 53 |
| T89-10 | 20 | 26 | 30 | 44 | 54 | 79 | 108 | 123 | 135 |
| T89-11 | 21 | 26 | 32 | 42 | 54 | 79 | 107 | 123 | 136 |
| T89-12 | 25 | 32 | 40 | 55 | 66 | 97 | 125 | 140 | 151 |
| T89-13 | 21 | 29 | 35 | 45 | 54 | 75 | 98 | 114 | 124 |
| T89-14 | 25 | 31 | 38 | 50 | 60 | 85 | 111 | 125 | 135 |
| T89-15 | 25 | 33 | 40 | 53 | 64 | 88 | 112 | 126 | 137 |
| T89-16 | 24 | 28 | 33 | 42 | 49 | 68 | 89 | 102 | 112 |
| T89-17 | 26 | 33 | 40 | 50 | 60 | 83 | 109 | 127 | 137 |
| T89-18 | 24 | 29 | 37 | 47 | 55 | 80 | 108 | 123 | 133 |
| T89-19 | 21 | 26 | 32 | 40 | 49 | 65 | 80 | 95 | 107 |
| T89-20 | 26 | 32 | 40 | 52 | 65 | 98 | 127 | 146 | 159 |
| T89-21 | 24 | 29 | 37 | 45 | 51 | 71 | 100 | 114 | 125 |
| T89-22 | 25 | 30 | 39 | 48 | 63 | 83 | 110 | 125 | 139 |
| T89-23 | 22 | 28 | 34 | 45 | 56 | 83 | 106 | 120 | 130 |
| T89-24 | 24 | 30 | 38 | 49 | 60 | 82 | 106 | 124 | 138 |
| T89-25 | 24 | 29 | 36 | 48 | 56 | 80 | 107 | 123 | 132 |
| T89-26 | 26 | 35 | 41 | 52 | 68 | 87 | 110 | 123 | 136 |
| T89-27 | 22 | 28 | 35 | 47 | 57 | 84 | 111 | 126 | 138 |
| T89-28 | 24 | 29 | 36 | 46 | 58 | 87 | 110 | 123 | 136 |
| T89-29 | 24 | 32 | 40 | 50 | 63 | 81 | 111 | 128 | 141 |
| T89-30 | 26 | 31 | 37 | 46 | 53 | 72 | 95 | 107 | 118 |
| T89-31 | 26 | 32 | 41 | 52 | 63 | 87 | 115 | 130 | 143 |
| T89-32 | 28 | 33 | 41 | 52 | 63 | 88 | 116 | 130 | 142 |
| T89-33 | 20 | 24 | 30 | 41 | 51 | 76 | 102 | 117 | 130 |
| T89-34 | 25 | 30 | 39 | 51 | 63 | 90 | 117 | 130 | 138 |
| T89-35 | 26 | 31 | 38 | 49 | 59 | 83 | 106 | 119 | 129 |
| T89-36 | 25 | 33 | 40 | 52 | 59 | 73 | 91 | 104 | 116 |
| T89-37 | 29 | 37 | 45 | 60 | 73 | 100 | 128 | 146 | 156 |

TABLE 1.4b

Diameter growth data for TF0002

| | Diameter (mm) Days in greenhouse | | | | | |
|---|---|---|---|---|---|---|
| | 29 | 32 | 39 | 46 | 50 | 53 |
| TF0002-1B | 3.4 | 4.7 | 6.0 | 7.3 | 7.5 | 8.1 |
| TF0002-2A | 3.5 | 4.1 | 5.7 | 7.0 | 7.4 | 7.3 |
| TF0002-2B | 2.9 | 3.3 | 4.3 | 5.7 | 6.2 | 7.0 |
| TF0002-3A | 3.8 | 4.8 | 6.2 | 7.4 | 8.3 | 8.8 |
| TF0002-3B | 3.5 | 4.4 | 5.7 | 6.7 | 7.4 | 8.1 |
| TF0002-4B | 3.4 | 4.8 | 5.8 | 7.1 | 7.5 | 8.0 |
| T89-01 | 3.8 | 4.6 | 5.9 | 7.2 | 7.6 | 8.1 |
| T89-02 | 5.0 | 5.9 | 7.0 | 8.4 | 9.5 | 8.9 |
| T89-03 | 4.9 | 6.4 | 7.3 | 8.8 | 8.8 | 9.6 |
| T89-04 | 5.1 | 6.2 | 8.1 | 9.0 | 8.6 | 10.2 |
| T89-05 | 3.8 | 4.2 | 5.0 | 6.1 | 5.9 | 6.7 |
| T89-06 | 5.0 | 5.9 | 7.0 | 7.9 | 8.9 | 9.1 |
| T89-07 | 4.0 | 5.0 | 6.4 | 7.5 | 8.3 | 9.3 |
| T89-08 | 4.6 | 5.6 | 7.1 | 8.1 | 8.6 | 9.9 |
| T89-09 | 5.1 | 6.2 | 8.0 | 9.3 | 9.7 | 10.3 |
| T89-10 | 3.7 | 5.0 | 6.2 | 7.3 | 8.3 | 8.7 |
| T89-11 | 3.8 | 4.5 | 6.0 | 7.4 | 8.2 | 8.7 |
| T89-12 | 4.6 | 6.3 | 7.1 | 8.6 | 9.4 | 10.8 |
| T89-13 | 5.0 | 5.2 | 6.0 | 6.8 | 7.2 | 7.7 |
| T89-14 | 4.3 | 5.1 | 6.5 | 7.3 | 7.7 | 8.5 |
| T89-15 | 5.6 | 6.0 | 7.4 | 8.4 | 8.9 | 9.6 |
| T89-16 | 4.1 | 5.0 | 6.1 | 6.9 | 7.0 | 7.8 |
| T89-17 | 5.5 | 6.2 | 7.2 | 7.9 | 8.7 | 9.0 |
| T89-18 | 4.6 | 4.9 | 6.0 | 7.2 | 7.9 | 8.7 |
| T89-19 | 4.0 | 5.2 | 6.5 | 7.7 | 7.0 | 8.4 |
| T89-20 | 4.6 | 6.0 | 7.5 | 9.8 | 10.3 | 8.8 |
| T89-21 | 4.5 | 4.7 | 5.6 | 6.8 | 5.8 | 7.8 |
| T89-22 | 4.7 | 5.4 | 6.1 | 6.9 | 6.9 | 8.1 |
| T89-23 | 4.0 | 5.0 | 6.2 | 7.7 | 8.5 | 9.0 |
| T89-24 | 4.4 | 5.0 | 5.5 | 6.8 | 6.9 | 7.9 |
| T89-25 | 4.4 | 5.5 | 6.1 | 7.8 | 8.2 | 7.3 |
| T89-26 | 4.4 | 4.8 | 6.2 | 7.6 | 6.3 | 8.5 |
| T89-27 | 4.4 | 5.1 | 5.8 | 7.1 | 9.0 | 7.2 |
| T89-28 | 4.0 | 5.0 | 6.3 | 7.4 | 8.1 | 8.9 |
| T89-29 | 4.7 | 6.0 | 7.1 | 8.3 | 7.8 | 9.3 |
| T89-30 | 4.3 | 4.8 | 5.5 | 6.0 | 6.6 | 7.1 |
| T89-31 | 4.6 | 5.5 | 6.4 | 7.8 | 9.0 | 9.3 |
| T89-32 | 4.5 | 5.2 | 6.1 | 7.0 | 7.9 | 8.7 |
| T89-33 | 3.9 | 4.4 | 5.6 | 6.5 | 5.7 | 7.7 |
| T89-34 | 4.5 | 5.7 | 6.6 | 8.3 | 9.0 | 9.5 |
| T89-35 | 4.2 | 5.4 | 7.1 | 8.5 | 9.3 | 10.0 |
| T89-36 | 5.0 | 5.6 | 7.0 | 8.3 | 7.1 | 8.9 |
| T89-37 | 5.1 | 6.0 | 6.9 | 8.1 | 9.1 | 9.6 |

Real-time RT-PCR was used to confirm over-expression of construct TF0002. Table 1.4c contains gene expression levels of construct gene relative to reference gene expression. All ratios between construct and reference gene expression levels shown are normalized to the average of wild type group ratios. All individuals of construction group TF0002 are over-expressed according to present RT-PCR data.

TABLE 1.4c

Real-time RT-PCR data for TF0002

| Sample | Relative gene expression level normalized to wild type average |
|---|---|
| TF0002-1B | 8.63 |
| TF0002-2A | 7.88 |
| TF0002-2B | 8.18 |
| TF0002-3A | 5.88 |
| TF0002-3B | 5.72 |
| TF0002-4B | 8.89 |
| T89-06 | 1.09 |
| T89-26 | 1.47 |
| T89-29 | 0.88 |
| T89-31 | 0.84 |
| T89-32 | 0.71 |

Results from growth analysis are specified in the overview table 1.4d. The determined growth effects of specified construction group are presented as ratios between construction and wild type group AFH, AFD, AMHGR, ADGR, MFH, MFD, MMHGR and MDC.

TABLE 1.4d

Overview table of growth effects of construct TF0002

| Construction group | Average Final Height | Average Final Diameter | Average Maximum Height Growth Rate | Average Diameter Growth Rate | Maximum Final Height | Maximum Final Diameter | Maximum of Maximum Height Growth Rate | Maximum Diameter Growth Rate |
|---|---|---|---|---|---|---|---|---|
| TF0002 | 1.12 | 0.90 | 1.31 | 1.06 | 1.04 | 0.81 | 1.13 | 0.85 |

Construction Group TF0052

This construct induces increased growth. The final height is 24% higher comparing the largest individuals of the construction group and wild type control group. The TF0052 construction group meets the more stringent level of growth difference selection criterion (4) as shown in table 1.5c.

Tables 1.5a and 1.5b contain growth data for specified construction group and corresponding wild type group. Table rows contain height and diameter measurements of individuals of specified construction group and corresponding wild type group. Time of measurement as number of days in greenhouse is shown in table headers.

TABLE 1.5a

Height growth data for TF0052

| | Height (cm) Days in greenhouse | | | | | | | | | |
|---|---|---|---|---|---|---|---|---|---|---|
| | 19 | 28 | 34 | 40 | 44 | 47 | 51 | 54 | 61 | 65 |
| TF0052-1A | 8 | 17 | 26 | 35 | 39 | 42 | 48 | 51 | 58 | 64 |
| TF0052-1B | 18 | 32 | 50 | 65 | 79 | 89 | 99 | 107 | 125 | 135 |
| TF0052-2A | 18 | 40 | 64 | 83 | 97 | 108 | 122 | 131 | 156 | 172 |
| TF0052-2B | 13 | 29 | 47 | 59 | 72 | 80 | 90 | 99 | 120 | 132 |
| TF0052-3A | 18 | 36 | 58 | 71 | 84 | 91 | 102 | 107 | 119 | 124 |
| TF0052-3B | 15 | 33 | 54 | 69 | 82 | 90 | 100 | 107 | 124 | 135 |
| TF0052-4A | 14 | 27 | 46 | 58 | 68 | 76 | 85 | 93 | 110 | 122 |
| TF0052-4B | 19 | 36 | 55 | 68 | 79 | 87 | 96 | 98 | 113 | 121 |
| T89-01 | 18 | 30 | 46 | 58 | 69 | 77 | 87 | 96 | 113 | 122 |
| T89-02 | 18 | 30 | 49 | 62 | 72 | 77 | 84 | 90 | 102 | 109 |
| T89-03 | 15 | 27 | 41 | 54 | 65 | 73 | 82 | 91 | 112 | 123 |
| T89-10 | N/A | N/A | N/A | N/A | N/A | N/A | N/A | N/A | N/A | N/A |
| T89-11 | 19 | 31 | 49 | 61 | 74 | 83 | 94 | 103 | 124 | 133 |
| T89-12 | 17 | 30 | 45 | 58 | 69 | 77 | 90 | 100 | 123 | 134 |
| T89-13 | 18 | 27 | 43 | 56 | 68 | 78 | 91 | 100 | 121 | 133 |
| T89-14 | 5 | 26 | 42 | 56 | 67 | 74 | 83 | 90 | 109 | 119 |
| T89-15 | 10 | 15 | 25 | 33 | 41 | 45 | 52 | 57 | 72 | 82 |
| T89-16 | 19 | 33 | 53 | 63 | 73 | 82 | 93 | 102 | 119 | 130 |
| T89-17 | 17 | 29 | 46 | 58 | 66 | 72 | 80 | 86 | 96 | 102 |
| T89-18 | 16 | 30 | 48 | 59 | 71 | 81 | 93 | 103 | 122 | 132 |
| T89-19 | 18 | 32 | 50 | 65 | 77 | 84 | 94 | 102 | 126 | 139 |
| T89-20 | 16 | 33 | 52 | 67 | 79 | 88 | 98 | 105 | 124 | 139 |
| T89-21 | 17 | 29 | 44 | 58 | 67 | 73 | 83 | 90 | 110 | 122 |
| T89-22 | 14 | 28 | 47 | 61 | 71 | 80 | 89 | 98 | 119 | 133 |
| T89-23 | 10 | 33 | 45 | 53 | 63 | 71 | 82 | 90 | 112 | 123 |
| T89-24 | 20 | 28 | 43 | 51 | 62 | 69 | 78 | 87 | 106 | 119 |
| T89-25 | 14 | 26 | 38 | 52 | 64 | 72 | 82 | 89 | 110 | 122 |
| T89-26 | 15 | 28 | 44 | 57 | 69 | 77 | 87 | 96 | 120 | 133 |
| T89-27 | 18 | 29 | 47 | 62 | 75 | 82 | 92 | 103 | 125 | 138 |
| T89-28 | 22 | 37 | 54 | 67 | 78 | 88 | 97 | 104 | 123 | 133 |
| T89-29 | 16 | 33 | 49 | 63 | 76 | 84 | 93 | 100 | 123 | 138 |
| T89-30 | 15 | 40 | 46 | 58 | 67 | 74 | 85 | 92 | 113 | 124 |

TABLE 1.5b

Diameter growth data for TF0052

| | Diameter (mm) Days in greenhouse | | | | | | | | |
|---|---|---|---|---|---|---|---|---|---|
| | 28 | 34 | 40 | 44 | 47 | 51 | 54 | 61 | 65 |
| TF0052-1A | 3.5 | 4.1 | 4.9 | 4.6 | 5.2 | 5.0 | 5.6 | 6.7 | 6.2 |
| TF0052-1B | 3.1 | 4.4 | 6.0 | 6.6 | 6.9 | 8.0 | 8.2 | 9.3 | 9.4 |
| TF0052-2A | 4.5 | 6.3 | 8.1 | 8.6 | 9.7 | 9.8 | 10.2 | 11.5 | 11.5 |
| TF0052-2B | 3.5 | 5.2 | 6.1 | 7.5 | 7.8 | 8.8 | 9.5 | 10.9 | 11.0 |
| TF0052-3A | 3.5 | 5.4 | 6.7 | 7.2 | 7.8 | 7.9 | 8.1 | 8.7 | 9.3 |
| TF0052-3B | 3.8 | 5.5 | 7.1 | 7.2 | 8.2 | 8.4 | 9.0 | 9.1 | 9.6 |
| TF0052-4A | 3.4 | 4.9 | 6.5 | 6.7 | 7.0 | 7.8 | 8.0 | 9.1 | 9.3 |
| TF0052-4B | 3.5 | 4.9 | 6.0 | 7.0 | 7.2 | 7.6 | 7.8 | 8.1 | 8.7 |
| T89-01 | 3.2 | 4.6 | 5.4 | 6.2 | 6.8 | 7.9 | 8.3 | 9.5 | 9.3 |
| T89-02 | 3.4 | 4.7 | 5.5 | 7.3 | 6.3 | 6.6 | 6.9 | 8.3 | 7.5 |
| T89-03 | 3.9 | 4.4 | 5.2 | 6.2 | 6.4 | 7.8 | 7.6 | 9.7 | 9.4 |
| T89-10 | N/A | N/A | N/A | N/A | N/A | N/A | N/A | N/A | N/A |
| T89-11 | 3.4 | 5.1 | 6.2 | 7.6 | 6.8 | 6.9 | 7.7 | 10.1 | 9.5 |
| T89-12 | 2.9 | 4.7 | 5.8 | 6.6 | 7.8 | 8.0 | 8.7 | 9.1 | 9.2 |
| T89-13 | 3.0 | 4.3 | 5.4 | 5.8 | 6.4 | 7.6 | 7.8 | 8.2 | 8.8 |
| T89-14 | 3.0 | 4.5 | 5.7 | 6.3 | 6.7 | 7.9 | 7.8 | 9.0 | 8.9 |
| T89-15 | N/A | 2.1 | 3.0 | 4.0 | 4.0 | 4.5 | 4.9 | 5.5 | 5.6 |
| T89-16 | 3.5 | 5.3 | 6.4 | 6.6 | 7.0 | 7.2 | 8.3 | 8.2 | 9.0 |
| T89-17 | 3.4 | 4.6 | 5.1 | 5.4 | 6.0 | 6.4 | 6.5 | 6.8 | 7.1 |
| T89-18 | 3.6 | 5.2 | 6.0 | 7.0 | 7.8 | 8.2 | 9.9 | 10.3 | 9.7 |
| T89-19 | 4.2 | 5.5 | 6.6 | 7.7 | 8.5 | 8.9 | 9.5 | 11.1 | 12.3 |
| T89-20 | 4.1 | 5.5 | 6.6 | 8.1 | 9.3 | 9.6 | 9.3 | 10.0 | 11.1 |
| T89-21 | 3.1 | 5.6 | 5.8 | 6.7 | 7.1 | 7.8 | 8.4 | 9.7 | 10.1 |
| T89-22 | 3.2 | 4.4 | 5.6 | 6.5 | 7.5 | 7.6 | 7.8 | 8.9 | 9.2 |
| T89-23 | 2.4 | 4.2 | 5.1 | 6.1 | 6.5 | 7.5 | 10.1 | 9.3 | 10.2 |
| T89-24 | 3.2 | 4.5 | 5.1 | 6.3 | 7.0 | 7.6 | 8.1 | 8.8 | 9.1 |
| T89-25 | 3.3 | 4.3 | 5.2 | 5.8 | 6.5 | 7.4 | 7.8 | 9.3 | 9.7 |
| T89-26 | 3.3 | 4.4 | 5.5 | 6.6 | 7.2 | 8.1 | 8.9 | 9.5 | 10.5 |
| T89-27 | 3.3 | 4.9 | 6.0 | 7.8 | 8.0 | 8.9 | 9.7 | 11.2 | 11.5 |
| T89-28 | 4.5 | 5.7 | 7.4 | 7.8 | 8.5 | 9.4 | 9.7 | 10.2 | 11.1 |
| T89-29 | 3.1 | 4.7 | 6.3 | 7.2 | 7.9 | 9.2 | 9.8 | 11.1 | 10.7 |
| T89-30 | 3.0 | 5.8 | 6.2 | 7.7 | 7.9 | 8.6 | 8.2 | 10.1 | 10.3 |

Results from growth analysis are specified in the overview table 1.5c. The determined growth effects of specified construction group are presented as ratios between construction and wild type group AFH, AFD, AMHGR, ADGR, MFH, MFD, MMHGR and MDC.

TABLE 1.5c

Overview table of growth effects of construct TF0052

| Construction group | Average Final Height | Average Final Diameter | Average Maximum Height Growth Rate | Average Diameter Growth Rate | Maximum Final Height | Maximum Final Diameter | Maximum of Maximum Height Growth Rate | Maximum Diameter Growth Rate |
|---|---|---|---|---|---|---|---|---|
| TF0052 | 1.00 | 0.98 | 0.95 | 0.89 | 1.24 | 0.93 | 1.08 | 0.91 |

Construction Group TF0065

This construct induces increased growth. The final height is 8% higher comparing the average of the construction group and wild type control group. The maximum height growth rate is 11% higher comparing the average of the construction group and wild type control group. The TF0065 construction group meets growth difference selection criterion (1) as shown in table 1.6c.

Tables 1.6a and 1.6b contain growth data for specified construction group and corresponding wild type group. Table rows contain height and diameter measurements of individuals of specified construction group and corresponding wild type group. Time of measurement as number of days in greenhouse is shown in table headers.

TABLE 1.6a

Height growth data for TF0065

| | Height (cm) Days in greenhouse | | | | | | | | | | |
|---|---|---|---|---|---|---|---|---|---|---|---|
| | 18 | 22 | 25 | 29 | 32 | 39 | 43 | 46 | 50 | 53 | 57 |
| TF0065-1AA | 20 | 26 | 33 | 46 | 58 | 88 | 101 | 111 | 123 | 134 | 151 |
| TF0065-1AB | 23 | 27 | 34 | 48 | 60 | 89 | 106 | 115 | 133 | 146 | 164 |
| TF0065-1BA | 21 | 27 | 33 | 45 | 56 | 82 | 97 | 107 | 122 | 135 | 153 |
| TF0065-1BB | 22 | 26 | 32 | 44 | 56 | 84 | 101 | 113 | 130 | 144 | 164 |
| TF0065-2B | 24 | 29 | 37 | 51 | 64 | 96 | 115 | 127 | 145 | 162 | 181 |
| TF0065-3A | 20 | 28 | 33 | 43 | 54 | 79 | 94 | 106 | 124 | 138 | 155 |
| TF0065-4B | 16 | 20 | 28 | 40 | 49 | 73 | 85 | 94 | 108 | 121 | 138 |
| T89-01 | 14 | 17 | 22 | 31 | 40 | 64 | 76 | 88 | 102 | 118 | 135 |
| T89-02 | 17 | 20 | 25 | 36 | 45 | 69 | 79 | 90 | 104 | 118 | 133 |
| T89-03 | 21 | 29 | 35 | 47 | 57 | 81 | 94 | 104 | 119 | 132 | 147 |
| T89-04 | 13 | 14 | 17 | 25 | 33 | 45 | 52 | 57 | 70 | 79 | 92 |
| T89-05 | 15 | 18 | 24 | 33 | 42 | 69 | 83 | 94 | 106 | 120 | 137 |
| T89-06 | 18 | 23 | 29 | 40 | 51 | 78 | 91 | 103 | 120 | 134 | 152 |
| T89-07 | 20 | 24 | 30 | 41 | 51 | 74 | 88 | 96 | 109 | 121 | 130 |
| T89-08 | 27 | 32 | 40 | 52 | 62 | 88 | 99 | 111 | 124 | 134 | 148 |
| T89-09 | 23 | 27 | 34 | 46 | 56 | 83 | 97 | 106 | 122 | 132 | 149 |
| T89-10 | 13 | 15 | 20 | 27 | 37 | 59 | 72 | 83 | 98 | 111 | 128 |
| T89-11 | N/A | N/A | N/A | N/A | N/A | N/A | N/A | N/A | N/A | N/A | N/A |
| T89-12 | 26 | 33 | 40 | 54 | 66 | 92 | 107 | 120 | 135 | 149 | 166 |
| T89-13 | 21 | 26 | 34 | 45 | 55 | 79 | 94 | 105 | 122 | 134 | 150 |
| T89-14 | 18 | 23 | 31 | 42 | 53 | 80 | 97 | 107 | 120 | 128 | 145 |
| T89-15 | 26 | 33 | 40 | 53 | 63 | 88 | 103 | 111 | 125 | 138 | 154 |
| T89-16 | 27 | 32 | 39 | 51 | 63 | 89 | 104 | 116 | 132 | 146 | 162 |
| T89-17 | 17 | 21 | 27 | 38 | 45 | 72 | 87 | 97 | 110 | 124 | 139 |
| T89-18 | 23 | 30 | 35 | 46 | 55 | 80 | 94 | 105 | 117 | 131 | 145 |
| T89-19 | 23 | 29 | 35 | 45 | 54 | 78 | 91 | 102 | 114 | 125 | 137 |
| T89-20 | 22 | 28 | 34 | 49 | 60 | 87 | 100 | 110 | 125 | 137 | 155 |
| T89-21 | 27 | 31 | 35 | 42 | 48 | 66 | 77 | 87 | 100 | 110 | 124 |
| T89-22 | 13 | 16 | 23 | 32 | 48 | 67 | 81 | 92 | 105 | 118 | 134 |
| T89-23 | 23 | 29 | 35 | 48 | 58 | 83 | 97 | 107 | 122 | 136 | 154 |
| T89-24 | 23 | 29 | 36 | 48 | 59 | 86 | 101 | 113 | 128 | 141 | 159 |
| T89-25 | 16 | 21 | 28 | 40 | 51 | 80 | 97 | 107 | 122 | 137 | 153 |
| T89-26 | 27 | 35 | 40 | 54 | 66 | 93 | 107 | 118 | 132 | 144 | 162 |
| T89-27 | 26 | 31 | 38 | 49 | 59 | 82 | 96 | 106 | 120 | 131 | 146 |
| T89-28 | 25 | 29 | 36 | 49 | 59 | 83 | 97 | 106 | 119 | 131 | 147 |
| T89-29 | 26 | 32 | 38 | 51 | 62 | 88 | 103 | 113 | 128 | 142 | 159 |
| T89-30 | 24 | 29 | 36 | 48 | 56 | 80 | 93 | 104 | 117 | 131 | 145 |
| T89-31 | 24 | 31 | 36 | 47 | 57 | 81 | 94 | 105 | 117 | 131 | 144 |
| T89-32 | 26 | 32 | 38 | 49 | 58 | 83 | 98 | 107 | 120 | 134 | 148 |
| T89-33 | 24 | 29 | 36 | 48 | 57 | 85 | 100 | 112 | 124 | 134 | 149 |
| T89-34 | 21 | 26 | 32 | 43 | 53 | 79 | 90 | 102 | 117 | 131 | 148 |
| T89-35 | 21 | 28 | 36 | 46 | 55 | 80 | 94 | 105 | 120 | 133 | 149 |
| T89-36 | 16 | 21 | 28 | 39 | 51 | 74 | 88 | 100 | 115 | 128 | 144 |
| T89-37 | 28 | 35 | 41 | 52 | 63 | 88 | 101 | 111 | 125 | 137 | 154 |
| T89-38 | 27 | 32 | 39 | 51 | 62 | 86 | 101 | 113 | 128 | 140 | 155 |
| T89-39 | 21 | 26 | 33 | 46 | 55 | 83 | 101 | 112 | 126 | 139 | 156 |
| T89-40 | 21 | 26 | 33 | 45 | 55 | 77 | 88 | 99 | 113 | 124 | 139 |
| T89-41 | 13 | 16 | 23 | 32 | 42 | 68 | 85 | 95 | 107 | 118 | 133 |
| T89-42 | 24 | 30 | 37 | 49 | 61 | 86 | 101 | 113 | 128 | 143 | 150 |

TABLE 1.6a-continued

Height growth data for TF0065

| | Height (cm) Days in greenhouse | | | | | | | | | | |
|---|---|---|---|---|---|---|---|---|---|---|---|
| | 18 | 22 | 25 | 29 | 32 | 39 | 43 | 46 | 50 | 53 | 57 |
| T89-43 | 25 | 31 | 38 | 51 | 61 | 86 | 102 | 114 | 130 | 144 | 163 |
| T89-44 | 23 | 31 | 39 | 51 | 64 | 90 | 105 | 118 | 135 | 151 | 169 |
| T89-45 | 26 | 32 | 37 | 49 | 58 | 85 | 100 | 110 | 124 | 137 | 153 |
| T89-46 | 20 | 25 | 34 | 43 | 55 | 81 | 97 | 109 | 122 | 133 | 149 |

TABLE 1.6b

Diameter growth data for TF0065

| | Diameter (mm) Days in greenhouse | | | | | | | |
|---|---|---|---|---|---|---|---|---|
| | 29 | 32 | 39 | 43 | 46 | 50 | 53 | 57 |
| TF0065-1AA | 3.9 | 5.0 | 6.2 | 6.7 | 6.9 | 7.3 | 8.5 | 8.3 |
| TF0065-1AB | 4.0 | 5.1 | 6.9 | 8.4 | 8.0 | 9.5 | 9.5 | 10.6 |
| TF0065-1BA | 4.3 | 4.9 | 5.9 | 6.3 | 6.8 | 7.5 | 7.8 | 8.4 |
| TF0065-1BB | 3.8 | 4.8 | 6.0 | 7.1 | 7.4 | 8.4 | 9.3 | 10.1 |
| TF0065-2B | 5.9 | 4.8 | 7.1 | 8.0 | 8.6 | 9.5 | 9.7 | 10.2 |
| TF0065-3A | 4.2 | 4.9 | 6.0 | 6.9 | 7.1 | 7.6 | 8.4 | 9.2 |
| TF0065-4B | 3.3 | 4.0 | 4.8 | 5.5 | 5.8 | N/A | 6.9 | 7.9 |
| T89-01 | 3.2 | 3.7 | 5.3 | 6.2 | 6.9 | 7.9 | 8.3 | 8.7 |
| T89-02 | 3.2 | 3.9 | 5.1 | 6.4 | 7.0 | 7.6 | 8.6 | 8.6 |
| T89-03 | 4.2 | 5.3 | 6.4 | 6.9 | 6.9 | N/A | 8.8 | 9.8 |
| T89-04 | 2.2 | 3.0 | 4.2 | 4.5 | 5.4 | 5.0 | 5.4 | 6.1 |
| T89-05 | 3.0 | 3.7 | 4.8 | 5.9 | 6.4 | 7.0 | 7.6 | 7.9 |
| T89-06 | 3.6 | 4.8 | 6.5 | 7.6 | 8.7 | 9.1 | 9.6 | 10.1 |
| T89-07 | 3.8 | 4.9 | 6.8 | 7.6 | 8.0 | 8.6 | 9.0 | 9.7 |
| T89-08 | 4.4 | 5.8 | 6.2 | 7.3 | 7.6 | 8.5 | 9.4 | 9.7 |
| T89-09 | 4.5 | 5.5 | 6.5 | 7.1 | 7.6 | 9.1 | 9.4 | 9.8 |
| T89-10 | 3.7 | 3.9 | 5.0 | 6.1 | 6.8 | 7.6 | 8.5 | 9.2 |
| T89-11 | N/A | N/A | N/A | N/A | N/A | N/A | N/A | N/A |
| T89-12 | 4.6 | 5.5 | 7.3 | 8.6 | 8.8 | 9.6 | 10.2 | 10.2 |
| T89-13 | 3.8 | 4.6 | 5.7 | 6.5 | 6.6 | 7.4 | 8.1 | 8.6 |
| T89-14 | 3.7 | 4.2 | 5.3 | 5.6 | 6.1 | 7.0 | 7.1 | 7.8 |
| T89-15 | 4.6 | 5.0 | 6.4 | 7.0 | 7.4 | 8.0 | 8.4 | 9.1 |
| T89-16 | 5.0 | 5.5 | 7.0 | 7.6 | 8.0 | 8.6 | 9.0 | 9.7 |
| T89-17 | 3.1 | 4.3 | 5.7 | 7.1 | 7.4 | 7.9 | 8.4 | 9.2 |
| T89-18 | 4.5 | 5.3 | 7.8 | 8.0 | 8.1 | 9.2 | 9.9 | 10.3 |
| T89-19 | 4.2 | 5.8 | 6.7 | 8.2 | 8.5 | 8.5 | 9.0 | 9.5 |
| T89-20 | 4.0 | 4.7 | 6.7 | 8.1 | 7.6 | 8.5 | 8.6 | 9.4 |
| T89-21 | 3.5 | 3.9 | 5.0 | 5.7 | 5.8 | 7.1 | 6.7 | 7.4 |
| T89-22 | 3.6 | 4.3 | 5.5 | 6.3 | 6.8 | 7.9 | 8.4 | 8.8 |
| T89-23 | 4.1 | 5.2 | 7.0 | 7.6 | 8.2 | 8.9 | 9.2 | 10.0 |
| T89-24 | 4.1 | 5.4 | 6.7 | 7.5 | 7.8 | 8.6 | 9.6 | 10.4 |
| T89-25 | 3.7 | 4.6 | 6.0 | 7.0 | 7.7 | 8.3 | 8.5 | 9.4 |
| T89-26 | 4.8 | 5.6 | 6.9 | 7.3 | 7.8 | 8.6 | 9.2 | 9.5 |
| T89-27 | 3.8 | 4.9 | 6.2 | 6.7 | 6.9 | 7.6 | 8.4 | 9.3 |
| T89-28 | 4.5 | 5.5 | 6.8 | 7.3 | 7.8 | 9.1 | 9.1 | 9.5 |
| T89-29 | 4.4 | 5.3 | 6.8 | 6.8 | 7.4 | 8.2 | 9.2 | 8.9 |
| T89-30 | 3.7 | 4.7 | 5.4 | 6.6 | 7.0 | 7.0 | 7.7 | 8.5 |
| T89-31 | 4.0 | 4.5 | 5.5 | 6.9 | 7.0 | 8.0 | 9.1 | 9.6 |
| T89-32 | 3.6 | 4.5 | 5.7 | 7.0 | 7.2 | 8.0 | 9.1 | 9.4 |
| T89-33 | 3.9 | 4.6 | 6.7 | 7.3 | 8.0 | 8.6 | 9.4 | 10.5 |
| T89-34 | 3.6 | 4.5 | 5.9 | 6.9 | 7.5 | 8.2 | 9.1 | 9.4 |
| T89-35 | 3.9 | 4.5 | 5.7 | 7.1 | 7.5 | 7.9 | 8.8 | 9.6 |
| T89-36 | 3.6 | 5.0 | 5.7 | 6.5 | 6.8 | 7.9 | 8.2 | 9.1 |
| T89-37 | 4.3 | 5.6 | 7.1 | 8.0 | 8.0 | 8.9 | 9.7 | 10.2 |
| T89-38 | 4.7 | 5.8 | 6.7 | 7.8 | 8.0 | 8.7 | 9.2 | 9.7 |
| T89-39 | 4.2 | 5.0 | 6.2 | 7.3 | 8.2 | 8.1 | 8.7 | 9.6 |
| T89-40 | 3.6 | 4.4 | 5.2 | 5.7 | 6.0 | 7.2 | 7.2 | 8.0 |
| T89-41 | 3.5 | 4.3 | 5.5 | 6.5 | 7.0 | 7.5 | 7.7 | 8.4 |
| T89-42 | 4.4 | 5.1 | 7.5 | 8.4 | 9.5 | 9.9 | 10.0 | 10.3 |
| T89-43 | 4.3 | 5.0 | 6.5 | 7.3 | 7.8 | 8.3 | 8.9 | 9.1 |
| T89-44 | 4.3 | 5.8 | 6.8 | 8.1 | 8.6 | 9.5 | 9.9 | 10.5 |
| T89-45 | 4.2 | 4.9 | 6.8 | 7.5 | 7.6 | 8.5 | 9.4 | 9.7 |
| T89-46 | 3.5 | 4.4 | 5.7 | 7.0 | 7.5 | 8.6 | 9.4 | 9.8 |

Results from growth analysis are specified in the overview table 1.6c. The determined growth effects of specified construction group are presented as ratios between construction and wild type group AFH, AFD, AMHGR, ADGR, MFH, MFD, MMHGR and MDC.

TABLE 1.6c

Overview table of growth effects of construct TF0065

| Construction group | Average Final Height | Average Final Diameter | Average Maximum Height Growth Rate | Average Maximum Diameter Growth Rate | Maximum Final Height | Maximum Final Diameter | Maximum of Maximum Height Growth Rate | Maximum Diameter Growth Rate |
|---|---|---|---|---|---|---|---|---|
| TF0065 | 1.08 | 0.99 | 1.11 | 0.96 | 1.07 | 1.01 | 1.06 | 0.97 |

Construction Group TF0076

This construct induces increased growth. The final height is 10% higher comparing the average of the construction group and wild type control group. The final height is 18% higher comparing the largest individuals of the construction group and wild type control group. The maximum height growth rate is 13% higher comparing the average of the construction group and wild type control group. The maximum height growth rate is 18% higher comparing the largest individuals of the construction group and wild type control group. The TF0076 construction group meets the more stringent level of growth difference selection criterion (1) and the less stringent level of growth difference selection criterion (4) as shown in table 1.7d.

Tables 1.7a and 1.7b contain growth data for specified construction group and corresponding wild type group. Table rows contain height and diameter measurements of individuals of specified construction group and corresponding wild type group. Time of measurement as number of days in greenhouse is shown in table headers.

TABLE 1.7a

Height growth data for TF0076

| | Height (cm) Days in greenhouse | | | | | | | | | | |
|---|---|---|---|---|---|---|---|---|---|---|---|
| | 18 | 22 | 25 | 29 | 32 | 39 | 43 | 46 | 50 | 53 | 57 |
| TF0076-2AA | 18 | 24 | 30 | 42 | 52 | 76 | 92 | 103 | 118 | 133 | 150 |
| TF0076-2AB | 18 | 25 | 33 | 44 | 55 | 81 | 94 | 104 | 117 | 128 | 143 |
| TF0076-3BA | 16 | 20 | 26 | 36 | 47 | 70 | 86 | 97 | 112 | 126 | 142 |
| TF0076-3BB | 23 | 28 | 35 | 49 | 61 | 90 | 104 | 115 | 130 | 143 | 155 |
| TF0076-4B | N/A | N/A | N/A | N/A | N/A | N/A | N/A | N/A | N/A | N/A | N/A |
| TF0076-5BA | 20 | 25 | 33 | 45 | 55 | 87 | 106 | 121 | 140 | 157 | 177 |
| TF0076-5BB | 24 | 32 | 40 | 57 | 71 | 105 | 127 | 140 | 160 | 180 | 200 |
| T89-01 | 14 | 17 | 22 | 31 | 40 | 64 | 76 | 88 | 102 | 118 | 135 |
| T89-02 | 17 | 20 | 25 | 36 | 45 | 69 | 79 | 90 | 104 | 118 | 133 |
| T89-03 | 21 | 29 | 35 | 47 | 57 | 81 | 94 | 104 | 119 | 132 | 147 |
| T89-04 | 13 | 14 | 17 | 25 | 33 | 45 | 52 | 57 | 70 | 79 | 92 |
| T89-05 | 15 | 18 | 24 | 33 | 42 | 69 | 83 | 94 | 106 | 120 | 137 |
| T89-06 | 18 | 23 | 29 | 40 | 51 | 78 | 91 | 103 | 120 | 134 | 152 |
| T89-07 | 20 | 24 | 30 | 41 | 51 | 74 | 88 | 96 | 109 | 121 | 130 |
| T89-08 | 27 | 32 | 40 | 52 | 62 | 88 | 99 | 111 | 124 | 134 | 148 |
| T89-09 | 23 | 27 | 34 | 46 | 56 | 83 | 97 | 106 | 122 | 132 | 149 |
| T89-10 | 13 | 15 | 20 | 27 | 37 | 59 | 72 | 83 | 98 | 111 | 128 |
| T89-11 | N/A | N/A | N/A | N/A | N/A | N/A | N/A | N/A | N/A | N/A | N/A |
| T89-12 | 26 | 33 | 40 | 54 | 66 | 92 | 107 | 120 | 135 | 149 | 166 |
| T89-13 | 21 | 26 | 34 | 45 | 55 | 79 | 94 | 105 | 122 | 134 | 150 |
| T89-14 | 18 | 23 | 31 | 42 | 53 | 80 | 97 | 107 | 120 | 128 | 145 |
| T89-15 | 26 | 33 | 40 | 53 | 63 | 88 | 103 | 111 | 125 | 138 | 154 |
| T89-16 | 27 | 32 | 39 | 51 | 63 | 89 | 104 | 116 | 132 | 146 | 162 |
| T89-17 | 17 | 21 | 27 | 38 | 45 | 72 | 87 | 97 | 110 | 124 | 139 |
| T89-18 | 23 | 30 | 35 | 46 | 55 | 80 | 94 | 105 | 117 | 131 | 145 |
| T89-19 | 23 | 29 | 35 | 45 | 54 | 78 | 91 | 102 | 114 | 125 | 137 |
| T89-20 | 22 | 28 | 34 | 49 | 60 | 87 | 100 | 110 | 125 | 137 | 155 |
| T89-21 | 27 | 31 | 35 | 42 | 48 | 66 | 77 | 87 | 100 | 110 | 124 |
| T89-22 | 13 | 16 | 23 | 32 | 48 | 67 | 81 | 92 | 105 | 118 | 134 |
| T89-23 | 23 | 29 | 35 | 48 | 58 | 83 | 97 | 107 | 122 | 136 | 154 |
| T89-24 | 23 | 29 | 36 | 48 | 59 | 86 | 101 | 113 | 128 | 141 | 159 |
| T89-25 | 16 | 21 | 28 | 40 | 51 | 80 | 97 | 107 | 122 | 137 | 153 |
| T89-26 | 27 | 35 | 40 | 54 | 66 | 93 | 107 | 118 | 132 | 144 | 162 |
| T89-27 | 26 | 31 | 38 | 49 | 59 | 82 | 96 | 106 | 120 | 131 | 146 |
| T89-28 | 25 | 29 | 36 | 49 | 59 | 83 | 97 | 106 | 119 | 131 | 147 |
| T89-29 | 26 | 32 | 38 | 51 | 62 | 88 | 103 | 113 | 128 | 142 | 159 |
| T89-30 | 24 | 29 | 36 | 48 | 56 | 80 | 93 | 104 | 117 | 131 | 145 |
| T89-31 | 24 | 31 | 36 | 47 | 57 | 81 | 94 | 105 | 117 | 131 | 144 |
| T89-32 | 26 | 32 | 38 | 49 | 58 | 83 | 98 | 107 | 120 | 134 | 148 |
| T89-33 | 24 | 29 | 36 | 48 | 57 | 85 | 100 | 112 | 124 | 134 | 149 |
| T89-34 | 21 | 26 | 32 | 43 | 53 | 79 | 90 | 102 | 117 | 131 | 148 |
| T89-35 | 21 | 28 | 36 | 46 | 55 | 80 | 94 | 105 | 120 | 133 | 149 |
| T89-36 | 16 | 21 | 28 | 39 | 51 | 74 | 88 | 100 | 115 | 128 | 144 |
| T89-37 | 28 | 35 | 41 | 52 | 63 | 88 | 101 | 111 | 125 | 137 | 154 |
| T89-38 | 27 | 32 | 39 | 51 | 62 | 86 | 101 | 113 | 128 | 140 | 155 |
| T89-39 | 21 | 26 | 33 | 46 | 55 | 83 | 101 | 112 | 126 | 139 | 156 |
| T89-40 | 21 | 26 | 33 | 45 | 55 | 77 | 88 | 99 | 113 | 124 | 139 |
| T89-41 | 13 | 16 | 23 | 32 | 42 | 68 | 85 | 95 | 107 | 118 | 133 |
| T89-42 | 24 | 30 | 37 | 49 | 61 | 86 | 101 | 113 | 128 | 143 | 150 |
| T89-43 | 25 | 31 | 38 | 51 | 61 | 86 | 102 | 114 | 130 | 144 | 163 |
| T89-44 | 23 | 31 | 39 | 51 | 64 | 90 | 105 | 118 | 135 | 151 | 169 |
| T89-45 | 26 | 32 | 37 | 49 | 58 | 85 | 100 | 110 | 124 | 137 | 153 |
| T89-46 | 20 | 25 | 34 | 43 | 55 | 81 | 97 | 109 | 122 | 133 | 149 |

TABLE 1.7b

Diameter growth data for TF0076

| | Diameter (mm) Days in greenhouse | | | | | | | |
|---|---|---|---|---|---|---|---|---|
| | 29 | 32 | 39 | 43 | 46 | 50 | 53 | 57 |
| TF0076-2AA | 3.8 | 4.5 | 6.6 | 7.5 | 8.0 | 9.1 | 9.9 | 10.4 |
| TF0076-2AB | 4.8 | 5.0 | 5.6 | 6.3 | 6.8 | 7.3 | 7.9 | 8.1 |
| TF0076-3BA | 3.1 | 3.8 | 5.5 | 6.6 | 7.5 | 7.6 | 8.8 | 8.9 |
| TF0076-3BB | 3.8 | 4.7 | 6.2 | 7.4 | 8.5 | 8.7 | 9.4 | 10.0 |
| TF0076-4B | N/A | N/A | N/A | N/A | N/A | N/A | N/A | N/A |
| TF0076-5BA | 3.7 | 4.9 | 6.1 | 7.0 | 7.8 | 9.1 | 9.7 | 9.8 |
| TF0076-5BB | 4.2 | 6.0 | 7.2 | 8.9 | 8.9 | 9.8 | 10.1 | 10.6 |
| T89-01 | 3.2 | 3.7 | 5.3 | 6.2 | 6.9 | 7.9 | 8.3 | 8.7 |
| T89-02 | 3.2 | 3.9 | 5.1 | 6.4 | 7.0 | 7.6 | 8.6 | 8.6 |
| T89-03 | 4.2 | 5.3 | 6.4 | 6.9 | 6.9 | N/A | 8.8 | 9.8 |
| T89-04 | 2.2 | 3.0 | 4.2 | 4.5 | 5.4 | 5.0 | 5.4 | 6.1 |
| T89-05 | 3.0 | 3.7 | 4.8 | 5.9 | 6.4 | 7.0 | 7.6 | 7.9 |
| T89-06 | 3.6 | 4.8 | 6.5 | 7.6 | 8.7 | 9.1 | 9.6 | 10.1 |
| T89-07 | 3.8 | 4.9 | 6.8 | 7.6 | 8.0 | 8.6 | 9.0 | 9.7 |
| T89-08 | 4.4 | 5.8 | 6.2 | 7.3 | 7.6 | 8.5 | 9.4 | 9.7 |
| T89-09 | 4.5 | 5.5 | 6.5 | 7.1 | 7.6 | 9.1 | 9.4 | 9.8 |
| T89-10 | 3.7 | 3.9 | 5.0 | 6.1 | 6.8 | 7.6 | 8.5 | 9.2 |
| T89-11 | N/A | N/A | N/A | N/A | N/A | N/A | N/A | N/A |
| T89-12 | 4.6 | 5.5 | 7.3 | 8.6 | 8.8 | 9.6 | 10.2 | 10.2 |
| T89-13 | 3.8 | 4.6 | 5.7 | 6.5 | 6.6 | 7.4 | 8.1 | 8.6 |
| T89-14 | 3.7 | 4.2 | 5.3 | 5.6 | 6.1 | 7.0 | 7.1 | 7.8 |
| T89-15 | 4.6 | 5.0 | 6.4 | 7.0 | 7.4 | 8.0 | 8.4 | 9.1 |
| T89-16 | 5.0 | 5.5 | 7.0 | 7.6 | 8.0 | 8.6 | 9.0 | 9.7 |
| T89-17 | 3.1 | 4.3 | 5.7 | 7.1 | 7.4 | 7.9 | 8.4 | 9.2 |
| T89-18 | 4.5 | 5.3 | 7.8 | 8.0 | 8.1 | 9.2 | 9.9 | 10.3 |
| T89-19 | 4.2 | 5.8 | 6.7 | 8.2 | 8.5 | 8.5 | 9.0 | 9.5 |
| T89-20 | 4.0 | 4.7 | 6.7 | 8.1 | 7.6 | 8.5 | 8.6 | 9.4 |
| T89-21 | 3.5 | 3.9 | 5.0 | 5.7 | 5.8 | 7.1 | 6.7 | 7.4 |
| T89-22 | 3.6 | 4.3 | 5.5 | 6.3 | 6.8 | 7.9 | 8.4 | 8.8 |
| T89-23 | 4.1 | 5.2 | 7.0 | 7.6 | 8.2 | 8.9 | 9.2 | 10.0 |
| T89-24 | 4.1 | 5.4 | 6.7 | 7.5 | 7.8 | 8.6 | 9.6 | 10.4 |
| T89-25 | 3.7 | 4.6 | 6.0 | 7.0 | 7.7 | 8.3 | 8.5 | 9.4 |
| T89-26 | 4.8 | 5.6 | 6.9 | 7.3 | 7.8 | 8.6 | 9.2 | 9.5 |
| T89-27 | 3.8 | 4.9 | 6.2 | 6.7 | 6.9 | 7.6 | 8.4 | 9.3 |
| T89-28 | 4.5 | 5.5 | 6.8 | 7.3 | 7.8 | 9.1 | 9.1 | 9.5 |
| T89-29 | 4.4 | 5.3 | 6.8 | 6.8 | 7.4 | 8.2 | 9.2 | 8.9 |
| T89-30 | 3.7 | 4.7 | 5.4 | 6.6 | 7.0 | 7.0 | 7.7 | 8.5 |
| T89-31 | 4.0 | 4.5 | 5.5 | 6.9 | 7.0 | 8.0 | 9.1 | 9.6 |
| T89-32 | 3.6 | 4.5 | 5.7 | 7.0 | 7.2 | 8.0 | 9.1 | 9.4 |
| T89-33 | 3.9 | 4.6 | 6.7 | 7.3 | 8.0 | 8.6 | 9.4 | 10.5 |
| T89-34 | 3.6 | 4.5 | 5.9 | 6.9 | 7.5 | 8.2 | 9.1 | 9.4 |
| T89-35 | 3.9 | 4.5 | 5.7 | 7.1 | 7.5 | 7.9 | 8.8 | 9.6 |
| T89-36 | 3.6 | 5.0 | 5.7 | 6.5 | 6.8 | 7.9 | 8.2 | 9.1 |
| T89-37 | 4.3 | 5.6 | 7.1 | 8.0 | 8.0 | 8.9 | 9.7 | 10.2 |
| T89-38 | 4.7 | 5.8 | 6.7 | 7.8 | 8.0 | 8.7 | 9.2 | 9.7 |
| T89-39 | 4.2 | 5.0 | 6.2 | 7.3 | 8.2 | 8.1 | 8.7 | 9.6 |
| T89-40 | 3.6 | 4.4 | 5.2 | 5.7 | 6.0 | 7.2 | 7.2 | 8.0 |
| T89-41 | 3.5 | 4.3 | 5.5 | 6.5 | 7.0 | 7.5 | 7.7 | 8.4 |
| T89-42 | 4.4 | 5.1 | 7.5 | 8.4 | 9.5 | 9.9 | 10.0 | 10.3 |
| T89-43 | 4.3 | 5.0 | 6.5 | 7.3 | 7.8 | 8.3 | 8.9 | 9.1 |
| T89-44 | 4.3 | 5.8 | 6.8 | 8.1 | 8.6 | 9.5 | 9.9 | 10.5 |
| T89-45 | 4.2 | 4.9 | 6.8 | 7.5 | 7.6 | 8.5 | 9.4 | 9.7 |
| T89-46 | 3.5 | 4.4 | 5.7 | 7.0 | 7.5 | 8.6 | 9.4 | 9.8 |

Real-time RT-PCR was used to confirm over-expression of construct TF0076. Table 1.7c contains gene expression levels of construct gene relative to reference gene expression. All ratios between construct and reference gene expression levels shown are normalized to the average of wild type group ratios. 4 of 6 individuals of construction group TF0076 are over-expressed according to present RT-PCR data.

TABLE 1.7c

Real-time RT-PCR data for TF0076

| Sample | Relative gene expression level normalized to wild type average |
|---|---|
| TF0076-2AA | 0.43 |
| TF0076-2AB | 3.25 |
| TF0076-3BA | 3.61 |
| TF0076-3BB | 0.65 |
| TF0076-5BA | 3.70 |
| TF0076-5BB | 3.63 |
| T89-03 | 1.46 |
| T89-36 | 1.54 |
| T89-37 | 0.52 |
| T89-38 | 0.66 |
| T89-39 | 0.82 |

Results from growth analysis are specified in the overview table 1.7d. The determined growth effects of specified construction group are presented as ratios between construction and wild type group AFH, AFD, AMHGR, ADGR, MFH, MFD, MMHGR and MDC.

TABLE 1.7d

Overview table of growth effects of construct TF0076

| Construction group | Average Final Height | Average Final Diameter | Average Maximum Height Growth Rate | Average Diameter Growth Rate | Maximum Final Height | Maximum Final Diameter | Maximum of Maximum Height Growth Rate | Maximum Diameter Growth Rate |
|---|---|---|---|---|---|---|---|---|
| TF0076 | 1.10 | 1.04 | 1.13 | 1.09 | 1.18 | 1.01 | 1.18 | 1.02 |

Construction Group TF0089

This construct induces increased growth. The final height is 7% higher comparing the average of the construction group and wild type control group. The final height is 17% higher comparing the largest individuals of the construction group and wild type control group. The maximum height growth rate is 12% higher comparing the average of the construction group and wild type control group. The maximum height growth rate is 17% higher comparing the largest individuals of the construction group and wild type control group. The TF0089 construction group meets growth difference selection criterion (1) as shown in table 1.8c.

Tables 1.8a and 1.8b contain growth data for specified construction group and corresponding wild type group. Table rows contain height and diameter measurements of individuals of specified construction group and corresponding wild type group. Time of measurement as number of days in greenhouse is shown in table headers.

TABLE 1.8a

Height growth data for TF0089

Height (cm) Days in greenhouse

| | 18 | 21 | 26 | 32 | 35 | 39 | 43 | 46 | 53 | 60 | 64 |
|---|---|---|---|---|---|---|---|---|---|---|---|
| TF0089-1A | 4 | 7 | 13 | 25 | 35 | 48 | 60 | 71 | 94 | 122 | 140 |
| TF0089-1BA | 19 | 22 | 31 | 51 | 61 | 71 | 84 | 92 | 115 | 138 | 152 |
| TF0089-1BB | 10 | 13 | 19 | 34 | 41 | 52 | 67 | 78 | 103 | 125 | 138 |
| TF0089-2AA | 23 | 29 | 37 | 52 | 61 | 71 | 86 | 97 | 119 | 144 | 158 |
| TF0089-2AB | 20 | 25 | 33 | 47 | 56 | 68 | 80 | 90 | 113 | 137 | 148 |
| TF0089-2B | 24 | 30 | 32 | 60 | 70 | 80 | 98 | 111 | 140 | 168 | 184 |
| T89-01 | 20 | 27 | 35 | 54 | 61 | 72 | 84 | 93 | 112 | 130 | 141 |
| T89-02 | 19 | 25 | 31 | 48 | 56 | 67 | 79 | 90 | 113 | 137 | 149 |
| T89-03 | 21 | 26 | 33 | 48 | 55 | 64 | 75 | 83 | 100 | 117 | 128 |
| T89-04 | 21 | 26 | 33 | 52 | 59 | 69 | 83 | 96 | 120 | 140 | 152 |
| T89-05 | 20 | 25 | 34 | 52 | 59 | 70 | 84 | | 120 | 144 | 156 |
| T89-06 | 20 | 26 | 35 | 52 | 61 | 73 | 87 | 98 | 121 | 143 | 156 |
| T89-07 | 17 | 21 | 27 | 45 | 53 | 63 | 74 | 85 | 107 | 129 | 140 |
| T89-08 | 18 | 24 | 31 | 48 | 56 | 64 | 75 | 86 | 106 | 128 | 141 |
| T89-09 | 24 | 28 | 34 | 48 | 55 | 65 | 78 | 91 | 112 | 136 | 153 |
| T89-10 | 18 | 24 | 30 | 44 | 52 | 62 | 75 | 87 | 107 | 129 | 142 |
| T89-11 | 11 | 14 | 20 | 32 | 41 | 52 | 62 | 72 | 95 | 118 | 132 |
| T89-12 | 17 | 24 | 30 | 44 | 52 | 62 | 74 | 85 | 106 | 129 | 141 |
| T89-13 | 21 | 28 | 35 | 48 | 56 | 67 | 78 | 85 | 103 | 122 | 134 |
| T89-14 | 20 | 25 | 34 | 51 | 60 | 69 | 80 | 90 | 110 | 135 | 148 |
| T89-15 | 19 | 24 | 32 | 45 | 52 | 62 | 74 | 84 | 106 | 129 | 142 |
| T89-16 | 20 | 24 | 30 | 45 | 53 | 63 | 75 | 86 | 108 | 131 | 141 |
| T89-17 | 18 | 23 | 28 | 42 | 50 | 61 | 74 | 82 | 104 | 129 | 143 |
| T89-18 | 17 | 22 | 28 | 44 | 53 | 62 | 75 | 85 | 108 | 130 | 144 |
| T89-19 | 19 | 24 | 30 | 43 | 50 | 59 | 72 | 84 | 103 | 125 | 140 |
| T89-20 | 18 | 23 | 30 | 43 | 50 | 60 | 71 | 80 | 102 | 123 | 136 |
| T89-21 | 19 | 24 | 31 | 45 | 53 | 62 | 76 | 87 | 107 | 134 | 149 |
| T89-22 | 15 | 19 | 23 | 30 | 39 | 47 | 58 | 66 | 82 | 99 | 109 |
| T89-23 | 19 | 24 | 34 | 50 | 60 | 69 | 83 | 94 | 118 | 141 | 154 |
| T89-24 | 23 | 27 | 36 | 51 | 61 | 72 | 85 | 95 | 120 | 145 | 157 |
| T89-25 | 19 | 21 | 29 | 44 | 52 | 63 | 74 | 84 | 102 | 124 | 138 |
| T89-26 | 20 | 25 | 32 | 45 | 53 | 63 | 75 | 85 | 108 | 128 | 139 |
| T89-27 | 22 | 25 | 33 | 48 | 56 | 66 | 80 | 92 | 112 | 134 | 147 |
| T89-28 | 21 | 28 | 33 | 47 | 57 | 68 | 80 | 89 | 111 | 137 | 148 |
| T89-29 | 18 | 23 | 28 | 43 | 51 | 61 | 73 | 84 | 105 | 125 | 136 |
| T89-30 | 19 | 20 | 25 | 38 | 45 | 53 | 63 | 71 | 91 | 114 | 125 |
| T89-31 | 15 | 21 | 29 | 48 | 57 | 66 | 80 | 91 | 114 | 134 | 148 |
| T89-32 | 20 | 24 | 33 | 50 | 55 | 65 | 77 | 88 | 110 | 134 | 146 |
| T89-33 | 20 | 26 | 33 | 49 | 57 | 68 | 79 | 89 | 113 | 135 | 149 |
| T89-34 | 19 | 25 | 33 | 51 | 58 | 70 | 84 | 98 | 120 | 140 | 154 |
| T89-35 | 19 | 24 | 31 | 46 | 54 | 64 | 78 | 90 | 112 | 135 | 147 |
| T89-36 | 21 | 25 | 33 | 49 | 57 | 68 | 80 | 89 | 109 | 130 | 140 |
| T89-37 | 17 | 23 | 32 | 49 | 58 | 68 | 78 | 88 | 110 | 133 | 146 |

TABLE 1.8a-continued

Height growth data for TF0089

Height (cm) Days in greenhouse

| | 18 | 21 | 26 | 32 | 35 | 39 | 43 | 46 | 53 | 60 | 64 |
|---|---|---|---|---|---|---|---|---|---|---|---|
| T89-38 | 18 | 24 | 31 | 46 | 54 | 65 | 79 | 91 | 112 | 138 | 152 |
| T89-39 | 20 | 25 | 32 | 50 | 59 | 69 | 82 | 92 | 118 | 138 | 151 |
| T89-40 | 22 | 27 | 35 | 49 | 56 | 66 | 77 | 88 | 109 | 131 | 145 |
| T89-41 | 20 | 24 | 30 | 44 | 51 | 60 | 73 | 82 | 106 | 129 | 141 |
| T89-42 | 21 | 26 | 32 | 50 | 58 | 68 | 82 | 92 | 115 | 134 | 148 |
| T89-43 | 17 | 24 | 32 | 47 | 55 | 65 | 79 | 89 | 113 | 139 | 154 |
| T89-44 | 18 | 24 | 31 | 47 | 56 | 65 | 78 | 89 | 112 | 135 | 152 |
| T89-45 | 20 | 23 | 29 | 45 | 55 | 63 | 75 | 86 | 106 | 129 | 141 |
| T89-46 | 21 | 24 | 32 | 45 | 55 | 67 | 78 | 85 | 103 | 122 | 138 |
| T89-47 | 19 | 24 | 30 | 46 | 53 | 67 | 74 | 84 | 105 | 131 | 144 |

TABLE 1.8b

Diameter growth data for TF0089

Diameter (mm) Days in greenhouse

| | 32 | 35 | 39 | 43 | 46 | 53 | 60 | 64 |
|---|---|---|---|---|---|---|---|---|
| TF0089-1A | 3.0 | 3.3 | 4.2 | 5.1 | 6.0 | 7.5 | 8.3 | 8.2 |
| TF0089-1BA | 4.9 | 6.0 | 6.5 | 7.8 | 8.1 | 9.1 | 9.5 | 10.1 |
| TF0089-1BB | 4.0 | 4.2 | 5.3 | 6.1 | 6.8 | 7.6 | 8.7 | 9.2 |
| TF0089-2AA | 5.7 | 6.3 | 7.3 | 8.6 | 8.1 | 9.6 | 10.9 | 11.5 |
| TF0089-2AB | 4.8 | 6.0 | 6.5 | 7.5 | 8.1 | 8.8 | 10.4 | 10.4 |
| TF0089-2B | 5.3 | 6.0 | 6.8 | 8.6 | 9.4 | 10.0 | 12.4 | 12.2 |
| T89-01 | 5.1 | 5.8 | 6.6 | 7.4 | 8.5 | 8.3 | 9.5 | 9.7 |
| T89-02 | 5.1 | 5.8 | 6.7 | 7.5 | 8.6 | 9.5 | 10.9 | 11.4 |
| T89-03 | 4.6 | 5.3 | 5.8 | 6.4 | 7.0 | 7.5 | 8.2 | 8.7 |
| T89-04 | 5.4 | 6.2 | 7.3 | 8.1 | 8.6 | 9.8 | 10.8 | 10.9 |
| T89-05 | 5.1 | 6.0 | 7.1 | 7.7 | 8.7 | 9.3 | 10.7 | 11.0 |
| T89-06 | 5.6 | 5.6 | 6.8 | 7.4 | 8.6 | 10.3 | 10.8 | 11.3 |
| T89-07 | 4.1 | 4.8 | 5.6 | 6.7 | 7.3 | 8.5 | 9.8 | 9.9 |
| T89-08 | 4.8 | 5.5 | 6.2 | 7.5 | 7.4 | 8.2 | 9.0 | 9.0 |
| T89-09 | 5.1 | 5.5 | 6.5 | 7.6 | 7.9 | 9.7 | 10.6 | 10.8 |
| T89-10 | 5.8 | 5.8 | 6.5 | 7.2 | 7.5 | 9.3 | 10.2 | 10.9 |
| T89-11 | 3.8 | 4.4 | 5.5 | 6.1 | 6.7 | 8.6 | 9.9 | 10.1 |
| T89-12 | 4.8 | 5.8 | 6.2 | 7.0 | 6.9 | 10.0 | 9.3 | 9.7 |
| T89-13 | 5.9 | 5.8 | 7.3 | 8.7 | 9.0 | 10.7 | 11.2 | 11.6 |
| T89-14 | 5.4 | 6.3 | 6.7 | 8.5 | 8.6 | 10.0 | 10.8 | 11.3 |
| T89-15 | 5.0 | 5.5 | 6.6 | 7.3 | 8.1 | 9.7 | 10.3 | 10.3 |
| T89-16 | 4.8 | 5.3 | 5.9 | 6.8 | 7.6 | 8.1 | 9.8 | 10.0 |
| T89-17 | 4.0 | 4.7 | 6.1 | 6.6 | 6.8 | 9.0 | 9.6 | 10.5 |
| T89-18 | 4.7 | 5.7 | 6.5 | 7.2 | 7.8 | 8.8 | 9.0 | 9.8 |
| T89-19 | 4.5 | 5.4 | 6.1 | 6.8 | 7.2 | 8.4 | 9.8 | 10.1 |
| T89-20 | 5.4 | 5.9 | 7.3 | 7.9 | 8.6 | 9.8 | 11.2 | 11.6 |
| T89-21 | 5.0 | 5.8 | 5.7 | 8.2 | 8.0 | 9.3 | 10.1 | 11.2 |
| T89-22 | 3.1 | 3.6 | 3.8 | 4.2 | 4.1 | 5.0 | 5.3 | 5.5 |
| T89-23 | 5.2 | 5.8 | 6.7 | 7.8 | 8.1 | 10.2 | 11.5 | 12.3 |
| T89-24 | 5.3 | 6.2 | 7.0 | 7.7 | 8.0 | 9.2 | 9.9 | 10.9 |
| T89-25 | 4.6 | 5.0 | 6.0 | 6.7 | 7.0 | 9.0 | 8.9 | 9.3 |
| T89-26 | 5.2 | 4.9 | 5.9 | 6.3 | 7.0 | 7.7 | 9.5 | 9.7 |
| T89-27 | 4.6 | 5.3 | 6.0 | 6.8 | 7.3 | 9.0 | 9.8 | 10.9 |
| T89-28 | 4.7 | 5.7 | 6.1 | 6.7 | 7.8 | 9.1 | 10.3 | 10.6 |
| T89-29 | 4.5 | 4.9 | 5.7 | 7.4 | 7.3 | 7.6 | 8.5 | 9.4 |
| T89-30 | 3.7 | 4.9 | 5.3 | 6.0 | 6.3 | 7.6 | 8.5 | 9.3 |
| T89-31 | 5.2 | 6.1 | 7.1 | 8.3 | 8.2 | 9.4 | 10.2 | 10.7 |
| T89-32 | 5.1 | 5.9 | 7.0 | 7.8 | 8.5 | 9.7 | 10.6 | 12.1 |
| T89-33 | 4.9 | 5.6 | 6.7 | 7.8 | 8.6 | 10.0 | 10.3 | 11.1 |
| T89-34 | 7.0 | 6.7 | 7.9 | 9.1 | 9.6 | 11.0 | 11.3 | 12.1 |
| T89-35 | 4.9 | 5.4 | 6.8 | 7.5 | 8.5 | 11.1 | 10.3 | 10.9 |
| T89-36 | 5.3 | 6.3 | 6.5 | 7.2 | 7.3 | 8.1 | 9.5 | 9.8 |
| T89-37 | 5.0 | 5.7 | 6.4 | 6.9 | 6.9 | 7.7 | 9.2 | 9.1 |
| T89-38 | 4.4 | 4.9 | 6.2 | 7.2 | 7.6 | 9.0 | 10.1 | 11.3 |
| T89-39 | 4.8 | 5.1 | 6.2 | 6.6 | 7.5 | 8.5 | 9.7 | 10.2 |
| T89-40 | 5.1 | 5.8 | 6.9 | 7.4 | 7.8 | 9.0 | 10.3 | 10.7 |
| T89-41 | 4.2 | 5.3 | 6.1 | 7.2 | 8.0 | 8.9 | 10.4 | 10.5 |
| T89-42 | 4.9 | 6.1 | 6.2 | 7.2 | 8.0 | 9.2 | 10.2 | 10.7 |
| T89-43 | 4.6 | 5.8 | 6.4 | 7.8 | 7.8 | 9.6 | 11.1 | 11.5 |
| T89-44 | 5.0 | 5.6 | 6.3 | 7.0 | 7.4 | 9.0 | 10.9 | 10.6 |

TABLE 1.8b-continued

Diameter growth data for TF0089

| | Diameter (mm) Days in greenhouse | | | | | | | |
|---|---|---|---|---|---|---|---|---|
| | 32 | 35 | 39 | 43 | 46 | 53 | 60 | 64 |
| T89-45 | 5.0 | 5.1 | 5.4 | 6.8 | 6.2 | 7.9 | 8.7 | 9.3 |
| T89-46 | 5.2 | 5.8 | 6.7 | 7.6 | 8.2 | 9.4 | 10.8 | 11.4 |
| T89-47 | 4.6 | 5.8 | 6.3 | 7.3 | 8.2 | 9.1 | 9.8 | 10.3 |

Results from growth analysis are specified in the overview table 1.8c. The determined growth effects of specified construction group are presented as ratios between construction and wild type group AFH, AFD, AMHGR, ADGR, MFH, MFD, MMHGR and MDC.

TABLE 1.8c

Overview table of growth effects of construct TF0089

| Construction group | Average Final Height | Average Final Diameter | Average Maximum Height Growth Rate | Average Diameter Growth Rate | Maximum Final Height | Maximum Final Diameter | Maximum of Maximum Height Growth Rate | Maximum Diameter Growth Rate |
|---|---|---|---|---|---|---|---|---|
| TF0089 | 1.07 | 0.98 | 1.12 | 1.02 | 1.17 | 0.99 | 1.17 | 0.96 |

Construction Group TF0109

This construct induces increased growth. The final height is 24% higher comparing the average of the construction group and wild type control group. The final height is 39% higher comparing the largest individuals of the construction group and wild type control group. The maximum height growth rate is 27% higher comparing the average of the construction group and wild type control group. The maximum height growth rate is 44% higher comparing the largest individuals of the construction group and wild type control group. The TF0109 construction group meets the more stringent level of growth difference selection criteria (1), (3) and (4) as shown in table 1.9d.

Tables 1.9a and 1.9b contain growth data for specified construction group and corresponding wild type group. Table rows contain height and diameter measurements of individuals of specified construction group and corresponding wild type group. Time of measurement as number of days in greenhouse is shown in table headers.

TABLE 1.9a

Height growth data for TF0109

| | Height (cm) Days in greenhouse | | | | | | |
|---|---|---|---|---|---|---|---|
| | 17 | 20 | 27 | 34 | 41 | 48 | 56 |
| TF0109-1B-1 | 17 | 20 | 34 | 56 | 81 | 108 | 138 |
| TF0109-1B-2 | 19 | 23 | 42 | 62 | 88 | 113 | 142 |
| TF0109-2A | 16 | 21 | 39 | 59 | 87 | 118 | 150 |
| TF0109-2B | 19 | 25 | 45 | 75 | 121 | 157 | 185 |
| TF0109-3B | 19 | 25 | 46 | 70 | 96 | 123 | 159 |
| TF0109-4A | 15 | 20 | 36 | 56 | 81 | 105 | 133 |
| TF0109-4B | 20 | 28 | 51 | 84 | 122 | 162 | 210 |
| T89-01 | 18 | 20 | 29 | 46 | 65 | 87 | 111 |
| T89-02 | 20 | 23 | 38 | 54 | 75 | 98 | 122 |
| T89-03 | 16 | 19 | 32 | 49 | 72 | 95 | 124 |
| T89-04 | 19 | 24 | 40 | 57 | 81 | 103 | 133 |
| T89-05 | 18 | 22 | 35 | 52 | 71 | 95 | 124 |
| T89-06 | 16 | 21 | 33 | 53 | 77 | 100 | 132 |
| T89-07 | 18 | 22 | 37 | 57 | 82 | 107 | 138 |
| T89-08 | 12 | 14 | 25 | 42 | 64 | 87 | 117 |
| T89-09 | 12 | 16 | 33 | 52 | 75 | 101 | 128 |
| T89-10 | 16 | 20 | 31 | 51 | 75 | 100 | 133 |
| T89-11 | 12 | 17 | 31 | 52 | 75 | 98 | 122 |
| T89-12 | 17 | 22 | 39 | 43 | N/A | N/A | N/A |
| T89-13 | 18 | 23 | 39 | 59 | 83 | 110 | 145 |
| T89-14 | 19 | 23 | 40 | 61 | 81 | 100 | 127 |
| T89-15 | 19 | 21 | 33 | 51 | 77 | 99 | 127 |
| T89-16 | 21 | 24 | 40 | 57 | 82 | 107 | 140 |
| T89-17 | 20 | 24 | 37 | 56 | 77 | 103 | 136 |
| T89-18 | 19 | 24 | 39 | 58 | 83 | 110 | 140 |
| T89-19 | 20 | 24 | 35 | 51 | 76 | 102 | 132 |
| T89-20 | 19 | 23 | 39 | 59 | 82 | 111 | 146 |
| T89-21 | 21 | 24 | 37 | 57 | 81 | 107 | 136 |
| T89-22 | 20 | 24 | 39 | 61 | 85 | 110 | 142 |
| T89-23 | 19 | 22 | 37 | 54 | 77 | 102 | 128 |
| T89-24 | 17 | 22 | 35 | 55 | 80 | 107 | 140 |
| T89-25 | 19 | 23 | 38 | 57 | 78 | 101 | 131 |
| T89-26 | 18 | 20 | 35 | 53 | 71 | 99 | 128 |
| T89-27 | 23 | 27 | 42 | 59 | 85 | 106 | 129 |
| T89-28 | 19 | 25 | 37 | 55 | 76 | 96 | 126 |
| T89-29 | 12 | 13 | 19 | 29 | 46 | 66 | 91 |
| T89-30 | 19 | 23 | 36 | 58 | 81 | 107 | 136 |
| T89-31 | 19 | 21 | 33 | 48 | 71 | 95 | 124 |
| T89-32 | 16 | 20 | 31 | 48 | 71 | 97 | 126 |
| T89-33 | 19 | 22 | 36 | 56 | 78 | 103 | 132 |
| T89-34 | 18 | 21 | 36 | 52 | 74 | 97 | 120 |
| T89-35 | 20 | 22 | 36 | 54 | 76 | 97 | 125 |
| T89-36 | 21 | 28 | 43 | 65 | 87 | 115 | 151 |
| T89-37 | 16 | 19 | 32 | 50 | 73 | 97 | 126 |

TABLE 1.9a-continued

Height growth data for TF0109

| | Height (cm) Days in greenhouse | | | | | | |
|---|---|---|---|---|---|---|---|
| | 17 | 20 | 27 | 34 | 41 | 48 | 56 |
| T89-38 | 17 | 21 | 35 | 52 | 74 | 92 | 113 |
| T89-39 | 17 | 19 | 28 | 45 | 60 | 89 | 116 |
| T89-40 | 21 | 26 | 38 | 55 | 79 | 104 | 130 |

TABLE 1.9b

Diameter growth data for TF0109

| | Diameter (mm) Days in greenhouse | | | | |
|---|---|---|---|---|---|
| | 27 | 34 | 41 | 48 | 56 |
| TF0109-1B-1 | 3.9 | 5.2 | 6.9 | 9.0 | 10.5 |
| TF0109-1B-2 | 4.3 | 5.7 | 7.2 | 8.8 | 9.8 |
| TF0109-2A | 4.1 | 5.8 | 7.9 | 9.9 | 11.1 |
| TF0109-2B | 4.0 | 5.8 | 7.2 | 8.8 | 9.4 |
| TF0109-3B | 4.4 | 6.0 | 7.9 | 9.6 | 10.2 |
| TF0109-4A | 4.2 | 5.4 | 7.5 | 8.4 | 10.0 |
| TF0109-4B | 4.2 | 5.5 | 7.1 | 8.6 | 10.0 |
| T89-01 | 3.5 | 4.3 | 5.4 | 7.0 | 8.1 |
| T89-02 | 4.2 | 6.0 | 7.6 | 8.0 | 9.7 |
| T89-03 | 3.6 | 5.9 | 7.0 | 8.0 | 9.9 |
| T89-04 | 4.0 | 6.0 | 7.7 | 8.9 | 10.7 |
| T89-05 | 4.0 | 5.6 | 7.4 | 9.0 | 10.4 |
| T89-06 | 4.7 | 6.2 | 7.8 | 9.9 | 11.2 |
| T89-07 | 5.3 | 5.8 | 7.0 | 8.4 | 10.0 |
| T89-08 | 4.0 | 4.6 | 6.4 | 7.8 | 9.4 |
| T89-09 | 4.2 | 4.9 | 7.0 | 9.4 | 10.5 |
| T89-10 | 3.9 | 5.0 | 7.0 | 9.0 | 9.7 |
| T89-11 | 3.8 | 5.0 | 6.6 | 7.7 | 9.1 |
| T89-12 | 4.8 | N/A | N/A | N/A | N/A |
| T89-13 | 4.0 | 5.5 | 7.2 | 8.9 | 10.1 |
| T89-14 | 4.4 | 5.8 | 6.9 | 8.2 | 8.0 |
| T89-15 | 3.6 | 4.6 | 6.5 | 7.4 | 8.7 |
| T89-16 | 4.0 | 5.3 | 6.4 | 8.8 | 9.3 |
| T89-17 | 3.8 | 6.4 | 6.7 | 8.5 | 9.6 |
| T89-18 | 4.3 | 5.8 | 6.9 | 8.1 | 9.7 |
| T89-19 | 3.7 | 5.0 | 6.9 | 7.9 | 9.3 |
| T89-20 | 3.9 | 5.2 | 7.1 | 8.4 | 9.8 |
| T89-21 | 4.3 | 5.4 | 7.0 | 8.5 | 11.0 |
| T89-22 | 4.3 | 5.6 | 7.0 | 9.0 | 10.0 |
| T89-23 | 4.0 | 5.2 | 7.3 | 8.6 | 10.8 |
| T89-24 | 4.6 | 5.8 | 7.5 | 8.5 | 10.0 |
| T89-25 | 4.0 | 5.9 | 6.7 | 7.3 | 8.8 |
| T89-26 | 4.2 | 5.4 | 6.4 | 8.0 | 8.4 |
| T89-27 | 4.2 | 5.1 | 6.5 | 7.5 | 7.7 |
| T89-28 | 3.6 | 4.5 | 6.4 | 7.5 | 8.9 |
| T89-29 | N/A | 2.5 | 3.4 | 4.9 | 5.9 |
| T89-30 | 4.2 | 5.2 | 6.6 | 8.0 | 9.4 |
| T89-31 | 3.8 | 4.9 | 6.5 | 8.3 | 9.7 |
| T89-32 | 3.9 | 4.8 | 6.0 | 7.5 | 9.2 |
| T89-33 | 3.7 | 5.0 | 7.7 | 7.8 | 9.4 |
| T89-34 | 3.9 | 5.1 | 6.2 | 7.5 | 7.5 |

TABLE 1.9b-continued

Diameter growth data for TF0109

| | Diameter (mm) Days in greenhouse | | | | |
|---|---|---|---|---|---|
| | 27 | 34 | 41 | 48 | 56 |
| T89-35 | 3.6 | 5.5 | 6.7 | 7.6 | 8.9 |
| T89-36 | 4.1 | 5.6 | 7.3 | 8.8 | 10.4 |
| T89-37 | 3.8 | 4.9 | 6.9 | 7.8 | 9.5 |
| T89-38 | 3.4 | 4.6 | 5.4 | 5.9 | 6.5 |
| T89-39 | 2.8 | 4.0 | 5.4 | 6.2 | 7.2 |
| T89-40 | 3.7 | 5.8 | 6.4 | 8.3 | 9.2 |

Real-time RT-PCR was used to confirm over-expression of construct TF0109. Table 1.9c contains gene expression levels of construct gene relative to reference gene expression. All ratios between construct and reference gene expression levels shown are normalized to the average of wild type group ratios. 4 of 7 individuals of construction group TF0109 are over-expressed according to present RT-PCR data. 2 of 7 individuals of construction group TF0109 are down-regulated according to present RT-PCR data. Individuals having higher expression levels of construct TF0109 are correlatively tall and fast growing while individuals having lower expression levels of construct TF0109 are shorter.

TABLE 1.9c

Real-time RT-PCR data for TF0109

| Sample | Relative gene expression level normalized to wild type average |
|---|---|
| TF0109-1B-1 | 0.39 |
| TF0109-1B-2 | 0.55 |
| TF0109-2A | 2.16 |
| TF0109-2B | 9.21 |
| TF0109-3B | 1.80 |
| TF0109-4A | 0.95 |
| TF0109-4B | 6.24 |
| T89-03 | 1.08 |
| T89-07 | 1.17 |
| T89-08 | 1.11 |
| T89-10 | 0.79 |
| T89-11 | 0.85 |

Results from growth analysis are specified in the overview table 1.9d. The determined growth effects of specified construction group are presented as ratios between construction and wild type group AFH, AFD, AMHGR, ADGR, MFH, MFD, MMHGR and MDC.

TABLE 1.9d

Overview table of growth effects of construct TF0109

| Construction group | Average Final Height | Average Final Diameter | Average Maximum Height Growth Rate | Average Diameter Growth Rate | Maximum Final Height | Maximum Final Diameter | Maximum of Maximum Height Growth Rate | Maximum Diameter Growth Rate |
|---|---|---|---|---|---|---|---|---|
| TF0109 | 1.24 | 1.09 | 1.27 | 1.12 | 1.39 | 1.00 | 1.44 | 1.02 |

Construction Group TF0132

This construct induces increased growth. The final height is 13% higher comparing the average of the construction group and wild type control group. The final height is 26% higher comparing the largest individuals of the construction group and wild type control group. The maximum height growth rate is 18% higher comparing the average of the construction group and wild type control group. The maximum height growth rate is 18% higher comparing the largest individuals of the construction group and wild type control group. The TF0132 construction group meets the more stringent level of growth difference selection criteria (1) and (4) as shown in table 1.10c.

Tables 1.10a and 1.10b contain growth data for specified construction group and corresponding wild type group. Table rows contain height and diameter measurements of individuals of specified construction group and corresponding wild type group. Time of measurement as number of days in greenhouse is shown in table headers.

TABLE 1.10a

Height growth data for TF0132

| | Height (cm) Days in greenhouse | | | | | | | | |
|---|---|---|---|---|---|---|---|---|---|
| | 20 | 28 | 34 | 37 | 41 | 48 | 51 | 55 | 59 |
| TF0132-3A-1 | 23 | 38 | 53 | 60 | 70 | 89 | 96 | 107 | 119 |
| TF0132-3A-2 | 15 | 28 | 42 | 49 | 58 | 75 | 81 | 93 | 100 |
| TF0132-3A-3 | 26 | 41 | 54 | 61 | 72 | 89 | 96 | 107 | 119 |
| TF0132-3B-1 | 27 | 47 | 63 | 73 | 84 | 113 | 125 | 142 | 156 |
| TF0132-3B-2 | 30 | 51 | 71 | 80 | 94 | N/A | 134 | 148 | 160 |
| TF0132-3BB | 32 | 58 | 87 | 96 | 112 | 141 | 155 | 171 | 182 |
| TF0132-4AA | 20 | 39 | 59 | 67 | 78 | 102 | 112 | 129 | 143 |
| TF0132-4AB | 21 | 43 | 63 | 74 | 87 | 114 | 126 | 142 | 156 |
| TF0132-4AC | 27 | 48 | 67 | 76 | 89 | 117 | 129 | 146 | 156 |
| T89-02 | 27 | 40 | 51 | 58 | 66 | 86 | 94 | 105 | 115 |
| T89-03 | 27 | 44 | 58 | 67 | 77 | 97 | 104 | 114 | 126 |
| T89-04 | 27 | 39 | 56 | 65 | 74 | 92 | 100 | 109 | 118 |
| T89-07 | 28 | 47 | 66 | 77 | 88 | 107 | 116 | 130 | 140 |
| T89-08 | 19 | 37 | 51 | 59 | 69 | 90 | 99 | 109 | 119 |
| T89-09 | 25 | 43 | 58 | 67 | 78 | 100 | 109 | 121 | 131 |
| T89-11 | 29 | 45 | 60 | 69 | 81 | 104 | 111 | 121 | 132 |
| T89-12 | 26 | 41 | 58 | 65 | 77 | 105 | 114 | 127 | 136 |
| T89-13 | 31 | 47 | 70 | 78 | 90 | 110 | 119 | 131 | 143 |
| T89-14 | 26 | 46 | 70 | 78 | 88 | 108 | 116 | 127 | 137 |
| T89-18 | 22 | 41 | 55 | 65 | 74 | 95 | 104 | 115 | 126 |
| T89-19 | 27 | 43 | 60 | 70 | 81 | 102 | 110 | 121 | 131 |
| T89-20 | 25 | 40 | 57 | N/A | 74 | 94 | 103 | 118 | 130 |
| T89-21 | 27 | 45 | 61 | 72 | 84 | 108 | 115 | 126 | 137 |
| T89-22 | 25 | 38 | 55 | 65 | 77 | 95 | 104 | 115 | 125 |
| T89-23 | 23 | 37 | 50 | 57 | 65 | 82 | 92 | 106 | 115 |
| T89-24 | 25 | 41 | 54 | 60 | 69 | 87 | 94 | 102 | 110 |
| T89-25 | 25 | 38 | 55 | 66 | 80 | 100 | 109 | 121 | 133 |
| T89-26 | 24 | 38 | 53 | 61 | 69 | 81 | 87 | 95 | 104 |
| T89-27 | 26 | 39 | 54 | 62 | 70 | 90 | 97 | 109 | 120 |
| T89-28 | 27 | 46 | 67 | 75 | 86 | 107 | 114 | 126 | 136 |
| T89-29 | 24 | 39 | 57 | 64 | 74 | 91 | 98 | 108 | 128 |
| T89-31 | 27 | 43 | 57 | 65 | 73 | 91 | 97 | 105 | 113 |
| T89-32 | 25 | 41 | 55 | 63 | 75 | 96 | 107 | 121 | 135 |
| T89-35 | 25 | 38 | 53 | 62 | 73 | 88 | 96 | 103 | 112 |
| T89-36 | 27 | 45 | 67 | 78 | 90 | 113 | 122 | 134 | 145 |
| T89-37 | 20 | 43 | 59 | 68 | 79 | 101 | 112 | 124 | 137 |
| T89-39 | 25 | 45 | 61 | 69 | 79 | 99 | 108 | 120 | 132 |
| T89-40 | 23 | 32 | 43 | 49 | 60 | 76 | 84 | 94 | 104 |
| T89-41 | 27 | 45 | 66 | 75 | 87 | 112 | 120 | 133 | 144 |
| T89-43 | 26 | 38 | 54 | 61 | 70 | 93 | 100 | 109 | 120 |
| T89-46 | 26 | 45 | 66 | 76 | 88 | 109 | 114 | 125 | 133 |

TABLE 1.10b

Diameter growth data for TF0132

| | Diameter (mm) Days in greenhouse | | | | |
|---|---|---|---|---|---|
| | 34 | 41 | 48 | 55 | 59 |
| TF0132-3A-1 | 6.1 | 7.3 | 7.8 | 9.0 | 8.9 |
| TF0132-3A-2 | 5.8 | 7.3 | 7.8 | 9.0 | 9.0 |
| TF0132-3A-3 | 6.6 | 8.5 | 8.6 | 9.2 | 9.7 |
| TF0132-3B-1 | 6.2 | 7.0 | 8.6 | 9.2 | 9.7 |
| TF0132-3B-2 | 5.7 | 7.3 | 8.8 | 9.8 | 9.2 |
| TF0132-3BB | 6.4 | 7.3 | 8.0 | 9.1 | 9.2 |
| TF0132-4AA | 5.3 | 6.0 | 7.4 | 8.8 | 9.1 |
| TF0132-4AB | 5.6 | 7.0 | 7.0 | 8.4 | 8.4 |
| TF0132-4AC | 6.2 | 7.2 | 9.1 | 9.6 | 10.0 |
| T89-02 | 5.6 | 6.4 | 7.8 | 9.0 | 8.4 |
| T89-03 | 6.6 | 7.7 | 8.5 | 8.9 | 9.6 |
| T89-04 | 7.2 | 7.8 | 9.1 | 9.8 | 9.7 |
| T89-07 | 7.3 | 7.9 | 9.5 | 9.9 | 10.1 |
| T89-08 | 5.5 | 7.8 | 8.3 | 10.0 | 9.8 |
| T89-09 | 6.7 | 7.8 | 9.3 | 9.7 | 9.8 |
| T89-11 | 6.4 | 8.1 | 9.2 | 9.4 | 9.7 |
| T89-12 | 7.0 | 8.0 | 9.0 | 10.1 | 9.9 |
| T89-13 | 6.8 | 8.5 | 9.1 | 10.7 | 10.8 |
| T89-14 | 6.1 | 6.9 | 7.7 | 8.4 | 8.8 |
| T89-18 | 5.5 | 6.5 | 7.9 | 9.5 | 9.4 |
| T89-19 | 7.5 | 8.3 | 9.0 | 9.5 | 10.4 |
| T89-20 | 7.3 | 7.1 | 8.7 | 9.3 | 9.7 |
| T89-21 | 7.0 | 8.6 | 9.3 | 10.3 | 10.3 |
| T89-22 | 7.0 | 7.8 | 8.4 | 10.0 | 9.5 |
| T89-23 | 5.8 | 6.8 | 7.9 | 9.9 | 9.7 |
| T89-24 | 6.1 | 6.8 | 8.1 | 9.0 | 9.4 |
| T89-25 | 6.5 | 8.8 | 9.5 | 10.0 | 10.9 |
| T89-26 | 5.8 | 6.7 | 7.0 | 7.5 | 7.7 |
| T89-27 | 6.3 | 7.4 | 8.6 | 9.0 | 9.5 |
| T89-28 | 7.0 | 8.1 | 8.8 | 9.7 | 10.5 |
| T89-29 | 7.5 | 7.4 | 8.5 | 10.7 | 10.0 |
| T89-31 | 5.6 | 6.3 | 7.2 | 7.6 | 8.6 |
| T89-32 | 6.0 | 7.0 | 8.2 | 8.7 | 9.3 |
| T89-35 | 5.4 | 6.4 | 6.8 | 7.9 | 8.0 |
| T89-36 | 6.7 | 8.2 | 8.9 | 9.6 | 9.4 |
| T89-37 | 7.4 | 8.5 | 8.6 | 9.3 | 10.8 |
| T89-39 | 7.1 | 7.9 | 9.6 | 10.2 | 10.2 |
| T89-40 | 3.9 | 5.2 | 5.7 | 6.8 | 6.6 |
| T89-41 | 7.2 | 8.7 | N/A | 9.7 | 10.3 |
| T89-43 | 6.9 | 7.5 | 8.6 | 9.7 | 10.4 |
| T89-46 | 6.4 | 7.2 | 8.2 | 8.7 | 9.7 |

Results from growth analysis are specified in the overview table 1.10c. The determined growth effects of specified construction group are presented as ratios between construction and wild type group AFH, AFD, AMHGR, ADGR, MFH, MFD, MMHGR and MDC.

TABLE 1.10c

Overview table of growth effects of construct TF0132

| Construction group | Average Final Height | Average Final Diameter | Average Maximum Height Growth Rate | Average Diameter Growth Rate | Maximum Final Height | Maximum Final Diameter | Maximum of Maximum Height Growth Rate | Maximum Diameter Growth Rate |
|---|---|---|---|---|---|---|---|---|
| TF0132 | 1.13 | 0.97 | 1.18 | 1.04 | 1.26 | 0.92 | 1.18 | 0.99 |

Construction Group TFSTT051

This construct induces increased growth. The final height is 7% higher comparing the average of the construction group and wild type control group. The final height is 11% higher comparing the largest individuals of the construction group and wild type control group. The maximum height growth rate is 5% higher comparing the average of the construction group and wild type control group. The maximum height growth rate is 10% higher comparing the largest individuals of the construction group and wild type control group. The TFSTT051 construction group meets growth difference selection criterion (1) as shown in table 1.11d.

Tables 1.11a and 1.11b contain growth data for specified construction group and corresponding wild type group. Table rows contain height and diameter measurements of individuals of specified construction group and corresponding wild type group. Time of measurement as number of days in greenhouse is shown in table headers.

TABLE 1.11a

Height growth data for TFSTT051

| | Height (cm) Days in greenhouse | | | | | | | | | |
|---|---|---|---|---|---|---|---|---|---|---|
| | 19 | 28 | 34 | 40 | 44 | 47 | 51 | 54 | 61 | 65 |
| TFSTT051-1B | 13 | 24 | 43 | 57 | 69 | 76 | 83 | 89 | 104 | 112 |
| TFSTT051-2A | 18 | 33 | 48 | 61 | 72 | 81 | 93 | 103 | 120 | 131 |
| TFSTT051-2B | 17 | 28 | 44 | 56 | 67 | 76 | 88 | 96 | 117 | 129 |
| TFSTT051-3A | 19 | 31 | 46 | 59 | 70 | 77 | 87 | 96 | 120 | 130 |
| TFSTT051-3B | 16 | 33 | 52 | 67 | 79 | 90 | 101 | 112 | 134 | 145 |
| TFSTT051-4A | 18 | 36 | 57 | 71 | 86 | 98 | 111 | 119 | 140 | 154 |
| TFSTT051-4B-1 | 18 | 34 | 52 | 67 | 81 | 87 | 96 | 103 | 123 | 136 |
| TFSTT051-4B-2 | 17 | 31 | 51 | 66 | 78 | 85 | 95 | 105 | 124 | 135 |
| T89-01 | 18 | 30 | 46 | 58 | 69 | 77 | 87 | 96 | 113 | 122 |
| T89-02 | 18 | 30 | 49 | 62 | 72 | 77 | 84 | 90 | 102 | 109 |
| T89-03 | 15 | 27 | 41 | 54 | 65 | 73 | 82 | 91 | 112 | 123 |
| T89-10 | N/A | N/A | N/A | N/A | N/A | N/A | N/A | N/A | N/A | N/A |
| T89-11 | 19 | 31 | 49 | 61 | 74 | 83 | 94 | 103 | 124 | 133 |
| T89-12 | 17 | 30 | 45 | 58 | 69 | 77 | 90 | 100 | 123 | 134 |
| T89-13 | 18 | 27 | 43 | 56 | 68 | 78 | 91 | 100 | 121 | 133 |
| T89-14 | 5 | 26 | 42 | 56 | 67 | 74 | 83 | 90 | 109 | 119 |
| T89-15 | 10 | 15 | 25 | 33 | 41 | 45 | 52 | 57 | 72 | 82 |
| T89-16 | 19 | 33 | 53 | 63 | 73 | 82 | 93 | 102 | 119 | 130 |
| T89-17 | 17 | 29 | 46 | 58 | 66 | 72 | 80 | 86 | 96 | 102 |
| T89-18 | 16 | 30 | 48 | 59 | 71 | 81 | 93 | 103 | 122 | 132 |
| T89-19 | 18 | 32 | 50 | 65 | 77 | 84 | 94 | 102 | 126 | 139 |
| T89-20 | 16 | 33 | 52 | 67 | 79 | 88 | 98 | 105 | 124 | 139 |
| T89-21 | 17 | 29 | 44 | 58 | 67 | 73 | 83 | 90 | 110 | 122 |
| T89-22 | 14 | 28 | 47 | 61 | 71 | 80 | 89 | 98 | 119 | 133 |
| T89-23 | 10 | 33 | 45 | 53 | 63 | 71 | 82 | 90 | 112 | 123 |
| T89-24 | 20 | 28 | 43 | 51 | 62 | 69 | 78 | 87 | 106 | 119 |
| T89-25 | 14 | 26 | 38 | 52 | 64 | 72 | 82 | 89 | 110 | 122 |
| T89-26 | 15 | 28 | 44 | 57 | 69 | 77 | 87 | 96 | 120 | 133 |
| T89-27 | 18 | 29 | 47 | 62 | 75 | 82 | 92 | 103 | 125 | 138 |
| T89-28 | 22 | 37 | 54 | 67 | 78 | 88 | 97 | 104 | 123 | 133 |
| T89-29 | 16 | 33 | 49 | 63 | 76 | 84 | 93 | 100 | 123 | 138 |
| T89-30 | 15 | 40 | 46 | 58 | 67 | 74 | 85 | 92 | 113 | 124 |

TABLE 1.11b

Diameter growth data for TFSTT051

| | Diameter (mm) Days in greenhouse | | | | | | | | |
|---|---|---|---|---|---|---|---|---|---|
| | 28 | 34 | 40 | 44 | 47 | 51 | 54 | 61 | 65 |
| TFSTT051-1B | 3.2 | 4.6 | 5.6 | 6.4 | 6.6 | 7.3 | 7.2 | 7.8 | 8.0 |
| TFSTT051-2A | 3.2 | 4.5 | 5.7 | 6.7 | 7.4 | 8.6 | 9.3 | 8.8 | 8.9 |
| TFSTT051-2B | 3.1 | 4.4 | 6.0 | 6.0 | 6.8 | 8.0 | 8.2 | 9.0 | 9.2 |
| TFSTT051-3A | 3.5 | 5.0 | 6.1 | 6.6 | 7.1 | 8.2 | 8.7 | 9.8 | 10.5 |
| TFSTT051-3B | 4.2 | 5.6 | 6.8 | 8.0 | 8.5 | 9.4 | 9.8 | 10.2 | 11.1 |
| TFSTT051-4A | 4.5 | 5.9 | 7.1 | 8.8 | 8.7 | 9.4 | 10.1 | 11.1 | 11.1 |
| TFSTT051-4B-1 | 4.1 | 5.6 | 6.8 | 7.9 | 8.1 | 8.6 | 9.7 | 10.7 | 11.6 |
| TFSTT051-4B-2 | 3.9 | 5.5 | 6.3 | 7.6 | 8.2 | 9.4 | 8.8 | 9.6 | 10.3 |
| T89-01 | 3.2 | 4.6 | 5.4 | 6.2 | 6.8 | 7.9 | 8.3 | 9.5 | 9.3 |
| T89-02 | 3.4 | 4.7 | 5.5 | 7.3 | 6.3 | 6.6 | 6.9 | 8.3 | 7.5 |
| T89-03 | 3.9 | 4.4 | 5.2 | 6.2 | 6.4 | 7.8 | 7.6 | 9.7 | 9.4 |
| T89-10 | N/A | N/A | N/A | N/A | N/A | N/A | N/A | N/A | N/A |
| T89-11 | 3.4 | 5.1 | 6.2 | 7.6 | 6.8 | 6.9 | 7.7 | 10.1 | 9.5 |
| T89-12 | 2.9 | 4.7 | 5.8 | 6.6 | 7.8 | 8.0 | 8.7 | 9.1 | 9.2 |
| T89-13 | 3.0 | 4.3 | 5.4 | 5.8 | 6.4 | 7.6 | 7.8 | 8.2 | 8.8 |
| T89-14 | 3.0 | 4.5 | 5.7 | 6.3 | 6.7 | 7.9 | 7.8 | 9.0 | 8.9 |
| T89-15 | N/A | 2.1 | 3.0 | 4.0 | 4.0 | 4.5 | 4.9 | 5.5 | 5.6 |
| T89-16 | 3.5 | 5.3 | 6.4 | 6.6 | 7.0 | 7.2 | 8.3 | 8.2 | 9.0 |
| T89-17 | 3.4 | 4.6 | 5.1 | 5.4 | 6.0 | 6.4 | 6.5 | 6.8 | 7.1 |
| T89-18 | 3.6 | 5.2 | 6.0 | 7.0 | 7.8 | 8.2 | 9.9 | 10.3 | 9.7 |
| T89-19 | 4.2 | 5.5 | 6.6 | 7.7 | 8.5 | 8.9 | 9.5 | 11.1 | 12.3 |
| T89-20 | 4.1 | 5.5 | 6.6 | 8.1 | 9.3 | 9.6 | 9.3 | 10.0 | 11.1 |
| T89-21 | 3.1 | 5.6 | 5.8 | 6.7 | 7.1 | 7.8 | 8.4 | 9.7 | 10.1 |
| T89-22 | 3.2 | 4.4 | 5.6 | 6.5 | 7.5 | 7.6 | 7.8 | 8.9 | 9.2 |
| T89-23 | 2.4 | 4.2 | 5.1 | 6.1 | 6.5 | 7.5 | 10.1 | 9.3 | 10.2 |
| T89-24 | 3.2 | 4.5 | 5.1 | 6.3 | 7.0 | 7.6 | 8.1 | 8.8 | 9.1 |
| T89-25 | 3.3 | 4.3 | 5.2 | 5.8 | 6.5 | 7.4 | 7.8 | 9.3 | 9.7 |
| T89-26 | 3.3 | 4.4 | 5.5 | 6.6 | 7.2 | 8.1 | 8.9 | 9.5 | 10.5 |
| T89-27 | 3.3 | 4.9 | 6.0 | 7.8 | 8.0 | 8.9 | 9.7 | 11.2 | 11.5 |
| T89-28 | 4.5 | 5.7 | 7.4 | 7.8 | 8.5 | 9.4 | 9.7 | 10.2 | 11.1 |
| T89-29 | 3.1 | 4.7 | 6.3 | 7.2 | 7.9 | 9.2 | 9.8 | 11.1 | 10.7 |
| T89-30 | 3.0 | 5.8 | 6.2 | 7.7 | 7.9 | 8.6 | 8.2 | 10.1 | 10.3 |

Real-time RT-PCR was used to confirm over-expression of construct TFSTT051. Table 1.11c contains gene expression levels of construct gene relative to reference gene expression. All ratios between construct and reference gene expression levels shown are normalized to the average of wild type group ratios. 1 of 8 individuals of construction group TFSTT051 are over-expressed according to present RT-PCR data.

TABLE 1.11c

Real-time RT-PCR data for TFSTT051

| Sample | Relative gene expression level normalized to wild type average |
|---|---|
| TFSTT051-1B | 1.18 |
| TFSTT051-2A | 7.42 |
| TFSTT051-2B | 1.13 |
| TFSTT051-3A | 0.30 |
| TFSTT051-3B | 1.06 |

TABLE 1.11c-continued

Real-time RT-PCR data for TFSTT051

| Sample | Relative gene expression level normalized to wild type average |
|---|---|
| TFSTT051-4A | 0.65 |
| TFSTT051-4B-1 | 1.34 |
| TFSTT051-4B-2 | 0.76 |
| T89-11 | 0.42 |
| T89-12 | 1.65 |
| T89-24 | 1.27 |
| T89-25 | 0.66 |

Results from growth analysis are specified in the overview table 1.11d. The determined growth effects of specified construction group are presented as ratios between construction and wild type group AFH, AFD, AMHGR, ADGR, MFH, MFD, MMHGR and MDC.

TABLE 1.11d

Overview table of growth effects of construct TFSTT051

| Construction group | Average Final Height | Average Final Diameter | Average Maximum Height Growth Rate | Average Diameter Growth Rate | Maximum Final Height | Maximum Final Diameter | Maximum of Maximum Height Growth Rate | Maximum Diameter Growth Rate |
|---|---|---|---|---|---|---|---|---|
| TFSTT051 | 1.07 | 1.06 | 1.05 | 1.01 | 1.11 | 0.94 | 1.10 | 0.90 |

Construction Group TF0013

This construct induces increased growth. The final height is 12% higher comparing the average of the construction group and wild type control group. The final height is 6% higher comparing the largest individuals of the construction group and wild type control group. The maximum height growth rate is 20% higher comparing the average of the construction group and wild type control group. The maximum height growth rate is 33% higher comparing the largest individuals of the construction group and wild type control group. The TF0013 construction group meets the more stringent level of growth difference selection criterion (4) and the less stringent level of growth difference selection criterion (1) and (3) as shown in table 1.12d.

Tables 1.12a and 1.12b contain growth data for specified construction group and corresponding wild type group. Table rows contain height and diameter measurements of individuals of specified construction group and corresponding wild type group. Time of measurement as number of days in greenhouse is shown in table headers.

TABLE 1.12a

Height growth data for TF0013

| | Height (cm) Days in greenhouse | | | | | | | | | | |
|---|---|---|---|---|---|---|---|---|---|---|---|
| | 18 | 22 | 25 | 29 | 32 | 39 | 43 | 46 | 50 | 53 | 57 |
| TF0013-1A-1 | 19 | 24 | 31 | 43 | 53 | 81 | 98 | 111 | 128 | 144 | 161 |
| TF0013-1A-2 | 12 | 15 | 19 | 27 | 37 | 62 | 77 | 90 | 108 | 125 | 159 |
| TF0013-2A | N/A | N/A | N/A | N/A | N/A | N/A | N/A | N/A | N/A | N/A | N/A |
| TF0013-2B | 20 | 25 | 32 | 45 | 57 | 85 | 102 | 112 | 128 | 142 | 157 |
| TF0013-3A | 19 | 25 | 33 | 47 | 58 | 88 | 103 | 116 | 134 | 151 | 170 |
| TF0013-3BA | 24 | 30 | 37 | 52 | 64 | 94 | 112 | 125 | 144 | 159 | 179 |
| TF0013-3BB | 19 | 26 | 31 | 43 | 53 | 84 | 100 | 114 | 130 | 144 | 164 |
| TF0013-4BA | 25 | 31 | 40 | 52 | 63 | 89 | 107 | 117 | 130 | 141 | 155 |
| TF0013-4BB | 20 | 25 | 31 | 45 | 57 | 83 | 100 | 111 | 128 | 145 | 162 |
| T89-01 | 14 | 17 | 22 | 31 | 40 | 64 | 76 | 88 | 102 | 118 | 135 |
| T89-02 | 17 | 20 | 25 | 36 | 45 | 69 | 79 | 90 | 104 | 118 | 133 |
| T89-03 | 21 | 29 | 35 | 47 | 57 | 81 | 94 | 104 | 119 | 132 | 147 |
| T89-04 | 13 | 14 | 17 | 25 | 33 | 45 | 52 | 57 | 70 | 79 | 92 |
| T89-05 | 15 | 18 | 24 | 33 | 42 | 69 | 83 | 94 | 106 | 120 | 137 |
| T89-06 | 18 | 23 | 29 | 40 | 51 | 78 | 91 | 103 | 120 | 134 | 152 |
| T89-07 | 20 | 24 | 30 | 41 | 51 | 74 | 88 | 96 | 109 | 121 | 130 |
| T89-08 | 27 | 32 | 40 | 52 | 62 | 88 | 99 | 111 | 124 | 134 | 148 |
| T89-09 | 23 | 27 | 34 | 46 | 56 | 83 | 97 | 106 | 122 | 132 | 149 |
| T89-10 | 13 | 15 | 20 | 27 | 37 | 59 | 72 | 83 | 98 | 111 | 128 |
| T89-11 | N/A | N/A | N/A | N/A | N/A | N/A | N/A | N/A | N/A | N/A | N/A |
| T89-12 | 26 | 33 | 40 | 54 | 66 | 92 | 107 | 120 | 135 | 149 | 166 |
| T89-13 | 21 | 26 | 34 | 45 | 55 | 79 | 94 | 105 | 122 | 134 | 150 |
| T89-14 | 18 | 23 | 31 | 42 | 53 | 80 | 97 | 107 | 120 | 128 | 145 |
| T89-15 | 26 | 33 | 40 | 53 | 63 | 88 | 103 | 111 | 125 | 138 | 154 |
| T89-16 | 27 | 32 | 39 | 51 | 63 | 89 | 104 | 116 | 132 | 146 | 162 |
| T89-17 | 17 | 21 | 27 | 38 | 45 | 72 | 87 | 97 | 110 | 124 | 139 |
| T89-18 | 23 | 30 | 35 | 46 | 55 | 80 | 94 | 105 | 117 | 131 | 145 |
| T89-19 | 23 | 29 | 35 | 45 | 54 | 78 | 91 | 102 | 114 | 125 | 137 |
| T89-20 | 22 | 28 | 34 | 49 | 60 | 87 | 100 | 110 | 125 | 137 | 155 |
| T89-21 | 27 | 31 | 35 | 42 | 48 | 66 | 77 | 87 | 100 | 110 | 124 |
| T89-22 | 13 | 16 | 23 | 32 | 48 | 67 | 81 | 92 | 105 | 118 | 134 |
| T89-23 | 23 | 29 | 35 | 48 | 58 | 83 | 97 | 107 | 122 | 136 | 154 |
| T89-24 | 23 | 29 | 36 | 48 | 59 | 86 | 101 | 113 | 128 | 141 | 159 |
| T89-25 | 16 | 21 | 28 | 40 | 51 | 80 | 97 | 107 | 122 | 137 | 153 |
| T89-26 | 27 | 35 | 40 | 54 | 66 | 93 | 107 | 118 | 132 | 144 | 162 |
| T89-27 | 26 | 31 | 38 | 49 | 59 | 82 | 96 | 106 | 120 | 131 | 146 |
| T89-28 | 25 | 29 | 36 | 49 | 59 | 83 | 97 | 106 | 119 | 131 | 147 |
| T89-29 | 26 | 32 | 38 | 51 | 62 | 88 | 103 | 113 | 128 | 142 | 159 |
| T89-30 | 24 | 29 | 36 | 48 | 56 | 80 | 93 | 104 | 117 | 131 | 145 |
| T89-31 | 24 | 31 | 36 | 47 | 57 | 81 | 94 | 105 | 117 | 131 | 144 |
| T89-32 | 26 | 32 | 38 | 49 | 58 | 83 | 98 | 107 | 120 | 134 | 148 |
| T89-33 | 24 | 29 | 36 | 48 | 57 | 85 | 100 | 112 | 124 | 134 | 149 |
| T89-34 | 21 | 26 | 32 | 43 | 53 | 79 | 90 | 102 | 117 | 131 | 148 |
| T89-35 | 21 | 28 | 36 | 46 | 55 | 80 | 94 | 105 | 120 | 133 | 149 |
| T89-36 | 16 | 21 | 28 | 39 | 51 | 74 | 88 | 100 | 115 | 128 | 144 |
| T89-37 | 28 | 35 | 41 | 52 | 63 | 88 | 101 | 111 | 125 | 137 | 154 |
| T89-38 | 27 | 32 | 39 | 51 | 62 | 86 | 101 | 113 | 128 | 140 | 155 |
| T89-39 | 21 | 26 | 33 | 46 | 55 | 83 | 101 | 112 | 126 | 139 | 156 |
| T89-40 | 21 | 26 | 33 | 45 | 55 | 77 | 88 | 99 | 113 | 124 | 139 |
| T89-41 | 13 | 16 | 23 | 32 | 42 | 68 | 85 | 95 | 107 | 118 | 133 |
| T89-42 | 24 | 30 | 37 | 49 | 61 | 86 | 101 | 113 | 128 | 143 | 150 |
| T89-43 | 25 | 31 | 38 | 51 | 61 | 86 | 102 | 114 | 130 | 144 | 163 |
| T89-44 | 23 | 31 | 39 | 51 | 64 | 90 | 105 | 118 | 135 | 151 | 169 |
| T89-45 | 26 | 32 | 37 | 49 | 58 | 85 | 100 | 110 | 124 | 137 | 153 |
| T89-46 | 20 | 25 | 34 | 43 | 55 | 81 | 97 | 109 | 122 | 133 | 149 |

TABLE 1.12b

Diameter growth data for TF0013

| | Diameter (mm) Days in greenhouse | | | | | | | |
|---|---|---|---|---|---|---|---|---|
| | 29 | 32 | 39 | 43 | 46 | 50 | 53 | 57 |
| TF0013-1A-1 | 3.9 | 5.1 | 6.6 | 7.6 | 8.6 | 9.8 | 9.9 | 10.5 |
| TF0013-1A-2 | 3.0 | 2.8 | 5.5 | 6.5 | 7.2 | 8.3 | 8.6 | 8.6 |
| TF0013-2A | N/A | N/A | N/A | N/A | N/A | N/A | N/A | N/A |
| TF0013-2B | 4.3 | 5.0 | 6.4 | 7.4 | 8.0 | 8.5 | 9.2 | 10.2 |
| TF0013-3A | 4.6 | 5.4 | 7.1 | 8.2 | 8.7 | 9.7 | 10.3 | 10.7 |
| TF0013-3BA | 4.4 | 5.0 | 7.2 | 7.5 | 9.1 | 9.1 | 9.8 | 10.6 |
| TF0013-3BB | 3.8 | 5.2 | 6.7 | 7.5 | 7.5 | 8.4 | 9.0 | 9.8 |
| TF0013-4BA | 4.7 | 5.7 | 6.1 | 6.8 | 7.4 | 8.8 | 9.0 | 9.6 |
| TF0013-4BB | 3.8 | 4.9 | N/A | 8.4 | 8.3 | 9.0 | 9.6 | 9.9 |
| T89-01 | 3.2 | 3.7 | 5.3 | 6.2 | 6.9 | 7.9 | 8.3 | 8.7 |
| T89-02 | 3.2 | 3.9 | 5.1 | 6.4 | 7.0 | 7.6 | 8.6 | 8.6 |
| T89-03 | 4.2 | 5.3 | 6.4 | 6.9 | 6.9 | N/A | 8.8 | 9.8 |
| T89-04 | 2.2 | 3.0 | 4.2 | 4.5 | 5.4 | 5.0 | 5.4 | 6.1 |
| T89-05 | 3.0 | 3.7 | 4.8 | 5.9 | 6.4 | 7.0 | 7.6 | 7.9 |
| T89-06 | 3.6 | 4.8 | 6.5 | 7.6 | 8.7 | 9.1 | 9.6 | 10.1 |
| T89-07 | 3.8 | 4.9 | 6.8 | 7.6 | 8.0 | 8.6 | 9.0 | 9.7 |
| T89-08 | 4.4 | 5.8 | 6.2 | 7.3 | 7.6 | 8.5 | 9.4 | 9.7 |
| T89-09 | 4.5 | 5.5 | 6.5 | 7.1 | 7.6 | 9.1 | 9.4 | 9.8 |
| T89-10 | 3.7 | 3.9 | 5.0 | 6.1 | 6.8 | 7.6 | 8.5 | 9.2 |
| T89-11 | N/A | N/A | N/A | N/A | N/A | N/A | N/A | N/A |
| T89-12 | 4.6 | 5.5 | 7.3 | 8.6 | 8.8 | 9.6 | 10.2 | 10.2 |
| T89-13 | 3.8 | 4.6 | 5.7 | 6.5 | 6.6 | 7.4 | 8.1 | 8.6 |
| T89-14 | 3.7 | 4.2 | 5.3 | 5.6 | 6.1 | 7.0 | 7.1 | 7.8 |
| T89-15 | 4.6 | 5.0 | 6.4 | 7.0 | 7.4 | 8.0 | 8.4 | 9.1 |
| T89-16 | 5.0 | 5.5 | 7.0 | 7.6 | 8.0 | 8.6 | 9.0 | 9.7 |
| T89-17 | 3.1 | 4.3 | 5.7 | 7.1 | 7.4 | 7.9 | 8.4 | 9.2 |
| T89-18 | 4.5 | 5.3 | 7.8 | 8.0 | 8.1 | 9.2 | 9.9 | 10.3 |
| T89-19 | 4.2 | 5.8 | 6.7 | 8.2 | 8.5 | 8.5 | 9.0 | 9.5 |
| T89-20 | 4.0 | 4.7 | 6.7 | 8.1 | 7.6 | 8.5 | 8.6 | 9.4 |
| T89-21 | 3.5 | 3.9 | 5.0 | 5.7 | 5.8 | 7.1 | 6.7 | 7.4 |
| T89-22 | 3.6 | 4.3 | 5.5 | 6.3 | 6.8 | 7.9 | 8.4 | 8.8 |
| T89-23 | 4.1 | 5.2 | 7.0 | 7.6 | 8.2 | 8.9 | 9.2 | 10.0 |
| T89-24 | 4.1 | 5.4 | 6.7 | 7.5 | 7.8 | 8.6 | 9.6 | 10.4 |
| T89-25 | 3.7 | 4.6 | 6.0 | 7.0 | 7.7 | 8.3 | 8.5 | 9.4 |
| T89-26 | 4.8 | 5.6 | 6.9 | 7.3 | 7.8 | 8.6 | 9.2 | 9.5 |
| T89-27 | 3.8 | 4.9 | 6.2 | 6.7 | 6.9 | 7.6 | 8.4 | 9.3 |
| T89-28 | 4.5 | 5.5 | 6.8 | 7.3 | 7.8 | 9.1 | 9.1 | 9.5 |
| T89-29 | 4.4 | 5.3 | 6.8 | 6.8 | 7.4 | 8.2 | 9.2 | 8.9 |
| T89-30 | 3.7 | 4.7 | 5.4 | 6.6 | 7.0 | 7.0 | 7.7 | 8.5 |
| T89-31 | 4.0 | 4.5 | 5.5 | 6.9 | 7.0 | 8.0 | 9.1 | 9.6 |
| T89-32 | 3.6 | 4.5 | 5.7 | 7.0 | 7.2 | 8.0 | 9.1 | 9.4 |
| T89-33 | 3.9 | 4.6 | 6.7 | 7.3 | 8.0 | 8.6 | 9.4 | 10.5 |
| T89-34 | 3.6 | 4.5 | 5.9 | 6.9 | 7.5 | 8.2 | 9.1 | 9.4 |
| T89-35 | 3.9 | 4.5 | 5.7 | 7.1 | 7.5 | 7.9 | 8.8 | 9.6 |
| T89-36 | 3.6 | 5.0 | 5.7 | 6.5 | 6.8 | 7.9 | 8.2 | 9.1 |
| T89-37 | 4.3 | 5.6 | 7.1 | 8.0 | 8.0 | 8.9 | 9.7 | 10.2 |
| T89-38 | 4.7 | 5.8 | 6.7 | 7.8 | 8.0 | 8.7 | 9.2 | 9.7 |
| T89-39 | 4.2 | 5.0 | 6.2 | 7.3 | 8.2 | 8.1 | 8.7 | 9.6 |
| T89-40 | 3.6 | 4.4 | 5.2 | 5.7 | 6.0 | 7.2 | 7.2 | 8.0 |
| T89-41 | 3.5 | 4.3 | 5.5 | 6.5 | 7.0 | 7.5 | 7.7 | 8.4 |
| T89-42 | 4.4 | 5.1 | 7.5 | 8.4 | 9.5 | 9.9 | 10.0 | 10.3 |
| T89-43 | 4.3 | 5.0 | 6.5 | 7.3 | 7.8 | 8.3 | 8.9 | 9.1 |
| T89-44 | 4.3 | 5.8 | 6.8 | 8.1 | 8.6 | 9.5 | 9.9 | 10.5 |
| T89-45 | 4.2 | 4.9 | 6.8 | 7.5 | 7.6 | 8.5 | 9.4 | 9.7 |
| T89-46 | 3.5 | 4.4 | 5.7 | 7 | 7.5 | 8.6 | 9.4 | 9.8 | m

Real-time RT-PCR was used to confirm over-expression of construct TF0013. Table 1.12c contains gene expression levels of construct gene relative to reference gene expression. All ratios between construct and reference gene expression levels shown are normalized to the average of wild type group ratios. 3 of 8 individuals of construction group TF0013 are over-expressed according to present RT-PCR data.

TABLE 1.12c

Real-time RT-PCR data for TF0013

| Sample | Relative gene expression level normalized to wild type average |
|---|---|
| TF0013-1A-1 | 0.59 |
| TF0013-1A-2 | 1.02 |
| TF0013-2B | 2.32 |
| TF0013-3A | 0.90 |
| TF0013-3BA | 0.86 |
| TF0013-3BB | 0.80 |
| TF0013-4BA | 1.38 |
| TF0013-4BB | 1.65 |
| T89-03 | 1.22 |
| T89-36 | 1.04 |
| T89-37 | 0.90 |
| T89-38 | 0.85 |

Results from growth analysis are specified in the overview table 1.12d. The determined growth effects of specified construction group are presented as ratios between construction and wild type group AFH, AFD, AMHGR, ADGR, MFH, MFD, MMHGR and MDC.

TABLE 1.12d

Overview table of growth effects of construct TF0013

| Construction group | Average Final Height | Average Final Diameter | Average Maximum Height Growth Rate | Average Diameter Growth Rate | Maximum Final Height | Maximum Final Diameter | Maximum of Maximum Height Growth Rate | Maximum Diameter Growth Rate |
|---|---|---|---|---|---|---|---|---|
| TF0013 | 1.12 | 1.07 | 1.20 | 1.12 | 1.06 | 1.02 | 1.33 | 1.01 |

1.3.10 Construction Group TF0097

This construct induces increased growth. The final height is 10% higher comparing the average of the construction group and wild type control group. The final height is 16% higher comparing the largest individuals of the construction group and wild type control group. The maximum height growth rate is 15% higher comparing the average of the construction group and wild type control group. The maximum height growth rate is 15% higher comparing the largest individuals of the construction group and wild type control group. The diameter growth rate is 7% higher comparing the average of the construction group and wild type control group. The diameter growth rate is 21% higher comparing the largest individuals of the construction group and wild type control group. The TF0097 construction group meets the more stringent level of growth difference selection criterion (1) and the less stringent level of growth difference selection criterion (4) as shown in table 1.13d.

Tables 1.13a and 1.13b contain growth data for specified construction group and corresponding wild type group. Table rows contain height and diameter measurements of individuals of specified construction group and corresponding wild type group. Time of measurement as number of days in greenhouse is shown in table headers.

TABLE 1.13a

Height growth data for TF0097

| | Height (cm) Days in greenhouse | | | | | |
|---|---|---|---|---|---|---|
| | 16 | 20 | 29 | 34 | 41 | 48 |
| TF0097-1A | 28 | 35 | 71 | 93 | 133 | 176 |
| TF0097-1B | 26 | 36 | 72 | 100 | 137 | 171 |
| TF0097-2A | 19 | 22 | 42 | 57 | 79 | 101 |
| TF0097-2B | 31 | 40 | 79 | 105 | 138 | 175 |
| TF0097-3A-1 | 28 | 36 | 73 | 96 | 130 | 166 |
| TF0097-3A-2 | 30 | 38 | 72 | 100 | 141 | 178 |
| TF0097-4A-1 | 27 | 32 | 48 | 68 | 103 | 140 |
| TF0097-4A-2 | 28 | 34 | 65 | 85 | 118 | 141 |
| TF0097-4B | 25 | 10 | 23 | 37 | 65 | 92 |
| T89-01 | 28 | 35 | 66 | 89 | 122 | 150 |
| T89-02 | 25 | 35 | 62 | 80 | 103 | 128 |
| T89-03 | 24 | 33 | 61 | 83 | 113 | 142 |
| T89-04 | 27 | 34 | 65 | 87 | 120 | 152 |
| T89-05 | 27 | 32 | 59 | 80 | 107 | 138 |
| T89-06 | 25 | 32 | 61 | 77 | 106 | 135 |
| T89-07 | 22 | 28 | 50 | 67 | 92 | 120 |
| T89-08 | 24 | 29 | 56 | 75 | 103 | 122 |
| T89-09 | 20 | 24 | 45 | 61 | 91 | 115 |
| T89-10 | 22 | 28 | 52 | 70 | 99 | 124 |
| T89-11 | 26 | 32 | 63 | 80 | 110 | 142 |
| T89-12 | 27 | 32 | 60 | 80 | 109 | 132 |
| T89-13 | 23 | 30 | 59 | 79 | 107 | 133 |
| T89-14 | 26 | 31 | 60 | 79 | 106 | 131 |
| T89-15 | 26 | 32 | 58 | 79 | 110 | 133 |
| T89-16 | 29 | 32 | 65 | 87 | 121 | 151 |
| T89-17 | 25 | 32 | 59 | 79 | 105 | 133 |
| T89-18 | 29 | 37 | 67 | 86 | 114 | 136 |
| T89-19 | 29 | 35 | 66 | 84 | 111 | 129 |
| T89-20 | 27 | 38 | 64 | 83 | 112 | 122 |
| T89-21 | 28 | 33 | 58 | 79 | 108 | 132 |
| T89-22 | 25 | 33 | 54 | 83 | 113 | 140 |
| T89-23 | 24 | 31 | 56 | 75 | 104 | 134 |
| T89-24 | 25 | 33 | 58 | 78 | 106 | 136 |
| T89-25 | 26 | 33 | 62 | 80 | 111 | 142 |
| T89-26 | 28 | 35 | 64 | 81 | 113 | 146 |
| T89-27 | 26 | 31 | 60 | 75 | 107 | 140 |
| T89-28 | 28 | 34 | 61 | 83 | 116 | 147 |
| T89-29 | 19 | 24 | 49 | 70 | 101 | 132 |
| T89-30 | 26 | 33 | 57 | 77 | 110 | 140 |
| T89-31 | 25 | 35 | 63 | 81 | 115 | 140 |
| T89-32 | 28 | 36 | 67 | 89 | 121 | 151 |
| T89-33 | 26 | 33 | 63 | 85 | 110 | 126 |

TABLE 1.13a-continued

Height growth data for TF0097

| | Height (cm) Days in greenhouse | | | | | |
|---|---|---|---|---|---|---|
| | 16 | 20 | 29 | 34 | 41 | 48 |
| T89-34 | 28 | 35 | 59 | 77 | 107 | 135 |
| T89-35 | 26 | 34 | 59 | 77 | 107 | 132 |
| T89-36 | 26 | 32 | 61 | 79 | 107 | 136 |
| T89-37 | 22 | 23 | 39 | 54 | 78 | 106 |
| T89-38 | 27 | 35 | 58 | 74 | 98 | 124 |
| T89-39 | 24 | 29 | 53 | 73 | 103 | 128 |
| T89-40 | 22 | 27 | 52 | 70 | 101 | 121 |
| T89-41 | 27 | 34 | 64 | 81 | 111 | 143 |
| T89-42 | 25 | 33 | 63 | 79 | 111 | 142 |
| T89-43 | 26 | 33 | 62 | 84 | 117 | 148 |
| T89-44 | 26 | 32 | 64 | 82 | 115 | 149 |
| T89-45 | 24 | 33 | 60 | 79 | 107 | 134 |
| T89-46 | 27 | 34 | 64 | 88 | 121 | 147 |
| T89-47 | 24 | 32 | 61 | 78 | 101 | 121 |
| T89-48 | 24 | 31 | 62 | 79 | 108 | 140 |
| T89-49 | 27 | 35 | 63 | 80 | 109 | 138 |
| T89-50 | 26 | 33 | 61 | 80 | 108 | 135 |
| T89-51 | 20 | 25 | 52 | 70 | 98 | 116 |
| T89-52 | 24 | 28 | 53 | 73 | 99 | 128 |
| T89-53 | 21 | 31 | 58 | 75 | 100 | 115 |
| T89-54 | 22 | 30 | 54 | 72 | 105 | 133 |
| T89-55 | 21 | 27 | 53 | 73 | 105 | 129 |
| T89-56 | 29 | 36 | 67 | 84 | 115 | 147 |
| T89-57 | 27 | 32 | 60 | 80 | 111 | 139 |
| T89-58 | 29 | 38 | 67 | 86 | 119 | 150 |
| T89-59 | 25 | 32 | 63 | 86 | 120 | 149 |
| T89-60 | 27 | 33 | 62 | 84 | 119 | 154 |
| T89-61 | 26 | 35 | 65 | 89 | 124 | 152 |
| T89-62 | 24 | 30 | 57 | 79 | 107 | 134 |
| T89-63 | 25 | 33 | 62 | 81 | 111 | 134 |
| T89-64 | 21 | 29 | 58 | 79 | 110 | 139 |
| T89-65 | 23 | 31 | 55 | 70 | 96 | 122 |
| T89-66 | 25 | 32 | 61 | 82 | 113 | 142 |
| T89-67 | 25 | 30 | 50 | 75 | 105 | 131 |
| T89-68 | 22 | 31 | 61 | 80 | 110 | 138 |
| T89-69 | 25 | 33 | 56 | 74 | 101 | 128 |
| T89-70 | 21 | 28 | 59 | 77 | 105 | 135 |
| T89-71 | 20 | 26 | 57 | 73 | 101 | 129 |
| T89-72 | 26 | 33 | 62 | 82 | 115 | 144 |

TABLE 1.13b

Diameter growth data for TF0097

| | Diameter (mm) Days in greenhouse | | | |
|---|---|---|---|---|
| | 29 | 34 | 41 | 48 |
| TF0097-1A | 4.7 | 5.0 | 6.9 | 8.2 |
| TF0097-1B | 4.2 | 5.1 | 6.9 | 8.2 |
| TF0097-2A | 3.0 | 3.6 | 4.1 | 7.9 |
| TF0097-2B | 5.9 | 6.6 | 7.1 | 8.6 |
| TF0097-3A-1 | 4.9 | 5.9 | 7.0 | 8.1 |
| TF0097-3A-2 | 5.2 | 6.4 | 8.1 | 9.3 |
| TF0097-4A-1 | 3.9 | 5.7 | 5.0 | 6.2 |
| TF0097-4A-2 | 4.7 | 4.8 | 5.6 | 6.4 |
| TF0097-4B | 2.5 | 2.9 | 4.0 | 4.8 |
| T89-01 | 5.3 | 6.3 | 8.0 | 8.8 |
| T89-02 | 4.8 | 5.3 | 6.7 | 7.1 |
| T89-03 | 5.3 | 6.4 | 8.2 | 8.7 |
| T89-04 | 5.3 | 6.5 | 7.9 | 9.3 |
| T89-05 | 5.4 | 6.5 | 7.6 | 8.1 |
| T89-06 | 5.3 | 6.0 | 7.2 | 8.4 |
| T89-07 | 4.0 | 4.8 | 7.2 | 7.7 |
| T89-08 | 4.5 | 5.4 | 6.3 | 7.1 |
| T89-09 | 3.7 | 4.7 | 6.1 | 7.5 |
| T89-10 | 4.4 | 5.5 | 6.9 | 7.6 |
| T89-11 | 5.4 | 6.4 | 7.1 | 8.0 |
| T89-12 | 5.5 | 5.7 | 6.8 | 8.1 |

TABLE 1.13b-continued

Diameter growth data for TF0097

| | Diameter (mm) Days in greenhouse | | | |
|---|---|---|---|---|
| | 29 | 34 | 41 | 48 |
| T89-13 | 5.2 | 6.0 | 6.7 | 7.4 |
| T89-14 | 5.3 | 6.4 | 6.7 | 7.9 |
| T89-15 | 5.1 | 6.4 | 6.9 | 7.8 |
| T89-16 | 5.2 | 6.4 | 7.6 | 9.2 |
| T89-17 | 5.0 | 5.7 | 6.5 | 7.9 |
| T89-18 | 5.8 | 6.4 | 7.1 | 7.7 |
| T89-19 | 5.4 | 6.4 | 7.5 | 8.0 |
| T89-20 | 5.6 | 6.6 | 8.3 | 8.6 |
| T89-21 | 5.0 | 5.8 | 6.9 | 7.8 |
| T89-22 | 5.4 | 6.5 | 8.2 | 8.9 |
| T89-23 | 4.7 | 5.3 | 7.1 | 8.0 |
| T89-24 | 4.8 | 6.3 | 6.9 | 8.4 |
| T89-25 | 5.0 | 6.3 | 6.9 | 7.8 |
| T89-26 | 5.6 | 6.6 | 7.5 | 8.5 |
| T89-27 | 5.5 | 6.0 | 7.5 | 8.8 |
| T89-28 | 6.0 | 7.1 | 7.7 | 8.8 |
| T89-29 | 4.2 | 5.3 | 6.8 | 8.5 |
| T89-30 | 5.5 | 6.4 | 8.0 | 9.3 |
| T89-31 | 5.7 | 5.7 | 8.4 | 8.9 |
| T89-32 | 5.4 | 6.5 | 7.8 | 9.0 |
| T89-33 | 5.6 | 6.3 | 6.8 | 7.4 |
| T89-34 | 5.1 | 6.1 | 7.2 | 8.1 |
| T89-35 | 5.6 | 6.7 | 7.7 | 8.2 |
| T89-36 | 5.4 | 6.2 | 7.7 | 9.4 |
| T89-37 | 2.8 | 3.3 | 4.7 | 5.5 |
| T89-38 | 5.1 | 5.5 | 7.1 | 8.4 |
| T89-39 | 4.9 | 5.5 | 6.5 | 7.4 |
| T89-40 | 4.9 | 6.4 | 7.6 | 7.6 |
| T89-41 | 5.6 | 7 | 7.3 | 9.1 |
| T89-42 | 5.9 | 6.4 | 7.7 | 8.4 |
| T89-43 | 5.4 | 6.7 | 8.2 | 9.1 |
| T89-44 | 6.4 | 6.4 | 8.1 | 9.3 |
| T89-45 | 5.6 | 6.4 | 7.8 | 8.0 |
| T89-46 | 6.1 | 6.4 | 7.9 | 9.5 |
| T89-47 | 5.2 | 5.9 | 6.5 | 6.9 |
| T89-48 | 5.1 | 6.1 | 7.3 | 8.8 |
| T89-49 | 5.3 | 5.9 | 7.3 | 7.7 |
| T89-50 | 5.3 | 6.8 | 7.7 | 8.2 |
| T89-51 | 4.7 | 5.7 | 7 | 7.5 |
| T89-52 | 4.9 | 5.5 | 6.9 | 8.2 |
| T89-53 | 5.1 | 6.1 | 6.8 | 7.5 |
| T89-54 | 4.7 | 5.9 | 6.7 | 7.7 |
| T89-55 | 4.8 | 5.9 | 7.1 | 7.9 |
| T89-56 | 5.4 | 6.9 | 7.7 | 9.1 |
| T89-57 | 5.3 | 6.5 | 7.5 | 9.2 |
| T89-58 | 5.5 | 6.5 | 8 | 8.8 |
| T89-59 | 5.8 | 6.4 | 7.7 | 8.4 |
| T89-60 | 5.6 | 6.2 | 7.9 | 9.6 |
| T89-61 | 5.6 | 7 | 8.3 | 9.4 |
| T89-62 | 5.1 | 6.3 | 7.2 | 7.7 |
| T89-63 | 5.5 | 7.1 | 8 | 8.4 |
| T89-64 | 4.7 | 6.2 | 8.4 | 8.1 |
| T89-65 | 5.3 | 6.1 | 6.9 | 8.2 |
| T89-66 | 5.2 | 6 | 7.2 | 8.4 |
| T89-67 | 5.8 | 6.5 | 7.7 | 8.9 |
| T89-68 | 5 | 6.1 | 7.5 | 8.2 |
| T89-69 | 5.1 | 6.4 | 7.2 | 9.0 |
| T89-70 | 5 | 6.1 | 6.6 | 7.4 |
| T89-71 | 4.9 | 6.4 | 7.2 | 8.7 |
| T89-72 | 5.8 | 6.8 | 7.9 | 9.1 |

Real-time RT-PCR was used to confirm over-expression of construct TF0097. Table 1.13c contains gene expression levels of construct gene relative to reference gene expression. All ratios between construct and reference gene expression levels shown are normalized to the average of wild type group ratios. 2 of 9 individuals of construction group TF0097 are over-expressed according to present RT-PCR data.

TABLE 1.13c

Real-time RT-PCR data for TF0097

| Sample | Relative gene expression level normalized to wild type average |
|---|---|
| TF0097-1A | 1.85 |
| TF0097-1B | 1.66 |
| TF0097-2A | 1.45 |
| TF0097-2B | 1.57 |
| TF0097-3A-1 | 1.09 |
| TF0097-3A-2 | 1.71 |
| TF0097-4A-1 | 0.79 |
| TF0097-4A-2 | 4.64 |
| TF0097-4B | 3.20 |
| T89-03 | 1.98 |
| T89-17 | 0.38 |
| T89-19 | 0.64 |

Results from growth analysis are specified in the overview table 1.13d. The determined growth effects of specified construction group are presented as ratios between construction and wild type group AFH, AFD, AMHGR, ADGR, MFH, MFD, MMHGR and MDC.

TABLE 1.13d

Overview table of growth effects of construct TF0097

| Construction group | Average Final Height | Average Final Diameter | Average Maximum Height Growth Rate | Average Diameter Growth Rate | Maximum Final Height | Maximum Final Diameter | Maximum of Maximum Height Growth Rate | Maximum Diameter Growth Rate |
|---|---|---|---|---|---|---|---|---|
| TF0097 | 1.10 | 0.91 | 1.15 | 1.07 | 1.16 | 0.97 | 1.15 | 1.21 |

1.3.11 Construction Group TFSTT019

This construct induces increased growth. The final diameter is 11% higher comparing the average of the construction group and wild type control group. The final diameter is 8% higher comparing the largest individuals of the construction group and wild type control group. The diameter growth rate is 18% higher comparing the average of the construction group and wild type control group. The diameter growth rate is 9% higher comparing the largest individuals of the construction group and wild type control group. The TFSTT019 construction group meets growth difference selection criterion (2) as shown in table 1.14c.

Tables 1.14a and 1.14b contain growth data for specified construction group and corresponding wild type group. Table rows contain height and diameter measurements of individuals of specified construction group and corresponding wild type group. Time of measurement as number of days in greenhouse is shown in table headers.

TABLE 1.14a

Height growth data for TFSTT019

Height (cm)
Days in greenhouse

|  | 18 | 22 | 25 | 29 | 32 | 39 | 43 | 46 | 50 | 53 | 57 |
|---|---|---|---|---|---|---|---|---|---|---|---|
| TFSTT019-1A | N/A | N/A | N/A | N/A | N/A | N/A | N/A | N/A | N/A | N/A | N/A |
| TFSTT019-1BA | 18 | 22 | 29 | 39 | 49 | 73 | 84 | 91 | 103 | 115 | 129 |
| TFSTT019-1BB | 21 | 26 | 34 | 46 | 55 | 82 | 99 | 107 | 120 | 132 | 145 |
| TFSTT019-2A | 24 | 30 | 37 | 51 | 61 | 88 | 104 | 114 | 128 | 140 | 157 |
| TFSTT019-2B | 11 | 14 | 18 | 28 | 37 | 60 | 73 | 86 | 102 | 115 | 132 |
| TFSTT019-3A | 23 | 31 | 37 | 50 | 57 | 81 | 94 | 106 | 119 | 129 | 144 |
| TFSTT019-4BA | 27 | 32 | 39 | 49 | 58 | 84 | 99 | 110 | 124 | 137 | 152 |
| TFSTT019-4BB | 21 | 27 | 35 | 47 | 57 | 84 | 99 | 110 | 124 | 137 | 151 |
| T89-01 | 14 | 17 | 22 | 31 | 40 | 64 | 76 | 88 | 102 | 118 | 135 |
| T89-02 | 17 | 20 | 25 | 36 | 45 | 69 | 79 | 90 | 104 | 118 | 133 |
| T89-03 | 21 | 29 | 35 | 47 | 57 | 81 | 94 | 104 | 119 | 132 | 147 |
| T89-04 | 13 | 14 | 17 | 25 | 33 | 45 | 52 | 57 | 70 | 79 | 92 |
| T89-05 | 15 | 18 | 24 | 33 | 42 | 69 | 83 | 94 | 106 | 120 | 137 |
| T89-06 | 18 | 23 | 29 | 40 | 51 | 78 | 91 | 103 | 120 | 134 | 152 |
| T89-07 | 20 | 24 | 30 | 41 | 51 | 74 | 88 | 96 | 109 | 121 | 130 |
| T89-08 | 27 | 32 | 40 | 52 | 62 | 88 | 99 | 111 | 124 | 134 | 148 |
| T89-09 | 23 | 27 | 34 | 46 | 56 | 83 | 97 | 106 | 122 | 132 | 149 |
| T89-10 | 13 | 15 | 20 | 27 | 37 | 59 | 72 | 83 | 98 | 111 | 128 |
| T89-11 | N/A | N/A | N/A | N/A | N/A | N/A | N/A | N/A | N/A | N/A | N/A |
| T89-12 | 26 | 33 | 40 | 54 | 66 | 92 | 107 | 120 | 135 | 149 | 166 |
| T89-13 | 21 | 26 | 34 | 45 | 55 | 79 | 94 | 105 | 122 | 134 | 150 |
| T89-14 | 18 | 23 | 31 | 42 | 53 | 80 | 97 | 107 | 120 | 128 | 145 |
| T89-15 | 26 | 33 | 40 | 53 | 63 | 88 | 103 | 111 | 125 | 138 | 154 |
| T89-16 | 27 | 32 | 39 | 51 | 63 | 89 | 104 | 116 | 132 | 146 | 162 |
| T89-17 | 17 | 21 | 27 | 38 | 45 | 72 | 87 | 97 | 110 | 124 | 139 |
| T89-18 | 23 | 30 | 35 | 46 | 55 | 80 | 94 | 105 | 117 | 131 | 145 |
| T89-19 | 23 | 29 | 35 | 45 | 54 | 78 | 91 | 102 | 114 | 125 | 137 |
| T89-20 | 22 | 28 | 34 | 49 | 60 | 87 | 100 | 110 | 125 | 137 | 155 |
| T89-21 | 27 | 31 | 35 | 42 | 48 | 66 | 77 | 87 | 100 | 110 | 124 |
| T89-22 | 13 | 16 | 23 | 32 | 48 | 67 | 81 | 92 | 105 | 118 | 134 |
| T89-23 | 23 | 29 | 35 | 48 | 58 | 83 | 97 | 107 | 122 | 136 | 154 |
| T89-24 | 23 | 29 | 36 | 48 | 59 | 86 | 101 | 113 | 128 | 141 | 159 |
| T89-25 | 16 | 21 | 28 | 40 | 51 | 80 | 97 | 107 | 122 | 137 | 153 |
| T89-26 | 27 | 35 | 40 | 54 | 66 | 93 | 107 | 118 | 132 | 144 | 162 |
| T89-27 | 26 | 31 | 38 | 49 | 59 | 82 | 96 | 106 | 120 | 131 | 146 |
| T89-28 | 25 | 29 | 36 | 49 | 59 | 83 | 97 | 106 | 119 | 131 | 147 |
| T89-29 | 26 | 32 | 38 | 51 | 62 | 88 | 103 | 113 | 128 | 142 | 159 |
| T89-30 | 24 | 29 | 36 | 48 | 56 | 80 | 93 | 104 | 117 | 131 | 145 |
| T89-31 | 24 | 31 | 36 | 47 | 57 | 81 | 94 | 105 | 117 | 131 | 144 |
| T89-32 | 26 | 32 | 38 | 49 | 58 | 83 | 98 | 107 | 120 | 134 | 148 |
| T89-33 | 24 | 29 | 36 | 48 | 57 | 85 | 100 | 112 | 124 | 134 | 149 |
| T89-34 | 21 | 26 | 32 | 43 | 53 | 79 | 90 | 102 | 117 | 131 | 148 |
| T89-35 | 21 | 28 | 36 | 46 | 55 | 80 | 94 | 105 | 120 | 133 | 149 |
| T89-36 | 16 | 21 | 28 | 39 | 51 | 74 | 88 | 100 | 115 | 128 | 144 |
| T89-37 | 28 | 35 | 41 | 52 | 63 | 88 | 101 | 111 | 125 | 137 | 154 |
| T89-38 | 27 | 32 | 39 | 51 | 62 | 86 | 101 | 113 | 128 | 140 | 155 |
| T89-39 | 21 | 26 | 33 | 46 | 55 | 83 | 101 | 112 | 126 | 139 | 156 |
| T89-40 | 21 | 26 | 33 | 45 | 55 | 77 | 88 | 99 | 113 | 124 | 139 |
| T89-41 | 13 | 16 | 23 | 32 | 42 | 68 | 85 | 95 | 107 | 118 | 133 |
| T89-42 | 24 | 30 | 37 | 49 | 61 | 86 | 101 | 113 | 128 | 143 | 150 |
| T89-43 | 25 | 31 | 38 | 51 | 61 | 86 | 102 | 114 | 130 | 144 | 163 |
| T89-44 | 23 | 31 | 39 | 51 | 64 | 90 | 105 | 118 | 135 | 151 | 169 |
| T89-45 | 26 | 32 | 37 | 49 | 58 | 85 | 100 | 110 | 124 | 137 | 153 |
| T89-46 | 20 | 25 | 34 | 43 | 55 | 81 | 97 | 109 | 122 | 133 | 149 |

TABLE 1.14b

Diameter growth data for TFSTT019

| | Diameter (mm) Days in greenhouse | | | | | | | |
|---|---|---|---|---|---|---|---|---|
| | 29 | 32 | 39 | 43 | 46 | 50 | 53 | 57 |
| TFSTT019-1A | N/A | N/A | N/A | N/A | N/A | N/A | N/A | N/A |
| TFSTT019-1BA | 3.7 | 5.0 | 7.1 | 7.9 | 8.4 | 8.6 | 9.7 | 10.2 |
| TFSTT019-1BB | 4.0 | 4.7 | 6.4 | 7.3 | 8.0 | 8.7 | 9.2 | 9.4 |
| TFSTT019-2A | 4.5 | 5.1 | 7.2 | 7.8 | 9.0 | 9.8 | 10.2 | 10.7 |
| TFSTT019-2B | 3.5 | 4.2 | 6.0 | 7.1 | 7.6 | 8.5 | 9.0 | 9.1 |
| TFSTT019-3A | 4.1 | 5.1 | 6.9 | 8.4 | 9.0 | 10.5 | 10.8 | 11.1 |
| TFSTT019-4BA | 4.4 | 5.5 | 7.3 | 8.4 | 9.2 | 9.5 | 10.1 | 11.3 |
| TFSTT019-4BB | 4.5 | 5.7 | 7.1 | 8.1 | 8.4 | 9.5 | 10.2 | 10.6 |
| T89-01 | 3.2 | 3.7 | 5.3 | 6.2 | 6.9 | 7.9 | 8.3 | 8.7 |
| T89-02 | 3.2 | 3.9 | 5.1 | 6.4 | 7.0 | 7.6 | 8.6 | 8.6 |
| T89-03 | 4.2 | 5.3 | 6.4 | 6.9 | 6.9 | N/A | 8.8 | 9.8 |
| T89-04 | 2.2 | 3.0 | 4.2 | 4.5 | 5.4 | 5.0 | 5.4 | 6.1 |
| T89-05 | 3.0 | 3.7 | 4.8 | 5.9 | 6.4 | 7.0 | 7.6 | 7.9 |
| T89-06 | 3.6 | 4.8 | 6.5 | 7.6 | 8.7 | 9.1 | 9.6 | 10.1 |
| T89-07 | 3.8 | 4.9 | 6.8 | 7.6 | 8.0 | 8.6 | 9.0 | 9.7 |
| T89-08 | 4.4 | 5.8 | 6.2 | 7.3 | 7.6 | 8.5 | 9.4 | 9.7 |
| T89-09 | 4.5 | 5.5 | 6.5 | 7.1 | 7.6 | 9.1 | 9.4 | 9.8 |
| T89-10 | 3.7 | 3.9 | 5.0 | 6.1 | 6.8 | 7.6 | 8.5 | 9.2 |
| T89-11 | N/A | N/A | N/A | N/A | N/A | N/A | N/A | N/A |
| T89-12 | 4.6 | 5.5 | 7.3 | 8.6 | 8.8 | 9.6 | 10.2 | 10.2 |
| T89-13 | 3.8 | 4.6 | 5.7 | 6.5 | 6.6 | 7.4 | 8.1 | 8.6 |
| T89-14 | 3.7 | 4.2 | 5.3 | 5.6 | 6.1 | 7.0 | 7.1 | 7.8 |
| T89-15 | 4.6 | 5.0 | 6.4 | 7.0 | 7.4 | 8.0 | 8.4 | 9.1 |
| T89-16 | 5.0 | 5.5 | 7.0 | 7.6 | 8.0 | 8.6 | 9.0 | 9.7 |
| T89-17 | 3.1 | 4.3 | 5.7 | 7.1 | 7.4 | 7.9 | 8.4 | 9.2 |
| T89-18 | 4.5 | 5.3 | 7.8 | 8.0 | 8.1 | 9.2 | 9.9 | 10.3 |
| T89-19 | 4.2 | 5.8 | 6.7 | 8.2 | 8.5 | 8.5 | 9.0 | 9.5 |
| T89-20 | 4.0 | 4.7 | 6.7 | 8.1 | 7.6 | 8.5 | 8.6 | 9.4 |
| T89-21 | 3.5 | 3.9 | 5.0 | 5.7 | 5.8 | 7.1 | 6.7 | 7.4 |
| T89-22 | 3.6 | 4.3 | 5.5 | 6.3 | 6.8 | 7.9 | 8.4 | 8.8 |
| T89-23 | 4.1 | 5.2 | 7.0 | 7.6 | 8.2 | 8.9 | 9.2 | 10.0 |
| T89-24 | 4.1 | 5.4 | 6.7 | 7.5 | 7.8 | 8.6 | 9.6 | 10.4 |
| T89-25 | 3.7 | 4.6 | 6.0 | 7.0 | 7.7 | 8.3 | 8.5 | 9.4 |
| T89-26 | 4.8 | 5.6 | 6.9 | 7.3 | 7.8 | 8.6 | 9.2 | 9.5 |
| T89-27 | 3.8 | 4.9 | 6.2 | 6.7 | 6.9 | 7.6 | 8.4 | 9.3 |
| T89-28 | 4.5 | 5.5 | 6.8 | 7.3 | 7.8 | 9.1 | 9.1 | 9.5 |
| T89-29 | 4.4 | 5.3 | 6.8 | 6.8 | 7.4 | 8.2 | 9.2 | 8.9 |
| T89-30 | 3.7 | 4.7 | 5.4 | 6.6 | 7.0 | 7.0 | 7.7 | 8.5 |
| T89-31 | 4.0 | 4.5 | 5.5 | 6.9 | 7.0 | 8.0 | 9.1 | 9.6 |
| T89-32 | 3.6 | 4.5 | 5.7 | 7.0 | 7.2 | 8.0 | 9.1 | 9.4 |
| T89-33 | 3.9 | 4.6 | 6.7 | 7.3 | 8.0 | 8.6 | 9.4 | 10.5 |
| T89-34 | 3.6 | 4.5 | 5.9 | 6.9 | 7.5 | 8.2 | 9.1 | 9.4 |
| T89-35 | 3.9 | 4.5 | 5.7 | 7.1 | 7.5 | 7.9 | 8.8 | 9.6 |
| T89-36 | 3.6 | 5.0 | 5.7 | 6.5 | 6.8 | 7.9 | 8.2 | 9.1 |
| T89-37 | 4.3 | 5.6 | 7.1 | 8.0 | 8.0 | 8.9 | 9.7 | 10.2 |
| T89-38 | 4.7 | 5.8 | 6.7 | 7.8 | 8.0 | 8.7 | 9.2 | 9.7 |
| T89-39 | 4.2 | 5.0 | 6.2 | 7.3 | 8.2 | 8.1 | 8.7 | 9.6 |
| T89-40 | 3.6 | 4.4 | 5.2 | 5.7 | 6.0 | 7.2 | 7.2 | 8.0 |
| T89-41 | 3.5 | 4.3 | 5.5 | 6.5 | 7.0 | 7.5 | 7.7 | 8.4 |
| T89-42 | 4.4 | 5.1 | 7.5 | 8.4 | 9.5 | 9.9 | 10.0 | 10.3 |
| T89-43 | 4.3 | 5.0 | 6.5 | 7.3 | 7.8 | 8.3 | 8.9 | 9.1 |
| T89-44 | 4.3 | 5.8 | 6.8 | 8.1 | 8.6 | 9.5 | 9.9 | 10.5 |
| T89-45 | 4.2 | 4.9 | 6.8 | 7.5 | 7.6 | 8.5 | 9.4 | 9.7 |
| T89-46 | 3.5 | 4.4 | 5.7 | 7 | 7.5 | 8.6 | 9.4 | 9.8 |

Results from growth analysis are specified in the overview table 1.14c. The determined growth effects of specified construction group are presented as ratios between construction and wild type group AFH, AFD, AMHGR, ADGR, MFH, MFD, MMHGR and MDC.

TABLE 1.14c

Overview table of growth effects of construct TFSTT019

| Construction group | Average Final Height | Average Final Diameter | Average Maximum Height Growth Rate | Average Maximum Diameter Growth Rate | Maximum Final Height | Maximum Final Diameter | Maximum of Maximum Height Growth Rate | Maximum Diameter Growth Rate |
|---|---|---|---|---|---|---|---|---|
| TFSTT019 | 0.99 | 1.11 | 0.96 | 1.18 | 0.93 | 1.08 | 0.89 | 1.09 |

1.3.12 Construction Group TFSTT035

This construct induces increased growth. The final diameter is 8% higher comparing the average of the construction group and wild type control group. The final diameter is 11% higher comparing the largest individuals of the construction group and wild type control group. The diameter growth rate is 12% higher comparing the average of the construction group and wild type control group. The diameter growth rate is 8% higher comparing the largest individuals of the construction group and wild type control group. The TFSTT035 construction group meets growth difference selection criterion (2) as shown in table 1.15c.

Tables 1.15a and 1.15b contain growth data for specified construction group and corresponding wild type group. Table rows contain height and diameter measurements of individuals of specified construction group and corresponding wild type group. Time of measurement as number of days in greenhouse is shown in table headers.

TABLE 1.15a

Height growth data for TFSTT035

| | Height (cm) Days in greenhouse | | | | | | | | | | |
|---|---|---|---|---|---|---|---|---|---|---|---|
| | 18 | 22 | 25 | 29 | 32 | 39 | 43 | 46 | 50 | 53 | 57 |
| TFSTT035-1A | 23 | 30 | 36 | 49 | 60 | 88 | 101 | 112 | 127 | 141 | 158 |
| TFSTT035-1BA | 21 | 27 | 34 | 47 | 58 | 83 | 97 | 109 | 125 | 138 | 150 |
| TFSTT035-1BB | 23 | 28 | 35 | 47 | 56 | 80 | 94 | 105 | 118 | 129 | 143 |
| TFSTT035-2AA | 22 | 28 | 36 | 49 | 59 | 84 | 98 | 107 | 122 | 135 | 150 |
| TFSTT035-2AB | 20 | 25 | 31 | 41 | 49 | 70 | 83 | 95 | 109 | 121 | 137 |
| TFSTT035-2B | 18 | 23 | 29 | 40 | 51 | 75 | 90 | 100 | 112 | 125 | 138 |
| TFSTT035-3B | 20 | 26 | 31 | 42 | 52 | 77 | 93 | 103 | 116 | 129 | 145 |
| TFSTT035-4B | 14 | 19 | 25 | 35 | 44 | 73 | 88 | 98 | 113 | 127 | 141 |
| T89-01 | 14 | 17 | 22 | 31 | 40 | 64 | 76 | 88 | 102 | 118 | 135 |
| T89-02 | 17 | 20 | 25 | 36 | 45 | 69 | 79 | 90 | 104 | 118 | 133 |
| T89-03 | 21 | 29 | 35 | 47 | 57 | 81 | 94 | 104 | 119 | 132 | 147 |
| T89-04 | 13 | 14 | 17 | 25 | 33 | 45 | 52 | 57 | 70 | 79 | 92 |
| T89-05 | 15 | 18 | 24 | 33 | 42 | 69 | 83 | 94 | 106 | 120 | 137 |
| T89-06 | 18 | 23 | 29 | 40 | 51 | 78 | 91 | 103 | 120 | 134 | 152 |
| T89-07 | 20 | 24 | 30 | 41 | 51 | 74 | 88 | 96 | 109 | 121 | 130 |
| T89-08 | 27 | 32 | 40 | 52 | 62 | 88 | 99 | 111 | 124 | 134 | 148 |
| T89-09 | 23 | 27 | 34 | 46 | 56 | 83 | 97 | 106 | 122 | 132 | 149 |
| T89-10 | 13 | 15 | 20 | 27 | 37 | 59 | 72 | 83 | 98 | 111 | 128 |
| T89-11 | N/A | N/A | N/A | N/A | N/A | N/A | N/A | N/A | N/A | N/A | N/A |
| T89-12 | 26 | 33 | 40 | 54 | 66 | 92 | 107 | 120 | 135 | 149 | 166 |
| T89-13 | 21 | 26 | 34 | 45 | 55 | 79 | 94 | 105 | 122 | 134 | 150 |
| T89-14 | 18 | 23 | 31 | 42 | 53 | 80 | 97 | 107 | 120 | 128 | 145 |
| T89-15 | 26 | 33 | 40 | 53 | 63 | 88 | 103 | 111 | 125 | 138 | 154 |
| T89-16 | 27 | 32 | 39 | 51 | 63 | 89 | 104 | 116 | 132 | 146 | 162 |
| T89-17 | 17 | 21 | 27 | 38 | 45 | 72 | 87 | 97 | 110 | 124 | 139 |
| T89-18 | 23 | 30 | 35 | 46 | 55 | 80 | 94 | 105 | 117 | 131 | 145 |
| T89-19 | 23 | 29 | 35 | 45 | 54 | 78 | 91 | 102 | 114 | 125 | 137 |
| T89-20 | 22 | 28 | 34 | 49 | 60 | 87 | 100 | 110 | 125 | 137 | 155 |
| T89-21 | 27 | 31 | 35 | 42 | 48 | 66 | 77 | 87 | 100 | 110 | 124 |
| T89-22 | 13 | 16 | 23 | 32 | 48 | 67 | 81 | 92 | 105 | 118 | 134 |
| T89-23 | 23 | 29 | 35 | 48 | 58 | 83 | 97 | 107 | 122 | 136 | 154 |
| T89-24 | 23 | 29 | 36 | 48 | 59 | 86 | 101 | 113 | 128 | 141 | 159 |
| T89-25 | 16 | 21 | 28 | 40 | 51 | 80 | 97 | 107 | 122 | 137 | 153 |
| T89-26 | 27 | 35 | 40 | 54 | 66 | 93 | 107 | 118 | 132 | 144 | 162 |
| T89-27 | 26 | 31 | 38 | 49 | 59 | 82 | 96 | 106 | 120 | 131 | 146 |
| T89-28 | 25 | 29 | 36 | 49 | 59 | 83 | 97 | 106 | 119 | 131 | 147 |
| T89-29 | 26 | 32 | 38 | 51 | 62 | 88 | 103 | 113 | 128 | 142 | 159 |
| T89-30 | 24 | 29 | 36 | 48 | 56 | 80 | 93 | 104 | 117 | 131 | 145 |
| T89-31 | 24 | 31 | 36 | 47 | 57 | 81 | 94 | 105 | 117 | 131 | 144 |
| T89-32 | 26 | 32 | 38 | 49 | 58 | 83 | 98 | 107 | 120 | 134 | 148 |
| T89-33 | 24 | 29 | 36 | 48 | 57 | 85 | 100 | 112 | 124 | 134 | 149 |
| T89-34 | 21 | 26 | 32 | 43 | 53 | 79 | 90 | 102 | 117 | 131 | 148 |
| T89-35 | 21 | 28 | 36 | 46 | 55 | 80 | 94 | 105 | 120 | 133 | 149 |
| T89-36 | 16 | 21 | 28 | 39 | 51 | 74 | 88 | 100 | 115 | 128 | 144 |
| T89-37 | 28 | 35 | 41 | 52 | 63 | 88 | 101 | 111 | 125 | 137 | 154 |
| T89-38 | 27 | 32 | 39 | 51 | 62 | 86 | 101 | 113 | 128 | 140 | 155 |
| T89-39 | 21 | 26 | 33 | 46 | 55 | 83 | 101 | 112 | 126 | 139 | 156 |
| T89-40 | 21 | 26 | 33 | 45 | 55 | 77 | 88 | 99 | 113 | 124 | 139 |
| T89-41 | 13 | 16 | 23 | 32 | 42 | 68 | 85 | 95 | 107 | 118 | 133 |
| T89-42 | 24 | 30 | 37 | 49 | 61 | 86 | 101 | 113 | 128 | 143 | 150 |
| T89-43 | 25 | 31 | 38 | 51 | 61 | 86 | 102 | 114 | 130 | 144 | 163 |
| T89-44 | 23 | 31 | 39 | 51 | 64 | 90 | 105 | 118 | 135 | 151 | 169 |
| T89-45 | 26 | 32 | 37 | 49 | 58 | 85 | 100 | 110 | 124 | 137 | 153 |
| T89-46 | 20 | 25 | 34 | 43 | 55 | 81 | 97 | 109 | 122 | 133 | 149 |

TABLE 1.15b

Diameter growth data for TFSTT035

| | Diameter (mm) Days in greenhouse | | | | | | | |
|---|---|---|---|---|---|---|---|---|
| | 29 | 32 | 39 | 43 | 46 | 50 | 53 | 57 |
| TFSTT035-1A | 4.6 | 5.6 | 7.0 | 8.3 | 8.7 | 8.8 | 9.1 | 10.4 |
| TFSTT035-1BA | 4.5 | 5.7 | 7.3 | 8.8 | 9.0 | 10.0 | 11.0 | 11.7 |
| TFSTT035-1BB | 4.1 | 5.3 | 6.5 | 7.1 | 7.5 | 8.3 | 9.0 | 9.5 |
| TFSTT035-2AA | 4.1 | 5.0 | 7.0 | 8.0 | 8.7 | 9.2 | 10.0 | 10.3 |
| TFSTT035-2AB | 4.0 | 4.9 | 6.5 | 7.5 | 8.0 | 8.6 | 9.2 | 9.8 |
| TFSTT035-2B | 3.6 | 5.0 | 6.6 | 7.3 | 8.0 | 8.3 | 8.9 | 9.5 |
| TFSTT035-3B | 3.5 | 4.2 | 5.8 | 6.8 | 7.2 | 8.0 | 8.9 | 9.5 |
| TFSTT035-4B | 3.4 | 4.5 | 5.5 | 7.0 | 7.4 | 7.7 | 9.0 | 9.5 |
| T89-01 | 3.2 | 3.7 | 5.3 | 6.2 | 6.9 | 7.9 | 8.3 | 8.7 |
| T89-02 | 3.2 | 3.9 | 5.1 | 6.4 | 7.0 | 7.6 | 8.6 | 8.6 |
| T89-03 | 4.2 | 5.3 | 6.4 | 6.9 | 6.9 | N/A | 8.8 | 9.8 |
| T89-04 | 2.2 | 3.0 | 4.2 | 4.5 | 5.4 | 5.0 | 5.4 | 6.1 |
| T89-05 | 3.0 | 3.7 | 4.8 | 5.9 | 6.4 | 7.0 | 7.6 | 7.9 |
| T89-06 | 3.6 | 4.8 | 6.5 | 7.6 | 8.7 | 9.1 | 9.6 | 10.1 |
| T89-07 | 3.8 | 4.9 | 6.8 | 7.6 | 8.0 | 8.6 | 9.0 | 9.7 |
| T89-08 | 4.4 | 5.8 | 6.2 | 7.3 | 7.6 | 8.5 | 9.4 | 9.7 |
| T89-09 | 4.5 | 5.5 | 6.5 | 7.1 | 7.6 | 9.1 | 9.4 | 9.8 |
| T89-10 | 3.7 | 3.9 | 5.0 | 6.1 | 6.8 | 7.6 | 8.5 | 9.2 |
| T89-11 | N/A | N/A | N/A | N/A | N/A | N/A | N/A | N/A |
| T89-12 | 4.6 | 5.5 | 7.3 | 8.6 | 8.8 | 9.6 | 10.2 | 10.2 |
| T89-13 | 3.8 | 4.6 | 5.7 | 6.5 | 6.6 | 7.4 | 8.1 | 8.6 |
| T89-14 | 3.7 | 4.2 | 5.3 | 5.6 | 6.1 | 7.0 | 7.1 | 7.8 |
| T89-15 | 4.6 | 5.0 | 6.4 | 7.0 | 7.4 | 8.0 | 8.4 | 9.1 |
| T89-16 | 5.0 | 5.5 | 7.0 | 7.6 | 8.0 | 8.6 | 9.0 | 9.7 |
| T89-17 | 3.1 | 4.3 | 5.7 | 7.1 | 7.4 | 7.9 | 8.4 | 9.2 |
| T89-18 | 4.5 | 5.3 | 7.8 | 8.0 | 8.1 | 9.2 | 9.9 | 10.3 |
| T89-19 | 4.2 | 5.8 | 6.7 | 8.2 | 8.5 | 8.5 | 9.0 | 9.5 |
| T89-20 | 4.0 | 4.7 | 6.7 | 8.1 | 7.6 | 8.5 | 8.6 | 9.4 |
| T89-21 | 3.5 | 3.9 | 5.0 | 5.7 | 5.8 | 7.1 | 6.7 | 7.4 |
| T89-22 | 3.6 | 4.3 | 5.5 | 6.3 | 6.8 | 7.9 | 8.4 | 8.8 |
| T89-23 | 4.1 | 5.2 | 7.0 | 7.6 | 8.2 | 8.9 | 9.2 | 10.0 |
| T89-24 | 4.1 | 5.4 | 6.7 | 7.5 | 7.8 | 8.6 | 9.6 | 10.4 |
| T89-25 | 3.7 | 4.6 | 6.0 | 7.0 | 7.7 | 8.3 | 8.5 | 9.4 |
| T89-26 | 4.8 | 5.6 | 6.9 | 7.3 | 7.8 | 8.6 | 9.2 | 9.5 |
| T89-27 | 3.8 | 4.9 | 6.2 | 6.7 | 6.9 | 7.6 | 8.4 | 9.3 |
| T89-28 | 4.5 | 5.5 | 6.8 | 7.3 | 7.8 | 9.1 | 9.1 | 9.5 |
| T89-29 | 4.4 | 5.3 | 6.8 | 6.8 | 7.4 | 8.2 | 9.2 | 8.9 |
| T89-30 | 3.7 | 4.7 | 5.4 | 6.6 | 7.0 | 7.0 | 7.7 | 8.5 |
| T89-31 | 4.0 | 4.5 | 5.5 | 6.9 | 7.0 | 8.0 | 9.1 | 9.6 |
| T89-32 | 3.6 | 4.5 | 5.7 | 7.0 | 7.2 | 8.0 | 9.1 | 9.4 |
| T89-33 | 3.9 | 4.6 | 6.7 | 7.3 | 8.0 | 8.6 | 9.4 | 10.5 |
| T89-34 | 3.6 | 4.5 | 5.9 | 6.9 | 7.5 | 8.2 | 9.1 | 9.4 |
| T89-35 | 3.9 | 4.5 | 5.7 | 7.1 | 7.5 | 7.9 | 8.8 | 9.6 |
| T89-36 | 3.6 | 5.0 | 5.7 | 6.5 | 6.8 | 7.9 | 8.2 | 9.1 |
| T89-37 | 4.3 | 5.6 | 7.1 | 8.0 | 8.0 | 8.9 | 9.7 | 10.2 |
| T89-38 | 4.7 | 5.8 | 6.7 | 7.8 | 8.0 | 8.7 | 9.2 | 9.7 |
| T89-39 | 4.2 | 5.0 | 6.2 | 7.3 | 8.2 | 8.1 | 8.7 | 9.6 |
| T89-40 | 3.6 | 4.4 | 5.2 | 5.7 | 6.0 | 7.2 | 7.2 | 8.0 |
| T89-41 | 3.5 | 4.3 | 5.5 | 6.5 | 7.0 | 7.5 | 7.7 | 8.4 |
| T89-42 | 4.4 | 5.1 | 7.5 | 8.4 | 9.5 | 9.9 | 10.0 | 10.3 |
| T89-43 | 4.3 | 5.0 | 6.5 | 7.3 | 7.8 | 8.3 | 8.9 | 9.1 |
| T89-44 | 4.3 | 5.8 | 6.8 | 8.1 | 8.6 | 9.5 | 9.9 | 10.5 |
| T89-45 | 4.2 | 4.9 | 6.8 | 7.5 | 7.6 | 8.5 | 9.4 | 9.7 |
| T89-46 | 3.5 | 4.4 | 5.7 | 7 | 7.5 | 8.6 | 9.4 | 9.8 |

Results from growth analysis are specified in the overview table 1.15c. The determined growth effects of specified construction group are presented as ratios between construction and wild type group AFH, AFD, AMHGR, ADGR, MFH, MFD, MMHGR and MDC.

TABLE 1.15c

Overview table of growth effects of construct TFSTT035

| Construction group | Average Final Height | Average Final Diameter | Average Maximum Height Growth Rate | Average Maximum Diameter Growth Rate | Maximum Final Height | Maximum Final Diameter | Maximum of Maximum Height Growth Rate | Maximum Diameter Growth Rate |
|---|---|---|---|---|---|---|---|---|
| TFSTT035 | 0.99 | 1.08 | 0.98 | 1.12 | 0.93 | 1.11 | 0.90 | 1.08 |

1.3.13 Construction Group TFSTT047

This construct induces increased growth. The final diameter is 8% higher comparing the average of the construction group and wild type control group. The final diameter is 11% higher comparing the largest individuals of the construction group and wild type control group. The diameter growth rate is 12% higher comparing the average of the construction group and wild type control group. The diameter growth rate is 8% higher comparing the largest individuals of the construction group and wild type control group. The TFSTT047 construction group meets growth difference selection criterion (3) as shown in table 1.16c.

Tables 1.16a and 1.16b contain growth data for specified construction group and corresponding wild type group. Table rows contain height and diameter measurements of individuals of specified construction group and corresponding wild type group. Time of measurement as number of days in greenhouse is shown in table headers.

TABLE 1.16a

Height growth data for TFSTT047

| | Height (cm) Days in greenhouse | | | | | | | | |
|---|---|---|---|---|---|---|---|---|---|
| | 20 | 28 | 34 | 37 | 41 | 48 | 51 | 55 | 59 |
| TFSTT047-1B | 29 | 44 | 56 | 64 | 73 | 91 | 99 | 111 | 121 |
| TFSTT047-2A | 29 | 47 | 67 | 76 | 87 | 114 | 122 | 135 | 147 |
| TFSTT047-2B | 26 | 44 | 67 | 76 | 90 | 116 | 125 | 139 | 150 |
| TFSTT047-3B | 25 | 43 | 65 | 74 | 87 | 109 | 118 | 131 | 143 |
| TFSTT047-4A | 25 | 45 | 68 | 75 | 87 | 108 | 115 | 128 | 138 |
| T89-02 | 27 | 40 | 51 | 58 | 66 | 86 | 94 | 105 | 115 |
| T89-03 | 27 | 44 | 58 | 67 | 77 | 97 | 104 | 114 | 126 |
| T89-04 | 27 | 39 | 56 | 65 | 74 | 92 | 100 | 109 | 118 |
| T89-07 | 28 | 47 | 66 | 77 | 88 | 107 | 116 | 130 | 140 |
| T89-08 | 19 | 37 | 51 | 59 | 69 | 90 | 99 | 109 | 119 |
| T89-09 | 25 | 43 | 58 | 67 | 78 | 100 | 109 | 121 | 131 |
| T89-11 | 29 | 45 | 60 | 69 | 81 | 104 | 111 | 121 | 132 |
| T89-12 | 26 | 41 | 58 | 65 | 77 | 105 | 114 | 127 | 136 |
| T89-13 | 31 | 47 | 70 | 78 | 90 | 110 | 119 | 131 | 143 |
| T89-14 | 26 | 46 | 70 | 78 | 88 | 108 | 116 | 127 | 137 |
| T89-18 | 22 | 41 | 55 | 65 | 74 | 95 | 104 | 115 | 126 |
| T89-19 | 27 | 43 | 60 | 70 | 81 | 102 | 110 | 121 | 131 |
| T89-20 | 25 | 40 | 57 | N/A | 74 | 94 | 103 | 118 | 130 |
| T89-21 | 27 | 45 | 61 | 72 | 84 | 108 | 115 | 126 | 137 |
| T89-22 | 25 | 38 | 55 | 65 | 77 | 95 | 104 | 115 | 125 |
| T89-23 | 23 | 37 | 50 | 57 | 65 | 82 | 92 | 106 | 115 |
| T89-24 | 25 | 41 | 54 | 60 | 69 | 87 | 94 | 102 | 110 |
| T89-25 | 25 | 38 | 55 | 66 | 80 | 100 | 109 | 121 | 133 |
| T89-26 | 24 | 38 | 53 | 61 | 69 | 81 | 87 | 95 | 104 |
| T89-27 | 26 | 39 | 54 | 62 | 70 | 90 | 97 | 109 | 120 |
| T89-28 | 27 | 46 | 67 | 75 | 86 | 107 | 114 | 126 | 136 |
| T89-29 | 24 | 39 | 57 | 64 | 74 | 91 | 98 | 108 | 128 |
| T89-31 | 27 | 43 | 57 | 65 | 73 | 91 | 97 | 105 | 113 |
| T89-32 | 25 | 41 | 55 | 63 | 75 | 96 | 107 | 121 | 135 |
| T89-35 | 25 | 38 | 53 | 62 | 73 | 88 | 96 | 103 | 112 |
| T89-36 | 27 | 45 | 67 | 78 | 90 | 113 | 122 | 134 | 145 |
| T89-37 | 20 | 43 | 59 | 68 | 79 | 101 | 112 | 124 | 137 |
| T89-39 | 25 | 45 | 61 | 69 | 79 | 99 | 108 | 120 | 132 |
| T89-40 | 23 | 32 | 43 | 49 | 60 | 76 | 84 | 94 | 104 |
| T89-41 | 27 | 45 | 66 | 75 | 87 | 112 | 120 | 133 | 144 |
| T89-43 | 26 | 38 | 54 | 61 | 70 | 93 | 100 | 109 | 120 |
| T89-46 | 26 | 45 | 66 | 76 | 88 | 109 | 114 | 125 | 133 |

TABLE 1.16b

Diameter growth data for TFSTT047

| | Diameter (mm) Days in greenhouse | | | | |
|---|---|---|---|---|---|
| | 34 | 41 | 48 | 55 | 59 |
| TFSTT047-1B | 6.1 | 7.0 | 8.3 | 9.3 | 9.4 |
| TFSTT047-2A | 6.7 | 7.6 | 8.7 | 10.0 | 10.4 |
| TFSTT047-2B | 6.9 | 7.5 | N/A | 9.5 | 10.6 |
| TFSTT047-3B | 6.8 | 7.8 | 8.9 | 9.9 | 10.1 |
| TFSTT047-4A | 5.7 | 6.9 | 8.2 | 9.1 | 9.8 |
| T89-02 | 5.6 | 6.4 | 7.8 | 9.0 | 8.4 |
| T89-03 | 6.6 | 7.7 | 8.5 | 8.9 | 9.6 |
| T89-04 | 7.2 | 7.8 | 9.1 | 9.8 | 9.7 |
| T89-07 | 7.3 | 7.9 | 9.5 | 9.9 | 10.1 |
| T89-08 | 5.5 | 7.8 | 8.3 | 10.0 | 9.8 |
| T89-09 | 6.7 | 7.8 | 9.3 | 9.7 | 9.8 |
| T89-11 | 6.4 | 8.1 | 9.2 | 9.4 | 9.7 |
| T89-12 | 7.0 | 8.0 | 9.0 | 10.1 | 9.9 |
| T89-13 | 6.8 | 8.5 | 9.1 | 10.7 | 10.8 |
| T89-14 | 6.1 | 6.9 | 7.7 | 8.4 | 8.8 |
| T89-18 | 5.5 | 6.5 | 7.9 | 9.5 | 9.4 |
| T89-19 | 7.5 | 8.3 | 9.0 | 9.5 | 10.4 |
| T89-20 | 7.3 | 7.1 | 8.7 | 9.3 | 9.7 |
| T89-21 | 7.0 | 8.6 | 9.3 | 10.3 | 10.3 |
| T89-22 | 7.0 | 7.8 | 8.4 | 10.0 | 9.5 |
| T89-23 | 5.8 | 6.8 | 7.9 | 9.9 | 9.7 |
| T89-24 | 6.1 | 6.8 | 8.1 | 9.0 | 9.4 |
| T89-25 | 6.5 | 8.8 | 9.5 | 10.0 | 10.9 |
| T89-26 | 5.8 | 6.7 | 7.0 | 7.5 | 7.7 |
| T89-27 | 6.3 | 7.4 | 8.6 | 9.0 | 9.5 |
| T89-28 | 7.0 | 8.1 | 8.8 | 9.7 | 10.5 |
| T89-29 | 7.5 | 7.4 | 8.5 | 10.7 | 10.0 |
| T89-31 | 5.6 | 6.3 | 7.2 | 7.6 | 8.6 |
| T89-32 | 6.0 | 7.0 | 8.2 | 8.7 | 9.3 |
| T89-35 | 5.4 | 6.4 | 6.8 | 7.9 | 8.0 |
| T89-36 | 6.7 | 8.2 | 8.9 | 9.6 | 9.4 |
| T89-37 | 7.4 | 8.5 | 8.6 | 9.3 | 10.8 |
| T89-39 | 7.1 | 7.9 | 9.6 | 10.2 | 10.2 |
| T89-40 | 3.9 | 5.2 | 5.7 | 6.8 | 6.6 |
| T89-41 | 7.2 | 8.7 | N/A | 9.7 | 10.3 |
| T89-43 | 6.9 | 7.5 | 8.6 | 9.7 | 10.4 |
| T89-46 | 6.4 | 7.2 | 8.2 | 8.7 | 9.7 |

Results from growth analysis are specified in the overview table 1.16c. The determined growth effects of specified construction group are presented as ratios between construction and wild type group AFH, AFD, AMHGR, ADGR, MFH, MFD, MMHGR and MDC.

TABLE 1.16c

Overview table of growth effects of construct TFSTT047

| Construction group | Average Final Height | Average Final Diameter | Average Maximum Height Growth Rate | Average Diameter Growth Rate | Maximum Final Height | Maximum Final Diameter | Maximum of Maximum Height Growth Rate | Maximum Diameter Growth Rate |
|---|---|---|---|---|---|---|---|---|
| TFSTT047 | 1.10 | 1.05 | 1.08 | 1.20 | 1.03 | 0.97 | 0.99 | 1.00 |

Example 2

Construction Group TF0002Rp2

This construct induces increased growth. The final height is 29% higher comparing the average of the construction group and wild type control group. The final height is 27% higher comparing the largest individuals of the construction group and wild type control group. The maximum height growth rate is 36% higher comparing the average of the construction group and wild type control group. The maximum height growth rate is 38% higher comparing the largest individuals of the construction group and wild type control group. The diameter growth rate is 10% higher comparing the average of the construction group and wild type control group. The diameter growth rate is 9% higher comparing the largest individuals of the construction group and wild type control group. The TF0002Rp2 construction group meets the more stringent level of growth difference selection criteria (1), (3) and (4) as shown in table 2.3.

Tables 2.1 and 2.2 contain growth data for specified construction group and corresponding wild type group. Table rows contain height and diameter measurements of individuals of specified construction group and corresponding wild type group. Time of measurement as number of days in greenhouse is shown in table headers.

TABLE 2.1

Height growth data for TF0002Rp2

| | Height (cm) Days in greenhouse | | | | | | | | | |
|---|---|---|---|---|---|---|---|---|---|---|
| | 20 | 25 | 29 | 35 | 41 | 46 | 50 | 53 | 57 | 60 |
| TF0002rp2-1B-1 | 18 | 25 | 33 | 50 | 72 | 91 | 106 | 120 | 132 | 143 |
| TF0002rp2-1B-2 | 21 | 31 | 42 | 62 | 85 | 106 | 120 | 132 | 146 | 155 |
| TF0002rp2-1B-3 | 19 | 26 | 36 | 54 | 77 | 100 | 113 | 125 | 140 | 153 |
| TF0002rp2-2A-1 | 19 | 28 | 38 | 52 | 72 | 91 | 103 | 115 | 127 | 138 |
| TF0002rp2-2A-2 | 20 | 23 | 28 | 36 | 53 | 73 | 83 | 94 | 106 | 116 |
| TF0002rp2-2A-3 | 22 | 31 | 40 | 57 | 73 | 94 | 101 | 109 | 116 | 124 |
| TF0002rp2-3B-1 | 17 | 18 | 23 | 36 | 52 | 70 | 81 | 92 | 106 | 118 |
| TF0002rp2-3B-2 | 19 | 28 | 37 | 56 | 78 | 103 | 115 | 125 | 139 | 150 |
| TF0002rp2-3B-3 | 19 | 29 | 41 | 60 | 85 | 111 | 126 | 137 | 150 | 161 |
| T89-01 | 17 | 26 | 31 | 45 | 61 | 76 | 87 | 95 | 107 | 116 |
| T89-02 | 16 | 21 | 26 | 38 | 53 | 67 | 76 | 83 | N/A | N/A |
| T89-03 | 18 | 24 | 32 | 47 | 64 | 78 | 87 | 96 | 106 | 115 |
| T89-04 | 18 | 26 | 35 | 50 | 66 | 80 | 87 | 96 | 107 | 115 |
| T89-05 | 17 | 26 | 33 | 44 | 57 | 73 | 81 | 91 | 100 | 107 |
| T89-06 | 16 | 21 | 28 | 40 | 55 | 74 | 79 | 89 | 99 | 106 |
| T89-07 | 17 | 23 | 31 | 43 | 57 | 71 | 80 | 88 | 98 | 107 |
| T89-08 | 15 | 20 | 26 | 37 | 51 | 65 | 75 | 84 | 94 | 100 |
| T89-09 | 18 | 25 | 32 | 46 | 61 | 74 | 85 | 93 | 103 | 112 |
| T89-10 | 19 | 25 | 32 | 46 | 60 | 75 | 86 | 95 | 104 | 112 |
| T89-11 | 20 | 27 | 36 | 51 | 68 | 86 | 98 | 107 | 120 | 127 |
| T89-12 | 19 | 27 | 36 | 50 | 67 | 80 | 89 | 97 | 108 | 118 |
| T89-13 | 18 | 25 | 32 | 45 | 59 | 75 | 83 | 92 | 101 | 108 |
| T89-14 | 18 | 23 | 26 | 36 | 51 | 65 | 72 | 79 | 89 | 96 |
| T89-15 | 17 | 21 | 28 | 39 | 53 | 70 | 78 | 87 | 97 | 105 |
| T89-16 | 19 | 25 | 32 | 43 | 57 | 71 | 81 | 90 | 101 | 109 |
| T89-17 | 16 | 20 | 29 | 41 | 54 | 68 | 78 | 84 | 93 | 101 |
| T89-18 | 16 | 23 | 30 | 45 | 63 | 78 | 87 | 94 | 103 | 110 |
| T89-19 | 16 | 22 | 28 | 42 | 56 | 69 | 79 | 89 | 100 | 107 |
| T89-20 | 18 | 25 | 32 | 47 | 63 | 78 | 89 | 99 | 109 | 115 |
| T89-21 | 19 | 27 | 34 | 50 | 67 | 82 | 92 | 102 | 111 | 120 |
| T89-22 | 19 | 25 | 32 | 44 | 58 | 76 | 84 | 93 | 102 | 109 |

TABLE 2.1-continued

Height growth data for TF0002Rp2

| | Height (cm) Days in greenhouse | | | | | | | | | |
|---|---|---|---|---|---|---|---|---|---|---|
| | 20 | 25 | 29 | 35 | 41 | 46 | 50 | 53 | 57 | 60 |
| T89-23 | 18 | 26 | 33 | 47 | 63 | 79 | 88 | 99 | 108 | 116 |
| T89-24 | 16 | 24 | 28 | 42 | 53 | 70 | 78 | 85 | 94 | 103 |
| T89-25 | 16 | 25 | 32 | 45 | 61 | 76 | 85 | 95 | 107 | 114 |
| T89-26 | 16 | 20 | 26 | 38 | 52 | 68 | 78 | 86 | 97 | 103 |
| T89-27 | 16 | 21 | 25 | 35 | 48 | 61 | 70 | 78 | N/A | 98 |
| T89-28 | 14 | 18 | 25 | 38 | 51 | 64 | 73 | 81 | 90 | 96 |
| T89-29 | 7 | 13 | 18 | 30 | 45 | 60 | 69 | 77 | 90 | 98 |
| T89-30 | 15 | 22 | 29 | 42 | 55 | 69 | 80 | 88 | 97 | 106 |
| T89-31 | 21 | 29 | 37 | 50 | 65 | 80 | 88 | 98 | 108 | 116 |
| T89-32 | 19 | 24 | 32 | 42 | 55 | 70 | 78 | 87 | 96 | 105 |

TABLE 2.2

Diameter growth data for TF0002Rp2

| | Diameter (mm) Days in greenhouse | | | | |
|---|---|---|---|---|---|
| | 35 | 41 | 46 | 53 | 60 |
| TF0002rp2-1B-1 | 4.6 | 5.4 | 6.3 | 8.0 | 8.2 |
| TF0002rp2-1B-2 | 4.5 | 5.4 | 6.5 | 7.7 | 8.7 |
| TF0002rp2-1B-3 | 4.9 | 5.9 | 6.4 | 7.2 | 8.0 |
| TF0002rp2-2A-1 | 4.3 | 4.9 | 6.0 | 7.4 | 8.0 |
| TF0002rp2-2A-2 | 4.1 | 5.3 | 6.3 | 6.5 | 7.6 |
| TF0002rp2-2A-3 | 4.7 | 6.3 | 6.2 | 7.7 | 9.8 |
| TF0002rp2-3B-1 | 3.4 | 4.4 | 5.1 | 6.9 | 7.1 |
| TF0002rp2-3B-2 | 4.9 | 6.5 | 6.8 | 8.5 | 9.3 |
| TF0002rp2-3B-3 | 4.7 | 6.3 | 6.9 | 8.5 | 8.7 |
| T89-01 | 4.7 | 6.0 | 6.5 | 6.9 | 8.3 |
| T89-02 | 4.4 | 5.7 | 6.6 | 7.6 | 7.8 |
| T89-03 | 4.7 | 6.3 | 6.7 | 7.7 | 8.4 |
| T89-04 | 4.7 | 6.0 | 7.1 | 8.0 | 8.5 |
| T89-05 | 4.0 | 5.3 | 6.3 | 7.8 | 8.1 |
| T89-06 | 4.6 | 5.9 | 6.3 | 7.7 | 8.2 |
| T89-07 | 4.6 | 6.1 | 6.5 | 7.9 | 8.5 |
| T89-08 | 4.0 | 5.2 | 5.8 | 6.9 | 7.1 |
| T89-09 | 4.4 | 5.8 | 6.4 | 7.6 | 8.2 |
| T89-09 | 4.4 | 5.8 | 6.4 | 7.6 | 8.2 |
| T89-10 | 4.9 | 6.0 | 6.6 | 7.4 | 8.5 |
| T89-11 | 4.7 | 5.8 | 6.4 | 7.9 | 8.3 |
| T89-12 | 4.7 | 5.9 | 7.3 | 7.4 | 7.6 |
| T89-13 | 5.9 | 5.9 | 6.7 | 7.5 | 8.3 |
| T89-14 | 4.5 | 5.2 | 5.8 | 6.1 | 7.0 |
| T89-15 | 4.7 | NA | 6.0 | 6.4 | 7.3 |
| T89-16 | 4.5 | 5.6 | 7.7 | 7.5 | 8.6 |
| T89-17 | 4.1 | 5.4 | 6.0 | 6.8 | 7.5 |
| T89-18 | 4.4 | 5.8 | 6.0 | 7.7 | 8.3 |
| T89-19 | 4.7 | 5.8 | 7.1 | 8.5 | 9.4 |
| T89-20 | 4.7 | 5.8 | 6.6 | 7.4 | 8.3 |
| T89-21 | 4.7 | 6.2 | 6.3 | 7.7 | 8.5 |
| T89-22 | 4.2 | 5.1 | 6.3 | 6.9 | 8.0 |
| T89-23 | 4.6 | 5.8 | 7.1 | 7.5 | 8.3 |
| T89-24 | 4.4 | 5.8 | 6.9 | 7.7 | 8.8 |
| T89-25 | 4.5 | 5.4 | 6.2 | 8.0 | 8.7 |
| T89-26 | 4.1 | 5.4 | 6.0 | 7.2 | 8.0 |
| T89-27 | 4.5 | 5.7 | 6.5 | 7.9 | 9.2 |
| T89-28 | 4.3 | 5.1 | 6.0 | 6.6 | 7.7 |
| T89-29 | 3.5 | 4.7 | 5.5 | 6.3 | 7.1 |
| T89-30 | 4.1 | 5.4 | 5.8 | 7.2 | 7.8 |
| T89-31 | 5.0 | 5.8 | 6.8 | 7.3 | 8.2 |
| T89-32 | 4.4 | 6.4 | 6.6 | 8.0 | 8.4 |

Results from growth analysis are specified in the overview table 2.3. The determined growth effects of specified construction group are presented as ratios between construction and wild type group AFH, AFD, AMHGR, ADGR, MFH, MFD, MMHGR and MDC.

TABLE 2.3

Overview table of growth effects of construct TF0002Rp2

| Construction group | Average Final Height | Average Final Diameter | Average Maximum Height Growth Rate | Average Maximum Diameter Growth Rate | Maximum Final Height | Maximum Final Diameter | Maximum of Maximum Height Growth Rate | Maximum Maximum Diameter Growth Rate |
|---|---|---|---|---|---|---|---|---|
| TF0002Rp2 | 1.29 | 1.03 | 1.36 | 1.10 | 1.27 | 1.05 | 1.38 | 1.09 |

Construction Group TF0003

Tables 2.4 and 2.5 contain growth data for specified construction group and corresponding wild type group. Table rows contain height and diameter measurements of individuals of specified construction group and corresponding wild type group. Time of measurement as number of days in greenhouse is shown in table headers.

TABLE 2.4

Height growth data for TF0003

| | Height (cm) Days in greenhouse | | | | | | |
|---|---|---|---|---|---|---|---|
| | 18 | 25 | 35 | 39 | 46 | 49 | 53 |
| TF0003-1A | 32 | 55 | 94 | 113 | 145 | 156 | 168 |
| TF0003-1B | 37 | 58 | 104 | 120 | 143 | 155 | 170 |
| TF0003-2A | 30 | 49 | 86 | 107 | 142 | 159 | 178 |
| TF0003-3A | 38 | 59 | 100 | 114 | 142 | 152 | 167 |
| TF0003-3B | 29 | 51 | 98 | 117 | 147 | 162 | 183 |
| TF0003-4A | 30 | 52 | 97 | 116 | 149 | 162 | 176 |
| TF0003-4B | 32 | 52 | 91 | 112 | 146 | 162 | 179 |
| T89-01 | 33 | 57 | 108 | 128 | 161 | 173 | 192 |
| T89-02 | 32 | 55 | 94 | 112 | 145 | 160 | 180 |
| T89-03 | 31 | 53 | 95 | 114 | 147 | 160 | 173 |
| T89-04 | 27 | 48 | 91 | 110 | 143 | 157 | 179 |
| T89-05 | 26 | 43 | 86 | 107 | 141 | 155 | 171 |
| T89-06 | 28 | 47 | 86 | 106 | 142 | 157 | 175 |
| T89-07 | 34 | 56 | 101 | 120 | 153 | 168 | 184 |
| T89-08 | 26 | 44 | 83 | 101 | 133 | 148 | 166 |
| T89-09 | 29 | 51 | 88 | 106 | 141 | 154 | 171 |
| T89-10 | 25 | 45 | 90 | 108 | 141 | 156 | 178 |
| T89-11 | 26 | 46 | 80 | 96 | 128 | 143 | 166 |
| T89-12 | 27 | 45 | 84 | 102 | 132 | 143 | 156 |
| T89-13 | 29 | 50 | 96 | 115 | 149 | 163 | 185 |
| T89-14 | 28 | 49 | 89 | 109 | 147 | 163 | 185 |
| T89-15 | 25 | 43 | 81 | 99 | 134 | 146 | 161 |
| T89-16 | 27 | 46 | 88 | 106 | 146 | 162 | 185 |
| T89-17 | 31 | 52 | 90 | 107 | 142 | 158 | 179 |
| T89-18 | 28 | 45 | 82 | 101 | 140 | 158 | 180 |
| T89-19 | 27 | 42 | 82 | 101 | 132 | 146 | 163 |
| T89-20 | 28 | 42 | 81 | 101 | 135 | 150 | 169 |
| T89-21 | 26 | 36 | 67 | 76 | 100 | 113 | 128 |
| T89-22 | 31 | 51 | 97 | 115 | 150 | 165 | 181 |
| T89-23 | 29 | 49 | 83 | 101 | 132 | 144 | 163 |
| T89-24 | 30 | 48 | 89 | 107 | 144 | 159 | 177 |
| T89-25 | 26 | 45 | 89 | 103 | 136 | 152 | 175 |
| T89-26 | 28 | 48 | 87 | 105 | 140 | 156 | 177 |
| T89-27 | 28 | 46 | 86 | 103 | 138 | 153 | 170 |
| T89-28 | 29 | 47 | 86 | 103 | 135 | 152 | 173 |
| T89-29 | 26 | 43 | 81 | 101 | 139 | 156 | 179 |
| T89-30 | 32 | 53 | 94 | 114 | 150 | 166 | 187 |
| T89-31 | 30 | 48 | 85 | 103 | 134 | 148 | 169 |
| T89-32 | 31 | 51 | 91 | 109 | 140 | 154 | 173 |
| T89-33 | 31 | 52 | 94 | 113 | 151 | 167 | 186 |
| T89-34 | 23 | 40 | 84 | 105 | 140 | 153 | 171 |
| T89-35 | 29 | 48 | 88 | 106 | 137 | 150 | 165 |
| T89-36 | 29 | 49 | 88 | 107 | 143 | 159 | 176 |
| T89-37 | 32 | 49 | 91 | 105 | 141 | 154 | 168 |
| T89-38 | 29 | 50 | 88 | 106 | 144 | 158 | 172 |
| T89-39 | 31 | 48 | 89 | 106 | 139 | 152 | 172 |
| T89-40 | 32 | 49 | 97 | 117 | 149 | 163 | 185 |
| T89-41 | 24 | 46 | 86 | 104 | 138 | 155 | 176 |
| T89-42 | 26 | 41 | 80 | 98 | 133 | 151 | 172 |
| T89-43 | 29 | 48 | 92 | 110 | 145 | 163 | 188 |
| T89-44 | 28 | 49 | 89 | 109 | 146 | 163 | 186 |
| T89-45 | 28 | 48 | 83 | 97 | 119 | 129 | 145 |
| T89-46 | 32 | 52 | 95 | 115 | 149 | 165 | 185 |
| T89-47 | 26 | 42 | 83 | 101 | 133 | 147 | 166 |
| T89-48 | 26 | 41 | 82 | 101 | 135 | 152 | 173 |
| T89-49 | 33 | 52 | 103 | 123 | 153 | 166 | 180 |

TABLE 2.5

Diameter growth data for TF0003

| | Diameter (mm) Days in greenhouse | | | |
|---|---|---|---|---|
| | 35 | 39 | 46 | 53 |
| TF0003-1A | 5.3 | 6.7 | 7.5 | 8.8 |
| TF0003-1B | 6.0 | 6.6 | 7.3 | 7.7 |
| TF0003-2A | 6.3 | 6.9 | 8.8 | 9.7 |
| TF0003-3A | 6.3 | 7.1 | 7.9 | 9.3 |
| TF0003-3B | 6.0 | 6.9 | 8.5 | 9.2 |
| TF0003-4A | 6.6 | 7.5 | 7.9 | 9.0 |
| TF0003-4B | 6.0 | 7.0 | 8.6 | 10.4 |
| T89-01 | 7.2 | 8.0 | 9.6 | 10.7 |
| T89-02 | 6.2 | 7.1 | 8.0 | 9.1 |
| T89-03 | 6.3 | 7.3 | 8.3 | 9.3 |
| T89-04 | 5.5 | 6.7 | 8.0 | 9.0 |
| T89-05 | 5.3 | 6.5 | 7.4 | 8.3 |
| T89-06 | 5.8 | 6.8 | 8.0 | 9.1 |
| T89-07 | 6.3 | 7.3 | 9.1 | 10.9 |
| T89-08 | 5.7 | 6.3 | 7.1 | 7.6 |
| T89-09 | 6.0 | 6.6 | 8.1 | 9.1 |
| T89-10 | 5.6 | 6.5 | 7.7 | 9.1 |
| T89-11 | 5.8 | 6.6 | 7.7 | 8.6 |
| T89-12 | 6.2 | 6.8 | 7.3 | 8.1 |
| T89-13 | 5.7 | 6.6 | 7.7 | 8.8 |
| T89-14 | 6.3 | 7.0 | 8.5 | 10.0 |
| T89-15 | 5.2 | 6.0 | 6.9 | 7.6 |
| T89-16 | 6.3 | 7.2 | 8.4 | 9.3 |
| T89-17 | 5.9 | 6.8 | 8.0 | 9.1 |
| T89-18 | 6.2 | 6.8 | 8.2 | 9.6 |
| T89-19 | 6.1 | 6.8 | 7.9 | 9.1 |
| T89-20 | 5.3 | 6.3 | 7.4 | 9.0 |
| T89-21 | 3.5 | 4.2 | 5.0 | 9.2 |
| T89-22 | 5.9 | 6.6 | 7.7 | 8.4 |
| T89-23 | 6.1 | 7.0 | 8.4 | 9.7 |
| T89-24 | 5.7 | 6.7 | 8.0 | 9.4 |
| T89-25 | 5.9 | 6.8 | 8.1 | 8.7 |
| T89-26 | 6.4 | 7.2 | 8.4 | 9.7 |
| T89-27 | 5.7 | 6.9 | 8.8 | 10.1 |
| T89-28 | 5.7 | 6.6 | 7.7 | 8.7 |
| T89-29 | 5.1 | 6.4 | 7.7 | 9.1 |
| T89-30 | 6.0 | 6.9 | 8.1 | 10.1 |
| T89-31 | 5.8 | 6.7 | 8.2 | 9.3 |
| T89-32 | 6.2 | 6.9 | 7.8 | 8.8 |

TABLE 2.5-continued

Diameter growth data for TF0003

| | Diameter (mm) Days in greenhouse | | | |
|---|---|---|---|---|
| | 35 | 39 | 46 | 53 |
| T89-33 | 6.3 | 7.1 | 8.5 | 10.2 |
| T89-34 | 5.8 | 6.8 | 8.1 | 9.8 |
| T89-35 | 6.1 | 7.2 | 7.7 | 8.9 |
| T89-36 | 6.3 | 6.9 | 8.7 | 10.0 |
| T89-37 | 5.9 | 7.0 | 8.4 | 9.2 |
| T89-38 | 6.0 | 6.6 | 7.5 | 8.2 |
| T89-39 | 7.1 | 7.6 | 8.4 | 9.7 |
| T89-40 | 6.1 | 7.0 | 8.3 | 9.7 |
| T89-41 | 5.5 | 6.4 | 6.9 | 7.9 |
| T89-42 | 5.4 | 6.2 | 7.8 | 9.1 |
| T89-43 | 6.0 | 6.9 | 8.3 | 9.5 |
| T89-44 | 5.9 | 7.2 | 9.0 | 10.5 |
| T89-45 | 5.0 | 5.7 | 6.2 | 7.8 |
| T89-46 | 6.2 | 7.5 | 8.6 | 9.8 |
| T89-47 | 5.3 | 6.1 | 7.8 | 8.8 |
| T89-48 | 5.4 | 6.2 | 7.6 | 8.2 |
| T89-49 | 7.0 | 8.2 | 9.4 | 10.3 |

Results from growth analysis are specified in the overview table 2.6. The determined growth effects of specified construction group are presented as ratios between construction and wild type group AFH, AFD, AMHGR, ADGR, MFH, MFD, MMHGR and MDC.

TABLE 2.6

Overview table of growth effects of construct TF0003

| Construction group | Average Final Height | Average Final Diameter | Average Maximum Height Growth Rate | Average Maximum Diameter Growth Rate | Maximum Final Height | Maximum Final Diameter | Maximum of Maximum Height Growth Rate | Maximum Maximum Diameter Growth Rate |
|---|---|---|---|---|---|---|---|---|
| TF0003 | 1.00 | 1.00 | 0.93 | 0.93 | 0.95 | 0.96 | 0.91 | 0.73 |

Construction Group TF0011

Tables 2.7 and 2.8 contain growth data for specified construction group and corresponding wild type group. Table rows contain height and diameter measurements of individuals of specified construction group and corresponding wild type group. Time of measurement as number of days in greenhouse is shown in table headers.

TABLE 2.7

Height growth data for TF0011

| | Height (cm) Days in greenhouse | | | | | | |
|---|---|---|---|---|---|---|---|
| | 19 | 25 | 32 | 39 | 48 | 54 | 56 |
| TF0011-1A-1 | 17 | 28 | 48 | 73 | 107 | 133 | 141 |
| TF0011-1A-2 | 23 | 35 | 58 | 80 | 101 | 114 | 118 |
| TF0011-1B | 17 | 27 | 45 | 66 | 94 | 111 | 117 |
| TF0011-2A-1 | 23 | 32 | 56 | 81 | 110 | 125 | 131 |
| TF0011-2A-2 | 18 | 33 | 55 | 76 | 105 | 127 | 134 |
| TF0011-3A-1 | 19 | 31 | 53 | 75 | 105 | 125 | 131 |
| TF0011-3A-2 | 17 | 27 | 47 | 67 | 95 | 116 | 121 |
| TF0011-3B-1 | 17 | 29 | 47 | 72 | 100 | 121 | 127 |
| TF0011-3B-2 | 14 | 24 | 45 | 67 | 101 | 123 | 130 |
| TF0011-4A | 19 | 33 | 57 | 81 | 114 | 135 | 143 |
| T89-01 | 18 | 28 | 49 | 70 | 100 | 126 | 133 |
| T89-02 | 19 | 29 | 51 | 76 | 105 | 128 | 136 |
| T89-03 | 11 | 18 | 36 | 47 | 76 | 93 | 98 |
| T89-04 | 16 | 25 | 48 | 74 | 102 | 126 | 133 |
| T89-05 | 17 | 29 | 49 | 73 | 106 | 128 | 135 |
| T89-06 | 16 | 28 | 51 | 74 | 105 | 127 | 132 |
| T89-07 | 19 | 28 | 51 | 73 | 104 | 125 | 136 |
| T89-08 | 19 | 31 | 52 | 77 | 110 | 130 | 137 |
| T89-09 | 17 | 26 | 44 | 67 | 93 | 114 | 122 |
| T89-10 | 16 | 25 | 44 | 63 | 89 | 108 | 115 |
| T89-11 | 20 | 31 | 47 | 68 | 87 | 114 | 118 |
| T89-12 | 17 | 28 | 48 | 70 | 101 | 117 | 124 |
| T89-13 | 18 | 30 | 52 | 73 | 105 | 125 | 130 |
| T89-14 | 19 | 29 | 44 | 67 | 96 | 116 | 123 |
| T89-15 | 17 | 29 | 49 | 72 | 102 | 124 | 131 |
| T89-16 | 18 | 29 | 50 | 74 | 108 | 129 | 135 |
| T89-17 | 14 | 23 | 43 | 65 | 93 | 116 | 123 |
| T89-18 | 15 | 26 | 48 | 72 | 103 | 128 | 136 |
| T89-19 | 11 | 19 | 38 | 63 | 93 | 115 | 122 |
| T89-20 | 19 | 30 | 52 | 75 | 104 | 126 | 133 |
| T89-21 | 17 | 28 | 48 | 72 | 104 | 128 | 135 |
| T89-22 | 19 | 29 | 49 | 73 | 105 | 123 | 129 |
| T89-23 | 21 | 30 | 54 | 79 | 112 | 135 | 138 |
| T89-24 | 19 | 24 | 37 | 54 | 77 | 100 | 103 |
| T89-25 | 15 | 27 | 46 | 69 | 98 | 117 | 123 |
| T89-26 | 19 | 29 | 50 | 73 | 103 | 127 | 135 |
| T89-27 | 15 | 27 | 47 | 70 | 106 | 129 | 135 |
| T89-28 | 20 | 33 | 55 | 80 | 109 | 130 | 137 |
| T89-29 | 24 | 38 | 62 | 88 | 122 | 143 | 151 |
| T89-30 | 21 | 33 | 56 | 78 | 113 | 132 | 138 |
| T89-31 | 21 | 31 | 52 | 76 | 105 | 126 | 133 |
| T89-32 | 18 | 29 | 50 | 73 | 105 | 129 | 138 |
| T89-33 | 23 | 37 | 61 | 89 | 121 | 143 | 150 |
| T89-34 | 19 | 30 | 52 | 78 | 108 | 130 | 138 |
| T89-35 | 19 | 31 | 55 | 79 | 111 | 134 | 142 |
| T89-36 | 18 | 29 | 52 | 75 | 105 | 127 | 134 |
| T89-37 | 22 | 32 | 52 | 73 | 103 | 124 | 130 |
| T89-38 | 18 | 29 | 51 | 74 | 105 | 128 | 134 |
| T89-39 | 21 | 31 | 51 | 72 | 102 | 119 | 124 |
| T89-40 | 20 | 32 | 51 | 74 | 99 | 121 | 128 |
| T89-41 | 19 | 29 | 50 | 73 | 108 | 130 | 135 |
| T89-42 | 15 | 26 | 46 | 68 | 95 | 113 | 119 |
| T89-43 | 16 | 28 | 48 | 67 | 93 | 113 | 119 |
| T89-44 | 21 | 31 | 50 | 70 | 97 | 116 | 122 |
| T89-45 | 16 | 26 | 48 | 72 | 101 | 123 | 131 |
| T89-46 | 21 | 29 | 50 | 75 | 106 | 129 | 138 |
| T89-47 | 9 | 16 | 34 | 55 | 82 | 106 | 114 |
| T89-48 | 5 | 8 | 17 | 24 | 42 | 52 | 56 |
| T89-49 | 20 | 30 | 50 | 71 | 96 | 117 | 125 |
| T89-50 | 16 | 28 | 50 | 74 | 105 | 128 | 136 |

TABLE 2.7-continued

Height growth data for TF0011

| | Height (cm) Days in greenhouse | | | | | | |
|---|---|---|---|---|---|---|---|
| | 19 | 25 | 32 | 39 | 48 | 54 | 56 |
| T89-51 | 19 | 29 | 51 | 75 | 107 | 128 | 136 |
| T89-52 | 20 | 29 | 50 | 75 | 104 | 124 | 131 |
| T89-53 | 21 | 32 | 50 | 72 | 101 | 118 | 125 |
| T89-54 | 21 | 32 | 55 | 81 | 112 | 133 | 142 |
| T89-55 | 21 | 32 | 56 | 83 | 112 | 133 | 141 |

TABLE 2.8

Diameter growth data for TF0011

| | Diameter (mm) Days in greenhouse | | | |
|---|---|---|---|---|
| | 39 | 48 | 54 | 56 |
| TF0011-1A-1 | 5.7 | 6.9 | 7.6 | 7.9 |
| TF0011-1A-2 | 5.0 | 5.6 | 5.6 | 6.0 |
| TF0011-1B | 5.2 | 7.1 | 7.7 | 7.6 |
| TF0011-2A-1 | 5.8 | 7.9 | 8.1 | 8.0 |
| TF0011-2A-2 | 6.2 | 7.9 | 9.2 | 9.3 |
| TF0011-3A-1 | 6.0 | 8.4 | 8.4 | 8.8 |
| TF0011-3A-2 | 6.0 | 7.5 | 8.0 | 8.5 |
| TF0011-3B-1 | 6.3 | 8.5 | 9.5 | 9.7 |
| TF0011-3B-2 | 7.7 | 8.4 | 9.3 | 9.5 |
| TF0011-4A | 6.7 | 8.1 | 9.2 | 9.6 |
| T89-01 | 6.6 | 8.4 | 8.5 | 9.2 |
| T89-02 | 6.8 | 8.3 | 9.4 | 10.1 |
| T89-03 | 4.6 | 4.9 | 6.1 | 6.1 |
| T89-04 | 6.9 | 8.7 | 10.0 | 9.4 |
| T89-05 | 5.6 | 7.6 | 8.2 | 8.8 |
| T89-06 | 6.9 | 8.2 | 9.6 | 9.3 |
| T89-07 | 6.6 | 7.9 | 9.5 | 9.5 |
| T89-08 | 6.9 | 8.9 | 9.6 | 9.8 |
| T89-09 | 6.1 | 7.6 | 8.6 | 8.7 |
| T89-10 | 5.5 | 7.5 | 8.6 | 8.6 |
| T89-11 | 7.4 | 8.4 | 9.3 | 8.7 |
| T89-12 | 5.9 | 7.4 | 8.7 | 9.5 |
| T89-13 | 6.2 | 7.7 | 9.2 | 9.5 |
| T89-14 | 5.9 | 7.8 | 9.2 | 8.7 |
| T89-15 | 6.8 | 8.1 | 9.4 | 9.7 |
| T89-16 | 7.3 | 9.2 | 10.6 | 10.3 |
| T89-17 | 6.4 | 8.0 | 8.9 | 9.1 |
| T89-18 | 7.0 | 7.5 | 8.1 | 8.8 |
| T89-19 | 5.6 | 7.4 | 8.6 | 8.9 |
| T89-20 | 6.5 | 8.3 | 8.6 | 9.5 |
| T89-21 | 6.2 | 8.1 | 8.0 | 8.7 |
| T89-22 | 6.2 | 8.5 | 9.3 | 10.1 |
| T89-23 | 6.2 | 8.1 | 9.2 | 9.5 |
| T89-24 | 3.1 | 4.6 | 5.0 | 4.5 |
| T89-25 | 5.9 | 7.7 | 8.5 | 8.9 |
| T89-26 | 6.2 | 7.8 | 8.6 | 9.5 |
| T89-27 | 6.1 | 7.6 | 8.2 | 8.6 |
| T89-28 | 6.9 | 9.0 | 10.7 | 10.5 |
| T89-29 | 7.8 | 8.4 | 10.3 | 10.2 |
| T89-30 | 6.4 | 8.5 | 9.4 | 9.9 |
| T89-31 | 6.8 | 8.6 | 8.8 | 9.5 |
| T89-32 | 6.7 | 8.4 | 10.2 | 10.9 |
| T89-33 | 7.1 | 8.7 | 9.4 | 11.4 |
| T89-34 | 7.1 | 8.5 | 11.1 | 10.9 |
| T89-35 | 6.7 | 9.0 | 8.9 | 11.4 |
| T89-36 | 6.2 | 8.0 | 8.5 | 8.5 |
| T89-37 | 5.6 | 7.1 | 7.8 | 8.7 |
| T89-38 | 5.8 | 7.8 | 8.8 | 8.7 |
| T89-39 | 6.2 | 8.1 | 9.2 | 9.3 |
| T89-40 | 6.2 | 7.9 | 9.6 | 9.5 |
| T89-41 | 5.9 | 8.2 | 8.9 | 9.5 |
| T89-42 | 6.8 | 8.4 | 9.1 | 10.4 |
| T89-43 | 6.7 | 8.5 | 9.7 | 9.3 |
| T89-44 | 7.1 | 9.1 | 9.2 | 9.4 |
| T89-45 | 6.6 | 7.8 | 9.2 | 9.2 |
| T89-46 | 6.8 | 9.3 | 10.2 | 10.0 |
| T89-47 | 5.3 | 7.0 | 7.9 | 8.4 |
| T89-48 | 2.3 | 3.0 | 3.2 | 3.5 |
| T89-49 | 7.5 | 8.7 | 9.1 | 9.8 |
| T89-50 | 6.8 | 8.6 | 9.3 | 8.9 |
| T89-51 | 7.2 | 8.3 | 9.2 | 9.1 |
| T89-52 | 7.5 | 8.8 | 9.4 | 9.7 |
| T89-53 | 7.3 | 9.3 | 9.5 | 10.2 |
| T89-54 | 7.0 | 9.0 | 9.2 | 9.6 |
| T89-55 | 7.0 | 8.9 | 9.2 | 9.8 |

Results from growth analysis are specified in the overview table 2.9. The determined growth effects of specified construction group are presented as ratios between construction and wild type group AFH, AFD, AMHGR, ADGR, MFH, MFD, MMHGR and MDC.

TABLE 2.9

Overview table of growth effects of construct TF0011

| Construction group | Average Final Height | Average Final Diameter | Average Maximum Height Growth Rate | Average Diameter Growth Rate | Maximum Final Height | Maximum Final Diameter | Maximum of Maximum Height Growth Rate | Maximum Diameter Growth Rate |
|---|---|---|---|---|---|---|---|---|
| TF0011 | 1.00 | 0.92 | 1.00 | 0.83 | 0.95 | 0.85 | 1.04 | 0.77 |

Construction Group TF0013rp2

Tables 2.10 and 2.11 contain growth data for specified construction group and corresponding wild type group. Table rows contain height and diameter measurements of individuals of specified construction group and corresponding wild type group. Time of measurement as number of days in greenhouse is shown in table headers.

TABLE 2.10

Height growth data for TF0013rp2

| | Height (cm) Days in greenhouse | | | | | | | | |
|---|---|---|---|---|---|---|---|---|---|
| | 15 | 19 | 26 | 33 | 37 | 40 | 47 | 51 | 54 |
| TF0013rp2-1A-1 | 20 | 25 | 39 | 48 | 59 | 68 | 89 | 100 | 111 |
| TF0013rp2-1A-2 | 18 | 22 | 34 | 52 | 64 | 74 | 101 | 115 | 131 |
| TF0013rp2-1A-3 | 21 | 25 | 38 | 54 | 67 | 75 | 104 | 116 | 133 |
| TF0013rp2-3BA-1 | 21 | 26 | 39 | 57 | 73 | 84 | 113 | 125 | 137 |
| TF0013rp2-3BA-2 | 20 | 23 | 34 | 52 | 65 | 75 | 101 | 113 | 128 |
| TF0013rp2-3BA-3 | 20 | 24 | 36 | 55 | 71 | 83 | 115 | 131 | 145 |
| T89-20 | 21 | 26 | 39 | 58 | 73 | 82 | 111 | 130 | 134 |
| T89-21 | 21 | 24 | 34 | 51 | 64 | 72 | 97 | 103 | 125 |
| T89-22 | 19 | 23 | 32 | 48 | 60 | 70 | 96 | 111 | 123 |
| T89-23 | 21 | 24 | 34 | 51 | 63 | 70 | 94 | 112 | 122 |
| T89-24 | 19 | 22 | 30 | 46 | 59 | 68 | 90 | 103 | 115 |
| T89-25 | 22 | 30 | 39 | 57 | 72 | 81 | 106 | 112 | 130 |
| T89-26 | 21 | 24 | 35 | 48 | 60 | 70 | 98 | 111 | 130 |
| T89-27 | 21 | 24 | 34 | 48 | 60 | 70 | 93 | 106 | 120 |
| T89-28 | 20 | 22 | 32 | 48 | 60 | 70 | 93 | 105 | 116 |

TABLE 2.11

Diameter growth data for TF0013rp2

| | Diameter (mm) Days in greenhouse | | | |
|---|---|---|---|---|
| | 33 | 40 | 47 | 54 |
| TF0013rp2-1A-1 | 3.8 | 5.0 | 6.3 | 6.8 |
| TF0013rp2-1A-2 | 5.4 | 5.7 | 7.3 | 8.1 |
| TF0013rp2-1A-3 | 4.4 | 5.4 | 6.6 | 7.6 |
| TF0013rp2-3BA-1 | 5.0 | 6.3 | 7.1 | 8.5 |
| TF0013rp2-3BA-2 | 4.2 | 5.4 | 7.0 | 8.5 |
| TF0013rp2-3BA-3 | 5.0 | 6.5 | 7.3 | 8.1 |
| T89-20 | 4.8 | 6.2 | 6.3 | 6.9 |
| T89-21 | 3.8 | 5.5 | 6.0 | 6.9 |
| T89-22 | 4.5 | 6.2 | 6.6 | 7.5 |
| T89-21 | 3.8 | 5.5 | 6.0 | 6.9 |
| T89-22 | 4.5 | 6.2 | 6.6 | 7.5 |
| T89-23 | 3.8 | 4.8 | 5.6 | 6.2 |
| T89-24 | 3.8 | 4.9 | 5.8 | 7.2 |
| T89-25 | 4.8 | 5.9 | 7.4 | 8.9 |
| T89-26 | 4.4 | 6.2 | 7.0 | 7.8 |
| T89-27 | 4.9 | 6.4 | 7.3 | 8.3 |
| T89-28 | 4.5 | 4.8 | 5.8 | 7.2 |

Results from growth analysis are specified in the overview table 2.12. The determined growth effects of specified construction group are presented as ratios between construction and wild type group AFH, AFD, AMHGR, ADGR, MFH, MFD, MMHGR and MDC.

TABLE 2.12

Overview table of growth effects of construct TF0013rp2

| Construction group | Average Final Height | Average Final Diameter | Average Maximum Height Growth Rate | Average Diameter Growth Rate | Maximum Final Height | Maximum Final Diameter | Maximum of Maximum Height Growth Rate | Maximum Diameter Growth Rate |
|---|---|---|---|---|---|---|---|---|
| TF0013rp2 | 1.04 | 1.03 | 1.08 | 1.06 | 1.08 | 0.91 | 1.06 | 0.96 |

Construction Group TF0045

This construct induces increased growth. The final height is 6% higher comparing the average of the construction group and wild type control group. The final height is 11% higher comparing the largest individuals of the construction group and wild type control group. The maximum height growth rate is 9% higher comparing the average of the construction group and wild type control group. The maximum height growth rate is 12% higher comparing the largest individuals of the construction group and wild type control group. The final diameter is 10% higher comparing the average of the construction group and wild type control group. The final diameter is 9% higher comparing the largest individuals of the construction group and wild type control group. The TF0045 construction group meets growth difference selection criterion (1) as shown in table 2.15.

Tables 2.13 and 2.14 contain growth data for specified construction group and corresponding wild type group. Table rows contain height and diameter measurements of individuals of specified construction group and corresponding wild type group. Time of measurement as number of days in greenhouse is shown in table headers.

TABLE 2.13

Height growth data for TF0045

| | Height (cm) Days in greenhouse | | | | | | | | |
|---|---|---|---|---|---|---|---|---|---|
| | 18 | 25 | 28 | 32 | 36 | 39 | 46 | 53 | 55 |
| TF0045-1A-1 | 25 | 39 | 53 | 66 | 79 | 87 | 106 | 125 | 128 |
| TF0045-1A-2 | 15 | 25 | 34 | 44 | 57 | 66 | 89 | 114 | 121 |
| TF0045-1A-3 | 18 | 34 | 45 | 55 | 68 | 79 | 104 | 133 | 141 |
| TF0045-1B-1 | 24 | 43 | 57 | 68 | 84 | 95 | 126 | 150 | 156 |
| TF0045-1B-2 | 24 | 43 | 57 | 70 | 85 | 95 | 120 | 147 | 154 |
| TF0045-1B-3 | 25 | 30 | 34 | 43 | 54 | 64 | 84 | 107 | 115 |
| TF0045-2B-1 | 21 | 33 | 45 | 53 | 64 | 76 | 103 | 128 | 136 |
| TF0045-2B-3 | 19 | 32 | 42 | 51 | 64 | 72 | 96 | 120 | 128 |
| T89-01 | 18 | 32 | 43 | 54 | 66 | 76 | 98 | 124 | 133 |
| T89-02 | 20 | 33 | 43 | 53 | 67 | 76 | 101 | 124 | 129 |
| T89-03 | 17 | 31 | 43 | 53 | 68 | 76 | 102 | 128 | 135 |
| T89-04 | 19 | 33 | 44 | 54 | 67 | 74 | 97 | 122 | 129 |
| T89-05 | 20 | 33 | 44 | 54 | 67 | 76 | 100 | 121 | 129 |
| T89-06 | 18 | 31 | 42 | 53 | 67 | 76 | 97 | 121 | 128 |
| T89-07 | 16 | 28 | 41 | 53 | 65 | 74 | 96 | 121 | 129 |
| T89-08 | 19 | 34 | 43 | 53 | 65 | 75 | 98 | 123 | 131 |
| T89-09 | 20 | 30 | 40 | 52 | 64 | 73 | 97 | 119 | 125 |
| T89-10 | 21 | 33 | 41 | 49 | 61 | 70 | 92 | 114 | 121 |
| T89-11 | 18 | 31 | 40 | 49 | 61 | 71 | 94 | 117 | 123 |
| T89-12 | 18 | 31 | 40 | N/A | 60 | 68 | 90 | 107 | 115 |
| T89-13 | 19 | 35 | 47 | 58 | 70 | 78 | 103 | 128 | 135 |
| T89-14 | 19 | 31 | 40 | 50 | 61 | 72 | 93 | 118 | 124 |
| T89-15 | 20 | 32 | 41 | 50 | 62 | 70 | 91 | 114 | 120 |
| T89-16 | 18 | 30 | 39 | 49 | 62 | 71 | 92 | 114 | 122 |
| T89-17 | 17 | 33 | 45 | 55 | 70 | 78 | 104 | 129 | 136 |

TABLE 2.13-continued

Height growth data for TF0045

| | Height (cm) Days in greenhouse | | | | | | | | |
|---|---|---|---|---|---|---|---|---|---|
| | 18 | 25 | 28 | 32 | 36 | 39 | 46 | 53 | 55 |
| T89-18 | 19 | 32 | 44 | 56 | 71 | 82 | 106 | 130 | 137 |
| T89-19 | 16 | 26 | 36 | 46 | 51 | 69 | 89 | 112 | 119 |
| T89-20 | 16 | 31 | 41 | 49 | 60 | 71 | 91 | 111 | 118 |
| T89-21 | 20 | 31 | 44 | 54 | 68 | 76 | 99 | 122 | 127 |
| T89-22 | 14 | 26 | 37 | 46 | 61 | 72 | 96 | 120 | 127 |
| T89-23 | 19 | 32 | 40 | 50 | 63 | 73 | 100 | 121 | 127 |
| T89-24 | 20 | 31 | 41 | 47 | 58 | 68 | 90 | 111 | 117 |
| T89-25 | 20 | 36 | 45 | 57 | 69 | 78 | 101 | 127 | 134 |
| T89-26 | 20 | 37 | 49 | 58 | 71 | 80 | 107 | 131 | 140 |
| T89-27 | 19 | 34 | 44 | 55 | 71 | 81 | 107 | 131 | 138 |
| T89-28 | 17 | 35 | 44 | 56 | 68 | 76 | 99 | 126 | 132 |
| T89-29 | 17 | 32 | 45 | 55 | 68 | 78 | 101 | 125 | 132 |
| T89-30 | 18 | 31 | 41 | 50 | 63 | 72 | 95 | 119 | 125 |
| T89-31 | 17 | 27 | 35 | 45 | 58 | 67 | 87 | 108 | 116 |
| T89-32 | 19 | 32 | 44 | 52 | 65 | 74 | 98 | 121 | 127 |
| T89-33 | 20 | 33 | 43 | 53 | 64 | 74 | 96 | 119 | 126 |
| T89-34 | 19 | 34 | 44 | 55 | 68 | 78 | 100 | 124 | 130 |
| T89-35 | 17 | 30 | 40 | 51 | 64 | 74 | 95 | 116 | 122 |
| T89-36 | 18 | 30 | 40 | 49 | 62 | 71 | 91 | 114 | 121 |
| T89-82 | 21 | 33 | 43 | 54 | 65 | 75 | 98 | 118 | 125 |
| T89-83 | 22 | 35 | 47 | 55 | 71 | 80 | 105 | 130 | 137 |
| T89-85 | 21 | 36 | 46 | 56 | 67 | 76 | 98 | 123 | 131 |

TABLE 2.14

Diameter growth data for TF0045

| | Diameter (mm) Days in greenhouse | | | | |
|---|---|---|---|---|---|
| | 32 | 39 | 46 | 53 | 55 |
| TF0045-1A-1 | 5.8 | 6.5 | 6.9 | 7.5 | 7.6 |
| TF0045-1A-2 | 4.3 | 6.8 | 8.4 | 8.7 | 9.2 |
| TF0045-1A-3 | 5.6 | 6.7 | 7.9 | 9.2 | 9.2 |
| TF0045-1B-1 | 5.9 | 7.1 | 8.8 | 9.7 | 10.0 |
| TF0045-1B-2 | 6.8 | 7.8 | 8.4 | 10.1 | 9.9 |
| TF0045-1B-3 | 4.3 | 4.4 | 4.6 | 5.9 | 5.9 |
| TF0045-2B-1 | 5.3 | 7.1 | 7.4 | 8.5 | 8.8 |
| TF0045-2B-3 | 5.4 | 6.2 | 8.0 | 8.9 | 8.8 |
| T89-01 | 5.2 | 6.0 | 6.8 | 8.2 | 7.6 |
| T89-02 | 4.5 | 5.8 | 7.1 | 8.6 | 8.3 |
| T89-03 | 4.4 | 5.7 | 6.8 | 7.9 | 8.1 |
| T89-04 | 4.4 | 6.0 | 6.9 | 8.6 | 8.5 |
| T89-05 | 4.6 | 5.8 | 6.7 | 7.9 | 8.0 |
| T89-06 | 4.7 | 5.9 | 7.2 | 8.1 | 9.2 |
| T89-07 | 4.8 | 5.5 | 6.2 | 6.9 | 7.1 |
| T89-08 | 4.5 | 5.4 | 6.0 | 6.9 | 7.1 |
| T89-09 | 4.7 | 5.6 | 6.7 | 8.8 | 8.0 |
| T89-10 | 4.1 | 4.9 | 5.6 | 7.1 | 7.0 |
| T89-11 | 3.8 | 5.3 | 7.3 | 8.0 | 7.6 |
| T89-12 | N/A | 5.1 | 6.2 | 7.3 | 6.9 |
| T89-13 | 4.8 | 5.7 | 6.5 | 7.6 | 7.6 |
| T89-14 | 4.2 | 5.5 | 6.6 | 7.6 | 6.5 |
| T89-15 | 5.0 | 6.1 | 7.2 | 7.9 | 8.3 |
| T89-16 | 4.4 | 5.6 | 6.2 | 7.3 | 7.9 |
| T89-17 | 4.8 | 6.7 | 7.0 | 8.3 | 8.4 |
| T89-18 | 4.2 | 5.5 | 6.7 | 7.3 | 7.4 |
| T89-19 | 4.7 | 5.5 | 6.8 | 7.2 | 7.8 |
| T89-20 | 4.5 | 5.6 | 6.5 | 7.0 | 7.3 |
| T89-21 | 4.9 | 5.6 | 6.4 | 7.4 | 7.6 |
| T89-22 | 4.3 | 5.4 | 6.5 | 7.3 | 7.6 |
| T89-23 | 3.9 | 5.5 | 6.7 | 7.7 | 7.0 |
| T89-24 | 4.3 | 5.9 | 6.8 | 8.1 | 7.9 |
| T89-25 | 4.7 | 6.5 | 7.5 | 9.2 | 9.1 |
| T89-26 | 5.4 | 5.9 | 7.7 | 8.6 | 8.8 |
| T89-27 | 4.7 | 5.6 | 7.4 | 7.9 | 8.0 |
| T89-28 | 4.7 | 5.7 | 6.3 | 7.2 | 7.4 |
| T89-29 | 4.8 | 5.6 | 6.6 | 7.7 | 8.1 |
| T89-30 | 4.6 | 5.5 | 6.7 | 7.3 | 7.3 |
| T89-31 | 4.3 | 5.8 | 6.3 | 7.5 | 7.6 |
| T89-32 | 4.6 | 5.9 | 7.6 | 9.3 | 9.1 |
| T89-33 | 4.4 | 5.3 | 6.2 | 7.1 | 7.1 |
| T89-34 | 4.6 | 5.6 | 6.8 | 8.1 | 8.7 |
| T89-35 | 5.3 | 6.0 | 7.5 | 8.8 | 8.9 |
| T89-36 | 4.4 | 6.1 | 6.9 | 8.1 | 8.6 |
| T89-82 | 4.7 | 5.3 | 6.5 | 7.5 | 7.4 |
| T89-83 | 4.7 | 6.1 | 7.1 | 8.3 | 8.3 |
| T89-85 | 5.1 | 6.3 | 7.3 | 7.7 | 8.2 |

Results from growth analysis are specified in the overview table 2.15. The determined growth effects of specified construction group are presented as ratios between construction and wild type group AFH, AFD, AMHGR, ADGR, MFH, MFD, MMHGR and MDC.

TABLE 2.15

Overview table of growth effects of construct TF0045

| Construction group | Average Final Height | Average Final Diameter | Average Maximum Height Growth Rate | Average Diameter Growth Rate | Maximum Final Height | Maximum Final Diameter | Maximum of Maximum Height Growth Rate | Maximum Maximum Diameter Growth Rate |
|---|---|---|---|---|---|---|---|---|
| TF0045 | 1.06 | 1.10 | 1.09 | 0.98 | 1.11 | 1.09 | 1.12 | 0.94 |

Construction Group TF0052Rp1

Tables 2.16 and 2.17 contain growth data for specified construction group and corresponding wild type group. Table rows contain height and diameter measurements of individuals of specified construction group and corresponding wild type group. Time of measurement as number of days in greenhouse is shown in table headers.

TABLE 2.16

Height growth data for TF0052Rp1

| | Height (cm) Days in greenhouse | | | | | | | | | |
|---|---|---|---|---|---|---|---|---|---|---|
| | 20 | 25 | 29 | 35 | 41 | 46 | 50 | 53 | 57 | 60 |
| TF0052rp1-2A-1 | 21 | 29 | 38 | 53 | 74 | 90 | 103 | 115 | 127 | 138 |
| TF0052rp1-2A-2 | 19 | 28 | 37 | 52 | 68 | 83 | 97 | 105 | 116 | 126 |
| TF0052rp1-2A-3 | 15 | 23 | 33 | 50 | 69 | 85 | 97 | 108 | 117 | 129 |
| TF0052rp1-2B-1 | 18 | 26 | 32 | 47 | 59 | 75 | 82 | 91 | 100 | 109 |
| TF0052rp1-2B-2 | 18 | 23 | 27 | 35 | 49 | 67 | 75 | 84 | 94 | 101 |
| TF0052rp1-2B-3 | 18 | 21 | 28 | 38 | 50 | 63 | 68 | 75 | 83 | 89 |
| T89-01 | 17 | 26 | 31 | 45 | 61 | 76 | 87 | 95 | 107 | 116 |
| T89-02 | 16 | 21 | 26 | 38 | 53 | 67 | 76 | 83 | N/A | N/A |
| T89-03 | 18 | 24 | 32 | 47 | 64 | 78 | 87 | 96 | 106 | 115 |
| T89-04 | 18 | 26 | 35 | 50 | 66 | 80 | 87 | 96 | 107 | 115 |
| T89-05 | 17 | 26 | 33 | 44 | 57 | 73 | 81 | 91 | 100 | 107 |
| T89-06 | 16 | 21 | 28 | 40 | 55 | 74 | 79 | 89 | 99 | 106 |
| T89-07 | 17 | 23 | 31 | 43 | 57 | 71 | 80 | 88 | 98 | 107 |
| T89-08 | 15 | 20 | 26 | 37 | 51 | 65 | 75 | 84 | 94 | 100 |
| T89-09 | 18 | 25 | 32 | 46 | 61 | 74 | 85 | 93 | 103 | 112 |
| T89-10 | 19 | 25 | 32 | 46 | 60 | 75 | 86 | 95 | 104 | 112 |
| T89-11 | 20 | 27 | 36 | 51 | 68 | 86 | 98 | 107 | 120 | 127 |
| T89-12 | 19 | 27 | 36 | 50 | 67 | 80 | 89 | 97 | 108 | 118 |
| T89-13 | 18 | 25 | 32 | 45 | 59 | 75 | 83 | 92 | 101 | 108 |
| T89-14 | 18 | 23 | 26 | 36 | 51 | 65 | 72 | 79 | 89 | 96 |
| T89-15 | 17 | 21 | 28 | 39 | 53 | 70 | 78 | 87 | 97 | 105 |
| T89-16 | 19 | 25 | 32 | 43 | 57 | 71 | 81 | 90 | 101 | 109 |
| T89-17 | 16 | 20 | 29 | 41 | 54 | 68 | 78 | 84 | 93 | 101 |
| T89-18 | 16 | 23 | 30 | 45 | 63 | 78 | 87 | 94 | 103 | 110 |
| T89-19 | 16 | 22 | 28 | 42 | 56 | 69 | 79 | 89 | 100 | 107 |
| T89-20 | 18 | 25 | 32 | 47 | 63 | 78 | 89 | 99 | 109 | 115 |
| T89-21 | 19 | 27 | 34 | 50 | 67 | 82 | 92 | 102 | 111 | 120 |
| T89-22 | 19 | 25 | 32 | 44 | 58 | 76 | 84 | 93 | 102 | 109 |
| T89-23 | 18 | 26 | 33 | 47 | 63 | 79 | 88 | 99 | 108 | 116 |
| T89-24 | 16 | 24 | 28 | 42 | 53 | 70 | 78 | 85 | 94 | 103 |
| T89-25 | 16 | 25 | 32 | 45 | 61 | 76 | 85 | 95 | 107 | 114 |
| T89-26 | 16 | 20 | 26 | 38 | 52 | 68 | 78 | 86 | 97 | 103 |
| T89-27 | 16 | 21 | 25 | 35 | 48 | 61 | 70 | 78 | N/A | 98 |
| T89-28 | 14 | 18 | 25 | 38 | 51 | 64 | 73 | 81 | 90 | 96 |
| T89-29 | 7 | 13 | 18 | 30 | 45 | 60 | 69 | 77 | 90 | 98 |
| T89-30 | 15 | 22 | 29 | 42 | 55 | 69 | 80 | 88 | 97 | 106 |
| T89-31 | 21 | 29 | 37 | 50 | 65 | 80 | 88 | 98 | 108 | 116 |
| T89-32 | 19 | 24 | 32 | 42 | 55 | 70 | 78 | 87 | 96 | 105 |

TABLE 2.17

Diameter growth data for TF0052Rp1

| | Diameter (mm) Days in greenhouse | | | | |
|---|---|---|---|---|---|
| | 35 | 41 | 46 | 53 | 60 |
| TF0052rp1-2A-1 | 5.4 | 6.5 | 7.2 | 8.6 | 9.4 |
| TF0052rp1-2A-2 | 4.9 | 6.6 | 6.9 | 7.3 | 8.3 |
| TF0052rp1-2A-3 | 5.3 | 6.7 | 7.5 | 8.4 | 9.5 |
| TF0052rp1-2B-1 | 5.0 | 6.2 | 6.9 | 9.0 | 8.0 |
| TF0052rp1-2B-2 | 4.9 | 5.9 | 6.6 | 6.8 | 8.1 |
| TF0052rp1-2B-3 | 3.3 | 4.2 | 4.4 | 5.1 | 5.7 |
| T89-01 | 4.7 | 6.0 | 6.5 | 6.9 | 8.3 |
| T89-02 | 4.4 | 5.7 | 6.6 | 7.6 | 7.8 |
| T89-03 | 4.7 | 6.3 | 6.7 | 7.7 | 8.4 |
| T89-04 | 4.7 | 6.0 | 7.1 | 8.0 | 8.5 |
| T89-05 | 4.0 | 5.3 | 6.3 | 7.8 | 8.1 |
| T89-06 | 4.6 | 5.9 | 6.3 | 7.7 | 8.2 |
| T89-07 | 4.6 | 6.1 | 6.5 | 7.9 | 8.5 |
| T89-08 | 4.0 | 5.2 | 5.8 | 6.9 | 7.1 |
| T89-09 | 4.4 | 5.8 | 6.4 | 7.6 | 8.2 |
| T89-10 | 4.9 | 6.0 | 6.6 | 7.4 | 8.5 |
| T89-11 | 4.7 | 5.8 | 6.4 | 7.9 | 8.3 |
| T89-12 | 4.7 | 5.9 | 7.3 | 7.4 | 7.6 |
| T89-13 | 5.9 | 5.9 | 6.7 | 7.5 | 8.3 |
| T89-14 | 4.5 | 5.2 | 5.8 | 6.1 | 7.0 |
| T89-15 | 4.7 | N/A | 6.0 | 6.4 | 7.3 |
| T89-16 | 4.5 | 5.6 | 7.7 | 7.5 | 8.6 |
| T89-17 | 4.1 | 5.4 | 6.0 | 6.8 | 7.5 |
| T89-18 | 4.4 | 5.8 | 6.0 | 7.7 | 8.3 |
| T89-19 | 4.7 | 5.8 | 7.1 | 8.5 | 9.4 |
| T89-20 | 4.7 | 5.8 | 6.6 | 7.4 | 8.3 |
| T89-21 | 4.7 | 6.2 | 6.3 | 7.7 | 8.5 |
| T89-22 | 4.2 | 5.1 | 6.3 | 6.9 | 8.0 |
| T89-23 | 4.6 | 5.8 | 7.1 | 7.5 | 8.3 |
| T89-24 | 4.4 | 5.8 | 6.9 | 7.7 | 8.8 |
| T89-25 | 4.5 | 5.4 | 6.2 | 8.0 | 8.7 |
| T89-26 | 4.1 | 5.4 | 6.0 | 7.2 | 8.0 |
| T89-27 | 4.5 | 5.7 | 6.5 | 7.9 | 9.2 |
| T89-28 | 4.3 | 5.1 | 6.0 | 6.6 | 7.7 |
| T89-29 | 3.5 | 4.7 | 5.5 | 6.3 | 7.1 |
| T89-30 | 4.1 | 5.4 | 5.8 | 7.2 | 7.8 |
| T89-31 | 5.0 | 5.8 | 6.8 | 7.3 | 8.2 |
| T89-32 | 4.4 | 6.4 | 6.6 | 8.0 | 8.4 |

Results from growth analysis are specified in the overview table 2.18. The determined growth effects of specified construction group are presented as ratios between construction and wild type group AFH, AFD, AMHGR, ADGR, MFH, MFD, MMHGR and MDC.

TABLE 2.18

Overview table of growth effects of construct TF0052Rp1

| Construction group | Average Final Height | Average Final Diameter | Average Maximum Height Growth Rate | Average Diameter Growth Rate | Maximum Final Height | Maximum Final Diameter | Maximum of Maximum Height Growth Rate | Maximum Diameter Growth Rate |
|---|---|---|---|---|---|---|---|---|
| TF0052Rp1 | 1.06 | 1.00 | 1.04 | 0.91 | 1.09 | 1.02 | 1.06 | 0.86 |

Construction Group TF0076Rp2

This construct induces increased growth. The final height is 13% higher comparing the average of the construction group and wild type control group. The final height is 13% higher comparing the largest individuals of the construction group and wild type control group. The maximum height growth rate is 13% higher comparing the average of the construction group and wild type control group. The maximum height growth rate is 18% higher comparing the largest individuals of the construction group and wild type control group. The TF0076Rp2 construction group meets the more stringent level of growth difference selection criterion (1) as shown in table 2.21.

Tables 2.19 and 2.20 contain growth data for specified construction group and corresponding wild type group. Table rows contain height and diameter measurements of individuals of specified construction group and corresponding wild type group. Time of measurement as number of days in greenhouse is shown in table headers.

TABLE 2.19

Height growth data for TF0076Rp2

| | Height (cm) Days in greenhouse | | | | | | | | | |
|---|---|---|---|---|---|---|---|---|---|---|
| | 20 | 25 | 29 | 35 | 41 | 46 | 50 | 53 | 57 | 60 |
| TF0076rp2-3BB-1 | 15 | 22 | 29 | 43 | 59 | 72 | 84 | 93 | 103 | 111 |
| TF0076rp2-3BB-2 | 20 | 28 | 39 | 53 | 70 | 85 | 95 | 104 | 115 | 120 |
| TF0076rp2-3BB-3 | 17 | 25 | 33 | 48 | 67 | 81 | 92 | 101 | 112 | 122 |
| TF0076rp2-4B-1 | 15 | 26 | 35 | 55 | 76 | 97 | 111 | 122 | 134 | 143 |
| TF0076rp2-4B-2 | 19 | 28 | 37 | 53 | 72 | 89 | 103 | 111 | 124 | 135 |
| TF0076rp2-4B-3 | 20 | 28 | 40 | 53 | 74 | 93 | 104 | 114 | 124 | 134 |
| TF0076rp2-5BA-1 | 18 | 24 | 30 | 39 | 49 | 65 | 74 | 84 | 96 | 103 |
| TF0076rp2-5BA-2 | 17 | 26 | 36 | 49 | 63 | 82 | 92 | 100 | 112 | 121 |
| TF0076rp2-5BA-3 | 16 | 24 | 31 | 46 | 65 | 84 | 93 | 103 | 116 | 126 |
| TF0076rp2-5BB-1 | 17 | 24 | 30 | 45 | 61 | 76 | 86 | 97 | 109 | 119 |
| TF0076rp2-5BB-2 | 15 | 22 | 29 | 42 | 58 | 73 | 86 | 95 | 106 | 118 |
| TF0076rp2-5BB-3 | 20 | 27 | 36 | 50 | 69 | N/A | 94 | 100 | 109 | 118 |
| T89-01 | 17 | 26 | 31 | 45 | 61 | 76 | 87 | 95 | 107 | 116 |
| T89-02 | 16 | 21 | 26 | 38 | 53 | 67 | 76 | 83 | N/A | N/A |
| T89-03 | 18 | 24 | 32 | 47 | 64 | 78 | 87 | 96 | 106 | 115 |
| T89-04 | 18 | 26 | 35 | 50 | 66 | 80 | 87 | 96 | 107 | 115 |
| T89-05 | 17 | 26 | 33 | 44 | 57 | 73 | 81 | 91 | 100 | 107 |
| T89-06 | 16 | 21 | 28 | 40 | 55 | 74 | 79 | 89 | 99 | 106 |
| T89-07 | 17 | 23 | 31 | 43 | 57 | 71 | 80 | 88 | 98 | 107 |
| T89-08 | 15 | 20 | 26 | 37 | 51 | 65 | 75 | 84 | 94 | 100 |
| T89-09 | 18 | 25 | 32 | 46 | 61 | 74 | 85 | 93 | 103 | 112 |

TABLE 2.19-continued

Height growth data for TF0076Rp2

| | Height (cm) Days in greenhouse | | | | | | | | | |
|---|---|---|---|---|---|---|---|---|---|---|
| | 20 | 25 | 29 | 35 | 41 | 46 | 50 | 53 | 57 | 60 |
| T89-10 | 19 | 25 | 32 | 46 | 60 | 75 | 86 | 95 | 104 | 112 |
| T89-11 | 20 | 27 | 36 | 51 | 68 | 86 | 98 | 107 | 120 | 127 |
| T89-12 | 19 | 27 | 36 | 50 | 67 | 80 | 89 | 97 | 108 | 118 |
| T89-13 | 18 | 25 | 32 | 45 | 59 | 75 | 83 | 92 | 101 | 108 |
| T89-14 | 18 | 23 | 26 | 36 | 51 | 65 | 72 | 79 | 89 | 96 |
| T89-15 | 17 | 21 | 28 | 39 | 53 | 70 | 78 | 87 | 97 | 105 |
| T89-16 | 19 | 25 | 32 | 43 | 57 | 71 | 81 | 90 | 101 | 109 |
| T89-17 | 16 | 20 | 29 | 41 | 54 | 68 | 78 | 84 | 93 | 101 |
| T89-18 | 16 | 23 | 30 | 45 | 63 | 78 | 87 | 94 | 103 | 110 |
| T89-19 | 16 | 22 | 28 | 42 | 56 | 69 | 79 | 89 | 100 | 107 |
| T89-20 | 18 | 25 | 32 | 47 | 63 | 78 | 89 | 99 | 109 | 115 |
| T89-21 | 19 | 27 | 34 | 50 | 67 | 82 | 92 | 102 | 111 | 120 |
| T89-22 | 19 | 25 | 32 | 44 | 58 | 76 | 84 | 93 | 102 | 109 |
| T89-23 | 18 | 26 | 33 | 47 | 63 | 79 | 88 | 99 | 108 | 116 |
| T89-24 | 16 | 24 | 28 | 42 | 53 | 70 | 78 | 85 | 94 | 103 |
| T89-25 | 16 | 25 | 32 | 45 | 61 | 76 | 85 | 95 | 107 | 114 |
| T89-26 | 16 | 20 | 26 | 38 | 52 | 68 | 78 | 86 | 97 | 103 |
| T89-27 | 16 | 21 | 25 | 35 | 48 | 61 | 70 | 78 | N/A | 98 |
| T89-28 | 14 | 18 | 25 | 38 | 51 | 64 | 73 | 81 | 90 | 96 |
| T89-29 | 7 | 13 | 18 | 30 | 45 | 60 | 69 | 77 | 90 | 98 |
| T89-30 | 15 | 22 | 29 | 42 | 55 | 69 | 80 | 88 | 97 | 106 |
| T89-31 | 21 | 29 | 37 | 50 | 65 | 80 | 88 | 98 | 108 | 116 |
| T89-32 | 19 | 24 | 32 | 42 | 55 | 70 | 78 | 87 | 96 | 105 |

TABLE 2.20

Diameter growth data for TF0076Rp2

| | Diameter (mm) Days in greenhouse | | | | |
|---|---|---|---|---|---|
| | 35 | 41 | 46 | 53 | 60 |
| TF0076rp2-3BB-1 | 4.1 | 5.3 | 6.4 | 8.3 | 8.2 |
| TF0076rp2-3BB-2 | 4.6 | 5.5 | 6.9 | 7.4 | 8.4 |
| TF0076rp2-3BB-3 | 5.3 | 6.6 | 7.3 | 8.5 | 9.1 |
| TF0076rp2-4B-1 | 4.4 | 5.8 | 6.8 | 7.5 | 8.0 |
| TF0076rp2-4B-2 | 4.4 | 5.7 | 6.5 | 7.0 | 7.9 |
| TF0076rp2-4B-3 | 4.9 | 6.2 | 7.5 | 8.2 | 9.1 |
| TF0076rp2-5BA-1 | 4.7 | 5.5 | 6.5 | 6.8 | 7.3 |
| TF0076rp2-5BA-2 | 4.4 | 6.2 | 6.4 | 7.4 | 8.1 |
| TF0076rp2-5BA-3 | 4.4 | 5.5 | 6.8 | 7.8 | 8.6 |
| TF0076rp2-5BB-1 | 4.5 | 5.8 | 6.1 | 7.3 | 8.0 |
| TF0076rp2-5BB-2 | 4.1 | 5.9 | 6.5 | 7.1 | 8.2 |
| TF0076rp2-5BB-3 | 4.1 | 6.1 | 6.1 | 6.4 | 8.1 |
| T89-01 | 4.7 | 6.0 | 6.5 | 6.9 | 8.3 |
| T89-02 | 4.4 | 5.7 | 6.6 | 7.6 | 7.8 |
| T89-03 | 4.7 | 6.3 | 6.7 | 7.7 | 8.4 |
| T89-04 | 4.7 | 6.0 | 7.1 | 8.0 | 8.5 |
| T89-05 | 4.0 | 5.3 | 6.3 | 7.8 | 8.1 |
| T89-06 | 4.6 | 5.9 | 6.3 | 7.7 | 8.2 |
| T89-07 | 4.6 | 6.1 | 6.5 | 7.9 | 8.5 |
| T89-08 | 4.0 | 5.2 | 5.8 | 6.9 | 7.1 |
| T89-09 | 4.4 | 5.8 | 6.4 | 7.6 | 8.2 |
| T89-10 | 4.9 | 6.0 | 6.6 | 7.4 | 8.5 |

TABLE 2.20-continued

Diameter growth data for TF0076Rp2

| | Diameter (mm) Days in greenhouse | | | | |
|---|---|---|---|---|---|
| | 35 | 41 | 46 | 53 | 60 |
| T89-11 | 4.7 | 5.8 | 6.4 | 7.9 | 8.3 |
| T89-12 | 4.7 | 5.9 | 7.3 | 7.4 | 7.6 |
| T89-13 | 5.9 | 5.9 | 6.7 | 7.5 | 8.3 |
| T89-14 | 4.5 | 5.2 | 5.8 | 6.1 | 7.0 |
| T89-15 | 4.7 | N/A | 6.0 | 6.4 | 7.3 |
| T89-16 | 4.5 | 5.6 | 7.7 | 7.5 | 8.6 |
| T89-17 | 4.1 | 5.4 | 6.0 | 6.8 | 7.5 |
| T89-18 | 4.4 | 5.8 | 6.0 | 7.7 | 8.3 |
| T89-19 | 4.7 | 5.8 | 7.1 | 8.5 | 9.4 |
| T89-20 | 4.7 | 5.8 | 6.6 | 7.4 | 8.3 |
| T89-21 | 4.7 | 6.2 | 6.3 | 7.7 | 8.5 |
| T89-22 | 4.2 | 5.1 | 6.3 | 6.9 | 8.0 |
| T89-23 | 4.6 | 5.8 | 7.1 | 7.5 | 8.3 |
| T89-24 | 4.4 | 5.8 | 6.9 | 7.7 | 8.8 |
| T89-25 | 4.5 | 5.4 | 6.2 | 8.0 | 8.7 |
| T89-26 | 4.1 | 5.4 | 6.0 | 7.2 | 8.0 |
| T89-27 | 4.5 | 5.7 | 6.5 | 7.9 | 9.2 |
| T89-28 | 4.3 | 5.1 | 6.0 | 6.6 | 7.7 |
| T89-29 | 3.5 | 4.7 | 5.5 | 6.3 | 7.1 |
| T89-30 | 4.1 | 5.4 | 5.8 | 7.2 | 7.8 |
| T89-31 | 5.0 | 5.8 | 6.8 | 7.3 | 8.2 |
| T89-32 | 4.4 | 6.4 | 6.6 | 8.0 | 8.4 |

Results from growth analysis are specified in the overview table 2.21. The determined growth effects of specified construction group are presented as ratios between construction and wild type group AFH, AFD, AMHGR, ADGR, MFH, MFD, MMHGR and MDC.

TABLE 2.21

Overview table of growth effects of construct TF0076Rp2

| Construction group | Average Final Height | Average Final Diameter | Average Maximum Height Growth Rate | Average Maximum Diameter Growth Rate | Maximum Final Height | Maximum Final Diameter | Maximum of Maximum Height Growth Rate | Maximum Diameter Growth Rate |
|---|---|---|---|---|---|---|---|---|
| TF0076Rp2 | 1.13 | 1.01 | 1.13 | 1.01 | 1.13 | 0.97 | 1.18 | 0.87 |

Construction Group TF0096

This construct induces increased growth. The final height is 11% higher comparing the average of the construction group and wild type control group. The final height is 8% higher comparing the largest individuals of the construction group and wild type control group. The maximum height growth rate is 18% higher comparing the average of the construction group and wild type control group. The maximum height growth rate is 14% higher comparing the largest individuals of the construction group and wild type control group. The final diameter is 15% higher comparing the average of the construction group and wild type control group. The final diameter is 8% higher comparing the largest individuals of the construction group and wild type control group. The diameter growth rate is 27% higher comparing the average of the construction group and wild type control group. The diameter growth rate is 14% higher comparing the largest individuals of the construction group and wild type control group. The TF0096 construction group meets the more stringent level of growth difference selection criterion (3) and the less stringent level of growth difference selection criteria (1) and (2) as shown in table 2.24.

Tables 2.22 and 2.23 contain growth data for specified construction group and corresponding wild type group. Table rows contain height and diameter measurements of individuals of specified construction group and corresponding wild type group. Time of measurement as number of days in greenhouse is shown in table headers.

TABLE 2.22

Height growth data for TF0096

| | Height (cm) Days in greenhouse | | | | | | | | |
|---|---|---|---|---|---|---|---|---|---|
| | 18 | 25 | 28 | 32 | 36 | 39 | 46 | 53 | 55 |
| TF0096-2A | 14 | 27 | 41 | 51 | 68 | 80 | 109 | 138 | 148 |
| TF0096-2B | 13 | 24 | 36 | 47 | 62 | 72 | 101 | 126 | 131 |
| TF0096-3A | 12 | 26 | 38 | 50 | 65 | 77 | 106 | 133 | 141 |
| TF0096-3B | 16 | 29 | 39 | 50 | 62 | 72 | 101 | 127 | 134 |
| TF0096-4A | 24 | 42 | 54 | 67 | 82 | 93 | 120 | N/A | 151 |
| T89-01 | 18 | 32 | 43 | 54 | 66 | 76 | 98 | 124 | 133 |
| T89-02 | 20 | 33 | 43 | 53 | 67 | 76 | 101 | 124 | 129 |
| T89-03 | 17 | 31 | 43 | 53 | 68 | 76 | 102 | 128 | 135 |
| T89-04 | 19 | 33 | 44 | 54 | 67 | 74 | 97 | 122 | 129 |
| T89-05 | 20 | 33 | 44 | 54 | 67 | 76 | 100 | 121 | 129 |
| T89-06 | 18 | 31 | 42 | 53 | 67 | 76 | 97 | 121 | 128 |
| T89-07 | 16 | 28 | 41 | 53 | 65 | 74 | 96 | 121 | 129 |
| T89-08 | 19 | 34 | 43 | 53 | 65 | 75 | 98 | 123 | 131 |
| T89-09 | 20 | 30 | 40 | 52 | 64 | 73 | 97 | 119 | 125 |
| T89-10 | 21 | 33 | 41 | 49 | 61 | 70 | 92 | 114 | 121 |
| T89-11 | 18 | 31 | 40 | 49 | 61 | 71 | 94 | 117 | 123 |
| T89-12 | 18 | 31 | 40 | N/A | 60 | 68 | 90 | 107 | 115 |
| T89-13 | 19 | 35 | 47 | 58 | 70 | 78 | 103 | 128 | 135 |
| T89-14 | 19 | 31 | 40 | 50 | 61 | 72 | 93 | 118 | 124 |
| T89-15 | 20 | 32 | 41 | 50 | 62 | 70 | 91 | 114 | 120 |

TABLE 2.22-continued

Height growth data for TF0096

| | Height (cm) Days in greenhouse | | | | | | | | |
|---|---|---|---|---|---|---|---|---|---|
| | 18 | 25 | 28 | 32 | 36 | 39 | 46 | 53 | 55 |
| T89-16 | 18 | 30 | 39 | 49 | 62 | 71 | 92 | 114 | 122 |
| T89-17 | 17 | 33 | 45 | 55 | 70 | 78 | 104 | 129 | 136 |
| T89-18 | 19 | 32 | 44 | 56 | 71 | 82 | 106 | 130 | 137 |
| T89-19 | 16 | 26 | 36 | 46 | 51 | 69 | 89 | 112 | 119 |
| T89-20 | 16 | 31 | 41 | 49 | 60 | 71 | 91 | 111 | 118 |
| T89-21 | 20 | 31 | 44 | 54 | 68 | 76 | 99 | 122 | 127 |
| T89-22 | 14 | 26 | 37 | 46 | 61 | 72 | 96 | 120 | 127 |
| T89-23 | 19 | 32 | 40 | 50 | 63 | 73 | 100 | 121 | 127 |
| T89-24 | 20 | 31 | 41 | 47 | 58 | 68 | 90 | 111 | 117 |
| T89-25 | 20 | 36 | 45 | 57 | 69 | 78 | 101 | 127 | 134 |
| T89-26 | 20 | 37 | 49 | 58 | 71 | 80 | 107 | 131 | 140 |
| T89-27 | 19 | 34 | 44 | 55 | 71 | 81 | 107 | 131 | 138 |
| T89-28 | 17 | 35 | 44 | 56 | 68 | 76 | 99 | 126 | 132 |
| T89-29 | 17 | 32 | 45 | 55 | 68 | 78 | 101 | 125 | 132 |
| T89-30 | 18 | 31 | 41 | 50 | 63 | 72 | 95 | 119 | 125 |
| T89-31 | 17 | 27 | 35 | 45 | 58 | 67 | 87 | 108 | 116 |
| T89-32 | 19 | 32 | 44 | 52 | 65 | 74 | 98 | 121 | 127 |

TABLE 2.22-continued

Height growth data for TF0096

| | Height (cm) Days in greenhouse | | | | | | | | |
|---|---|---|---|---|---|---|---|---|---|
| | 18 | 25 | 28 | 32 | 36 | 39 | 46 | 53 | 55 |
| T89-33 | 20 | 33 | 43 | 53 | 64 | 74 | 96 | 119 | 126 |
| T89-34 | 19 | 34 | 44 | 55 | 68 | 78 | 100 | 124 | 130 |
| T89-35 | 17 | 30 | 40 | 51 | 64 | 74 | 95 | 116 | 122 |
| T89-36 | 18 | 30 | 40 | 49 | 62 | 71 | 91 | 114 | 121 |
| T89-82 | 21 | 33 | 43 | 54 | 65 | 75 | 98 | 118 | 125 |
| T89-83 | 22 | 35 | 47 | 55 | 71 | 80 | 105 | 130 | 137 |
| T89-85 | 21 | 36 | 46 | 56 | 67 | 76 | 98 | 123 | 131 |

TABLE 2.23

Diameter growth data for TF0096

| | Diameter (mm) Days in greenhouse | | | | |
|---|---|---|---|---|---|
| | 32 | 39 | 46 | 53 | 55 |
| TF0096-2A | 4.8 | 6.0 | 7.3 | 8.4 | 8.6 |
| TF0096-2B | 4.4 | 6.2 | 8.2 | 9.2 | 9.9 |
| TF0096-3A | 5.5 | 6.8 | 7.4 | 9.2 | 9.2 |
| TF0096-3B | 3.9 | 5.5 | 7.3 | 8.2 | 8.4 |
| TF0096-4A | 5.5 | 6.9 | 7.6 | 9.2 | 9.1 |
| T89-01 | 5.2 | 6.0 | 6.8 | 8.2 | 7.6 |
| T89-02 | 4.5 | 5.8 | 7.1 | 8.6 | 8.3 |
| T89-03 | 4.4 | 5.7 | 6.8 | 7.9 | 8.1 |
| T89-04 | 4.4 | 6.0 | 6.9 | 8.6 | 8.5 |
| T89-05 | 4.6 | 5.8 | 6.7 | 7.9 | 8.0 |
| T89-06 | 4.7 | 5.9 | 7.2 | 8.1 | 9.2 |
| T89-07 | 4.8 | 5.5 | 6.2 | 6.9 | 7.1 |
| T89-08 | 4.5 | 5.4 | 6.0 | 6.9 | 7.1 |
| T89-09 | 4.7 | 5.6 | 6.7 | 8.8 | 8.0 |
| T89-10 | 4.1 | 4.9 | 5.6 | 7.1 | 7.0 |
| T89-11 | 3.8 | 5.3 | 7.3 | 8.0 | 7.6 |
| T89-12 | N/A | 5.1 | 6.2 | 7.3 | 6.9 |
| T89-13 | 4.8 | 5.7 | 6.5 | 7.6 | 7.6 |
| T89-14 | 4.2 | 5.5 | 6.6 | 7.6 | 6.5 |
| T89-15 | 5.0 | 6.1 | 7.2 | 7.9 | 8.3 |
| T89-16 | 4.4 | 5.6 | 6.2 | 7.3 | 7.9 |
| T89-17 | 4.8 | 6.7 | 7.0 | 8.3 | 8.4 |
| T89-18 | 4.2 | 5.5 | 6.7 | 7.3 | 7.4 |
| T89-19 | 4.7 | 5.5 | 6.8 | 7.2 | 7.8 |
| T89-20 | 4.5 | 5.6 | 6.5 | 7.0 | 7.3 |
| T89-21 | 4.9 | 5.6 | 6.4 | 7.4 | 7.6 |
| T89-22 | 4.3 | 5.4 | 6.5 | 7.3 | 7.6 |
| T89-23 | 3.9 | 5.5 | 6.7 | 7.7 | 7.0 |
| T89-24 | 4.3 | 5.9 | 6.8 | 8.1 | 7.9 |
| T89-25 | 4.7 | 6.5 | 7.5 | 9.2 | 9.1 |
| T89-26 | 5.4 | 5.9 | 7.7 | 8.6 | 8.8 |
| T89-27 | 4.7 | 5.6 | 7.4 | 7.9 | 8.0 |
| T89-28 | 4.7 | 5.7 | 6.3 | 7.2 | 7.4 |
| T89-29 | 4.8 | 5.6 | 6.6 | 7.7 | 8.1 |
| T89-30 | 4.6 | 5.5 | 6.7 | 7.3 | 7.3 |
| T89-31 | 4.3 | 5.8 | 6.3 | 7.5 | 7.6 |
| T89-32 | 4.6 | 5.9 | 7.6 | 9.3 | 9.1 |
| T89-33 | 4.4 | 5.3 | 6.2 | 7.1 | 7.1 |
| T89-34 | 4.6 | 5.6 | 6.8 | 8.1 | 8.7 |
| T89-35 | 5.3 | 6.0 | 7.5 | 8.8 | 8.9 |
| T89-36 | 4.4 | 6.1 | 6.9 | 8.1 | 8.6 |
| T89-82 | 4.7 | 5.3 | 6.5 | 7.5 | 7.4 |
| T89-83 | 4.7 | 6.1 | 7.1 | 8.3 | 8.3 |
| T89-85 | 5.1 | 6.3 | 7.3 | 7.7 | 8.2 |

Results from growth analysis are specified in the overview table 2.24. The determined growth effects of specified construction group are presented as ratios between construction and wild type group AFH, AFD, AMHGR, ADGR, MFH, MFD, MMHGR and MDC.

TABLE 2.24

Overview table of growth effects of construct TF0096

| Construction group | Average Final Height | Average Final Diameter | Average Maximum Height Growth Rate | Average Maximum Diameter Growth Rate | Maximum Final Height | Maximum Final Diameter | Maximum of Maximum Height Growth Rate | Maximum Diameter Growth Rate |
|---|---|---|---|---|---|---|---|---|
| TF0096 | 1.11 | 1.15 | 1.18 | 1.27 | 1.08 | 1.08 | 1.14 | 1.14 |

Construction Group TF0097Rp1

This construct induces increased growth. The final height is 33% higher comparing the average of the construction group and wild type control group. The final height is 43% higher comparing the largest individuals of the construction group and wild type control group. The maximum height growth rate is 32% higher comparing the average of the construction group and wild type control group. The maximum height growth rate is 41% higher comparing the largest individuals of the construction group and wild type control group. The final diameter is 11% higher comparing the average of the construction group and wild type control group. The final diameter is 13% higher comparing the largest individuals of the construction group and wild type control group. The diameter growth rate is 20% higher comparing the average of the construction group and wild type control group. The diameter growth rate is 26% higher comparing the largest individuals of the construction group and wild type control group. The TF0097Rp1 construction group meets the more stringent level of growth difference selection criteria (1), (2), (3) and (4) as shown in table 2.27.

Tables 2.25 and 2.26 contain growth data for specified construction group and corresponding wild type group. Table rows contain height and diameter measurements of individuals of specified construction group and corresponding wild type group. Time of measurement as number of days in greenhouse is shown in table headers.

TABLE 2.25

Height growth data for TF0097Rp1

| | Height (cm) Days in greenhouse | | | | | | | | | |
|---|---|---|---|---|---|---|---|---|---|---|
| | 20 | 25 | 29 | 35 | 41 | 46 | 50 | 53 | 57 | 60 |
| TF0097rp1-1A-1 | 25 | 32 | 41 | 61 | 86 | 107 | 123 | 137 | 153 | 166 |
| TF0097rp1-1A-2 | 29 | 40 | 52 | 69 | 91 | 113 | 129 | 140 | 155 | 170 |
| TF0097rp1-1A-3 | 27 | 35 | 40 | 57 | 81 | 99 | 115 | 126 | 140 | 151 |
| TF0097rp1-2A-1 | 23 | 32 | 43 | 61 | 75 | 92 | 102 | 111 | 123 | 132 |
| TF0097rp1-2A-2 | 19 | 31 | 41 | 57 | 75 | 92 | 102 | 111 | 122 | 132 |
| TF0097rp1-2A-3 | 19 | 29 | 38 | 52 | 68 | 86 | 94 | 103 | 112 | 121 |
| TF0097rp1-2B-1 | 26 | 33 | 43 | 61 | 80 | 93 | 102 | 110 | 118 | 124 |
| TF0097rp1-2B-2 | 26 | 34 | 45 | 62 | 83 | 102 | 114 | 125 | 138 | 147 |
| TF0097rp1-2B-3 | 22 | 32 | 44 | 63 | 86 | 101 | 117 | 127 | 144 | 155 |
| TF0097rp1-3A-1 | 27 | 40 | 49 | 72 | 96 | 115 | 137 | 150 | 165 | 181 |
| TF0097rp1-3A-2 | 13 | 23 | 34 | 50 | 73 | 93 | 108 | 119 | 132 | 143 |
| TF0097rp1-3A-3 | 19 | 31 | 44 | 63 | 88 | 109 | 125 | 137 | 151 | 162 |
| TF0097rp1-4A-1 | 24 | 35 | 42 | 48 | 62 | 81 | 91 | 99 | 108 | 116 |
| TF0097rp1-4A-2 | 14 | 22 | 28 | 39 | 55 | 80 | 90 | 103 | 115 | 126 |
| TF0097rp1-4A-3 | 19 | 25 | 29 | 46 | 67 | 80 | 99 | 109 | 125 | 136 |
| T89-01 | 17 | 26 | 31 | 45 | 61 | 76 | 87 | 95 | 107 | 116 |
| T89-02 | 16 | 21 | 26 | 38 | 53 | 67 | 76 | 83 | N/A | N/A |
| T89-03 | 18 | 24 | 32 | 47 | 64 | 78 | 87 | 96 | 106 | 115 |
| T89-04 | 18 | 26 | 35 | 50 | 66 | 80 | 87 | 96 | 107 | 115 |
| T89-05 | 17 | 26 | 33 | 44 | 57 | 73 | 81 | 91 | 100 | 107 |
| T89-06 | 16 | 21 | 28 | 40 | 55 | 74 | 79 | 89 | 99 | 106 |
| T89-07 | 17 | 23 | 31 | 43 | 57 | 71 | 80 | 88 | 98 | 107 |
| T89-08 | 15 | 20 | 26 | 37 | 51 | 65 | 75 | 84 | 94 | 100 |

TABLE 2.25-continued

Height growth data for TF0097Rp1

| | Height (cm) Days in greenhouse | | | | | | | | | |
|---|---|---|---|---|---|---|---|---|---|---|
| | 20 | 25 | 29 | 35 | 41 | 46 | 50 | 53 | 57 | 60 |
| T89-09 | 18 | 25 | 32 | 46 | 61 | 74 | 85 | 93 | 103 | 112 |
| T89-10 | 19 | 25 | 32 | 46 | 60 | 75 | 86 | 95 | 104 | 112 |
| T89-11 | 20 | 27 | 36 | 51 | 68 | 86 | 98 | 107 | 120 | 127 |
| T89-12 | 19 | 27 | 36 | 50 | 67 | 80 | 89 | 97 | 108 | 118 |
| T89-13 | 18 | 25 | 32 | 45 | 59 | 75 | 83 | 92 | 101 | 108 |
| T89-14 | 18 | 23 | 26 | 36 | 51 | 65 | 72 | 79 | 89 | 96 |
| T89-15 | 17 | 21 | 28 | 39 | 53 | 70 | 78 | 87 | 97 | 105 |
| T89-16 | 19 | 25 | 32 | 43 | 57 | 71 | 81 | 90 | 101 | 109 |
| T89-17 | 16 | 20 | 29 | 41 | 54 | 68 | 78 | 84 | 93 | 101 |
| T89-18 | 16 | 23 | 30 | 45 | 63 | 78 | 87 | 94 | 103 | 110 |
| T89-19 | 16 | 22 | 28 | 42 | 56 | 69 | 79 | 89 | 100 | 107 |
| T89-20 | 18 | 25 | 32 | 47 | 63 | 78 | 89 | 99 | 109 | 115 |
| T89-21 | 19 | 27 | 34 | 50 | 67 | 82 | 92 | 102 | 111 | 120 |
| T89-22 | 19 | 25 | 32 | 44 | 58 | 76 | 84 | 93 | 102 | 109 |
| T89-23 | 18 | 26 | 33 | 47 | 63 | 79 | 88 | 99 | 108 | 116 |
| T89-24 | 16 | 24 | 28 | 42 | 53 | 70 | 78 | 85 | 94 | 103 |
| T89-25 | 16 | 25 | 32 | 45 | 61 | 76 | 85 | 95 | 107 | 114 |
| T89-26 | 16 | 20 | 26 | 38 | 52 | 68 | 78 | 86 | 97 | 103 |
| T89-27 | 16 | 21 | 25 | 35 | 48 | 61 | 70 | 78 | N/A | 98 |
| T89-28 | 14 | 18 | 25 | 38 | 51 | 64 | 73 | 81 | 90 | 96 |
| T89-29 | 7 | 13 | 18 | 30 | 45 | 60 | 69 | 77 | 90 | 98 |
| T89-30 | 15 | 22 | 29 | 42 | 55 | 69 | 80 | 88 | 97 | 106 |
| T89-31 | 21 | 29 | 37 | 50 | 65 | 80 | 88 | 98 | 108 | 116 |
| T89-32 | 19 | 24 | 32 | 42 | 55 | 70 | 78 | 87 | 96 | 105 |

TABLE 2.26

Diameter growth data for TF0097Rp1

| | Diameter (mm) Days in greenhouse | | | | |
|---|---|---|---|---|---|
| | 35 | 41 | 46 | 53 | 60 |
| TF0097rp1-1A-1 | 4.3 | 5.3 | 6.2 | 8.0 | 9.5 |
| TF0097rp1-1A-2 | 4.5 | 5.3 | 6.0 | 7.4 | 8.8 |
| TF0097rp1-1A-3 | 4.4 | 5.2 | 5.3 | 6.4 | 8.1 |
| TF0097rp1-2A-1 | 5.7 | 6.9 | 7.8 | 9.6 | 9.9 |
| TF0097rp1-2A-2 | 5.3 | 6.7 | 7.5 | 7.9 | 9.3 |
| TF0097rp1-2A-3 | 5.1 | 6.5 | 7.5 | 7.8 | 9.2 |
| TF0097rp1-2B-1 | 4.6 | 5.5 | 6.2 | 6.8 | 7.5 |
| TF0097rp1-2B-2 | 4.9 | 6.0 | 7.1 | 7.6 | 10.2 |
| TF0097rp1-2B-3 | 5.3 | 7.7 | 8.2 | 9.9 | 10.6 |
| TF0097rp1-3A-1 | 5.7 | 7.0 | 7.7 | 9.4 | 9.8 |
| TF0097rp1-3A-2 | 4.7 | 6.2 | 7.0 | 7.3 | 9.5 |
| TF0097rp1-3A-3 | 5.0 | 6.5 | 7.1 | 9.0 | 10.2 |
| TF0097rp1-4A-1 | 4.4 | 5.0 | 6.0 | 7.3 | 6.7 |
| TF0097rp1-4A-2 | 4.1 | 5.4 | 5.9 | 6.3 | 7.2 |
| TF0097rp1-4A-3 | 3.7 | 4.9 | 6.0 | 8.6 | 9.4 |
| T89-01 | 4.7 | 6.0 | 6.5 | 6.9 | 8.3 |
| T89-02 | 4.4 | 5.7 | 6.6 | 7.6 | 7.8 |
| T89-03 | 4.7 | 6.3 | 6.7 | 7.7 | 8.4 |
| T89-04 | 4.7 | 6.0 | 7.1 | 8.0 | 8.5 |
| T89-05 | 4.0 | 5.3 | 6.3 | 7.8 | 8.1 |
| T89-06 | 4.6 | 5.9 | 6.3 | 7.7 | 8.2 |
| T89-07 | 4.6 | 6.1 | 6.5 | 7.9 | 8.5 |
| T89-08 | 4.0 | 5.2 | 5.8 | 6.9 | 7.1 |
| T89-09 | 4.4 | 5.8 | 6.4 | 7.6 | 8.2 |
| T89-10 | 4.9 | 6.0 | 6.6 | 7.4 | 8.5 |
| T89-11 | 4.7 | 5.8 | 6.4 | 7.9 | 8.3 |
| T89-12 | 4.7 | 5.9 | 7.3 | 7.4 | 7.6 |
| T89-13 | 5.9 | 5.9 | 6.7 | 7.5 | 8.3 |
| T89-14 | 4.5 | 5.2 | 5.8 | 6.1 | 7.0 |
| T89-15 | 4.7 | N/A | 6.0 | 6.4 | 7.3 |
| T89-16 | 4.5 | 5.6 | 7.7 | 7.5 | 8.6 |
| T89-17 | 4.1 | 5.4 | 6.0 | 6.8 | 7.5 |
| T89-18 | 4.4 | 5.8 | 6.0 | 7.7 | 8.3 |
| T89-19 | 4.7 | 5.8 | 7.1 | 8.5 | 9.4 |
| T89-20 | 4.7 | 5.8 | 6.6 | 7.4 | 8.3 |
| T89-21 | 4.7 | 6.2 | 6.3 | 7.7 | 8.5 |

TABLE 2.26-continued

Diameter growth data for TF0097Rp1

| | Diameter (mm) Days in greenhouse | | | | |
|---|---|---|---|---|---|
| | 35 | 41 | 46 | 53 | 60 |
| T89-22 | 4.2 | 5.1 | 6.3 | 6.9 | 8.0 |
| T89-23 | 4.6 | 5.8 | 7.1 | 7.5 | 8.3 |
| T89-24 | 4.4 | 5.8 | 6.9 | 7.7 | 8.8 |
| T89-25 | 4.5 | 5.4 | 6.2 | 8.0 | 8.7 |
| T89-26 | 4.1 | 5.4 | 6.0 | 7.2 | 8.0 |
| T89-27 | 4.5 | 5.7 | 6.5 | 7.9 | 9.2 |
| T89-28 | 4.3 | 5.1 | 6.0 | 6.6 | 7.7 |
| T89-29 | 3.5 | 4.7 | 5.5 | 6.3 | 7.1 |
| T89-30 | 4.1 | 5.4 | 5.8 | 7.2 | 7.8 |
| T89-31 | 5.0 | 5.8 | 6.8 | 7.3 | 8.2 |
| T89-32 | 4.4 | 6.4 | 6.6 | 8.0 | 8.4 |

Results from growth analysis are specified in the overview table 2.27. The determined growth effects of specified construction group are presented as ratios between construction and wild type group AFH, AFD, AMHGR, ADGR, MFH, MFD, MMHGR and MDC.

TABLE 2.27

Overview table of growth effects of construct TF0097Rp1

| Construction group | Average Final Height | Average Final Diameter | Average Maximum Height Growth Rate | Average Maximum Diameter Growth Rate | Maximum Final Height | Maximum Final Diameter | Maximum of Maximum Height Growth Rate | Maximum Diameter Growth Rate |
|---|---|---|---|---|---|---|---|---|
| TF0097Rp1 | 1.33 | 1.11 | 1.32 | 1.20 | 1.43 | 1.13 | 1.41 | 1.26 |

Construction Group TF0104

This construct induces increased growth. The final height is 15% higher comparing the average of the construction group and wild type control group. The final height is 12% higher comparing the largest individuals of the construction group and wild type control group. The maximum height growth rate is 16% higher comparing the average of the construction group and wild type control group. The maximum height growth rate is 14% higher comparing the largest individuals of the construction group and wild type control group. The final diameter is 23% higher comparing the average of the construction group and wild type control group. The final diameter is 20% higher comparing the largest individuals of the construction group and wild type control group. The diameter growth rate is 20% higher comparing the average of the construction group and wild type control group. The diameter growth rate is 10% higher comparing the largest individuals of the construction group and wild type control group. The TF0104 construction group meets the more stringent level of growth difference selection criteria (1), (2) and (3) and the less stringent level of growth difference selection criterion (4) as shown in table 2.30.

Tables 2.28 and 2.29 contain growth data for specified construction group and corresponding wild type group. Table rows contain height and diameter measurements of individuals of specified construction group and corresponding wild type group. Time of measurement as number of days in greenhouse is shown in table headers.

TABLE 2.28

Height growth data for TF0104

| | Height (cm) Days in greenhouse | | | | | | | | |
|---|---|---|---|---|---|---|---|---|---|
| | 18 | 25 | 28 | 32 | 36 | 39 | 46 | 53 | 55 |
| TF0104-1A | 20 | 35 | 48 | 60 | 77 | 90 | 117 | 149 | 157 |
| TF0104-1B | 23 | 37 | 50 | 63 | 78 | 90 | 120 | 148 | 155 |
| TF0104-2A | 21 | 37 | 50 | 62 | 75 | 85 | 114 | 140 | 147 |
| TF0104-3A | 20 | 37 | 50 | 61 | 74 | 85 | 102 | 115 | 119 |
| TF0104-3B | 20 | 35 | 50 | 62 | 78 | 89 | 118 | 145 | 152 |
| T89-01 | 18 | 32 | 43 | 54 | 66 | 76 | 98 | 124 | 133 |
| T89-02 | 20 | 33 | 43 | 53 | 67 | 76 | 101 | 124 | 129 |
| T89-03 | 17 | 31 | 43 | 53 | 68 | 76 | 102 | 128 | 135 |
| T89-04 | 19 | 33 | 44 | 54 | 67 | 74 | 97 | 122 | 129 |
| T89-05 | 20 | 33 | 44 | 54 | 67 | 76 | 100 | 121 | 129 |
| T89-06 | 18 | 31 | 42 | 53 | 67 | 76 | 97 | 121 | 128 |
| T89-07 | 16 | 28 | 41 | 53 | 65 | 74 | 96 | 121 | 129 |
| T89-08 | 19 | 34 | 43 | 53 | 65 | 75 | 98 | 123 | 131 |
| T89-09 | 20 | 30 | 40 | 52 | 64 | 73 | 97 | 119 | 125 |
| T89-10 | 21 | 33 | 41 | 49 | 61 | 70 | 92 | 114 | 121 |
| T89-11 | 18 | 31 | 40 | 49 | 61 | 71 | 94 | 117 | 123 |
| T89-12 | 18 | 31 | 40 | N/A | 60 | 68 | 90 | 107 | 115 |
| T89-13 | 19 | 35 | 47 | 58 | 70 | 78 | 103 | 128 | 135 |
| T89-14 | 19 | 31 | 40 | 50 | 61 | 72 | 93 | 118 | 124 |
| T89-15 | 20 | 32 | 41 | 50 | 62 | 70 | 91 | 114 | 120 |
| T89-16 | 18 | 30 | 39 | 49 | 62 | 71 | 92 | 114 | 122 |
| T89-17 | 17 | 33 | 45 | 55 | 70 | 78 | 104 | 129 | 136 |
| T89-18 | 19 | 32 | 44 | 56 | 71 | 82 | 106 | 130 | 137 |
| T89-19 | 16 | 26 | 36 | 46 | 51 | 69 | 89 | 112 | 119 |
| T89-20 | 16 | 31 | 41 | 49 | 60 | 71 | 91 | 111 | 118 |
| T89-21 | 20 | 31 | 44 | 54 | 68 | 76 | 99 | 122 | 127 |
| T89-22 | 14 | 26 | 37 | 46 | 61 | 72 | 96 | 120 | 127 |
| T89-23 | 19 | 32 | 40 | 50 | 63 | 73 | 100 | 121 | 127 |
| T89-24 | 20 | 31 | 41 | 47 | 58 | 68 | 90 | 111 | 117 |
| T89-25 | 20 | 36 | 45 | 57 | 69 | 78 | 101 | 127 | 134 |
| T89-26 | 20 | 37 | 49 | 58 | 71 | 80 | 107 | 131 | 140 |
| T89-27 | 19 | 34 | 44 | 55 | 71 | 81 | 107 | 131 | 138 |
| T89-28 | 17 | 35 | 44 | 56 | 68 | 76 | 99 | 126 | 132 |
| T89-29 | 17 | 32 | 45 | 55 | 68 | 78 | 101 | 125 | 132 |
| T89-30 | 18 | 31 | 41 | 50 | 63 | 72 | 95 | 119 | 125 |
| T89-31 | 17 | 27 | 35 | 45 | 58 | 67 | 87 | 108 | 116 |
| T89-32 | 19 | 32 | 44 | 52 | 65 | 74 | 98 | 121 | 127 |
| T89-33 | 20 | 33 | 43 | 53 | 64 | 74 | 96 | 119 | 126 |
| T89-34 | 19 | 34 | 44 | 55 | 68 | 78 | 100 | 124 | 130 |
| T89-35 | 17 | 30 | 40 | 51 | 64 | 74 | 95 | 116 | 122 |
| T89-36 | 18 | 30 | 40 | 49 | 62 | 71 | 91 | 114 | 121 |
| T89-82 | 21 | 33 | 43 | 54 | 65 | 75 | 98 | 118 | 125 |
| T89-83 | 22 | 35 | 47 | 55 | 71 | 80 | 105 | 130 | 137 |
| T89-85 | 21 | 36 | 46 | 56 | 67 | 76 | 98 | 123 | 131 |

TABLE 2.29

Diameter growth data for TF0104

| | Diameter (mm) Days in greenhouse | | | | |
|---|---|---|---|---|---|
| | 32 | 39 | 46 | 53 | 55 |
| TF0104-1A | 6.0 | 7.2 | 8.7 | 10.4 | 11.0 |
| TF0104-1B | 5.7 | 7.9 | 8.8 | 10.0 | 10.6 |
| TF0104-2A | 5.7 | 8.0 | 9.0 | 10.4 | 10.2 |
| TF0104-3A | 5.3 | 6.3 | 6.7 | 7.5 | 7.1 |
| TF0104-3B | 5.7 | 6.9 | 8.2 | 9.8 | 9.5 |
| T89-01 | 5.2 | 6.0 | 6.8 | 8.2 | 7.6 |
| T89-02 | 4.5 | 5.8 | 7.1 | 8.6 | 8.3 |
| T89-03 | 4.4 | 5.7 | 6.8 | 7.9 | 8.1 |
| T89-04 | 4.4 | 6.0 | 6.9 | 8.6 | 8.5 |
| T89-05 | 4.6 | 5.8 | 6.7 | 7.9 | 8.0 |
| T89-06 | 4.7 | 5.9 | 7.2 | 8.1 | 9.2 |
| T89-07 | 4.8 | 5.5 | 6.2 | 6.9 | 7.1 |
| T89-08 | 4.5 | 5.4 | 6.0 | 6.9 | 7.1 |
| T89-09 | 4.7 | 5.6 | 6.7 | 8.8 | 8.0 |
| T89-10 | 4.1 | 4.9 | 5.6 | 7.1 | 7.0 |
| T89-11 | 3.8 | 5.3 | 7.3 | 8.0 | 7.6 |
| T89-12 | N/A | 5.1 | 6.2 | 7.3 | 6.9 |
| T89-13 | 4.8 | 5.7 | 6.5 | 7.6 | 7.6 |
| T89-14 | 4.2 | 5.5 | 6.6 | 7.6 | 6.5 |
| T89-15 | 5.0 | 6.1 | 7.2 | 7.9 | 8.3 |
| T89-16 | 4.4 | 5.6 | 6.2 | 7.3 | 7.9 |
| T89-17 | 4.8 | 6.7 | 7.0 | 8.3 | 8.4 |
| T89-18 | 4.2 | 5.5 | 6.7 | 7.3 | 7.4 |
| T89-19 | 4.7 | 5.5 | 6.8 | 7.2 | 7.8 |
| T89-20 | 4.5 | 5.6 | 6.5 | 7.0 | 7.3 |
| T89-21 | 4.9 | 5.6 | 6.4 | 7.4 | 7.6 |
| T89-22 | 4.3 | 5.4 | 6.5 | 7.3 | 7.6 |
| T89-23 | 3.9 | 5.5 | 6.7 | 7.7 | 7.0 |
| T89-24 | 4.3 | 5.9 | 6.8 | 8.1 | 7.9 |
| T89-25 | 4.7 | 6.5 | 7.5 | 9.2 | 9.1 |
| T89-26 | 5.4 | 5.9 | 7.7 | 8.6 | 8.8 |
| T89-27 | 4.7 | 5.6 | 7.4 | 7.9 | 8.0 |
| T89-28 | 4.7 | 5.7 | 6.3 | 7.2 | 7.4 |
| T89-29 | 4.8 | 5.6 | 6.6 | 7.7 | 8.1 |
| T89-30 | 4.6 | 5.5 | 6.7 | 7.3 | 7.3 |
| T89-31 | 4.3 | 5.8 | 6.3 | 7.5 | 7.6 |
| T89-32 | 4.6 | 5.9 | 7.6 | 9.3 | 9.1 |
| T89-33 | 4.4 | 5.3 | 6.2 | 7.1 | 7.1 |
| T89-34 | 4.6 | 5.6 | 6.8 | 8.1 | 8.7 |
| T89-35 | 5.3 | 6.0 | 7.5 | 8.8 | 8.9 |
| T89-36 | 4.4 | 6.1 | 6.9 | 8.1 | 8.6 |
| T89-82 | 4.7 | 5.3 | 6.5 | 7.5 | 7.4 |
| T89-83 | 4.7 | 6.1 | 7.1 | 8.3 | 8.3 |
| T89-85 | 5.1 | 6.3 | 7.3 | 7.7 | 8.2 |

Results from growth analysis are specified in the overview table 2.30. The determined growth effects of specified construction group are presented as ratios between construction and wild type group AFH, AFD, AMHGR, ADGR, MFH, MFD, MMHGR and MDC.

TABLE 2.30

Overview table of growth effects of construct TF0104

| Construction group | Average Final Height | Average Final Diameter | Average Maximum Height Growth Rate | Average Diameter Growth Rate | Maximum Final Height | Maximum Final Diameter | Maximum of Maximum Height Growth Rate | Maximum Diameter Growth Rate |
|---|---|---|---|---|---|---|---|---|
| TF0104 | 1.15 | 1.23 | 1.16 | 1.20 | 1.12 | 1.20 | 1.14 | 1.10 |

Construction Group TF0109Rp1

This construct induces increased growth. The final height is 22% higher comparing the average of the construction group and wild type control group. The final height is 32% higher comparing the largest individuals of the construction group and wild type control group. The maximum height growth rate is 26% higher comparing the average of the construction group and wild type control group. The maximum height growth rate is 40% higher comparing the largest individuals of the construction group and wild type control group. The final diameter is 15% higher comparing the average of the construction group and wild type control group. The final diameter is 14% higher comparing the largest individuals of the construction group and wild type control group. The diameter growth rate is 25% higher comparing the average of the construction group and wild type control group. The diameter growth rate is 27% higher comparing the largest individuals of the construction group and wild type control group. The TF0109Rp1 construction group meets the more stringent level of growth difference selection criteria (1), (2), (3) and (4) as shown in table 2.33.

Tables 2.31 and 2.32 contain growth data for specified construction group and corresponding wild type group. Table rows contain height and diameter measurements of individuals of specified construction group and corresponding wild type group. Time of measurement as number of days in greenhouse is shown in table headers.

TABLE 2.31

Height growth data for TF0109Rp1

| | Height (cm) Days in greenhouse | | | | | | | | | |
|---|---|---|---|---|---|---|---|---|---|---|
| | 20 | 25 | 29 | 35 | 41 | 46 | 50 | 53 | 57 | 60 |
| TF0109rp1-2A-1 | 21 | 31 | 39 | 55 | 73 | 89 | 100 | 109 | 122 | 130 |
| TF0109rp1-2A-2 | 18 | 25 | 33 | 47 | 65 | 79 | 91 | 101 | 111 | 120 |
| TF0109rp1-2A-3 | 17 | 23 | 31 | 47 | 63 | 77 | 87 | 96 | 109 | 118 |
| TF0109rp1-2B-1 | 19 | 26 | 35 | 54 | 78 | 103 | 117 | 129 | 141 | 149 |
| TF0109rp1-2B-2 | 21 | 31 | 39 | 57 | 82 | 105 | 124 | 136 | 151 | 168 |
| TF0109rp1-2B-3 | 16 | 27 | 40 | 51 | 80 | 102 | 117 | 122 | 137 | 150 |
| TF0109rp1-3B-1 | 18 | 29 | 39 | 59 | 77 | 94 | 104 | 114 | 126 | 136 |
| TF0109rp1-3B-2 | 18 | 28 | 37 | 54 | 70 | 88 | 98 | 108 | 118 | 125 |
| TF0109rp1-3B-3 | 17 | 28 | 37 | 51 | 65 | 87 | 94 | 103 | 115 | 120 |
| TF0109rp1-4A-1 | 16 | 25 | 32 | 46 | 64 | 79 | 94 | 104 | 116 | 126 |
| TF0109rp1-4A-2 | 17 | 24 | 32 | 46 | 65 | 83 | 94 | 106 | 118 | 126 |
| TF0109rp1-4A-3 | 17 | 19 | 26 | 38 | 57 | 73 | 85 | 96 | 110 | 121 |
| T89-01 | 17 | 26 | 31 | 45 | 61 | 76 | 87 | 95 | 107 | 116 |
| T89-02 | 16 | 21 | 26 | 38 | 53 | 67 | 76 | 83 | N/A | N/A |
| T89-03 | 18 | 24 | 32 | 47 | 64 | 78 | 87 | 96 | 106 | 115 |
| T89-04 | 18 | 26 | 35 | 50 | 66 | 80 | 87 | 96 | 107 | 115 |
| T89-05 | 17 | 26 | 33 | 44 | 57 | 73 | 81 | 91 | 100 | 107 |
| T89-06 | 16 | 21 | 28 | 40 | 55 | 74 | 79 | 89 | 99 | 106 |
| T89-07 | 17 | 23 | 31 | 43 | 57 | 71 | 80 | 88 | 98 | 107 |
| T89-08 | 15 | 20 | 26 | 37 | 51 | 65 | 75 | 84 | 94 | 100 |
| T89-09 | 18 | 25 | 32 | 46 | 61 | 74 | 85 | 93 | 103 | 112 |
| T89-10 | 19 | 25 | 32 | 46 | 60 | 75 | 86 | 95 | 104 | 112 |
| T89-11 | 20 | 27 | 36 | 51 | 68 | 86 | 98 | 107 | 120 | 127 |
| T89-12 | 19 | 27 | 36 | 50 | 67 | 80 | 89 | 97 | 108 | 118 |
| T89-13 | 18 | 25 | 32 | 45 | 59 | 75 | 83 | 92 | 101 | 108 |
| T89-14 | 18 | 23 | 26 | 36 | 51 | 65 | 72 | 79 | 89 | 96 |

TABLE 2.31-continued

Height growth data for TF0109Rp1

| | Height (cm) Days in greenhouse | | | | | | | | | |
|---|---|---|---|---|---|---|---|---|---|---|
| | 20 | 25 | 29 | 35 | 41 | 46 | 50 | 53 | 57 | 60 |
| T89-15 | 17 | 21 | 28 | 39 | 53 | 70 | 78 | 87 | 97 | 105 |
| T89-16 | 19 | 25 | 32 | 43 | 57 | 71 | 81 | 90 | 101 | 109 |
| T89-17 | 16 | 20 | 29 | 41 | 54 | 68 | 78 | 84 | 93 | 101 |
| T89-18 | 16 | 23 | 30 | 45 | 63 | 78 | 87 | 94 | 103 | 110 |
| T89-19 | 16 | 22 | 28 | 42 | 56 | 69 | 79 | 89 | 100 | 107 |
| T89-20 | 18 | 25 | 32 | 47 | 63 | 78 | 89 | 99 | 109 | 115 |
| T89-21 | 19 | 27 | 34 | 50 | 67 | 82 | 92 | 102 | 111 | 120 |
| T89-22 | 19 | 25 | 32 | 44 | 58 | 76 | 84 | 93 | 102 | 109 |
| T89-23 | 18 | 26 | 33 | 47 | 63 | 79 | 88 | 99 | 108 | 116 |
| T89-24 | 16 | 24 | 28 | 42 | 53 | 70 | 78 | 85 | 94 | 103 |
| T89-25 | 16 | 25 | 32 | 45 | 61 | 76 | 85 | 95 | 107 | 114 |
| T89-26 | 16 | 20 | 26 | 38 | 52 | 68 | 78 | 86 | 97 | 103 |
| T89-27 | 16 | 21 | 25 | 35 | 48 | 61 | 70 | 78 | N/A | 98 |
| T89-28 | 14 | 18 | 25 | 38 | 51 | 64 | 73 | 81 | 90 | 96 |
| T89-29 | 7 | 13 | 18 | 30 | 45 | 60 | 69 | 77 | 90 | 98 |
| T89-30 | 15 | 22 | 29 | 42 | 55 | 69 | 80 | 88 | 97 | 106 |
| T89-31 | 21 | 29 | 37 | 50 | 65 | 80 | 88 | 98 | 108 | 116 |
| T89-32 | 19 | 24 | 32 | 42 | 55 | 70 | 78 | 87 | 96 | 105 |

TABLE 2.32

Diameter growth data for TF0109Rp1

| | Diameter (mm) Days in greenhouse | | | | |
|---|---|---|---|---|---|
| | 35 | 41 | 46 | 53 | 60 |
| TF0109rp1-2A-1 | 5.7 | 7.3 | 8.1 | 9.1 | 9.9 |
| TF0109rp1-2A-2 | 4.7 | 5.7 | 6.7 | 7.8 | 8.8 |
| TF0109rp1-2A-3 | 4.6 | 6.2 | 6.5 | 8.1 | 9.3 |
| TF0109rp1-2B-1 | 3.8 | 5.2 | 5.6 | 6.7 | 8.0 |
| TF0109rp1-2B-2 | 4.3 | 5.4 | 6.3 | 6.9 | 7.9 |
| TF0109rp1-2B-3 | 5.1 | 6.2 | 7.3 | 8.2 | 9.3 |
| TF0109rp1-3B-1 | 5.1 | 7.0 | 7.3 | 7.7 | 9.1 |
| TF0109rp1-3B-2 | 5.3 | 6.1 | 7.5 | 7.7 | 8.7 |
| TF0109rp1-3B-3 | 4.9 | 5.3 | 6.7 | 8.1 | 9.3 |
| TF0109rp1-4A-1 | 5.2 | 6.5 | 7.5 | 8.7 | 10.5 |
| TF0109rp1-4A-2 | 5.4 | 6.5 | 7.8 | 9.2 | 10.7 |
| TF0109rp1-4A-3 | 4.8 | 6.2 | 7.3 | 9.1 | 10.7 |
| T89-01 | 4.7 | 6.0 | 6.5 | 6.9 | 8.3 |
| T89-02 | 4.4 | 5.7 | 6.6 | 7.6 | 7.8 |
| T89-03 | 4.7 | 6.3 | 6.7 | 7.7 | 8.4 |
| T89-04 | 4.7 | 6.0 | 7.1 | 8.0 | 8.5 |
| T89-05 | 4.0 | 5.3 | 6.3 | 7.8 | 8.1 |
| T89-06 | 4.6 | 5.9 | 6.3 | 7.7 | 8.2 |
| T89-07 | 4.6 | 6.1 | 6.5 | 7.9 | 8.5 |
| T89-08 | 4.0 | 5.2 | 5.8 | 6.9 | 7.1 |
| T89-09 | 4.4 | 5.8 | 6.4 | 7.6 | 8.2 |
| T89-10 | 4.9 | 6.0 | 6.6 | 7.4 | 8.5 |
| T89-11 | 4.7 | 5.8 | 6.4 | 7.9 | 8.3 |
| T89-12 | 4.7 | 5.9 | 7.3 | 7.4 | 7.6 |
| T89-13 | 5.9 | 5.9 | 6.7 | 7.5 | 8.3 |
| T89-14 | 4.5 | 5.2 | 5.8 | 6.1 | 7.0 |
| T89-15 | 4.7 | N/A | 6.0 | 6.4 | 7.3 |
| T89-16 | 4.5 | 5.6 | 7.7 | 7.5 | 8.6 |
| T89-17 | 4.1 | 5.4 | 6.0 | 6.8 | 7.5 |
| T89-18 | 4.4 | 5.8 | 6.0 | 7.7 | 8.3 |
| T89-19 | 4.7 | 5.8 | 7.1 | 8.5 | 9.4 |
| T89-20 | 4.7 | 5.8 | 6.6 | 7.4 | 8.3 |
| T89-21 | 4.7 | 6.2 | 6.3 | 7.7 | 8.5 |
| T89-22 | 4.2 | 5.1 | 6.3 | 6.9 | 8.0 |
| T89-23 | 4.6 | 5.8 | 7.1 | 7.5 | 8.3 |
| T89-24 | 4.4 | 5.8 | 6.9 | 7.7 | 8.8 |
| T89-25 | 4.5 | 5.4 | 6.2 | 8.0 | 8.7 |

TABLE 2.32-continued

Diameter growth data for TF0109Rp1

| | Diameter (mm) Days in greenhouse | | | | |
|---|---|---|---|---|---|
| | 35 | 41 | 46 | 53 | 60 |
| T89-26 | 4.1 | 5.4 | 6.0 | 7.2 | 8.0 |
| T89-27 | 4.5 | 5.7 | 6.5 | 7.9 | 9.2 |
| T89-28 | 4.3 | 5.1 | 6.0 | 6.6 | 7.7 |
| T89-29 | 3.5 | 4.7 | 5.5 | 6.3 | 7.1 |
| T89-30 | 4.1 | 5.4 | 5.8 | 7.2 | 7.8 |
| T89-31 | 5.0 | 5.8 | 6.8 | 7.3 | 8.2 |
| T89-32 | 4.4 | 6.4 | 6.6 | 8.0 | 8.4 |

Results from growth analysis are specified in the overview table 2.33. The determined growth effects of specified construction group are presented as ratios between construction and wild type group AFH, AFD, AMHGR, ADGR, MFH, MFD, MMHGR and MDC.

TABLE 2.33

Overview table of growth effects of construct TF0109Rp1

| Construction group | Average Final Height | Average Final Diameter | Average Maximum Height Growth Rate | Average Maximum Diameter Growth Rate | Maximum Final Height | Maximum Final Diameter | Maximum of Maximum Height Growth Rate | Maximum Diameter Growth Rate |
|---|---|---|---|---|---|---|---|---|
| TF0109Rp1 | 1.22 | 1.15 | 1.26 | 1.25 | 1.32 | 1.14 | 1.40 | 1.27 |

Construction Group TF0116

Tables 2.34 and 2.35 contain growth data for specified construction group and corresponding wild type group. Table rows contain height and diameter measurements of individuals of specified construction group and corresponding wild type group. Time of measurement as number of days in greenhouse is shown in table headers.

TABLE 2.34

Height growth data for TF0116

| | Height (cm) Days in greenhouse | | | | | | | | | |
|---|---|---|---|---|---|---|---|---|---|---|
| | 19 | 28 | 34 | 40 | 44 | 47 | 51 | 54 | 61 | 65 |
| TF0116-1B | N/A | N/A | N/A | N/A | N/A | N/A | N/A | N/A | N/A | N/A |
| TF0116-2A | 18 | 37 | 51 | 67 | 77 | 86 | 98 | 106 | 123 | 133 |
| TF0116-2B-1 | 18 | 34 | 50 | 65 | 76 | 84 | 98 | 106 | 126 | 139 |
| TF0116-2B-2 | 17 | 31 | 48 | 61 | 75 | 82 | 93 | 101 | 120 | 133 |
| TF0116-4A | 16 | 33 | 53 | 68 | 81 | 91 | 103 | 113 | 133 | 142 |
| TF0116-5B | 21 | 40 | 56 | 70 | 78 | 88 | 98 | 105 | 124 | 136 |
| TF0116-6A | 21 | 36 | 55 | 71 | 83 | 90 | 101 | 110 | 131 | 143 |
| TF0116-6B | 17 | 29 | 45 | 59 | 70 | 80 | 92 | 102 | 125 | 138 |
| T89-01 | 18 | 30 | 46 | 58 | 69 | 77 | 87 | 96 | 113 | 122 |
| T89-02 | 18 | 30 | 49 | 62 | 72 | 77 | 84 | 90 | 102 | 109 |
| T89-03 | 15 | 27 | 41 | 54 | 65 | 73 | 82 | 91 | 112 | 123 |
| T89-10 | N/A | N/A | N/A | N/A | N/A | N/A | N/A | N/A | N/A | N/A |
| T89-11 | 19 | 31 | 49 | 61 | 74 | 83 | 94 | 103 | 124 | 133 |
| T89-12 | 17 | 30 | 45 | 58 | 69 | 77 | 90 | 100 | 123 | 134 |
| T89-13 | 18 | 27 | 43 | 56 | 68 | 78 | 91 | 100 | 121 | 133 |
| T89-14 | 5 | 26 | 42 | 56 | 67 | 74 | 83 | 90 | 109 | 119 |
| T89-15 | 10 | 15 | 25 | 33 | 41 | 45 | 52 | 57 | 72 | 82 |
| T89-16 | 19 | 33 | 53 | 63 | 73 | 82 | 93 | 102 | 119 | 130 |
| T89-17 | 17 | 29 | 46 | 58 | 66 | 72 | 80 | 86 | 96 | 102 |
| T89-18 | 16 | 30 | 48 | 59 | 71 | 81 | 93 | 103 | 122 | 132 |
| T89-19 | 18 | 32 | 50 | 65 | 77 | 84 | 94 | 102 | 126 | 139 |
| T89-20 | 16 | 33 | 52 | 67 | 79 | 88 | 98 | 105 | 124 | 139 |
| T89-21 | 17 | 29 | 44 | 58 | 67 | 73 | 83 | 90 | 110 | 122 |
| T89-22 | 14 | 28 | 47 | 61 | 71 | 80 | 89 | 98 | 119 | 133 |
| T89-23 | 10 | 33 | 45 | 53 | 63 | 71 | 82 | 90 | 112 | 123 |
| T89-24 | 20 | 28 | 43 | 51 | 62 | 69 | 78 | 87 | 106 | 119 |

TABLE 2.34-continued

Height growth data for TF0116

| | Height (cm) Days in greenhouse | | | | | | | | | |
|---|---|---|---|---|---|---|---|---|---|---|
| | 19 | 28 | 34 | 40 | 44 | 47 | 51 | 54 | 61 | 65 |
| T89-25 | 14 | 26 | 38 | 52 | 64 | 72 | 82 | 89 | 110 | 122 |
| T89-26 | 15 | 28 | 44 | 57 | 69 | 77 | 87 | 96 | 120 | 133 |
| T89-27 | 18 | 29 | 47 | 62 | 75 | 82 | 92 | 103 | 125 | 138 |
| T89-28 | 22 | 37 | 54 | 67 | 78 | 88 | 97 | 104 | 123 | 133 |
| T89-29 | 16 | 33 | 49 | 63 | 76 | 84 | 93 | 100 | 123 | 138 |
| T89-30 | 15 | 40 | 46 | 58 | 67 | 74 | 85 | 92 | 113 | 124 |

TABLE 2.35

Diameter growth data for TF0116

| | Diameter (mm) Days in greenhouse | | | | | | | | |
|---|---|---|---|---|---|---|---|---|---|
| | 28 | 34 | 40 | 44 | 47 | 51 | 54 | 61 | 65 |
| TF0116-1B | N/A | N/A | N/A | N/A | N/A | N/A | N/A | N/A | N/A |
| TF0116-2A | 3.7 | 5.9 | 7.3 | 8.2 | 8.6 | 9.2 | 10.0 | 10.5 | 10.9 |
| TF0116-2B-1 | 3.5 | 5.3 | 6.2 | 6.9 | 8.0 | 8.4 | 9.0 | 10.0 | 10.2 |
| TF0116-2B-2 | 3.4 | 5.0 | 5.8 | 6.6 | 7.3 | 8.4 | 8.4 | 10.7 | 10.3 |
| TF0116-4A | 3.8 | 5.8 | 6.5 | 7.2 | 8.0 | 8.7 | 9.4 | 10.2 | 10.9 |
| TF0116-5B | 3.9 | 5.0 | 6.3 | 6.9 | 7.6 | 8.2 | 8.4 | 10.3 | 10.4 |
| TF0116-6A | 3.9 | 4.9 | 6.7 | 7.5 | 7.9 | 9.0 | 9.4 | 10.7 | 11.1 |
| TF0116-6B | 3.7 | 4.7 | 5.9 | 7.2 | 7.7 | 9.2 | 9.7 | 10.5 | 10.8 |
| T89-01 | 3.2 | 4.6 | 5.4 | 6.2 | 6.8 | 7.9 | 8.3 | 9.5 | 9.3 |
| T89-02 | 3.4 | 4.7 | 5.5 | 7.3 | 6.3 | 6.6 | 6.9 | 8.3 | 7.5 |
| T89-03 | 3.9 | 4.4 | 5.2 | 6.2 | 6.4 | 7.8 | 7.6 | 9.7 | 9.4 |
| T89-10 | N/A | N/A | N/A | N/A | N/A | N/A | N/A | N/A | N/A |
| T89-11 | 3.4 | 5.1 | 6.2 | 7.6 | 6.8 | 6.9 | 7.7 | 10.1 | 9.5 |
| T89-12 | 2.9 | 4.7 | 5.8 | 6.6 | 7.8 | 8.0 | 8.7 | 9.1 | 9.2 |
| T89-13 | 3.0 | 4.3 | 5.4 | 5.8 | 6.4 | 7.6 | 7.8 | 8.2 | 8.8 |
| T89-14 | 3.0 | 4.5 | 5.7 | 6.3 | 6.7 | 7.9 | 7.8 | 9.0 | 8.9 |
| T89-15 | N/A | 2.1 | 3.0 | 4.0 | 4.0 | 4.5 | 4.9 | 5.5 | 5.6 |
| T89-16 | 3.5 | 5.3 | 6.4 | 6.6 | 7.0 | 7.2 | 8.3 | 8.2 | 9.0 |
| T89-17 | 3.4 | 4.6 | 5.1 | 5.4 | 6.0 | 6.4 | 6.5 | 6.8 | 7.1 |
| T89-18 | 3.6 | 5.2 | 6.0 | 7.0 | 7.8 | 8.2 | 9.9 | 10.3 | 9.7 |
| T89-19 | 4.2 | 5.5 | 6.6 | 7.7 | 8.5 | 8.9 | 9.5 | 11.1 | 12.3 |
| T89-20 | 4.1 | 5.5 | 6.6 | 8.1 | 9.3 | 9.6 | 9.3 | 10.0 | 11.1 |
| T89-21 | 3.1 | 5.6 | 5.8 | 6.7 | 7.1 | 7.8 | 8.4 | 9.7 | 10.1 |
| T89-22 | 3.2 | 4.4 | 5.6 | 6.5 | 7.5 | 7.6 | 7.8 | 8.9 | 9.2 |
| T89-23 | 2.4 | 4.2 | 5.1 | 6.1 | 6.5 | 7.5 | 10.1 | 9.3 | 10.2 |
| T89-24 | 3.2 | 4.5 | 5.1 | 6.3 | 7.0 | 7.6 | 8.1 | 8.8 | 9.1 |
| T89-25 | 3.3 | 4.3 | 5.2 | 5.8 | 6.5 | 7.4 | 7.8 | 9.3 | 9.7 |
| T89-26 | 3.3 | 4.4 | 5.5 | 6.6 | 7.2 | 8.1 | 8.9 | 9.5 | 10.5 |
| T89-27 | 3.3 | 4.9 | 6.0 | 7.8 | 8.0 | 8.9 | 9.7 | 11.2 | 11.5 |
| T89-28 | 4.5 | 5.7 | 7.4 | 7.8 | 8.5 | 9.4 | 9.7 | 10.2 | 11.1 |
| T89-29 | 3.1 | 4.7 | 6.3 | 7.2 | 7.9 | 9.2 | 9.8 | 11.1 | 10.7 |
| T89-30 | 3.0 | 5.8 | 6.2 | 7.7 | 7.9 | 8.6 | 8.2 | 10.1 | 10.3 |

Results from growth analysis are specified in the overview table 2.36. The determined growth effects of specified construction group are presented as ratios between construction and wild type group AFH, AFD, AMHGR, ADGR, MFH, MFD, MMHGR and MDC.

TABLE 2.36

Overview table of growth effects of construct TF0116

| Construction group | Average Final Height | Average Final Diameter | Average Maximum Height Growth Rate | Average Maximum Diameter Growth Rate | Maximum Final Height | Maximum Final Diameter | Maximum of Maximum Height Growth Rate | Maximum Diameter Growth Rate |
|---|---|---|---|---|---|---|---|---|
| TF0116 | 1.10 | 1.12 | 1.03 | 1.13 | 1.03 | 0.90 | 0.99 | 0.90 |

Construction Group TF0132.2nd

This construct induces increased growth. The final height is 27% higher comparing the average of the construction group and wild type control group. The final height is 32% higher comparing the largest individuals of the construction group and wild type control group. The maximum height growth rate is 38% higher comparing the average of the construction group and wild type control group. The maximum height growth rate is 41% higher comparing the largest individuals of the construction group and wild type control group. The final diameter is 12% higher comparing the average of the construction group and wild type control group. The final diameter is 9% higher comparing the largest individuals of the construction group and wild type control group. The diameter growth rate is 15% higher comparing the average of the construction group and wild type control group. The diameter growth rate is 8% higher comparing the largest individuals of the construction group and wild type control group. The TF0132.2nd construction group meets the more stringent level of growth difference selection criteria (1), (3) and (4) and the less stringent level of growth difference selection criterion (2) as shown in table 2.39.

Tables 2.37 and 2.38 contain growth data for specified construction group and corresponding wild type group. Table rows contain height and diameter measurements of individuals of specified construction group and corresponding wild type group. Time of measurement as number of days in greenhouse is shown in table headers.

TABLE 2.37

Height growth data for TF0132.2nd

| | Height (cm) Days in greenhouse | | | | | | | | |
|---|---|---|---|---|---|---|---|---|---|
| | 18 | 25 | 28 | 32 | 36 | 39 | 46 | 53 | 55 |
| TF0132.2nd-1A | 17 | 30 | 40 | 51 | 66 | 78 | 103 | 132 | 139 |
| TF0132.2nd-1B | 19 | 34 | 48 | 63 | 82 | 96 | 132 | 168 | 178 |
| TF0132.2nd-2A | 19 | 32 | 40 | 52 | 67 | 77 | 93 | 108 | 112 |
| TF0132.2nd-4B | 22 | 41 | 57 | 73 | 93 | 106 | 138 | 175 | 185 |
| TF0132.2nd-5A | 19 | 33 | 47 | 62 | 73 | 84 | 110 | 143 | 153 |
| TF0132.2nd-5B | 19 | 35 | 49 | 63 | 84 | 101 | 136 | 168 | 177 |
| TF0132.2nd-6B | 21 | 37 | 51 | 64 | 83 | 98 | 133 | 170 | 180 |
| TF0132.2nd-7A | 20 | 34 | 47 | 59 | 77 | 92 | 125 | 160 | 175 |
| T89-01 | 18 | 32 | 43 | 54 | 66 | 76 | 98 | 124 | 133 |
| T89-02 | 20 | 33 | 43 | 53 | 67 | 76 | 101 | 124 | 129 |
| T89-03 | 17 | 31 | 43 | 53 | 68 | 76 | 102 | 128 | 135 |
| T89-04 | 19 | 33 | 44 | 54 | 67 | 74 | 97 | 122 | 129 |
| T89-05 | 20 | 33 | 44 | 54 | 67 | 76 | 100 | 121 | 129 |
| T89-06 | 18 | 31 | 42 | 53 | 67 | 76 | 97 | 121 | 128 |
| T89-07 | 16 | 28 | 41 | 53 | 65 | 74 | 96 | 121 | 129 |
| T89-08 | 19 | 34 | 43 | 53 | 65 | 75 | 98 | 123 | 131 |
| T89-09 | 20 | 30 | 40 | 52 | 64 | 73 | 97 | 119 | 125 |
| T89-10 | 21 | 33 | 41 | 49 | 61 | 70 | 92 | 114 | 121 |
| T89-11 | 18 | 31 | 40 | 49 | 61 | 71 | 94 | 117 | 123 |
| T89-12 | 18 | 31 | 40 | N/A | 60 | 68 | 90 | 107 | 115 |
| T89-13 | 19 | 35 | 47 | 58 | 70 | 78 | 103 | 128 | 135 |
| T89-14 | 19 | 31 | 40 | 50 | 61 | 72 | 93 | 118 | 124 |
| T89-15 | 20 | 32 | 41 | 50 | 62 | 70 | 91 | 114 | 120 |
| T89-16 | 18 | 30 | 39 | 49 | 62 | 71 | 92 | 114 | 122 |
| T89-17 | 17 | 33 | 45 | 55 | 70 | 78 | 104 | 129 | 136 |
| T89-18 | 19 | 32 | 44 | 56 | 71 | 82 | 106 | 130 | 137 |
| T89-19 | 16 | 26 | 36 | 46 | 51 | 69 | 89 | 112 | 119 |
| T89-20 | 16 | 31 | 41 | 49 | 60 | 71 | 91 | 111 | 118 |
| T89-21 | 20 | 31 | 44 | 54 | 68 | 76 | 99 | 122 | 127 |
| T89-22 | 14 | 26 | 37 | 46 | 61 | 72 | 96 | 120 | 127 |
| T89-23 | 19 | 32 | 40 | 50 | 63 | 73 | 100 | 121 | 127 |
| T89-24 | 20 | 31 | 41 | 47 | 58 | 68 | 90 | 111 | 117 |
| T89-25 | 20 | 36 | 45 | 57 | 69 | 78 | 101 | 127 | 134 |
| T89-26 | 20 | 37 | 49 | 58 | 71 | 80 | 107 | 131 | 140 |
| T89-27 | 19 | 34 | 44 | 55 | 71 | 81 | 107 | 131 | 138 |
| T89-28 | 17 | 35 | 44 | 56 | 68 | 76 | 99 | 126 | 132 |
| T89-29 | 17 | 32 | 45 | 55 | 68 | 78 | 101 | 125 | 132 |
| T89-30 | 18 | 31 | 41 | 50 | 63 | 72 | 95 | 119 | 125 |

TABLE 2.37-continued

Height growth data for TF0132.2nd

| | Height (cm) Days in greenhouse | | | | | | | | |
|---|---|---|---|---|---|---|---|---|---|
| | 18 | 25 | 28 | 32 | 36 | 39 | 46 | 53 | 55 |
| T89-31 | 17 | 27 | 35 | 45 | 58 | 67 | 87 | 108 | 116 |
| T89-32 | 19 | 32 | 44 | 52 | 65 | 74 | 98 | 121 | 127 |
| T89-33 | 20 | 33 | 43 | 53 | 64 | 74 | 96 | 119 | 126 |
| T89-34 | 19 | 34 | 44 | 55 | 68 | 78 | 100 | 124 | 130 |
| T89-35 | 17 | 30 | 40 | 51 | 64 | 74 | 95 | 116 | 122 |
| T89-36 | 18 | 30 | 40 | 49 | 62 | 71 | 91 | 114 | 121 |
| T89-82 | 21 | 33 | 43 | 54 | 65 | 75 | 98 | 118 | 125 |
| T89-83 | 22 | 35 | 47 | 55 | 71 | 80 | 105 | 130 | 137 |
| T89-85 | 21 | 36 | 46 | 56 | 67 | 76 | 98 | 123 | 131 |

TABLE 2.38

Diameter growth data for TF0132.2nd

| | Diameter (mm) Days in greenhouse | | | | |
|---|---|---|---|---|---|
| | 32 | 39 | 46 | 53 | 55 |
| TF0132.2nd-1A | 4.7 | 6.1 | 7.5 | 8.8 | 9.3 |
| TF0132.2nd-1B | 5.3 | 6.3 | 7.6 | 10.2 | 10.0 |
| TF0132.2nd-2A | 5.0 | 6.0 | 6.5 | 7.2 | 6.7 |
| TF0132.2nd-4B | 5.8 | 6.5 | 7.5 | 9.6 | 9.6 |
| TF0132.2nd-5A | 5.1 | 6.0 | 6.4 | 7.7 | 8.0 |
| TF0132.2nd-5B | 5.2 | 6.4 | 7.2 | 8.4 | 8.3 |
| TF0132.2nd-6B | 4.9 | 6.3 | 7.6 | 9.1 | 9.3 |
| TF0132.2nd-7A | 4.9 | 6.7 | 8.0 | 9.1 | 9.5 |
| T89-01 | 5.2 | 6.0 | 6.8 | 8.2 | 7.6 |
| T89-02 | 4.5 | 5.8 | 7.1 | 8.6 | 8.3 |
| T89-03 | 4.4 | 5.7 | 6.8 | 7.9 | 8.1 |
| T89-04 | 4.4 | 6.0 | 6.9 | 8.6 | 8.5 |
| T89-05 | 4.6 | 5.8 | 6.7 | 7.9 | 8.0 |
| T89-06 | 4.7 | 5.9 | 7.2 | 8.1 | 9.2 |
| T89-07 | 4.8 | 5.5 | 6.2 | 6.9 | 7.1 |
| T89-08 | 4.5 | 5.4 | 6.0 | 6.9 | 7.1 |
| T89-09 | 4.7 | 5.6 | 6.7 | 8.8 | 8.0 |
| T89-10 | 4.1 | 4.9 | 5.6 | 7.1 | 7.0 |
| T89-11 | 3.8 | 5.3 | 7.3 | 8.0 | 7.6 |
| T89-12 | N/A | 5.1 | 6.2 | 7.3 | 6.9 |
| T89-13 | 4.8 | 5.7 | 6.5 | 7.6 | 7.6 |
| T89-14 | 4.2 | 5.5 | 6.6 | 7.6 | 6.5 |
| T89-15 | 5.0 | 6.1 | 7.2 | 7.9 | 8.3 |
| T89-16 | 4.4 | 5.6 | 6.2 | 7.3 | 7.9 |
| T89-17 | 4.8 | 6.7 | 7.0 | 8.3 | 8.4 |
| T89-18 | 4.2 | 5.5 | 6.7 | 7.3 | 7.4 |
| T89-19 | 4.7 | 5.5 | 6.8 | 7.2 | 7.8 |
| T89-20 | 4.5 | 5.6 | 6.5 | 7.0 | 7.3 |
| T89-21 | 4.9 | 5.6 | 6.4 | 7.4 | 7.6 |
| T89-22 | 4.3 | 5.4 | 6.5 | 7.3 | 7.6 |
| T89-23 | 3.9 | 5.5 | 6.7 | 7.7 | 7.0 |
| T89-24 | 4.3 | 5.9 | 6.8 | 8.1 | 7.9 |
| T89-25 | 4.7 | 6.5 | 7.5 | 9.2 | 9.1 |
| T89-26 | 5.4 | 5.9 | 7.7 | 8.6 | 8.8 |
| T89-27 | 4.7 | 5.6 | 7.4 | 7.9 | 8.0 |
| T89-28 | 4.7 | 5.7 | 6.3 | 7.2 | 7.4 |
| T89-29 | 4.8 | 5.6 | 6.6 | 7.7 | 8.1 |
| T89-30 | 4.6 | 5.5 | 6.7 | 7.3 | 7.3 |
| T89-31 | 4.3 | 5.8 | 6.3 | 7.5 | 7.6 |
| T89-32 | 4.6 | 5.9 | 7.6 | 9.3 | 9.1 |
| T89-33 | 4.4 | 5.3 | 6.2 | 7.1 | 7.1 |
| T89-34 | 4.6 | 5.6 | 6.8 | 8.1 | 8.7 |
| T89-35 | 5.3 | 6.0 | 7.5 | 8.8 | 8.9 |
| T89-36 | 4.4 | 6.1 | 6.9 | 8.1 | 8.6 |
| T89-82 | 4.7 | 5.3 | 6.5 | 7.5 | 7.4 |
| T89-83 | 4.7 | 6.1 | 7.1 | 8.3 | 8.3 |
| T89-85 | 5.1 | 6.3 | 7.3 | 7.7 | 8.2 |

Results from growth analysis are specified in the overview table 2.39. The determined growth effects of specified construction group are presented as ratios between construction and wild type group AFH, AFD, AMHGR, ADGR, MFH, MFD, MMHGR and MDC.

TABLE 2.39

Overview table of growth effects of construct TF0132.2nd

| Construction group | Average Final Height | Average Final Diameter | Average Maximum Height Growth Rate | Average Diameter Growth Rate | Maximum Final Height | Maximum Final Diameter | Maximum of Maximum Height Growth Rate | Maximum Diameter Growth Rate |
|---|---|---|---|---|---|---|---|---|
| TF0132.2nd | 1.27 | 1.12 | 1.38 | 1.15 | 1.32 | 1.09 | 1.41 | 1.08 |

Construction Group TF0132rp1

This construct induces increased growth. The final height is 29% higher comparing the average of the construction group and wild type control group. The final height is 28% higher comparing the largest individuals of the construction group and wild type control group. The maximum height growth rate is 31% higher comparing the average of the construction group and wild type control group. The maximum height growth rate is 23% higher comparing the largest individuals of the construction group and wild type control group.

The TF0132rp1 construction group meets the more stringent level of growth difference selection criteria (1), (3) and (4) as shown in table 2.42.

Tables 2.40 and 2.41 contain growth data for specified construction group and corresponding wild type group. Table rows contain height and diameter measurements of individuals of specified construction group and corresponding wild type group. Time of measurement as number of days in greenhouse is shown in table headers.

TABLE 2.40

Height growth data for TF0132rp1

| | Height (cm) Days in greenhouse | | | | | | | | |
|---|---|---|---|---|---|---|---|---|---|
| | 15 | 19 | 26 | 33 | 37 | 40 | 47 | 51 | 54 |
| TF0132rp1-1B-1 | 25 | 30 | 48 | 70 | 88 | 103 | 137 | 153 | 170 |
| TF0132rp1-1B-2 | 23 | 26 | 38 | 63 | 80 | 96 | 133 | 151 | 168 |
| TF0132rp1-1B-3 | 23 | 27 | 42 | 66 | 86 | 98 | 131 | 151 | 167 |
| TF0132rp1-3BB-1 | 21 | 25 | 36 | 58 | 76 | 90 | 124 | 140 | 157 |
| TF0132rp1-3BB-2 | 21 | 28 | 46 | 68 | 88 | 101 | 135 | 147 | 171 |
| TF0132rp1-3BB-3 | 18 | 22 | 38 | 66 | 81 | 94 | 129 | 144 | 161 |
| TF0132rp1-4AC-1 | 22 | 27 | 42 | 65 | 83 | 95 | 127 | 142 | 159 |
| TF0132rp1-4AC-2 | 20 | 25 | 41 | 65 | 81 | 94 | 125 | 140 | 156 |
| TF0132rp1-4AC-3 | 21 | 24 | 38 | 61 | 77 | 88 | 122 | 139 | 154 |
| TF0132rp1-4B-1 | 26 | 30 | 45 | 70 | 87 | 100 | 133 | 144 | 162 |
| TF0132rp1-4B-2 | 20 | 26 | 43 | 64 | 77 | 90 | 121 | 135 | 152 |
| TF0132rp1-4B-3 | 20 | 24 | 41 | 67 | 85 | 100 | 132 | 147 | 163 |
| TF0132rp1-6B-1 | 23 | 26 | 41 | 65 | 83 | 95 | 127 | 141 | 157 |
| TF0132rp1-6B-2 | 23 | 28 | 41 | 64 | 82 | 96 | 132 | 152 | 165 |
| TF0132rp1-6B-3 | 20 | 26 | 45 | 73 | 93 | 107 | 140 | 156 | 169 |
| T89-20 | 21 | 26 | 39 | 58 | 73 | 82 | 111 | 130 | 134 |
| T89-21 | 21 | 24 | 34 | 51 | 64 | 72 | 97 | 103 | 125 |
| T89-22 | 19 | 23 | 32 | 48 | 60 | 70 | 96 | 111 | 123 |
| T89-23 | 21 | 24 | 34 | 51 | 63 | 70 | 94 | 112 | 122 |

TABLE 2.40-continued

Height growth data for TF0132rp1

| | Height (cm) Days in greenhouse | | | | | | | | |
|---|---|---|---|---|---|---|---|---|---|
| | 15 | 19 | 26 | 33 | 37 | 40 | 47 | 51 | 54 |
| T89-24 | 19 | 22 | 30 | 46 | 59 | 68 | 90 | 103 | 115 |
| T89-25 | 22 | 30 | 39 | 57 | 72 | 81 | 106 | 112 | 130 |
| T89-26 | 21 | 24 | 35 | 48 | 60 | 70 | 98 | 111 | 130 |
| T89-27 | 21 | 24 | 34 | 48 | 60 | 70 | 93 | 106 | 120 |
| T89-28 | 20 | 22 | 32 | 48 | 60 | 70 | 93 | 105 | 116 |

TABLE 2.41

Diameter growth data for TF0132rp1

| | Diameter (mm) Days in greenhouse | | | |
|---|---|---|---|---|
| | 33 | 40 | 47 | 54 |
| TF0132rp1-1B-1 | 5.1 | 6.3 | 7.4 | 9.1 |
| TF0132rp1-1B-2 | 4.8 | 5.8 | 6.9 | 8.1 |
| TF0132rp1-1B-3 | 4.2 | 5.8 | 7.0 | 7.6 |
| TF0132rp1-3BB-1 | 4.0 | 5.5 | 6.7 | 7.4 |
| TF0132rp1-3BB-2 | 5.1 | 6.1 | 6.8 | 8.2 |
| TF0132rp1-3BB-3 | 4.9 | 5.7 | 6.8 | 8.4 |
| TF0132rp1-4AC-1 | 4.3 | 6.2 | 8.0 | 9.1 |
| TF0132rp1-4AC-2 | 5.0 | 6.6 | 8.5 | 9.4 |
| TF0132rp1-4AC-3 | 4.8 | 6.5 | 7.5 | 8.5 |
| TF0132rp1-4B-1 | 4.8 | 5.1 | 6.5 | 7.9 |
| TF0132rp1-4B-2 | 4.8 | 5.3 | 6.3 | 7.2 |
| TF0132rp1-4B-3 | 4.5 | 5.6 | 7.7 | 8.4 |
| TF0132rp1-6B-1 | 4.2 | 5.3 | 6.6 | 6.9 |
| TF0132rp1-6B-2 | 4.5 | 5.8 | 7.6 | 8.2 |
| TF0132rp1-6B-3 | 6.5 | 6.7 | 7.3 | 8.4 |
| T89-20 | 4.8 | 6.2 | 6.3 | 6.9 |
| T89-21 | 3.8 | 5.5 | 6.0 | 6.9 |
| T89-22 | 4.5 | 6.2 | 6.6 | 7.5 |
| T89-23 | 3.8 | 4.8 | 5.6 | 6.2 |
| T89-24 | 3.8 | 4.9 | 5.8 | 7.2 |
| T89-25 | 4.8 | 5.9 | 7.4 | 8.9 |
| T89-26 | 4.4 | 6.2 | 7.0 | 7.8 |
| T89-27 | 4.9 | 6.4 | 7.3 | 8.3 |
| T89-28 | 4.5 | 4.8 | 5.8 | 7.2 |

Results from growth analysis are specified in the overview table 2.42. The determined growth effects of specified construction group are presented as ratios between construction and wild type group AFH, AFD, AMHGR, ADGR, MFH, MFD, MMHGR and MDC.

TABLE 2.42

Overview table of growth effects of construct TF0132rp1

| Construction group | Average Final Height | Average Final Diameter | Average Maximum Height Growth Rate | Average Diameter Growth Rate | Maximum Final Height | Maximum Final Diameter | Maximum of Maximum Height Growth Rate | Maximum Diameter Growth Rate |
|---|---|---|---|---|---|---|---|---|
| TF0132rp1 | 1.29 | 1.07 | 1.31 | 1.10 | 1.28 | 1.01 | 1.23 | 1.02 |

Construction Group TF0146

This construct induces increased growth. The final height is 13% higher comparing the average of the construction group and wild type control group. The final height is 16% higher comparing the largest individuals of the construction group and wild type control group. The maximum height growth rate is 18% higher comparing the average of the construction group and wild type control group. The maximum height growth rate is 25% higher comparing the largest individuals of the construction group and wild type control group. The final diameter is 8% higher comparing the average of the construction group and wild type control group. The final diameter is 8% higher comparing the largest individuals of the construction group and wild type control group. The TF0146 construction group meets the more stringent level of growth difference selection criteria (1) and (4) as shown in table 2.45.

Tables 2.43 and 2.44 contain growth data for specified construction group and corresponding wild type group. Table rows contain height and diameter measurements of individuals of specified construction group and corresponding wild type group. Time of measurement as number of days in greenhouse is shown in table headers.

TABLE 2.43

Height growth data for TF0146

Height (cm)
Days in greenhouse

| | 18 | 25 | 28 | 32 | 36 | 39 | 46 | 53 | 55 |
|---|---|---|---|---|---|---|---|---|---|
| TF0146-1A | 25 | 43 | 51 | 60 | 80 | 94 | 125 | 152 | 158 |
| TF0146-1B | 16 | 32 | 42 | 55 | 68 | 82 | 113 | 140 | 148 |
| TF0146-2A | 18 | 31 | 41 | 51 | 64 | 74 | 98 | 124 | 132 |
| TF0146-2B | 22 | 42 | 55 | 64 | 81 | 95 | 125 | 156 | 162 |
| TF0146-3A | 24 | 38 | 51 | 63 | 77 | 89 | 116 | 139 | 144 |
| TF0146-3B | 18 | 30 | 38 | 49 | 64 | 74 | 95 | 114 | 122 |
| TF0146-4A | 20 | 34 | 47 | 58 | 72 | 84 | 107 | 124 | 132 |
| TF0146-4B | 24 | 39 | 52 | 63 | 79 | 91 | 120 | 149 | 158 |
| T89-01 | 18 | 32 | 43 | 54 | 66 | 76 | 98 | 124 | 133 |
| T89-02 | 20 | 33 | 43 | 53 | 67 | 76 | 101 | 124 | 129 |
| T89-03 | 17 | 31 | 43 | 53 | 68 | 76 | 102 | 128 | 135 |
| T89-04 | 19 | 33 | 44 | 54 | 67 | 74 | 97 | 122 | 129 |
| T89-05 | 20 | 33 | 44 | 54 | 67 | 76 | 100 | 121 | 129 |
| T89-06 | 18 | 31 | 42 | 53 | 67 | 76 | 97 | 121 | 128 |
| T89-07 | 16 | 28 | 41 | 53 | 65 | 74 | 96 | 121 | 129 |
| T89-08 | 19 | 34 | 43 | 53 | 65 | 75 | 98 | 123 | 131 |
| T89-09 | 20 | 30 | 40 | 52 | 64 | 73 | 97 | 119 | 125 |
| T89-10 | 21 | 33 | 41 | 49 | 61 | 70 | 92 | 114 | 121 |
| T89-11 | 18 | 31 | 40 | 49 | 61 | 71 | 94 | 117 | 123 |
| T89-12 | 18 | 31 | 40 | N/A | 60 | 68 | 90 | 107 | 115 |
| T89-13 | 19 | 35 | 47 | 58 | 70 | 78 | 103 | 128 | 135 |
| T89-14 | 19 | 31 | 40 | 50 | 61 | 72 | 93 | 118 | 124 |
| T89-15 | 20 | 32 | 41 | 50 | 62 | 70 | 91 | 114 | 120 |
| T89-16 | 18 | 30 | 39 | 49 | 62 | 71 | 92 | 114 | 122 |
| T89-17 | 17 | 33 | 45 | 55 | 70 | 78 | 104 | 129 | 136 |
| T89-18 | 19 | 32 | 44 | 56 | 71 | 82 | 106 | 130 | 137 |
| T89-19 | 16 | 26 | 36 | 46 | 51 | 69 | 89 | 112 | 119 |
| T89-20 | 16 | 31 | 41 | 49 | 60 | 71 | 91 | 111 | 118 |

TABLE 2.43-continued

Height growth data for TF0146

Height (cm)
Days in greenhouse

| | 18 | 25 | 28 | 32 | 36 | 39 | 46 | 53 | 55 |
|---|---|---|---|---|---|---|---|---|---|
| T89-21 | 20 | 31 | 44 | 54 | 68 | 76 | 99 | 122 | 127 |
| T89-22 | 14 | 26 | 37 | 46 | 61 | 72 | 96 | 120 | 127 |
| T89-23 | 19 | 32 | 40 | 50 | 63 | 73 | 100 | 121 | 127 |
| T89-24 | 20 | 31 | 41 | 47 | 58 | 68 | 90 | 111 | 117 |
| T89-25 | 20 | 36 | 45 | 57 | 69 | 78 | 101 | 127 | 134 |
| T89-26 | 20 | 37 | 49 | 58 | 71 | 80 | 107 | 131 | 140 |
| T89-27 | 19 | 34 | 44 | 55 | 71 | 81 | 107 | 131 | 138 |
| T89-28 | 17 | 35 | 44 | 56 | 68 | 76 | 99 | 126 | 132 |
| T89-29 | 17 | 32 | 45 | 55 | 68 | 78 | 101 | 125 | 132 |
| T89-30 | 18 | 31 | 41 | 50 | 63 | 72 | 95 | 119 | 125 |
| T89-31 | 17 | 27 | 35 | 45 | 58 | 67 | 87 | 108 | 116 |
| T89-32 | 19 | 32 | 44 | 52 | 65 | 74 | 98 | 121 | 127 |
| T89-33 | 20 | 33 | 43 | 53 | 64 | 74 | 96 | 119 | 126 |
| T89-34 | 19 | 34 | 44 | 55 | 68 | 78 | 100 | 124 | 130 |
| T89-35 | 17 | 30 | 40 | 51 | 64 | 74 | 95 | 116 | 122 |
| T89-36 | 18 | 30 | 40 | 49 | 62 | 71 | 91 | 114 | 121 |
| T89-82 | 21 | 33 | 43 | 54 | 65 | 75 | 98 | 118 | 125 |
| T89-83 | 22 | 35 | 47 | 55 | 71 | 80 | 105 | 130 | 137 |
| T89-85 | 21 | 36 | 46 | 56 | 67 | 76 | 98 | 123 | 131 |

TABLE 2.44

Diameter growth data for TF0146

Diameter (mm)
Days in greenhouse

| | 32 | 39 | 46 | 53 | 55 |
|---|---|---|---|---|---|
| TF0146-1A | 5.4 | 6.2 | 7.2 | 6.9 | 7.5 |
| TF0146-1B | 4.2 | 5.7 | 7.0 | 8.3 | 8.6 |
| TF0146-2A | 6.1 | 6.4 | 7.4 | 8.7 | 9.4 |
| TF0146-2B | 5.5 | 7.0 | 8.5 | 9.9 | 9.9 |
| TF0146-3A | 6.0 | 7.1 | 8.1 | 8.3 | 8.3 |
| TF0146-3B | 4.2 | 5.6 | 6.8 | 8.5 | 8.4 |
| TF0146-4A | 4.8 | 5.1 | 6.9 | 7.2 | 7.2 |
| TF0146-4B | 5.5 | 8.8 | 8.5 | 10.0 | 9.1 |
| T89-01 | 5.2 | 6.0 | 6.8 | 8.2 | 7.6 |
| T89-02 | 4.5 | 5.8 | 7.1 | 8.6 | 8.3 |
| T89-03 | 4.4 | 5.7 | 6.8 | 7.9 | 8.1 |
| T89-04 | 4.4 | 6.0 | 6.9 | 8.6 | 8.5 |
| T89-05 | 4.6 | 5.8 | 6.7 | 7.9 | 8.0 |
| T89-06 | 4.7 | 5.9 | 7.2 | 8.1 | 9.2 |
| T89-07 | 4.8 | 5.5 | 6.2 | 6.9 | 7.1 |
| T89-08 | 4.5 | 5.4 | 6.0 | 6.9 | 7.1 |
| T89-09 | 4.7 | 5.6 | 6.7 | 8.8 | 8.0 |
| T89-10 | 4.1 | 4.9 | 5.6 | 7.1 | 7.0 |
| T89-11 | 3.8 | 5.3 | 7.3 | 8.0 | 7.6 |
| T89-12 | N/A | 5.1 | 6.2 | 7.3 | 6.9 |
| T89-13 | 4.8 | 5.7 | 6.5 | 7.6 | 7.6 |
| T89-14 | 4.2 | 5.5 | 6.6 | 7.6 | 6.5 |
| T89-15 | 5.0 | 6.1 | 7.2 | 7.9 | 8.3 |
| T89-16 | 4.4 | 5.6 | 6.2 | 7.3 | 7.9 |
| T89-17 | 4.8 | 6.7 | 7.0 | 8.3 | 8.4 |
| T89-18 | 4.2 | 5.5 | 6.7 | 7.3 | 7.4 |

TABLE 2.44-continued

Diameter growth data for TF0146

| | Diameter (mm) Days in greenhouse | | | | |
|---|---|---|---|---|---|
| | 32 | 39 | 46 | 53 | 55 |
| T89-19 | 4.7 | 5.5 | 6.8 | 7.2 | 7.8 |
| T89-20 | 4.5 | 5.6 | 6.5 | 7.0 | 7.3 |
| T89-21 | 4.9 | 5.6 | 6.4 | 7.4 | 7.6 |
| T89-22 | 4.3 | 5.4 | 6.5 | 7.3 | 7.6 |
| T89-23 | 3.9 | 5.5 | 6.7 | 7.7 | 7.0 |
| T89-24 | 4.3 | 5.9 | 6.8 | 8.1 | 7.9 |
| T89-25 | 4.7 | 6.5 | 7.5 | 9.2 | 9.1 |
| T89-26 | 5.4 | 5.9 | 7.7 | 8.6 | 8.8 |
| T89-27 | 4.7 | 5.6 | 7.4 | 7.9 | 8.0 |
| T89-28 | 4.7 | 5.7 | 6.3 | 7.2 | 7.4 |
| T89-29 | 4.8 | 5.6 | 6.6 | 7.7 | 8.1 |
| T89-30 | 4.6 | 5.5 | 6.7 | 7.3 | 7.3 |
| T89-31 | 4.3 | 5.8 | 6.3 | 7.5 | 7.6 |
| T89-32 | 4.6 | 5.9 | 7.6 | 9.3 | 9.1 |
| T89-33 | 4.4 | 5.3 | 6.2 | 7.1 | 7.1 |
| T89-34 | 4.6 | 5.6 | 6.8 | 8.1 | 8.7 |
| T89-35 | 5.3 | 6.0 | 7.5 | 8.8 | 8.9 |
| T89-36 | 4.4 | 6.1 | 6.9 | 8.1 | 8.6 |
| T89-82 | 4.7 | 5.3 | 6.5 | 7.5 | 7.4 |
| T89-83 | 4.7 | 6.1 | 7.1 | 8.3 | 8.3 |
| T89-85 | 5.1 | 6.3 | 7.3 | 7.7 | 8.2 |

Results from growth analysis are specified in the overview table 2.45. The determined growth effects of specified construction group are presented as ratios between construction and wild type group AFH, AFD, AMHGR, ADGR, MFH, MFD, MMHGR and MDC.

TABLE 2.45

Overview table of growth effects of construct TF0146

| Construction group | Average Final Height | Average Final Diameter | Average Maximum Height Growth Rate | Average Diameter Growth Rate | Maximum Final Height | Maximum Final Diameter | Maximum of Maximum Height Growth Rate | Maximum Diameter Growth Rate |
|---|---|---|---|---|---|---|---|---|
| TF0146 | 1.13 | 1.08 | 1.18 | 0.99 | 1.16 | 1.08 | 1.25 | 0.95 |

Construction Group TF0173

This construct induces increased growth. The diameter growth rate is 19% higher comparing the average of the construction group and wild type control group. The TF0173 construction group meets growth difference selection criterion (3) as shown in table 2.48.

Tables 2.46 and 2.47 contain growth data for specified construction group and corresponding wild type group. Table rows contain height and diameter measurements of individuals of specified construction group and corresponding wild type group. Time of measurement as number of days in greenhouse is shown in table headers.

TABLE 2.46

Height growth data for TF0173

| | Height (cm) Days in greenhouse | | | | | | | | | |
|---|---|---|---|---|---|---|---|---|---|---|
| | 22 | 27 | 31 | 34 | 38 | 41 | 45 | 48 | 52 | 56 |
| TF0173-3A-1 | 28 | 39 | 51 | 60 | 73 | 81 | 93 | 104 | 120 | 134 |
| TF0173-3A-2 | 24 | 34 | 44 | 53 | 65 | 74 | 87 | 98 | 111 | 123 |
| TF0173-3B-1 | 30 | 42 | 57 | 67 | 81 | 94 | 108 | 120 | 136 | 155 |
| TF0173-3B-2 | 26 | 37 | 50 | 62 | 76 | 88 | 103 | 114 | 131 | 147 |
| TF0173-4A-1 | 26 | 37 | 51 | 60 | 76 | 87 | 101 | 112 | 125 | 141 |
| TF0173-4A-2 | 28 | 40 | 54 | 64 | 77 | 88 | 102 | 111 | 125 | 142 |
| TF0173-4B-1 | 30 | 41 | 57 | 65 | 80 | 91 | 105 | 115 | N/A | 136 |
| TF0173-4B-2 | 30 | 38 | 49 | 58 | 71 | 82 | 95 | 105 | 116 | 140 |
| T89-01 | 27 | 37 | 47 | 58 | 69 | 79 | 93 | 100 | 114 | 129 |
| T89-02 | 28 | 38 | 48 | 57 | 69 | 75 | 84 | 91 | 97 | 104 |
| T89-03 | 26 | 38 | 49 | 59 | 69 | 82 | 94 | 106 | 122 | 139 |
| T89-04 | 27 | 37 | 49 | 58 | 70 | 82 | 99 | 110 | 124 | 140 |
| T89-05 | 29 | 40 | 52 | 60 | 74 | 83 | 96 | 106 | 120 | 134 |
| T89-06 | 29 | 39 | 51 | 59 | 70 | 85 | 97 | 105 | 118 | 133 |
| T89-07 | 24 | 32 | 43 | 52 | 61 | 71 | 81 | 90 | 96 | 102 |
| T89-08 | 27 | 35 | 45 | 54 | 67 | 76 | 88 | 99 | 114 | 129 |
| T89-09 | 30 | 40 | 53 | 64 | 75 | 86 | 99 | 110 | 123 | 136 |
| T89-10 | 26 | 37 | 48 | 59 | 73 | 80 | 92 | 101 | 115 | 129 |
| T89-12 | 32 | 43 | 56 | 68 | 80 | 93 | 108 | 117 | 131 | 144 |
| T89-13 | 29 | 41 | 50 | 61 | 72 | 82 | 93 | 104 | 118 | 136 |
| T89-14 | 28 | 36 | 47 | 58 | 69 | 77 | 89 | 100 | 115 | 132 |
| T89-15 | 24 | 38 | 48 | 57 | 68 | 78 | 93 | 106 | 120 | 135 |
| T89-16 | 29 | 40 | 53 | 63 | 74 | 85 | N/A | 109 | 122 | 137 |
| T89-18 | 30 | 40 | 52 | 61 | 73 | 81 | 93 | 104 | 115 | 124 |
| T89-19 | 30 | 43 | 56 | 67 | 80 | 92 | 108 | 117 | 132 | 149 |
| T89-20 | 31 | 42 | 56 | 65 | 78 | 89 | 102 | 113 | 129 | 145 |
| T89-21 | 31 | 42 | 55 | 64 | 78 | 89 | 102 | 116 | 132 | 147 |
| T89-23 | 32 | 41 | 52 | 62 | 74 | 85 | 97 | 107 | 120 | 135 |
| T89-24 | 25 | 36 | 47 | 55 | 69 | 78 | 92 | 101 | 113 | 128 |
| T89-25 | 30 | 40 | 52 | 61 | 73 | 84 | 101 | 112 | 125 | 139 |
| T89-26 | 28 | 40 | 50 | 60 | 72 | 85 | 97 | 109 | 122 | 136 |
| T89-27 | 27 | 36 | 46 | 53 | 65 | 74 | 85 | 96 | 109 | 123 |
| T89-31 | 30 | 41 | 51 | 61 | 73 | 84 | 98 | 109 | 123 | 138 |
| T89-32 | 28 | 38 | 52 | 62 | 75 | 85 | 98 | 107 | 121 | 135 |
| T89-35 | 29 | 40 | 54 | 64 | 76 | 88 | 101 | 110 | 124 | 139 |
| T89-36 | 24 | 34 | 43 | 52 | 63 | 72 | 84 | 95 | 108 | 120 |
| T89-37 | 27 | 40 | 52 | 63 | 73 | 84 | 97 | 105 | 122 | 137 |
| T89-38 | 13 | 14 | 18 | 22 | 39 | 46 | 55 | 62 | 72 | 81 |
| T89-39 | 28 | 39 | 51 | 60 | 73 | 85 | 98 | 106 | 120 | 134 |
| T89-40 | 23 | 42 | 45 | 54 | 68 | 75 | 86 | 97 | 108 | 122 |
| T89-41 | 29 | 40 | 53 | 63 | 75 | 85 | 99 | 107 | 117 | 131 |
| T89-42 | 33 | 43 | 58 | 69 | 83 | 97 | 111 | 121 | 136 | 150 |
| T89-45 | 23 | 36 | 48 | 58 | 69 | 78 | 93 | 103 | 119 | N/A |
| T89-46 | 25 | 34 | 44 | 51 | 60 | 68 | 77 | 87 | 99 | 113 |
| T89-69 | 28 | 38 | 49 | 61 | 75 | 86 | 100 | 110 | 126 | 142 |

TABLE 2.47

Diameter growth data for TF0173

| | Diameter (mm) Days in greenhouse | | | |
|---|---|---|---|---|
| | 34 | 45 | 48 | 56 |
| TF0173-3A-1 | 5.6 | 6.4 | 7.3 | 8.0 |
| TF0173-3A-2 | 6.5 | 6.8 | 7.3 | 9.2 |
| TF0173-3B-1 | 6.0 | 8.9 | 9.0 | 9.8 |
| TF0173-3B-2 | 5.7 | 8.2 | 8.7 | 9.5 |
| TF0173-4A-1 | 6.0 | 7.9 | 8.5 | 10.1 |
| TF0173-4A-2 | 5.6 | 8.0 | 8.5 | 10.7 |
| TF0173-4B-1 | 6.3 | 8.1 | 9.0 | 11.5 |
| TF0173-4B-2 | 5.2 | 6.8 | 8.7 | 9.3 |
| T89-01 | 7.0 | N/A | 9.0 | 10.2 |
| T89-02 | 5.9 | 6.0 | 6.4 | 6.8 |
| T89-03 | 6.2 | 7.9 | 10.3 | 9.8 |
| T89-04 | 6.2 | 9.0 | 8.2 | 9.5 |
| T89-05 | 6.2 | 8.0 | 8.4 | 9.8 |
| T89-06 | 6.6 | 8.9 | 9.7 | 9.9 |
| T89-07 | 5.2 | 6.3 | 6.7 | 7.0 |
| T89-08 | 5.7 | 6.9 | 7.9 | 9.1 |
| T89-09 | 4.1 | 7.6 | 9.0 | 9.8 |
| T89-10 | 6.3 | 8.5 | 8.4 | 9.9 |
| T89-12 | 5.8 | 7.8 | 8.3 | 9.7 |
| T89-13 | 5.7 | 7.8 | 8.0 | 9.3 |
| T89-14 | 6.5 | 6.8 | 7.1 | 8.8 |
| T89-15 | 6.0 | 7.6 | 8.3 | 9.5 |
| T89-16 | 6.3 | 8.6 | 7.8 | 9.3 |
| T89-18 | 7.2 | 7.7 | 8.4 | 8.3 |
| T89-19 | 6.1 | 8.1 | 8.7 | 9.4 |
| T89-20 | 6.8 | 8.0 | 8.2 | 9.7 |
| T89-21 | 6.3 | 7.3 | 8.3 | 9.6 |
| T89-23 | 5.7 | 7.9 | 7.8 | 9.6 |
| T89-24 | 5.7 | 6.9 | 7.1 | 8.4 |
| T89-25 | 5.7 | 8.0 | 9.2 | 10.3 |
| T89-26 | 6.5 | 8.7 | 9.5 | 10.3 |
| T89-27 | 6.4 | 7.7 | 8.6 | 10.1 |
| T89-31 | 5.6 | 8.6 | 7.7 | 9.2 |
| T89-32 | 7.2 | 9.0 | 9.2 | 10.6 |
| T89-35 | 6.9 | 8.1 | 8.6 | 9.6 |
| T89-36 | 5.3 | 7.4 | 8.2 | 9.7 |
| T89-37 | 5.5 | 8.0 | 8.7 | 9.2 |
| T89-38 | 5.4 | N/A | 6.1 | 7.0 |
| T89-39 | 6.0 | 8.3 | 8.8 | 10.4 |
| T89-40 | 5.3 | 7.0 | 7.7 | 8.7 |
| T89-41 | 5.4 | 7.4 | 7.8 | 9.3 |
| T89-42 | 6.2 | 8.5 | 9.1 | 10.5 |
| T89-45 | 5.4 | 8.5 | 8.7 | 9.9 |
| T89-46 | 7.3 | 7.4 | 8.0 | 9.6 |
| T89-69 | 5.7 | 8.0 | 8.7 | 8.9 |

Results from growth analysis are specified in the overview table 2.48. The determined growth effects of specified construction group are presented as ratios between construction and wild type group AFH, AFD, AMHGR, ADGR, MFH, MFD, MMHGR and MDC.

TABLE 2.48

Overview table of growth effects of construct TF0173

| Construction group | Average Final Height | Average Final Diameter | Average Maximum Height Growth Rate | Average Diameter Growth Rate | Maximum Final Height | Maximum Final Diameter | Maximum of Maximum Height Growth Rate | Maximum Diameter Growth Rate |
|---|---|---|---|---|---|---|---|---|
| TF0173 | 1.06 | 1.04 | 1.07 | 1.19 | 1.03 | 1.09 | 1.04 | 0.99 |

Construction Group TF0247

This construct induces increased growth. The final height is 7% higher comparing the average of the construction group and wild type control group. The final height is 10% higher comparing the largest individuals of the construction group and wild type control group. The maximum height growth rate is 5% higher comparing the average of the construction group and wild type control group. The maximum height growth rate is 7% higher comparing the largest individuals of the construction group and wild type control group. The final diameter is 18% higher comparing the average of the construction group and wild type control group. The final diameter is 9% higher comparing the largest individuals of the construction group and wild type control group. The diameter growth rate is 22% higher comparing the average of the construction group and wild type control group. The diameter growth rate is 18% higher comparing the largest individuals of the construction group and wild type control group. The TF0247 construction group meets the more stringent level of growth difference selection criterion (2) and the less stringent level of growth difference selection criteria (1), (3) and (4) as shown in table 2.51.

Tables 2.49 and 2.50 contain growth data for specified construction group and corresponding wild type group. Table rows contain height and diameter measurements of individuals of specified construction group and corresponding wild type group. Time of measurement as number of days in greenhouse is shown in table headers.

TABLE 2.49

Height growth data for TF0247

| | Height (cm) Days in greenhouse | | | | | | | | |
|---|---|---|---|---|---|---|---|---|---|
| | 18 | 25 | 28 | 32 | 36 | 39 | 46 | 53 | 55 |
| TF0247-1A | 18 | 29 | 40 | 52 | 67 | 76 | 98 | 123 | 131 |
| TF0247-3A | 22 | 38 | 51 | 63 | 78 | 90 | 118 | 145 | 154 |
| TF0247-3B | 23 | 37 | 50 | 61 | 76 | 87 | 114 | 139 | 145 |
| TF0247-4A | 17 | 30 | 41 | 53 | 68 | 77 | 103 | 127 | 134 |
| TF0247-6B | 25 | 40 | 52 | 63 | 73 | 83 | 97 | 111 | 116 |
| T89-01 | 18 | 32 | 43 | 54 | 66 | 76 | 98 | 124 | 133 |
| T89-02 | 20 | 33 | 43 | 53 | 67 | 76 | 101 | 124 | 129 |
| T89-03 | 17 | 31 | 43 | 53 | 68 | 76 | 102 | 128 | 135 |
| T89-04 | 19 | 33 | 44 | 54 | 67 | 74 | 97 | 122 | 129 |
| T89-05 | 20 | 33 | 44 | 54 | 67 | 76 | 100 | 121 | 129 |
| T89-06 | 18 | 31 | 42 | 53 | 67 | 76 | 97 | 121 | 128 |
| T89-07 | 16 | 28 | 41 | 53 | 65 | 74 | 96 | 121 | 129 |
| T89-08 | 19 | 34 | 43 | 53 | 65 | 75 | 98 | 123 | 131 |
| T89-09 | 20 | 30 | 40 | 52 | 64 | 73 | 97 | 119 | 125 |
| T89-10 | 21 | 33 | 41 | 49 | 61 | 70 | 92 | 114 | 121 |
| T89-11 | 18 | 31 | 40 | 49 | 61 | 71 | 94 | 117 | 123 |
| T89-12 | 18 | 31 | 40 | N/A | 60 | 68 | 90 | 107 | 115 |
| T89-13 | 19 | 35 | 47 | 58 | 70 | 78 | 103 | 128 | 135 |
| T89-14 | 19 | 31 | 40 | 50 | 61 | 72 | 93 | 118 | 124 |
| T89-15 | 20 | 32 | 41 | 50 | 62 | 70 | 91 | 114 | 120 |
| T89-16 | 18 | 30 | 39 | 49 | 62 | 71 | 92 | 114 | 122 |
| T89-17 | 17 | 33 | 45 | 55 | 70 | 78 | 104 | 129 | 136 |
| T89-18 | 19 | 32 | 44 | 56 | 71 | 82 | 106 | 130 | 137 |
| T89-19 | 16 | 26 | 36 | 46 | 51 | 69 | 89 | 112 | 119 |
| T89-20 | 16 | 31 | 41 | 49 | 60 | 71 | 91 | 111 | 118 |
| T89-21 | 20 | 31 | 44 | 54 | 68 | 76 | 99 | 122 | 127 |
| T89-22 | 14 | 26 | 37 | 46 | 61 | 72 | 96 | 120 | 127 |
| T89-23 | 19 | 32 | 40 | 50 | 63 | 73 | 100 | 121 | 127 |
| T89-24 | 20 | 31 | 41 | 47 | 58 | 68 | 90 | 111 | 117 |
| T89-25 | 20 | 36 | 45 | 57 | 69 | 78 | 101 | 127 | 134 |
| T89-26 | 20 | 37 | 49 | 58 | 71 | 80 | 107 | 131 | 140 |
| T89-27 | 19 | 34 | 44 | 55 | 71 | 81 | 107 | 131 | 138 |
| T89-28 | 17 | 35 | 44 | 56 | 68 | 76 | 99 | 126 | 132 |
| T89-29 | 17 | 32 | 45 | 55 | 68 | 78 | 101 | 125 | 132 |
| T89-30 | 18 | 31 | 41 | 50 | 63 | 72 | 95 | 119 | 125 |
| T89-31 | 17 | 27 | 35 | 45 | 58 | 67 | 87 | 108 | 116 |
| T89-32 | 19 | 32 | 44 | 52 | 65 | 74 | 98 | 121 | 127 |

TABLE 2.49-continued

Height growth data for TF0247

| | Height (cm) Days in greenhouse | | | | | | | | |
|---|---|---|---|---|---|---|---|---|---|
| | 18 | 25 | 28 | 32 | 36 | 39 | 46 | 53 | 55 |
| T89-33 | 20 | 33 | 43 | 53 | 64 | 74 | 96 | 119 | 126 |
| T89-34 | 19 | 34 | 44 | 55 | 68 | 78 | 100 | 124 | 130 |
| T89-35 | 17 | 30 | 40 | 51 | 64 | 74 | 95 | 116 | 122 |
| T89-36 | 18 | 30 | 40 | 49 | 62 | 71 | 91 | 114 | 121 |
| T89-82 | 21 | 33 | 43 | 54 | 65 | 75 | 98 | 118 | 125 |
| T89-83 | 22 | 35 | 47 | 55 | 71 | 80 | 105 | 130 | 137 |
| T89-85 | 21 | 36 | 46 | 56 | 67 | 76 | 98 | 123 | 131 |

TABLE 2.50

Diameter growth data for TF0247

| | Diameter (mm) Days in greenhouse | | | | |
|---|---|---|---|---|---|
| | 32 | 39 | 46 | 53 | 55 |
| TF0247-1A | 4.9 | 6.0 | 7.4 | 8.5 | 9.7 |
| TF0247-3A | 5.8 | 6.8 | 7.6 | 8.7 | 9.1 |
| TF0247-3B | 5.4 | 7.0 | 8.1 | 9.5 | 10.0 |
| TF0247-4A | 4.6 | 5.7 | 7.4 | 10.3 | 9.7 |
| TF0247-6B | 6.0 | 6.8 | 7.0 | 7.3 | 7.9 |
| T89-01 | 5.2 | 6.0 | 6.8 | 8.2 | 7.6 |
| T89-02 | 4.5 | 5.8 | 7.1 | 8.6 | 8.3 |
| T89-03 | 4.4 | 5.7 | 6.8 | 7.9 | 8.1 |
| T89-04 | 4.4 | 6.0 | 6.9 | 8.6 | 8.5 |
| T89-05 | 4.6 | 5.8 | 6.7 | 7.9 | 8.0 |
| T89-06 | 4.7 | 5.9 | 7.2 | 8.1 | 9.2 |
| T89-07 | 4.8 | 5.5 | 6.2 | 6.9 | 7.1 |
| T89-08 | 4.5 | 5.4 | 6.0 | 6.9 | 7.1 |
| T89-09 | 4.7 | 5.6 | 6.7 | 8.8 | 8.0 |
| T89-10 | 4.1 | 4.9 | 5.6 | 7.1 | 7.0 |
| T89-11 | 3.8 | 5.3 | 7.3 | 8.0 | 7.6 |
| T89-12 | N/A | 5.1 | 6.2 | 7.3 | 6.9 |
| T89-13 | 4.8 | 5.7 | 6.5 | 7.6 | 7.6 |
| T89-14 | 4.2 | 5.5 | 6.6 | 7.6 | 6.5 |
| T89-15 | 5.0 | 6.1 | 7.2 | 7.9 | 8.3 |
| T89-16 | 4.4 | 5.6 | 6.2 | 7.3 | 7.9 |
| T89-17 | 4.8 | 6.7 | 7.0 | 8.3 | 8.4 |
| T89-18 | 4.2 | 5.5 | 6.7 | 7.3 | 7.4 |
| T89-19 | 4.7 | 5.5 | 6.8 | 7.2 | 7.8 |
| T89-20 | 4.5 | 5.6 | 6.5 | 7.0 | 7.3 |
| T89-21 | 4.9 | 5.6 | 6.4 | 7.4 | 7.6 |
| T89-22 | 4.3 | 5.4 | 6.5 | 7.3 | 7.6 |
| T89-23 | 3.9 | 5.5 | 6.7 | 7.7 | 7.0 |
| T89-24 | 4.3 | 5.9 | 6.8 | 8.1 | 7.9 |
| T89-25 | 4.7 | 6.5 | 7.5 | 9.2 | 9.1 |
| T89-26 | 5.4 | 5.9 | 7.7 | 8.6 | 8.8 |
| T89-27 | 4.7 | 5.6 | 7.4 | 7.9 | 8.0 |
| T89-28 | 4.7 | 5.7 | 6.3 | 7.2 | 7.4 |
| T89-29 | 4.8 | 5.6 | 6.6 | 7.7 | 8.1 |
| T89-30 | 4.6 | 5.5 | 6.7 | 7.3 | 7.3 |
| T89-31 | 4.3 | 5.8 | 6.3 | 7.5 | 7.6 |
| T89-32 | 4.6 | 5.9 | 7.6 | 9.3 | 9.1 |
| T89-33 | 4.4 | 5.3 | 6.2 | 7.1 | 7.1 |
| T89-34 | 4.6 | 5.6 | 6.8 | 8.1 | 8.7 |
| T89-35 | 5.3 | 6.0 | 7.5 | 8.8 | 8.9 |
| T89-36 | 4.4 | 6.1 | 6.9 | 8.1 | 8.6 |
| T89-82 | 4.7 | 5.3 | 6.5 | 7.5 | 7.4 |
| T89-83 | 4.7 | 6.1 | 7.1 | 8.3 | 8.3 |
| T89-85 | 5.1 | 6.3 | 7.3 | 7.7 | 8.2 |

Results from growth analysis are specified in the overview table 2.51. The determined growth effects of specified construction group are presented as ratios between construction and wild type group AFH, AFD, AMHGR, ADGR, MFH, MFD, MMHGR and MDC.

TABLE 2.51

Overview table of growth effects of construct TF0247

| Construction group | Average Final Height | Average Final Diameter | Average Maximum Height Growth Rate | Average Maximum Diameter Growth Rate | Maximum Final Height | Maximum Final Diameter | Maximum of Maximum Height Growth Rate | Maximum Diameter Growth Rate |
|---|---|---|---|---|---|---|---|---|
| TF0247 | 1.07 | 1.18 | 1.05 | 1.22 | 1.10 | 1.09 | 1.07 | 1.18 |

Construction Group TF0405

This construct induces increased growth. The final height is 10% higher comparing the average of the construction group and wild type control group. The final height is 9% higher comparing the largest individuals of the construction group and wild type control group. The maximum height growth rate is 13% higher comparing the average of the construction group and wild type control group. The maximum height growth rate is 15% higher comparing the largest individuals of the construction group and wild type control group. The final diameter is 15% higher comparing the average of the construction group and wild type control group. The final diameter is 10% higher comparing the largest individuals of the construction group and wild type control group. The diameter growth rate is 22% higher comparing the average of the construction group and wild type control group. The diameter growth rate is 19% higher comparing the largest individuals of the construction group and wild type control group. The TF0405 construction group meets the more stringent level of growth difference selection criteria (1) and (2) and the less stringent level of growth difference selection criteria (3) and (4) as shown in table 2.54.

Tables 2.52 and 2.53 contain growth data for specified construction group and corresponding wild type group. Table rows contain height and diameter measurements of individuals of specified construction group and corresponding wild type group. Time of measurement as number of days in greenhouse is shown in table headers.

TABLE 2.52

Height growth data for TF0405

| | Height (cm) Days in greenhouse | | | | | | | | |
|---|---|---|---|---|---|---|---|---|---|
| | 18 | 25 | 28 | 32 | 36 | 39 | 46 | 53 | 55 |
| TF0405-2A-1 | 7 | 17 | 25 | 36 | 46 | 57 | 83 | 109 | 117 |
| TF0405-2A-2 | 21 | 36 | 50 | 60 | 74 | 87 | 118 | 146 | 153 |
| TF0405-2B-2 | 19 | 34 | 47 | 58 | 73 | 84 | 108 | 130 | 136 |
| TF0405-3A-1 | 24 | 41 | 54 | 63 | 77 | 88 | 117 | 144 | 150 |
| TF0405-3A-2 | 25 | 38 | 52 | 64 | 79 | 91 | 117 | 142 | 150 |
| TF0405-3B-1 | 19 | 33 | 44 | 54 | 65 | 75 | 98 | 123 | 130 |
| TF0405-3B-2 | 22 | 36 | 49 | 59 | 72 | 86 | 112 | 136 | 145 |
| T89-01 | 18 | 32 | 43 | 54 | 66 | 76 | 98 | 124 | 133 |
| T89-02 | 20 | 33 | 43 | 53 | 67 | 76 | 101 | 124 | 129 |
| T89-03 | 17 | 31 | 43 | 53 | 68 | 76 | 102 | 128 | 135 |
| T89-04 | 19 | 33 | 44 | 54 | 67 | 74 | 97 | 122 | 129 |
| T89-05 | 20 | 33 | 44 | 54 | 67 | 76 | 100 | 121 | 129 |
| T89-06 | 18 | 31 | 42 | 53 | 67 | 76 | 97 | 121 | 128 |
| T89-07 | 16 | 28 | 41 | 53 | 65 | 74 | 96 | 121 | 129 |
| T89-08 | 19 | 34 | 43 | 53 | 65 | 75 | 98 | 123 | 131 |
| T89-09 | 20 | 30 | 40 | 52 | 64 | 73 | 97 | 119 | 125 |
| T89-10 | 21 | 33 | 41 | 49 | 61 | 70 | 92 | 114 | 121 |
| T89-11 | 18 | 31 | 40 | 49 | 61 | 71 | 94 | 117 | 123 |
| T89-12 | 18 | 31 | 40 | N/A | 60 | 68 | 90 | 107 | 115 |
| T89-13 | 19 | 35 | 47 | 58 | 70 | 78 | 103 | 128 | 135 |
| T89-14 | 19 | 31 | 40 | 50 | 61 | 72 | 93 | 118 | 124 |

TABLE 2.52-continued

Height growth data for TF0405

| | Height (cm) Days in greenhouse | | | | | | | | |
|---|---|---|---|---|---|---|---|---|---|
| | 18 | 25 | 28 | 32 | 36 | 39 | 46 | 53 | 55 |
| T89-15 | 20 | 32 | 41 | 50 | 62 | 70 | 91 | 114 | 120 |
| T89-16 | 18 | 30 | 39 | 49 | 62 | 71 | 92 | 114 | 122 |
| T89-17 | 17 | 33 | 45 | 55 | 70 | 78 | 104 | 129 | 136 |
| T89-18 | 19 | 32 | 44 | 56 | 71 | 82 | 106 | 130 | 137 |
| T89-19 | 16 | 26 | 36 | 46 | 51 | 69 | 89 | 112 | 119 |
| T89-20 | 16 | 31 | 41 | 49 | 60 | 71 | 91 | 111 | 118 |
| T89-21 | 20 | 31 | 44 | 54 | 68 | 76 | 99 | 122 | 127 |
| T89-22 | 14 | 26 | 37 | 46 | 61 | 72 | 96 | 120 | 127 |
| T89-23 | 19 | 32 | 40 | 50 | 63 | 73 | 100 | 121 | 127 |
| T89-24 | 20 | 31 | 41 | 47 | 58 | 68 | 90 | 111 | 117 |
| T89-25 | 20 | 36 | 45 | 57 | 69 | 78 | 101 | 127 | 134 |
| T89-26 | 20 | 37 | 49 | 58 | 71 | 80 | 107 | 131 | 140 |
| T89-27 | 19 | 34 | 44 | 55 | 71 | 81 | 107 | 131 | 138 |
| T89-28 | 17 | 35 | 44 | 56 | 68 | 76 | 99 | 126 | 132 |
| T89-29 | 17 | 32 | 45 | 55 | 68 | 78 | 101 | 125 | 132 |
| T89-30 | 18 | 31 | 41 | 50 | 63 | 72 | 95 | 119 | 125 |
| T89-31 | 17 | 27 | 35 | 45 | 58 | 67 | 87 | 108 | 116 |
| T89-32 | 19 | 32 | 44 | 52 | 65 | 74 | 98 | 121 | 127 |
| T89-33 | 20 | 33 | 43 | 53 | 64 | 74 | 96 | 119 | 126 |
| T89-34 | 19 | 34 | 44 | 55 | 68 | 78 | 100 | 124 | 130 |
| T89-35 | 17 | 30 | 40 | 51 | 64 | 74 | 95 | 116 | 122 |
| T89-36 | 18 | 30 | 40 | 49 | 62 | 71 | 91 | 114 | 121 |
| T89-82 | 21 | 33 | 43 | 54 | 65 | 75 | 98 | 118 | 125 |
| T89-83 | 22 | 35 | 47 | 55 | 71 | 80 | 105 | 130 | 137 |
| T89-85 | 21 | 36 | 46 | 56 | 67 | 76 | 98 | 123 | 131 |

TABLE 2.53

Diameter growth data for TF0405

| | Diameter (mm) Days in greenhouse | | | | |
|---|---|---|---|---|---|
| | 32 | 39 | 46 | 53 | 55 |
| TF0405-2A-1 | 4.0 | 5.1 | 6.8 | 9.1 | 9.2 |
| TF0405-2A-2 | 5.3 | 6.9 | 8.3 | 10.2 | 10.1 |
| TF0405-2B-2 | 5.3 | 7.0 | 7.7 | 8.9 | 9.0 |
| TF0405-3A-1 | 5.2 | 6.9 | 8.1 | 9.1 | 8.9 |
| TF0405-3A-2 | 5.4 | 6.7 | 8.0 | 9.2 | 9.0 |
| TF0405-3B-1 | 5.1 | 5.8 | 7.3 | 7.8 | 7.9 |
| TF0405-3B-2 | 5.3 | 6.3 | 7.8 | 9.2 | 9.1 |
| T89-01 | 5.2 | 6.0 | 6.8 | 8.2 | 7.6 |
| T89-02 | 4.5 | 5.8 | 7.1 | 8.6 | 8.3 |
| T89-03 | 4.4 | 5.7 | 6.8 | 7.9 | 8.1 |
| T89-04 | 4.4 | 6.0 | 6.9 | 8.6 | 8.5 |
| T89-05 | 4.6 | 5.8 | 6.7 | 7.9 | 8.0 |
| T89-06 | 4.7 | 5.9 | 7.2 | 8.1 | 9.2 |
| T89-07 | 4.8 | 5.5 | 6.2 | 6.9 | 7.1 |
| T89-08 | 4.5 | 5.4 | 6.0 | 6.9 | 7.1 |
| T89-09 | 4.7 | 5.6 | 6.7 | 8.8 | 8.0 |
| T89-10 | 4.1 | 4.9 | 5.6 | 7.1 | 7.0 |
| T89-11 | 3.8 | 5.3 | 7.3 | 8.0 | 7.6 |
| T89-12 | N/A | 5.1 | 6.2 | 7.3 | 6.9 |
| T89-13 | 4.8 | 5.7 | 6.5 | 7.6 | 7.6 |

TABLE 2.53-continued

Diameter growth data for TF0405

| | Diameter (mm) Days in greenhouse | | | | |
|---|---|---|---|---|---|
| | 32 | 39 | 46 | 53 | 55 |
| T89-14 | 4.2 | 5.5 | 6.6 | 7.6 | 6.5 |
| T89-15 | 5.0 | 6.1 | 7.2 | 7.9 | 8.3 |
| T89-16 | 4.4 | 5.6 | 6.2 | 7.3 | 7.9 |
| T89-17 | 4.8 | 6.7 | 7.0 | 8.3 | 8.4 |
| T89-18 | 4.2 | 5.5 | 6.7 | 7.3 | 7.4 |
| T89-19 | 4.7 | 5.5 | 6.8 | 7.2 | 7.8 |
| T89-20 | 4.5 | 5.6 | 6.5 | 7.0 | 7.3 |
| T89-21 | 4.9 | 5.6 | 6.4 | 7.4 | 7.6 |
| T89-22 | 4.3 | 5.4 | 6.5 | 7.3 | 7.6 |
| T89-23 | 3.9 | 5.5 | 6.7 | 7.7 | 7.0 |
| T89-24 | 4.3 | 5.9 | 6.8 | 8.1 | 7.9 |
| T89-25 | 4.7 | 6.5 | 7.5 | 9.2 | 9.1 |
| T89-26 | 5.4 | 5.9 | 7.7 | 8.6 | 8.8 |
| T89-27 | 4.7 | 5.6 | 7.4 | 7.9 | 8.0 |
| T89-28 | 4.7 | 5.7 | 6.3 | 7.2 | 7.4 |
| T89-29 | 4.8 | 5.6 | 6.6 | 7.7 | 8.1 |
| T89-30 | 4.6 | 5.5 | 6.7 | 7.3 | 7.3 |
| T89-31 | 4.3 | 5.8 | 6.3 | 7.5 | 7.6 |
| T89-32 | 4.6 | 5.9 | 7.6 | 9.3 | 9.1 |
| T89-33 | 4.4 | 5.3 | 6.2 | 7.1 | 7.1 |
| T89-34 | 4.6 | 5.6 | 6.8 | 8.1 | 8.7 |
| T89-35 | 5.3 | 6.0 | 7.5 | 8.8 | 8.9 |
| T89-36 | 4.4 | 6.1 | 6.9 | 8.1 | 8.6 |
| T89-82 | 4.7 | 5.3 | 6.5 | 7.5 | 7.4 |
| T89-83 | 4.7 | 6.1 | 7.1 | 8.3 | 8.3 |
| T89-85 | 5.1 | 6.3 | 7.3 | 7.7 | 8.2 |

Results from growth analysis are specified in the overview table 2.54. The determined growth effects of specified construction group are presented as ratios between construction and wild type group AFH, AFD, AMHGR, ADGR, MFH, MFD, MMHGR and MDC.

TABLE 2.54

Overview table of growth effects of construct TF0405

| Construction group | Average Final Height | Average Final Diameter | Average Maximum Height Growth Rate | Average Diameter Growth Rate | Maximum Final Height | Maximum Final Diameter | Maximum of Maximum Height Growth Rate | Maximum Diameter Growth Rate |
|---|---|---|---|---|---|---|---|---|
| TF0405 | 1.10 | 1.15 | 1.13 | 1.22 | 1.09 | 1.10 | 1.15 | 1.19 |

Construction Group TFSTT004

Tables 2.55 and 2.56 contain growth data for specified construction group and corresponding wild type group. Table rows contain height and diameter measurements of individuals of specified construction group and corresponding wild type group. Time of measurement as number of days in greenhouse is shown in table headers.

TABLE 2.55

Height growth data for TFSTT004

| | Height (cm) Days in greenhouse | | | | | | | | | |
|---|---|---|---|---|---|---|---|---|---|---|
| | 19 | 28 | 34 | 40 | 44 | 47 | 51 | 54 | 61 | 65 |
| TFSTT004-1A | 18 | 35 | 55 | 71 | 84 | 95 | 105 | 114 | 135 | 145 |
| TFSTT004-2A-1 | 16 | 33 | 54 | 67 | 82 | 89 | 100 | 108 | 130 | 141 |
| TFSTT004-2A-2 | 19 | 39 | 57 | 71 | 84 | 94 | 106 | 112 | 130 | 140 |
| TFSTT004-2B-1 | 20 | 41 | 61 | 78 | 90 | 99 | 110 | 119 | 139 | 150 |
| TFSTT004-2B-2 | 20 | 38 | 59 | 74 | 85 | 93 | 103 | 113 | 135 | 146 |
| TFSTT004-3B | 19 | 35 | 53 | 66 | 77 | 87 | 98 | 107 | 124 | 134 |
| TFSTT004-4B-1 | 18 | 33 | 51 | 63 | 76 | 86 | 98 | 108 | 129 | 142 |
| TFSTT004-4B-2 | 18 | 35 | 57 | 74 | 86 | 96 | 108 | 116 | 141 | 152 |
| T89-01 | 18 | 30 | 46 | 58 | 69 | 77 | 87 | 96 | 113 | 122 |
| T89-02 | 18 | 30 | 49 | 62 | 72 | 77 | 84 | 90 | 102 | 109 |
| T89-03 | 15 | 27 | 41 | 54 | 65 | 73 | 82 | 91 | 112 | 123 |
| T89-10 | N/A | N/A | N/A | N/A | N/A | N/A | N/A | N/A | N/A | N/A |
| T89-11 | 19 | 31 | 49 | 61 | 74 | 83 | 94 | 103 | 124 | 133 |
| T89-12 | 17 | 30 | 45 | 58 | 69 | 77 | 90 | 100 | 123 | 134 |
| T89-13 | 18 | 27 | 43 | 56 | 68 | 78 | 91 | 100 | 121 | 133 |
| T89-14 | 5 | 26 | 42 | 56 | 67 | 74 | 83 | 90 | 109 | 119 |
| T89-15 | 10 | 15 | 25 | 33 | 41 | 45 | 52 | 57 | 72 | 82 |
| T89-16 | 19 | 33 | 53 | 63 | 73 | 82 | 93 | 102 | 119 | 130 |
| T89-17 | 17 | 29 | 46 | 58 | 66 | 72 | 80 | 86 | 96 | 102 |
| T89-18 | 16 | 30 | 48 | 59 | 71 | 81 | 93 | 103 | 122 | 132 |

TABLE 2.55-continued

Height growth data for TFSTT004

| | Height (cm) Days in greenhouse | | | | | | | | | |
|---|---|---|---|---|---|---|---|---|---|---|
| | 19 | 28 | 34 | 40 | 44 | 47 | 51 | 54 | 61 | 65 |
| T89-19 | 18 | 32 | 50 | 65 | 77 | 84 | 94 | 102 | 126 | 139 |
| T89-20 | 16 | 33 | 52 | 67 | 79 | 88 | 98 | 105 | 124 | 139 |
| T89-21 | 17 | 29 | 44 | 58 | 67 | 73 | 83 | 90 | 110 | 122 |
| T89-22 | 14 | 28 | 47 | 61 | 71 | 80 | 89 | 98 | 119 | 133 |
| T89-23 | 10 | 33 | 45 | 53 | 63 | 71 | 82 | 90 | 112 | 123 |
| T89-24 | 20 | 28 | 43 | 51 | 62 | 69 | 78 | 87 | 106 | 119 |
| T89-25 | 14 | 26 | 38 | 52 | 64 | 72 | 82 | 89 | 110 | 122 |
| T89-26 | 15 | 28 | 44 | 57 | 69 | 77 | 87 | 96 | 120 | 133 |
| T89-27 | 18 | 29 | 47 | 62 | 75 | 82 | 92 | 103 | 125 | 138 |
| T89-28 | 22 | 37 | 54 | 67 | 78 | 88 | 97 | 104 | 123 | 133 |
| T89-29 | 16 | 33 | 49 | 63 | 76 | 84 | 93 | 100 | 123 | 138 |
| T89-30 | 15 | 40 | 46 | 58 | 67 | 74 | 85 | 92 | 113 | 124 |

TABLE 2.56

Diameter growth data for TFSTT004

| | Diameter (mm) Days in greenhouse | | | | | | | | |
|---|---|---|---|---|---|---|---|---|---|
| | 28 | 34 | 40 | 44 | 47 | 51 | 54 | 61 | 65 |
| TFSTT004-1A | 4.6 | 6.0 | 8.5 | 7.9 | 8.6 | 9.0 | 10.3 | 11.2 | 11.3 |
| TFSTT004-2A-1 | 4.6 | 5.7 | 6.5 | 7.4 | 8.8 | 9.1 | 9.8 | 10.6 | 10.7 |
| TFSTT004-2A-2 | 4.2 | 5.9 | 6.9 | 7.5 | 8.5 | 8.9 | 9.6 | 10.2 | 10.3 |
| TFSTT004-2B-1 | 5.0 | 6.5 | 7.8 | 8.9 | 9.6 | 10.9 | 10.9 | 12.1 | 12.6 |
| TFSTT004-2B-2 | 4.5 | 6.2 | 7.3 | 8.3 | 8.3 | 9.3 | 8.9 | 10.7 | 11.0 |
| TFSTT004-3B | 4.1 | 5.6 | 6.8 | 7.5 | 8.2 | 9.0 | 9.9 | 10.6 | 10.7 |
| TFSTT004-4B-1 | 3.6 | 5.0 | 6.0 | 7.0 | 7.5 | 9.3 | 9.2 | 10.6 | 11.0 |
| TFSTT004-4B-2 | 4.2 | 5.7 | 7.5 | 8.6 | 9.2 | 9.5 | 10.4 | 11.1 | 11.7 |
| T89-01 | 3.2 | 4.6 | 5.4 | 6.2 | 6.8 | 7.9 | 8.3 | 9.5 | 9.3 |
| T89-02 | 3.4 | 4.7 | 5.5 | 7.3 | 6.3 | 6.6 | 6.9 | 8.3 | 7.5 |
| T89-03 | 3.9 | 4.4 | 5.2 | 6.2 | 6.4 | 7.8 | 7.6 | 9.7 | 9.4 |
| T89-10 | N/A | N/A | N/A | N/A | N/A | N/A | N/A | N/A | N/A |
| T89-11 | 3.4 | 5.1 | 6.2 | 7.6 | 6.8 | 6.9 | 7.7 | 10.1 | 9.5 |
| T89-12 | 2.9 | 4.7 | 5.8 | 6.6 | 7.8 | 8.0 | 8.7 | 9.1 | 9.2 |
| T89-13 | 3.0 | 4.3 | 5.4 | 5.8 | 6.4 | 7.6 | 7.8 | 8.2 | 8.8 |
| T89-14 | 3.0 | 4.5 | 5.7 | 6.3 | 6.7 | 7.9 | 7.8 | 9.0 | 8.9 |
| T89-15 | N/A | 2.1 | 3.0 | 4.0 | 4.0 | 4.5 | 4.9 | 5.5 | 5.6 |
| T89-16 | 3.5 | 5.3 | 6.4 | 6.6 | 7.0 | 7.2 | 8.3 | 8.2 | 9.0 |
| T89-17 | 3.4 | 4.6 | 5.1 | 5.4 | 6.0 | 6.4 | 6.5 | 6.8 | 7.1 |
| T89-18 | 3.6 | 5.2 | 6.0 | 7.0 | 7.8 | 8.2 | 9.9 | 10.3 | 9.7 |
| T89-19 | 4.2 | 5.5 | 6.6 | 7.7 | 8.5 | 8.9 | 9.5 | 11.1 | 12.3 |
| T89-20 | 4.1 | 5.5 | 6.6 | 8.1 | 9.3 | 9.6 | 9.3 | 10.0 | 11.1 |
| T89-21 | 3.1 | 5.6 | 5.8 | 6.7 | 7.1 | 7.8 | 8.4 | 9.7 | 10.1 |
| T89-22 | 3.2 | 4.4 | 5.6 | 6.5 | 7.5 | 7.6 | 7.8 | 8.9 | 9.2 |
| T89-23 | 2.4 | 4.2 | 5.1 | 6.1 | 6.5 | 7.5 | 10.1 | 9.3 | 10.2 |
| T89-24 | 3.2 | 4.5 | 5.1 | 6.3 | 7.0 | 7.6 | 8.1 | 8.8 | 9.1 |
| T89-25 | 3.3 | 4.3 | 5.2 | 5.8 | 6.5 | 7.4 | 7.8 | 9.3 | 9.7 |
| T89-26 | 3.3 | 4.4 | 5.5 | 6.6 | 7.2 | 8.1 | 8.9 | 9.5 | 10.5 |
| T89-27 | 3.3 | 4.9 | 6.0 | 7.8 | 8.0 | 8.9 | 9.7 | 11.2 | 11.5 |
| T89-28 | 4.5 | 5.7 | 7.4 | 7.8 | 8.5 | 9.4 | 9.7 | 10.2 | 11.1 |
| T89-29 | 3.1 | 4.7 | 6.3 | 7.2 | 7.9 | 9.2 | 9.8 | 11.1 | 10.7 |
| T89-30 | 3.0 | 5.8 | 6.2 | 7.7 | 7.9 | 8.6 | 8.2 | 10.1 | 10.3 |

Results from growth analysis are specified in the overview table 2.57. The determined growth effects of specified construction group are presented as ratios between construction and wild type group AFH, AFD, AMHGR, ADGR, MFH, MFD, MMHGR and MDC.

TABLE 2.57

Overview table of growth effects of construct TFSTT004

| Construction group | Average Final Height | Average Final Diameter | Average Maximum Height Growth Rate | Average Diameter Growth Rate | Maximum Final Height | Maximum Final Diameter | Maximum of Maximum Height Growth Rate | Maximum Diameter Growth Rate |
|---|---|---|---|---|---|---|---|---|
| TFSTT004 | 1.15 | 1.17 | 1.06 | 1.09 | 1.09 | 1.02 | 0.97 | 0.91 |

Construction Group TFSTT013

The gene over-expressed with construct TFSTT013 generates the same top hits as the gene over-expressed with construct TFSTT038, when using BLAST search against the *P. trichocarpa* Jamboree Gene Model database at the Joint Genome Institute web page, indicating high homology between the two genes.

Tables 2.58 and 2.59 contain growth data for specified construction group and corresponding wild type group. Table rows contain height and diameter measurements of individuals of specified construction group and corresponding wild type group. Time of measurement as number of days in greenhouse is shown in table headers.

TABLE 2.58

Height growth data for TFSTT013

| | Height (cm) Days in greenhouse | | | | | | |
|---|---|---|---|---|---|---|---|
| | 19 | 25 | 32 | 39 | 48 | 54 | 56 |
| TFSTT013-1A | 18 | 30 | 54 | 81 | 113 | 137 | 140 |
| TFSTT013-1B | 19 | 31 | 54 | 75 | 108 | 124 | 127 |
| TFSTT013-2B | 16 | 28 | 48 | 67 | 98 | 115 | 121 |
| TFSTT013-3A | 17 | 29 | 48 | 70 | 89 | 103 | 110 |
| TFSTT013-3B | 20 | 32 | 53 | 75 | 106 | 128 | 136 |
| TFSTT013-4A | 23 | 37 | 59 | 83 | 116 | 141 | 149 |
| TFSTT013-4B | 21 | 33 | 57 | 85 | 120 | 140 | 147 |
| TFSTT013-5B | 18 | 30 | 52 | 77 | 109 | 126 | 133 |
| T89-01 | 18 | 28 | 49 | 70 | 100 | 126 | 133 |
| T89-02 | 19 | 29 | 51 | 76 | 105 | 128 | 136 |
| T89-03 | 11 | 18 | 36 | 47 | 76 | 93 | 98 |
| T89-04 | 16 | 25 | 48 | 74 | 102 | 126 | 133 |
| T89-05 | 17 | 29 | 49 | 73 | 106 | 128 | 135 |
| T89-06 | 16 | 28 | 51 | 74 | 105 | 127 | 132 |
| T89-07 | 19 | 28 | 51 | 73 | 104 | 125 | 136 |
| T89-08 | 19 | 31 | 52 | 77 | 110 | 130 | 137 |
| T89-09 | 17 | 26 | 44 | 67 | 93 | 114 | 122 |
| T89-10 | 16 | 25 | 44 | 63 | 89 | 108 | 115 |
| T89-11 | 20 | 31 | 47 | 68 | 87 | 114 | 118 |
| T89-12 | 17 | 28 | 48 | 70 | 101 | 117 | 124 |
| T89-13 | 18 | 30 | 52 | 73 | 105 | 125 | 130 |
| T89-14 | 19 | 29 | 44 | 67 | 96 | 116 | 123 |
| T89-15 | 17 | 29 | 49 | 72 | 102 | 124 | 131 |
| T89-16 | 18 | 29 | 50 | 74 | 108 | 129 | 135 |
| T89-17 | 14 | 23 | 43 | 65 | 93 | 116 | 123 |
| T89-18 | 15 | 26 | 48 | 72 | 103 | 128 | 136 |
| T89-19 | 11 | 19 | 38 | 63 | 93 | 115 | 122 |
| T89-20 | 19 | 30 | 52 | 75 | 104 | 126 | 133 |
| T89-21 | 17 | 28 | 48 | 72 | 104 | 128 | 135 |
| T89-22 | 19 | 29 | 49 | 73 | 105 | 123 | 129 |
| T89-23 | 21 | 30 | 54 | 79 | 112 | 135 | 138 |
| T89-24 | 19 | 24 | 37 | 54 | 77 | 100 | 103 |
| T89-25 | 15 | 27 | 46 | 69 | 98 | 117 | 123 |
| T89-26 | 19 | 29 | 50 | 73 | 103 | 127 | 135 |
| T89-27 | 15 | 27 | 47 | 70 | 106 | 129 | 135 |
| T89-28 | 20 | 33 | 55 | 80 | 109 | 130 | 137 |
| T89-29 | 24 | 38 | 62 | 88 | 122 | 143 | 151 |
| T89-30 | 21 | 33 | 56 | 78 | 113 | 132 | 138 |
| T89-31 | 21 | 31 | 52 | 76 | 105 | 126 | 133 |
| T89-32 | 18 | 29 | 50 | 73 | 105 | 129 | 138 |

TABLE 2.58-continued

Height growth data for TFSTT013

| | Height (cm) Days in greenhouse | | | | | | |
|---|---|---|---|---|---|---|---|
| | 19 | 25 | 32 | 39 | 48 | 54 | 56 |
| T89-33 | 23 | 37 | 61 | 89 | 121 | 143 | 150 |
| T89-34 | 19 | 30 | 52 | 78 | 108 | 130 | 138 |
| T89-35 | 19 | 31 | 55 | 79 | 111 | 134 | 142 |
| T89-36 | 18 | 29 | 52 | 75 | 105 | 127 | 134 |
| T89-37 | 22 | 32 | 52 | 73 | 103 | 124 | 130 |
| T89-38 | 18 | 29 | 51 | 74 | 105 | 128 | 134 |
| T89-39 | 21 | 31 | 51 | 72 | 102 | 119 | 124 |
| T89-40 | 20 | 32 | 51 | 74 | 99 | 121 | 128 |
| T89-41 | 19 | 29 | 50 | 73 | 108 | 130 | 135 |
| T89-42 | 15 | 26 | 46 | 68 | 95 | 113 | 119 |
| T89-43 | 16 | 28 | 48 | 67 | 93 | 113 | 119 |
| T89-44 | 21 | 31 | 50 | 70 | 97 | 116 | 122 |
| T89-45 | 16 | 26 | 48 | 72 | 101 | 123 | 131 |
| T89-46 | 21 | 29 | 50 | 75 | 106 | 129 | 138 |
| T89-47 | 9 | 16 | 34 | 55 | 82 | 106 | 114 |
| T89-48 | 5 | 8 | 17 | 24 | 42 | 52 | 56 |
| T89-49 | 20 | 30 | 50 | 71 | 96 | 117 | 125 |
| T89-50 | 16 | 28 | 50 | 74 | 105 | 128 | 136 |
| T89-51 | 19 | 29 | 51 | 75 | 107 | 128 | 136 |
| T89-52 | 20 | 29 | 50 | 75 | 104 | 124 | 131 |
| T89-53 | 21 | 32 | 50 | 72 | 101 | 118 | 125 |
| T89-54 | 21 | 32 | 55 | 81 | 112 | 133 | 142 |
| T89-55 | 21 | 32 | 56 | 83 | 112 | 133 | 141 |

TABLE 2.59

Diameter growth data for TFSTT013

| | Diameter (mm) Days in greenhouse | | | |
|---|---|---|---|---|
| | 39 | 48 | 54 | 56 |
| TFSTT013-1A | 5.9 | 7.9 | 8.6 | 9.4 |
| TFSTT013-1B | 5.9 | 8.4 | 8.5 | 8.6 |
| TFSTT013-2B | 5.7 | 5.6 | 7.8 | 8.1 |
| TFSTT013-3A | 6.4 | 6.9 | 7.5 | 7.8 |
| TFSTT013-3B | 5.9 | 7.9 | 8.8 | 9.8 |
| TFSTT013-4A | 6.8 | 8.3 | 9.0 | 9.9 |
| TFSTT013-4B | 7.2 | 9.1 | 10.4 | 10.1 |
| TFSTT013-5B | 7.5 | 9.0 | 10.3 | 9.5 |
| T89-01 | 6.6 | 8.4 | 8.5 | 9.2 |
| T89-02 | 6.8 | 8.3 | 9.4 | 10.1 |
| T89-03 | 4.6 | 4.9 | 6.1 | 6.1 |
| T89-04 | 6.9 | 8.7 | 10.0 | 9.4 |
| T89-05 | 5.6 | 7.6 | 8.2 | 8.8 |
| T89-06 | 6.9 | 8.2 | 9.6 | 9.3 |
| T89-07 | 6.6 | 7.9 | 9.5 | 9.5 |
| T89-08 | 6.9 | 8.9 | 9.6 | 9.8 |
| T89-09 | 6.1 | 7.6 | 8.6 | 8.7 |
| T89-10 | 5.5 | 7.5 | 8.6 | 8.6 |
| T89-11 | 7.4 | 8.4 | 9.3 | 8.7 |
| T89-12 | 5.9 | 7.4 | 8.7 | 9.5 |
| T89-13 | 6.2 | 7.7 | 9.2 | 9.5 |
| T89-14 | 5.9 | 7.8 | 9.2 | 8.7 |

TABLE 2.59-continued

Diameter growth data for TFSTT013

| | Diameter (mm) Days in greenhouse | | | |
|---|---|---|---|---|
| | 39 | 48 | 54 | 56 |
| T89-15 | 6.8 | 8.1 | 9.4 | 9.7 |
| T89-16 | 7.3 | 9.2 | 10.6 | 10.3 |
| T89-17 | 6.4 | 8.0 | 8.9 | 9.1 |
| T89-18 | 7.0 | 7.5 | 8.1 | 8.8 |
| T89-19 | 5.6 | 7.4 | 8.6 | 8.9 |
| T89-20 | 6.5 | 8.3 | 8.6 | 9.5 |
| T89-21 | 6.2 | 8.1 | 8.0 | 8.7 |
| T89-22 | 6.2 | 8.5 | 9.3 | 10.1 |
| T89-23 | 6.2 | 8.1 | 9.2 | 9.5 |
| T89-24 | 3.1 | 4.6 | 5.0 | 4.5 |
| T89-24 | 3.1 | 4.6 | 5.0 | 4.5 |
| T89-25 | 5.9 | 7.7 | 8.5 | 8.9 |
| T89-26 | 6.2 | 7.8 | 8.6 | 9.5 |
| T89-27 | 6.1 | 7.6 | 8.2 | 8.6 |
| T89-28 | 6.9 | 9.0 | 10.7 | 10.5 |
| T89-29 | 7.8 | 8.4 | 10.3 | 10.2 |
| T89-30 | 6.4 | 8.5 | 9.4 | 9.9 |
| T89-31 | 6.8 | 8.6 | 8.8 | 9.5 |
| T89-32 | 6.7 | 8.4 | 10.2 | 10.9 |
| T89-33 | 7.1 | 8.7 | 9.4 | 11.4 |
| T89-34 | 7.1 | 8.5 | 11.1 | 10.9 |
| T89-35 | 6.7 | 9.0 | 8.9 | 11.4 |
| T89-36 | 6.2 | 8.0 | 8.5 | 8.5 |
| T89-37 | 5.6 | 7.1 | 7.8 | 8.7 |
| T89-38 | 5.8 | 7.8 | 8.8 | 8.7 |
| T89-39 | 6.2 | 8.1 | 9.2 | 9.3 |
| T89-40 | 6.2 | 7.9 | 9.6 | 9.5 |
| T89-41 | 5.9 | 8.2 | 8.9 | 9.5 |
| T89-42 | 6.8 | 8.4 | 9.1 | 10.4 |
| T89-43 | 6.7 | 8.5 | 9.7 | 9.3 |
| T89-44 | 7.1 | 9.1 | 9.2 | 9.4 |
| T89-45 | 6.6 | 7.8 | 9.2 | 9.2 |
| T89-46 | 6.8 | 9.3 | 10.2 | 10.0 |
| T89-47 | 5.3 | 7.0 | 7.9 | 8.4 |
| T89-48 | 2.3 | 3.0 | 3.2 | 3.5 |
| T89-49 | 7.5 | 8.7 | 9.1 | 9.8 |
| T89-50 | 6.8 | 8.6 | 9.3 | 8.9 |
| T89-51 | 7.2 | 8.3 | 9.2 | 9.1 |
| T89-52 | 7.5 | 8.8 | 9.4 | 9.7 |
| T89-53 | 7.3 | 9.3 | 9.5 | 10.2 |
| T89-54 | 7.0 | 9.0 | 9.2 | 9.6 |
| T89-55 | 7.0 | 8.9 | 9.2 | 9.8 |

Results from growth analysis are specified in the overview table 2.60. The determined growth effects of specified construction group are presented as ratios between construction and wild type group AFH, AFD, AMHGR, ADGR, MFH, MFD, MMHGR and MDC.

TABLE 2.60

Overview table of growth effects of construct TFSTT013

| Construction group | Average Final Height | Average Final Diameter | Average Maximum Height Growth Rate | Average Diameter Growth Rate | Maximum Final Height | Maximum Final Diameter | Maximum of Maximum Height Growth Rate | Maximum Diameter Growth Rate |
|---|---|---|---|---|---|---|---|---|
| TFSTT013 | 1.03 | 0.99 | 1.01 | 0.96 | 0.99 | 0.88 | 1.01 | 0.87 |

Construction Group TFSTT016

Tables 2.61 and 2.62 contain growth data for specified construction group and corresponding wild type group. Table rows contain height and diameter measurements of individuals of specified construction group and corresponding wild type group. Time of measurement as number of days in greenhouse is shown in table headers.

TABLE 2.61

Height growth data for TFSTT016

| | Height (cm) Days in greenhouse | | | | | | | | | |
|---|---|---|---|---|---|---|---|---|---|---|
| | 19 | 28 | 34 | 40 | 44 | 47 | 51 | 54 | 61 | 65 |
| TFSTT016-1A | 19 | 37 | 57 | 71 | 83 | 91 | 101 | 111 | 127 | 137 |
| TFSTT016-1B | 19 | 36 | 54 | 67 | 78 | 87 | 98 | 107 | 126 | 138 |
| TFSTT016-2A | 18 | 34 | 51 | 67 | 76 | 84 | 93 | 101 | 118 | 130 |
| TFSTT016-2B | 18 | 34 | 55 | 70 | 80 | 87 | 97 | 105 | 125 | 137 |
| TFSTT016-3A-1 | 19 | 34 | 51 | 65 | 76 | 84 | 95 | 106 | 125 | 137 |
| TFSTT016-3A-2 | 17 | 33 | 50 | 64 | 76 | 85 | 96 | 107 | 129 | 143 |
| TFSTT016-4A | 16 | 33 | 52 | 69 | 83 | 91 | 103 | 112 | 136 | 151 |
| T89-01 | 18 | 30 | 46 | 58 | 69 | 77 | 87 | 96 | 113 | 122 |
| T89-02 | 18 | 30 | 49 | 62 | 72 | 77 | 84 | 90 | 102 | 109 |
| T89-03 | 15 | 27 | 41 | 54 | 65 | 73 | 82 | 91 | 112 | 123 |
| T89-10 | N/A | N/A | N/A | N/A | N/A | N/A | N/A | N/A | N/A | N/A |
| T89-11 | 19 | 31 | 49 | 61 | 74 | 83 | 94 | 103 | 124 | 133 |

TABLE 2.61-continued

Height growth data for TFSTT016

| | Height (cm) Days in greenhouse | | | | | | | | | |
|---|---|---|---|---|---|---|---|---|---|---|
| | 19 | 28 | 34 | 40 | 44 | 47 | 51 | 54 | 61 | 65 |
| T89-12 | 17 | 30 | 45 | 58 | 69 | 77 | 90 | 100 | 123 | 134 |
| T89-13 | 18 | 27 | 43 | 56 | 68 | 78 | 91 | 100 | 121 | 133 |
| T89-14 | 5 | 26 | 42 | 56 | 67 | 74 | 83 | 90 | 109 | 119 |
| T89-15 | 10 | 15 | 25 | 33 | 41 | 45 | 52 | 57 | 72 | 82 |
| T89-16 | 19 | 33 | 53 | 63 | 73 | 82 | 93 | 102 | 119 | 130 |
| T89-17 | 17 | 29 | 46 | 58 | 66 | 72 | 80 | 86 | 96 | 102 |
| T89-18 | 16 | 30 | 48 | 59 | 71 | 81 | 93 | 103 | 122 | 132 |
| T89-19 | 18 | 32 | 50 | 65 | 77 | 84 | 94 | 102 | 126 | 139 |
| T89-20 | 16 | 33 | 52 | 67 | 79 | 88 | 98 | 105 | 124 | 139 |
| T89-21 | 17 | 29 | 44 | 58 | 67 | 73 | 83 | 90 | 110 | 122 |
| T89-22 | 14 | 28 | 47 | 61 | 71 | 80 | 89 | 98 | 119 | 133 |
| T89-23 | 10 | 33 | 45 | 53 | 63 | 71 | 82 | 90 | 112 | 123 |
| T89-24 | 20 | 28 | 43 | 51 | 62 | 69 | 78 | 87 | 106 | 119 |
| T89-25 | 14 | 26 | 38 | 52 | 64 | 72 | 82 | 89 | 110 | 122 |
| T89-26 | 15 | 28 | 44 | 57 | 69 | 77 | 87 | 96 | 120 | 133 |
| T89-27 | 18 | 29 | 47 | 62 | 75 | 82 | 92 | 103 | 125 | 138 |
| T89-28 | 22 | 37 | 54 | 67 | 78 | 88 | 97 | 104 | 123 | 133 |
| T89-29 | 16 | 33 | 49 | 63 | 76 | 84 | 93 | 100 | 123 | 138 |
| T89-30 | 15 | 40 | 46 | 58 | 67 | 74 | 85 | 92 | 113 | 124 |

TABLE 2.62

Diameter growth data for TFSTT016

| | Diameter (mm) Days in greenhouse | | | | | | | | |
|---|---|---|---|---|---|---|---|---|---|
| | 28 | 34 | 40 | 44 | 47 | 51 | 54 | 61 | 65 |
| TFSTT016-1A | 3.9 | 5.8 | 7.3 | 8.5 | 8.1 | 9.4 | 9.6 | 9.9 | 10.7 |
| TFSTT016-1B | 4.1 | 5.7 | 6.4 | 7.2 | 8.3 | 9.1 | 9.3 | 10.9 | 11.1 |
| TFSTT016-2A | 3.6 | 5.5 | 6.4 | 7.2 | 8.3 | 8.6 | 9.2 | 10.0 | 10.5 |
| TFSTT016-2B | 4.3 | 5.7 | 7.0 | 7.5 | 7.8 | 7.9 | 8.6 | 8.9 | 9.1 |
| TFSTT016-3A-1 | 3.8 | 5.6 | 6.7 | 7.8 | 8.9 | 9.9 | 10.7 | 11.4 | 11.7 |
| TFSTT016-3A-2 | 3.6 | 5.0 | 6.5 | 7.7 | 7.8 | 9.3 | 9.1 | 10.4 | 10.9 |
| TFSTT016-4A | 4.2 | 5.2 | 6.6 | 8.0 | 8.6 | 9.7 | 9.7 | 11.3 | 11.5 |
| T89-01 | 3.2 | 4.6 | 5.4 | 6.2 | 6.8 | 7.9 | 8.3 | 9.5 | 9.3 |
| T89-02 | 3.4 | 4.7 | 5.5 | 7.3 | 6.3 | 6.6 | 6.9 | 8.3 | 7.5 |
| T89-03 | 3.9 | 4.4 | 5.2 | 6.2 | 6.4 | 7.8 | 7.6 | 9.7 | 9.4 |
| T89-10 | N/A | N/A | N/A | N/A | N/A | N/A | N/A | N/A | N/A |
| T89-11 | 3.4 | 5.1 | 6.2 | 7.6 | 6.8 | 6.9 | 7.7 | 10.1 | 9.5 |
| T89-12 | 2.9 | 4.7 | 5.8 | 6.6 | 7.8 | 8.0 | 8.7 | 9.1 | 9.2 |
| T89-13 | 3.0 | 4.3 | 5.4 | 5.8 | 6.4 | 7.6 | 7.8 | 8.2 | 8.8 |
| T89-14 | 3.0 | 4.5 | 5.7 | 6.3 | 6.7 | 7.9 | 7.8 | 9.0 | 8.9 |
| T89-15 | N/A | 2.1 | 3.0 | 4.0 | 4.0 | 4.5 | 4.9 | 5.5 | 5.6 |
| T89-16 | 3.5 | 5.3 | 6.4 | 6.6 | 7.0 | 7.2 | 8.3 | 8.2 | 9.0 |
| T89-17 | 3.4 | 4.6 | 5.1 | 5.4 | 6.0 | 6.4 | 6.5 | 6.8 | 7.1 |
| T89-18 | 3.6 | 5.2 | 6.0 | 7.0 | 7.8 | 8.2 | 9.9 | 10.3 | 9.7 |
| T89-19 | 4.2 | 5.5 | 6.6 | 7.7 | 8.5 | 8.9 | 9.5 | 11.1 | 12.3 |
| T89-20 | 4.1 | 5.5 | 6.6 | 8.1 | 9.3 | 9.6 | 9.3 | 10.0 | 11.1 |
| T89-21 | 3.1 | 5.6 | 5.8 | 6.7 | 7.1 | 7.8 | 8.4 | 9.7 | 10.1 |
| T89-22 | 3.2 | 4.4 | 5.6 | 6.5 | 7.5 | 7.6 | 7.8 | 8.9 | 9.2 |
| T89-23 | 2.4 | 4.2 | 5.1 | 6.1 | 6.5 | 7.5 | 10.1 | 9.3 | 10.2 |
| T89-24 | 3.2 | 4.5 | 5.1 | 6.3 | 7.0 | 7.6 | 8.1 | 8.8 | 9.1 |
| T89-25 | 3.3 | 4.3 | 5.2 | 5.8 | 6.5 | 7.4 | 7.8 | 9.3 | 9.7 |
| T89-26 | 3.3 | 4.4 | 5.5 | 6.6 | 7.2 | 8.1 | 8.9 | 9.5 | 10.5 |
| T89-27 | 3.3 | 4.9 | 6.0 | 7.8 | 8.0 | 8.9 | 9.7 | 11.2 | 11.5 |
| T89-28 | 4.5 | 5.7 | 7.4 | 7.8 | 8.5 | 9.4 | 9.7 | 10.2 | 11.1 |
| T89-29 | 3.1 | 4.7 | 6.3 | 7.2 | 7.9 | 9.2 | 9.8 | 11.1 | 10.7 |
| T89-30 | 3.0 | 5.8 | 6.2 | 7.7 | 7.9 | 8.6 | 8.2 | 10.1 | 10.3 |

Results from growth analysis are specified in the overview table 2.63. The determined growth effects of specified construction group are presented as ratios between construction and wild type group AFH, AFD, AMHGR, ADGR, MFH, MFD, MMHGR and MDC.

TABLE 2.63

Overview table of growth effects of construct TFSTT016

| Construction group | Average Final Height | Average Final Diameter | Average Maximum Height Growth Rate | Average Diameter Growth Rate | Maximum Final Height | Maximum Final Diameter | Maximum of Maximum Height Growth Rate | Maximum Diameter Growth Rate |
|---|---|---|---|---|---|---|---|---|
| TFSTT016 | 1.11 | 1.13 | 1.03 | 1.09 | 1.09 | 0.95 | 1.04 | 0.96 |

Construction Group TFSTT019Rp1

Tables 2.64 and 2.65 contain growth data for specified construction group and corresponding wild type group. Table rows contain height and diameter measurements of individuals of specified construction group and corresponding wild type group. Time of measurement as number of days in greenhouse is shown in table headers.

TABLE 2.64

Height growth data for TFSTT019Rp1

Height (cm)
Days in greenhouse

| | 20 | 25 | 29 | 35 | 41 | 46 | 50 | 53 | 57 | 60 |
|---|---|---|---|---|---|---|---|---|---|---|
| TFSTT019rp1-2A-1 | 17 | 24 | 32 | 45 | 58 | 71 | 81 | 88 | 98 | 104 |
| TFSTT019rp1-2A-2 | 15 | 23 | 30 | 42 | 57 | 72 | 80 | 88 | 99 | 108 |
| TFSTT019rp1-2A-3 | 16 | 22 | 28 | 40 | 55 | 67 | 78 | 87 | 97 | 105 |
| TFSTT019rp1-3A-1 | 16 | 24 | 32 | 47 | 62 | 79 | 87 | 96 | 104 | 111 |
| TFSTT019rp1-3A-2 | 14 | 20 | 24 | 28 | 38 | 54 | 61 | 69 | 79 | 85 |
| TFSTT019rp1-3A-3 | 18 | 30 | 35 | 47 | 62 | 79 | 89 | 97 | 107 | 116 |
| TFSTT019rp1-4BA-1 | 18 | 23 | 29 | 40 | 54 | 66 | 78 | 86 | 96 | 104 |
| TFSTT019rp1-4BA-2 | 19 | 27 | 35 | 48 | 65 | 79 | 92 | 101 | 112 | 121 |
| TFSTT019rp1-4BA-3 | N/A | N/A | N/A | N/A | N/A | N/A | N/A | N/A | N/A | N/A |
| TFSTT019rp1-4BB-1 | 18 | 27 | 35 | 50 | 65 | 80 | 90 | 99 | 111 | 117 |
| TFSTT019rp1-4BB-2 | 17 | 23 | 31 | 43 | 57 | 70 | 80 | 86 | 96 | 104 |
| TFSTT019rp1-4BB-3 | 17 | 23 | 30 | 42 | 60 | 74 | 82 | 90 | 98 | 107 |
| T89-01 | 17 | 26 | 31 | 45 | 61 | 76 | 87 | 95 | 107 | 116 |
| T89-02 | 16 | 21 | 26 | 38 | 53 | 67 | 76 | 83 | N/A | N/A |
| T89-03 | 18 | 24 | 32 | 47 | 64 | 78 | 87 | 96 | 106 | 115 |
| T89-04 | 18 | 26 | 35 | 50 | 66 | 80 | 87 | 96 | 107 | 115 |
| T89-05 | 17 | 26 | 33 | 44 | 57 | 73 | 81 | 91 | 100 | 107 |
| T89-06 | 16 | 21 | 28 | 40 | 55 | 74 | 79 | 89 | 99 | 106 |
| T89-07 | 17 | 23 | 31 | 43 | 57 | 71 | 80 | 88 | 98 | 107 |
| T89-08 | 15 | 20 | 26 | 37 | 51 | 65 | 75 | 84 | 94 | 100 |
| T89-09 | 18 | 25 | 32 | 46 | 61 | 74 | 85 | 93 | 103 | 112 |
| T89-10 | 19 | 25 | 32 | 46 | 60 | 75 | 86 | 95 | 104 | 112 |
| T89-11 | 20 | 27 | 36 | 51 | 68 | 86 | 98 | 107 | 120 | 127 |
| T89-12 | 19 | 27 | 36 | 50 | 67 | 80 | 89 | 97 | 108 | 118 |
| T89-13 | 18 | 25 | 32 | 45 | 59 | 75 | 83 | 92 | 101 | 108 |
| T89-14 | 18 | 23 | 26 | 36 | 51 | 65 | 72 | 79 | 89 | 96 |
| T89-15 | 17 | 21 | 28 | 39 | 53 | 70 | 78 | 87 | 97 | 105 |
| T89-16 | 19 | 25 | 32 | 43 | 57 | 71 | 81 | 90 | 101 | 109 |
| T89-17 | 16 | 20 | 29 | 41 | 54 | 68 | 78 | 84 | 93 | 101 |
| T89-18 | 16 | 23 | 30 | 45 | 63 | 78 | 87 | 94 | 103 | 110 |
| T89-19 | 16 | 22 | 28 | 42 | 56 | 69 | 79 | 89 | 100 | 107 |
| T89-20 | 18 | 25 | 32 | 47 | 63 | 78 | 89 | 99 | 109 | 115 |
| T89-21 | 19 | 27 | 34 | 50 | 67 | 82 | 92 | 102 | 111 | 120 |
| T89-22 | 19 | 25 | 32 | 44 | 58 | 76 | 84 | 93 | 102 | 109 |
| T89-23 | 18 | 26 | 33 | 47 | 63 | 79 | 88 | 99 | 108 | 116 |
| T89-24 | 16 | 24 | 28 | 42 | 53 | 70 | 78 | 85 | 94 | 103 |
| T89-25 | 16 | 25 | 32 | 45 | 61 | 76 | 85 | 95 | 107 | 114 |
| T89-26 | 16 | 20 | 26 | 38 | 52 | 68 | 78 | 86 | 97 | 103 |
| T89-27 | 16 | 21 | 25 | 35 | 48 | 61 | 70 | 78 | N/A | 98 |
| T89-28 | 14 | 18 | 25 | 38 | 51 | 64 | 73 | 81 | 90 | 96 |
| T89-29 | 7 | 13 | 18 | 30 | 45 | 60 | 69 | 77 | 90 | 98 |
| T89-30 | 15 | 22 | 29 | 42 | 55 | 69 | 80 | 88 | 97 | 106 |
| T89-31 | 21 | 29 | 37 | 50 | 65 | 80 | 88 | 98 | 108 | 116 |
| T89-32 | 19 | 24 | 32 | 42 | 55 | 70 | 78 | 87 | 96 | 105 |

TABLE 2.65

Diameter growth data for TFSTT019Rp1

| | Diameter (mm) Days in greenhouse | | | | |
|---|---|---|---|---|---|
| | 35 | 41 | 46 | 53 | 60 |
| TFSTT019rp1-2A-1 | 5.4 | 6.1 | 7.3 | 8.2 | 8.5 |
| TFSTT019rp1-2A-2 | 5.2 | 6.6 | 8.0 | 8.9 | 9.3 |
| TFSTT019rp1-2A-3 | 5.0 | 6.4 | 7.1 | 8.9 | 9.0 |
| TFSTT019rp1-3A-1 | 5.5 | 6.5 | 7.4 | 8.2 | 8.9 |
| TFSTT019rp1-3A-2 | 4.2 | 5.8 | 5.9 | 6.0 | 6.9 |
| TFSTT019rp1-3A-3 | 5.1 | 6.6 | 7.8 | 8.9 | 9.4 |
| TFSTT019rp1-4BA-1 | 4.8 | 6.5 | 8.5 | 7.9 | 9.1 |
| TFSTT019rp1-4BA-2 | 5.0 | 6.4 | 6.9 | 8.3 | 9.2 |
| TFSTT019rp1-4BA-3 | N/A | N/A | N/A | N/A | N/A |
| TFSTT019rp1-4BB-1 | 5.2 | 6.6 | 7.5 | 8.1 | 8.8 |
| TFSTT019rp1-4BB-2 | 4.7 | N/A | 7.1 | 8.2 | 8.6 |
| TFSTT019rp1-4BB-3 | 5.5 | 6.9 | 7.5 | 8.1 | 8.8 |
| T89-01 | 4.7 | 6.0 | 6.5 | 6.9 | 8.3 |
| T89-02 | 4.4 | 5.7 | 6.6 | 7.6 | 7.8 |
| T89-03 | 4.7 | 6.3 | 6.7 | 7.7 | 8.4 |
| T89-04 | 4.7 | 6.0 | 7.1 | 8.0 | 8.5 |
| T89-05 | 4.0 | 5.3 | 6.3 | 7.8 | 8.1 |
| T89-06 | 4.6 | 5.9 | 6.3 | 7.7 | 8.2 |
| T89-07 | 4.6 | 6.1 | 6.5 | 7.9 | 8.5 |
| T89-08 | 4.0 | 5.2 | 5.8 | 6.9 | 7.1 |
| T89-09 | 4.4 | 5.8 | 6.4 | 7.6 | 8.2 |
| T89-10 | 4.9 | 6.0 | 6.6 | 7.4 | 8.5 |
| T89-11 | 4.7 | 5.8 | 6.4 | 7.9 | 8.3 |
| T89-12 | 4.7 | 5.9 | 7.3 | 7.4 | 7.6 |
| T89-13 | 5.9 | 5.9 | 6.7 | 7.5 | 8.3 |
| T89-14 | 4.5 | 5.2 | 5.8 | 6.1 | 7.0 |
| T89-15 | 4.7 | N/A | 6.0 | 6.4 | 7.3 |
| T89-16 | 4.5 | 5.6 | 7.7 | 7.5 | 8.6 |
| T89-17 | 4.1 | 5.4 | 6.0 | 6.8 | 7.5 |
| T89-18 | 4.4 | 5.8 | 6.0 | 7.7 | 8.3 |
| T89-19 | 4.7 | 5.8 | 7.1 | 8.5 | 9.4 |
| T89-20 | 4.7 | 5.8 | 6.6 | 7.4 | 8.3 |
| T89-21 | 4.7 | 6.2 | 6.3 | 7.7 | 8.5 |
| T89-22 | 4.2 | 5.1 | 6.3 | 6.9 | 8.0 |
| T89-23 | 4.6 | 5.8 | 7.1 | 7.5 | 8.3 |
| T89-24 | 4.4 | 5.8 | 6.9 | 7.7 | 8.8 |
| T89-25 | 4.5 | 5.4 | 6.2 | 8.0 | 8.7 |
| T89-26 | 4.1 | 5.4 | 6.0 | 7.2 | 8.0 |
| T89-27 | 4.5 | 5.7 | 6.5 | 7.9 | 9.2 |
| T89-28 | 4.3 | 5.1 | 6.0 | 6.6 | 7.7 |
| T89-29 | 3.5 | 4.7 | 5.5 | 6.3 | 7.1 |
| T89-30 | 4.1 | 5.4 | 5.8 | 7.2 | 7.8 |
| T89-31 | 5.0 | 5.8 | 6.8 | 7.3 | 8.2 |
| T89-32 | 4.4 | 6.4 | 6.6 | 8.0 | 8.4 |

Results from growth analysis are specified in the overview table 2.66. The determined growth effects of specified construction group are presented as ratios between construction and wild type group AFH, AFD, AMHGR, ADGR, MFH, MFD, MMHGR and MDC.

TABLE 2.66

Overview table of growth effects of construct TFSTT019Rp1

| Construction group | Average Final Height | Average Final Diameter | Average Maximum Height Growth Rate | Average Diameter Growth Rate | Maximum Final Height | Maximum Final Diameter | Maximum of Maximum Height Growth Rate | Maximum Diameter Growth Rate |
|---|---|---|---|---|---|---|---|---|
| TFSTT019Rp1 | 0.99 | 1.08 | 0.98 | 0.99 | 0.95 | 1.00 | 0.93 | 0.88 |

Construction Group TFSTT036

This construct induces increased growth. The final height is 10% higher comparing the average of the construction group and wild type control group. The final height is 8% higher comparing the largest individuals of the construction group and wild type control group. The maximum height growth rate is 14% higher comparing the average of the construction group and wild type control group. The maximum height growth rate is 12% higher comparing the largest individuals of the construction group and wild type control group. The final diameter is 7% higher comparing the average of the construction group and wild type control group. The final diameter is 14% higher comparing the largest individuals of the construction group and wild type control group. The TFSTT036 construction group meets growth difference selection criterion (1) as shown in table 2.69.

Tables 2.67 and 2.68 contain growth data for specified construction group and corresponding wild type group. Table rows contain height and diameter measurements of individuals of specified construction group and corresponding wild type group. Time of measurement as number of days in greenhouse is shown in table headers.

TABLE 2.67

Height growth data for TFSTT036

| | Height (cm) Days in greenhouse | | | | | | | | |
|---|---|---|---|---|---|---|---|---|---|
| | 18 | 25 | 28 | 32 | 36 | 39 | 46 | 53 | 55 |
| TFSTT036-1B | 23 | 37 | 46 | 56 | 68 | 79 | 103 | 126 | 132 |
| TFSTT036-2A | 18 | 36 | 46 | 57 | 72 | 83 | 108 | 126 | 132 |
| TFSTT036-2B | 21 | 33 | 45 | 54 | 67 | 80 | 111 | 135 | 143 |
| TFSTT036-3A | 21 | 36 | 48 | 59 | 77 | 90 | 113 | 133 | 140 |
| TFSTT036-4A | 25 | 39 | 51 | 61 | 76 | 88 | 117 | 141 | 151 |
| TFSTT036-4B | 23 | 38 | 53 | 67 | 83 | 92 | 119 | 144 | 148 |
| TFSTT036-5B | 21 | 33 | 44 | 55 | 69 | 81 | 106 | 130 | 139 |
| T89-01 | 18 | 32 | 43 | 54 | 66 | 76 | 98 | 124 | 133 |
| T89-02 | 20 | 33 | 43 | 53 | 67 | 76 | 101 | 124 | 129 |
| T89-03 | 17 | 31 | 43 | 53 | 68 | 76 | 102 | 128 | 135 |
| T89-04 | 19 | 33 | 44 | 54 | 67 | 74 | 97 | 122 | 129 |
| T89-05 | 20 | 33 | 44 | 54 | 67 | 76 | 100 | 121 | 129 |
| T89-06 | 18 | 31 | 42 | 53 | 67 | 76 | 97 | 121 | 128 |
| T89-07 | 16 | 28 | 41 | 53 | 65 | 74 | 96 | 121 | 129 |
| T89-08 | 19 | 34 | 43 | 53 | 65 | 75 | 98 | 123 | 131 |
| T89-09 | 20 | 30 | 40 | 52 | 64 | 73 | 97 | 119 | 125 |
| T89-10 | 21 | 33 | 41 | 49 | 61 | 70 | 92 | 114 | 121 |
| T89-11 | 18 | 31 | 40 | 49 | 61 | 71 | 94 | 117 | 123 |
| T89-12 | 18 | 31 | 40 | N/A | 60 | 68 | 90 | 107 | 115 |
| T89-13 | 19 | 35 | 47 | 58 | 70 | 78 | 103 | 128 | 135 |
| T89-14 | 19 | 31 | 40 | 50 | 61 | 72 | 93 | 118 | 124 |
| T89-15 | 20 | 32 | 41 | 50 | 62 | 70 | 91 | 114 | 120 |
| T89-16 | 18 | 30 | 39 | 49 | 62 | 71 | 92 | 114 | 122 |
| T89-17 | 17 | 33 | 45 | 55 | 70 | 78 | 104 | 129 | 136 |
| T89-18 | 19 | 32 | 44 | 56 | 71 | 82 | 106 | 130 | 137 |
| T89-19 | 16 | 26 | 36 | 46 | 51 | 69 | 89 | 112 | 119 |
| T89-20 | 16 | 31 | 41 | 49 | 60 | 71 | 91 | 111 | 118 |
| T89-21 | 20 | 31 | 44 | 54 | 68 | 76 | 99 | 122 | 127 |
| T89-22 | 14 | 26 | 37 | 46 | 61 | 72 | 96 | 120 | 127 |
| T89-23 | 19 | 32 | 40 | 50 | 63 | 73 | 100 | 121 | 127 |
| T89-24 | 20 | 31 | 41 | 47 | 58 | 68 | 90 | 111 | 117 |
| T89-25 | 20 | 36 | 45 | 57 | 69 | 78 | 101 | 127 | 134 |
| T89-26 | 20 | 37 | 49 | 58 | 71 | 80 | 107 | 131 | 140 |
| T89-27 | 19 | 34 | 44 | 55 | 71 | 81 | 107 | 131 | 138 |
| T89-28 | 17 | 35 | 44 | 56 | 68 | 76 | 99 | 126 | 132 |
| T89-29 | 17 | 32 | 45 | 55 | 68 | 78 | 101 | 125 | 132 |
| T89-30 | 18 | 31 | 41 | 50 | 63 | 72 | 95 | 119 | 125 |
| T89-31 | 17 | 27 | 35 | 45 | 58 | 67 | 87 | 108 | 116 |
| T89-32 | 19 | 32 | 44 | 52 | 65 | 74 | 98 | 121 | 127 |
| T89-33 | 20 | 33 | 43 | 53 | 64 | 74 | 96 | 119 | 126 |
| T89-34 | 19 | 34 | 44 | 55 | 68 | 78 | 100 | 124 | 130 |
| T89-35 | 17 | 30 | 40 | 51 | 64 | 74 | 95 | 116 | 122 |
| T89-36 | 18 | 30 | 40 | 49 | 62 | 71 | 91 | 114 | 121 |
| T89-82 | 21 | 33 | 43 | 54 | 65 | 75 | 98 | 118 | 125 |

TABLE 2.67-continued

Height growth data for TFSTT036

| | Height (cm) Days in greenhouse | | | | | | | | |
|---|---|---|---|---|---|---|---|---|---|
| | 18 | 25 | 28 | 32 | 36 | 39 | 46 | 53 | 55 |
| T89-83 | 22 | 35 | 47 | 55 | 71 | 80 | 105 | 130 | 137 |
| T89-85 | 21 | 36 | 46 | 56 | 67 | 76 | 98 | 123 | 131 |

TABLE 2.68

Diameter growth data for TFSTT036

| | Diameter (mm) Days in greenhouse | | | | |
|---|---|---|---|---|---|
| | 32 | 39 | 46 | 53 | 55 |
| TFSTT036-1B | 5.2 | 6.6 | 7.4 | 8.1 | 8.5 |
| TFSTT036-2A | 5.8 | 6.8 | 8.0 | 9.5 | 8.7 |
| TFSTT036-2B | 3.9 | 5.1 | 6.2 | 7.5 | 7.5 |
| TFSTT036-3A | 4.2 | 4.2 | 5.1 | 6.2 | 6.4 |
| TFSTT036-4A | 6.3 | 6.9 | 8.9 | 10.1 | 10.5 |
| TFSTT036-4B | 5.5 | 6.8 | 8.2 | 8.7 | 8.4 |
| TFSTT036-5B | 5.7 | 6.8 | 7.6 | 8.7 | 8.9 |
| T89-01 | 5.2 | 6.0 | 6.8 | 8.2 | 7.6 |
| T89-02 | 4.5 | 5.8 | 7.1 | 8.6 | 8.3 |
| T89-03 | 4.4 | 5.7 | 6.8 | 7.9 | 8.1 |
| T89-04 | 4.4 | 6.0 | 6.9 | 8.6 | 8.5 |
| T89-05 | 4.6 | 5.8 | 6.7 | 7.9 | 8.0 |
| T89-06 | 4.7 | 5.9 | 7.2 | 8.1 | 9.2 |
| T89-07 | 4.8 | 5.5 | 6.2 | 6.9 | 7.1 |
| T89-08 | 4.5 | 5.4 | 6.0 | 6.9 | 7.1 |
| T89-09 | 4.7 | 5.6 | 6.7 | 8.8 | 8.0 |
| T89-10 | 4.1 | 4.9 | 5.6 | 7.1 | 7.0 |
| T89-11 | 3.8 | 5.3 | 7.3 | 8.0 | 7.6 |
| T89-12 | N/A | 5.1 | 6.2 | 7.3 | 6.9 |
| T89-13 | 4.8 | 5.7 | 6.5 | 7.6 | 7.6 |
| T89-14 | 4.2 | 5.5 | 6.6 | 7.6 | 6.5 |
| T89-15 | 5.0 | 6.1 | 7.2 | 7.9 | 8.3 |
| T89-16 | 4.4 | 5.6 | 6.2 | 7.3 | 7.9 |
| T89-17 | 4.8 | 6.7 | 7.0 | 8.3 | 8.4 |
| T89-17 | 4.8 | 6.7 | 7.0 | 8.3 | 8.4 |
| T89-18 | 4.2 | 5.5 | 6.7 | 7.3 | 7.4 |
| T89-19 | 4.7 | 5.5 | 6.8 | 7.2 | 7.8 |
| T89-20 | 4.5 | 5.6 | 6.5 | 7.0 | 7.3 |
| T89-21 | 4.9 | 5.6 | 6.4 | 7.4 | 7.6 |
| T89-22 | 4.3 | 5.4 | 6.5 | 7.3 | 7.6 |
| T89-23 | 3.9 | 5.5 | 6.7 | 7.7 | 7.0 |
| T89-24 | 4.3 | 5.9 | 6.8 | 8.1 | 7.9 |
| T89-25 | 4.7 | 6.5 | 7.5 | 9.2 | 9.1 |
| T89-26 | 5.4 | 5.9 | 7.7 | 8.6 | 8.8 |
| T89-27 | 4.7 | 5.6 | 7.4 | 7.9 | 8.0 |
| T89-28 | 4.7 | 5.7 | 6.3 | 7.2 | 7.4 |
| T89-29 | 4.8 | 5.6 | 6.6 | 7.7 | 8.1 |
| T89-30 | 4.6 | 5.5 | 6.7 | 7.3 | 7.3 |
| T89-31 | 4.3 | 5.8 | 6.3 | 7.5 | 7.6 |
| T89-32 | 4.6 | 5.9 | 7.6 | 9.3 | 9.1 |
| T89-33 | 4.4 | 5.3 | 6.2 | 7.1 | 7.1 |
| T89-34 | 4.6 | 5.6 | 6.8 | 8.1 | 8.7 |
| T89-35 | 5.3 | 6.0 | 7.5 | 8.8 | 8.9 |
| T89-36 | 4.4 | 6.1 | 6.9 | 8.1 | 8.6 |
| T89-82 | 4.7 | 5.3 | 6.5 | 7.5 | 7.4 |
| T89-83 | 4.7 | 6.1 | 7.1 | 8.3 | 8.3 |
| T89-85 | 5.1 | 6.3 | 7.3 | 7.7 | 8.2 |

Results from growth analysis are specified in the overview table 2.69. The determined growth effects of specified construction group are presented as ratios between construction and wild type group AFH, AFD, AMHGR, ADGR, MFH, MFD, MMHGR and MDC.

TABLE 2.69

Overview table of growth effects of construct TFSTT036

| Construction group | Average Final Height | Average Final Diameter | Average Maximum Height Growth Rate | Average Diameter Growth Rate | Maximum Final Height | Maximum Final Diameter | Maximum of Maximum Height Growth Rate | Maximum Diameter Growth Rate |
|---|---|---|---|---|---|---|---|---|
| TFSTT036 | 1.10 | 1.07 | 1.14 | 0.99 | 1.08 | 1.14 | 1.12 | 0.95 |

Construction Group TFSTT038

The gene over-expressed with construct TFSTT038 generates the same top hits as the gene over-expressed with construct TFSTT013, when using BLAST search against the *P. trichocarpa* Jamboree Gene Model database at the Joint Genome Institute web page, indicating high homology between the two genes Tables 2.70 and 2.71 contain growth data for specified construction group and corresponding wild type group. Table rows contain height and diameter measurements of individuals of specified construction group and corresponding wild type group. Time of measurement as number of days in greenhouse is shown in table headers.

TABLE 2.70

Height growth data for TFSTT038

| | Height (cm) Days in greenhouse | | | | | | | | | |
|---|---|---|---|---|---|---|---|---|---|---|
| | 19 | 28 | 34 | 40 | 44 | 47 | 51 | 54 | 61 | 65 |
| TFSTT038-1A-1 | 23 | 42 | 62 | 82 | 92 | 100 | 110 | 118 | 138 | 153 |
| TFSTT038-1A-2 | 19 | 38 | 58 | 70 | 83 | 90 | 102 | 110 | 130 | 142 |
| TFSTT038-1B | 18 | 33 | 48 | 62 | 73 | 83 | 93 | 99 | 117 | 128 |
| TFSTT038-2A | 21 | 38 | 58 | 71 | 85 | 96 | 108 | 119 | 143 | 157 |
| TFSTT038-2B | 14 | 29 | 46 | 60 | 70 | 78 | 87 | 96 | 118 | 130 |
| TFSTT038-3A | 18 | 38 | 57 | 70 | 83 | 92 | 105 | 116 | 133 | 142 |
| TFSTT038-3B | 21 | 38 | 57 | 72 | 84 | 92 | 102 | 110 | 122 | 126 |
| TFSTT038-4B | 17 | 34 | 52 | 67 | 78 | 87 | 96 | 104 | 123 | 133 |
| T89-01 | 18 | 30 | 46 | 58 | 69 | 77 | 87 | 96 | 113 | 122 |
| T89-02 | 18 | 30 | 49 | 62 | 72 | 77 | 84 | 90 | 102 | 109 |
| T89-03 | 15 | 27 | 41 | 54 | 65 | 73 | 82 | 91 | 112 | 123 |
| T89-10 | N/A | N/A | N/A | N/A | N/A | N/A | N/A | N/A | N/A | N/A |
| T89-11 | 19 | 31 | 49 | 61 | 74 | 83 | 94 | 103 | 124 | 133 |
| T89-12 | 17 | 30 | 45 | 58 | 69 | 77 | 90 | 100 | 123 | 134 |
| T89-13 | 18 | 27 | 43 | 56 | 68 | 78 | 91 | 100 | 121 | 133 |
| T89-14 | 5 | 26 | 42 | 56 | 67 | 74 | 83 | 90 | 109 | 119 |
| T89-15 | 10 | 15 | 25 | 33 | 41 | 45 | 52 | 57 | 72 | 82 |
| T89-16 | 19 | 33 | 53 | 63 | 73 | 82 | 93 | 102 | 119 | 130 |
| T89-17 | 17 | 29 | 46 | 58 | 66 | 72 | 80 | 86 | 96 | 102 |
| T89-18 | 16 | 30 | 48 | 59 | 71 | 81 | 93 | 103 | 122 | 132 |
| T89-19 | 18 | 32 | 50 | 65 | 77 | 84 | 94 | 102 | 126 | 139 |
| T89-20 | 16 | 33 | 52 | 67 | 79 | 88 | 98 | 105 | 124 | 139 |
| T89-21 | 17 | 29 | 44 | 58 | 67 | 73 | 83 | 90 | 110 | 122 |
| T89-22 | 14 | 28 | 47 | 61 | 71 | 80 | 89 | 98 | 119 | 133 |
| T89-23 | 10 | 33 | 45 | 53 | 63 | 71 | 82 | 90 | 112 | 123 |
| T89-24 | 20 | 28 | 43 | 51 | 62 | 69 | 78 | 87 | 106 | 119 |
| T89-25 | 14 | 26 | 38 | 52 | 64 | 72 | 82 | 89 | 110 | 122 |
| T89-26 | 15 | 28 | 44 | 57 | 69 | 77 | 87 | 96 | 120 | 133 |
| T89-27 | 18 | 29 | 47 | 62 | 75 | 82 | 92 | 103 | 125 | 138 |
| T89-28 | 22 | 37 | 54 | 67 | 78 | 88 | 97 | 104 | 123 | 133 |
| T89-29 | 16 | 33 | 49 | 63 | 76 | 84 | 93 | 100 | 123 | 138 |
| T89-30 | 15 | 40 | 46 | 58 | 67 | 74 | 85 | 92 | 113 | 124 |

TABLE 2.71

Diameter growth data for TFSTT038

| | Diameter (mm) Days in greenhouse | | | | | | | | |
|---|---|---|---|---|---|---|---|---|---|
| | 28 | 34 | 40 | 44 | 47 | 51 | 54 | 61 | 65 |
| TFSTT038-1A-1 | 4.4 | 6.1 | 7.4 | 8.4 | 9.3 | 9.8 | 10.5 | 11.3 | 11.8 |
| TFSTT038-1A-2 | 3.8 | 5.5 | 6.6 | 7.7 | 7.9 | 8.9 | 9.4 | 10.6 | 11.2 |
| TFSTT038-1B | 3.4 | 5.1 | 6.5 | 7.2 | 7.8 | 8.3 | 10.1 | 9.3 | 9.5 |
| TFSTT038-2A | 3.8 | 5.4 | 6.7 | 7.2 | 8.7 | 9.6 | 9.8 | 11.5 | 11.3 |

TABLE 2.71-continued

Diameter growth data for TFSTT038

| | Diameter (mm) Days in greenhouse | | | | | | | | |
|---|---|---|---|---|---|---|---|---|---|
| | 28 | 34 | 40 | 44 | 47 | 51 | 54 | 61 | 65 |
| TFSTT038-2B | 3.8 | 4.4 | 5.4 | 6.4 | 7.2 | 7.8 | 8.5 | 10.1 | 10.7 |
| TFSTT038-3A | 3.9 | 5.7 | 7.4 | 7.8 | 8.4 | 9.3 | 9.8 | 10.6 | 11.1 |
| TFSTT038-3B | 4.3 | 5.9 | 6.8 | 7.8 | 8.0 | 8.0 | 8.4 | 9.0 | 9.9 |
| TFSTT038-4B | 4.2 | 4.5 | 6.3 | 6.8 | 7.3 | 8.2 | 8.6 | 9.0 | 9.1 |
| T89-01 | 3.2 | 4.6 | 5.4 | 6.2 | 6.8 | 7.9 | 8.3 | 9.5 | 9.3 |
| T89-02 | 3.4 | 4.7 | 5.5 | 7.3 | 6.3 | 6.6 | 6.9 | 8.3 | 7.5 |
| T89-03 | 3.9 | 4.4 | 5.2 | 6.2 | 6.4 | 7.8 | 7.6 | 9.7 | 9.4 |
| T89-10 | N/A | N/A | N/A | N/A | N/A | N/A | N/A | N/A | N/A |
| T89-11 | 3.4 | 5.1 | 6.2 | 7.6 | 6.8 | 6.9 | 7.7 | 10.1 | 9.5 |
| T89-12 | 2.9 | 4.7 | 5.8 | 6.6 | 7.8 | 8.0 | 8.7 | 9.1 | 9.2 |
| T89-13 | 3.0 | 4.3 | 5.4 | 5.8 | 6.4 | 7.6 | 7.8 | 8.2 | 8.8 |
| T89-14 | 3.0 | 4.5 | 5.7 | 6.3 | 6.7 | 7.9 | 7.8 | 9.0 | 8.9 |
| T89-15 | N/A | 2.1 | 3.0 | 4.0 | 4.0 | 4.5 | 4.9 | 5.5 | 5.6 |
| T89-16 | 3.5 | 5.3 | 6.4 | 6.6 | 7.0 | 7.2 | 8.3 | 8.2 | 9.0 |
| T89-17 | 3.4 | 4.6 | 5.1 | 5.4 | 6.0 | 6.4 | 6.5 | 6.8 | 7.1 |
| T89-18 | 3.6 | 5.2 | 6.0 | 7.0 | 7.8 | 8.2 | 9.9 | 10.3 | 9.7 |
| T89-19 | 4.2 | 5.5 | 6.6 | 7.7 | 8.5 | 8.9 | 9.5 | 11.1 | 12.3 |
| T89-20 | 4.1 | 5.5 | 6.6 | 8.1 | 9.3 | 9.6 | 9.3 | 10.0 | 11.1 |
| T89-21 | 3.1 | 5.6 | 5.8 | 6.7 | 7.1 | 7.8 | 8.4 | 9.7 | 10.1 |
| T89-22 | 3.2 | 4.4 | 5.6 | 6.5 | 7.5 | 7.6 | 7.8 | 8.9 | 9.2 |
| T89-23 | 2.4 | 4.2 | 5.1 | 6.1 | 6.5 | 7.5 | 10.1 | 9.3 | 10.2 |
| T89-24 | 3.2 | 4.5 | 5.1 | 6.3 | 7.0 | 7.6 | 8.1 | 8.8 | 9.1 |
| T89-25 | 3.3 | 4.3 | 5.2 | 5.8 | 6.5 | 7.4 | 7.8 | 9.3 | 9.7 |
| T89-26 | 3.3 | 4.4 | 5.5 | 6.6 | 7.2 | 8.1 | 8.9 | 9.5 | 10.5 |
| T89-27 | 3.3 | 4.9 | 6.0 | 7.8 | 8.0 | 8.9 | 9.7 | 11.2 | 11.5 |
| T89-28 | 4.5 | 5.7 | 7.4 | 7.8 | 8.5 | 9.4 | 9.7 | 10.2 | 11.1 |
| T89-29 | 3.1 | 4.7 | 6.3 | 7.2 | 7.9 | 9.2 | 9.8 | 11.1 | 10.7 |
| T89-30 | 3.0 | 5.8 | 6.2 | 7.7 | 7.9 | 8.6 | 8.2 | 10.1 | 10.3 |

Results from growth analysis are specified in the overview table 2.72. The determined growth effects of specified construction group are presented as ratios between construction and wild type group AFH, AFD, AMHGR, ADGR, MFH, MFD, MMHGR and MDC.

TABLE 2.72

Overview table of growth effects of construct TFSTT038

| Construction group | Average Final Height | Average Final Diameter | Average Maximum Height Growth Rate | Average Diameter Growth Rate | Maximum Final Height | Maximum Final Diameter | Maximum of Maximum Height Growth Rate | Maximum Diameter Growth Rate |
|---|---|---|---|---|---|---|---|---|
| TFSTT038 | 1.11 | 1.11 | 1.04 | 1.06 | 1.13 | 0.96 | 1.05 | 0.92 |

Construction Group TFSTT045

Tables 2.73 and 2.74 contain growth data for specified construction group and corresponding wild type group. Table rows contain height and diameter measurements of individuals of specified construction group and corresponding wild type group. Time of measurement as number of days in greenhouse is shown in table headers.

TABLE 2.73

Height growth data for TFSTT045

| | Height (cm) Days in greenhouse | | | | | | | | |
|---|---|---|---|---|---|---|---|---|---|
| | 18 | 25 | 28 | 32 | 36 | 39 | 46 | 53 | 55 |
| TFSTT045-1B | 19 | 33 | 43 | 52 | 64 | 75 | 94 | 116 | 123 |
| TFSTT045-2B | 24 | 37 | 49 | 58 | 71 | 80 | 105 | 127 | 133 |
| TFSTT045-3A | 20 | 35 | 48 | 60 | 76 | 87 | 113 | 143 | 153 |
| TFSTT045-3B | 16 | 28 | 37 | 47 | 57 | 65 | 86 | 111 | 118 |
| TFSTT045-4A | 23 | 34 | 45 | 56 | 70 | 82 | 105 | 133 | 139 |
| TFSTT045-4B | 25 | 38 | 51 | 60 | 75 | 87 | 109 | 119 | 120 |
| TFSTT045-7B | 23 | 35 | 46 | 60 | 70 | 80 | N/A | 124 | 130 |
| T89-01 | 18 | 32 | 43 | 54 | 66 | 76 | 98 | 124 | 133 |
| T89-02 | 20 | 33 | 43 | 53 | 67 | 76 | 101 | 124 | 129 |
| T89-03 | 17 | 31 | 43 | 53 | 68 | 76 | 102 | 128 | 135 |
| T89-04 | 19 | 33 | 44 | 54 | 67 | 74 | 97 | 122 | 129 |
| T89-05 | 20 | 33 | 44 | 54 | 67 | 76 | 100 | 121 | 129 |
| T89-06 | 18 | 31 | 42 | 53 | 67 | 76 | 97 | 121 | 128 |
| T89-07 | 16 | 28 | 41 | 53 | 65 | 74 | 96 | 121 | 129 |
| T89-08 | 19 | 34 | 43 | 53 | 65 | 75 | 98 | 123 | 131 |
| T89-09 | 20 | 30 | 40 | 52 | 64 | 73 | 97 | 119 | 125 |
| T89-10 | 21 | 33 | 41 | 49 | 61 | 70 | 92 | 114 | 121 |
| T89-11 | 18 | 31 | 40 | 49 | 61 | 71 | 94 | 117 | 123 |
| T89-12 | 18 | 31 | 40 | N/A | 60 | 68 | 90 | 107 | 115 |
| T89-13 | 19 | 35 | 47 | 58 | 70 | 78 | 103 | 128 | 135 |
| T89-14 | 19 | 31 | 40 | 50 | 61 | 72 | 93 | 118 | 124 |
| T89-15 | 20 | 32 | 41 | 50 | 62 | 70 | 91 | 114 | 120 |
| T89-16 | 18 | 30 | 39 | 49 | 62 | 71 | 92 | 114 | 122 |
| T89-17 | 17 | 33 | 45 | 55 | 70 | 78 | 104 | 129 | 136 |
| T89-18 | 19 | 32 | 44 | 56 | 71 | 82 | 106 | 130 | 137 |
| T89-19 | 16 | 26 | 36 | 46 | 51 | 69 | 89 | 112 | 119 |
| T89-20 | 16 | 31 | 41 | 49 | 60 | 71 | 91 | 111 | 118 |
| T89-21 | 20 | 31 | 44 | 54 | 68 | 76 | 99 | 122 | 127 |
| T89-22 | 14 | 26 | 37 | 46 | 61 | 72 | 96 | 120 | 127 |
| T89-23 | 19 | 32 | 40 | 50 | 63 | 73 | 100 | 121 | 127 |
| T89-24 | 20 | 31 | 41 | 47 | 58 | 68 | 90 | 111 | 117 |
| T89-25 | 20 | 36 | 45 | 57 | 69 | 78 | 101 | 127 | 134 |
| T89-26 | 20 | 37 | 49 | 58 | 71 | 80 | 107 | 131 | 140 |
| T89-27 | 19 | 34 | 44 | 55 | 71 | 81 | 107 | 131 | 138 |
| T89-28 | 17 | 35 | 44 | 56 | 68 | 76 | 99 | 126 | 132 |
| T89-29 | 17 | 32 | 45 | 55 | 68 | 78 | 101 | 125 | 132 |
| T89-30 | 18 | 31 | 41 | 50 | 63 | 72 | 95 | 119 | 125 |
| T89-31 | 17 | 27 | 35 | 45 | 58 | 67 | 87 | 108 | 116 |
| T89-32 | 19 | 32 | 44 | 52 | 65 | 74 | 98 | 121 | 127 |
| T89-33 | 20 | 33 | 43 | 53 | 64 | 74 | 96 | 119 | 126 |
| T89-34 | 19 | 34 | 44 | 55 | 68 | 78 | 100 | 124 | 130 |
| T89-35 | 17 | 30 | 40 | 51 | 64 | 74 | 95 | 116 | 122 |
| T89-36 | 18 | 30 | 40 | 49 | 62 | 71 | 91 | 114 | 121 |
| T89-82 | 21 | 33 | 43 | 54 | 65 | 75 | 98 | 118 | 125 |
| T89-83 | 22 | 35 | 47 | 55 | 71 | 80 | 105 | 130 | 137 |
| T89-85 | 21 | 36 | 46 | 56 | 67 | 76 | 98 | 123 | 131 |

TABLE 2.74

Diameter growth data for TFSTT045

| | Diameter (mm) Days in greenhouse | | | | |
|---|---|---|---|---|---|
| | 32 | 39 | 46 | 53 | 55 |
| TFSTT045-1B | 5.2 | 5.7 | 7.0 | 8.1 | 8.6 |
| TFSTT045-2B | 5.5 | 6.7 | 7.8 | 8.8 | 9.1 |
| TFSTT045-3A | 6.5 | 7.2 | 8.7 | 10.4 | 10.6 |
| TFSTT045-3B | 4.8 | 5.6 | 7.4 | 8.0 | 8.6 |
| TFSTT045-4A | 5.1 | 6.3 | 7.0 | 7.9 | 8.2 |
| TFSTT045-4B | 5.5 | 6.1 | 7.3 | 8.0 | 8.8 |
| TFSTT045-7B | 5.1 | 6.9 | 8.3 | 9.0 | 9.6 |
| T89-01 | 5.2 | 6.0 | 6.8 | 8.2 | 7.6 |
| T89-02 | 4.5 | 5.8 | 7.1 | 8.6 | 8.3 |
| T89-03 | 4.4 | 5.7 | 6.8 | 7.9 | 8.1 |
| T89-04 | 4.4 | 6.0 | 6.9 | 8.6 | 8.5 |
| T89-05 | 4.6 | 5.8 | 6.7 | 7.9 | 8.0 |
| T89-06 | 4.7 | 5.9 | 7.2 | 8.1 | 9.2 |
| T89-07 | 4.8 | 5.5 | 6.2 | 6.9 | 7.1 |
| T89-08 | 4.5 | 5.4 | 6.0 | 6.9 | 7.1 |
| T89-09 | 4.7 | 5.6 | 6.7 | 8.8 | 8.0 |
| T89-10 | 4.1 | 4.9 | 5.6 | 7.1 | 7.0 |
| T89-11 | 3.8 | 5.3 | 7.3 | 8.0 | 7.6 |
| T89-12 | N/A | 5.1 | 6.2 | 7.3 | 6.9 |
| T89-13 | 4.8 | 5.7 | 6.5 | 7.6 | 7.6 |
| T89-13 | 4.8 | 5.7 | 6.5 | 7.6 | 7.6 |
| T89-14 | 4.2 | 5.5 | 6.6 | 7.6 | 6.5 |
| T89-15 | 5.0 | 6.1 | 7.2 | 7.9 | 8.3 |
| T89-16 | 4.4 | 5.6 | 6.2 | 7.3 | 7.9 |
| T89-17 | 4.8 | 6.7 | 7.0 | 8.3 | 8.4 |
| T89-18 | 4.2 | 5.5 | 6.7 | 7.3 | 7.4 |
| T89-19 | 4.7 | 5.5 | 6.8 | 7.2 | 7.8 |
| T89-20 | 4.5 | 5.6 | 6.5 | 7.0 | 7.3 |
| T89-21 | 4.9 | 5.6 | 6.4 | 7.4 | 7.6 |
| T89-22 | 4.3 | 5.4 | 6.5 | 7.3 | 7.6 |
| T89-23 | 3.9 | 5.5 | 6.7 | 7.7 | 7.0 |
| T89-24 | 4.3 | 5.9 | 6.8 | 8.1 | 7.9 |
| T89-25 | 4.7 | 6.5 | 7.5 | 9.2 | 9.1 |
| T89-26 | 5.4 | 5.9 | 7.7 | 8.6 | 8.8 |
| T89-27 | 4.7 | 5.6 | 7.4 | 7.9 | 8.0 |
| T89-28 | 4.7 | 5.7 | 6.3 | 7.2 | 7.4 |
| T89-29 | 4.8 | 5.6 | 6.6 | 7.7 | 8.1 |
| T89-30 | 4.6 | 5.5 | 6.7 | 7.3 | 7.3 |
| T89-31 | 4.3 | 5.8 | 6.3 | 7.5 | 7.6 |
| T89-32 | 4.6 | 5.9 | 7.6 | 9.3 | 9.1 |
| T89-33 | 4.4 | 5.3 | 6.2 | 7.1 | 7.1 |
| T89-34 | 4.6 | 5.6 | 6.8 | 8.1 | 8.7 |
| T89-35 | 5.3 | 6.0 | 7.5 | 8.8 | 8.9 |
| T89-36 | 4.4 | 6.1 | 6.9 | 8.1 | 8.6 |
| T89-82 | 4.7 | 5.3 | 6.5 | 7.5 | 7.4 |
| T89-83 | 4.7 | 6.1 | 7.1 | 8.3 | 8.3 |
| T89-85 | 5.1 | 6.3 | 7.3 | 7.7 | 8.2 |

Results from growth analysis are specified in the overview table 2.75. The determined growth effects of specified construction group are presented as ratios between construction and wild type group AFH, AFD, AMHGR, ADGR, MFH, MFD, MMHGR and MDC.

TABLE 2.75

Overview table of growth effects of construct TFSTT045

| Construction group | Average Final Height | Average Final Diameter | Average Maximum Height Growth Rate | Average Diameter Growth Rate | Maximum Final Height | Maximum Final Diameter | Maximum of Maximum Height Growth Rate | Maximum Diameter Growth Rate |
|---|---|---|---|---|---|---|---|---|
| TFSTT045 | 1.03 | 1.15 | 1.03 | 1.14 | 1.09 | 1.16 | 1.11 | 0.94 |

Construction Group TFSTT051Rp1

Tables 2.76 and 2.77 contain growth data for specified construction group and corresponding wild type group. Table rows contain height and diameter measurements of individuals of specified construction group and corresponding wild type group. Time of measurement as number of days in greenhouse is shown in table headers.

TABLE 2.76

Height growth data for TFSTT051Rp1

| | Height (cm) Days in greenhouse | | | | | | | | | |
|---|---|---|---|---|---|---|---|---|---|---|
| | 20 | 25 | 29 | 35 | 41 | 46 | 50 | 53 | 57 | 60 |
| TFSTT051rp1-3B-1 | 19 | 25 | 29 | 44 | 60 | 70 | 76 | 83 | 90 | 97 |
| TFSTT051rp1-3B-2 | 17 | 24 | 30 | 43 | 56 | 68 | 75 | 82 | 89 | 97 |
| TFSTT051rp1-3B-3 | 18 | 24 | 28 | 37 | 49 | 63 | 69 | 75 | 83 | 90 |
| TFSTT051rp1-4A-1 | 18 | 23 | 30 | 43 | 58 | 71 | 81 | 90 | 101 | 110 |
| TFSTT051rp1-4A-2 | 16 | 25 | 33 | 45 | 62 | 78 | 88 | 97 | 109 | 119 |
| TFSTT051rp1-4A-3 | 20 | 28 | 38 | 54 | 73 | 90 | 101 | 110 | 122 | 132 |
| T89-01 | 17 | 26 | 31 | 45 | 61 | 76 | 87 | 95 | 107 | 116 |
| T89-02 | 16 | 21 | 26 | 38 | 53 | 67 | 76 | 83 | N/A | N/A |
| T89-03 | 18 | 24 | 32 | 47 | 64 | 78 | 87 | 96 | 106 | 115 |
| T89-04 | 18 | 26 | 35 | 50 | 66 | 80 | 87 | 96 | 107 | 115 |
| T89-05 | 17 | 26 | 33 | 44 | 57 | 73 | 81 | 91 | 100 | 107 |
| T89-06 | 16 | 21 | 28 | 40 | 55 | 74 | 79 | 89 | 99 | 106 |
| T89-07 | 17 | 23 | 31 | 43 | 57 | 71 | 80 | 88 | 98 | 107 |
| T89-08 | 15 | 20 | 26 | 37 | 51 | 65 | 75 | 84 | 94 | 100 |
| T89-09 | 18 | 25 | 32 | 46 | 61 | 74 | 85 | 93 | 103 | 112 |
| T89-10 | 19 | 25 | 32 | 46 | 60 | 75 | 86 | 95 | 104 | 112 |
| T89-11 | 20 | 27 | 36 | 51 | 68 | 86 | 98 | 107 | 120 | 127 |
| T89-12 | 19 | 27 | 36 | 50 | 67 | 80 | 89 | 97 | 108 | 118 |
| T89-13 | 18 | 25 | 32 | 45 | 59 | 75 | 83 | 92 | 101 | 108 |
| T89-14 | 18 | 23 | 26 | 36 | 51 | 65 | 72 | 79 | 89 | 96 |
| T89-15 | 17 | 21 | 28 | 39 | 53 | 70 | 78 | 87 | 97 | 105 |
| T89-16 | 19 | 25 | 32 | 43 | 57 | 71 | 81 | 90 | 101 | 109 |
| T89-17 | 16 | 20 | 29 | 41 | 54 | 68 | 78 | 84 | 93 | 101 |
| T89-18 | 16 | 23 | 30 | 45 | 63 | 78 | 87 | 94 | 103 | 110 |
| T89-19 | 16 | 22 | 28 | 42 | 56 | 69 | 79 | 89 | 100 | 107 |
| T89-20 | 18 | 25 | 32 | 47 | 63 | 78 | 89 | 99 | 109 | 115 |
| T89-21 | 19 | 27 | 34 | 50 | 67 | 82 | 92 | 102 | 111 | 120 |
| T89-22 | 19 | 25 | 32 | 44 | 58 | 76 | 84 | 93 | 102 | 109 |
| T89-23 | 18 | 26 | 33 | 47 | 63 | 79 | 88 | 99 | 108 | 116 |
| T89-24 | 16 | 24 | 28 | 42 | 53 | 70 | 78 | 85 | 94 | 103 |
| T89-25 | 16 | 25 | 32 | 45 | 61 | 76 | 85 | 95 | 107 | 114 |
| T89-26 | 16 | 20 | 26 | 38 | 52 | 68 | 78 | 86 | 97 | 103 |
| T89-27 | 16 | 21 | 25 | 35 | 48 | 61 | 70 | 78 | N/A | 98 |
| T89-28 | 14 | 18 | 25 | 38 | 51 | 64 | 73 | 81 | 90 | 96 |
| T89-29 | 7 | 13 | 18 | 30 | 45 | 60 | 69 | 77 | 90 | 98 |
| T89-30 | 15 | 22 | 29 | 42 | 55 | 69 | 80 | 88 | 97 | 106 |
| T89-31 | 21 | 29 | 37 | 50 | 65 | 80 | 88 | 98 | 108 | 116 |
| T89-32 | 19 | 24 | 32 | 42 | 55 | 70 | 78 | 87 | 96 | 105 |

TABLE 2.77

Diameter growth data for TFSTT051Rp1

| | Diameter (mm) Days in greenhouse | | | | |
|---|---|---|---|---|---|
| | 35 | 41 | 46 | 53 | 60 |
| TFSTT051rp1-3B-1 | 4.6 | 5.9 | 6.4 | 7.2 | 7.7 |
| TFSTT051rp1-3B-2 | 4.3 | 5.6 | 6.0 | 6.1 | 7.3 |
| TFSTT051rp1-3B-3 | 4.2 | 5.4 | 6.8 | 6.9 | 8.3 |
| TFSTT051rp1-4A-1 | 4.5 | 5.9 | 6.6 | 7.8 | 9.1 |
| TFSTT051rp1-4A-2 | 4.5 | 5.9 | 6.6 | 7.4 | 8.1 |
| TFSTT051rp1-4A-3 | 5.2 | 6.4 | 7.1 | 7.9 | 8.3 |
| T89-01 | 4.7 | 6.0 | 6.5 | 6.9 | 8.3 |
| T89-02 | 4.4 | 5.7 | 6.6 | 7.6 | 7.8 |
| T89-03 | 4.7 | 6.3 | 6.7 | 7.7 | 8.4 |
| T89-04 | 4.7 | 6.0 | 7.1 | 8.0 | 8.5 |
| T89-05 | 4.0 | 5.3 | 6.3 | 7.8 | 8.1 |
| T89-06 | 4.6 | 5.9 | 6.3 | 7.7 | 8.2 |
| T89-07 | 4.6 | 6.1 | 6.5 | 7.9 | 8.5 |
| T89-08 | 4.0 | 5.2 | 5.8 | 6.9 | 7.1 |
| T89-09 | 4.4 | 5.8 | 6.4 | 7.6 | 8.2 |
| T89-10 | 4.9 | 6.0 | 6.6 | 7.4 | 8.5 |
| T89-11 | 4.7 | 5.8 | 6.4 | 7.9 | 8.3 |
| T89-12 | 4.7 | 5.9 | 7.3 | 7.4 | 7.6 |
| T89-13 | 5.9 | 5.9 | 6.7 | 7.5 | 8.3 |
| T89-14 | 4.5 | 5.2 | 5.8 | 6.1 | 7.0 |
| T89-15 | 4.7 | N/A | 6.0 | 6.4 | 7.3 |
| T89-16 | 4.5 | 5.6 | 7.7 | 7.5 | 8.6 |
| T89-17 | 4.1 | 5.4 | 6.0 | 6.8 | 7.5 |
| T89-18 | 4.4 | 5.8 | 6.0 | 7.7 | 8.3 |
| T89-19 | 4.7 | 5.8 | 7.1 | 8.5 | 9.4 |
| T89-20 | 4.7 | 5.8 | 6.6 | 7.4 | 8.3 |
| T89-21 | 4.7 | 6.2 | 6.3 | 7.7 | 8.5 |
| T89-22 | 4.2 | 5.1 | 6.3 | 6.9 | 8.0 |
| T89-23 | 4.6 | 5.8 | 7.1 | 7.5 | 8.3 |
| T89-24 | 4.4 | 5.8 | 6.9 | 7.7 | 8.8 |
| T89-25 | 4.5 | 5.4 | 6.2 | 8.0 | 8.7 |
| T89-26 | 4.1 | 5.4 | 6.0 | 7.2 | 8.0 |
| T89-27 | 4.5 | 5.7 | 6.5 | 7.9 | 9.2 |
| T89-28 | 4.3 | 5.1 | 6.0 | 6.6 | 7.7 |
| T89-29 | 3.5 | 4.7 | 5.5 | 6.3 | 7.1 |
| T89-30 | 4.1 | 5.4 | 5.8 | 7.2 | 7.8 |
| T89-31 | 5.0 | 5.8 | 6.8 | 7.3 | 8.2 |
| T89-32 | 4.4 | 6.4 | 6.6 | 8.0 | 8.4 |

Results from growth analysis are specified in the overview table 2.78. The determined growth effects of specified construction group are presented as ratios between construction and wild type group AFH, AFD, AMHGR, ADGR, MFH, MFD, MMHGR and MDC.

TABLE 2.78

Overview table of growth effects of construct TFSTT051Rp1

| Construction group | Average Final Height | Average Final Diameter | Average Maximum Height Growth Rate | Average Diameter Growth Rate | Maximum Final Height | Maximum Final Diameter | Maximum of Maximum Height Growth Rate | Maximum Diameter Growth Rate |
|---|---|---|---|---|---|---|---|---|
| TFSTT051Rp1 | 0.99 | 1.00 | 0.96 | 0.95 | 1.04 | 0.97 | 0.98 | 0.95 |

Example 3

Volumetric Growth Calculation

The volume of the stem of each individual plant is approximated from final height and final diameter measurements using cone volume.

Stem Volume Approximation $$V = \frac{\pi * h * r^2}{3}$$

where
V=Volume
h=height (Final height)
r=radius (Final diameter/2)

Average final volumes of each construction group population and corresponding wild type population are subsequently calculated. A volumetric growth selection criterion is applied, where a construction group is considered having a significant or pronounced volume increase compared to the wild type population if construction group average final volume is at least 25% (or 50% in the second more stringent level) greater than corresponding wild type group average final volume.

Results from volume approximation are specified in the overview table 3.1. The determined growth effects are presented as ratios between construction and wild type group average final volumes AFV.

The following construction groups meet the volumetric growth criterion. Construction group TF0002Rp2 has an average final volume increase of 36%; construction group TF0013 has an average final volume increase of 27%; construction group TF0045 has an average final volume increase of 33%; construction group TF0096 has an average final volume increase of 44%; construction group TF0109 has an average final volume increase of 44%; construction group TF0116 has an average final volume increase of 31%; construction group TF0132rp1 has an average final volume increase of 46%, where construction group line TF0132rp1-4AC has an average final volume increase of 70% (+/−20%); construction group TF0146 has an average final volume increase of 34%; construction group TF0247 has an average final volume increase of 49%; construction group TF0405 has an average final volume increase of 45%; construction group TFSTT016 has an average final volume increase of 36%; construction group TFSTT036 has an average final volume increase of 28%; construction group TFSTT038 has an average final volume increase of 32%; construction group TFSTT045 has an average final volume increase of 38%.

The following construction groups meet the more stringent level of the volumetric growth criterion (5) as shown in table 3.1. Construction group TF0097Rp1 has an average final volume increase of 68%, where construction group line TF0097Rp1-3A has an average final volume increase of 116% (+/−37%); construction group TF0104 has an average final volume increase of 79%; construction group TF0109Rp1 has an average final volume increase of 58%, where construction group line TF0109Rp1-4A has an average final volume increase of 92% (+/−5%);%; construction group TF0132.2nd has an average final volume increase of 65%; construction group TFSTT004 has an average final volume increase of 51%. These construction groups meet the more stringent level of volumetric growth criterion (5) as shown in table 3.1.

TABLE 3.1

| Construction group | Average Final Volume |
|---|---|
| TF0002Rp2 | 1.36 |
| TF0013 | 1.27 |
| TF0045 | 1.33 |
| TF0096 | 1.44 |
| TF0097Rp1 | 1.68 |
| TF0104 | 1.79 |
| TF0109 | 1.44 |
| TF0109Rp1 | 1.58 |
| TF0116 | 1.31 |
| TF0132.2nd | 1.65 |
| TF0132rp1 | 1.46 |
| TF0146 | 1.34 |
| TF0247 | 1.49 |
| TF0405 | 1.45 |
| TFSTT004 | 1.51 |
| TFSTT016 | 1.36 |
| TFSTT036 | 1.28 |
| TFSTT038 | 1.32 |
| TFSTT045 | 1.38 |

Example 4

Dry Weight Measurements

Dry weight measurements were performed on replanted construction groups. Plants were harvested according to a standard procedure: stem, bark, five fully developed leafs, rest of leafs and roots were collected as separate samples. The leaf area were measured of the five fully developed leafs and the length of 20 fully developed internodes were measured. The separate samples of plant material were put in a drier oven for more than 48 hours. The dry weights were measured and analysed according differences compared to corresponding wild type groups. Abbreviations and parameters used for dry weight analyses is shown in table 4.1.

TABLE 4.1

| | Abbreviations and parameters associated with dry weight |
|---|---|
| Stem (g) | Dry weight of stem of one plant individual |
| Bark (g) | Dry weight of bark of one plant individual |
| Root (g) | Dry weight of root of one plant individual |
| Leaf (g) | Dry weight of all leafs of one plant individual |
| TOTAL(g) | Total dry weight of stem, bark and leafs of one plant individual |
| SLA (m2/kg) | Specific Leaf Area, square meter per kg leaf dry weight, calculated from five fully developed leaf of one plant individual |
| Internode (cm) | Average internode length, calculated from 20 internodes of one plant individual |
| Average Stem | Average stem dry weight of the wild type population and each construction group population |
| Average Bark | Average bark dry weight of the wild type population and each construction group population |
| Average Root | Average root dry weight of the wild type population and each construction group population |
| Average Leaf | Average Leaf dry weight of the wild type population and each construction group population |
| Average TOTAL | Average TOTAL dry weight of the wild type population and each construction group population |
| Average SLA | Average SLA of the wild type population and each construction group population |
| Average Internode | Average internode of the wild type population and each construction group population |
| Maximum Stem | Maximum stem dry weight of the wild type population and each construction group population |
| Maximum Bark | Maximum bark dry weight of the wild type population and each construction group population |
| Maximum Root | Maximum root dry weight of the wild type population and each construction group population |
| Maximum Leaf | Maximum Leaf dry weight of the wild type population and each construction group population |
| Maximum TOTAL | Maximum TOTAL dry weight of the wild type population and each construction group population |
| Line Average Stem | Average stem dry weight of the wild type population and each construction group line |
| Line Average Bark | Average bark dry weight of the wild type population and each construction group line |
| Line Average Root | Average root dry weight of the wild type population and each construction group line |
| Line Average Leaf | Average leaf dry weight of the wild type population and each construction group line |
| Line Average TOTAL | Average TOTAL dry weight of the wild type population and each construction group line |
| Line Average SLA | Average SLA of the wild type population and each construction group line |
| Line Average Internode | Average internode length of the wild type population and each construction group line |

Dry Weight Experiment Results
Construction Group TF0013

This construct induce increase of biomass production. Dry weight measurements of the construction group show 20% increase of average stem, 14% increase of average bark, 14% increase of average leaf and 16% increase of average TOTAL compared to the corresponding wildtype group. One of the construction group lines show 48% increase of average stem, 37% increase of average bark, 31% increase of average leaf and 36% increase of average TOTAL compared to the corresponding wildtype group.

Table 4.2 contains dry weight data for specified construction group and corresponding wild type group.

TABLE 4.2

| Construction Group Individual | Stem (g) | Bark (g) | Root (g) | Leaf (g) | TOTAL (g) | SLA (m2/kg) | Internode (cm) |
|---|---|---|---|---|---|---|---|
| TF0013rp2-1A-1 | 4.4 | 2.1 | | 15.1 | 21.6 | 33.7 | 3.0 |
| TF0013rp2-1A-2 | 6.5 | 2.7 | | 15.0 | 24.2 | 41.2 | 3.6 |
| TF0013rp2-1A-3 | 5.9 | 2.8 | | 14.4 | 23.0 | 33.6 | 3.5 |
| TF0013rp2-3BA-1 | 8.7 | 3.7 | | 19.5 | 31.9 | 34.4 | 3.8 |
| TF0013rp2-3BA-2 | 9.1 | 3.9 | | 20.6 | 33.6 | 32.8 | 3.7 |
| TF0013rp2-3BA-3 | 8.7 | 3.7 | | 19.8 | 32.2 | 34.2 | 4.1 |
| T89-20 | 5.8 | 2.7 | 6.4 | 14.0 | 22.5 | 35.4 | 3.7 |
| T89-21 | 5.9 | 3.0 | 8.5 | 16.9 | 25.8 | 30.3 | 3.2 |
| T89-22 | 6.0 | 2.7 | | 15.4 | 24.1 | 34.4 | 3.7 |
| T89-23 | 4.3 | 2.0 | 4.6 | 12.1 | 18.4 | 48.9 | 3.3 |
| T89-24 | 5.5 | 2.5 | 6.5 | 14.3 | 22.2 | 32.8 | 3.6 |
| T89-25 | 7.6 | 3.4 | 8.0 | 18.8 | 29.8 | 31.2 | 3.3 |

TABLE 4.2-continued

| Construction Group Individual | Stem (g) | Bark (g) | Root (g) | Leaf (g) | TOTAL (g) | SLA (m2/kg) | Internode (cm) |
|---|---|---|---|---|---|---|---|
| T89-26 | 6.6 | 3.0 | | 17.2 | 26.8 | 33.5 | 3.7 |
| T89-27 | 6.9 | 3.1 | | 16.0 | 26.0 | 31.4 | 3.8 |
| T89-28 | 5.2 | 2.6 | | 12.8 | 20.5 | 32.7 | 3.4 |

Table 4.3 contains the dry weight ratios of specified construction group relative to corresponding wildtype group of average stem, average bark, average root, average leaf and average TOTAL. Table 4.3 also show ratios of average SLA and average internode length of specified construction group relative to corresponding wildtype group.

TABLE 4.3

| Construction Group | Average Stem | Average Bark | Average Root | Average Leaf | Average TOTAL | Average SLA | Average Internode |
|---|---|---|---|---|---|---|---|
| TF0013rp2 | 1.20 | 1.14 | | 1.14 | 1.16 | 1.01 | 1.03 |

Table 4.4 contains the dry weight ratios for specified construction group relative to corresponding wildtype group for maximum stem, maximum bark, maximum root, maximum leaf and maximum TOTAL.

TABLE 4.4

| Construction Group | Maximum Stem | Maximum Bark | Maximum Root | Maximum Leaf | Maximum TOTAL |
|---|---|---|---|---|---|
| TF0013rp2 | 1.20 | 1.16 | | 1.09 | 1.13 |

Table 4.5 contains dry weight ratios for specified construction group line relative to corresponding wildtype group of average stem, average bark, average root, average leaf and average TOTAL. Table 4.5 also show ratios of average SLA and average internode length of specified construction group line relative to corresponding wildtype group.

TABLE 4.5

| Construction Group Line | Line Average Stem | Line Average Bark | Line Average Root | Line Average Leaf | Line Average TOTAL | Line Average SLA | Line Average Internode |
|---|---|---|---|---|---|---|---|
| TF0013rp2-1A | 0.93 | 0.91 | | 0.97 | 0.95 | 1.05 | 0.96 |
| TF0013rp2-3BA | 1.48 | 1.37 | | 1.31 | 1.36 | 0.98 | 1.10 |

Construction Group TF0132

This construct induce increase of biomass production. Dry weight measurements of the construction group show 83% increase of average stem, 58% increase of average bark, 34% increase of average leaf and 49% increase of average TOTAL compared to the corresponding wildtype group. One of the construction group lines show 119% increase of average stem, 82% increase of average bark, 53% increase of average leaf and 73% increase of average TOTAL compared to the corresponding wildtype group. For the lines were root dry weight were measured an increase in the shot-root ratio were observed.

Table 4.6 contains dry weight data for specified construction group and corresponding wild type group.

TABLE 4.6

| Construction Group Individual | Stem (g) | Bark (g) | Root (g) | Leaf (g) | TOTAL (g) | SLA (m2/kg) | Internode (cm) |
|---|---|---|---|---|---|---|---|
| TF0132rp1-1B-2 | 11.7 | 4.6 | 10.3 | 18.1 | 34.5 | 33.3 | |
| TF0132rp1-1B-3 | 9.1 | 3.5 | 6.0 | 15.7 | 28.4 | 33.3 | 4.2 |
| TF0132rp1-3BB-1 | 9.8 | 4.1 | 10.7 | 18.7 | 32.6 | 33.7 | 4.2 |
| TF0132rp1-3BB-2 | 11.4 | 4.9 | 9.8 | 24.8 | 41.2 | 30.8 | 4.3 |
| TF0132rp1-3BB-3 | 10.8 | 4.3 | 10.7 | 20.4 | 35.5 | 34.1 | 4.3 |
| TF0132rp1-4AC-1 | 13.3 | 5.1 | | 20.7 | 39.1 | 32.8 | 3.6 |
| TF0132rp1-4AC-2 | 14.5 | 5.5 | | 26.7 | 46.7 | 34.2 | 3.9 |
| TF0132rp1-4AC-3 | 11.4 | 4.5 | | 22.5 | 38.4 | 34.6 | 3.7 |
| TF0132rp1-4B-1 | 10.7 | 4.3 | | 18.2 | 33.2 | 32.4 | 4.1 |
| TF0132rp1-4B-2 | 6.7 | 2.9 | | 16.9 | 26.4 | 34.3 | 4.0 |
| TF0132rp1-4B-3 | 10.2 | 3.8 | | 17.7 | 31.7 | 38.9 | 4.1 |
| TF0132rp1-6B-1 | 7.5 | 3.6 | | 21.3 | 32.5 | 32.5 | 4.0 |
| TF0132rp1-6B-2 | 11.9 | 4.6 | | 20.7 | 37.2 | 34.0 | 4.3 |

TABLE 4.6-continued

| Construction Group Individual | Stem (g) | Bark (g) | Root (g) | Leaf (g) | TOTAL (g) | SLA (m2/kg) | Internode (cm) |
|---|---|---|---|---|---|---|---|
| TF0132rp1-6B-3 | 11.1 | 4.6 | | 22.5 | 38.2 | 31.4 | 4.3 |
| T89-20 | 5.8 | 2.7 | 6.4 | 14.0 | 22.5 | 35.4 | 3.7 |
| T89-21 | 5.9 | 3.0 | 8.5 | 16.9 | 25.8 | 30.3 | 3.2 |
| T89-22 | 6.0 | 2.7 | | 15.4 | 24.1 | 34.4 | 3.7 |
| T89-23 | 4.3 | 2.0 | 4.6 | 12.1 | 18.4 | 48.9 | 3.3 |
| T89-24 | 5.5 | 2.5 | 6.5 | 14.3 | 22.2 | 32.8 | 3.6 |
| T89-25 | 7.6 | 3.4 | 8.0 | 18.8 | 29.8 | 31.2 | 3.3 |
| T89-26 | 6.6 | 3.0 | | 17.2 | 26.8 | 33.5 | 3.7 |
| T89-27 | 6.9 | 3.1 | | 16.0 | 26.0 | 31.4 | 3.8 |
| T89-28 | 5.2 | 2.6 | | 12.8 | 20.5 | 32.7 | 3.4 |

Table 4.7 contains the dry weight ratios of specified construction group relative to corresponding wildtype group of average stem, average bark, average root, average leaf and average TOTAL. Table 4.7 also show ratios of average SLA and average internode length of specified construction group relative to corresponding wildtype group.

TABLE 4.7

| Construction Group | Average Stem | Average Bark | Average Root | Average Leaf | Average TOTAL | Average SLA | Average Internode |
|---|---|---|---|---|---|---|---|
| TF0132rp1 | 1.83 | 1.58 | 1.58 | 1.34 | 1.49 | 0.96 | 1.17 |

Table 4.8 contains the dry weight ratios for specified construction group relative to corresponding wildtype group for maximum stem, maximum bark, maximum root, maximum leaf and maximum TOTAL.

TABLE 4.8

| Construction Group | Maximum Stem | Maximum Bark | Maximum Root | Maximum Leaf | Maximum TOTAL |
|---|---|---|---|---|---|
| TF0132rp1 | 1.92 | 1.62 | 1.99 | 1.42 | 1.57 |

Table 4.9 contains dry weight ratios for specified construction group line relative to corresponding wildtype group of average stem, average bark, average root, average leaf and average TOTAL. Table 4.9 also show ratios of average SLA and average internode length of specified construction group line relative to corresponding wildtype group.

TABLE 4.9

| Construction Group Line | Line Average Stem | Line Average Bark | Line Average Root | Line Average Leaf | Line Average TOTAL | Line Average SLA | Line Average Internode |
|---|---|---|---|---|---|---|---|
| TF0132rp1-1B | 1.93 | 1.61 | 1.63 | 1.24 | 1.45 | 0.92 | 1.25 |
| TF0132rp1-3BB | 1.79 | 1.59 | 1.53 | 1.40 | 1.52 | 0.95 | 1.22 |
| TF0132rp1-4AC | 2.19 | 1.82 | | 1.53 | 1.73 | 0.98 | 1.07 |
| TF0132rp1-4B | 1.54 | 1.32 | | 1.15 | 1.27 | 1.02 | 1.15 |
| TF0132rp1-6B | 1.70 | 1.53 | | 1.41 | 1.50 | 0.95 | 1.20 |

Construction Group TF0002

This construct induce increase of biomass production. Dry weight measurements of the construction group show 50% increase of average stem, 52% increase of average bark, 6% increase of average leaf and 20% increase of average TOTAL compared to the corresponding wildtype group. One of the construction group lines show 72% increase of average stem, 61% increase of average bark, 20% increase of average leaf and 35% increase of average TOTAL compared to the corresponding wildtype group. For the line were root dry weight were measured an increase in the shot-root ratio were observed.

Table 4.10 contains dry weight data for specified construction group and corresponding wild type group.

TABLE 4.10

| Construction Group Individual | Stem (g) | Bark (g) | Root (g) | Leaf (g) | TOTAL (g) | SLA (m2/kg) | Internode (cm) |
|---|---|---|---|---|---|---|---|
| TF0002rp2-1B-1 | 8.5 | 3.4 | 8.1 | 17.4 | 29.4 | 33.4 | 3.5 |
| TF0002rp2-1B-2 | 10.7 | 4.7 | 12.6 | 20.5 | 35.8 | 32.2 | 3.2 |
| TF0002rp2-1B-3 | 10.0 | 3.7 | 8.0 | 19.2 | 32.9 | 36.2 | 3.3 |

TABLE 4.10-continued

| Construction Group Individual | Stem (g) | Bark (g) | Root (g) | Leaf (g) | TOTAL (g) | SLA (m2/kg) | Internode (cm) |
|---|---|---|---|---|---|---|---|
| TF0002rp2-2A-1 | 8.0 | 3.4 | | 14.5 | 25.9 | 34.3 | 3.3 |
| TF0002rp2-2A-2 | 5.0 | 2.4 | | 10.1 | 17.4 | 35.9 | 3.0 |
| TF0002rp2-2A-3 | 6.4 | 3.3 | | 12.2 | 22.0 | 25.3 | 3.1 |
| TF0002rp2-3B-1 | 4.7 | 2.3 | | 12.0 | 19.0 | 34.5 | 3.0 |
| TF0002rp2-3B-2 | 10.7 | 4.7 | | 20.7 | 36.1 | 32.1 | 3.3 |
| TF0002rp2-3B-3 | 12.3 | 5.8 | | 25.3 | 43.3 | 27.4 | 2.5 |
| T89-01 | 5.1 | 2.2 | | 13.1 | 20.4 | 39.9 | 2.7 |
| T89-02 | | | | 13.8 | 28.4 | 36.3 | 2.6 |
| T89-03 | 6.8 | 2.7 | | 17.1 | 26.6 | 37.8 | 2.6 |
| T89-04 | 6.9 | 2.7 | | 17.3 | 27.0 | 37.1 | 2.4 |
| T89-05 | 5.7 | 2.5 | | 16.6 | 24.9 | 31.8 | 2.6 |
| T89-06 | 6.1 | 2.7 | 8.2 | 18.4 | 27.1 | 31.7 | 2.7 |
| T89-07 | 5.8 | 2.5 | 9.2 | 15.9 | 24.2 | 31.7 | 2.6 |
| T89-08 | 3.9 | 2.1 | | 16.1 | 22.0 | 29.2 | 2.6 |
| T89-09 | 6.9 | 3.1 | | 20.7 | 30.7 | 30.3 | 2.5 |
| T89-10 | 5.5 | 2.5 | 10.3 | 16.6 | 24.6 | 36.9 | 2.6 |
| T89-11 | 6.9 | 3.0 | | 17.9 | 27.8 | 34.0 | 3.0 |
| T89-12 | 6.6 | 3.0 | | 15.2 | 24.8 | 31.9 | 2.8 |
| T89-13 | 5.9 | 2.2 | | 15.0 | 23.1 | 39.6 | 2.4 |
| T89-14 | 3.4 | 1.7 | | 13.2 | 18.3 | 32.7 | 2.5 |
| T89-15 | 4.6 | 2.0 | | 14.9 | 21.6 | 33.4 | 2.7 |
| T89-16 | 6.1 | 2.7 | | 17.7 | 26.4 | 31.8 | 2.6 |
| T89-17 | 4.4 | 2.1 | | 15.9 | 22.4 | 31.5 | 2.6 |
| T89-18 | 5.6 | 2.6 | | 15.0 | 23.3 | 32.7 | 2.7 |
| T89-19 | 6.2 | 2.7 | | 18.4 | 27.3 | 33.6 | 2.5 |
| T89-20 | 5.9 | 2.7 | 8.4 | 16.5 | 25.2 | 35.9 | 2.7 |
| T89-21 | 6.9 | 2.8 | | 17.8 | 27.5 | 39.0 | 2.6 |
| T89-22 | 5.4 | 2.2 | | 13.7 | 21.3 | 37.9 | 2.7 |
| T89-23 | 7.0 | 2.9 | | 17.7 | 27.5 | 33.3 | 2.9 |
| T89-24 | 6.6 | 2.7 | | 17.3 | 26.6 | 33.8 | 2.6 |
| T89-25 | 6.5 | 2.8 | 7.4 | 17.2 | 26.5 | 32.4 | 2.8 |
| T89-26 | 4.7 | 2.2 | 6.2 | 14.3 | 21.2 | 33.0 | 2.8 |
| T89-27 | 5.4 | 2.4 | | 16.1 | 23.9 | 31.3 | 2.5 |
| T89-28 | 3.6 | 1.5 | | 11.7 | 16.7 | 39.5 | 2.5 |
| T89-29 | 3.1 | 1.3 | | 9.9 | 14.4 | 36.3 | 3.0 |
| T89-30 | 5.0 | 2.1 | | 13.7 | 20.8 | 36.2 | 2.9 |
| T89-31 | 7.0 | 2.9 | | 17.2 | 27.2 | 32.7 | 2.7 |
| T89-32 | 6.0 | 2.5 | | 16.7 | 25.2 | 32.3 | 2.5 |

Table 4.11 contains the dry weight ratios of specified construction group relative to corresponding wildtype group of average stem, average bark, average root, average leaf and average TOTAL. Table 4.11 also show ratios of average SLA and average internode length of specified construction group relative to corresponding wildtype group.

TABLE 4.11

| Construction Group | Average Stem | Average Bark | Average Root | Average Leaf | Average TOTAL | Average SLA | Average Internode |
|---|---|---|---|---|---|---|---|
| TF0002rp2 | 1.50 | 1.52 | 1.16 | 1.06 | 1.20 | 0.94 | 1.19 |

Table 4.12 contains the dry weight ratios for specified construction group relative to corresponding wildtype group for maximum stem, maximum bark, maximum root, maximum leaf and maximum TOTAL.

TABLE 4.12

| Construction Group | Maximum Stem | Maximum Bark | Maximum Root | Maximum Leaf | Maximum TOTAL |
|---|---|---|---|---|---|
| TF0002rp2 | 1.76 | 1.85 | 1.23 | 1.22 | 1.41 |

Table 4.13 contains dry weight ratios for specified construction group line relative to corresponding wildtype group of average stem, average bark, average root, average leaf and average TOTAL. Table 4.13 also show ratios of average SLA and average internode length of specified construction group line relative to corresponding wildtype group.

TABLE 4.13

| Construction Group Line | Line Average Stem | Line Average Bark | Line Average Root | Line Average Leaf | Line Average TOTAL | Line Average SLA | Line Average Internode |
|---|---|---|---|---|---|---|---|
| TF0002rp2-1B | 1.72 | 1.61 | 1.16 | 1.20 | 1.35 | 0.99 | 1.27 |
| TF0002rp2-2A | 1.15 | 1.23 | | 0.77 | 0.90 | 0.93 | 1.18 |
| TF0002rp2-3B | 1.63 | 1.73 | | 1.22 | 1.36 | 0.91 | 1.12 |

Construction Group TF0052

This construct induce increase of biomass production. Dry weight measurements of one of the construction group lines show 49% increase of average stem, 64% increase of average bark, 32% increase of average leaf and 38% increase of average TOTAL compared to the corresponding wildtype group.

Table 4.14 contains dry weight data for specified construction group and corresponding wild type group.

TABLE 4.14

| Construction Group Individual | Stem (g) | Bark (g) | Root (g) | Leaf (g) | TOTAL (g) | SLA (m2/kg) | Internode (cm) |
|---|---|---|---|---|---|---|---|
| TF0052rp1-2A-1 | 9.5 | 4.5 | | 23.8 | 37.8 | 30.0 | 3.0 |
| TF0052rp1-2A-2 | 7.3 | 3.6 | | 18.4 | 29.2 | 33.7 | 3.0 |
| TF0052rp1-2A-3 | 8.5 | 4.0 | | 21.0 | 33.4 | 37.8 | 3.0 |
| TF0052rp1-2B-1 | 4.7 | 2.2 | | 14.1 | 21.0 | 39.8 | 2.6 |
| TF0052rp1-2B-2 | 4.0 | 2.0 | | 13.5 | 19.6 | 32.3 | 2.6 |
| TF0052rp1-2B-3 | 2.4 | 1.3 | | 7.3 | 11.0 | 31.0 | 2.5 |
| T89-01 | 5.1 | 2.2 | | 13.1 | 20.4 | 39.9 | 2.7 |
| T89-02 | | | | 13.8 | 28.4 | 36.3 | 2.6 |
| T89-03 | 6.8 | 2.7 | | 17.1 | 26.6 | 37.8 | 2.6 |
| T89-04 | 6.9 | 2.7 | | 17.3 | 27.0 | 37.1 | 2.4 |
| T89-05 | 5.7 | 2.5 | | 16.6 | 24.9 | 31.8 | 2.6 |
| T89-06 | 6.1 | 2.7 | 8.2 | 18.4 | 27.1 | 31.7 | 2.7 |
| T89-07 | 5.8 | 2.5 | 9.2 | 15.9 | 24.2 | 31.7 | 2.6 |
| T89-08 | 3.9 | 2.1 | | 16.1 | 22.0 | 29.2 | 2.6 |
| T89-09 | 6.9 | 3.1 | | 20.7 | 30.7 | 30.3 | 2.5 |
| T89-10 | 5.5 | 2.5 | 10.3 | 16.6 | 24.6 | 36.9 | 2.6 |
| T89-11 | 6.9 | 3.0 | | 17.9 | 27.8 | 34.0 | 3.0 |
| T89-12 | 6.6 | 3.0 | | 15.2 | 24.8 | 31.9 | 2.8 |
| T89-13 | 5.9 | 2.2 | | 15.0 | 23.1 | 39.6 | 2.4 |
| T89-14 | 3.4 | 1.7 | | 13.2 | 18.3 | 32.7 | 2.5 |
| T89-15 | 4.6 | 2.0 | | 14.9 | 21.6 | 33.4 | 2.7 |
| T89-16 | 6.1 | 2.7 | | 17.7 | 26.4 | 31.8 | 2.6 |
| T89-17 | 4.4 | 2.1 | | 15.9 | 22.4 | 31.5 | 2.6 |
| T89-18 | 5.6 | 2.6 | | 15.0 | 23.3 | 32.7 | 2.7 |
| T89-19 | 6.2 | 2.7 | | 18.4 | 27.3 | 33.6 | 2.5 |
| T89-20 | 5.9 | 2.7 | 8.4 | 16.5 | 25.2 | 35.9 | 2.7 |
| T89-21 | 6.9 | 2.8 | | 17.8 | 27.5 | 39.0 | 2.6 |
| T89-22 | 5.4 | 2.2 | | 13.7 | 21.3 | 37.9 | 2.7 |
| T89-23 | 7.0 | 2.9 | | 17.7 | 27.5 | 33.3 | 2.9 |
| T89-24 | 6.6 | 2.7 | | 17.3 | 26.6 | 33.8 | 2.6 |
| T89-25 | 6.5 | 2.8 | 7.4 | 17.2 | 26.5 | 32.4 | 2.8 |
| T89-26 | 4.7 | 2.2 | 6.2 | 14.3 | 21.2 | 33.0 | 2.8 |
| T89-27 | 5.4 | 2.4 | | 16.1 | 23.9 | 31.3 | 2.5 |
| T89-28 | 3.6 | 1.5 | | 11.7 | 16.7 | 39.5 | 2.5 |
| T89-29 | 3.1 | 1.3 | | 9.9 | 14.4 | 36.3 | 3.0 |
| T89-30 | 5.0 | 2.1 | | 13.7 | 20.8 | 36.2 | 2.9 |
| T89-31 | 7.0 | 2.9 | | 17.2 | 27.2 | 32.7 | 2.7 |
| T89-32 | 6.0 | 2.5 | | 16.7 | 25.2 | 32.3 | 2.5 |

Table 4.15 contains the dry weight ratios of specified construction group relative to corresponding wildtype group of average stem, average bark, average root, average leaf and average TOTAL. Table 4.15 also show ratios of average SLA and average internode length of specified construction group relative to corresponding wildtype group.

TABLE 4.15

| Construction Group | Average Stem | Average Bark | Average Root | Average Leaf | Average TOTAL | Average SLA | Average Internode |
|---|---|---|---|---|---|---|---|
| TF0052rp1 | 1.07 | 1.20 | 1.03 | 1.05 | 0.99 | 1.05 | |

Table 4.16 contains the dry weight ratios for specified construction group relative to corresponding wildtype group for maximum stem, maximum bark, maximum root, maximum leaf and maximum TOTAL.

TABLE 4.16

| Construction Group | Maximum Stem | Maximum Bark | Maximum Root | Maximum Leaf | Maximum TOTAL |
|---|---|---|---|---|---|
| TF0052rp1 | 1.36 | 1.43 | | 1.15 | 1.23 |

Table 4.17 contains dry weight ratios for specified construction group line relative to corresponding wildtype group of average stem, average bark, average root, average leaf and average TOTAL. Table 4.17 also show ratios of average SLA and average internode length of specified construction group line relative to corresponding wildtype group.

TABLE 4.17

| Construction Group Line | Line Average Stem | Line Average Bark | Line Average Root | Line Average Leaf | Line Average TOTAL | Line Average SLA | Line Average Internode |
|---|---|---|---|---|---|---|---|
| TF0052rp1-2A | 1.49 | 1.64 | | 1.32 | 1.38 | 0.99 | 1.12 |
| TF0052rp1-2B | 0.65 | 0.76 | | 0.73 | 0.71 | 1.00 | 0.97 |

Construction Group TF0076

This construct induce increase of biomass production. Dry weight measurements of the construction group show 16% increase of average stem, 11% increase of average bark, 4% increase of average leaf and 7% increase of average TOTAL compared to the corresponding wildtype group. One of the construction group lines show 42% increase of average stem, 29% increase of average bark, 16% increase of average leaf and 23% increase of average TOTAL compared to the corresponding wildtype group. For the line were root dry weight were measured an increase in the shot-root ratio were observed.

Table 4.18 contains dry weight data for specified construction group and corresponding wild type group.

TABLE 4.18

| Construction Group Individual | Stem (g) | Bark (g) | Root (g) | Leaf (g) | TOTAL (g) | SLA (m2/kg) | Internode (cm) |
|---|---|---|---|---|---|---|---|
| TF0076rp2-3BB-1 | 5.8 | 2.7 | | 15.7 | 24.2 | 32.9 | 3.0 |
| TF0076rp2-3BB-2 | 6.9 | 3.1 | | 17.0 | 27.1 | 29.3 | 2.7 |
| TF0076rp2-3BB-3 | 8.0 | 3.5 | | 23.1 | 34.6 | 33.0 | 2.8 |
| TF0076rp2-4B-1 | 7.9 | 3.2 | 7.8 | 19.6 | 30.6 | 33.1 | 2.6 |
| TF0076rp2-4B-2 | 7.5 | 3.2 | 7.7 | 18.0 | 28.7 | 35.4 | 2.7 |
| TF0076rp2-4B-3 | 8.7 | 3.1 | 8.1 | 17.9 | 29.6 | 37.3 | 2.3 |
| TF0076rp2-5BA-1 | 3.9 | 1.5 | | 9.0 | 14.4 | 43.8 | 2.3 |
| TF0076rp2-5BA-2 | 6.6 | 2.7 | | 14.7 | 23.9 | 36.8 | 2.8 |
| TF0076rp2-5BA-3 | 7.6 | 2.8 | | 18.1 | 28.5 | 36.2 | 2.9 |
| TF0076rp2-5BB-1 | 5.4 | 2.2 | | 14.9 | 22.4 | 39.2 | 3.0 |
| TF0076rp2-5BB-2 | 5.5 | 2.6 | | 17.2 | 25.3 | 32.6 | 2.9 |
| TF0076rp2-5BB-3 | 5.4 | 2.1 | | 12.8 | 20.2 | 28.5 | 2.5 |
| T89-01 | 5.1 | 2.2 | | 13.1 | 20.4 | 39.9 | 2.7 |
| T89-02 | | | | 13.8 | 28.4 | 36.3 | 2.6 |
| T89-03 | 6.8 | 2.7 | | 17.1 | 26.6 | 37.8 | 2.6 |
| T89-04 | 6.9 | 2.7 | | 17.3 | 27.0 | 37.1 | 2.4 |
| T89-05 | 5.7 | 2.5 | | 16.6 | 24.9 | 31.8 | 2.6 |
| T89-06 | 6.1 | 2.7 | 8.2 | 18.4 | 27.1 | 31.7 | 2.7 |
| T89-07 | 5.8 | 2.5 | 9.2 | 15.9 | 24.2 | 31.7 | 2.6 |
| T89-08 | 3.9 | 2.1 | | 16.1 | 22.0 | 29.2 | 2.6 |
| T89-09 | 6.9 | 3.1 | | 20.7 | 30.7 | 30.3 | 2.5 |
| T89-10 | 5.5 | 2.5 | 10.3 | 16.6 | 24.6 | 36.9 | 2.6 |
| T89-11 | 6.9 | 3.0 | | 17.9 | 27.8 | 34.0 | 3.0 |
| T89-12 | 6.6 | 3.0 | | 15.2 | 24.8 | 31.9 | 2.8 |
| T89-13 | 5.9 | 2.2 | | 15.0 | 23.1 | 39.6 | 2.4 |
| T89-14 | 3.4 | 1.7 | | 13.2 | 18.3 | 32.7 | 2.5 |
| T89-15 | 4.6 | 2.0 | | 14.9 | 21.6 | 33.4 | 2.7 |
| T89-16 | 6.1 | 2.7 | | 17.7 | 26.4 | 31.8 | 2.6 |
| T89-17 | 4.4 | 2.1 | | 15.9 | 22.4 | 31.5 | 2.6 |
| T89-18 | 5.6 | 2.6 | | 15.0 | 23.3 | 32.7 | 2.7 |
| T89-19 | 6.2 | 2.7 | | 18.4 | 27.3 | 33.6 | 2.5 |
| T89-20 | 5.9 | 2.7 | 8.4 | 16.5 | 25.2 | 35.9 | 2.7 |
| T89-21 | 6.9 | 2.8 | | 17.8 | 27.5 | 39.0 | 2.6 |
| T89-22 | 5.4 | 2.2 | | 13.7 | 21.3 | 37.9 | 2.7 |
| T89-23 | 7.0 | 2.9 | | 17.7 | 27.5 | 33.3 | 2.9 |
| T89-24 | 6.6 | 2.7 | | 17.3 | 26.6 | 33.8 | 2.6 |
| T89-25 | 6.5 | 2.8 | 7.4 | 17.2 | 26.5 | 32.4 | 2.8 |
| T89-26 | 4.7 | 2.2 | 6.2 | 14.3 | 21.2 | 33.0 | 2.8 |
| T89-27 | 5.4 | 2.4 | | 16.1 | 23.9 | 31.3 | 2.5 |
| T89-28 | 3.6 | 1.5 | | 11.7 | 16.7 | 39.5 | 2.5 |
| T89-29 | 3.1 | 1.3 | | 9.9 | 14.4 | 36.3 | 3.0 |
| T89-30 | 5.0 | 2.1 | | 13.7 | 20.8 | 36.2 | 2.9 |

TABLE 4.18-continued

| Construction Group Individual | Stem (g) | Bark (g) | Root (g) | Leaf (g) | TOTAL (g) | SLA (m2/kg) | Inter-node (cm) |
|---|---|---|---|---|---|---|---|
| T89-31 | 7.0 | 2.9 | | 17.2 | 27.2 | 32.7 | 2.7 |
| T89-32 | 6.0 | 2.5 | | 16.7 | 25.2 | 32.3 | 2.5 |

Table 4.19 contains the dry weight ratios of specified construction group relative to corresponding wildtype group of average stem, average bark, average root, average leaf and average TOTAL. Table 4.19 also show ratios of average SLA and average internode length of specified construction group relative to corresponding wildtype group.

TABLE 4.19

| Construction Group | Average Stem | Average Bark | Average Root | Average Leaf | Average TOTAL | Average SLA | Average Internode |
|---|---|---|---|---|---|---|---|
| TF0076rp2 | 1.16 | 1.11 | 0.95 | 1.04 | 1.07 | 1.02 | 1.02 |

Table 4.20 contains the dry weight ratios for specified construction group relative to corresponding wildtype group for maximum stem, maximum bark, maximum root, maximum leaf and maximum TOTAL.

TABLE 4.20

| Construction Group | Maximum Stem | Maximum Bark | Maximum Root | Maximum Leaf | Maximum TOTAL |
|---|---|---|---|---|---|
| TF0076rp2 | 1.24 | 1.13 | 0.79 | 1.12 | 1.13 |

Table 4.21 contains dry weight ratios for specified construction group line relative to corresponding wildtype group of average stem, average bark, average root, average leaf and average TOTAL. Table 4.21 also show ratios of average SLA and average internode length of specified construction group line relative to corresponding wildtype group.

TABLE 4.21

| Construction Group Line | Line Average Stem | Line Average Bark | Line Average Root | Line Average Leaf | Line Average TOTAL | Line Average SLA | Line Average Internode |
|---|---|---|---|---|---|---|---|
| TF0076rp2-3BB | 1.22 | 1.27 | | 1.17 | 1.18 | 0.92 | 1.06 |
| TF0076rp2-4B | 1.42 | 1.29 | 0.95 | 1.16 | 1.23 | 1.03 | 0.96 |
| TF0076rp2-5BA | 1.06 | 0.94 | | 0.88 | 0.92 | 1.14 | 1.00 |
| TF0076rp2-5BB | 0.95 | 0.94 | | 0.94 | 0.94 | 0.98 | 1.06 |

Construction Group TF0097

This construct induce increase of biomass production. Dry weight measurements of the construction group show 74% increase of average stem, 82% increase of average bark, 28% increase of average leaf and 43% increase of average TOTAL compared to the corresponding wildtype group. One of the construction group lines show 136% increase of average stem, 141% increase of average bark, 63% increase of average leaf and 87% increase of average TOTAL compared to the corresponding wildtype group. For the line were root dry weight were measured an increase in the shot-root ratio were observed.

Table 4.22 contains dry weight data for specified construction group and corresponding wild type group.

TABLE 4.22

| Construction Group Individual | Stem (g) | Bark (g) | Root (g) | Leaf (g) | TOTAL (g) | SLA (m2/kg) | Inter-node (cm) |
|---|---|---|---|---|---|---|---|
| TF0097rp1-1A-1 | 12.2 | 5.5 | | 21.8 | 39.4 | 27.1 | 3.6 |
| TF0097rp1-1A-2 | 11.1 | 5.3 | | 18.3 | 34.7 | 28.6 | 3.8 |
| TF0097rp1-1A-3 | 8.3 | 4.1 | | 16.6 | 29.0 | 28.2 | 3.6 |
| TF0097rp1-2A-1 | 9.1 | 3.3 | | 21.9 | 34.3 | 35.5 | 2.6 |
| TF0097rp1-2A-2 | 9.4 | 3.8 | | 23.8 | 37.0 | 33.6 | 2.7 |
| TF0097rp1-2A-3 | 8.2 | 3.2 | | 21.0 | 32.4 | 30.6 | 2.7 |
| TF0097rp1-2B-1 | 5.7 | 3.8 | | 13.4 | 22.8 | 20.5 | 3.1 |
| TF0097rp1-2B-2 | 10.5 | 5.3 | | 21.6 | 37.4 | 25.2 | 3.8 |
| TF0097rp1-2B-3 | 14.2 | 6.1 | | 27.9 | 48.1 | 25.1 | 3.3 |
| TF0097rp1-3A-1 | 15.3 | 7.2 | | 28.9 | 51.4 | 28.5 | 3.6 |
| TF0097rp1-3A-2 | 10.1 | 4.0 | 6.3 | 20.7 | 34.7 | 33.2 | 3.7 |
| TF0097rp1-3A-3 | 14.6 | 6.6 | 11.3 | 28.2 | 49.4 | 27.0 | 3.6 |
| TF0097rp1-4A-1 | 4.3 | 2.2 | | 8.9 | 15.4 | 27.9 | 2.8 |
| TF0097rp1-4A-2 | 5.1 | 2.5 | | 13.1 | 20.6 | 28.7 | 3.5 |
| TF0097rp1-4A-3 | 9.4 | 4.3 | | 18.6 | 32.4 | 26.5 | 3.6 |
| T89-01 | 5.1 | 2.2 | | 13.1 | 20.4 | 39.9 | 2.7 |
| T89-02 | | | | 13.8 | 28.4 | 36.3 | 2.6 |
| T89-03 | 6.8 | 2.7 | | 17.1 | 26.6 | 37.8 | 2.6 |
| T89-04 | 6.9 | 2.7 | | 17.3 | 27.0 | 37.1 | 2.4 |
| T89-05 | 5.7 | 2.5 | | 16.6 | 24.9 | 31.8 | 2.6 |
| T89-06 | 6.1 | 2.7 | 8.2 | 18.4 | 27.1 | 31.7 | 2.7 |
| T89-07 | 5.8 | 2.5 | 9.2 | 15.9 | 24.2 | 31.7 | 2.6 |
| T89-08 | 3.9 | 2.1 | | 16.1 | 22.0 | 29.2 | 2.6 |
| T89-09 | 6.9 | 3.1 | | 20.7 | 30.7 | 30.3 | 2.5 |
| T89-10 | 5.5 | 2.5 | 10.3 | 16.6 | 24.6 | 36.9 | 2.6 |
| T89-11 | 6.9 | 3.0 | | 17.9 | 27.8 | 34.0 | 3.0 |
| T89-12 | 6.6 | 3.0 | | 15.2 | 24.8 | 31.9 | 2.8 |
| T89-13 | 5.9 | 2.2 | | 15.0 | 23.1 | 39.6 | 2.4 |
| T89-14 | 3.4 | 1.7 | | 13.2 | 18.3 | 32.7 | 2.5 |
| T89-15 | 4.6 | 2.0 | | 14.9 | 21.6 | 33.4 | 2.7 |
| T89-16 | 6.1 | 2.7 | | 17.7 | 26.4 | 31.8 | 2.6 |
| T89-17 | 4.4 | 2.1 | | 15.9 | 22.4 | 31.5 | 2.6 |
| T89-18 | 5.6 | 2.6 | | 15.0 | 23.3 | 32.7 | 2.7 |
| T89-19 | 6.2 | 2.7 | | 18.4 | 27.3 | 33.6 | 2.5 |
| T89-20 | 5.9 | 2.7 | 8.4 | 16.5 | 25.2 | 35.9 | 2.7 |
| T89-21 | 6.9 | 2.8 | | 17.8 | 27.5 | 39.0 | 2.6 |
| T89-22 | 5.4 | 2.2 | | 13.7 | 21.3 | 37.9 | 2.7 |
| T89-23 | 7.0 | 2.9 | | 17.7 | 27.5 | 33.3 | 2.9 |
| T89-24 | 6.6 | 2.7 | | 17.3 | 26.6 | 33.8 | 2.6 |
| T89-25 | 6.5 | 2.8 | 7.4 | 17.2 | 26.5 | 32.4 | 2.8 |
| T89-26 | 4.7 | 2.2 | 6.2 | 14.3 | 21.2 | 33.0 | 2.8 |
| T89-27 | 5.4 | 2.4 | | 16.1 | 23.9 | 31.3 | 2.5 |
| T89-28 | 3.6 | 1.5 | | 11.7 | 16.7 | 39.5 | 2.5 |
| T89-29 | 3.1 | 1.3 | | 9.9 | 14.4 | 36.3 | 3.0 |
| T89-30 | 5.0 | 2.1 | | 13.7 | 20.8 | 36.2 | 2.9 |
| T89-31 | 7.0 | 2.9 | | 17.2 | 27.2 | 32.7 | 2.7 |
| T89-32 | 6.0 | 2.5 | | 16.7 | 25.2 | 32.3 | 2.5 |

Table 4.23 contains the dry weight ratios of specified construction group relative to corresponding wildtype group of average stem, average bark, average root, average leaf and average TOTAL. Table 4.23 also show ratios of average SLA and average internode length of specified construction group relative to corresponding wildtype group.

TABLE 4.23

| Construction Group | Average Stem | Average Bark | Average Root | Average Leaf | Average TOTAL | Average SLA | Average Internode |
|---|---|---|---|---|---|---|---|
| TF0097rp1 | 1.74 | 1.82 | 1.07 | 1.28 | 1.43 | 0.83 | 1.25 |

Table 4.24 contains the dry weight ratios for specified construction group relative to corresponding wildtype group for maximum stem, maximum bark, maximum root, maximum leaf and maximum TOTAL.

TABLE 4.24

| Construction Group | Maximum Stem | Maximum Bark | Maximum Root | Maximum Leaf | Maximum TOTAL |
|---|---|---|---|---|---|
| TF0097rp1 | 2.19 | 2.31 | 1.10 | 1.40 | 1.68 |

Table 4.25 contains dry weight ratios for specified construction group line relative to corresponding wildtype group of average stem, average bark, average root, average leaf and average TOTAL. Table 4.25 also show ratios of average SLA and average internode length of specified construction group line relative to corresponding wildtype group.

TABLE 4.25

| Construction Group Line | Line Average Stem | Line Average Bark | Line Average Root | Line Average Leaf | Line Average TOTAL | Line Average SLA | Line Average Internode |
|---|---|---|---|---|---|---|---|
| TF0097rp1-1A | 1.86 | 2.02 |  | 1.19 | 1.42 | 0.82 | 1.37 |
| TF0097rp1-2A | 1.58 | 1.41 |  | 1.40 | 1.43 | 0.97 | 1.00 |
| TF0097rp1-2B | 1.79 | 2.06 |  | 1.32 | 1.49 | 0.69 | 1.29 |
| TF0097rp1-3A | 2.36 | 2.41 | 1.07 | 1.63 | 1.87 | 0.86 | 1.36 |
| TF0097rp1-4A | 1.11 | 1.22 |  | 0.85 | 0.94 | 0.81 | 1.25 |

Construction Group TF0109

This construct induce increase of biomass production. Dry weight measurements of the construction group show 57% increase of average stem, 56% increase of average bark, 34% increase of average leaf and 40% increase of average TOTAL compared to the corresponding wildtype group. One of the construction group lines show 82% increase of average stem, 62% increase of average bark, 10% increase of average leaf and 31% increase of average TOTAL compared to the corresponding wildtype group. For the line were root dry weight were measured an increase in the shot-root ratio were observed.

Table 4.26 contains dry weight data for specified construction group and corresponding wild type group.

TABLE 4.26

| Construction Group Individual | Stem (g) | Bark (g) | Root (g) | Leaf (g) | TOTAL (g) | SLA (m2/kg) | Internode (cm) |
|---|---|---|---|---|---|---|---|
| TF0109rp1-2A-1 | 10.5 | 4.2 |  | 25.5 | 40.2 | 29.0 | 2.8 |
| TF0109rp1-2A-2 | 7.5 | 3.2 |  | 19.0 | 29.7 | 31.9 | 3.0 |
| TF0109rp1-2A-3 | 7.7 | 3.3 |  | 21.9 | 32.9 | 30.4 | 2.7 |
| TF0109rp1-2B-1 | 8.6 | 4.1 | 6.2 | 16.3 | 29.1 | 29.9 | 4.0 |
| TF0109rp1-2B-2 | 11.4 | 4.3 | 6.5 | 19.8 | 35.5 | 32.6 | 3.9 |
| TF0109rp1-2B-3 | 10.9 | 3.5 | 7.5 | 16.3 | 30.7 | 36.2 | 3.1 |
| TF0109rp1-3B-1 | 9.0 | 3.9 |  | 21.4 | 34.3 | 38.5 | 2.8 |
| TF0109rp1-3B-2 | 8.1 | 3.6 |  | 19.8 | 31.5 | 34.1 | 2.8 |
| TF0109rp1-3B-3 | 8.6 | 3.6 |  | 22.0 | 34.1 | 31.6 | 2.9 |
| TF0109rp1-4A-1 | 8.0 | 3.9 |  | 24.1 | 36.0 | 27.5 | 3.3 |
| TF0109rp1-4A-2 | 8.3 | 4.0 |  | 24.6 | 37.0 | 33.3 | 3.1 |
| TF0109rp1-4A-3 | 7.8 | 4.3 |  | 24.2 | 36.3 | 27.3 | 3.1 |
| T89-01 | 5.1 | 2.2 |  | 13.1 | 20.4 | 39.9 | 2.7 |
| T89-02 |  |  |  | 13.8 | 28.4 | 36.3 | 2.6 |
| T89-03 | 6.8 | 2.7 |  | 17.1 | 26.6 | 37.8 | 2.6 |
| T89-04 | 6.9 | 2.7 |  | 17.3 | 27.0 | 37.1 | 2.4 |
| T89-05 | 5.7 | 2.5 |  | 16.6 | 24.9 | 31.8 | 2.6 |
| T89-06 | 6.1 | 2.7 | 8.2 | 18.4 | 27.1 | 31.7 | 2.7 |
| T89-07 | 5.8 | 2.5 | 9.2 | 15.9 | 24.2 | 31.7 | 2.6 |
| T89-08 | 3.9 | 2.1 |  | 16.1 | 22.0 | 29.2 | 2.6 |
| T89-09 | 6.9 | 3.1 |  | 20.7 | 30.7 | 30.3 | 2.5 |
| T89-10 | 5.5 | 2.5 | 10.3 | 16.6 | 24.6 | 36.9 | 2.6 |
| T89-11 | 6.9 | 3.0 |  | 17.9 | 27.8 | 34.0 | 3.0 |
| T89-12 | 6.6 | 3.0 |  | 15.2 | 24.8 | 31.9 | 2.8 |
| T89-13 | 5.9 | 2.2 |  | 15.0 | 23.1 | 39.6 | 2.4 |
| T89-14 | 3.4 | 1.7 |  | 13.2 | 18.3 | 32.7 | 2.5 |

TABLE 4.26-continued

| Construction Group Individual | Stem (g) | Bark (g) | Root (g) | Leaf (g) | TOTAL (g) | SLA (m2/kg) | Internode (cm) |
|---|---|---|---|---|---|---|---|
| T89-15 | 4.6 | 2.0 |  | 14.9 | 21.6 | 33.4 | 2.7 |
| T89-16 | 6.1 | 2.7 |  | 17.7 | 26.4 | 31.8 | 2.6 |
| T89-17 | 4.4 | 2.1 |  | 15.9 | 22.4 | 31.5 | 2.6 |
| T89-18 | 5.6 | 2.6 |  | 15.0 | 23.3 | 32.7 | 2.7 |
| T89-19 | 6.2 | 2.7 |  | 18.4 | 27.3 | 33.6 | 2.5 |
| T89-20 | 5.9 | 2.7 | 8.4 | 16.5 | 25.2 | 35.9 | 2.7 |
| T89-21 | 6.9 | 2.8 |  | 17.8 | 27.5 | 39.0 | 2.6 |
| T89-22 | 5.4 | 2.2 |  | 13.7 | 21.3 | 37.9 | 2.7 |
| T89-23 | 7.0 | 2.9 |  | 17.7 | 27.5 | 33.3 | 2.9 |
| T89-24 | 6.6 | 2.7 |  | 17.3 | 26.6 | 33.8 | 2.6 |
| T89-25 | 6.5 | 2.8 | 7.4 | 17.2 | 26.5 | 32.4 | 2.8 |
| T89-26 | 4.7 | 2.2 | 6.2 | 14.3 | 21.2 | 33.0 | 2.8 |
| T89-27 | 5.4 | 2.4 |  | 16.1 | 23.9 | 31.3 | 2.5 |
| T89-28 | 3.6 | 1.5 |  | 11.7 | 16.7 | 39.5 | 2.5 |
| T89-29 | 3.1 | 1.3 |  | 9.9 | 14.4 | 36.3 | 3.0 |
| T89-30 | 5.0 | 2.1 |  | 13.7 | 20.8 | 36.2 | 2.9 |
| T89-31 | 7.0 | 2.9 |  | 17.2 | 27.2 | 32.7 | 2.7 |
| T89-32 | 6.0 | 2.5 |  | 16.7 | 25.2 | 32.3 | 2.5 |

Table 4.27 contains the dry weight ratios of specified construction group relative to corresponding wildtype group of average stem, average bark, average root, average leaf and average TOTAL. Table 4.27 also show ratios of average SLA and average internode length of specified construction group relative to corresponding wildtype group.

TABLE 4.27

| Construction Group | Average Stem | Average Bark | Average Root | Average Leaf | Average TOTAL | Average SLA | Average Internode |
|---|---|---|---|---|---|---|---|
| TF0109rp1 | 1.57 | 1.56 | 0.81 | 1.34 | 1.40 | 0.93 | 1.18 |

Table 4.28 contains the dry weight ratios for specified construction group relative to corresponding wildtype group for maximum stem, maximum bark, maximum root, maximum leaf and maximum TOTAL.

TABLE 4.28

| Construction Group | Maximum Stem | Maximum Bark | Maximum Root | Maximum Leaf | Maximum TOTAL |
|---|---|---|---|---|---|
| TF0109rp1 | 1.63 | 1.39 | 0.74 | 1.23 | 1.31 |

Table 4.29 contains dry weight ratios for specified construction group line relative to corresponding wildtype group of average stem, average bark, average root, average leaf and average TOTAL. Table 4.29 also show ratios of average SLA and average internode length of specified construction group line relative to corresponding wildtype group.

TABLE 4.29

| Construction Group Line | Line Average Stem | Line Average Bark | Line Average Root | Line Average Leaf | Line Average TOTAL | Line Average SLA | Line Average Internode |
|---|---|---|---|---|---|---|---|
| TF0109rp1-2A | 1.51 | 1.45 |  | 1.39 | 1.41 | 0.89 | 1.06 |
| TF0109rp1-2B | 1.82 | 1.62 | 0.81 | 1.10 | 1.31 | 0.96 | 1.39 |
| TF0109rp1-3B | 1.51 | 1.51 |  | 1.32 | 1.38 | 1.01 | 1.07 |
| TF0109rp1-4A | 1.42 | 1.66 |  | 1.53 | 1.50 | 0.86 | 1.19 |

Construction Group TFSTT019

This construct induce increase of biomass production. Dry weight measurements of one of the construction group lines show 19% increase of average stem, 12% increase of average bark, 10% increase of average leaf and 11% increase of average TOTAL compared to the corresponding wildtype group. This gene also gives an increased SLA in many lines, which in many cases are coupled to efficient growth.

Table 4.30 contains dry weight data for specified construction group and corresponding wild type group.

TABLE 4.30

| Construction Group Individual | Stem (g) | Bark (g) | Root (g) | Leaf (g) | TOTAL (g) | SLA (m2/kg) | Internode (cm) |
|---|---|---|---|---|---|---|---|
| TFSTT019rp1-2A-1 | 5.1 | 2.1 |  | 15.0 | 22.2 | 39.0 | 2.5 |
| TFSTT019rp1-2A-2 |  |  |  | 18.7 | 18.7 | 35.4 | 2.7 |
| TFSTT019rp1-2A-3 | 5.8 | 2.5 |  | 16.9 | 25.1 | 40.0 | 2.6 |
| TFSTT019rp1-3A-1 | 6.3 | 2.6 |  | 18.6 | 27.5 | 41.1 | 2.6 |
| TFSTT019rp1-3A-2 | 2.2 | 1.2 |  | 11.2 | 14.5 | 30.9 | 2.1 |
| TFSTT019rp1-3A-3 | 9.0 | 3.4 |  | 22.9 | 35.3 | 33.1 | 2.7 |
| TFSTT019rp1-4BA-1 | 5.9 | 2.4 |  | 15.7 | 24.0 | 35.5 | 2.6 |
| TFSTT019rp1-4BA-2 | 7.6 | 3.1 |  | 19.3 | 29.9 | 35.8 | 2.6 |
| TFSTT019rp1-4BA-3 |  |  |  |  |  |  |  |
| TFSTT019rp1-4BB-1 | 6.0 | 2.5 |  | 15.9 | 24.4 | 40.4 | 2.6 |
| TFSTT019rp1-4BB-2 | 5.7 | 2.4 |  | 17.6 | 25.6 | 40.0 | 2.2 |
| TFSTT019rp1-4BB-3 | 6.0 | 2.3 |  | 16.4 | 24.7 | 39.9 | 2.5 |
| T89-01 | 5.1 | 2.2 |  | 13.1 | 20.4 | 39.9 | 2.7 |
| T89-02 |  |  |  | 13.8 | 28.4 | 36.3 | 2.6 |
| T89-03 | 6.8 | 2.7 |  | 17.1 | 26.6 | 37.8 | 2.6 |
| T89-04 | 6.9 | 2.7 |  | 17.3 | 27.0 | 37.1 | 2.4 |
| T89-05 | 5.7 | 2.5 |  | 16.6 | 24.9 | 31.8 | 2.6 |
| T89-06 | 6.1 | 2.7 | 8.2 | 18.4 | 27.1 | 31.7 | 2.7 |
| T89-07 | 5.8 | 2.5 | 9.2 | 15.9 | 24.2 | 31.7 | 2.6 |
| T89-08 | 3.9 | 2.1 |  | 16.1 | 22.0 | 29.2 | 2.6 |
| T89-09 | 6.9 | 3.1 |  | 20.7 | 30.7 | 30.3 | 2.5 |
| T89-10 | 5.5 | 2.5 | 10.3 | 16.6 | 24.6 | 36.9 | 2.6 |
| T89-11 | 6.9 | 3.0 |  | 17.9 | 27.8 | 34.0 | 3.0 |
| T89-12 | 6.6 | 3.0 |  | 15.2 | 24.8 | 31.9 | 2.8 |
| T89-13 | 5.9 | 2.2 |  | 15.0 | 23.1 | 39.6 | 2.4 |
| T89-14 | 3.4 | 1.7 |  | 13.2 | 18.3 | 32.7 | 2.5 |
| T89-15 | 4.6 | 2.0 |  | 14.9 | 21.6 | 33.4 | 2.7 |
| T89-16 | 6.1 | 2.7 |  | 17.7 | 26.4 | 31.8 | 2.6 |
| T89-17 | 4.4 | 2.1 |  | 15.9 | 22.4 | 31.5 | 2.6 |
| T89-18 | 5.6 | 2.6 |  | 15.0 | 23.3 | 32.7 | 2.7 |
| T89-19 | 6.2 | 2.7 |  | 18.4 | 27.3 | 33.6 | 2.5 |
| T89-20 | 5.9 | 2.7 | 8.4 | 16.5 | 25.2 | 35.9 | 2.7 |
| T89-21 | 6.9 | 2.8 |  | 17.8 | 27.5 | 39.0 | 2.6 |
| T89-22 | 5.4 | 2.2 |  | 13.7 | 21.3 | 37.9 | 2.7 |
| T89-23 | 7.0 | 2.9 |  | 17.7 | 27.5 | 33.3 | 2.9 |
| T89-24 | 6.6 | 2.7 |  | 17.3 | 26.6 | 33.8 | 2.6 |
| T89-25 | 6.5 | 2.8 | 7.4 | 17.2 | 26.5 | 32.4 | 2.8 |
| T89-26 | 4.7 | 2.2 | 6.2 | 14.3 | 21.2 | 33.0 | 2.8 |
| T89-27 | 5.4 | 2.4 |  | 16.1 | 23.9 | 31.3 | 2.5 |
| T89-28 | 3.6 | 1.5 |  | 11.7 | 16.7 | 39.5 | 2.5 |
| T89-29 | 3.1 | 1.3 |  | 9.9 | 14.4 | 36.3 | 3.0 |
| T89-30 | 5.0 | 2.1 |  | 13.7 | 20.8 | 36.2 | 2.9 |
| T89-31 | 7.0 | 2.9 |  | 17.2 | 27.2 | 32.7 | 2.7 |
| T89-32 | 6.0 | 2.5 |  | 16.7 | 25.2 | 32.3 | 2.5 |

Table 4.31 contains the dry weight ratios of specified construction group relative to corresponding wildtype group of average stem, average bark, average root, average leaf and average TOTAL. Table 4.31 also show ratios of average SLA and average internode length of specified construction group relative to corresponding wildtype group.

TABLE 4.31

| Construction Group | Average Stem | Average Bark | Average Root | Average Leaf | Average TOTAL | Average SLA | Average Internode |
|---|---|---|---|---|---|---|---|
| TFSTT019rp1 | 1.05 | 1.00 | | 1.08 | 1.02 | 1.09 | 0.95 |

Table 4.32 contains the dry weight ratios for specified construction group relative to corresponding wildtype group for maximum stem, maximum bark, maximum root, maximum leaf and maximum TOTAL.

TABLE 4.32

| Construction Group | Maximum Stem | Maximum Bark | Maximum Root | Maximum Leaf | Maximum TOTAL |
|---|---|---|---|---|---|
| TFSTT019rp1 | 1.28 | 1.10 | | 1.11 | 1.15 |

Table 4.33 contains dry weight ratios for specified construction group line relative to corresponding wildtype group of average stem, average bark, average root, average leaf and average TOTAL. Table 4.33 also show ratios of average SLA and average internode length of specified construction group line relative to corresponding wildtype group.

TABLE 4.33

| Construction Group Line | Line Average Stem | Line Average Bark | Line Average Root | Line Average Leaf | Line Average TOTAL | Line Average SLA | Line Average Internode |
|---|---|---|---|---|---|---|---|
| TFSTT019rp1-2A | 0.97 | 0.93 | | 1.06 | 0.91 | 1.11 | 0.98 |
| TFSTT019rp1-3A | 1.03 | 0.98 | | 1.10 | 1.06 | 1.02 | 0.93 |
| TFSTT019rp1-4BA | 1.19 | 1.12 | | 1.10 | 1.11 | 1.04 | 0.97 |
| TFSTT019rp1-4BB | 1.04 | 0.98 | | 1.05 | 1.03 | 1.17 | 0.91 |

Construction Group TFSTT051

This construct induce increase of biomass production. Dry weight measurements of one of the construction group lines show 22% increase of average stem, 30% increase of average bark, 29% increase of average leaf and 26% increase of average TOTAL compared to the corresponding wildtype group.

Table 4.34 contains dry weight data for specified construction group and corresponding wild type group.

TABLE 4.34

| Construction Group Individual | Stem (g) | Bark (g) | Root (g) | Leaf (g) | TOTAL (g) | SLA (m2/kg) | Internode (cm) |
|---|---|---|---|---|---|---|---|
| TFSTT051rp1-3B-1 | 4.6 | 2.4 | | 12.4 | 19.4 | 24.6 | 2.1 |
| TFSTT051rp1-3B-2 | 4.0 | 2.3 | | 11.4 | 17.6 | 24.1 | 2.0 |
| TFSTT051rp1-3B-3 | 4.6 | 2.6 | | 13.1 | 20.3 | 22.5 | 2.0 |
| TFSTT051rp1-4A-1 | 6.7 | 2.9 | | 20.1 | 29.7 | 30.5 | 2.9 |
| TFSTT051rp1-4A-2 | 6.1 | 2.9 | | 18.5 | 27.4 | 33.3 | 2.8 |
| TFSTT051rp1-4A-3 | 8.0 | 3.7 | | 22.9 | 34.6 | 31.8 | 2.5 |
| T89-01 | 5.1 | 2.2 | | 13.1 | 20.4 | 39.9 | 2.7 |
| T89-02 | | | | 13.8 | 28.4 | 36.3 | 2.6 |
| T89-03 | 6.8 | 2.7 | | 17.1 | 26.6 | 37.8 | 2.6 |
| T89-04 | 6.9 | 2.7 | | 17.3 | 27.0 | 37.1 | 2.4 |
| T89-05 | 5.7 | 2.5 | | 16.6 | 24.9 | 31.8 | 2.6 |
| T89-06 | 6.1 | 2.7 | 8.2 | 18.4 | 27.1 | 31.7 | 2.7 |
| T89-07 | 5.8 | 2.5 | 9.2 | 15.9 | 24.2 | 31.7 | 2.6 |
| T89-08 | 3.9 | 2.1 | | 16.1 | 22.0 | 29.2 | 2.6 |
| T89-09 | 6.9 | 3.1 | | 20.7 | 30.7 | 30.3 | 2.5 |
| T89-10 | 5.5 | 2.5 | 10.3 | 16.6 | 24.6 | 36.9 | 2.6 |
| T89-11 | 6.9 | 3.0 | | 17.9 | 27.8 | 34.0 | 3.0 |
| T89-12 | 6.6 | 3.0 | | 15.2 | 24.8 | 31.9 | 2.8 |

TABLE 4.34-continued

| Construction Group Individual | Stem (g) | Bark (g) | Root (g) | Leaf (g) | TOTAL (g) | SLA (m2/kg) | Internode (cm) |
|---|---|---|---|---|---|---|---|
| T89-13 | 5.9 | 2.2 |  | 15.0 | 23.1 | 39.6 | 2.4 |
| T89-14 | 3.4 | 1.7 |  | 13.2 | 18.3 | 32.7 | 2.5 |
| T89-15 | 4.6 | 2.0 |  | 14.9 | 21.6 | 33.4 | 2.7 |
| T89-16 | 6.1 | 2.7 |  | 17.7 | 26.4 | 31.8 | 2.6 |
| T89-17 | 4.4 | 2.1 |  | 15.9 | 22.4 | 31.5 | 2.6 |
| T89-18 | 5.6 | 2.6 |  | 15.0 | 23.3 | 32.7 | 2.7 |
| T89-19 | 6.2 | 2.7 |  | 18.4 | 27.3 | 33.6 | 2.5 |
| T89-20 | 5.9 | 2.7 | 8.4 | 16.5 | 25.2 | 35.9 | 2.7 |
| T89-21 | 6.9 | 2.8 |  | 17.8 | 27.5 | 39.0 | 2.6 |
| T89-22 | 5.4 | 2.2 |  | 13.7 | 21.3 | 37.9 | 2.7 |
| T89-23 | 7.0 | 2.9 |  | 17.7 | 27.5 | 33.3 | 2.9 |
| T89-24 | 6.6 | 2.7 |  | 17.3 | 26.6 | 33.8 | 2.6 |
| T89-25 | 6.5 | 2.8 | 7.4 | 17.2 | 26.5 | 32.4 | 2.8 |
| T89-26 | 4.7 | 2.2 | 6.2 | 14.3 | 21.2 | 33.0 | 2.8 |
| T89-27 | 5.4 | 2.4 |  | 16.1 | 23.9 | 31.3 | 2.5 |
| T89-28 | 3.6 | 1.5 |  | 11.7 | 16.7 | 39.5 | 2.5 |
| T89-29 | 3.1 | 1.3 |  | 9.9 | 14.4 | 36.3 | 3.0 |
| T89-30 | 5.0 | 2.1 |  | 13.7 | 20.8 | 36.2 | 2.9 |
| T89-31 | 7.0 | 2.9 |  | 17.2 | 27.2 | 32.7 | 2.7 |
| T89-32 | 6.0 | 2.5 |  | 16.7 | 25.2 | 32.3 | 2.5 |

Table 4.35 contains the dry weight ratios of specified construction group relative to corresponding wildtype group of average stem, average bark, average root, average leaf and average TOTAL. Table 4.35 also show ratios of average SLA and average internode length of specified construction group relative to corresponding wildtype group.

TABLE 4.35

| Construction Group | Average Stem | Average Bark | Average Root | Average Leaf | Average TOTAL | Average SLA | Average Internode |
|---|---|---|---|---|---|---|---|
| TFSTT051rp1 | 1.00 | 1.15 |  | 1.03 | 1.03 | 0.81 | 0.90 |

Table 4.36 contains the dry weight ratios for specified construction group relative to corresponding wildtype group for maximum stem, maximum bark, maximum root, maximum leaf and maximum TOTAL.

TABLE 4.36

| Construction Group | Maximum Stem | Maximum Bark | Maximum Root | Maximum Leaf | Maximum TOTAL |
|---|---|---|---|---|---|
| TFSTT051rp1 | 1.15 | 1.20 |  | 1.11 | 1.13 |

Table 4.37 contains dry weight ratios for specified construction group line relative to corresponding wildtype group of average stem, average bark, average root, average leaf and average TOTAL. Table 4.37 also show ratios of average SLA and average internode length of specified construction group line relative to corresponding wildtype group.

TABLE 4.37

| Construction Group Line | Line Average Stem | Line Average Bark | Line Average Root | Line Average Leaf | Line Average TOTAL | Line Average SLA | Line Average Internode |
|---|---|---|---|---|---|---|---|
| TFSTT051rp1-3B | 0.77 | 1.00 | | 0.77 | 0.79 | 0.69 | 0.76 |
| TFSTT051rp1-4A | 1.22 | 1.30 | | 1.29 | 1.26 | 0.93 | 1.04 |

Example 5

Density Measurement

A 5 cm long steam section (the segment between 36 cm and 41 cm from the soil) of each plant was stored in a freezer (−20° C.) after harvest. Samples subjected to density measurement were first defrosted and debarked and then the central core was removed. The weight (w) was measured using a balance and the volume (v) was determent using the principle of Archimedes, the wood samples were pushed (using a needle) into a baker (placed on a balance) with water and the increase in weight is equivalent to weight of the water pushed aside by the wood sample and since the density of water is (1 g/cm$^3$) it is equivalent to the volume of the wood samples. The samples were then dried in oven for >48 h at 45° C. The dry weight (dw) were measured and the density (d) was calculated according to (1).

$$d = dw/v \quad (1)$$

Samples for each construction are compared with wild type samples (T89) from the same cultivation round. Each construction must fulfil two criteria's to be seen as a construction group with altered density.

1. Significant differences in average density according to a t-test (p-value<0.01). The t-test is two sided and assuming unequal variance.

2. Two or more individuals outside (on the same side) a 95% confidence interval around the wild type population.

Summary table density

| | Average KR | Average T89 | Average(KR)/ Average(T89) | T-Test 99% | Samples Above 95% conf int | Signifcant change |
|---|---|---|---|---|---|---|
| TF0002Rp2 | 0.335 | 0.284 | 1.179 | Sign | 4 | YES |
| TF0003 | 0.291 | 0.255 | 1.140 | Sign | 2 | YES |
| TF0011 | 0.314 | 0.284 | 1.106 | Sign | 2 | YES |
| TF0013 | 0.252 | 0.260 | 0.970 | Not sign | 0 | NO |
| TF0045 | 0.306 | 0.274 | 1.117 | Sign | 2 | YES |
| TF0052 | 0.302 | 0.275 | 1.099 | Not sign | 2 | NO |
| TF0065 | 0.273 | 0.260 | 1.051 | Not sign | 1 | NO |
| TF0076 | 0.267 | 0.260 | 1.027 | Not sign | 0 | NO |
| TF0076Rp2 | 0.285 | 0.284 | 1.002 | Not sign | 1 | NO |
| TF0096 | 0.307 | 0.274 | 1.121 | Not sign | 1 | NO |
| TF0097Rp1 | 0.314 | 0.284 | 1.107 | Sign | 7 | YES |
| TF0104 | 0.284 | 0.274 | 1.036 | Not sign | 0 | NO |
| TF0109Rp1 | 0.286 | 0.284 | 1.007 | Not sign | 3 | NO* |
| TF0116 | 0.277 | 0.275 | 1.008 | Not sign | 0 | NO |
| TF0132.2nd | 0.294 | 0.274 | 1.071 | Not sign | 1 | NO |
| TF0132rp1 | 0.272 | 0.255 | 1.068 | Sign | 4 | YES |
| TF0146 | 0.318 | 0.274 | 1.161 | Sign | 3 | YES |
| TF0173 | 0.256 | 0.254 | 1.008 | Not sign | 0 | NO |
| TF0247 | 0.294 | 0.274 | 1.073 | Not sign | 1 | NO |
| TF0405 | 0.287 | 0.274 | 1.045 | Not sign | 0 | NO |
| TFSTT004 | 0.284 | 0.275 | 1.033 | Not sign | 0 | NO |
| TFSTT013 | 0.319 | 0.284 | 1.123 | Sign | 2 | YES |
| TFSTT016 | 0.270 | 0.275 | 0.980 | Not sign | 0 | NO |
| TFSTT019 | 0.257 | 0.260 | 0.989 | Not sign | 0 | NO |
| TFSTT035 | 0.249 | 0.260 | 0.957 | Not sign | 0 | NO |
| TFSTT036 | 0.306 | 0.274 | 1.117 | Sign | 2 | YES |
| TFSTT038 | 0.295 | 0.275 | 1.073 | Not sign | 0 | NO |
| TFSTT045 | 0.274 | 0.274 | 1.000 | Not sign | 1 | NO |
| TFSTT051 | 0.278 | 0.275 | 1.013 | Not sign | 0 | NO |

*The construction group TF0109 (Replant 1) does not fulfil the criteria for altered density, but the construction group lines; TF0109Rp1-2B (+18%) and TF0109Rp1-4A (−16%) do.

Explanation of Construction Group Summary Tables Density.

All densities are given in g/cm$^3$

| | TFXXX |
|---|---|
| Average TFXXX: | Construction group average |
| Max TFXXX: | Construction group max |
| Min TFXXX: | Construction group min |
| Number of TFXXX: | Number of sample for the group construction |
| Number of TFXXX lines: | Number of lines (only shown when number of lines differs form number of samples) |
| Average T89: | Wild type average |
| Max T89: | Wild type max |
| Min T89: | Wild type min |
| Number of T89: | Number of wild type samples |
| Confidence interval (95%) | (Wild type mean) +/− ($t_{table}$(2-tailed 95%)* Standard deviation for wild type samples) |
| T-test | T-test |

| TFXXX | |
|---|---|
| Number of TFXXX > CI upper limit | Number TFXXX samples outside the confidence interval's upper limit |
| Number of TFXXX < CI lower limit | Number TFXXX samples outside the confidence interval's lower limit |
| Average (TFXXX)/ Average(T89) | Construction group average/ Wild type average |
| Max(TFXXX)/ Max(T89) | Construction group max/ Wild type max |

The following construction groups have not generated any data TF0089, TF0097, TF0109, TF0132 and TFSTT047.

Construction Group TF0002 (Replant 2)

| Raw data TF002Rp2 density | |
|---|---|
| TF0002Rp2 Individual name: | Density (g/cm$^3$) |
| TF0002Rp2-1B-1 | 0.317 |
| TF0002Rp2-1B-2 | 0.360 |
| TF0002Rp2-1B-3 | 0.323 |
| TF0002Rp2-2A-1 | 0.322 |
| TF0002Rp2-2A-2 | 0.323 |
| TF0002Rp2-2A-3 | 0.366 |
| TF0002Rp2-3B-1 | 0.330 |
| TF0002Rp2-3B-2 | 0.321 |
| TF0002Rp2-3B-3 | 0.352 |

| Summary density TF002Rp2 TF0002Rp2 | |
|---|---|
| Average TF0002Rp2: | 0.335 |
| Max TF0002Rp2: | 0.366 |
| Min TF0002Rp2: | 0.317 |
| Number of TF0002Rp2: | 9 |
| Number of TF0002Rp2 lines: | 3 |
| Average T89: | 0.284 |
| Max T89: | 0.338 |
| Min T89: | 0.252 |
| Number of T89: | 32 |
| Confidence interval (95%) | 0.284 +/- 0.041 |
| T-test | 4.066E-08 |
| Number of TF0002Rp2 > 0.325 | 4 |
| Number of TF0002Rp2 < 0.243 | 0 |
| Average (TF0002Rp2)/Average(T89) | 1.179 |
| Max(TF0002Rp2)/Max(T89) | 1.083 |

TF0002Rp2 has significant higher density (according to criteria 1 and 2) (+18% in average) than corresponding T89 group. The density change (compared to T89) for the 3 construction group lines of TF0002Rp2 (3 individuals of each line), TF0002Rp2-1B (+17% in average), TF0002Rp2-2A (+19% in average) and TF0002Rp2-3B (+18 in average). Line TF0002Rp2-3B itself fulfils the criteria 1 and 2.

Construction Group TF0003

| Raw data TF0003 density | |
|---|---|
| TF0003 Individual name: | Density (g/cm$^3$) |
| TF0003-1A | 0.318 |
| TF0003-1B | 0.323 |
| TF0003-2A | 0.242 |
| TF0003-3A | |
| TF0003-3B | |

| Raw data TF0003 density | |
|---|---|
| TF0003 Individual name: | Density (g/cm$^3$) |
| TF0003-4A | |
| TF0003-4B | 0.282 |

| Summary density TF0003 TF0003 | |
|---|---|
| Average TF0003: | 0.291 |
| Max TF0003: | 0.323 |
| Min TF0003: | 0.242 |
| Number of TF0003: | 4 |
| Number of TF0003 lines: | |
| Average T89: | 0.255 |
| Max T89: | 0.313 |
| Min T89: | 0.221 |
| Number of T89: | 39 |
| Confidence interval (95%) | 0.255 +/- 0.045 |
| T-test | 6.712E-03 |
| Number of TF0003 > 0.301 | 2 |
| Number of TF0003 < 0.21 | 0 |
| Average (TF0003)/Average(T89) | 1.140 |
| Max(TF0003)/Max(T89) | 1.032 |

Construction group TF0003 has significant higher density (according to criteria 1 and 2) (+14% in average) than corresponding T89 group.

Construction Group TF0011

| Raw data TF0011 density | |
|---|---|
| TF0011 Individual name: | Density (g/cm$^3$) |
| TF0011-1A-1 | 0.308 |
| TF0011-1A-2 | 0.360 |
| TF0011-1B | 0.264 |
| TF0011-2A-1 | 0.337 |
| TF0011-2A-2 | 0.298 |
| TF0011-3A-1 | 0.326 |
| TF0011-3A-2 | 0.350 |
| TF0011-3B-1 | 0.333 |
| TF0011-3B-2 | 0.303 |
| TF0011-4A | 0.261 |

| Summary density TF0011 TF0011 | |
|---|---|
| Average TF0011: | 0.314 |
| Max TF0011: | 0.360 |
| Min TF0011: | 0.261 |
| Number of TF0011: | 10 |
| Number of TF0011 lines: | |
| Average T89: | 0.284 |
| Max T89: | 0.361 |
| Min T89: | 0.222 |
| Number of T89: | 41 |
| Confidence interval (95%) | 0.284 +/- 0.06 |
| T-test | 7.377E-03 |
| Number of TF0011 > 0.344 | 2 |
| Number of TF0011 < 0.224 | 0 |
| Average (TF0011)/Average(T89) | 1.106 |
| Max(TF0011)/Max(T89) | 0.997 |

Construction group TF0011 has significant higher density (according to criteria 1 and 2) (+11% in average) than corresponding T89 group.

Construction Group TF0013

| Raw data TF0013 density | |
|---|---|
| TF0013 Individual name: | Density (g/cm³) |
| TF0013-1A-1 | 0.246 |
| TF0013-1A-2 | 0.236 |
| TF0013-2A | |
| TF0013-2B | 0.265 |
| TF0013-3A | 0.258 |
| TF0013-3BA | 0.254 |
| TF0013-3BB | 0.245 |
| TF0013-4BA | 0.258 |
| TF0013-4BB | 0.253 |

| Summary density TF0013 | |
|---|---|
| Average TF0013: | 0.252 |
| Max TF0013: | 0.265 |
| Min TF0013: | 0.236 |
| Number of TF0013: | 8 |
| Number of TF0013 lines: | |
| Average T89: | 0.260 |
| Max T89: | 0.358 |
| Min T89: | 0.218 |
| Number of T89: | 45 |
| Confidence interval (95%) | 0.26 +/− 0.049 |
| T-test | 3.760E−01 |
| Number of TF0013 > 0.309 | 0 |
| Number of TF0013 < 0.211 | 0 |
| Average (TF0013)/Average(T89) | 0.970 |
| Max(TF0013)/Max(T89) | 0.740 |

Construction group TF0013 has no significant difference in density (according to criteria 1 and 2) compared with corresponding T89 group.

Construction Group TF0045

| Raw data TF0045 density | |
|---|---|
| TF0045 Individual name: | Density (g/cm³) |
| TF0045-1A-1 | 0.344 |
| TF0045-1A-2 | |
| TF0045-1A-3 | 0.270 |
| TF0045-1B-1 | 0.320 |
| TF0045-1B-2 | 0.323 |
| TF0045-1B-3 | 0.328 |
| TF0045-2B-1 | 0.303 |
| TF0045-2B-3 | 0.255 |

| Summary density TF0045 | |
|---|---|
| Average TF0045: | 0.306 |
| Max TF0045: | 0.344 |
| Min TF0045: | 0.255 |
| Number of TF0045: | 7 |
| Number of TF0045 lines: | 3 |
| Average T89: | 0.274 |
| Max T89: | 0.354 |
| Min T89: | 0.226 |
| Number of T89: | 36 |
| Confidence interval (95%) | 0.274 +/− 0.052 |
| T-test | 5.760E−03 |
| Number of TF0045 > 0.326 | 2 |
| Number of TF0045 < 0.222 | 0 |
| Average (TF0045)/Average(T89) | 1.117 |
| Max(TF0045)/Max(T89) | 0.972 |

TF0045 has significant higher density (according to criteria 1 and 2) (+12% in average) than corresponding T89 group. The density change (compared to T89) for the 3 construction group lines of TF0045, TF0045-1A (+12% in average (2 measured individuals)), TF0045-1B (+18% in average (3 individuals)) and TF0045-2B (+2% in average (2 individuals)).

Construction Group TF0052

| Raw data TF0052 density | |
|---|---|
| TF0052 Individual name: | Density (g/cm³) |
| TF0052-1A | 0.241 |
| TF0052-1B | 0.346 |
| TF0052-2A | 0.323 |
| TF0052-2B | 0.251 |
| TF0052-3A | 0.393 |
| TF0052-3B | 0.278 |
| TF0052-4A | 0.261 |
| TF0052-4B | 0.322 |

| Summary density TF0052 | |
|---|---|
| Average TF0052: | 0.302 |
| Max TF0052: | 0.393 |
| Min TF0052: | 0.241 |
| Number of TF0052: | 8 |
| Number of TF0052 lines: | |
| Average T89: | 0.275 |
| Max T89: | 0.345 |
| Min T89: | 0.223 |
| Number of T89: | 23 |
| Confidence interval (95%) | 0.275 +/− 0.069 |
| T-test | 9.876E−02 |
| Number of TF0052 > 0.343 | 2 |
| Number of TF0052 < 0.206 | 0 |
| Average (TF0052)/Average(T89) | 1.099 |
| Max(TF0052)/Max(T89) | 1.139 |

Construction group TF0052 has no significant difference in density (according to criteria 1) compared with corresponding T89 group. Although TF0052 has an increased density (+10%) in average and fulfil criteria 2.

Construction Group TF0065

| Raw data TF0065 density | |
|---|---|
| TF0065 Individual name: | Density (g/cm³) |
| TF0065-1AA | 0.333 |
| TF0065-1AB | 0.245 |
| TF0065-1BA | 0.267 |
| TF0065-1BB | 0.253 |
| TF0065-2B | 0.278 |
| TF0065-3A | 0.262 |
| TF0065-4B | 0.272 |

| Summary density TF0065 TF0065 | |
|---|---|
| Average TF0065: | 0.273 |
| Max TF0065: | 0.333 |
| Min TF0065: | 0.245 |
| Number of TF0065: | 7 |
| Number of TF0065 lines: | |
| Average T89: | 0.260 |
| Max T89: | 0.358 |
| Min T89: | 0.218 |
| Number of T89: | 45 |
| Confidence interval (95%) | 0.26 +/− 0.049 |
| T-test | 2.012E−01 |
| Number of TF0065 > 0.309 | 1 |
| Number of TF0065 < 0.211 | 0 |
| Average (TF0065)/Average(T89) | 1.051 |
| Max(TF0065)/Max(T89) | 0.931 |

Construction group TF0065 has no significant difference in density (according to criteria 1 and 2) compared with corresponding T89 group.

Construction Group TF0076

| Raw data TF0076 density | |
|---|---|
| TF0076 Individual name: | Density (g/cm$^3$) |
| TF0076-2AA | 0.250 |
| TF0076-2AB | 0.253 |
| TF0076-3BA | 0.252 |
| TF0076-3BB | 0.257 |
| TF0076-4B | |
| TF0076-5BA | 0.288 |
| TF0076-5BB | 0.300 |

| Summary density TF0065 TF0076 | |
|---|---|
| Average TF0076: | 0.267 |
| Max TF0076: | 0.300 |
| Min TF0076: | 0.250 |
| Number of TF0076: | 6 |
| Number of TF0076 lines: | |
| Average T89: | 0.260 |
| Max T89: | 0.358 |
| Min T89: | 0.218 |
| Number of T89: | 45 |
| Confidence interval (95%) | 0.26 +/− 0.049 |
| T-test | 5.054E−01 |
| Number of TF0076 > 0.309 | 0 |
| Number of TF0076 < 0.211 | 0 |
| Average (TF0076)/Average(T89) | 1.027 |
| Max(TF0076)/Max(T89) | 0.839 |

Construction group TF0076 has no significant difference in density (according to criteria 1 and 2) compared with corresponding T89 group.

Construction Group TF0076 (Replant 21

| Raw data TF0076Rp2 density | |
|---|---|
| TF0076Rp2 Individual name: | Density (g/cm$^3$) |
| TF0076Rp2-3BB-1 | 0.237 |
| TF0076Rp2-3BB-2 | 0.311 |
| TF0076Rp2-3BB-3 | 0.274 |
| TF0076Rp2-4B-1 | 0.304 |
| TF0076Rp2-4B-2 | 0.293 |

| Raw data TF0076Rp2 density | |
|---|---|
| TF0076Rp2 Individual name: | Density (g/cm$^3$) |
| TF0076Rp2-4B-3 | 0.301 |
| TF0076Rp2-5BA-1 | 0.262 |
| TF0076Rp2-5BA-2 | 0.288 |
| TF0076Rp2-5BA-3 | 0.259 |
| TF0076Rp2-5BB-1 | 0.267 |
| TF0076Rp2-5BB-2 | 0.263 |
| TF0076Rp2-5BB-3 | 0.356 |

| Summary density TF0076Rp2 TF0076Rp2 | |
|---|---|
| Average TF0076Rp2: | 0.285 |
| Max TF0076Rp2: | 0.356 |
| Min TF0076Rp2: | 0.237 |
| Number of TF0076Rp2: | 12 |
| Number of TF0076Rp2 lines: | 4 |
| Average T89: | 0.284 |
| Max T89: | 0.338 |
| Min T89: | 0.252 |
| Number of T89: | 32 |
| Confidence interval (95%) | 0.284 +/− 0.041 |
| T-test | 9.407E−01 |
| Number of TF0076Rp2 > 0.325 | 1 |
| Number of TF0076Rp2 < 0.243 | 1 |
| Average (TF0076Rp2)/Average(T89) | 1.002 |
| Max(TF0076Rp2)/Max(T89) | 1.054 |

Construction group TF0076Rp2 has no significant difference in density (according to criteria 1 and 2) compared with corresponding T89 group.

Construction Group TF0096

| Raw data TF0096 density | |
|---|---|
| TF0096 Individual name: | Density (g/cm$^3$) |
| TF0096-2A | 0.296 |
| TF0096-2B | 0.249 |
| TF0096-3A | 0.321 |
| TF0096-3B | 0.308 |
| TF0096-4A | 0.363 |

| Summary density TF0096 TF0096 | |
|---|---|
| Average TF0096: | 0.307 |
| Max TF0096: | 0.363 |
| Min TF0096: | 0.249 |
| Number of TF0096: | 5 |
| Number of TF0096 lines: | |
| Average T89: | 0.274 |
| Max T89: | 0.354 |
| Min T89: | 0.226 |
| Number of T89: | 36 |
| Confidence interval (95%) | 0.274 +/− 0.052 |
| T-test | 1.562E−02 |
| Number of TF0096 > 0.326 | 1 |
| Number of TF0096 < 0.222 | 0 |
| Average (TF0096)/Average(T89) | 1.121 |
| Max(TF0096)/Max(T89) | 1.024 |

Construction group TF0096 has no significant difference in density (according to criteria 1 and 2) compared with corresponding T89 group.

Construction Group TF0097 (Replant 1)

| Raw data TF0097Rp1 density | |
|---|---|
| TF0097Rp1 Individual name: | Density (g/cm$^3$) |
| TF0097Rp1-1A-1 | 0.327 |
| TF0097Rp1-1A-2 | 0.335 |
| TF0097Rp1-1A-3 | 0.344 |
| TF0097Rp1-2A-1 | 0.275 |
| TF0097Rp1-2A-2 | 0.284 |
| TF0097Rp1-2A-3 | 0.308 |
| TF0097Rp1-2B-1 | 0.328 |
| TF0097Rp1-2B-2 | 0.351 |
| TF0097Rp1-2B-3 | 0.309 |
| TF0097Rp1-3A-1 | 0.309 |
| TF0097Rp1-3A-2 | 0.268 |
| TF0097Rp1-3A-3 | 0.297 |
| TF0097Rp1-4A-1 | 0.333 |
| TF0097Rp1-4A-2 | 0.325 |
| TF0097Rp1-4A-3 | 0.319 |

| Summary density TF0097Rp1 | |
|---|---|
| TF0097Rp1 | |
| Average TF0097Rp1: | 0.314 |
| Max TF0097Rp1: | 0.351 |
| Min TF0097Rp1: | 0.268 |
| Number of TF0097Rp1: | 15 |
| Number of TF0097Rp1 lines: | 5 |
| Average T89: | 0.284 |
| Max T89: | 0.338 |
| Min T89: | 0.252 |
| Number of T89: | 32 |
| Confidence interval (95%) | 0.284 +/− 0.041 |
| T-test | 4.607E−05 |
| Number of TF0097Rp1 > 0.325 | 7 |
| Number of TF0097Rp1 < 0.243 | 0 |
| Average (TF0097Rp1)/Average(T89) | 1.107 |
| Max(TF0097Rp1)/Max(T89) | 1.038 |

TF0097Rp1 has significant higher density (according to criteria 1 and 2) (+11% in average) than corresponding T89 group. The density change (compared to T89) for the 5 construction group lines of TF0097Rp1 (3 individuals of each line), TF00097Rp1-1A (+18% in average), TF00097Rp1-2A (+2% in average), TF00097Rp1-2B(+16% in average), TF00097Rp1-3A (+3% in average) and TF00097Rp1-4A (+15 in average). The lines TF00097Rp1-1A, TF00097Rp1-2B and TF00097Rp1-4A them self fulfil criteria 1 and 2.

Construction Group TF0104

| Raw data TF0104 density | |
|---|---|
| TF0104 Individual name: | Density (g/cm$^3$) |
| TF0104-1A | 0.282 |
| TF0104-1B | 0.282 |
| TF0104-2A | 0.297 |
| TF0104-3A | 0.298 |
| TF0104-3B | 0.261 |

| Summary density TF0104 | |
|---|---|
| TF0104 | |
| Average TF0104: | 0.284 |
| Max TF0104: | 0.298 |
| Min TF0104: | 0.261 |
| Number of TF0104: | 5 |
| Number of TF0104 lines: | |
| Average T89: | 0.274 |
| Max T89: | 0.354 |
| Min T89: | 0.226 |
| Number of T89: | 36 |
| Confidence interval (95%) | 0.274 +/− 0.052 |
| T-test | 4.063E−01 |
| Number of TF0104 > 0.326 | 0 |
| Number of TF0104 < 0.222 | 0 |
| Average (TF0104)/Average(T89) | 1.036 |
| Max(TF0104)/Max(T89) | 0.842 |

Construction group TF0104 has no significant difference in density (according to criteria 1 and 2) compared with corresponding T89 group.

Construction Group TF0109 (Replant 1)

| Raw data TF0109Rp1 density | |
|---|---|
| TF0109Rp1 Individual name: | Density (g/cm$^3$) |
| TF0109Rp1-2A-1 | 0.301 |
| TF0109Rp1-2A-2 | 0.294 |
| TF0109Rp1-2A-3 | 0.284 |
| TF0109Rp1-2B-1 | 0.329 |
| TF0109Rp1-2B-2 | 0.342 |
| TF0109Rp1-2B-3 | 0.336 |
| TF0109Rp1-3B-1 | 0.279 |
| TF0109Rp1-3B-2 | 0.279 |
| TF0109Rp1-3B-3 | 0.271 |
| TF0109Rp1-4A-1 | 0.253 |
| TF0109Rp1-4A-2 | 0.238 |
| TF0109Rp1-4A-3 | 0.222 |

| Summary density TF0109Rp1 | |
|---|---|
| TF0109Rp1 | |
| Average TF0109Rp1: | 0.286 |
| Max TF0109Rp1: | 0.342 |
| Min TF0109Rp1: | 0.222 |
| Number of TF0109Rp1: | 12 |
| Number of TF0109Rp1 lines: | 4 |
| Average T89: | 0.284 |
| Max T89: | 0.338 |
| Min T89: | 0.252 |
| Number of T89: | 32 |
| Confidence interval (95%) | 0.284 +/− 0.041 |
| T-test | 8.314E−01 |
| Number of TF0109Rp1 > 0.325 | 3 |
| Number of TF0109Rp1 < 0.243 | 2 |
| Average (TF0109Rp1)/Average(T89) | 1.007 |
| Max(TF0109Rp1)/Max(T89) | 1.014 |

Construction group TF0109Rp1 has no significant difference in density (according to criteria 1 and 2) compared with corresponding T89 group. The density change (compared to T89) for the 4 construction group lines of TF0109Rp1 (3 individuals of each line), TF0109Rp1-2A (+3% in average), TF0109Rp1-2B (+18% in average), TF0109Rp1-3B(−3% in average and TF0109Rp1-4A (−16 in average). The lines TF0109Rp1-2B and TF0109Rp1-4A them self fulfil criteria 1 and 2.

Construction Group TF0116

| Raw data TF0116 density | |
|---|---|
| TF0116 Individual name: | Density (g/cm³) |
| TF0116-1B | |
| TF0116-2A | 0.306 |
| TF0116-2B-1 | 0.293 |
| TF0116-2B-2 | 0.263 |
| TF0116-4A | 0.292 |
| TF0116-5B | 0.247 |
| TF0116-6A | 0.271 |
| TF0116-6B | 0.268 |

| Summary density TF0116 | |
|---|---|
| TF0116 | |
| Average TF0116: | 0.277 |
| Max TF0116: | 0.306 |
| Min TF0116: | 0.247 |
| Number of TF0116: | 7 |
| Number of TF0116 lines: | |
| Average T89: | 0.275 |
| Max T89: | 0.345 |
| Min T89: | 0.223 |
| Number of T89: | 23 |
| Confidence interval (95%) | 0.275 +/− 0.069 |
| T-test | 8.725E−01 |
| Number of TF0116 > 0.343 | 0 |
| Number of TF0116 < 0.206 | 0 |
| Average (TF0116)/Average(T89) | 1.008 |
| Max(TF0116)/Max(T89) | 0.887 |

Construction group TF0116 has no significant difference in density (according to criteria 1 and 2) compared with corresponding T89 group.

Construction Group TF0132 (2nd Set of Construction Group Lines)

| Raw data TF0132.2nd density | |
|---|---|
| TF0132.2nd Individual name: | Density (g/cm³) |
| TF0132.2nd-1A | 0.263 |
| TF0132.2nd-1B | 0.284 |
| TF0132.2nd-2A | 0.350 |
| TF0132.2nd-4B | 0.315 |
| TF0132.2nd-5A | 0.271 |
| TF0132.2nd-5B | 0.286 |
| TF0132.2nd-6B | 0.285 |
| TF0132.2nd-7A | 0.294 |

| Summary density TF0132.2nd | |
|---|---|
| TF0132.2nd | |
| Average TF0132.2nd: | 0.294 |
| Max TF0132.2nd: | 0.350 |
| Min TF0132.2nd: | 0.263 |
| Number of TF0132.2nd: | 8 |
| Number of TF0132.2nd lines: | |
| Average T89: | 0.274 |
| Max T89: | 0.354 |
| Min T89: | 0.226 |
| Number of T89: | 36 |
| Confidence interval (95%) | 0.274 +/− 0.052 |
| T-test | 6.257E−02 |
| Number of TF0132.2nd > 0.326 | 1 |
| Number of TF0132.2nd < 0.222 | 0 |
| Average (TF0132.2nd)/Average(T89) | 1.071 |
| Max(TF0132.2nd)/Max(T89) | 0.988 |

Construction group TF0132.2nd has no significant difference in density (according to criteria 1 and 2) compared with corresponding T89 group.

Construction Group TF0132 (Replant 1)

| Raw data TF0132rp1 density | |
|---|---|
| TF0132rp1 Individual name: | Density (g/cm³) |
| TF0132Rp1-1B-1 | 0.274 |
| TF0132Rp1-1B-2 | 0.265 |
| TF0132Rp1-1B-3 | 0.265 |
| TF0132Rp1-3BB-1 | 0.260 |
| TF0132Rp1-3BB-2 | 0.265 |
| TF0132Rp1-3BB-3 | 0.267 |
| TF0132Rp1-4AC-1 | 0.283 |
| TF0132Rp1-4AC-2 | 0.275 |
| TF0132Rp1-4AC-3 | 0.278 |
| TF0132Rp1-4B-1 | 0.291 |
| TF0132Rp1-4B-2 | 0.260 |
| TF0132Rp1-4B-3 | 0.282 |
| TF0132Rp1-6B-1 | 0.270 |
| TF0132Rp1-6B-2 | 0.281 |
| TF0132Rp1-6B-3 | 0.269 |

| Summary density TF0132Rp1 | |
|---|---|
| TF0132rp1 | |
| Average TF0132rp1: | 0.272 |
| Max TF0132rp1: | 0.291 |
| Min TF0132rp1: | 0.260 |
| Number of TF0132rp1: | 15 |
| Number of TF0132rp1 lines: | 5 |
| Average T89: | 0.255 |
| Max T89: | 0.275 |
| Min T89: | 0.232 |
| Number of T89: | 27 |
| Confidence interval (95%) | 0.255 +/− 0.025 |
| T-test | 2.603E−05 |
| Number of TF0132rp1 > 0.280 | 4 |
| Number of TF0132rp1 < 0.230 | 0 |
| Average (TF0132rp1)/Average(T89) | 1.068 |
| Max(TF0132rp1)/Max(T89) | 1.059 |

Construction group TF0132Rp1 has significant higher density (according to criteria 1 and 2) (+7% in average) than corresponding T89 group. The density change (compared to T89) for the 5 construction group lines of TF0132Rp1 (3 individuals of each line), T TF0132Rp1-1B (+5% in average), TF0132Rp1-3BB (+4% in average), TF0132Rp1-4AC (+9% in average), TF0132Rp1-4B (+9% in average) and TF0132Rp1-6B (+7% in average). The line TF0132Rp1-4B itself fulfil criteria 1 and 2.

Construction Group TF0146

| Raw data TF0146 density | |
|---|---|
| TF0146 Individual name: | Density (g/cm³) |
| TF0146-1A | 0.341 |
| TF0146-1B | 0.314 |
| TF0146-2A | 0.303 |
| TF0146-2B | 0.300 |
| TF0146-3A | 0.333 |
| TF0146-3B | 0.313 |
| TF0146-4A | 0.374 |
| TF0146-4B | 0.269 |

| Summary density TF0146 TF0146 | |
|---|---|
| Average TF0146: | 0.318 |
| Max TF0146: | 0.374 |
| Min TF0146: | 0.269 |
| Number of TF0146: | 8 |
| Number of TF0146 lines: | |
| Average T89: | 0.274 |
| Max T89: | 0.354 |
| Min T89: | 0.226 |
| Number of T89: | 36 |
| Confidence interval (95%) | 0.274 +/− 0.052 |
| T-test | 1.127E−04 |
| Number of TF0146 > 0.326 | 3 |
| Number of TF0146 < 0.222 | 0 |
| Average (TF0146)/Average(T89) | 1.161 |
| Max(TF0146)/Max(T89) | 1.054 |

Construction group TF0146 has significant higher density (according to criteria 1 and 2) (+16% in average) than corresponding T89 group.

Construction Group TF0173

| Raw data TF0173 density | |
|---|---|
| TF0173 Individual name: | Density (g/cm³) |
| TF0173-3A-1 | 0.232 |
| TF0173-3A-2 | 0.291 |
| TF0173-3B-1 | 0.239 |
| TF0173-3B-2 | 0.242 |
| TF0173-4A-1 | 0.251 |
| TF0173-4A-2 | 0.231 |
| TF0173-4B-1 | 0.256 |
| TF0173-4B-2 | 0.305 |

| Summary density TF0173 TF0173 | |
|---|---|
| Average TF0173: | 0.256 |
| Max TF0173: | 0.305 |
| Min TF0173: | 0.231 |
| Number of TF0173: | 8 |
| Number of TF0173 lines: | |
| Average T89: | 0.254 |
| Max T89: | 0.345 |
| Min T89: | 0.221 |
| Number of T89: | 34 |
| Confidence interval (95%) | 0.254 +/− 0.056 |
| T-test | 8.478E−01 |
| Number of TF0173 > 0.31 | 0 |
| Number of TF0173 < 0.198 | 0 |
| Average (TF0173)/Average(T89) | 1.008 |
| Max(TF0173)/Max(T89) | 0.884 |

Construction group TF0173 has no significant difference in density (according to criteria 1 and 2) compared with corresponding T89 group.

Construction Group TF0247

| Raw data TF0247 density | |
|---|---|
| TF0247 Individual name: | Density (g/cm³) |
| TF0247-1A | 0.257 |
| TF0247-3A | 0.250 |
| TF0247-3B | 0.309 |
| TF0247-4A | 0.288 |
| TF0247-6B | 0.366 |

| Summary density TF0247 TF0247 | |
|---|---|
| Average TF0247: | 0.294 |
| Max TF0247: | 0.366 |
| Min TF0247: | 0.250 |
| Number of TF0247: | 5 |
| Number of TF0247 lines: | |
| Average T89: | 0.274 |
| Max T89: | 0.354 |
| Min T89: | 0.226 |
| Number of T89: | 36 |
| Confidence interval (95%) | 0.274 +/− 0.052 |
| T-test | 1.498E−01 |
| Number of TF0247 > 0.326 | 1 |
| Number of TF0247 < 0.222 | 0 |
| Average (TF0247)/Average(T89) | 1.073 |
| Max(TF0247)/Max(T89) | 1.032 |

Construction group TF0247 has no significant difference in density (according to criteria 1 and 2) compared with corresponding T89 group.

Construction Group TF0405

| Raw data TF0405 density | |
|---|---|
| TF0405 Individual name: | Density (g/cm³) |
| TF0405-2A-1 | 0.271 |
| TF0405-2A-2 | 0.291 |
| TF0405-2B-2 | |
| TF0405-3A-1 | 0.275 |
| TF0405-3A-2 | 0.309 |
| TF0405-3B-1 | 0.295 |
| TF0405-3B-2 | 0.279 |

| Summary density TF0405 TF0405 | |
|---|---|
| Average TF0405: | 0.287 |
| Max TF0405: | 0.309 |
| Min TF0405: | 0.271 |
| Number of TF0405: | 6 |

-continued

| Summary density TF0405 TF0405 | |
|---|---|
| Number of TF0405 lines: | |
| Average T89: | 0.274 |
| Max T89: | 0.354 |
| Min T89: | 0.226 |
| Number of T89: | 36 |
| Confidence interval (95%) | 0.274 +/− 0.052 |
| T-test | 2.560E−01 |
| Number of TF0405 > 0.326 | 0 |
| Number of TF0405 < 0.222 | 0 |
| Average (TF0405)/Average(T89) | 1.045 |
| Max(TF0405)/Max(T89) | 0.871 |

Construction group TF0405 has no significant difference in density (according to criteria 1 and 2) compared with corresponding T89 group.

Construction Group TFSTT004

| Raw data TFSTT004 density | |
|---|---|
| TFSTT004 Individual name: | Density (g/cm$^3$) |
| TFSTT004-1A | 0.300 |
| TFSTT004-2A-1 | 0.285 |
| TFSTT004-2A-2 | 0.283 |
| TFSTT004-2B-1 | 0.272 |
| TFSTT004-2B-2 | 0.262 |
| TFSTT004-3B | 0.329 |
| TFSTT004-4B-1 | 0.266 |
| TFSTT004-4B-2 | 0.274 |

| Summary density TFSTT004 TFSTT004 | |
|---|---|
| Average TFSTT004: | 0.284 |
| Max TFSTT004: | 0.329 |
| Min TFSTT004: | 0.262 |
| Number of TFSTT004: | 8 |
| Number of TFSTT004 lines: | |
| Average T89: | 0.275 |
| Max T89: | 0.345 |
| Min T89: | 0.223 |
| Number of T89: | 23 |
| Confidence interval (95%) | 0.275 +/− 0.069 |
| T-test | 4.777E−01 |
| Number of TFSTT004 > 0.343 | 0 |
| Number of TFSTT004 < 0.206 | 0 |
| Average (TFSTT004)/Average(T89) | 1.033 |
| Max(TFSTT004)/Max(T89) | 0.955 |

Construction group TFSTT004 has no significant difference in density (according to criteria 1 and 2) compared with corresponding T89 group.

Construction Group TFSTT013

| Raw data TFSTT013 density | |
|---|---|
| TFSTT013 Individual name: | Density (g/cm$^3$) |
| TFSTT013-1A | 0.323 |
| TFSTT013-1B | 0.328 |
| TFSTT013-2B | 0.288 |
| TFSTT013-3A | 0.345 |
| TFSTT013-3B | 0.291 |
| TFSTT013-4A | 0.304 |
| TFSTT013-4B | 0.324 |
| TFSTT013-5B | 0.346 |

| Summary density TFSTT013 TFSTT013 | |
|---|---|
| Average TFSTT013: | 0.319 |
| Max TFSTT013: | 0.346 |
| Min TFSTT013: | 0.288 |
| Number of TFSTT013: | 8 |
| Number of TFSTT013 lines: | |
| Average T89: | 0.284 |
| Max T89: | 0.361 |
| Min T89: | 0.222 |
| Number of T89: | 41 |
| Confidence interval (95%) | 0.284 +/− 0.06 |
| T-test | 3.006E−03 |
| Number of TFSTT013 > 0.344 | 2 |
| Number of TFSTT013 < 0.224 | 0 |
| Average (TFSTT013)/Average(T89) | 1.123 |
| Max(TFSTT013)/Max(T89) | 0.958 |

Construction group TFSTT013 has significant higher density (according to criteria 1 and 2) (+12% in average) than corresponding T89 group.

Construction Group TFSTT016

| Raw data TFSTT016 density | |
|---|---|
| TFSTT016 Individual name: | Density (g/cm$^3$) |
| TFSTT016-1A | 0.306 |
| TFSTT016-1B | 0.254 |
| TFSTT016-2A | 0.249 |
| TFSTT016-2B | 0.279 |
| TFSTT016-3A-1 | 0.272 |
| TFSTT016-3A-2 | 0.274 |
| TFSTT016-4A | 0.252 |

| Summary density TFSTT016 TFSTT016 | |
|---|---|
| Average TFSTT016: | 0.270 |
| Max TFSTT016: | 0.306 |
| Min TFSTT016: | 0.249 |
| Number of TFSTT016: | 7 |
| Number of TFSTT016 lines: | |
| Average T89: | 0.275 |
| Max T89: | 0.345 |
| Min T89: | 0.223 |
| Number of T89: | 23 |
| Confidence interval (95%) | 0.275 +/− 0.069 |
| T-test | 6.884E−01 |
| Number of TFSTT016 > 0.343 | 0 |
| Number of TFSTT016 < 0.206 | 0 |
| Average (TFSTT016)/Average(T89) | 0.980 |
| Max(TFSTT016)/Max(T89) | 0.886 |

Construction group TFSTT016 has no significant difference in density (according to criteria 1 and 2) compared with corresponding T89 group.

Construction Group TFSTT019

| Raw data TFSTT019 density | |
|---|---|
| TFSTT019 Individual name: | Density (g/cm$^3$) |
| TFSTT019-1A | |
| TFSTT019-1BA | 0.216 |
| TFSTT019-1BB | 0.283 |
| TFSTT019-2A | 0.265 |
| TFSTT019-2B | 0.231 |
| TFSTT019-3A | 0.277 |
| TFSTT019-4BA | 0.244 |
| TFSTT019-4BB | 0.282 |

| Summary density TFSTT019 TFSTT019 | |
|---|---|
| Average TFSTT019: | 0.257 |
| Max TFSTT019: | 0.283 |
| Min TFSTT019: | 0.216 |
| Number of TFSTT019: | 7 |
| Number of TFSTT019 lines: | |
| Average T89: | 0.260 |
| Max T89: | 0.358 |
| Min T89: | 0.218 |
| Number of T89: | 45 |
| Confidence interval (95%) | 0.26 +/− 0.049 |
| T-test | 7.862E−01 |
| Number of TFSTT019 > 0.309 | 0 |
| Number of TFSTT019 < 0.211 | 0 |
| Average (TFSTT019)/Average(T89) | 0.989 |
| Max(TFSTT019)/Max(T89) | 0.789 |

Construction group TFSTT019 has no significant difference in density (according to criteria 1 and 2) compared with corresponding T89 group.

Construction Group TFSTT035

| Raw data TFSTT035 density | |
|---|---|
| TFSTT035 Individual name: | Density (g/cm$^3$) |
| TFSTT035-1A | 0.236 |
| TFSTT035-1BA | 0.260 |
| TFSTT035-1BB | 0.265 |
| TFSTT035-2AA | 0.247 |
| TFSTT035-2AB | 0.257 |
| TFSTT035-2B | 0.217 |
| TFSTT035-3B | 0.240 |
| TFSTT035-4B | 0.267 |

| Summary density TFSTT035 TFSTT035 | |
|---|---|
| Average TFSTT035: | 0.249 |
| Max TFSTT035: | 0.267 |
| Min TFSTT035: | 0.217 |
| Number of TFSTT035: | 8 |
| Number of TFSTT035 lines: | |
| Average T89: | 0.260 |
| Max T89: | 0.358 |
| Min T89: | 0.218 |
| Number of T89: | 45 |
| Confidence interval (95%) | 0.26 +/− 0.049 |
| T-test | 2.247E−01 |
| Number of TFSTT035 > 0.309 | 0 |
| Number of TFSTT035 < 0.211 | 0 |
| Average (TFSTT035)/Average(T89) | 0.957 |
| Max(TFSTT035)/Max(T89) | 0.745 |

Construction group TFSTT035 has no significant difference in density (according to criteria 1 and 2) compared with corresponding T89 group.

Construction Group TFSTT036

| Raw data TFSTT036 density | |
|---|---|
| TFSTT036 Individual name: | Density (g/cm$^3$) |
| TFSTT036-1B | 0.291 |
| TFSTT036-2A | 0.306 |
| TFSTT036-2B | 0.365 |
| TFSTT036-3A | 0.322 |
| TFSTT036-4A | 0.274 |
| TFSTT036-4B | 0.331 |
| TFSTT036-5B | 0.254 |

| Summary density TFSTT036 TFSTT036 | |
|---|---|
| Average TFSTT036: | 0.306 |
| Max TFSTT036: | 0.365 |
| Min TFSTT036: | 0.254 |
| Number of TFSTT036: | 7 |
| Number of TFSTT036 lines: | |
| Average T89: | 0.274 |
| Max T89: | 0.354 |
| Min T89: | 0.226 |
| Number of T89: | 36 |
| Confidence interval (95%) | 0.274 +/− 0.052 |
| T-test | 7.640E−03 |
| Number of TFSTT036 > 0.326 | 2 |
| Number of TFSTT036 < 0.222 | 0 |
| Average (TFSTT036)/Average(T89) | 1.117 |
| Max(TFSTT036)/Max(T89) | 1.030 |

Construction group TFSTT036 has significant higher density (according to criteria 1 and 2) (+12% in average) than corresponding T89 group.

Construction Group TFSTT038

| Raw data TFSTT038 density | |
|---|---|
| TFSTT038 Individual name: | Density (g/cm$^3$) |
| TFSTT038-1A-1 | 0.256 |
| TFSTT038-1A-2 | 0.292 |
| TFSTT038-1B | 0.312 |
| TFSTT038-2A | 0.308 |
| TFSTT038-2B | 0.264 |
| TFSTT038-3A | 0.301 |
| TFSTT038-3B | 0.343 |
| TFSTT038-4B | 0.284 |

| Summary density TFSTT038 TFSTT038 | |
|---|---|
| Average TFSTT038: | 0.295 |
| Max TFSTT038: | 0.343 |
| Min TFSTT038: | 0.256 |
| Number of TFSTT038: | 8 |
| Number of TFSTT038 lines: | |
| Average T89: | 0.275 |
| Max T89: | 0.345 |
| Min T89: | 0.223 |
| Number of T89: | 23 |
| Confidence interval (95%) | 0.275 +/− 0.069 |
| T-test | 1.343E−01 |
| Number of TFSTT038 > 0.343 | 0 |
| Number of TFSTT038 < 0.206 | 0 |
| Average (TFSTT038)/Average(T89) | 1.073 |
| Max(TFSTT038)/Max(T89) | 0.995 |

Construction group TFSTT038 has no significant difference in density (according to criteria 1 and 2) compared with corresponding T89 group.

Construction Group TFSTT045

| Raw data TFSTT045 density | |
|---|---|
| TFSTT045 Individual name: | Density (g/cm³) |
| TFSTT045-1B | 0.231 |
| TFSTT045-2B | 0.243 |
| TFSTT045-3A | 0.258 |
| TFSTT045-3B | 0.257 |
| TFSTT045-4A | 0.258 |
| TFSTT045-4B | 0.349 |
| TFSTT045-7B | 0.324 |

| Summary density TFSTT045 TFSTT045 | |
|---|---|
| Average TFSTT045: | 0.274 |
| Max TFSTT045: | 0.349 |
| Min TFSTT045: | 0.231 |
| Number of TFSTT045: | 7 |
| Number of TFSTT045 lines: | |
| Average T89: | 0.274 |
| Max T89: | 0.354 |
| Min T89: | 0.226 |
| Number of T89: | 36 |
| Confidence interval (95%) | 0.274 +/− 0.052 |
| T-test | 9.934E−01 |
| Number of TFSTT045 > 0.326 | 1 |
| Number of TFSTT045 < 0.222 | 0 |
| Average (TFSTT045)/Average(T89) | 1.000 |
| Max(TFSTT045)/Max(T89) | 0.984 |

Construction group TFSTT045 has no significant difference in density (according to criteria 1 and 2) compared with corresponding T89 group.

Construction Group TFSTT051

| Raw data TFSTT051 density | |
|---|---|
| TFSTT051 Individual name: | Density (g/cm³) |
| TFSTT051-1B | 0.315 |
| TFSTT051-2A | 0.318 |
| TFSTT051-2B | 0.292 |
| TFSTT051-3A | 0.289 |
| TFSTT051-3B | 0.270 |
| TFSTT051-4A | 0.240 |
| TFSTT051-4B-1 | 0.269 |
| TFSTT051-4B-2 | 0.234 |

| Summary density TFSTT051 TFSTT051 | |
|---|---|
| Average TFSTT051: | 0.278 |
| Max TFSTT051: | 0.318 |
| Min TFSTT051: | 0.234 |
| Number of TFSTT051: | 8 |
| Number of TFSTT051 lines: | |
| Average T89: | 0.275 |
| Max T89: | 0.345 |
| Min T89: | 0.223 |
| Number of T89: | 23 |
| Confidence interval (95%) | 0.275 +/− 0.069 |
| T-test | 7.969E−01 |
| Number of TFSTT051 > 0.343 | 0 |
| Number of TFSTT051 < 0.206 | 0 |
| Average (TFSTT051)/Average(T89) | 1.013 |
| Max(TFSTT051)/Max(T89) | 0.921 |

Construction group TFSTT051 has no significant difference in density (according to criteria 1 and 2) compared with corresponding T89 group.

Example 6

Fibre Measurements

Fibre measurements were performed on samples at 33 to 36 cm height of the stem. A piece of pure wood, about 1.5 mm×1.5 mm×15 mm was cut out from the stem piece. A maceration preparation (Franklin et al. 1945) was performed to get a macerate of single fibres from the small piece of wood. The sample was then measured using a KajaaniFibreLab™ from Metso Automation, giving the average of fibre length, average fibre width and an estimation of the fibre cell wall thickness. The supplied computer software calculates these numbers using the below formulas according to the manufacturer.

Fibre Length

Average of fibre length, L(n), using true length of fibres, measured along the centreline:

$$L(n) = \frac{\sum (n_i * l_i)}{\sum n_i} \; [mm]$$

where $n_i$=number of fibres in class i, i=1 ... 152, $l_i$=(0.05*0−0.025, $l_i$=length of class i, Fibre Width Average of fibre width, W; based on cross sectional measurements:

$$W = \frac{\sum (n_i * w_i)}{\sum n_i} \; [\mu m]$$

where
$n_i$=number of fibres in class i,
i=1 ... 100,
$w_i$=kw*(i−0.5),
$w_i$=width of class i,
kw=width calibration factor,
Cell Wall Thickness Average of cell wall thickness, CWT, based on cross sectional measurements:

$$CWT = \frac{\sum (n_i * CWT_i)}{\sum n_i} \; [\mu m]$$

where
$n_i$=number of fibres in class i,
i=1 ... 100,
$CWT_i$=kt*(i−0.5),
$CWT_i$=cell wall thickness of class i,
kt=cell wall thickness calibration factor.

Construction Groups with fibres with at least an 10% increase or 15% decrease in fibre length or widths were selected as being effected in genes useful for modifying fibre dimension according to the selection criteria's below.
Fibre Parameters Selection Criteria In Table 6.1 the abbreviations used for the phenotypes used for the fibre selection criteria are listed.

TABLE 6.1

Abbreviations for phenotypes

| | |
|---|---|
| AFL | average fibre length of the wild type population and each Construction group population |
| AFW | average fibre width of the wild type population and each Construction group population |
| maxFL | maximum fibre length of the wild type population and each Construction group population |
| maxFW | maximum fibre width of the wild type population and each Construction group population |
| minFL | minimum fibre length of the wild type population and each Construction group population |
| minFW | minimum fibre width of the wild type population and each Construction group population |

Construction groups that showed a difference compared to the wild type population in any of the fibre parameters mentioned above were scored as construction groups that are altered in their growth properties and therefore the corresponding genes can be used to alter these properties.

As a 10% increase or a 15% decrease in fibre dimensions are of interest for the industry, the selection criteria below were used to select genes that can be used to altered fibre dimensions.

The fibre parameters selection criteria are as follows:
1. If construction group AFL is at least 10% higher than corresponding wildtype group AFL, or
2. If construction group AFW is at least 10% higher than corresponding wildtype group AFW, or
3. If construction group maxFL is at least 10% higher than corresponding wildtype group maxFL, or
4. If construction group maxFW is at least 10% higher than corresponding wildtype group maxFW, or
5. If construction group AFL is at least 15% lower than corresponding wildtype group AFL, or
6. If construction group AFW is at least 15% lower than corresponding wildtype group AFW, or
7. If construction group minFL is at least 15% lower than corresponding wildtype group minFL, or
8. If construction group minFW is at least 15% lower than corresponding wildtype group minFW.

Construction groups meeting one or more of these criteria were selected.

The results below are presented according to construction group.

Construction Group TF0002

This construct induces changes in fibre parameters. The maximum fibre width is 16% higher than corresponding maximum wildtype. The TF0002 construction group meets the fibre parameters selection criterion (4).

Table 6.2 contains fibre measurements data for specified construction group and corresponding wild type group.

TABLE 6.2

| Construction group Individual | Fibre Length (mm) | Fibre Width (μm) | CWT (μm) |
|---|---|---|---|
| TF0002-1B | 0.37 | 17.73 | 4.32 |
| TF0002-2A | 0.39 | 19 | 4.8 |
| TF0002-2B | 0.34 | 14.57 | 3.47 |
| TF0002-3A | 0.36 | 16.23 | 3.9 |
| TF0002-3B | 0.34 | 14.71 | 3.51 |
| TF0002-4B | 0.36 | 15.86 | 3.85 |
| T89-1 | 0.33 | 14.2 | 3.37 |
| T89-18 | 0.35 | 14.1 | 3.23 |
| T89-20 | 0.35 | 14.57 | 3.37 |
| T89-24 | 0.36 | 14.39 | 3.34 |
| T89-27 | 0.37 | 16.03 | 3.87 |
| T89-3 | 0.36 | 14.89 | 3.5 |
| T89-30 | 0.37 | 14.11 | 3.3 |
| T89-31 | 0.38 | 15.44 | 3.63 |
| T89-32 | 0.37 | 15.34 | 3.63 |
| T89-34 | 0.37 | 15.56 | 3.71 |
| T89-36 | 0.36 | 14.43 | 3.39 |
| T89-4 | 0.37 | 16.4 | 3.93 |
| T89-6 | 0.37 | 14.68 | 3.46 |
| T89-7 | 0.33 | 14.25 | 3.36 |
| T89-9 | 0.38 | 15.94 | 3.8 |

Results from the fibre measurements are presented in table 6.3 as ratios of average fibre length (AFL), average fibre width (AFW), maximum fibre length (maxFL), maximum fibre width (maxFW), minimum fibre length (minFL), minimum fibre width (minFW) of specified construction group relative to corresponding wildtype group.

TABLE 6.3

| Construction Group | Average Fibre Length | Average Fibre Width | Max Fibre Length | Max Fibre Width | Min Fibre Length | Min Fibre Width |
|---|---|---|---|---|---|---|
| TF0002 | 1.00 | 1.09 | 1.03 | 1.16 | 1.03 | 1.03 |

Construction Group TF0052

This construct induces changes in fibre parameters. The average fibre width is 13% higher than of corresponding wildtype group. The maximum fibre width is 22% higher than corresponding maximum wildtype. The TF0052 construction group meets the fibre parameters selection criterion (2) and (4).

Table 6.4 contains fibre measurements data for specified construction group and corresponding wild type group.

TABLE 6.4

| Construction group Individual | Fibre Length (mm) | Fibre Width (μm) | CWT (μm) |
|---|---|---|---|
| TF0052-1A | 0.3 | 12.77 | 3.11 |
| TF0052-1B | 0.33 | 14.4 | 3.46 |
| TF0052-2A | 0.34 | 15.9 | 3.86 |
| TF0052-2B | 0.36 | 18.22 | 4.49 |
| TF0052-3A | 0.34 | 18.54 | 4.71 |
| TF0052-3B | 0.34 | 14.52 | 3.49 |
| TF0052-4A | 0.35 | 15.94 | 3.9 |
| TF0052-4B | 0.32 | 15.33 | 3.76 |
| T89-1 | 0.35 | 15.15 | 3.59 |
| T89-12 | 0.34 | 14.79 | 3.44 |
| T89-14 | 0.33 | 12.52 | 2.83 |
| T89-16 | 0.34 | 13.67 | 3.14 |
| T89-18 | 0.34 | 14.25 | 3.28 |
| T89-19 | 0.33 | 13.82 | 3.17 |
| T89-20 | 0.36 | 15.11 | 3.58 |
| T89-21 | 0.34 | 13.42 | 3.14 |
| T89-24 | 0.33 | 14.54 | 3.39 |
| T89-25 | 0.37 | 15.2 | 3.58 |
| T89-26 | 0.35 | 14.12 | 3.31 |
| T89-27 | 0.33 | 13.52 | 3.12 |
| T89-28 | 0.33 | 13.41 | 3.13 |
| T89-3 | 0.3 | 13.3 | 3.18 |
| T89-30 | 0.32 | 12.52 | 2.91 |

Results from the fibre measurements are presented in table 6.5 as ratios of average fibre length (AFL), average fibre width (AFW), maximum fibre length (maxFL), maximum fibre width (maxFW), minimum fibre length (minFL), minimum fibre width (minFW) of specified construction group relative to corresponding wildtype group.

TABLE 6.5

| Construction Group | Average Fibre Length | Average Fibre Width | Max Fibre Length | Max Fibre Width | Min Fibre Length | Min Fibre Width |
|---|---|---|---|---|---|---|
| TF0052 | 0.99 | 1.13 | 0.97 | 1.22 | 1.00 | 1.02 |

Construction Group TF0058

This construct induces changes in fibre parameters. The average fibre width is 16% higher than of corresponding wildtype group. The maximum fibre width is 23% higher than corresponding maximum wildtype. The TF0058 construction group meets the fibre parameters selection criterion (2) and (4).

Table 6.6 contains fibre measurements data for specified construction group and corresponding wild type group.

TABLE 6.6

| Construction group Individual | Fibre Length (mm) | Fibre Width (μm) | CWT (μm) |
|---|---|---|---|
| TF0058-1A | 0.34 | 15.29 | 3.74 |
| TF0058-1B | 0.31 | 15.07 | 3.66 |
| TF0058-2A | 0.36 | 16.98 | 4.21 |
| TF0058-2B | 0.34 | 15.89 | 3.89 |
| TF0058-3A | 0.36 | 15.28 | 3.67 |
| TF0058-3B | 0.36 | 15.62 | 3.77 |
| TF0058-4A | 0.37 | 16.97 | 4.14 |

TABLE 6.6-continued

| Construction group Individual | Fibre Length (mm) | Fibre Width (μm) | CWT (μm) |
|---|---|---|---|
| TF0058-4B | 0.39 | 18.7 | 4.57 |
| T89-1 | 0.35 | 15.15 | 3.59 |
| T89-12 | 0.34 | 14.79 | 3.44 |
| T89-14 | 0.33 | 12.52 | 2.83 |
| T89-16 | 0.34 | 13.67 | 3.14 |
| T89-18 | 0.34 | 14.25 | 3.28 |
| T89-19 | 0.33 | 13.82 | 3.17 |
| T89-20 | 0.36 | 15.11 | 3.58 |
| T89-21 | 0.34 | 13.42 | 3.14 |
| T89-24 | 0.33 | 14.54 | 3.39 |
| T89-25 | 0.37 | 15.2 | 3.58 |
| T89-26 | 0.35 | 14.12 | 3.31 |
| T89-27 | 0.33 | 13.52 | 3.12 |
| T89-28 | 0.33 | 13.41 | 3.13 |
| T89-3 | 0.3 | 13.3 | 3.18 |
| T89-30 | 0.32 | 12.52 | 2.91 |

Results from the fibre measurements are presented in table 6.7 as ratios of average fibre length (AFL), average fibre width (AFW), maximum fibre length (maxFL), maximum fibre width (maxFW), minimum fibre length (minFL), minimum fibre width (minFW) of specified construction group relative to corresponding wildtype group.

TABLE 6.7

| Construction Group | Average Fibre Length | Average Fibre Width | Max Fibre Length | Max Fibre Width | Min Fibre Length | Min Fibre Width |
|---|---|---|---|---|---|---|
| TF0058 | 1.05 | 1.16 | 1.05 | 1.23 | 1.03 | 1.20 |

Construction Group TF0097

This construct induces changes in fibre parameters. The maximum fibre width is 13% higher than corresponding maximum wildtype. The TF0097 construction group meets the fibre parameters selection criterion (4).

Table 6.8 contains fibre measurements data for specified construction group and corresponding wild type group.

TABLE 6.8

| Construction group Individual | Fibre Length (mm) | Fibre Width (μm) | CWT (μm) |
|---|---|---|---|
| TF0097-1A | 0.38 | 16.6 | 4.07 |
| TF0097-1B | 0.36 | 14.84 | 3.53 |
| TF0097-2A | 0.33 | 12.65 | 2.92 |
| TF0097-2B | 0.37 | 15.92 | 3.8 |
| TF0097-3A-1 | 0.38 | 17.11 | 4.13 |
| TF0097-3A-2 | 0.33 | 14.05 | 3.37 |
| TF0097-4A-1 | 0.34 | 12.27 | 2.79 |
| TF0097-4A-2 | 0.33 | 13.03 | 2.98 |
| TF0097-4B | 0.3 | 12.34 | 2.9 |
| T89-02 | 0.3 | 11.82 | 2.7 |
| T89-07 | 0.36 | 14.1 | 3.25 |
| T89-11 | 0.35 | 13.66 | 3.2 |
| T89-17 | 0.31 | 13.26 | 3.15 |
| T89-19 | 0.32 | 15.14 | 3.67 |
| T89-26 | 0.32 | 12.06 | 2.7 |
| T89-29 | 0.36 | 15.19 | 3.63 |
| T89-31 | 0.36 | 14.51 | 3.44 |
| T89-32 | 0.35 | 13.73 | 3.17 |
| T89-34 | 0.33 | 12.93 | 2.96 |
| T89-35 | 0.32 | 13.28 | 3.12 |
| T89-38 | 0.34 | 14.69 | 3.52 |
| T89-44 | 0.32 | 13.64 | 3.24 |
| T89-46 | 0.34 | 13.96 | 3.26 |

TABLE 6.8-continued

| Construction group Individual | Fibre Length (mm) | Fibre Width (μm) | CWT (μm) |
|---|---|---|---|
| T89-61 | 0.34 | 14.09 | 3.35 |
| T89-68 | 0.29 | 12.49 | 2.99 |

Results from the fibre measurements are presented in table 6.9 as ratios of average fibre length (AFL), average fibre width (AFW), maximum fibre length (maxFL), maximum fibre width (maxFW), minimum fibre length (minFL), minimum fibre width (minFW) of specified construction group relative to corresponding wildtype group.

TABLE 6.9

| Construction Group | Average Fibre Length | Average Fibre Width | Max Fibre Length | Max Fibre Width | Min Fibre Length | Min Fibre Width |
|---|---|---|---|---|---|---|
| TF0097 | 1.04 | 1.05 | 1.06 | 1.13 | 1.03 | 1.04 |

Construction Group TF0109

This construct induces changes in fibre parameters. The average fibre length is 11% higher than of corresponding wildtype group. The maximum fibre length is 25% higher than of corresponding maximum wildtype. The maximum fibre width is 23% higher than corresponding maximum wildtype. The TF0109 construction group meets the fibre parameters selection criterion (1) (3) and (4).

Table 6.10 contains fibre measurements data for specified construction group and corresponding wild type group.

TABLE 6.10

| Construction group Individual | Fibre Length (mm) | Fibre Width (μm) | CWT (μm) |
|---|---|---|---|
| TF0109-1B-1 | 0.35 | 15.06 | 3.54 |
| TF0109-1B-2 | 0.35 | 15.83 | 3.8 |
| TF0109-2A | 0.34 | 15.4 | 3.69 |
| TF0109-2B | 0.35 | 15.7 | 3.75 |
| TF0109-3B | 0.36 | 15.73 | 3.75 |
| TF0109-4A | 0.45 | 21.49 | 5.12 |
| TF0109-4B | 0.37 | 16.82 | 4.08 |
| T89-16 | 0.35 | 15.93 | 3.82 |
| T89-17 | 0.34 | 15.56 | 3.79 |
| T89-19 | 0.34 | 15.87 | 3.9 |
| T89-2 | 0.33 | 13.88 | 3.25 |
| T89-20 | 0.33 | 14.43 | 3.42 |
| T89-24 | 0.34 | 14.52 | 3.46 |
| T89-25 | 0.35 | 15.48 | 3.73 |
| T89-26 | 0.32 | 14.93 | 3.61 |
| T89-34 | 0.33 | 14.68 | 3.54 |
| T89-35 | 0.36 | 15.84 | 3.77 |
| T89-36 | 0.31 | 16.92 | 4.23 |
| T89-37 | 0.31 | 15.95 | 4.02 |
| T89-38 | 0.3 | 13.64 | 3.23 |
| T89-4 | 0.33 | 17.48 | 4.44 |
| T89-6 | 0.3 | 14.5 | 3.55 |

Results from the fibre measurements are presented in table 6.11 as ratios of average fibre length (AFL), average fibre width (AFW), maximum fibre length (maxFL), maximum fibre width (maxFW), minimum fibre length (minFL), minimum fibre width (minFW) of specified construction group relative to corresponding wildtype group.

TABLE 6.11

| Construction Group | Average Fibre Length | Average Fibre Width | Max Fibre Length | Max Fibre Width | Min Fibre Length | Min Fibre Width |
|---|---|---|---|---|---|---|
| TF0109 | 1.11 | 1.08 | 1.25 | 1.23 | 1.13 | 1.10 |

Construction Group TF0116

This construct induces changes in fibre parameters. The average fibre width is 11% higher than of corresponding wildtype group. The maximum fibre width is 20% higher than corresponding maximum wildtype. The TF0116 construction group meets the fibre parameters selection criterion (2) and (4).

Table 6.12 contains fibre measurements data for specified construction group and corresponding wild type group.

TABLE 6.12

| Construction group Individual | Fibre Length (mm) | Fibre Width (μm) | CWT (μm) |
|---|---|---|---|
| TF0116-2A | 0.33 | 14.84 | 3.55 |
| TF0116-2B-1 | 0.34 | 18.24 | 4.52 |
| TF0116-2B-2 | 0.34 | 15.66 | 3.7 |
| TF0116-4A | 0.37 | 15.85 | 3.76 |
| TF0116-5B | 0.33 | 12.15 | 2.82 |
| TF0116-6A | 0.33 | 15.2 | 3.69 |
| TF0116-6B | 0.37 | 16.5 | 3.94 |
| T89-1 | 0.35 | 15.15 | 3.59 |
| T89-12 | 0.34 | 14.79 | 3.44 |
| T89-14 | 0.33 | 12.52 | 2.83 |
| T89-16 | 0.34 | 13.67 | 3.14 |
| T89-18 | 0.34 | 14.25 | 3.28 |
| T89-19 | 0.33 | 13.82 | 3.17 |
| T89-20 | 0.36 | 15.11 | 3.58 |
| T89-21 | 0.34 | 13.42 | 3.14 |
| T89-24 | 0.33 | 14.54 | 3.39 |
| T89-25 | 0.37 | 15.2 | 3.58 |
| T89-26 | 0.35 | 14.12 | 3.31 |
| T89-27 | 0.33 | 13.52 | 3.12 |
| T89-28 | 0.33 | 13.41 | 3.13 |
| T89-3 | 0.3 | 13.3 | 3.18 |
| T89-30 | 0.32 | 12.52 | 2.91 |

Results from the fibre measurements are presented in table 6.13 as ratios of average fibre length (AFL), average fibre width (AFW), maximum fibre length (maxFL), maximum fibre width (maxFW), minimum fibre length (minFL), minimum fibre width (minFW) of specified construction group relative to corresponding wildtype group.

TABLE 6.13

| Construction Group | Average Fibre Length | Average Fibre Width | Max Fibre Length | Max Fibre Width | Min Fibre Length | Min Fibre Width |
|---|---|---|---|---|---|---|
| TF0116 | 1.02 | 1.11 | 1.00 | 1.20 | 1.10 | 0.97 |

Construction Group TFSTT001

This construct induces changes in fibre parameters. The average fibre width is 14% lower than of corresponding wildtype group. The minimum fibre length is 17% lower than corresponding minimum wildtype. The minimum fibre width is 30% lower than corresponding minimum wildtype. The TFSTT001 construction group meets the fibre parameters selection criterion (7) and (8).

Table 6.14 contains fibre measurements data for specified construction group and corresponding wild type group.

TABLE 6.14

| Construction group Individual | Fibre Length (mm) | Fibre Width (µm) | CWT (µm) |
|---|---|---|---|
| TFSTT001-1BX-2 | 0.31 | 11.68 | 2.7 |
| TFSTT001-1BY-1 | 0.3 | 12.11 | 2.83 |
| TFSTT001-1BY-2 | 0.25 | 9.57 | 2.51 |
| TFSTT001-2A-1 | 0.28 | 12.87 | 3.06 |
| TFSTT001-2A-2 | 0.36 | 15.23 | 3.65 |
| TFSTT001-3B-1 | 0.35 | 15.26 | 3.63 |
| TFSTT001-3B-2 | 0.35 | 15.66 | 3.77 |
| T89-16 | 0.35 | 15.93 | 3.82 |
| T89-17 | 0.34 | 15.56 | 3.79 |
| T89-19 | 0.34 | 15.87 | 3.9 |
| T89-2 | 0.33 | 13.88 | 3.25 |
| T89-20 | 0.33 | 14.43 | 3.42 |
| T89-24 | 0.34 | 14.52 | 3.46 |
| T89-25 | 0.35 | 15.48 | 3.73 |
| T89-26 | 0.32 | 14.93 | 3.61 |
| T89-34 | 0.33 | 14.68 | 3.54 |
| T89-35 | 0.36 | 15.84 | 3.77 |
| T89-36 | 0.31 | 16.92 | 4.23 |
| T89-37 | 0.31 | 15.95 | 4.02 |
| T89-38 | 0.3 | 13.64 | 3.23 |
| T89-4 | 0.33 | 17.48 | 4.44 |
| T89-6 | 0.3 | 14.5 | 3.55 |

Results from the fibre measurements are presented in table 6.15 as ratios of average fibre length (AFL), average fibre width (AFW), maximum fibre length (maxFL), maximum fibre width (maxFW), minimum fibre length (minFL), minimum fibre width (minFW) of specified construction group relative to corresponding wildtype group.

TABLE 6.15

| Construction Group | Average Fibre Length | Average Fibre Width | Max Fibre Length | Max Fibre Width | Min Fibre Length | Min Fibre Width |
|---|---|---|---|---|---|---|
| TFSTT001 | 0.95 | 0.86 | 1.00 | 0.90 | 0.83 | 0.70 |

Construction Group TFSTT004

This construct induces changes in fibre parameters. The average fibre width is 15% higher than of corresponding wildtype group. The maximum fibre width is 29% higher than corresponding maximum wildtype. The TFSTT004 construction group meets the fibre parameters selection criterion (2) and (4).

Table 6.16 contains fibre measurements data for specified construction group and corresponding wild type group.

TABLE 6.16

| Construction group Individual | Fibre Length (mm) | Fibre Width (µm) | CWT (µm) |
|---|---|---|---|
| TFSTT004-1A | 0.31 | 14.81 | 3.63 |
| TFSTT004-2A-1 | 0.35 | 16.07 | 3.84 |
| TFSTT004-2A-2 | 0.37 | 19.54 | 4.92 |
| TFSTT004-2B-1 | 0.37 | 16 | 3.86 |
| TFSTT004-2B-2 | 0.35 | 14.67 | 3.53 |
| TFSTT004-3B | 0.3 | 14.73 | 4.13 |
| TFSTT004-4B-1 | 0.35 | 16.72 | 4.1 |
| TFSTT004-4B-2 | 0.37 | 16.21 | 3.88 |
| T89-1 | 0.35 | 15.15 | 3.59 |
| T89-12 | 0.34 | 14.79 | 3.44 |
| T89-14 | 0.33 | 12.52 | 2.83 |
| T89-16 | 0.34 | 13.67 | 3.14 |
| T89-18 | 0.34 | 14.25 | 3.28 |
| T89-19 | 0.33 | 13.82 | 3.17 |
| T89-20 | 0.36 | 15.11 | 3.58 |

TABLE 6.16-continued

| Construction group Individual | Fibre Length (mm) | Fibre Width (µm) | CWT (µm) |
|---|---|---|---|
| T89-21 | 0.34 | 13.42 | 3.14 |
| T89-24 | 0.33 | 14.54 | 3.39 |
| T89-25 | 0.37 | 15.2 | 3.58 |
| T89-26 | 0.35 | 14.12 | 3.31 |
| T89-27 | 0.33 | 13.52 | 3.12 |
| T89-28 | 0.33 | 13.41 | 3.13 |
| T89-3 | 0.3 | 13.3 | 3.18 |
| T89-30 | 0.32 | 12.52 | 2.91 |

Results from the fibre measurements are presented in table 6.17 as ratios of average fibre length (AFL), average fibre width (AFW), maximum fibre length (maxFL), maximum fibre width (maxFW), minimum fibre length (minFL), minimum fibre width (minFW) of specified construction group relative to corresponding wildtype group.

TABLE 6.17

| Construction Group | Average Fibre Length | Average Fibre Width | Max Fibre Length | Max Fibre Width | Min Fibre Length | Min Fibre Width |
|---|---|---|---|---|---|---|
| TFSTT004 | 1.03 | 1.15 | 1.00 | 1.29 | 1.00 | 1.17 |

Construction Group TFSTT017

This construct induces changes in fibre parameters. The minimum fibre length is 17% lower than corresponding minimum wildtype. The TFSTT017 construction group meets the fibre parameters selection criterion (7).

Table 6.18 contains fibre measurements data for specified construction group and corresponding wild type group.

TABLE 6.18

| Construction group Individual | Fibre Length (mm) | Fibre Width (µm) | CWT (µm) |
|---|---|---|---|
| TFSTT017-1A-1 | 0.38 | 14.46 | 3.57 |
| TFSTT017-1A-2 | 0.25 | 12.95 | 3.23 |
| TFSTT017-1B | 0.28 | 12.88 | 3.41 |
| TFSTT017-2A-1 | 0.35 | 16.02 | 3.89 |
| TFSTT017-2A-2 | 0.33 | 13.46 | 3.1 |
| TFSTT017-2B | 0.31 | 13.48 | 3.25 |
| TFSTT017-3A | 0.32 | 14.97 | 3.63 |
| TFSTT017-3B | 0.3 | 12.75 | 3.01 |
| TFSTT017-4B | 0.29 | 11.93 | 2.77 |
| T89-1 | 0.35 | 15.15 | 3.59 |
| T89-12 | 0.34 | 14.79 | 3.44 |
| T89-14 | 0.33 | 12.52 | 2.83 |
| T89-16 | 0.34 | 13.67 | 3.14 |
| T89-18 | 0.34 | 14.25 | 3.28 |
| T89-19 | 0.33 | 13.82 | 3.17 |
| T89-20 | 0.36 | 15.11 | 3.58 |
| T89-21 | 0.34 | 13.42 | 3.14 |
| T89-24 | 0.33 | 14.54 | 3.39 |
| T89-25 | 0.37 | 15.2 | 3.58 |
| T89-26 | 0.35 | 14.12 | 3.31 |
| T89-27 | 0.33 | 13.52 | 3.12 |
| T89-28 | 0.33 | 13.41 | 3.13 |
| T89-3 | 0.3 | 13.3 | 3.18 |
| T89-30 | 0.32 | 12.52 | 2.91 |

Results from the fibre measurements are presented in table 6.19 as ratios of average fibre length (AFL), average fibre width (AFW), maximum fibre length (maxFL), maximum fibre width (maxFW), minimum fibre length (minFL), minimum fibre width (minFW) of specified construction group relative to corresponding wildtype group.

TABLE 6.19

| Construction Group | Average Fibre Length | Average Fibre Width | Max Fibre Length | Max Fibre Width | Min Fibre Length | Min Fibre Width |
|---|---|---|---|---|---|---|
| TFSTT017 | 0.93 | 0.98 | 1.03 | 1.05 | 0.83 | 0.95 |

Construction Group TFSTT038

This construct induces changes in fibre parameters. The average fibre width is 16% higher than of corresponding wildtype group. The maximum fibre width is 21% higher than corresponding maximum wildtype. The TFSTT038 construction group meets the fibre parameters selection criterion (2) and (4).

Table 6.20 contains fibre measurements data for specified construction group and corresponding wild type group.

TABLE 6.20

| Construction group Individual | Fibre Length (mm) | Fibre Width (µm) | CWT (µm) |
|---|---|---|---|
| TFSTT038-1A-1 | 0.35 | 16.43 | 4 |
| TFSTT038-1A-2 | 0.35 | 16.88 | 4.1 |
| TFSTT038-1B | 0.36 | 17.48 | 4.27 |
| TFSTT038-2A | 0.37 | 18.37 | 4.55 |
| TFSTT038-2B | 0.34 | 16.41 | 4.04 |
| TFSTT038-3A | 0.32 | 15.95 | 3.93 |
| TFSTT038-3B | 0.36 | 14.95 | 3.56 |
| TFSTT038-4B | 0.32 | 12.89 | 2.98 |
| T89-1 | 0.35 | 15.15 | 3.59 |
| T89-12 | 0.34 | 14.79 | 3.44 |
| T89-14 | 0.33 | 12.52 | 2.83 |
| T89-18 | 0.34 | 14.25 | 3.28 |
| T89-19 | 0.33 | 13.82 | 3.17 |
| T89-20 | 0.36 | 15.11 | 3.58 |
| T89-21 | 0.34 | 13.42 | 3.14 |
| T89-24 | 0.33 | 14.54 | 3.39 |
| T89-25 | 0.37 | 15.2 | 3.58 |
| T89-26 | 0.35 | 14.12 | 3.31 |
| T89-27 | 0.33 | 13.52 | 3.12 |
| T89-28 | 0.33 | 13.41 | 3.13 |
| T89-3 | 0.3 | 13.3 | 3.18 |
| T89-30 | 0.32 | 12.52 | 2.91 |

Results from the fibre measurements are presented in table 6.21 as ratios of average fibre length (AFL), average fibre width (AFW), maximum fibre length (maxFL), maximum fibre width (maxFW), minimum fibre length (minFL), minimum fibre width (minFW) of specified construction group relative to corresponding wildtype group.

TABLE 6.21

| Construction Group | Average Fibre Length | Average Fibre Width | Max Fibre Length | Max Fibre Width | Min Fibre Length | Min Fibre Width |
|---|---|---|---|---|---|---|
| TFSTT038 | 1.03 | 1.16 | 1.00 | 1.21 | 1.07 | 1.03 |

Example 7

Selected Constructs Used for Tobacco Transformation
Tobacco Transformation

Based on growth data from poplar experiments, a selected set of constructs, namely CaMV 35S: over-expression DNA constructs TF0097, TF0132 and TFSTT019, were used for transformation into tobacco (*Nicotiana tabacum* cv. SR1). Plants were transformed and regenerated essentially as described in Nilsson et al. (1992), but using leaf disc explants.

Approximately 10-15 independent lines were generated for each construct. One such group of transgenic plants produced using one construct is hereafter called a "construction group", e.g. different transgenic plants emanating from one construct. Each transgenic line within each construction group, e.g. TF0555-01, TF0555-02, TF0555-03 and so on, are different transformation events and therefore most probably have the recombinant DNA inserted into different locations in the plant genome. This makes the different lines within one construction group partly different. For example it is known that different transformation events will produce plants with different levels of gene over-expression.

Plant Growth

The transgenic tobacco plants, comprising three construction groups each having 9-15 independent lines, were grown together with 14 wildtype control plants, in a greenhouse under a photoperiod of 18 h and a temperature of 22° C./18° C. (day/night). The plants were fertilized with Weibulls Rika S NPK 7-1-5 diluted 1 to 100 (final concentrations $NO_3$, 55 g/l; $NH_4$, 29 g/l; P, 12 g/l; K, 56 g/l; Mg 7.2 g/l; S, 7.2 g/l; B, 0.18 g/l; Cu, 0.02 g/l; Fe, 0.84 g/l; Mn, 0.42 g/l; Mo, 0.03 g/l; Zn, 0.13 g/L). Plant height and diameter was measured regularly during growth in the greenhouse.

Observed growth effects in tobacco transformants included faster regeneration of tobacco plants transformed with construct TF0132, where regenerated plantlets had markedly larger leaves during early tissue culture phases. Also, in tobacco plants transformed with either of the selected constructs (i.e. TF0097, TF0132 or TFSTT019) a longer period of vegetative growth and hence later flowering than wild-type SR1 plants was observed.

REFERENCES

Aharoni et al. 2000 Plant Cell 2000 (12) 647-662
*Arabidopsis* Genome Initiative 2000 Nature. 2000 Dec. 14; 408(6814):796-815
Brady and Provart 2007. Journal of the Science of Food and Agriculture Vol 87, Pp 925-929.
Burke et al 2007. Current opinion in genetics and development vol 17, 525-532
Chern et al. (2001) Plant J. 27: 101 113
Fan and Dong (2002) Plant Cell 14: 1377 1389
Feng and Doolittle (1987) J. Mol. Evol. 25: 351 360
Gilmour et al. (1998) Plant J. 16: 433 442
Henikoff, Till, and Comai, Plant Physiol. 2004 June; 135(2): 630-6.
Hertzberg et al. 2001 Proc. Natl. Acad. Sci. USA, 2001 (98), 14372-14737,
Higgins et al. (1996) Methods Enzymol. 266: 383 402
Ichikawa et al. 1997 Nature 390 698-701;
Jaglo et al. (1998) Plant Physiol. 127: 910 917
Jin and Martin 1999 Plant Mol Biol 41 (5) 577-585
Journot-Catalino et al (2006).Plant Cell 18(11), 3289-3302
Kakimoto et al. 1996 Science 274: 982-985
Karimi, M. et al., Trends In plant Sciences 2002, Vol 7 no 5 pp 193-195.
Katou et al 2005 Plant Physiology, 139(4), 1914-1926
Kosugi and Ohashi, (2002) Plant J. 29: 45 59
Lee et al. (2002) Genome Res. 12: 493 502
Lichtenstein and Nellen (1997), Antisense Technology: A Practical Approach IRL Press at Oxford University, Oxford, England.
Moyle et al 2002 Volume 31 Issue 6 Page 675-685
Neurath H. and R. L In, The Proteins, Academic Press, New York.

Ng et al. 2007 Biochim Biophys Acta. 2007 May-June; 1769 (5-6):316-29

Nilsson et al. (1992) Transgenic Research 1, pp 209-220.

Ratcliffe et al. (2001) Plant Physiol. 126: 122 132

Remm et al. (2001) J. Mol. Biol. 314: 1041 1052

Riano-Pachon et al 2007. BMC Bioinformatics 2007, 8:42

Riechmann et al. 2000 Science 2000, vo1290 pp 2105-2110

Rognes T, 2001, Nucleic Acids Research, 29, 1647-1652, 1989.

Sambrook et al., Molecular Cloning: A Laboratory Manual, 2nd Ed., Cold Spring Harbor, Schrader et al. 2005 Plant Cell, (16), 2278-2292

Slade and Knauf, Transgenic Res. 2005 April; 14(2):109-15

Sterky et al. 2004 Proc Natl Acad Sci USA. 2004 Sep. 21; 101(38):13951-13956

Thompson et al. (1994) Nucleic Acids Res. 22: 4673 4680

Tuskan et al. 2006 Science. 2006 Sep. 15; 313(5793):1596-604

Ülker and Somssich 2004. Current Opinion in Plant Biology. Vol 7, Issue 5, Pp 491-498

Varshney et al 2005. Trends in Plant Science, Vol 10, 621-630.

Vasil et al. 1984, Cell Culture and Somatic Cell Genetics of Plants, Vol I, II and III, Laboratory Procedures White et al. 1999 Science 1999 (286) 2187-2184

Xiaoxing et al 2006 Plant Physiol. 2006 August; 141(4): 1167-1184

US 20020168707
US 20030226173
US 2003101481
US 20040019927
US 20060195944
US 20060272060
US 20070022495
US 20070039070
U.S. Pat. No. 4,987,071
U.S. Pat. No. 5,107,065
U.S. Pat. No. 5,231,020
U.S. Pat. No. 5,543,508
U.S. Pat. No. 5,583,021
U.S. Pat. No. 6,506,559
U.S. Pat. No. 7,238,860
U.S. Pat. No. 7,265,263
WO 2001035727
WO 2001036444
WO 2002015675
WO 2004087952
WO 2007003409
WO 2004097024
WO 2006078431
WO 91/14772
WO 96/06166
WO 98/53057
WO 98/53083
WO 99/53050
WO 99/61631

The invention claimed is:

1. A method of producing a tree having an increased growth and/or biomass compared to its wild type, said method comprising transforming said tree with a nucleic acid comprising a promoter operably linked to a polynucleotide encoding a functional gene product comprising a polypeptide sequence having at least 95% sequence identity to SEQ ID NO: 24, wherein said increased level of the functional gene product results in an increase in growth and/or biomass in said tree.

2. The method according to claim 1, comprising:
  (i) providing an expression vector comprising a nucleic acid that encodes a polypeptide having at least 95% sequence identity to SEQ ID NO: 24 and at least one regulatory element operably linked to the nucleotide sequence;
  (ii) introducing the expression vector into at least one plant; and
  (iii) selecting at least one transgenic plant that has an increased growth and/or biomass compared to its wild type.

3. The method according to claim 1, comprising
  (i) selecting plant species with high expression of the polypeptide having at least 95% sequence identity to the polypeptide shown as SEQ ID NO: 24;
  (ii) crossing a plant species selected in (i) with the same or another plant species selected in (i),
  (iii) selecting plants with increased expression of the polypeptide having at least 95% sequence identity to the polypeptide shown as SEQ ID NO: 24 compared to the plant species selected under (i);
  (iv) backcrossing one or more times the plants obtained in (iii) and selecting plants with increased expression of the polypeptide having at least 95% sequence identity to the polypeptide shown as SEQ ID NO: 24 compared to any of the plant species used in (i) and/or plants obtained in (iii).

4. The method according to claim 1, wherein the nucleic acid encodes a polypeptide comprising a conservatively substituted variant having at least 95% sequence identity to SEQ ID NO:24.

5. The method according to claim 1, wherein the nucleic acid which encodes the polypeptide shown as SEQ ID NO: 24 comprises a silent substitution.

6. A tree having an increased growth and/or biomass compared to its wild type, said tree being transformed with a nucleic acid comprising a promoter operably linked to a polynucleotide encoding functional gene product comprising a polypeptide sequence having at least 95% sequence identity to SEQ ID NO: 24, wherein said increased level of the functional gene product results in an increase in growth and/or biomass in said tree.

7. The tree according to claim 6, wherein the nucleic acid encodes a conservatively substituted variant having at least 95% sequence identity to SEQ ID NO:24.

8. The tree according to claim 6, wherein the nucleic acid comprises a silent substitution.

9. A tree cell or plant progeny of the tree according to claim 6, wherein said tree cell or said plant progeny of the tree comprises said functional gene product.

10. Wood produced by the tree according to claim 6.

* * * * *

UNITED STATES PATENT AND TRADEMARK OFFICE
CERTIFICATE OF CORRECTION

PATENT NO.        : 8,937,219 B2
APPLICATION NO.   : 12/810966
DATED             : January 20, 2015
INVENTOR(S)       : Magnus Hertzberg et al.

It is certified that error appears in the above-identified patent and that said Letters Patent is hereby corrected as shown below:

Title Page

Page 1 (item 73, Assignee) at line 1, Change "Sweetree" to --Swetree--.

In column 2 (page 2, item 56) at line 70, Under Other Publications, change "ncbi.nlmnih" to --ncbi.nlm.nih--.

Specification

In column 1 at line 46, Change "worlds" to --world's--.

In column 4 at line 31, Change "defense" to --defence--.

In column 6 at line 9, Change "rate;" to --rate.--.

In column 13 at line 36, Change "abscissic" to --abscisic--.

In column 13 at line 58, Change "50fold," to --50-fold--.

In column 22 at line 29, Change "FIG." to --fig--.

In column 25 at line 29, Change "FIG." to --fig--.

In column 31 at line 1, Change "e.g" to --e.g.,--.

In column 31 at line 7, Change "(0.2nd)" to --0.2--.

In column 141 at line 19, Change "genes" to --genes.--.

In column 172 at line 18 (approx.), Change "Signifcant" to --Significant--.

In column 177 at line 56, Change "21" to --2)--.

In column 201 at line 9, Change "vol290" to --Vol 290--.

Claims

In column 379 at line 60, In Claim 2, change "24and" to --24 and--.

In column 380 at line 61, In Claim 3, change "24compared" to --24 compared--.

In column 380 at line 67, In Claim 4, change "NO:24." to --NO: 24.--.

Signed and Sealed this
Tenth Day of November, 2015

Michelle K. Lee
*Director of the United States Patent and Trademark Office*

In column 381 at line 7, In Claim 6, after "encoding" insert --a--.

In column 381 at line 14, In Claim 7, change "NO:24." to --NO: 24.--.

SEQUENCE LISTING

```
<160> NUMBER OF SEQ ID NOS: 203

<210> SEQ ID NO 1
<211> LENGTH: 1044
<212> TYPE: DNA
<213> ORGANISM: Populus trichocarpa

<400> SEQUENCE: 1
atggctgtgg agcttatgat ggggtattct ggtgatagtt ttgctacaaa aatgcaagag      60
aatgatgtga gagaagccgc aactgctggg atacaaagcg ttgaggaagt cataaaactg     120
ctcaaacaaa atcaactgga acagcaacaa aaacaacaat actaccaaga gttgtctgca     180
gcctcttcaa gttccaatct tggcacggat aatatcatgg ctgttactga tatggccgtg     240
aacaatttca aaaaggttat ttctttactg ggtcgcacca caagaactgg ccatgctcga     300
tttagaagag ctcctgttgc ctgccctcct caacaacaaa tacaagaacc agaaccagga     360
ccgcaacagc aaaaacagca accaccagag caaggctctg cttttagagt ttatcaaccg     420
accccaattc atcgtctccc tcctttgcct cacaatcagc aacaaaagac actgctggtt     480
acgaaaaatg gattatcaga tcggaatgaa atggctacta cgatcaattt cgctaattcg     540
ccaacaatat ctgctccttc tttcttgtct ctttaacag gggaaactga tagcttccag      600
tgttctaagt cttctgggtt tcagtttacc caaccttctg ctggtaaacc tcctttgtcc     660
tcttcttctc ttaagagaaa gtgcaactcc atggatgatg ctgctctcaa gtgtggctct     720
tcttctagtc gctgccactg ctccaagaaa agcaggaaat caagaattaa aagggtggtt     780
agagttcctg caattagtag taagatggct gatatcccac ctgatgatta ttcctggaga     840
```

| | | |
|---|---|---|
| aagtatggcc aaaagcccat caaaggctct cctcatccca ggggatacta caagtgcagt | 900 | |
| agcgtgagag gatgtccggc acgcaaacac gtggagagag ctctagatga ctcgatgatg | 960 | |
| cttattgtga cctatgaagg ggaacacaac cactctcatc caatcgatga tgcacctggt | 1020 | |
| gctcttgtcc ttgaatcatc ttaa | 1044 | |

```
<210> SEQ ID NO 2
<211> LENGTH: 474
<212> TYPE: DNA
<213> ORGANISM: Populus trichocarpa

<400> SEQUENCE: 2
```

| | |
|---|---|
| atgtctttga acatgatcaa ctcttatgct tctaccgact ttgaaggtac tagggggaaat | 60 |
| ggattgttgg gattgatgca agagatgcaa gctccagcca gtttaaattt tgatgacatc | 120 |
| tctcagaaca gaggctttgt tgggtctgga attgagggga aattgggaaa gaataaggga | 180 |
| gaaaagaaga taagaaagcc caagtacgct tttcaaacaa ggagccgagt tgatatcctt | 240 |
| gatgatggat atcgatggag aaagtatggt caaaaggccg tcaagaacaa caaatttccc | 300 |
| agaagctact atcggtgtac acatcaaggg tgcaacgtga agaagcaggt tcagagatta | 360 |
| acaaaagacg aaggagtcgt ggtgacaacc tatgaaggaa tgcattctca tcagatcgaa | 420 |
| aagtctccag ataacttcga gcatatcttg agccagatgc aaatctactc ctga | 474 |

```
<210> SEQ ID NO 3
<211> LENGTH: 1428
<212> TYPE: DNA
<213> ORGANISM: Populus  trichocarpa

<400> SEQUENCE: 3
```

| | |
|---|---|
| atggagatca aggaatcaga gagggtggtt atagctaaac cagtagcttc caggcctagt | 60 |
| tactcaaatt ttacgtcttt ctcagagttg cttgcgggtg ccatcaatac cacaccctct | 120 |
| aatgtttgtt ctggaacagc agttgctgcc attagaccaa aaacagtgag gttcaggcca | 180 |
| ctggtgaatc gtgctccagg tgcactggtt tcttcacagg ctggactctc tggaacagca | 240 |
| gttagcaatt cgtttaataa agcttcaagt actgatagca aagccactat catatataaa | 300 |
| ccacaggcaa agcttgtgtc aaaggcaact gttctctac tggcgaatat gggaaacttc | 360 |
| aatactaatt cacaacaaat gttacaacca gttgagactc gtcctcagct ttcaaaacaa | 420 |
| gataaacaca atttctcatc ccagcttacc tcaaatcctc atcagaatat tccatcccct | 480 |
| gcagaagcag accacacaac tgaacccta aggttaacat ctctgaacca ggaggaggat | 540 |
| cctaaaactt tatctcatgc atctaatggg gaccgacctt catatgatgg ttataattgg | 600 |
| aggaaatatg gacaaaagca agtaaaagga agtaatatc cacggagcta ctacaagtgc | 660 |
| acctatccaa actgtccagt gaaaaagaag gtcgaaagat catttgacgg gcagattgca | 720 |
| gaaattgtct acaaggggga acacaaccat tcaaagcctc agcctccaaa gcgcaactca | 780 |
| tcaggaacac aaggactatc tgatggcaat gctccagata ggaacagcat cccattatgg | 840 |
| agtaatcaac tcaatgaaag aaatgaaggc tctgaaggta gagaagaaaa tcagaatgaa | 900 |
| attggattac cagtgcattc aatttatcag ggtaaagctc caccatctta tgatcctgct | 960 |
| ggaaccggca caattaatgc tggtacggga acttctgata actcatgtgg tgtcagcggg | 1020 |
| gaatgtgatg atggaagcaa gggattggag ggagccaatg atgaacctaa agtaaaagga | 1080 |
| aggaaaactg agatacaatc cactgaaggt ggcatgtcag ggagggagt acaagagccc | 1140 |
| cgtgtagtgg tgcaaagttc cacagattct gagattttgg gggatggttt tcgatggaga | 1200 |

```
aaatatgggc agaagattgt gaagggaat  ccatatccca ggagttacta tagatgtacc    1260
agtatcaaat gcaatgttcg caagcatgtg gaaagagtat cagatgatcc aagagctttt    1320
attacaacat atgaaggaaa acataaccat gagatccctc tgaagagcac aaacctagca    1380
gcctttgaac ctgattcaca ggcacctact actagagtca agcagtga                 1428
```

<210> SEQ ID NO 4
<211> LENGTH: 1068
<212> TYPE: DNA
<213> ORGANISM: Populus trichocarpa

<400> SEQUENCE: 4

```
atggaggagg ttgaggaggt acacaaggca gctattgaga gctgcaatag agttattggc     60
cttttgtgtc aacaaaaaga tcaagtccag ggtaggaact taatggtgga aactagagag    120
actgtgttta agtttaagag agttatatct cttttaagca ctggtttagg tcatggaaga    180
gtaagaaaga tgaagaagct tagaccatct ttgccccaaa acatcttcct agatagtcct    240
aattgcaaaa cagttttatc accaaaacct ctccaaatgg tgcctcctaa ttttcttgaa    300
accccactta ctgacatgga tgctaagtct aaaccttcta tccaaatttc ccagaaaatg    360
cttcttgaaa acccagtact tgagttgaac tcaaatatca ggcccctgt  gcaaattatg    420 caaacaaaac caccacaaaa cttccagctt ctccaacagc atcagcagac acaggatg     480 cactttcagc agcagcagca gcagcaaatg aagtatcagg ctgatagggt gtattctagg    540
agtaatggtg ggataaacct taagtttgat gggtctactt gcacaccaac catgtcatcc    600
acaagatcat tcatatcatc tctgagcatg gatggtgctg tgtctacttt tgatggagac    660
tctttccatt tgattggtat gcctcactca tctgatcaca tctcacaaca aacaaggagg    720
aggtgttctg gtagaggaga agatgggaat gccaaatgtt ctagcagtgg taaatgccat    780
tgttcaaaga ggaggaaact gagggtgaag agatctatca aagttcctgc aattagcaac    840
aaggtggcag atattcctcc tgatgagtat tcatggagga agtatggaca aaagccaatt    900
aagggctctc cgcatcctag gggatactat aaatgtagca gtctgagggg ttgcccggca    960
aggaagcacg ttgagagatg cctggaagac ccttcaatgc taattgtaac ctatgaaggt   1020
gagcataacc attccaggtt gatctcatca cagtctgcgc atacatga                1068
```

<210> SEQ ID NO 5
<211> LENGTH: 2157
<212> TYPE: DNA
<213> ORGANISM: Populus trichocarpa

<400> SEQUENCE: 5

```
atggctggga ttgatgataa cgttgctata attggtgatt gggtacctcc tagtccaagt     60
ccaagagctt ttttctcagc aatgttaggt gatgatatta actcaagaac aatcccagaa    120
tctcctgggg agaaaagaaa tgaagggctc tatctgggac aaccagagca gatggcaaca    180
ggaaattctg agaaaaagga tggagcacaa actagtggtg ttcagttgac tgaattaggt    240
acattttctg agcaaaaatc aaactttcgt ggaggtcttg ttgaaagaat tgcagccaga    300
gctggattta atgcaccgcg gttgaataca gaaagtatca ggtccactga agttctatg     360 aaccctgaga ttaggtcgcc ttatttgaca ataccacctg gtctcagccc gacaaccttg    420
ctggaatctc cagtttttcct ttcaaatttg gcacagccat ctccaacaac tggaaaattt    480 tcttttttttc caaatggtaa caccaagaac tccacagtgg gctctgaccc tcctgataaa    540
```

-continued

| | |
|---|---|
| agtaaagaaa cttctttga caacattgat tcatcttcat ttgcgttcaa gcctatggga | 600 |
| gaatcaggtt cttttttcct tggtggaaca agcaagcaat cctttcccag tatcgatgtt | 660 |
| tctgttcact ctgagaatgc ttttcagtcg catggtgtgg aacccgccaa aactcagttt | 720 |
| gagagtagaa acagcctcca tttccgagca gaattctcca aattgactac tgaaaaggat | 780 |
| aatggatgta ttactgtagc agatcagagg acctttgaca ctgttgctgg caacgccgag | 840 |
| cattcttccc ctcttgctga gcaacaagat gaagaaggag atcaaagagc cagtgaagat | 900 |
| tcaatggctg ctggaggcac accatctgag gatgcatata attggagaaa atatgggcag | 960 |
| aaacaagtaa aaggcagtga gtatccacgg agttattaca agtgcacgca tccaaattgc | 1020 |
| ccagttaaga gaaagtggaa cgttctcat gagggccata taacagagat catatataag | 1080 |
| ggggcacaca accatcccaa gccaccaccc aaccggaggt cagccactgg atcaatggat | 1140 |
| acacaactgg atattcctga caagctggg ccacaggttg gtgctgttaa tgattcggtt | 1200 |
| tgggcaggta cacaaaaagg aactgctgca ggaactcctg attggaggaa tgacaatgtc | 1260 |
| gaggtttcat cttcagcatc tgggggccta ggccctgaat tcgggaatcc atcttcctcg | 1320 |
| gtacagggtc agagcggaac tccctttgag tcagctgatg ctgtggatgc ctcgtctacc | 1380 |
| ttttcaaatg atgaagatga tgatcgggct acacatggca gtgtaggtta tgatggtgaa | 1440 |
| ggagaagaat ctgagtccaa gagaaggaaa gttgaaacat atgcaaccga aatgagtgga | 1500 |
| gccaccagag caatccgtga gcctagagtt gtggtccaga caaccagtga ggtggatatc | 1560 |
| cttgacgatg gatatcgctg gagaaagtat ggacagaaag ttgttaaagg aaatccaaat | 1620 |
| cctaggagtt attacaagtg cactagcgca ggctgcacag tgagaaagca tgtggagagg | 1680 |
| gcatcgcatg accttaagtc agtgatcact acgtatgagg ggaagcacaa tcatgatgtc | 1740 |
| cctgctgctc gcaatagcaa ccatgtcaac tctggcacct ctaatgccac accagcccaa | 1800 |
| gctggcatcg cagttcaaac ccaagttcac agacctgagg catcccaagt tcacaacagc | 1860 |
| atgactagta gatttgagag gcctcctgca tttggatcct tcaggcagca gctgggcct | 1920 |
| tcggctggct tctcatttgg aatgaatcaa cctgggtttg ccaatatggg aatggctggg | 1980 |
| ttaggtccag ggcaaccaag gatgccagtt atgcccatgc atccatactt agcacagcaa | 2040 |
| cgtgcagtga atgaaatggg gttgatgatg ccgaaaggag aagcaaaggt ggagccagtg | 2100 |
| acctccaaca atccaacagt gtatcagcaa ataatgagta ggctgcctca gatgtaa | 2157 |

<210> SEQ ID NO 6
<211> LENGTH: 906
<212> TYPE: DNA
<213> ORGANISM: Populus trichocarpa

<400> SEQUENCE: 6

| | |
|---|---|
| atggctgtgg atctagttag gtattcaaag atggaagatc agatggctat acaagaagct | 60 |
| gcatcagctg ggctcgagag catggagcac ttgatctttg cattctctaa ccaaactcga | 120 |
| caaagccacc aacttgactg cggagaaatc acaaacttca ccgttgctaa gttcaagcaa | 180 |
| gtcatctcca tgttgaaccg gaccggtcat gcccgttttc gccgtggacc aacttcttct | 240 |
| ccttcttcct acccggttcc cgtccgacct gtccctcaag agcctcaaaa actgaacctt | 300 |
| gattttgtta acagtaatag ccccctaaa gctgagtcga aaaatgacct gtctttgggt | 360 |
| agtcagtatt caaggataga ccttagctct ggcaccacta cctcatcctt cgtgtcttct | 420 |
| gttacagctg atgggagtgt ctctaatggg aaacaaggtg gctcttctct tttcggaact | 480 |
| caagcgcgat ctaccggaaa accacctctc tcatcgaccc accgcaagaa atgccacgat | 540 |

| | |
|---|---|
| catgccctct ccgccagaaa gatctcctcc ggtggaagct gtcattgctc caaaagaagg | 600 |
| aaatcaaggg ttaagaggac aataagggta ccagccgtga gttccaagat tgccgatata | 660 |
| ccagcagatg agtactcatg gagaaaatat ggtcaaaagc caatcaaggg ctcaccatac | 720 |
| ccaagagggt attacaagtg tagcagtgtt agaggatgtc cagcaaggaa gcatgtggag | 780 |
| cgtgccgtag atgactcggc catgcttatc gtgacttacg agggggagca ccgtcactca | 840 |
| catactccgt tgccgggaga cgtcaccgcg agtgctgcaa tgcgacacgt gtttcactca | 900 |
| acatga | 906 |

<210> SEQ ID NO 7
<211> LENGTH: 1044
<212> TYPE: DNA
<213> ORGANISM: Populus trichocarpa

<400> SEQUENCE: 7

| | |
|---|---|
| atggagggg ttgaagaagc taaccgggca gctgtggaga gctgccatag agttataagt | 60 |
| ttgctatccc aaccccaaga tcaggttcaa tataggaatt taatggtgga aactggagag | 120 |
| gctgtgttta ggttcaagaa agtagttttcc cttttaaata ctggtttagg tcatgcaaga | 180 |
| gttcgaaaac ttaagaagtt accgaccct ttatcccaaa gcatcctctt agacaaccca | 240 |
| ctgagcagta cagaccaccc atccaaaaca ccccagtttc tccagtccag tagttacctg | 300 |
| gaaagccaac caattcaaga attgggctca attgctaaaa attgtctatc tttgggaacc | 360 |
| ccatccctgg aattgagttc aaatgggaaa aaccctcttc agcttggcca acccacgcca | 420 |
| gcagcgcact atcagttcct tcagcaacag caactgcata ggctacagct tcaacagcag | 480 |
| cagcaaatga agcagcaagc tgagatgatg tttagaaaaa gcaatagtgg gattagcttg | 540 |
| aatttcgata gttctagctg cactcctaca atgtcatcta ccagatcttt tatatcgtcc | 600 |
| ttgagtattg atggtaatgt ggctaatttg gaaggaagtg cattccattt aacgggggcg | 660 |
| gctcgctcct cagatcagag ttcacagcaa cacaagagga aatgttctgg aaggggagaa | 720 |
| gatggaagta tgaaatgtgg aagcagcgtt agatgtcatt gctcaaagaa gaggaaacat | 780 |
| agggtgaaga ggtcgatcaa ggttcctgct attagcaaca agcttgctga tatccctcct | 840 |
| gatgattact catggagaaa gtatgggcaa aagccaatca agggttctcc tcatcccagg | 900 |
| ggatattaca aatgtagcag tatgagaggt tgtcctgcaa ggaagcatgt ggagaggtgc | 960 |
| ttggaagatc cgtccatgct tattgttacc tatgaaggtg aacataacca cccaaggatt | 1020 |
| ccagcacaat ccacaaacac gtaa | 1044 |

<210> SEQ ID NO 8
<211> LENGTH: 1098
<212> TYPE: DNA
<213> ORGANISM: Populus trichocarpa

<400> SEQUENCE: 8

| | |
|---|---|
| atggaattgt ccatggaatg ggagcacaag actctaataa gtgagctaac tcaagggaaa | 60 |
| gagctagcga acagcttag caaccatctt aacccttcct catctctcga agcacgtcaa | 120 |
| ttcctagtgg ataagatact ttcttcttat gagaaagcac tttcaatgct aaattggggg | 180 |
| gctttggctg ctgatcaacc aaagcccaca attggcacag tcgaaccact gcattcattt | 240 |
| gccaacagta gtcctaggag tgaggtctct gatcaggatt gcaaggagga atgtaacaaa | 300 |
| gatgtttaca agaagagaaa aatacaacct cgatggactg agcaagtgaa ggattgttca | 360 |

-continued

| | |
|---|---|
| gggaccggtc tagaagggcc tcttgatgat ggttatagct ggaggaaata cgggcaaaag | 420 |
| gatattctcg gagctaattt tccaagagga tactacagat gcactcaccg ccattcccaa | 480 |
| ggctgtttgg ccacgaagca agtgcaaaga tcagatgagg accattcaat ttttgaagtg | 540 |
| acctatcgag ggagacatac atgtaaccaa gcctctcctt cacccgtggc atcgccttcc | 600 |
| ccaaaaaatg attgctcaaa acaaagcaag tatcatcgta agcagcagca gcagcgtcaa | 660 |
| gagaaaccaa agccaacaga ggagatattt gttaactttg gatcagacat tgttcaagtt | 720 |
| aaaaatgagg acttgggctc caaggacgac attttcccat ccttttcctt cccatgtaca | 780 |
| tcattcggga atgaaaacga ggaaaacaac attttcaccg agtccatgat ggaaaacaac | 840 |
| ttcttgggta gcttttctcc aacatttata tctccggcaa catctgaatc caactacttc | 900 |
| tcaatgtcac catgccatat gaacagcttt ggaataggtt accaaaatgt gcagacccca | 960 |
| gagtctgaac tcaccacgga gataatatca gccccaactt cggtaaccaa ttcaccaatc | 1020 |
| ggggattttg atatctcaat cgataatgta gattttgata ccaccttccc atttgacaac | 1080 |
| ccagatttct ttgcttaa | 1098 |

<210> SEQ ID NO 9
<211> LENGTH: 1074
<212> TYPE: DNA
<213> ORGANISM: Populus tricocharpa

<400> SEQUENCE: 9

| | |
|---|---|
| atgatggaag aactttacgg tcttcaatcc accagctctg attactcttt gcaggttcca | 60 |
| tcagagaaca tggtttctcc agtggctaat tactaccatc ctgtggggtt cacctcccca | 120 |
| gctggggagc catcatttcc tgttttggga tcggagcaga tgttttgtgg ttcctcagta | 180 |
| tctgatgctg cttcaatggg ggccgagttg catcagaagc agcagcagca gagtgggggt | 240 |
| gttggtgttg gtgatcatag taatagaaat aattcagagg aggtttcttg tgcaattagg | 300 |
| gctaaaattg cttctcaccc gctttaccct aagttacttg aagcttatat tgattgccag | 360 |
| aaggtgggag caccgccgga gatggcttat ttattagatg aaatccggct agtgaatgat | 420 |
| gtttccaagg ggtccaatga tactgtcgcc tcttgcttgg gtgccgatcc cgagctcgac | 480 |
| gagttcatgg aaacttactg tgacgttctg atgaagtata agcggatct ctcaaggcct | 540 |
| ttcgatgaag ccactacttt cttgaatgat atagaagctc agtttaatac tctctgcaac | 600 |
| ggtccttcca gaagccaagt ttatggtctc cctctctctc tctcactctc tattttacta | 660 |
| ctcagtatgt tatctaatga agctgctggt tcatctgatg aagatgccag tggaggagag | 720 |
| gcaggcatgc aagattcaac ccgtataaac gaggatcgag agctgaagga caaactatta | 780 |
| cgtaaatata gtggttacat aagtacccta agcatgcgt tttcaaaaca gaagaagaaa | 840 |
| ggaaaactac caaaggaagc aaggcaaatc ctgttaaact ggtggaacat tcataacaaa | 900 |
| tggccatacc caacggaagc tgataaggtt gctttggccg aatcaactgg cctagatcag | 960 |
| aaacagataa acaactggtt catcaatcaa aggaaacgtc actggaaacc atcagagaac | 1020 |
| atgcaatttg ctgttgtgga tagtctgtat ggtcccttt tcatgaacga ctga | 1074 |

<210> SEQ ID NO 10
<211> LENGTH: 1707
<212> TYPE: DNA
<213> ORGANISM: Populus tricocharpa

<400> SEQUENCE: 10

| | |
|---|---|
| atggaaagag ataagttgtt tgtgagcgag ggagccaaca cagcagcaac catttggaat | 60 |

```
tcttgcagtt ttggaatgga aatgcaagcc aatgagctga gttgcggtcc agagaaactt    120
gccaattgct ttctcaatcc caattgggac aactcattgg atcagagcga tcccttcgag   180
tctgctttga gctccattgt ctcatcacct gttgcatccg gtgccaacgc aaacgccaac   240
gccattccta atgctggcgt tggtggtgac agtcttatga ttagagaact tattggaaga   300
ctaggaaaca tttgcaattc tggagacatt tcactacaat cttttgttaa caataataac   360
aatagcacta cacttcttg ctatagtacc ccaatgaatt cccctccaaa gctgaatctc    420
tcgatgatgg attcacaaat gagaggaaac ctgccaattc tggaaacag cgtagtaaag    480 catccaggtt tagcaccatt tccagctgat tttgtagaga gggctgcacg atattcttgc   540
tttggtagca acaatcctgg aggcatcaat aaacaattcg gattgaatga atccgaattg   600
attaataggt tgatgccacg agtagaacct ggtaagctct cgagagtttc gagtaacaat   660
tcaatgaagg tcactgtatc gcaagcaaat gttcaagaaa gcaacaagag ctcaccccag   720
gatgggagtt tgaattctga aagaaattc agtaggcagt caaggcctac aacatcagag    780
aatggagatt ccagggaaga atcttcattg tctgagcagg tcccaggtgg gaaattgagc   840
atgaaatccc agaatgacgc caattccagg aaaagaaaat caattcccag aggaaaagcc   900
aaagaaactc cctcttcatc tccatctgct tctgatgtca aggttgcagc agagaatgat   960
gaatcgaagg caaaagaag caaatcggat gaaactaatg gcagtgacaa ggatacagca   1020
aaggaaaagg aagaagaaaa tggaaatcag aaacagaaca aaataattc aaagccgcca    1080 gagccaccaa aggattatat ccatgtcaga gccagaaggg gtcaggctac agatagccac   1140
agtcttgctg aaagagttag aagagagaaa atcagtgaaa gaatgaagtt cctccaggat   1200
cttgttcccg gatgcaataa ggttactggg aaagcagtga tgcttgacga gattataaac   1260
tatgtacagt cattgcagcg ccaggttgag tttctgtcaa tgaagttgtc atctgtgaat   1320
ccgaggatgg agatcaacat ggaaacttg ttgtccaagg atattttcca atcccgtgga   1380
tctatgccac atagtcttta tccattagat gcctccacgc cggtattccc ttatggttac   1440
caatcccagc aagggttagc cctgcaaaat ggcatgccaa gcaatgccga acccagttc    1500 tctatgaacc cattaaatgc tgcgttgcgg cgaaacccga gcatgcattt gccacacctt   1560
gatggtttcg gtgatcctgc tgctcttcag gcctcagcca tgtgggaaga cgaccttcaa   1620
agtgttgtgc agatgggata tggtcagaat catcaggaga gctttcaagg ctcagtgccc   1680
tcaactcaca tgaaaattga gctataa                                        1707
```

<210> SEQ ID NO 11
<211> LENGTH: 1176
<212> TYPE: DNA
<213> ORGANISM: Populus tricocharpa

<400> SEQUENCE: 11

```
atgtctgttg gtgtaaacac agaaaccccta gtgagagttg aggagataca aggaagagga    60
agagggcttg tatccactca gcccttaaga ggtggccaaa tcgtcctcat agattctcca   120
atcctcctct attctgcact ccctttaacc aaacagcaac actcaacctt cctttactgt   180
gacaaatgct tcaaaactat acaatcagca tcagtatctt gtcccacctg ctctcaccag   240
cgtttctgta gccccacttg cctttccgct gctctggcat cttctcacac tccttgggtc   300
tgccaatctc ttagccgcct ccgcgactgc caagattttc tacagcatca ttctgtggaa   360
cgacaaatcc aagctcaatt cctcgttgct gcttacaatc ttgcattcgt ttcacccttcg  420
```

```
gattttcaaa ttttgctgtc gctgcaaggc cgcgctgaag atgaagatcc agctattgtc      480
cagtctctgc attctgtaat ctcatctctt tgtcctcctc caccaattga ggggttctct      540
tttagcttgg aacttattgc ggctttggtt gcgaaagaca gatttaatgc tttcggatta      600
atggagcctt tgaatcttaa tgaagagaat ggtgggcaaa gatcggtgag ggcttacggt      660
atttatccta aggcatctct ttttaatcac gattgccttc caaatgcttg taggtttgat      720
tatgttgata cgaataatag tgggaacact gatattgttg ttagaatgat tcatgatgtt      780
ccgcaaggaa gggagatttg tttgagttat tttcctgtaa acagtaatta ctccactaga      840
cggaaaagat tgcttgagga ctatggattt acctgtgact gtgatcgttg taaggtcgaa      900
gctacttggt ctgatgacga gggtgatggt gatgataatg ataatgaggt gatggaggag      960
gatgtcgatg agccaatgga ggccgaatct gatggtgaag aaatcggcaa tgataatagc     1020
actgactttc ctcatgccta tttcttttg cgatacatgt gtaatcgaaa taattgctgg      1080
ggtacactgg ctccttttcc tccttctgat gctaagccat caaatttatt ggagtgcaat     1140
gcctgtggtg atatcaagaa tgatgaggtt tgttga                               1176

<210> SEQ ID NO 12
<211> LENGTH: 1008
<212> TYPE: DNA
<213> ORGANISM: Populus tricocharpa

<400> SEQUENCE: 12
atgtatcagc tggagagcgt tcctagttca agttcggtcc ataaaaactt attagttaat      60
gatcagtatt tagattgtga tgatatgaca atggatccca tcaatggagg gaacaatctc     120
aacaacaatc ctaatcttgc ctcaaagcaa agattgcgtt ggactcatga gcttcacgaa     180
cgctttgttg atgctgtggc tcagcttggt gggccagatc gggctacgcc taaaggtgtt     240
cttagagtca tgggtgtgca aggcttaaca atataccatg ttaaaagcca tttacagaaa     300
tatcgacttg caaaatacct tcctgactcc tcatctgatg ggaaaaaagc ggacaagaag     360
gaaacagggg atatgatttc caatttggat ggttcatctg gcatgcaaat tacagaagca     420
ctcaagctgc agatggaggt gcagaagcgt ctacatgagc aattggaggt acagagacag     480
ctacaattac gcatagaagc ccaagggaag tatttgaaga agataattga agagcaacaa     540
cgattgagtg gagttcttga agatgtgcct ggctcggggg tcactgcccc agtatcaggt     600
gataactgcc cagaatctga caagacagac ccagcaaccc ctgccccaac ttctgaatca     660
ccctccaag acaaggctgc caaggaacgt gccccagcaa agagcctttc aattgatgaa      720
tcattctctt ctcagcctga gccactgaca ccagattcac gttgcaatgc tggctcccca     780
gcagagagcc ctagaggtga gagatctatg aagaagcaac gggtaagcat gggtgtaaca     840
tatggtaaac aagagatggt tcttacacac cagatactcg agtcaagctt aaattcctat     900
ccacgaccac actctgcctt cctgggtaga gagcagtttg atccttcatc tgggttatca     960
atgggaatcg aagatcaaat ggagaaagtt tcaggcagtg atgttag                   1008

<210> SEQ ID NO 13
<211> LENGTH: 1101
<212> TYPE: DNA
<213> ORGANISM: Populus tricocharpa

<400> SEQUENCE: 13
atgtctccac cactacttgg tgttgtggag gaggagggtc atagtaatgt cactctactg      60
gcttctccgg cctcagcaga aagtgcatgc ctgaatggtt tggaattgaa agagcgtaac     120
```

```
tacatgggtt tgtccgattg ttcttccgtg dacagctcgg cagtctctgc agcatctgat      180
gaaagaaaga ctagtttaaa tctgaaggct actgaattgc ggcttgggct tcctgggtcc      240
cagtctccag aaagaaatca tgagctttcc ctgttgagct cggcattact tgatgagaag      300
cccttcttcc ctttgcatcc ctcaaatgat ggtcactact cctcaacaca gaaaaatgtt      360
gtttcgggta caagagagt gttctctgat gccatggatg agttttcaga gagcaagttt       420
ctgtcaaatt cggaggtaaa tgcaatgctc tcacccaggc cctcaccgaa catgggattg      480
aaacctggca tgttggagaa ccttggagtt caacaagcta aagtgaaaga gatagtagcc      540
ccaaaggcag acaagagag acctcatgcg gcaaacgaga ccagaccact tcgtaacagc      600
tccgcaaaca acagcagtgc acctgctcca aaggcacaag ttgtgggttg gccacccatc      660
aaatcattta ggaagaattc ccttgccacc acctcaaaga acacagaaga agttgatggt      720
aaagcagggc caggtgcttt atttatcaaa gtcagcatgg atggtgctcc ttatcttaga      780
aaagtggatt tgagaaacta ctctgcatat caggaattgt cttctgccct cgagaagatg      840
ttcagctgtt tcaccatagg ccaatatgga tcccatggag ctccaggaag ggagatgctg      900
agcgagagca agctgaagga tctgctgcat ggctcagaat atgttctcac ttatgaggat      960
aaagacggag actggatgct tgttggcgat gttccctggg agatgtttat tgaaacatgc     1020
aagaggctga ggatcatgaa gagctctgat gccattggcc tagccccaag ggccatggag     1080
aaatgcaaaa acaggaatta g                                               1101
```

<210> SEQ ID NO 14
<211> LENGTH: 347
<212> TYPE: PRT
<213> ORGANISM: Populus tricocharpa

<400> SEQUENCE: 14

```
Met Ala Val Glu Leu Met Met Gly Tyr Ser Gly Asp Ser Phe Ala Thr
1               5                   10                  15

Lys Met Gln Glu Asn Asp Val Arg Glu Ala Ala Thr Ala Gly Ile Gln
            20                  25                  30

Ser Val Glu Glu Val Ile Lys Leu Leu Lys Gln Asn Gln Leu Glu Gln
        35                  40                  45

Gln Gln Lys Gln Gln Tyr Tyr Gln Glu Leu Ser Ala Ala Ser Ser Ser
    50                  55                  60

Ser Asn Leu Gly Thr Asp Asn Ile Met Ala Val Thr Asp Met Ala Val
65                  70                  75                  80

Asn Asn Phe Lys Lys Val Ile Ser Leu Leu Gly Arg Thr Thr Arg Thr
                85                  90                  95

Gly His Ala Arg Phe Arg Arg Ala Pro Val Ala Cys Pro Pro Gln Gln
            100                 105                 110

Gln Ile Gln Glu Pro Glu Pro Gly Pro Gln Gln Gln Lys Gln Gln Pro
        115                 120                 125

Pro Glu Gln Gly Ser Ala Phe Arg Val Tyr Gln Pro Thr Pro Ile His
    130                 135                 140

Arg Leu Pro Pro Leu Pro His Asn Gln Gln Gln Lys Thr Leu Leu Val
145                 150                 155                 160

Thr Lys Asn Gly Leu Ser Asp Arg Asn Glu Met Ala Thr Thr Ile Asn
                165                 170                 175

Phe Ala Asn Ser Pro Thr Ile Ser Ala Pro Ser Phe Leu Ser Ser Leu
            180                 185                 190
```

```
Thr Gly Glu Thr Asp Ser Phe Gln Cys Ser Lys Ser Ser Gly Phe Gln
            195                 200                 205

Phe Thr Gln Pro Ser Ala Gly Lys Pro Pro Leu Ser Ser Ser Ser Leu
    210                 215                 220

Lys Arg Lys Cys Asn Ser Met Asp Asp Ala Ala Leu Lys Cys Gly Ser
225                 230                 235                 240

Ser Ser Ser Arg Cys His Cys Ser Lys Lys Ser Arg Lys Ser Arg Ile
                245                 250                 255

Lys Arg Val Val Arg Val Pro Ala Ile Ser Ser Lys Met Ala Asp Ile
            260                 265                 270

Pro Pro Asp Asp Tyr Ser Trp Arg Lys Tyr Gly Gln Lys Pro Ile Lys
    275                 280                 285

Gly Ser Pro His Pro Arg Gly Tyr Tyr Lys Cys Ser Ser Val Arg Gly
290                 295                 300

Cys Pro Ala Arg Lys His Val Glu Arg Ala Leu Asp Asp Ser Met Met
305                 310                 315                 320

Leu Ile Val Thr Tyr Glu Gly Glu His Asn His Ser His Pro Ile Asp
                325                 330                 335

Asp Ala Pro Gly Ala Leu Val Leu Glu Ser Ser
            340                 345

<210> SEQ ID NO 15
<211> LENGTH: 157
<212> TYPE: PRT
<213> ORGANISM: Populus tricocharpa

<400> SEQUENCE: 15

Met Ser Leu Asn Met Ile Asn Ser Tyr Ala Ser Thr Asp Phe Glu Gly
1               5                   10                  15

Thr Arg Gly Asn Gly Leu Leu Gly Leu Met Gln Glu Met Gln Ala Pro
            20                  25                  30

Ala Ser Leu Asn Phe Asp Asp Ile Ser Gln Asn Arg Gly Phe Val Gly
        35                  40                  45

Ser Gly Ile Glu Gly Lys Leu Gly Lys Asn Lys Gly Glu Lys Lys Ile
    50                  55                  60

Arg Lys Pro Lys Tyr Ala Phe Gln Thr Arg Ser Arg Val Asp Ile Leu
65                  70                  75                  80

Asp Asp Gly Tyr Arg Trp Arg Lys Tyr Gly Gln Lys Ala Val Lys Asn
                85                  90                  95

Asn Lys Phe Pro Arg Ser Tyr Tyr Arg Cys Thr His Gln Gly Cys Asn
            100                 105                 110

Val Lys Lys Gln Val Gln Arg Leu Thr Lys Asp Glu Gly Val Val Val
        115                 120                 125

Thr Thr Tyr Glu Gly Met His Ser His Gln Ile Glu Lys Ser Pro Asp
    130                 135                 140

Asn Phe Glu His Ile Leu Ser Gln Met Gln Ile Tyr Ser
145                 150                 155

<210> SEQ ID NO 16
<211> LENGTH: 475
<212> TYPE: PRT
<213> ORGANISM: Populus tricocharpa

<400> SEQUENCE: 16

Met Glu Ile Lys Glu Ser Glu Arg Val Val Ile Ala Lys Pro Val Ala
1               5                   10                  15
```

-continued

Ser Arg Pro Ser Tyr Ser Asn Phe Thr Ser Phe Ser Glu Leu Leu Ala
             20                  25                  30

Gly Ala Ile Asn Thr Thr Pro Ser Asn Val Cys Ser Gly Thr Ala Val
         35                  40                  45

Ala Ala Ile Arg Pro Lys Thr Val Arg Phe Arg Pro Leu Val Asn Arg
50                  55                  60

Ala Pro Gly Ala Leu Val Ser Ser Gln Ala Gly Leu Ser Gly Thr Ala
65                  70                  75                  80

Val Ser Asn Ser Phe Asn Lys Ala Ser Ser Thr Asp Ser Lys Ala Thr
                 85                  90                  95

Ile Ile Tyr Lys Pro Gln Ala Lys Leu Val Ser Lys Ala Thr Val Ser
             100                 105                 110

Leu Leu Ala Asn Met Gly Asn Phe Asn Thr Asn Ser Gln Gln Met Leu
         115                 120                 125

Gln Pro Val Glu Thr Arg Pro Gln Leu Ser Lys Gln Asp Lys His Asn
130                 135                 140

Phe Ser Ser Gln Leu Thr Ser Asn Pro His Gln Asn Ile Pro Ser Pro
145                 150                 155                 160

Ala Glu Ala Asp His Thr Thr Glu Pro Leu Arg Leu Thr Ser Leu Asn
                 165                 170                 175

Gln Glu Glu Asp Pro Lys Thr Leu Ser His Ala Ser Asn Gly Asp Arg
             180                 185                 190

Pro Ser Tyr Asp Gly Tyr Asn Trp Arg Lys Tyr Gly Gln Lys Gln Val
         195                 200                 205

Lys Gly Ser Glu Tyr Pro Arg Ser Tyr Tyr Lys Cys Thr Tyr Pro Asn
210                 215                 220

Cys Pro Val Lys Lys Lys Val Glu Arg Ser Phe Asp Gly Gln Ile Ala
225                 230                 235                 240

Glu Ile Val Tyr Lys Gly Glu His Asn His Ser Lys Pro Gln Pro Pro
                 245                 250                 255

Lys Arg Asn Ser Ser Gly Thr Gln Gly Leu Ser Asp Gly Asn Ala Pro
             260                 265                 270

Asp Arg Asn Ser Ile Pro Leu Trp Ser Asn Gln Leu Asn Glu Arg Asn
         275                 280                 285

Glu Gly Ser Glu Gly Arg Glu Glu Asn Gln Asn Glu Ile Gly Leu Pro
290                 295                 300

Val His Ser Ile Tyr Gln Gly Lys Ala Pro Pro Ser Tyr Asp Pro Ala
305                 310                 315                 320

Gly Thr Gly Thr Ile Asn Ala Gly Thr Gly Thr Ser Asp Asn Ser Cys
                 325                 330                 335

Gly Val Ser Gly Glu Cys Asp Asp Gly Ser Lys Gly Leu Glu Gly Ala
             340                 345                 350

Asn Asp Glu Pro Lys Ser Lys Arg Arg Lys Thr Glu Ile Gln Ser Thr
         355                 360                 365

Glu Gly Gly Met Ser Gly Glu Gly Val Gln Glu Pro Arg Val Val Val
370                 375                 380

Gln Ser Ser Thr Asp Ser Glu Ile Leu Gly Asp Gly Phe Arg Trp Arg
385                 390                 395                 400

Lys Tyr Gly Gln Lys Ile Val Lys Gly Asn Pro Tyr Pro Arg Ser Tyr
                 405                 410                 415

Tyr Arg Cys Thr Ser Ile Lys Cys Asn Val Arg Lys His Val Glu Arg
             420                 425                 430

Val Ser Asp Asp Pro Arg Ala Phe Ile Thr Thr Tyr Glu Gly Lys His

```
                 435                 440                 445
Asn His Glu Ile Pro Leu Lys Ser Thr Asn Leu Ala Ala Phe Glu Pro
    450                 455                 460

Asp Ser Gln Ala Pro Thr Thr Arg Val Lys Gln
465                 470                 475

<210> SEQ ID NO 17
<211> LENGTH: 355
<212> TYPE: PRT
<213> ORGANISM: Populus tricocharpa

<400> SEQUENCE: 17

Met Glu Glu Val Glu Val His Lys Ala Ala Ile Glu Ser Cys Asn
1               5                  10                  15

Arg Val Ile Gly Leu Leu Cys Gln Gln Lys Asp Gln Val Gln Gly Arg
                20                  25                  30

Asn Leu Met Val Glu Thr Arg Glu Thr Val Phe Lys Phe Lys Arg Val
            35                  40                  45

Ile Ser Leu Leu Ser Thr Gly Leu Gly His Gly Arg Val Arg Lys Met
50                  55                  60

Lys Lys Leu Arg Pro Ser Leu Pro Gln Asn Ile Phe Leu Asp Ser Pro
65                  70                  75                  80

Asn Cys Lys Thr Val Leu Ser Pro Lys Pro Leu Gln Met Val Pro Pro
                85                  90                  95

Asn Phe Leu Glu Thr Pro Leu Thr Asp Met Asp Ala Lys Ser Lys Pro
            100                 105                 110

Ser Ile Gln Ile Ser Gln Lys Met Leu Leu Glu Asn Pro Val Leu Glu
        115                 120                 125

Leu Asn Ser Asn Ile Arg Pro Pro Val Gln Ile Met Gln Thr Lys Pro
130                 135                 140

Pro Gln Asn Phe Gln Leu Leu Gln Gln His Gln Gln Thr Gln Arg Met
145                 150                 155                 160

His Phe Gln Gln Gln Gln Gln Gln Met Lys Tyr Gln Ala Asp Arg
                165                 170                 175

Val Tyr Ser Arg Ser Asn Gly Gly Ile Asn Leu Lys Phe Asp Gly Ser
            180                 185                 190

Thr Cys Thr Pro Thr Met Ser Ser Thr Arg Ser Phe Ile Ser Ser Leu
        195                 200                 205

Ser Met Asp Gly Ala Val Ser Thr Phe Asp Gly Asp Ser Phe His Leu
210                 215                 220

Ile Gly Met Pro His Ser Ser Asp His Ile Ser Gln Gln Thr Arg Arg
225                 230                 235                 240

Arg Cys Ser Gly Arg Gly Glu Asp Gly Asn Ala Lys Cys Ser Ser Ser
                245                 250                 255

Gly Lys Cys His Cys Ser Lys Arg Arg Lys Leu Arg Val Lys Arg Ser
            260                 265                 270

Ile Lys Val Pro Ala Ile Ser Asn Lys Val Ala Asp Ile Pro Pro Asp
        275                 280                 285

Glu Tyr Ser Trp Arg Lys Tyr Gly Gln Lys Pro Ile Lys Gly Ser Pro
    290                 295                 300

His Pro Arg Gly Tyr Tyr Lys Cys Ser Ser Leu Arg Gly Cys Pro Ala
305                 310                 315                 320

Arg Lys His Val Glu Arg Cys Leu Glu Asp Pro Ser Met Leu Ile Val
                325                 330                 335
```

-continued

```
Thr Tyr Glu Gly Glu His Asn His Ser Arg Leu Ile Ser Ser Gln Ser
                340                 345                 350

Ala His Thr
        355

<210> SEQ ID NO 18
<211> LENGTH: 718
<212> TYPE: PRT
<213> ORGANISM: Populus tricocharpa

<400> SEQUENCE: 18

Met Ala Gly Ile Asp Asp Asn Val Ala Ile Gly Asp Trp Val Pro
1               5                   10                  15

Pro Ser Pro Ser Pro Arg Ala Phe Phe Ser Ala Met Leu Gly Asp Asp
                20                  25                  30

Ile Asn Ser Arg Thr Ile Pro Glu Ser Pro Gly Glu Lys Arg Asn Glu
                35                  40                  45

Gly Leu Tyr Leu Gly Gln Pro Glu Gln Met Ala Thr Gly Asn Ser Glu
        50                  55                  60

Lys Lys Asp Gly Ala Gln Thr Ser Gly Val Gln Leu Thr Glu Leu Gly
65                  70                  75                  80

Thr Phe Ser Glu Gln Lys Ser Asn Phe Arg Gly Gly Leu Val Glu Arg
                85                  90                  95

Ile Ala Arg Ala Gly Phe Asn Ala Pro Arg Leu Asn Thr Glu Ser
                100                 105                 110

Ile Arg Ser Thr Glu Ser Ser Met Asn Pro Glu Ile Arg Ser Pro Tyr
            115                 120                 125

Leu Thr Ile Pro Pro Gly Leu Ser Pro Thr Thr Leu Leu Glu Ser Pro
        130                 135                 140

Val Phe Leu Ser Asn Leu Ala Gln Pro Ser Pro Thr Thr Gly Lys Phe
145                 150                 155                 160

Ser Phe Phe Pro Asn Gly Asn Thr Lys Asn Ser Thr Val Gly Ser Asp
                165                 170                 175

Pro Pro Asp Lys Ser Lys Glu Thr Phe Phe Asp Asn Ile Asp Ser Ser
                180                 185                 190

Ser Phe Ala Phe Lys Pro Met Gly Glu Ser Gly Ser Phe Phe Leu Gly
            195                 200                 205

Gly Thr Ser Lys Gln Ser Phe Pro Ser Ile Asp Val Ser Val His Ser
        210                 215                 220

Glu Asn Ala Phe Gln Ser His Gly Val Glu Pro Ala Lys Thr Gln Phe
225                 230                 235                 240

Glu Ser Arg Asn Ser Leu His Phe Arg Ala Glu Phe Ser Lys Leu Thr
                245                 250                 255

Thr Glu Lys Asp Asn Gly Cys Ile Thr Val Ala Asp Gln Arg Thr Phe
                260                 265                 270

Asp Thr Val Ala Gly Asn Ala Glu His Ser Ser Pro Leu Ala Glu Gln
            275                 280                 285

Gln Asp Glu Glu Gly Asp Gln Arg Ala Ser Glu Asp Ser Met Ala Ala
        290                 295                 300

Gly Gly Thr Pro Ser Glu Asp Ala Tyr Asn Trp Arg Lys Tyr Gly Gln
305                 310                 315                 320

Lys Gln Val Lys Gly Ser Glu Tyr Pro Arg Ser Tyr Tyr Lys Cys Thr
                325                 330                 335

His Pro Asn Cys Pro Val Lys Lys Lys Val Glu Arg Ser His Glu Gly
                340                 345                 350
```

His Ile Thr Glu Ile Ile Tyr Lys Gly Ala His Asn His Pro Lys Pro
            355                 360                 365

Pro Pro Asn Arg Arg Ser Ala Thr Gly Ser Met Asp Thr Gln Leu Asp
    370                 375                 380

Ile Pro Glu Gln Ala Gly Pro Gln Val Gly Ala Val Asn Asp Ser Val
385                 390                 395                 400

Trp Ala Gly Thr Gln Lys Gly Thr Ala Ala Gly Thr Pro Asp Trp Arg
                405                 410                 415

Asn Asp Asn Val Glu Val Ser Ser Ala Ser Gly Gly Leu Gly Pro
            420                 425                 430

Glu Phe Gly Asn Pro Ser Ser Ser Val Gln Gly Gln Ser Gly Thr Pro
            435                 440                 445

Phe Glu Ser Ala Asp Ala Val Asp Ala Ser Ser Thr Phe Ser Asn Asp
    450                 455                 460

Glu Asp Asp Asp Arg Ala Thr His Gly Ser Val Gly Tyr Asp Gly Glu
465                 470                 475                 480

Gly Glu Glu Ser Glu Ser Lys Arg Arg Lys Val Glu Thr Tyr Ala Thr
                485                 490                 495

Glu Met Ser Gly Ala Thr Arg Ala Ile Arg Glu Pro Arg Val Val Val
            500                 505                 510

Gln Thr Thr Ser Glu Val Asp Ile Leu Asp Asp Gly Tyr Arg Trp Arg
            515                 520                 525

Lys Tyr Gly Gln Lys Val Val Lys Gly Asn Pro Asn Pro Arg Ser Tyr
    530                 535                 540

Tyr Lys Cys Thr Ser Ala Gly Cys Thr Val Arg Lys His Val Glu Arg
545                 550                 555                 560

Ala Ser His Asp Leu Lys Ser Val Ile Thr Thr Tyr Glu Gly Lys His
                565                 570                 575

Asn His Asp Val Pro Ala Ala Arg Asn Ser Asn His Val Asn Ser Gly
            580                 585                 590

Thr Ser Asn Ala Thr Pro Ala Gln Ala Gly Ile Ala Val Gln Thr Gln
            595                 600                 605

Val His Arg Pro Glu Ala Ser Gln Val His Asn Ser Met Thr Ser Arg
    610                 615                 620

Phe Glu Arg Pro Pro Ala Phe Gly Ser Phe Arg Gln Gln Leu Gly Pro
625                 630                 635                 640

Ser Ala Gly Phe Ser Phe Gly Met Asn Gln Pro Gly Phe Ala Asn Met
                645                 650                 655

Gly Met Ala Gly Leu Gly Pro Gly Gln Pro Arg Met Pro Val Met Pro
            660                 665                 670

Met His Pro Tyr Leu Ala Gln Gln Arg Ala Val Asn Glu Met Gly Leu
            675                 680                 685

Met Met Pro Lys Gly Glu Ala Lys Val Glu Pro Val Thr Ser Asn Asn
    690                 695                 700

Pro Thr Val Tyr Gln Gln Ile Met Ser Arg Leu Pro Gln Met
705                 710                 715

<210> SEQ ID NO 19
<211> LENGTH: 301
<212> TYPE: PRT
<213> ORGANISM: Populus tricocharpa

<400> SEQUENCE: 19

Met Ala Val Asp Leu Val Arg Tyr Ser Lys Met Glu Asp Gln Met Ala

```
  1               5                  10                 15
Ile Gln Glu Ala Ala Ser Ala Gly Leu Glu Ser Met Glu His Leu Ile
             20                 25                 30
Phe Ala Phe Ser Asn Gln Thr Arg Gln Ser His Gln Leu Asp Cys Gly
             35                 40                 45
Glu Ile Thr Asn Phe Thr Val Ala Lys Phe Lys Gln Val Ile Ser Met
             50                 55                 60
Leu Asn Arg Thr Gly His Ala Arg Phe Arg Gly Pro Thr Ser Ser
 65              70                 75                 80
Pro Ser Ser Tyr Pro Val Pro Val Arg Pro Val Pro Gln Glu Pro Gln
                 85                 90                 95
Lys Leu Asn Leu Asp Phe Val Asn Ser Asn Ser Pro Pro Lys Ala Glu
                100                105                110
Ser Lys Asn Asp Leu Ser Leu Gly Ser Gln Tyr Ser Lys Asp Ser Leu
                115                120                125
Ser Ser Gly Thr Thr Thr Ser Ser Phe Val Ser Ser Val Thr Ala Asp
                130                135                140
Gly Ser Val Ser Asn Gly Lys Gln Gly Gly Ser Ser Leu Phe Gly Thr
145                150                155                160
Gln Ala Arg Ser Thr Gly Lys Pro Pro Leu Ser Ser Thr His Arg Lys
                165                170                175
Lys Cys His Asp His Ala Leu Ser Ala Arg Lys Ile Ser Ser Gly Gly
                180                185                190
Ser Cys His Cys Ser Lys Arg Arg Lys Ser Arg Val Lys Arg Thr Ile
                195                200                205
Arg Val Pro Ala Val Ser Ser Lys Ile Ala Asp Ile Pro Ala Asp Glu
210                215                220
Tyr Ser Trp Arg Lys Tyr Gly Gln Lys Pro Ile Lys Gly Ser Pro Tyr
225                230                235                240
Pro Arg Gly Tyr Tyr Lys Cys Ser Ser Val Arg Gly Cys Pro Ala Arg
                245                250                255
Lys His Val Glu Arg Ala Val Asp Asp Ser Ala Met Leu Ile Val Thr
                260                265                270
Tyr Glu Gly Glu His Arg His Ser His Thr Pro Leu Pro Gly Asp Val
                275                280                285
Thr Ala Ser Ala Ala Met Arg His Val Phe His Ser Thr
290                295                300

<210> SEQ ID NO 20
<211> LENGTH: 347
<212> TYPE: PRT
<213> ORGANISM: Populus tricocharpa

<400> SEQUENCE: 20

Met Glu Gly Val Glu Glu Ala Asn Arg Ala Ala Val Glu Ser Cys His
 1               5                  10                 15
Arg Val Ile Ser Leu Leu Ser Gln Pro Gln Asp Val Gln Tyr Arg
             20                 25                 30
Asn Leu Met Val Glu Thr Gly Glu Ala Val Phe Arg Phe Lys Lys Val
             35                 40                 45
Val Ser Leu Leu Asn Thr Gly Leu Gly His Ala Arg Val Arg Lys Leu
             50                 55                 60
Lys Lys Leu Pro Thr Pro Leu Ser Gln Ser Ile Leu Leu Asp Asn Pro
 65              70                 75                 80
```

```
Leu Ser Ser Thr Asp His Pro Ser Lys Thr Pro Gln Phe Leu Gln Ser
            85                  90                  95

Ser Ser Tyr Leu Glu Ser Gln Pro Ile Gln Glu Leu Gly Ser Ile Ala
            100                 105                 110

Lys Asn Cys Leu Ser Leu Gly Thr Pro Ser Leu Glu Leu Ser Ser Asn
            115                 120                 125

Gly Lys Asn Pro Leu Gln Leu Gly Gln Pro Thr Pro Ala Ala His Tyr
130             135                 140

Gln Phe Leu Gln Gln Gln Leu His Arg Leu Gln Leu Gln Gln
145                 150                 155                 160

Gln Gln Met Lys Gln Gln Ala Glu Met Met Phe Arg Lys Ser Asn Ser
                165                 170                 175

Gly Ile Ser Leu Asn Phe Asp Ser Ser Ser Cys Thr Pro Thr Met Ser
            180                 185                 190

Ser Thr Arg Ser Phe Ile Ser Ser Leu Ser Ile Asp Gly Asn Val Ala
            195                 200                 205

Asn Leu Glu Gly Ser Ala Phe His Leu Thr Gly Ala Ala Arg Ser Ser
            210                 215                 220

Asp Gln Ser Ser Gln Gln His Lys Arg Lys Cys Ser Gly Arg Gly Glu
225                 230                 235                 240

Asp Gly Ser Met Lys Cys Gly Ser Ser Val Arg Cys His Cys Ser Lys
            245                 250                 255

Lys Arg Lys His Arg Val Lys Arg Ser Ile Lys Val Pro Ala Ile Ser
            260                 265                 270

Asn Lys Leu Ala Asp Ile Pro Pro Asp Asp Tyr Ser Trp Arg Lys Tyr
            275                 280                 285

Gly Gln Lys Pro Ile Lys Gly Ser Pro His Pro Arg Gly Tyr Tyr Lys
            290                 295                 300

Cys Ser Ser Met Arg Gly Cys Pro Ala Arg Lys His Val Glu Arg Cys
305                 310                 315                 320

Leu Glu Asp Pro Ser Met Leu Ile Val Thr Tyr Glu Gly Glu His Asn
            325                 330                 335

His Pro Arg Ile Pro Ala Gln Ser Thr Asn Thr
            340                 345

<210> SEQ ID NO 21
<211> LENGTH: 365
<212> TYPE: PRT
<213> ORGANISM: Populus tricocharpa

<400> SEQUENCE: 21

Met Glu Leu Ser Met Glu Trp Glu His Lys Thr Leu Ile Ser Glu Leu
1               5                   10                  15

Thr Gln Gly Lys Glu Leu Ala Lys Gln Leu Ser Asn His Leu Asn Pro
            20                  25                  30

Ser Ser Ser Leu Glu Ala Arg Gln Phe Leu Val Asp Lys Ile Leu Ser
            35                  40                  45

Ser Tyr Glu Lys Ala Leu Ser Met Leu Asn Trp Gly Ala Leu Ala Ala
        50                  55                  60

Asp Gln Pro Lys Pro Thr Ile Gly Thr Val Glu Pro Leu His Ser Phe
65                  70                  75                  80

Ala Asn Ser Ser Pro Arg Ser Glu Val Ser Asp Gln Asp Cys Lys Glu
            85                  90                  95

Glu Cys Asn Lys Asp Val Tyr Lys Lys Arg Lys Ile Gln Pro Arg Trp
            100                 105                 110
```

```
Thr Glu Gln Val Lys Asp Cys Ser Gly Thr Gly Leu Glu Gly Pro Leu
            115                 120                 125

Asp Asp Gly Tyr Ser Trp Arg Lys Tyr Gly Gln Lys Asp Ile Leu Gly
        130                 135                 140

Ala Asn Phe Pro Arg Gly Tyr Tyr Arg Cys Thr His Arg His Ser Gln
145                 150                 155                 160

Gly Cys Leu Ala Thr Lys Gln Val Gln Arg Ser Asp Glu Asp His Ser
            165                 170                 175

Ile Phe Glu Val Thr Tyr Arg Gly Arg His Thr Cys Asn Gln Ala Ser
            180                 185                 190

Pro Ser Pro Val Ala Ser Pro Pro Lys Asn Asp Cys Ser Lys Gln
            195                 200                 205

Ser Lys Tyr His Arg Lys Gln Gln Gln Arg Gln Glu Lys Pro Lys
            210                 215                 220

Pro Thr Glu Glu Ile Phe Val Asn Phe Gly Ser Asp Ile Val Gln Val
225                 230                 235                 240

Lys Asn Glu Asp Leu Gly Ser Lys Asp Ile Phe Pro Ser Phe Ser
            245                 250                 255

Phe Pro Cys Thr Ser Phe Gly Asn Glu Asn Glu Asn Asn Ile Phe
            260                 265                 270

Thr Glu Ser Met Met Glu Asn Asn Phe Leu Gly Ser Phe Ser Pro Thr
            275                 280                 285

Phe Ile Ser Pro Ala Thr Ser Glu Ser Asn Tyr Phe Ser Met Ser Pro
            290                 295                 300

Cys His Met Asn Ser Phe Gly Ile Gly Tyr Gln Asn Val Gln Thr Pro
305                 310                 315                 320

Glu Ser Glu Leu Thr Thr Glu Ile Ile Ser Ala Pro Thr Ser Val Thr
            325                 330                 335

Asn Ser Pro Ile Gly Asp Phe Asp Ile Ser Ile Asp Asn Val Asp Phe
            340                 345                 350

Asp Thr Thr Phe Pro Phe Asp Asn Pro Asp Phe Phe Ala
            355                 360                 365

<210> SEQ ID NO 22
<211> LENGTH: 357
<212> TYPE: PRT
<213> ORGANISM: Populus tricocharpa

<400> SEQUENCE: 22

Met Met Glu Glu Leu Tyr Gly Leu Gln Ser Thr Ser Ser Asp Tyr Ser
1               5                   10                  15

Leu Gln Val Pro Ser Glu Asn Met Val Ser Pro Val Ala Asn Tyr Tyr
            20                  25                  30

His Pro Val Gly Phe Thr Ser Pro Ala Gly Glu Pro Ser Phe Pro Val
        35                  40                  45

Phe Gly Ser Glu Gln Met Phe Cys Gly Ser Ser Val Ser Asp Ala Ala
    50                  55                  60

Ser Met Gly Ala Glu Leu His Gln Lys Gln Gln Gln Ser Gly Gly
65                  70                  75              80

Val Gly Val Gly Asp His Ser Asn Arg Asn Asn Ser Glu Glu Val Ser
            85                  90                  95

Cys Ala Ile Arg Ala Lys Ile Ala Ser His Pro Leu Tyr Pro Lys Leu
            100                 105                 110

Leu Glu Ala Tyr Ile Asp Cys Gln Lys Val Gly Ala Pro Pro Glu Met
```

```
            115                 120                 125
Ala Tyr Leu Leu Asp Glu Ile Arg Leu Val Asn Asp Val Ser Lys Gly
130                 135                 140

Ser Asn Asp Thr Val Ala Ser Cys Leu Gly Ala Asp Pro Glu Leu Asp
145                 150                 155                 160

Glu Phe Met Glu Thr Tyr Cys Asp Val Leu Met Lys Tyr Lys Ala Asp
                165                 170                 175

Leu Ser Arg Pro Phe Asp Glu Ala Thr Thr Phe Leu Asn Asp Ile Glu
            180                 185                 190

Ala Gln Phe Asn Thr Leu Cys Asn Gly Pro Ser Arg Ser Gln Val Tyr
        195                 200                 205

Gly Leu Pro Leu Ser Leu Ser Leu Ser Ile Leu Leu Leu Ser Met Leu
    210                 215                 220

Ser Asn Glu Ala Ala Gly Ser Ser Asp Glu Asp Ala Ser Gly Gly Glu
225                 230                 235                 240

Ala Gly Met Gln Asp Ser Thr Arg Ile Asn Glu Asp Arg Glu Leu Lys
                245                 250                 255

Asp Lys Leu Leu Arg Lys Tyr Ser Gly Tyr Ile Ser Thr Leu Lys His
            260                 265                 270

Ala Phe Ser Lys Gln Lys Lys Lys Gly Lys Leu Pro Lys Glu Ala Arg
        275                 280                 285

Gln Ile Leu Leu Asn Trp Trp Asn Ile His Asn Lys Trp Pro Tyr Pro
    290                 295                 300

Thr Glu Ala Asp Lys Val Ala Leu Ala Glu Ser Thr Gly Leu Asp Gln
305                 310                 315                 320

Lys Gln Ile Asn Asn Trp Phe Ile Asn Gln Arg Lys Arg His Trp Lys
                325                 330                 335

Pro Ser Glu Asn Met Gln Phe Ala Val Val Asp Ser Leu Tyr Gly Pro
            340                 345                 350

Phe Phe Met Asn Asp
        355

<210> SEQ ID NO 23
<211> LENGTH: 568
<212> TYPE: PRT
<213> ORGANISM: Populus tricocharpa

<400> SEQUENCE: 23

Met Glu Arg Asp Lys Leu Phe Val Ser Glu Gly Ala Asn Thr Ala Ala
1               5                   10                  15

Thr Ile Trp Asn Ser Cys Ser Phe Gly Met Glu Met Gln Ala Asn Glu
                20                  25                  30

Leu Ser Cys Gly Pro Glu Lys Leu Ala Asn Cys Phe Leu Asn Pro Asn
            35                  40                  45

Trp Asp Asn Ser Leu Asp Gln Ser Asp Pro Phe Glu Ser Ala Leu Ser
        50                  55                  60

Ser Ile Val Ser Ser Pro Val Ala Ser Gly Ala Asn Ala Asn Ala Asn
65                  70                  75                  80

Ala Ile Pro Asn Ala Gly Val Gly Gly Asp Ser Leu Met Ile Arg Glu
                85                  90                  95

Leu Ile Gly Arg Leu Gly Asn Ile Cys Asn Ser Gly Asp Ile Ser Leu
            100                 105                 110

Gln Ser Phe Val Asn Asn Asn Asn Ser Thr Asn Thr Ser Cys Tyr
        115                 120                 125
```

```
Ser Thr Pro Met Asn Ser Pro Pro Lys Leu Asn Leu Ser Met Met Asp
130                 135                 140

Ser Gln Met Arg Gly Asn Leu Pro Ile Pro Gly Asn Ser Val Val Lys
145                 150                 155                 160

His Pro Gly Leu Ala Pro Phe Pro Ala Asp Phe Val Glu Arg Ala Ala
                165                 170                 175

Arg Tyr Ser Cys Phe Gly Ser Asn Asn Pro Gly Gly Ile Asn Lys Gln
                180                 185                 190

Phe Gly Leu Asn Glu Ser Glu Leu Ile Asn Arg Leu Met Pro Arg Val
            195                 200                 205

Glu Pro Gly Lys Leu Ser Arg Val Ser Ser Asn Asn Ser Met Lys Val
210                 215                 220

Thr Val Ser Gln Ala Asn Val Gln Glu Ser Asn Lys Ser Ser Pro Gln
225                 230                 235                 240

Asp Gly Ser Leu Asn Ser Glu Lys Lys Phe Ser Arg Gln Ser Arg Pro
                245                 250                 255

Thr Thr Ser Glu Asn Gly Asp Ser Arg Glu Glu Ser Ser Leu Ser Glu
                260                 265                 270

Gln Val Pro Gly Gly Lys Leu Ser Met Lys Ser Gln Asn Asp Ala Asn
            275                 280                 285

Ser Arg Lys Arg Lys Ser Ile Pro Arg Gly Lys Ala Lys Glu Thr Pro
290                 295                 300

Ser Ser Ser Pro Ser Ala Ser Asp Val Lys Val Ala Ala Glu Asn Asp
305                 310                 315                 320

Glu Ser Lys Ala Lys Arg Ser Lys Ser Asp Glu Thr Asn Gly Ser Asp
                325                 330                 335

Lys Asp Thr Ala Lys Glu Lys Glu Glu Asn Gly Asn Gln Lys Gln
                340                 345                 350

Asn Lys Asn Asn Ser Lys Pro Pro Glu Pro Pro Lys Asp Tyr Ile His
                355                 360                 365

Val Arg Ala Arg Arg Gly Gln Ala Thr Asp Ser His Ser Leu Ala Glu
                370                 375                 380

Arg Val Arg Arg Glu Lys Ile Ser Glu Arg Met Lys Phe Leu Gln Asp
385                 390                 395                 400

Leu Val Pro Gly Cys Asn Lys Val Thr Gly Lys Ala Val Met Leu Asp
                405                 410                 415

Glu Ile Ile Asn Tyr Val Gln Ser Leu Gln Arg Gln Val Glu Phe Leu
                420                 425                 430

Ser Met Lys Leu Ser Ser Val Asn Pro Arg Met Glu Ile Asn Met Glu
                435                 440                 445

Thr Leu Leu Ser Lys Asp Ile Phe Gln Ser Arg Gly Ser Met Pro His
450                 455                 460

Ser Leu Tyr Pro Leu Asp Ala Ser Thr Pro Val Phe Pro Tyr Gly Tyr
465                 470                 475                 480

Gln Ser Gln Gln Gly Leu Ala Leu Gln Asn Gly Met Pro Ser Asn Ala
                485                 490                 495

Glu Thr Gln Phe Ser Met Asn Pro Leu Asn Ala Ala Leu Arg Arg Asn
                500                 505                 510

Pro Ser Met His Leu Pro His Leu Asp Gly Phe Gly Asp Pro Ala Ala
                515                 520                 525

Leu Gln Ala Ser Ala Met Trp Glu Asp Asp Leu Gln Ser Val Val Gln
530                 535                 540

Met Gly Tyr Gly Gln Asn His Gln Glu Ser Phe Gln Gly Ser Val Pro
```

Ser Thr His Met Lys Ile Glu Leu
              565

<210> SEQ ID NO 24
<211> LENGTH: 391
<212> TYPE: PRT
<213> ORGANISM: Populus tricocharpa

<400> SEQUENCE: 24

Met Ser Val Gly Val Asn Thr Glu Thr Leu Val Arg Val Glu Glu Ile
1               5                   10                  15

Gln Gly Arg Gly Arg Gly Leu Val Ser Thr Gln Pro Leu Arg Gly Gly
            20                  25                  30

Gln Ile Val Leu Ile Asp Ser Pro Ile Leu Leu Tyr Ser Ala Leu Pro
        35                  40                  45

Leu Thr Lys Gln Gln His Ser Thr Phe Leu Tyr Cys Asp Lys Cys Phe
    50                  55                  60

Lys Thr Ile Gln Ser Ala Ser Val Ser Cys Pro Thr Cys Ser His Gln
65                  70                  75                  80

Arg Phe Cys Ser Pro Thr Cys Leu Ser Ala Ala Leu Ala Ser Ser His
                85                  90                  95

Thr Pro Trp Val Cys Gln Ser Leu Ser Arg Leu Arg Asp Cys Gln Asp
            100                 105                 110

Phe Leu Gln His His Ser Val Glu Arg Gln Ile Gln Ala Gln Phe Leu
        115                 120                 125

Val Ala Ala Tyr Asn Leu Ala Phe Val Ser Pro Ser Asp Phe Gln Ile
    130                 135                 140

Leu Leu Ser Leu Gln Gly Arg Ala Glu Asp Glu Asp Pro Ala Ile Val
145                 150                 155                 160

Gln Ser Leu His Ser Val Ile Ser Ser Leu Cys Pro Pro Pro Ile
                165                 170                 175

Glu Gly Phe Ser Phe Ser Leu Glu Leu Ile Ala Ala Leu Val Ala Lys
            180                 185                 190

Asp Arg Phe Asn Ala Phe Gly Leu Met Glu Pro Leu Asn Leu Asn Glu
        195                 200                 205

Glu Asn Gly Gly Gln Arg Ser Val Arg Ala Tyr Gly Ile Tyr Pro Lys
    210                 215                 220

Ala Ser Leu Phe Asn His Asp Cys Leu Pro Asn Ala Cys Arg Phe Asp
225                 230                 235                 240

Tyr Val Asp Thr Asn Asn Ser Gly Asn Thr Asp Ile Val Val Arg Met
                245                 250                 255

Ile His Asp Val Pro Gln Gly Arg Glu Ile Cys Leu Ser Tyr Phe Pro
            260                 265                 270

Val Asn Ser Asn Tyr Ser Thr Arg Arg Lys Arg Leu Leu Glu Asp Tyr
        275                 280                 285

Gly Phe Thr Cys Asp Cys Arg Cys Lys Val Glu Ala Thr Trp Ser
    290                 295                 300

Asp Asp Glu Gly Asp Gly Asp Asn Asp Asn Glu Val Met Glu Glu
305                 310                 315                 320

Asp Val Asp Glu Pro Met Glu Ala Glu Ser Asp Gly Glu Glu Ile Gly
                325                 330                 335

Asn Asp Asn Ser Thr Asp Phe Pro His Ala Tyr Phe Phe Leu Arg Tyr
            340                 345                 350

```
Met Cys Asn Arg Asn Asn Cys Trp Gly Thr Leu Ala Pro Phe Pro Pro
            355                 360                 365

Ser Asp Ala Lys Pro Ser Asn Leu Leu Glu Cys Asn Ala Cys Gly Asp
            370                 375                 380

Ile Lys Asn Asp Glu Val Cys
385                 390

<210> SEQ ID NO 25
<211> LENGTH: 335
<212> TYPE: PRT
<213> ORGANISM: Populus tricocharpa

<400> SEQUENCE: 25

Met Tyr Gln Leu Glu Ser Val Pro Ser Ser Ser Val His Lys Asn
1               5                   10                  15

Leu Leu Val Asn Asp Gln Tyr Leu Asp Cys Asp Met Thr Met Asp
                20                  25                  30

Pro Ile Asn Gly Gly Asn Asn Leu Asn Asn Pro Asn Leu Ala Ser
            35                  40                  45

Lys Gln Arg Leu Arg Trp Thr His Glu Leu His Glu Arg Phe Val Asp
    50                  55                  60

Ala Val Ala Gln Leu Gly Gly Pro Asp Arg Ala Thr Pro Lys Gly Val
65                  70                  75                  80

Leu Arg Val Met Gly Val Gln Gly Leu Thr Ile Tyr His Val Lys Ser
                85                  90                  95

His Leu Gln Lys Tyr Arg Leu Ala Lys Tyr Leu Pro Asp Ser Ser Ser
                100                 105                 110

Asp Gly Lys Lys Ala Asp Lys Lys Glu Thr Gly Asp Met Ile Ser Asn
            115                 120                 125

Leu Asp Gly Ser Ser Gly Met Gln Ile Thr Glu Ala Leu Lys Leu Gln
    130                 135                 140

Met Glu Val Gln Lys Arg Leu His Glu Gln Leu Glu Val Gln Arg Gln
145                 150                 155                 160

Leu Gln Leu Arg Ile Glu Ala Gln Gly Lys Tyr Leu Lys Lys Ile Ile
                165                 170                 175

Glu Glu Gln Gln Arg Leu Ser Gly Val Leu Glu Asp Val Pro Gly Ser
            180                 185                 190

Gly Val Thr Ala Pro Val Ser Gly Asp Asn Cys Pro Glu Ser Asp Lys
        195                 200                 205

Thr Asp Pro Ala Thr Pro Ala Pro Thr Ser Glu Ser Pro Leu Gln Asp
    210                 215                 220

Lys Ala Ala Lys Glu Arg Ala Pro Ala Lys Ser Leu Ser Ile Asp Glu
225                 230                 235                 240

Ser Phe Ser Ser Gln Pro Glu Pro Leu Thr Pro Asp Ser Arg Cys Asn
                245                 250                 255

Ala Gly Ser Pro Ala Glu Ser Pro Arg Gly Glu Arg Ser Met Lys Lys
            260                 265                 270

Gln Arg Val Ser Met Gly Val Thr Tyr Gly Lys Gln Glu Met Val Leu
    275                 280                 285

Thr His Gln Ile Leu Glu Ser Ser Leu Asn Ser Tyr Pro Arg Pro His
    290                 295                 300

Ser Ala Phe Leu Gly Arg Glu Gln Phe Asp Pro Ser Ser Gly Leu Ser
305                 310                 315                 320

Met Gly Ile Glu Asp Gln Met Glu Lys Val Ser Gly Ser Asp Val
                325                 330                 335
```

<210> SEQ ID NO 26
<211> LENGTH: 366
<212> TYPE: PRT
<213> ORGANISM: Populus tricocharpa

<400> SEQUENCE: 26

```
Met Ser Pro Leu Leu Gly Val Val Glu Glu Gly His Ser Asn
1               5                   10                  15

Val Thr Leu Leu Ala Ser Pro Ala Ala Glu Ser Ala Cys Leu Asn
            20                  25                  30

Gly Leu Glu Leu Lys Glu Arg Asn Tyr Met Gly Leu Ser Asp Cys Ser
            35                  40                  45

Ser Val Asp Ser Ser Ala Val Ser Ala Ala Ser Asp Glu Arg Lys Thr
    50                  55                  60

Ser Leu Asn Leu Lys Ala Thr Glu Leu Arg Leu Gly Leu Pro Gly Ser
65                  70                  75                  80

Gln Ser Pro Glu Arg Asn His Glu Leu Ser Leu Leu Ser Ala Leu
                85                  90                  95

Leu Asp Glu Lys Pro Phe Phe Pro Leu His Pro Ser Asn Asp Gly His
            100                 105                 110

Tyr Ser Ser Thr Gln Lys Asn Val Val Ser Gly Asn Lys Arg Val Phe
            115                 120                 125

Ser Asp Ala Met Asp Glu Phe Ser Glu Ser Lys Phe Leu Ser Asn Ser
    130                 135                 140

Glu Val Asn Ala Met Leu Ser Pro Arg Pro Ser Pro Asn Met Gly Leu
145                 150                 155                 160

Lys Pro Gly Met Leu Glu Asn Leu Gly Val Gln Gln Ala Lys Val Lys
                165                 170                 175

Glu Ile Val Ala Pro Lys Ala Gly Gln Glu Arg Pro His Ala Ala Asn
            180                 185                 190

Glu Thr Arg Pro Leu Arg Asn Ser Ser Ala Asn Asn Ser Ser Ala Pro
            195                 200                 205

Ala Pro Lys Ala Gln Val Val Gly Trp Pro Pro Ile Lys Ser Phe Arg
    210                 215                 220

Lys Asn Ser Leu Ala Thr Thr Ser Lys Asn Thr Glu Glu Val Asp Gly
225                 230                 235                 240

Lys Ala Gly Pro Gly Ala Leu Phe Ile Lys Val Ser Met Asp Gly Ala
                245                 250                 255

Pro Tyr Leu Arg Lys Val Asp Leu Arg Asn Tyr Ser Ala Tyr Gln Glu
            260                 265                 270

Leu Ser Ser Ala Leu Glu Lys Met Phe Ser Cys Phe Thr Ile Gly Gln
            275                 280                 285

Tyr Gly Ser His Gly Ala Pro Gly Arg Glu Met Leu Ser Glu Ser Lys
    290                 295                 300

Leu Lys Asp Leu Leu His Gly Ser Glu Tyr Val Leu Thr Tyr Glu Asp
305                 310                 315                 320

Lys Asp Gly Asp Trp Met Leu Val Gly Asp Val Pro Trp Glu Met Phe
                325                 330                 335

Ile Glu Thr Cys Lys Arg Leu Arg Ile Met Lys Ser Ser Asp Ala Ile
            340                 345                 350

Gly Leu Ala Pro Arg Ala Met Glu Lys Cys Lys Asn Arg Asn
            355                 360                 365
```

```
<210> SEQ ID NO 27
<211> LENGTH: 21
<212> TYPE: DNA
<213> ORGANISM: Artificial
<220> FEATURE:
<223> OTHER INFORMATION: Forward cloning primer

<400> SEQUENCE: 27
atggctgtgg agcttatgat g                                              21

<210> SEQ ID NO 28
<211> LENGTH: 28
<212> TYPE: DNA
<213> ORGANISM: Artificial
<220> FEATURE:
<223> OTHER INFORMATION: Forward cloning primer

<400> SEQUENCE: 28
atgtctgtga acatgatcaa ctcttatg                                       28

<210> SEQ ID NO 29
<211> LENGTH: 24
<212> TYPE: DNA
<213> ORGANISM: Artificial
<220> FEATURE:
<223> OTHER INFORMATION: Forward cloning primer

<400> SEQUENCE: 29
atggagatca aggaatcaga gagg                                           24

<210> SEQ ID NO 30
<211> LENGTH: 22
<212> TYPE: DNA
<213> ORGANISM: Artificial
<220> FEATURE:
<223> OTHER INFORMATION: Forward cloning primer

<400> SEQUENCE: 30
atggaggagg ttgaggaggt ac                                             22

<210> SEQ ID NO 31
<211> LENGTH: 22
<212> TYPE: DNA
<213> ORGANISM: Artificial
<220> FEATURE:
<223> OTHER INFORMATION: Forward cloning primer

<400> SEQUENCE: 31
atggctggga ttgatgataa cg                                             22

<210> SEQ ID NO 32
<211> LENGTH: 26
<212> TYPE: DNA
<213> ORGANISM: Artificial
<220> FEATURE:
<223> OTHER INFORMATION: Forward cloning primer

<400> SEQUENCE: 32
atggctgtgg atctagttag gtattc                                         26

<210> SEQ ID NO 33
<211> LENGTH: 20
<212> TYPE: DNA
<213> ORGANISM: Artificial
<220> FEATURE:
<223> OTHER INFORMATION: Forward cloning primer
```

```
<400> SEQUENCE: 33
atggaggggg ttgaagaagc                                           20

<210> SEQ ID NO 34
<211> LENGTH: 22
<212> TYPE: DNA
<213> ORGANISM: Artificial
<220> FEATURE:
<223> OTHER INFORMATION: Forward cloning primer

<400> SEQUENCE: 34
atggaattgt ccatggaatg gg                                        22

<210> SEQ ID NO 35
<211> LENGTH: 25
<212> TYPE: DNA
<213> ORGANISM: Artificial
<220> FEATURE:
<223> OTHER INFORMATION: Forward cloning primer

<400> SEQUENCE: 35
atgatggaag aactttacgg tcttc                                     25

<210> SEQ ID NO 36
<211> LENGTH: 26
<212> TYPE: DNA
<213> ORGANISM: Artificial
<220> FEATURE:
<223> OTHER INFORMATION: Forward cloning primer

<400> SEQUENCE: 36
atggaaagag ataagttgtt tgtgag                                    26

<210> SEQ ID NO 37
<211> LENGTH: 26
<212> TYPE: DNA
<213> ORGANISM: Artificial
<220> FEATURE:
<223> OTHER INFORMATION: Forward cloning primer

<400> SEQUENCE: 37
atgtctgttg gtgtaaacac agaaac                                    26

<210> SEQ ID NO 38
<211> LENGTH: 22
<212> TYPE: DNA
<213> ORGANISM: Artificial
<220> FEATURE:
<223> OTHER INFORMATION: Forward cloning primer

<400> SEQUENCE: 38
atgtatcagc tggagagcgt tc                                        22

<210> SEQ ID NO 39
<211> LENGTH: 25
<212> TYPE: DNA
<213> ORGANISM: Artificial
<220> FEATURE:
<223> OTHER INFORMATION: Forward cloning primer

<400> SEQUENCE: 39
atgtctccac cactacttgg tgttg                                     25

<210> SEQ ID NO 40
<211> LENGTH: 22
```

```
<212> TYPE: DNA
<213> ORGANISM: Artificial
<220> FEATURE:
<223> OTHER INFORMATION: Reverse cloning primer

<400> SEQUENCE: 40
agtgtcttgt cttacacgga tg                                              22

<210> SEQ ID NO 41
<211> LENGTH: 21
<212> TYPE: DNA
<213> ORGANISM: Artificial
<220> FEATURE:
<223> OTHER INFORMATION: Reverse cloning primer

<400> SEQUENCE: 41
tggcgtttga ggcttaattt g                                               21

<210> SEQ ID NO 42
<211> LENGTH: 21
<212> TYPE: DNA
<213> ORGANISM: Artificial
<220> FEATURE:
<223> OTHER INFORMATION: Reverse cloning primer

<400> SEQUENCE: 42
cggcagcaaa gagaaaagat g                                               21

<210> SEQ ID NO 43
<211> LENGTH: 23
<212> TYPE: DNA
<213> ORGANISM: Artificial
<220> FEATURE:
<223> OTHER INFORMATION: Reverse cloning primer

<400> SEQUENCE: 43
gtttcatgta tgcgcagact gtg                                             23

<210> SEQ ID NO 44
<211> LENGTH: 25
<212> TYPE: DNA
<213> ORGANISM: Artificial
<220> FEATURE:
<223> OTHER INFORMATION: Reverse cloning primer

<400> SEQUENCE: 44
attttacatc tgaggcagcc tactc                                           25

<210> SEQ ID NO 45
<211> LENGTH: 24
<212> TYPE: DNA
<213> ORGANISM: Artificial
<220> FEATURE:
<223> OTHER INFORMATION: Reverse cloning primer

<400> SEQUENCE: 45
tcatgttgag tgaaacacgt gtcg                                            24

<210> SEQ ID NO 46
<211> LENGTH: 24
<212> TYPE: DNA
<213> ORGANISM: Artificial
<220> FEATURE:
<223> OTHER INFORMATION: Reverse cloning primer

<400> SEQUENCE: 46
```
gggtggttac gtgtttgtgg attg                                          24

<210> SEQ ID NO 47
<211> LENGTH: 24
<212> TYPE: DNA
<213> ORGANISM: Artificial
<220> FEATURE:
<223> OTHER INFORMATION: Reverse cloning primer

<400> SEQUENCE: 47
ttaagcaaag aaatctgggt tgtc                                          24

<210> SEQ ID NO 48
<211> LENGTH: 20
<212> TYPE: DNA
<213> ORGANISM: Artificial
<220> FEATURE:
<223> OTHER INFORMATION: Reverse cloning primer

<400> SEQUENCE: 48
catcagcatg aggccctgtc                                               20

<210> SEQ ID NO 49
<211> LENGTH: 22
<212> TYPE: DNA
<213> ORGANISM: Artificial
<220> FEATURE:
<223> OTHER INFORMATION: Reverse cloning primer

<400> SEQUENCE: 49
gggatcaggg actgtttatt gg                                            22

<210> SEQ ID NO 50
<211> LENGTH: 24
<212> TYPE: DNA
<213> ORGANISM: Artificial
<220> FEATURE:
<223> OTHER INFORMATION: Reverse cloning primer

<400> SEQUENCE: 50
cagcatcaac aaacctcatc attc                                          24

<210> SEQ ID NO 51
<211> LENGTH: 25
<212> TYPE: DNA
<213> ORGANISM: Artificial
<220> FEATURE:
<223> OTHER INFORMATION: Reverse cloning primer

<400> SEQUENCE: 51
ctaaacatca ctgcctgaaa ctttc                                         25

<210> SEQ ID NO 52
<211> LENGTH: 25
<212> TYPE: DNA
<213> ORGANISM: Artificial
<220> FEATURE:
<223> OTHER INFORMATION: Reverse cloning primer

<400> SEQUENCE: 52
ctaattcctg tttttgcatt tctcc                                         25

<210> SEQ ID NO 53
<211> LENGTH: 20
<212> TYPE: DNA
<213> ORGANISM: Artificial

```
<220> FEATURE:
<223> OTHER INFORMATION: Forward real-time RT PCR primer

<400> SEQUENCE: 53
cagaaccagg accgcaacag                                                    20

<210> SEQ ID NO 54
<211> LENGTH: 20
<212> TYPE: DNA
<213> ORGANISM: Artificial
<220> FEATURE:
<223> OTHER INFORMATION: Forward real-time RT PCR primer

<400> SEQUENCE: 54
atggtgccca attcttatgc                                                    20

<210> SEQ ID NO 55
<211> LENGTH: 21
<212> TYPE: DNA
<213> ORGANISM: Artificial
<220> FEATURE:
<223> OTHER INFORMATION: Forward real-time RT PCR primer

<400> SEQUENCE: 55
aagaaatgaa ggctctgaag g                                                  21

<210> SEQ ID NO 56
<211> LENGTH: 22
<212> TYPE: DNA
<213> ORGANISM: Artificial
<220> FEATURE:
<223> OTHER INFORMATION: Forward real-time RT PCR primer

<400> SEQUENCE: 56
attggtatgc ctcactcatc tg                                                 22

<210> SEQ ID NO 57
<211> LENGTH: 21
<212> TYPE: DNA
<213> ORGANISM: Artificial
<220> FEATURE:
<223> OTHER INFORMATION: Forward real-time RT PCR primer

<400> SEQUENCE: 57
gcagatggca acaggaaatt c                                                  21

<210> SEQ ID NO 58
<211> LENGTH: 21
<212> TYPE: DNA
<213> ORGANISM: Artificial
<220> FEATURE:
<223> OTHER INFORMATION: Forward real-time RT PCR primer

<400> SEQUENCE: 58
gactgcggag aaatcacaaa c                                                  21

<210> SEQ ID NO 59
<211> LENGTH: 23
<212> TYPE: DNA
<213> ORGANISM: Artificial
<220> FEATURE:
<223> OTHER INFORMATION: Forward real-time RT PCR primer

<400> SEQUENCE: 59
cattttccca tcctttcct tcc                                                 23
```

```
<210> SEQ ID NO 60
<211> LENGTH: 22
<212> TYPE: DNA
<213> ORGANISM: Artificial
<220> FEATURE:
<223> OTHER INFORMATION: Forward real-time RT PCR primer

<400> SEQUENCE: 60
tagtgaatga tgtttccaag gg                                              22

<210> SEQ ID NO 61
<211> LENGTH: 18
<212> TYPE: DNA
<213> ORGANISM: Artificial
<220> FEATURE:
<223> OTHER INFORMATION: Forward real-time RT PCR primer

<400> SEQUENCE: 61
agccaacaca gcagcaac                                                   18

<210> SEQ ID NO 62
<211> LENGTH: 22
<212> TYPE: DNA
<213> ORGANISM: Artificial
<220> FEATURE:
<223> OTHER INFORMATION: Forward real-time RT PCR primer

<400> SEQUENCE: 62
cactatgtcc tctacttcct tg                                              22

<210> SEQ ID NO 63
<211> LENGTH: 20
<212> TYPE: DNA
<213> ORGANISM: Artificial
<220> FEATURE:
<223> OTHER INFORMATION: Reverse real-time RT PCR primer

<400> SEQUENCE: 63
tgaggcaaag gagggagacg                                                 20

<210> SEQ ID NO 64
<211> LENGTH: 23
<212> TYPE: DNA
<213> ORGANISM: Artificial
<220> FEATURE:
<223> OTHER INFORMATION: Reverse real-time RT PCR primer

<400> SEQUENCE: 64
ctagttatag acccaacaaa gcc                                             23

<210> SEQ ID NO 65
<211> LENGTH: 21
<212> TYPE: DNA
<213> ORGANISM: Artificial
<220> FEATURE:
<223> OTHER INFORMATION: Reverse real-time RT PCR primer

<400> SEQUENCE: 65
gctgacacca catgagttat c                                               21

<210> SEQ ID NO 66
<211> LENGTH: 21
<212> TYPE: DNA
<213> ORGANISM: Artificial
<220> FEATURE:
<223> OTHER INFORMATION: Reverse real-time RT PCR primer
```

```
<400> SEQUENCE: 66
atctcttcac cctcagtttc c                                              21

<210> SEQ ID NO 67
<211> LENGTH: 21
<212> TYPE: DNA
<213> ORGANISM: Artificial
<220> FEATURE:
<223> OTHER INFORMATION: Reverse real-time RT PCR primer

<400> SEQUENCE: 67
tcaacaagac ctccacgaaa g                                              21

<210> SEQ ID NO 68
<211> LENGTH: 23
<212> TYPE: DNA
<213> ORGANISM: Artificial
<220> FEATURE:
<223> OTHER INFORMATION: Reverse real-time RT PCR primer

<400> SEQUENCE: 68
taggaagaag gagaagaagt tgg                                            23

<210> SEQ ID NO 69
<211> LENGTH: 23
<212> TYPE: DNA
<213> ORGANISM: Artificial
<220> FEATURE:
<223> OTHER INFORMATION: Reverse real-time RT PCR primer

<400> SEQUENCE: 69
agtagttgga ttcagatgtt gcc                                            23

<210> SEQ ID NO 70
<211> LENGTH: 23
<212> TYPE: DNA
<213> ORGANISM: Artificial
<220> FEATURE:
<223> OTHER INFORMATION: Reverse real-time RT PCR primer

<400> SEQUENCE: 70
ttgagagatc cgctttatac ttc                                            23

<210> SEQ ID NO 71
<211> LENGTH: 19
<212> TYPE: DNA
<213> ORGANISM: Artificial
<220> FEATURE:
<223> OTHER INFORMATION: Reverse real-time RT PCR primer

<400> SEQUENCE: 71
tttctctgga ccgcaactc                                                 19

<210> SEQ ID NO 72
<211> LENGTH: 19
<212> TYPE: DNA
<213> ORGANISM: Artificial
<220> FEATURE:
<223> OTHER INFORMATION: Reverse real-time RT PCR primer

<400> SEQUENCE: 72
atggtcttgg gtcttcctg                                                 19

<210> SEQ ID NO 73
```

<211> LENGTH: 1154
<212> TYPE: DNA
<213> ORGANISM: Populus tremula x Populus tremuloides

<400> SEQUENCE: 73

```
atggctgtgg agcttatgat ggggtattct ggcgatagtt ttgctacaaa aatgcaagag      60
aatgatgtga gagaagccgc aactgctggg atacaaagcg ttgaggaagt cataaaactg     120
ctcaaacaaa tcaactgga acagcaacaa aaacaacaat actaccagga gttgtctgca     180
gcctcctcaa gttccaatct tggcacggat aatatcatgg ctgttactga tatggccgtg     240
aacaatttca aaaggttat ttctttactg ggtcgtacca caagaactgg ccatgctcga     300
tttagaagag ctcctgttgc ctgccctcct caacaacgaa tgcaagaacc agaaccagaa     360
ccgcaacagc aaaaacagca agttcagag ccagtaccat atgttcgagc aattaattcg     420
cagccaacag agcaaggctc tgcttttaga gtttatcaac cgaccccaat tcatcgtctc     480
cctcctttgc ctcacaatca gcaacaaaag acactggtgg ttacgaaaaa tggattatca     540
gatcggaatg aaatggctac tacgatcaat ttctccaatt cgccaacaat atctgctcct     600
acttcttct tgtcttctgt aacagggaa actgatagct ccagcgttc tacgctttct     660
gggtttcagt ttacccaacc ttctgctggt aaaccccctt tgtcctcttc ttctcttaag     720
agaaagtgta actccatgga tgatgctgct ctcaagtgtg ctcctcttc tagtcgctgc     780
cactgctcca agaaaaggaa atcaagaatt aaaagggtgg ttagagttcc tgcaattagt     840
agtaagatgg ctgatatccc acctgatgat tattcctgga gaagtatgg tcaaaagccc     900
atcaaaggct ctcctcatcc caggggatac tacaagtgca gtagcgtgag aggatgtccg     960
gcacgcaaac acgtggagag agctctagat gactcgatga tgcttgttgt gacctatgaa    1020
ggggaacaca accactctca tccaatcgat gaagcacccg gtgctcttgt ccttgaatca    1080
tcttaagtca actgatcaat cgacatggaa atatcttcc ccggttcatt cacatccgtg    1140
taagacaaga cact                                                     1154
```

<210> SEQ ID NO 74
<211> LENGTH: 595
<212> TYPE: DNA
<213> ORGANISM: Populus tremula x Populus tremuloides

<400> SEQUENCE: 74

```
atgtctgtga acatgatcaa ctcttatgct tctaccgact ttgaaggtgc aaggggaaac      60
ggattgttgg gattgatgca agagatgcaa ggtccagcca gtttgaattt tgatgacatc     120
tctcaaaaca gaggctttgt tgggtctgga actgaggaga aattgggaaa gaataaggga     180
ggaaagaaga taagaaagcc caagtacgct tttcaaacaa ggagccgagt tgatatcctt     240
gatgatggat atcgatggag aaagtatggt caaaaagcag tgaagaacaa caaatttccc     300
agaagctact atcggtgtac acatcaaggg tgcgacgtga agaagcaggt tcagagatta     360
acaaaagacg aaggagtcgt ggtgacaacc tatgaaggaa tgcattctca tcagatcgaa     420
aagtctccag ataacttcga gcatatcttg agccagatgc aaatctactc ctaatccttc     480
taattaagtc cctagctagg cctctatatc atcgttacat aaggaaatta tggtatcgag     540
atatccgtag actcttacat caataaacta tagacaaatt aagcctcaaa cgcca          595
```

<210> SEQ ID NO 75
<211> LENGTH: 906
<212> TYPE: DNA
<213> ORGANISM: Populus tremula x Populus tremuloides

<400> SEQUENCE: 75

```
atggctgtgg atctagttag gtattcaaag atggaagatc agatggctat acaagaagct      60
gcatcagctg ggctcgagag catggagcac ttgatctttg cactctctaa ccaaactcga     120
caaagccacc aacttgactg cggagaaatc acaaacttca ccgttgccaa gttcaagcaa     180
gtcatctcca tgttgaaccg gaccggccat gcccgttttc gccgtggacc aacttcttct     240
ccttcttcct acccggttcc cgtccgacct gtccctcaag aacctcaaaa actgaacctt     300
gattttgtta acagtaagag ccccctaaa gctgagtcga aaatgaccct gtctttgggt      360
agtcagtatt caaaggatag ccttagctct ggcaccacta cctcatcctt cgtgtcttct     420
gttacagctg atgggagtgt ctctaatggg aaacaaggtg gctcttctct tttcggaact     480
caagctcgat ctaccggaaa gccacctctc tcatcgaccc accgcaagaa atgccacgat     540
catgcccttt ccgccagaaa gatctcctcc ggtggcagct gtcattgctc aaaagaagg      600
aaatcaaggg ttaagaggac aataagggta ccagccgtga gttccaagct tgccgatata     660
ccagcagatg agtactcatg agaaaatat ggtcaaaagc caatcaaggg ctcaccatac      720
ccaagagggt attacaagtg tagtagtgtg aggggatgtc ccgcaaagaa gcatgtggag     780
cgtgccgtag atgactcggc catgcttatt gtgacttacg aggggagca ccgtcactca      840
catactccgt tgccggaaga cgtcacggct agtgctgcaa tgcgacacgt gtttcactca     900
acatga                                                                906
```

<210> SEQ ID NO 76
<211> LENGTH: 470
<212> TYPE: DNA
<213> ORGANISM: Populus tremula x Populus tremuloides

<400> SEQUENCE: 76

```
atggagatca aggaatcaga gagggtggtt atagctaaac cagtagcttc caggcctagt      60
tactcaaatt ttacgtcttt ctcagagttg cttgcgggtg ccatcaatac cacaccctct     120
aatgtttgtt ctggaacagc agttgctgcc attaaaccaa aaacagtgag gttcaggcca     180
ctggtgaatc gtgctccagg tgcactggtt tcttcacagg ctggactctc tggaacagca     240
gttagcaatt cgtttaataa agcttcaagt actgatagca aagccactat catatataaa     300
ccacaggcaa agcttgtgtc aaaggcaact gtttctctac tggcgaatat gggaaacttc     360
aatactaatt cacaacaaat gttacaacca gttgagactc gtcctcagct ttcaaaacaa     420
gataaacaca atttctcatc ccagcttacc tcaaatcctc atcagaatat                 470
```

<210> SEQ ID NO 77
<211> LENGTH: 302
<212> TYPE: DNA
<213> ORGANISM: Populus tremula x Populus tremuloides

<400> SEQUENCE: 77

```
atggaggagg ttgaggaggt acacaaggca gctattgaga gctgcaatag agttattggc      60
cttttgtgtc aagaaaaaga tcaagtccag ggtaggaact taatggtgga aactagagag     120
actgtgttta agtttaagag agttatttct cttttaagca ctggtttagg tcatggaaga     180
gtaagaaaga tgaagaagct tagaccatct ttgccccaaa acatcttcct aaatagtcct     240
aattgcaaaa caatttttatc gccaaaacct ctccaaatgg tgcctcctaa ttttcttgaa     300
ac                                                                    302
```

```
<210> SEQ ID NO 78
<211> LENGTH: 482
<212> TYPE: DNA
<213> ORGANISM: Populus tremula x Populus tremuloides

<400> SEQUENCE: 78
atggctggga ttgatgataa tgttgctata attggtgatt gggtacctcc tagtccaagt      60
ccaagagctt ttttctcagc aatgttaggc gatgatatta actcaagaac aatctcagaa     120
tctcctgggg agaaaagaaa tgaagggctc tatctgggac aaccagagca gatgacaata     180
ggaaattctg agaaaaagga tggagcacaa actagtggtg ttcagttgac tgaattaggt     240
acattttctg agcaaaaatc aaactttcgt ggaggtcttg ttgaaagaat ggcagccaga     300
gctggattta atgcgccgcg gttgaataca gaaagtataa ggtctactga agttctatg      360 aaccctgaga ttaggtcgcc ttatttgaca ataccacctg gtttcagccc gacaaccttg     420
ctggaatctc cagttttcct ttcaaatttg gcacagccat ctccaacaac tggaaaattt     480
tc                                                                    482

<210> SEQ ID NO 79
<211> LENGTH: 538
<212> TYPE: DNA
<213> ORGANISM: Populus tremula x Populus tremuloides

<400> SEQUENCE: 79
atggaggggg ttgaagaagc taaccgggca gctgtggaga gctgccatag agttataact      60
ttgctatccc aacccaaga tcaggttcaa tataggaatt taatggtgga aactggagag      120
gctgtgttta ggttcaagaa agtagtttcc cttttaaata ctggtttagg tcatgcaaga     180
gttcgaaaac ttaagaagtt accgacccct ttatcccaaa gcatcctttt agacaaccca     240
ctgagcagta caggccaccc atccaaaaca tcccagtttc tccagtccag tagttacctg     300
gaaagccaat caattcaaga attgggctca attgctaaaa attgtctatc tctgggaacc     360
ccatccctgg aattgagttc aaatgggaaa aaccctcttc agcttggaca acccacgcca     420
gcagcgccct atcagttcct tcagcaacag caactgcata ggctacagct tcaacagcag     480
cagcaaatga agcagcaagc tgagataatg tttagaaaaa acaatagtgg gatgagct       538

<210> SEQ ID NO 80
<211> LENGTH: 192
<212> TYPE: DNA
<213> ORGANISM: Populus tremula x Populus tremuloides

<400> SEQUENCE: 80
atggaattgt ccatggaatg ggagcacaag actctaatta gtgagctaag tcaagggaag      60
gagctagcga aacagcttag caaccatctt aacccttcct catctctcga agcacgtcaa     120
ttcctagtgg ataagatact ttcttcttat gagaaagcac tttcactgct aaattggggg     180
gctttggtag at                                                         192

<210> SEQ ID NO 81
<211> LENGTH: 394
<212> TYPE: DNA
<213> ORGANISM: Populus tremula x Populus tremuloides

<400> SEQUENCE: 81
atgatggaag aactttacgg tcttcaatcc accagccctg attactcttt gcaggttcca      60
tcagagaaca tggttgctcc agtggctaat tactaccatc ctgcgggtt cacctcccca      120
```

```
gctgggggagc catcatttcc tgttttttgga tcggagcaga tgttttgtgg ttcctcagta    180
tctgatgctg cttcaatggt ggccgagttg catcagaagc agcagcagca gagagggggt    240
gttggtgtgg gtgatcatag taatagtaat aattcagagg aggtttcttg tgcaattagg    300
gctaaaattg cttctcaccc gctttaccct aagttacttg aagcttatat tgattgccag    360
aaggtgggag caccgccgga gatggcttat ttat                                 394

<210> SEQ ID NO 82
<211> LENGTH: 431
<212> TYPE: DNA
<213> ORGANISM: Populus tremula x Populus tremuloides

<400> SEQUENCE: 82
atggaaagag ataagttgtt tgtgagcgag ggagcgaaca cagcagcaac catttggaat     60
tcttgcagtt ttggaatgga aatacaagcc aatgagctga gttgtggtcc agagaaactt    120
gtcaattgct ttctcaatcc caattgggac aactcattgg atcagagcga tcccttttgag    180 tctgctttga gctccattgt atcctcacct gttgcatccg gtgccaatgc aaacgccaac    240
gccgttccta atgctggcgt tggtggtgac ggttttatga ttagagaact cattggaaga    300
ctaggaaaca tttgcaattc tggagacatt tcaccacaat cttttgttaa caataataac    360
aatagcacta cacttcttg ctatagtacc cctttgaatt cccctccaaa gctgaatctt    420
tcgatgatgg a                                                          431

<210> SEQ ID NO 83
<211> LENGTH: 182
<212> TYPE: DNA
<213> ORGANISM: Populus tremula x Populus tremuloides

<400> SEQUENCE: 83
atgtctgttg gtgtaaacac agaaacccta gtgagagttg aggagataca aggaagagga     60
agagggcttg tatccactca gcccttaaga ggtggccaaa tcgtcctcgt agattctcca    120
atcctcctct attctgcact ccctttaacc aaacagcaac actcaacctt cctttactgt    180
ga                                                                    182

<210> SEQ ID NO 84
<211> LENGTH: 463
<212> TYPE: DNA
<213> ORGANISM: Populus tremula x Populus tremuloides

<400> SEQUENCE: 84
atgtatcagc tggagagcgt tcctagttca agttcggtcc ataaaaactc attagttaat     60
gatcagtatt tagattgtga tgatatgaca atggatccca tcaatggagg gaacaatctc    120
aacaacaatc ctaatcttgc ctcaaagcaa agattgcgtt ggactcatga gcttcacgaa    180
cgctttgttg atgctgtggc tcagcttggt gggccagatc gggctacgcc taaaggtgtt    240
ctcagagtca tgggtgtgca aggcttaaca atataccatg ttaaaagcca tttacagaaa    300
tatcgacttg caaaataccct tcctgactcc tcatctgatg ggaaaaaagc ggacaagaag    360
gaaacagggg atatgatttc caatatggat ggttcatctg gcatgcaaat tacagaagca    420
ctcaagctgc agatggaggt gcaaaagcga ctacatgagc aat                       463

<210> SEQ ID NO 85
<211> LENGTH: 490
<212> TYPE: DNA
```

<213> ORGANISM: Populus tremula x Populus tremuloides

<400> SEQUENCE: 85

```
atgtctccac cactacttgg tgttgtggag gaggagggtc aaagtaatgt cactctactg        60
gcttctccgg cctctgcaga aagtgcatgc ctgaatggtt tggaattgaa agagcgtaac       120
tacatgggtt tgtccgattg ttcttccgtg dacagctcgg cagtctctgc agcatctgat       180
gaaagaaagg ctagtttaaa tctgaaggct actgaattgc ggcttgggct tcctgggtct       240
cagtctccgg aaaggaatca cgagctttcc ctgttgagct cggcattact tgatgagaag       300
cccttcttcc ctttgcatcc ctcaaatgat ggtcactact caacacagaa aaatgttgtt       360
tcgggtaaca agagagtgtt ctctgatgcc atggatgagt tttcagagag caagtttctg       420
tcaaattcgg aggtaaatgc aatgctctca cccaggccct caccgaacat gggattgaaa       480
cctggcatgt                                                             490
```

<210> SEQ ID NO 86
<211> LENGTH: 469
<212> TYPE: DNA
<213> ORGANISM: Populus tremula x Populus tremuloides

<400> SEQUENCE: 86

```
cggcagcaaa gagaaaagat gaaatgaaaa cgacacagcc tgtttcgata attctcatta        60
ccagcacaag actgacatca tgaagaagcc tccgtaactg aaacagcttt gttttgtttt       120
ttgattgtca tgttatttag cttttccgga gccctcatac tcttctgata tctgggccag       180
agaaagcatc aagttcgata tcaaatcctt ccatggctga tcactgct tgactctagt         240
agtaggtgcc tgtgaatcag gttcaaaggc tgctaggttt gtgctcttca gagggatctc       300
atggttatgt tttccttcat atgttgtaat aaaagctctt ggatcatctg atactctttc       360
cacatgcttg cgaacattgc atttgatact ggtacatcta tagtaactcc tgggatatgg       420
attccccttc acaatcttct gcccatattt tctccatcga aaccatcc                    469
```

<210> SEQ ID NO 87
<211> LENGTH: 440
<212> TYPE: DNA
<213> ORGANISM: Populus tremula x Populus tremuloides

<400> SEQUENCE: 87

```
gtttcatgta tgcgcagact gtgatgagat caacctggaa tggttatgct caccttcata        60
ggtgacaatt agcattgaag ggtcttccag gcatctctca acgtgcttcc ttgccgggca       120
accccctcaga ctgctacatt tatagtatcc cctaggatgc ggagagccct taattggctt      180
ttgtccatac ttcctccatg aatactcatc aggaggaata tctgccacct tgttgctaat       240
tgcaggaact ttgatagatc tcttcaccct cattttcctc ctctttgaac aatggcattt       300
accactgcta gaacatttgg cattcccatc ttctcctcta ccagaacacc tcctccttgt       360
ttgttgtgag atgtgatcag atgagtgagg cataccaatc aaatggaaag agtctccatc       420
aaaattagac acagcaccat                                                   440
```

<210> SEQ ID NO 88
<211> LENGTH: 514
<212> TYPE: DNA
<213> ORGANISM: Populus tremula x Populus tremuloides

<400> SEQUENCE: 88

```
attttacatc tgaggcagcc tactcattaa atgctgatac actgctgggt tgttggagga        60
```

```
caggctcata ttagcttcag tcactggctc cacctttgct tctcctttcg gcatcatcaa    120
ccccatttca ttcactgcac gttgctgtgc taggtatgga tgcatgggca taactggcat    180
ccttggttgc cctggaccta acccagccat tcccatattg gcaacccag gttgattcat     240 tccaaatgag aagccagccg gaggcccag ctgctgcctg aaggacccaa atgcaggagg     300
cctctcaaat ctaccagtca tgctgttgtg aacttggac gcctcaggtc tatgaacttg     360
ggtttgaacg gcgacgccag cttggggtgg tgtggcatta gaggtgccag agttgacatg    420
gttgctattg cgagcagcag ggacatcatg attgtgcttc ccctcgtacg tagtgatcac    480
tgacttaagg tcatgcgatg ccctctccac atgc                                514

<210> SEQ ID NO 89
<211> LENGTH: 454
<212> TYPE: DNA
<213> ORGANISM: Populus tremula x Populus tremuloides

<400> SEQUENCE: 89
gggtggttac gtgtttgtgg attgtgctgg aatccttggg tggttatgtt caccctcata    60
ggtaacaata agcatggacg gatcttccaa gcacctctcc acatgcttcc ttgcaggaca    120
acctctcata ctgctacatt tgtaatatcc cctaggatga ggagaaccct tgattggctt    180
ttgcccatac tttctccatg agtaatcatc aggagggata tcagcaagct tgttgctaat    240
agcaggaacc ttgatcgacc tcttcaccct atgtttcctc ttctttgagc aatgacatct    300
aacgctgctt ccacatttca tactcccatc ttctcccctt ccggaacatt tcctcttgtg    360
ttgctgtgaa ctctgatctg aggagcgagc cgccccgtt aaatggaatg cagttccttc     420
caaattagcc acattaccgt caatactcaa ggac                                454

<210> SEQ ID NO 90
<211> LENGTH: 270
<212> TYPE: DNA
<213> ORGANISM: Populus tremula x Populus tremuloides

<400> SEQUENCE: 90
ttaagcaaag aaatctgggt tgtcaaatgg gaaagtggta tcaaaatcta cattatcgat    60
tgagatatca aaatccccga ttggtgaatt ggttaccgaa gttggggctg atattatctc    120
cgtggtgagt tcagactccg gggtctgcac atttgggtaa cctattccaa agctgttcat    180
atggcatggt gacattgaga agtagttgga ttcagatgtt gccggagata taaatgtcgg    240
agaaaagcta cccaagaagt tgttttccat                                     270

<210> SEQ ID NO 91
<211> LENGTH: 465
<212> TYPE: DNA
<213> ORGANISM: Populus tremula x Populus tremuloides

<400> SEQUENCE: 91
catcagcatg aggccctgtc caagcatgta caaaaaaagg cgtagtgaga gctaagaggg    60
aacaccccac ctcagtcgtt catgaaaaag ggaccataaa gactatccac aacagcaaat    120
tgcatgttct ctgatggttt ccagcgacgt ttcctttgat tgatgaacca gttgtttatc    180
tgtttctgat ccaggccagt tgattcagcc aacgcaacct tgtcagcttc cgttgggtat    240
ggccatttgt tatgaacgtt ccaccagttt agcaggattt gccttgcttc ctttggtagt    300
tttcctttct tcttctgttt tgaaaacgca tgctttaggg tacttatgta accactatat    360
```

```
ttacgtagta gtttgtcctt gagctctcga tcctcgttta tacgggtaga atcttgcaag    420
tctgcctctc ctccactggc atcgtcatca gatgaaccgg cagct                   465
```

<210> SEQ ID NO 92
<211> LENGTH: 389
<212> TYPE: DNA
<213> ORGANISM: Populus tremula x Populus tremuloides

<400> SEQUENCE: 92

```
gggatcaggg actgtttatt ggttaattac agctcaattt tcatgtgagt tgagggcact     60
gagccttgaa agctctcctg atgattctga ccatatccca tctgcacaac actttgaagg    120
tcgtcttccc acatggctga ggcctgaaga acagcaggat caccaaaacc atcaaggggt    180
ggcagatgca tgctcgggtt tcgccgcaac gcagcgttta atgggttcat ggagaactgg    240
gtttctgcat tgcttggcat gccattttgc agggccagcc cttgctggga ttggtatcca    300
taagggaatg ccggcgtgga ggcatctgat ggataaagac tatgaggcat ggatccacgg    360
gattggaaaa tatccttgga caacagagt                                     389
```

<210> SEQ ID NO 93
<211> LENGTH: 201
<212> TYPE: DNA
<213> ORGANISM: Populus tremula x Populus tremuloides

<400> SEQUENCE: 93

```
cagcatcaac aaacctcatc attcttgata acaccacagg cattgcattc caataaattt     60
gatggcttag catcagaagg aggaagagga gctagtgtac cccaacaatt atttcgatta    120
cacatgtatc tcaaaaagaa ataggcatga ggaaagtcag cgctgttatc attgtcgatt    180
tcttcaccat tagattcggc c                                             201
```

<210> SEQ ID NO 94
<211> LENGTH: 483
<212> TYPE: DNA
<213> ORGANISM: Populus tremula x Populus tremuloides

<400> SEQUENCE: 94

```
ctaaacatca ctgcctgaaa cttctctccat ttgatcttcg attcccatcg ataacccaga    60
tgaaggatca aactgctctc tacccaggaa ggcagagtgt ggtcgtggat aggaatttaa    120
gcttgactcg agtatctggt gtgtaagaac catctcttgt ttactgtatg ttacacccat    180
gcttacccgt tgcttcttca tcgatctctc acctctaggg ctctctgctg gggagccagc    240
attacaacgt gaatctggtg tcagtggctc aggctgagaa gagaatgatt catcaattga    300
aaggctcttt gctggggcac gttccttggc agccttgtct tggagggtg attcagaagt    360 tggggcaggg gttgctgggt ctgtcttgtc agattctggg cagttatcac ctgatactgg    420
ggcagcgacc cccgagccag gcacatcttc aagaactcca ctcaatcgtt gttgctcttc    480
aat                                                                 483
```

<210> SEQ ID NO 95
<211> LENGTH: 374
<212> TYPE: DNA
<213> ORGANISM: Populus tremula x Populus tremuloides

<400> SEQUENCE: 95

```
ctaattcctg tttttgcatt tctccatggc ccttggtgct aggccaatgg catcagagct     60
cttcatgatc ctcagcctct tgcatgtttc aataaacatc tcccagggaa catcgccaac    120
```

```
aagcatccag tctccgtctt tatcctcata agtgagaaca tatttctgagc catgcagcag      180 atccttcagc ttgctctcgc tcagcatctc ccttcctgga gctccatggg atccatattg      240
gcctatggtg aaacagctga acatcttctc gagggcagaa gacaattcct gatatgcaga      300
gtagtttctc aaatccactt ttctaagata aggagcacca tccatgctga ctttgataaa      360
taaagcacct ggcc                                                        374
```

<210> SEQ ID NO 96
<211> LENGTH: 11135
<212> TYPE: DNA
<213> ORGANISM: Artificial
<220> FEATURE:
<223> OTHER INFORMATION: Binary destinatin vector: pK2GW7

<400> SEQUENCE: 96

```
ctcccatatg gtcgactaga gccaagctga tctcctttgc cccggagatc accatggacg       60
actttctcta tctctacgat ctaggaagaa agttcgacgg agaaggtgac gataccatgt      120
tcaccaccga taatgagaag attagcctct tcaatttcag aaagaatgct gacccacaga      180
tggttagaga ggcctacgcg gcaggtctca tcaagacgat ctacccgagt aataatctcc      240
aggagatcaa ataccttccc aagaaggtta agatgcagt caaaagattc aggactaact      300
gcatcaagaa cacagagaaa gatatatttc tcaagatcag aagtactatt ccagtatgga      360
cgattcaagg cttgcttcat aaaccaaggc aagtaataga gattggagtc tctaagaaag      420
tagttcctac tgaatcaaag gccatggagt caaaaattca gatcgaggat ctaacagaac      480
tcgccgtgaa gactggcgaa cagttcatac agagtctttt acgactcaat gacaagaaga      540
aaatcttcgt caacatggtg gagcacgaca ctctcgtcta ctccaagaat atcaaagata      600
cagtctcaga agaccaaagg gctattgaga cttttcaaca aagggtaata tcgggaaacc      660
tcctcggatt ccattgccca gctatctgtc acttcatcaa aggacagta gaaaaggaag      720 gtggcaccta caaatgccat cattgcgata aaggaaaggc tatcgttcaa gatgcctctg      780
ccgacagtgg tcccaaagat ggaccccac ccacgaggag catcgtggaa aaagaagacg      840
ttccaaccac gtcttcaaag caagtggatt gatgtgatat ctccactgac gtaagggatg      900
acgcacaatc ccactatcct tcgcaagacc cttcctctat ataaggaagt tcatttcatt      960
tggagaggac tccggtattt ttacaacaat accacaacaa acaaacaac aaacaacatt     1020 acaatttact attctagtcg acctgcaggc ggccgcacta gtgatatcac aagtttgtac     1080
aaaaaagctg aacgagaaac gtaaaatgat ataaatatca atatattaaa ttagattttg     1140
cataaaaaac agactacata atactgtaaa acacaacata tccagtcact atggcggccg     1200
cattaggcac cccaggcttt acactttatg cttccggctc gtataatgtg tggatttga     1260 gttaggatcc ggcgagattt tcaggagcta aggaagctaa aatggagaaa aaaatcactg     1320
gatataccac cgttgatata tcccaatggc atcgtaaaga acattttgag gcatttcagt     1380
cagttgctca atgtacctat aaccagaccg ttcagctgga tattacggcc tttttaaaga     1440
ccgtaaagaa aaataagcac aagttttatc cggcctttat tcacattctt gcccgcctga     1500
tgaatgctca tccggaattc cgtatggcaa tgaaagacgg tgagctggtg atatgggata     1560
gtgttcaccc ttgttacacc gttttccatg agcaaactga aacgttttca tcgctctgga     1620
gtgaatacca cgacgatttc cggcagtttc tacacatata ttcgcaagat gtggcgtgtt     1680
acggtgaaaa cctggcctat ttccctaaag ggtttattga gaatatgttt ttcgtctcag     1740
```

```
ccaatccctg ggtgagtttc accagttttg atttaaacgt ggccaatatg gcaacttct   1800
tcgccccgt  tttcaccatg gcaaatatt  atacgcaagg cgacaaggtg ctgatgccgc   1860
tggcgattca ggttcatcat gccgtctgtg atggcttcca tgtcggcaga atgcttaatg   1920
aattacaaca gtactgcgat gagtggcagg gcggggcgta aacgcgtgga tccggcttac   1980
taaaagccag ataacagtat gcgtatttgc gcgctgattt ttgcggtata agaatatata   2040
ctgatatgta tacccgaagt atgtcaaaaa gaggtgtgct atgaagcagc gtattacagt   2100
gacagttgac agcgacagct atcagttgct caaggcatat atgatgtcaa tatctccggt   2160
ctggtaagca caaccatgca gaatgaagcc cgtcgtctgc gtgccgaacg ctggaaagcg   2220
gaaaatcagg aagggatggc tgaggtcgcc cggtttattg aaatgaacgg ctcttttgct   2280
gacgagaaca gggactggtg aaatgcagtt aaggtttac  acctataaaa gagagagccg   2340
ttatcgtctg tttgtggatg tacagagtga tattattgac acgcccgggc gacggatggt   2400
gatcccctg  gccagtgcac gtctgctgtc agataaagtc tcccgtgaac tttacccggt   2460
ggtgcatatc ggggatgaaa gctggcgcat gatgaccacc gatatggcca gtgtgccggt   2520
ctccgttatc ggggaagaag tggctgatct cagccaccgc gaaaatgaca tcaaaaacgc   2580
cattaaccta atgttctggg aatataaat  gtcaggctcc cttatacaca gccagtctgc   2640
aggtcgacca tagtgactgg atatgttgtg ttttacagta ttatgtagtc tgttttttat   2700
gcaaaatcta atttaatata ttgatattta tatcatttta cgtttctcgt tcagcttttct  2760
tgtacaaagt ggtgatatcc cgcggccatg ctagagtccg caaaaatcac cagtctctct   2820
ctacaaatct atctctctct atttttctcc agaataatgt gtgagtagtt cccagataag   2880
ggaattaggg ttcttatagg gtttcgctca tgtgttgagc atataagaaa cccttagtat   2940
gtatttgtat ttgtaaaata cttctatcaa taaaatttct aattcctaaa accaaaatcc   3000
agtgacctgc aggcatgcga cgtcgggccc aagcttagct tgagcttgga tcagattgtc   3060
gtttcccgcc ttcagtttaa actatcagtg tttgacagga tatattggcg ggtaaaccta   3120
agagaaaaga gcgtttatta gaataacgga tatttaaaag ggcgtgaaaa ggtttatccg   3180
ttcgtccatt tgtatgtgca tgccaaccac agggttcccc tcgggatcaa agtactttga   3240
tccaacccct ccgctgctat agtgcagtcg gcttctgacg ttcagtgcag ccgtcttctg   3300
aaaacgacat gtcgcacaag tcctaagtta cgcgacaggc tgccgccctg ccctttctcct  3360
ggcgttttct tgtcgcgtgt tttagtcgca taaagtagaa tacttgcgac tagaaccgga   3420
gacattacgc catgaacaag agcgccgccg ctggcctgct gggctatgcc cgcgtcagca   3480
ccgacgacca ggacttgacc aaccaacggg ccgaactgca cgcggccggc tgcaccaagc   3540
tgttttccga agatcacc  ggcaccaggc gcgaccgccc ggagctggcc aggatgcttg   3600
accacctacg ccctggcgac gttgtgacag tgaccaggct agaccgcctg gcccgcagca   3660
cccgcgacct actggacatt gccgagcgca tccaggaggc cggcgcgggc ctgcgtagcc   3720
tggcagagcc gtgggccgac accaccacgc cggccggccg catggtgttg accgtgttcg   3780
ccggcattgc cgagttcgag cgttccctaa tcatcgaccg cacccggagc gggcgcgagg   3840
ccgccaaggc ccgaggcgtg aagtttggcc ccgccctac  cctcaccccg gcacagatcg   3900
cgcacgcccg cgagctgatc gaccaggaag gccgcaccgt gaagaggcg  gctgcactgc   3960
ttggcgtgca tcgctcgacc ctgtaccgcg cacttgagcg cagcgaggaa gtgacgccca   4020
ccgaggccag gcggcgcggt gccttccgtg aggacgcatt gaccgaggcc gacgccctgg   4080
cggccgccga gaatgaacgc caagaggaac aagcatgaaa ccgcaccagg acggccagga   4140
```

```
cgaaccgttt tcattaccg aagagatcga ggcggagatg atcgcggccg ggtacgtgtt    4200
cgagccgccc gcgcacgtct caaccgtgcg gctgcatgaa atcctggccg gtttgtctga    4260
tgccaagctg gcggcctggc cggccagctt ggccgctgaa gaaaccgagc gccgccgtct    4320
aaaaaggtga tgtgtatttg agtaaaaacag cttgcgtcat gcggtcgctg cgtatatgat    4380
gcgatgagta aataaacaaa tacgcaaggg gaacgcatga aggttatcgc tgtacttaac    4440
cagaaaggcg ggtcaggcaa gacgaccatc gcaacccatc tagcccgcgc cctgcaactc    4500
gccggggccg atgttctgtt agtcgattcc gatccccagg gcagtgcccg cgattgggcg    4560
gccgtgcggg aagatcaacc gctaaccgtt gtcggcatcg accgcccgac gattgaccgc    4620
gacgtgaagg ccatcggccg gcgcgacttc gtagtgatcg acggagcgcc ccaggcggcg    4680
gacttggctg tgtccgcgat caaggcagcc gacttcgtgc tgattccggt gcagccaagc    4740
ccttacgaca tatgggccac cgccgacctg gtggagctgg ttaagcagcg cattgaggtc    4800
acggatggaa ggctacaagc ggcctttgtc gtgtcgcggg cgatcaaagg cacgcgcatc    4860
ggcggtgagg ttgccgaggc gctggccggg tacgagctgc ccattcttga gtcccgtatc    4920
acgcagcgcg tgagctaccc aggcactgcc gccgccggca caaccgttct tgaatcagaa    4980
cccgagggcg acgctgcccg cgaggtccag gcgctggccg ctgaaattaa atcaaaactc    5040
atttgagtta atgaggtaaa gagaaaatga gcaaaagcac aaacacgcta agtgccggcc    5100
gtccgagcgc acgcagcagc aaggctgcaa cgttggccag cctggcagac acgccagcca    5160
tgaagcgggt caactttcag ttgccggcgg aggatcacac caagctgaag atgtacgcgg    5220
tacgccaagg caagaccatt accgagctgc tatctgaata catcgcgcag ctaccagagt    5280
aaatgagcaa atgaataaat gagtagatga attttagcgg ctaaaggagg cggcatggaa    5340
aatcaagaac aaccaggcac cgacgccgtg gaatgcccca tgtgtggagg aacgggcggt    5400
tggccaggcg taagcggctg ggttgtctgc cggccctgca atggcactgg aacccccaag    5460
cccgaggaat cggcgtgacg gtcgcaaacc atccggcccg gtacaaatcg cgcggcgct    5520 gggtgatgac ctggtggaga agttgaaggc cgcgcaggcc gcccagcggc aacgcatcga    5580
ggcagaagca cgccccggtg aatcgtggca agcggccgct gatcgaatcc gcaaagaatc    5640
ccggcaaccg ccggcagccg gtgcgccgtc gattaggaag ccgcccaagg cgacgagca    5700 accagatttt tcgttccga tgctctatga cgtgggcacc cgcgatagtc gcagcatcat    5760
ggacgtggcc gttttccgtc tgtcgaagcg tgaccgacga gctggcgagg tgatccgcta    5820
cgagcttcca gacgggcacg tagaggtttc cgcagggccg gccggcatgg ccagtgtgtg    5880
ggattacgac ctggtactga tggcggtttc ccatctaacc gaatccatga accgataccg    5940
ggaagggaag ggagacaagc ccggccgcgt gttccgtcca cacgttgcgg acgtactcaa    6000
gttctgccgg cgagccgatg gcggaaagca gaaagacgac ctggtagaaa cctgcattcg    6060
gttaaacacc acgcacgttg ccatgcagcg tacgaagaag gccaagaacg gccgcctggt    6120
gacggtatcc gagggtgaag ccttgattag ccgctacaag atcgtaaaga gcgaaaccgg    6180
gcggccggag tacatcgaga tcgagctagc tgattggatg taccgcgaga tcacagaagg    6240
caagaacccg gacgtgctga cggttcaccc cgattacttt tgatcgatc ccggcatcgg    6300 ccgttttctc taccgcctgg cacgccgcgc cgcaggcaag gcagaagcca gatggttgtt    6360
caagacgatc tacgaacgca gtggcagcgc cggagagttc aagaagttct gtttcaccgt    6420
gcgcaagctg atcgggtcaa atgaccctgcc ggagtacgat ttgaaggagg aggcggggca    6480
```

```
ggctggcccg atcctagtca tgcgctaccg caacctgatc gagggcgaag catccgccgg    6540
ttcctaatgt acggagcaga tgctagggca aattgcccta gcaggggaaa aaggtcgaaa    6600
aggtctcttt cctgtggata gcacgtacat tgggaaccca aagccgtaca ttgggaaccg    6660
gaacccgtac attgggaacc caaagccgta cattgggaac cggtcacaca tgtaagtgac    6720
tgatataaaa gagaaaaaag gcgattttc cgcctaaaac tctttaaaac ttattaaaac    6780
tcttaaaacc cgcctggcct gtgcataact gtctggccag cgcacagccg aagagctgca    6840
aaaagcgcct acccttcggt cgctgcgctc cctacgcccc gccgcttcgc gtcggcctat    6900
cgcggccgct ggccgctcaa aaatggctgg cctacggcca gcaatctac cagggcgcgg    6960
acaagccgcg ccgtcgccac tcgaccgccg gcgcccacat caaggcaccc tgcctcgcgc    7020
gtttcggtga tgacggtgaa aacctctgac acatgcagct cccggagacg gtcacagctt    7080
gtctgtaagc ggatgccggg agcagacaag cccgtcaggg cgcgtcagcg ggtgttggcg    7140
ggtgtcgggg cgcagccatg acccagtcac gtagcgatag cggagtgtat actggcttaa    7200
ctatgcggca tcagagcaga ttgtactgag agtgcaccat atgcggtgtg aaataccgca    7260
cagatgcgta aggagaaaat accgcatcag gcgctcttcc gcttcctcgc tcactgactc    7320
gctgcgctcg gtcgttcggc tgcggcgagc ggtatcagct cactcaaagg cggtaatacg    7380
gttatccaca gaatcagggg ataacgcagg aaagaacatg tgagcaaaag gccagcaaaa    7440
ggccaggaac cgtaaaaagg ccgcgttgct ggcgtttttc cataggctcc gcccccctga    7500
cgagcatcac aaaaatcgac gctcaagtca gaggtggcga aacccgacag gactataaag    7560
ataccaggcg tttccccctg gaagctccct cgtgcgctct cctgttccga ccctgccgct    7620
taccggatac ctgtccgcct ttctcccttc gggaagcgtg gcgctttctc atagctcacg    7680
ctgtaggtat ctcagttcgg tgtaggtcgt tcgctccaag ctgggctgtg tgcacgaacc    7740
ccccgttcag cccgaccgct gcgccttatc cggtaactat cgtcttgagt ccaacccggt    7800
aagacacgac ttatcgccac tggcagcagc cactggtaac aggattagca gagcgaggta    7860
tgtaggcggt gctacagagt tcttgaagtg gtggcctaac tacggctaca ctagaaggac    7920
agtatttggt atctgcgctc tgctgaagcc agttaccttc ggaaaaagag ttggtagctc    7980
ttgatccggc aaacaaacca ccgctggtag cggtggtttt tttgtttgca agcagcagat    8040
tacgcgcaga aaaaaggat ctcaagaaga tcctttgatc ttttctacgg ggtctgacgc    8100
tcagtggaac gaaaactcac gttaagggat tttggtcatg catgatatat ctcccaattt    8160
gtgtagggct tattatgcac gcttaaaaat aataaaagca gacttgacct gatagtttgg    8220
ctgtgagcaa ttatgtgctt agtgcatcta atcgcttgag ttaacgccgg cgaagcggcg    8280
tcggcttgaa cgaatttcta gctagacatt atttgccgac taccttggtg atctcgcctt    8340
tcacgtagtg gacaaattct tccaactgat ctgcgcgcga ggccaagcga tcttcttctt    8400
gtccaagata agcctgtcta gcttcaagta tgacgggctg atactgggcc ggcaggcgct    8460
ccattgccca gtcggcagcg acatccttcg gcgcgatttt gccggttact gcgctgtacc    8520
aaatgcggga caacgtaagc actacatttc gctcatcgcc agcccagtcg gcggcgagt    8580
tccatagcgt taaggtttca tttagcgcct caaatagatc ctgttcagga accggatcaa    8640
agagttcctc cgccgctgga cctaccaagg caacgctatg ttctcttgct tttgtcagca    8700
agatagccag atcaatgtcg atcgtggctg gctcgaagat acctgcaaga atgtcattgc    8760
gctgccattc tccaaattgc agttcgcgct tagctggata cgccacggaa tgatgtcgt    8820
cgtgcacaac aatggtgact tctacagcgc ggagaatctc gctctctcca gggaagccg    8880
```

```
aagtttccaa aaggtcgttg atcaaagctc gccgcgttgt ttcatcaagc cttacggtca   8940
ccgtaaccag caaatcaata tcactgtgtg gcttcaggcc gccatccact gcggagccgt   9000
acaaatgtac ggccagcaac gtcggttcga gatggcgctc gatgacgcca actacctctg   9060
atagttgagt cgatacttcg gcgatcaccg cttcccccat gatgtttaac tttgttttag   9120
ggcgactgcc ctgctgcgta acatcgttgc tgctccataa catcaaacat cgacccacgg   9180
cgtaacgcgc ttgctgcttg gatgcccgag gcatagactg taccccaaaa aaacatgtca   9240
taacaagaag ccatgaaaac cgccactgcg ccgttaccac cgctgcgttc ggtcaaggtt   9300
ctggaccagt tgcgtgacgg cagttacgct acttgcatta cagcttacga accgaacgag   9360
gcttatgtcc actgggttcg tgcccgaatt gatcacaggc agcaacgctc tgtcatcgtt   9420
acaatcaaca tgctaccctc cgcgagatca tccgtgtttc aaacccggca gcttagttgc   9480
cgttcttccg aatagcatcg gtaacatgag caaagtctgc cgccttacaa cggctctccc   9540
gctgacgccg tcccgactg  atgggctgcc tgtatcgagt ggtgattttg tgccgagctg   9600
ccggtcgggg agctgttggc tggctggtgg caggatatat tgtggtgtaa acaaattgac   9660
gcttagacaa cttaataaca cattgcggac gttttttaatg tactgaatta acgccgaatt   9720
gaattatcag cttgcatgcc ggtcgatcta gtaacataga tgacaccgcg cgcgataatt   9780
tatcctagtt tgcgcgctat attttgtttt ctatcgcgta ttaaatgtat aattgcggga   9840
ctctaatcat aaaaacccat ctcataaata acgtcatgca ttacatgtta attattacat   9900
gcttaacgta attcaacaga aattatatga taatcatcgc aagaccggca acaggattca   9960
atcttaagaa actttattgc caaatgtttg aacgatctgc ttgactctag ctagagtccg  10020
aaccccagag tcccgctcag aagaactcgt caagaaggcg atagaaggcg atgcgctgcg  10080
aatcgggagc ggcgataccg taaagcacga ggaagcggtc agcccattcg ccgccaagct  10140
cttcagcaat atcacgggta gccaacgcta tgtcctgata gcggtccgcc acacccagcc  10200
ggccacagtc gatgaatcca gaaaagcggc cattttccac catgatattc ggcaagcagg  10260
catcgccgtg ggtcacgacg agatcctcgc cgtcgggcat ccgcgccttg agcctggcga  10320
acagttcggc tggcgcgagc ccctgatgct cttcgtccag atcatcctga tcgacaagac  10380
cggcttccat ccgagtacgt gctcgctcga tgcgatgttt cgcttggtgg tcgaatgggc  10440
aggtagccgg atcaagcgta tgcagccgcc gcattgcatc agccatgatg gatactttct  10500
cggcaggagc aaggtgagat gacaggagat cctgccccgg cacttcgccc aatagcagcc  10560
agtcccttcc cgcttcagtg acaacgtcga gcacagctgc gcaaggaacg cccgtcgtgg  10620
ccagccacga tagccgcgct gcctcgtctt ggagttcatt cagggcaccg gacaggtcgg  10680
tcttgacaaa aagaaccggg cgcccctgcg ctgacagccg aacacggcg  gcatcagagc  10740
agccgattgt ctgttgtgcc cagtcatagc cgaatagcct ctccacccaa gcggccggag  10800
aacctgcgtg caatccatct tgttcaatca tgcctcgatc gagttgagag tgaatatgag  10860
actctaattg ataccgagg  ggaatttatg gaacgtcagt ggagcatttt tgacaagaaa  10920
tatttgctag ctgatagtga ccttaggcga cttttgaacg cgcaataatg gtttctgacg  10980
tatgtgctta gctcattaaa ctccagaaac ccgcggctga gtggctcctt caacgttgcg  11040
gttctgtcag ttccaaacgt aaaacggctt gtcccgcgtc atcggcgggg gtcataacgt  11100
gactcccctta attctcatgt atgataattc gagct                             11135
```

<210> SEQ ID NO 97

<211> LENGTH: 564
<212> TYPE: DNA
<213> ORGANISM: Populus Trichoocarpa

<400> SEQUENCE: 97

| | | | | | |
|---|---|---|---|---|---|
| atgcaaccag | gcttggatga | gatcacaatg | acggcgtgga | agaatctaaa | gcaacggctc | 60 |
| tcattcaagg | gcctgggtag | ttgctgcggg | agcacaagct | ggagttccag | aagtgccacc | 120 |
| ccaaccatgc | cctttatcga | tatagagcaa | gaagaagagg | aagagcccat | catgcaaaac | 180 |
| caagctcaaa | gaggaggagg | agctgcagca | gcagcagcag | cgccaggtgc | tgggatgaat | 240 |
| ctggcaatgg | cattagctgc | tgagcgcaat | ttaggggatt | caaatgtcaa | gacattgatg | 300 |
| agtttgatcg | aagaaacgga | cggtgttgat | tggaggaaga | agaataacag | taatgataaa | 360 |
| agtaggaggg | acaaggaaca | ggaacagaag | caggaagaag | agaaggattg | ggtatgctgc | 420 |
| gtttgcatgg | agagaaataa | aggcgcagct | tttattccat | gtggacacac | cttttgtagg | 480 |
| gtttgttcaa | gagaaatgtg | ggttaatcga | gggtgctgtc | ctatctgcaa | ccgttccatt | 540 |
| ctcgacatcc | ttgatatctt | ctag | | | | 564 |

<210> SEQ ID NO 98
<211> LENGTH: 645
<212> TYPE: DNA
<213> ORGANISM: Populus Trichocarpa

<400> SEQUENCE: 98

| | | | | | |
|---|---|---|---|---|---|
| atggcgagag | gaaaggttca | gctgaaaagg | atagagaatg | caactagcag | gcaagtgacc | 60 |
| ttctccaaga | gaaaaaatgg | gttattgaag | aaagcttatg | agctatcaat | tctgtgcgat | 120 |
| gctgaagttg | cagtgatcat | cttttcacag | aaaggaacac | tctttaagtt | tgcaagcatt | 180 |
| gatcagatac | aaaagacgat | tgatcggtac | cgtaaaaatg | caaagcaatt | gcacactgac | 240 |
| aggattgatg | tggaacaatc | taaggagcaa | ttaagacaag | aatcagcaaa | catggccaag | 300 |
| aagattgaga | taatcgagat | tttgcaacga | aagcttttag | gcaagatttt | agattcatgt | 360 |
| tctcccgaag | agctccatga | cattgacaat | cagcttgaga | tcagtttaag | caatatcagg | 420 |
| gctagaaaga | ctcagttatt | caaggagcag | atagaacagc | tgcaagcaaa | ggaaagattg | 480 |
| ttgttaatgg | agaatgcaag | gttaactaaa | cagtgtgatg | cacagccatt | gcagcaatca | 540 |
| actcaatcga | accaagtggt | gtcatacttg | acctcatgta | gcaagagttc | agatatcgtg | 600 |
| gagactgatc | tgtacattgg | actgccacac | atgcgctgct | tgtag | | 645 |

<210> SEQ ID NO 99
<211> LENGTH: 1755
<212> TYPE: DNA
<213> ORGANISM: Populus trichocarpa

<400> SEQUENCE: 99

| | | | | | |
|---|---|---|---|---|---|
| atggcatata | tgtgtgcaga | tagcggaaat | ctaatggcaa | tagcccaaca | agttattaag | 60 |
| caaaaacaac | aacaagaaca | acagcagcaa | caaagccacc | accaccacca | taaccaacag | 120 |
| caacaatttc | ttggcctaaa | cccatttttct | ttaaatcctt | ggccgactaa | tataatgtct | 180 |
| gctaacccaa | acttgggtta | cgggctctcg | ggtccggctg | ctttctctga | cccttttcag | 240 |
| agtggacaag | aaacaggtga | cccacctgtg | tttagtttct | cgaacatgga | gcagcaccac | 300 |
| tcaagcgggt | tcggcttcc | ttattttact | ggagctggtg | gtgagtttga | ctcggatgag | 360 |
| tggatggaca | gttaatgaa | cggtggagat | tcaacggata | gttctaatct | tccttctggt | 420 |
| tgtgacgcgt | ggcaaaacag | tactgatttt | gggatgtaca | cttctgatcc | gtttaatact | 480 |

```
tgccccagtc gacttactgt tggctgctct ccaccgtctg atcttaacgg ggttctctct      540
aattcgctct gggtcgcccc atctcctcct caagaaatca agcccacaac gtcacccccg      600
ccactgcttc cgccaacagt aaaaaatgaa accgtcggag ggtcagagga aattgtacag      660
ttatcttcct cgccggtttt gaaagcgctt gttgagtgcg ctcaacttgt cgagtccaaa      720
gctgatcaag ccgtgaaatc gttggttaag tgcaaggact tggtgagtga aaacggtgat      780
ccagttgagc gagctggttt ctacttcgcg gaaggattat gccgaagagt tgctgtagga      840
gagcttgatg tcttgaaaaa ttttgatcag acaagtgaag agttcactct gtcctataaa      900
gctttgaatg atgcctgtcc atattcaaag tttgctcatt aacagcaaa ccaagcaatt       960 cttgaggcaa ctgagaaagc aagcaagatt cacatagttg attttggtat tgttcatgga     1020
gttcaatggg ctgctctttt acaagcttta gctacacgtt cagctggaaa acctgttaga     1080
attcggatct caggtatacc tgctccagtt cttggtaaga atccagctgc ctctctttta     1140
gctactggta ataggcttct tgattatgcc aagcttcttg gtttgaattt cgagtttgag     1200
cctattctga ctccaattca ggagttaaat gaatcttgtt ttcgagccga gccggatgag     1260
gttttggctg ttaatttcat gcttcaattg tataatttat tggatgagtc tccagttgct     1320
gtagaaactg ctttaaagat ggctaaatcg ttgaacccga taattgtcac tcttggtgaa     1380
tatgaagcta gtttgaaccg ggttgggtac ttgactcggt ttaagaatgc tttgagatac     1440
tacactgctg ttttttgagtc tcttgagcct aacatgagta gagactcacc agagaggctt     1500
caagttgaga gattgttatt gggtcgagaa tttctagtgt tggaaaggat ggaggataaa     1560
gatcaatggg gagttttaat ggaaagttca ggttttgaat cggtttcgct tagccattat     1620
gcaatgagtc aggctaagat actcttatgg tattgcaatt acagtgattt gtattctctt     1680
gatgattctc agcctgggtt cttaacttta gcttggaatg aggtgccact actcacagtt     1740
tcgtcatggc gataa                                                      1755
```

<210> SEQ ID NO 100
<211> LENGTH: 729
<212> TYPE: DNA
<213> ORGANISM: Populus trichocarpa

<400> SEQUENCE: 100

```
atggggagag gtagggttga gttgaagaga attgagaaca agatcaacag gcaagtaaca       60
tttgcaaaga gaaggaatgg acttttgaag aaagcctatg agctttccgt tctttgtgat      120
gcagaggttg ctctcatcat cttctccaat agaggaaagc tgtacgagtt ttgcagtagt      180
tcaagcatgc tcaaaactct tgagaggtac cagaagtgca attatggagc accagagcca      240
aatgtgtctg caagggaggc cctggaactg agtagtcagc aggaatatct gaagcttaaa      300
gcacgttatg aagccctgca aagaacccaa aggaatcttt tgggagaaga acttggccct      360
ctaagcagca aagagctaga atcacttgaa aggcagcttg atatgtcatt gaagcagatc      420
agatcaacaa ggacccaata catgctggat cagctccatg acctacagca taaggagcac      480
atgctgactg cagctaataa gtccctgaaa gaaaggttga tggaaggcta ccaattaaat      540
tcactccagt tgaatccaag tgcagaagat gtggagtacg ctagacaaca agcccaaccc      600
cagggtgatg ggttttttca tgctttggag tgtgaaccta cactacaaat tgggtatcag      660
ccagaaaata taacaatggt cactgctggc ccaagtatga ctacttacat gccaggttgg      720
ttagcatga                                                             729
```

```
<210> SEQ ID NO 101
<211> LENGTH: 1758
<212> TYPE: DNA
<213> ORGANISM: Populus trichocarpa

<400> SEQUENCE: 101
atgtctttag ttggacctgc agaactttct gcaacaccat acggaaatca taagctgtac     60
tcactgaagg ggagcaatga caactctggc ttgtctgccc aaatattctg ccctgataaa    120
cgtcagaaca tgtatatgac cgattcttac tccagtgaga gttatgagaa gtacttcctt    180
gattccccaa cagaagagct aatacaacca tcaagttctg catttcagg gaattcagct    240 ccacctcaag gcacatcttc ctaccagcta agaaagaatt taggtccatc catgtcccct    300
caagatgatc catacgacgc ttgtttcaca ttgacgacac cctgtgatgg ctatcaattc    360
aattccgagt cagattactt ggacatcgag agcccagatc cactaaacta tgatgaatat    420
aagatgaaat taaagtttca ggaacttgag agagcgcttc taaatgataa tgatgaggat    480
ggcatgtttg aaatagtca gagcatgaa atggatggag agtggtctga tccaatccag    540
aatgggatgc tccatgattc tcccaaggag tcatcatctt ctgattctag cctaagtagc    600
atcagcagta ataagaagt atcacagtta tctcctcgaa ctcccaggcg attgcttttt    660
gaatgtgcta atgcaatctc agagggaaac attgagaaag catcaacttt aataaacgag    720
ctccgtcaat tggtgtcaat tcaaggagat cctccgcaga ggattgcagc ctacatggtg    780
gaaggtcttg cagctcgtat ggctgaatct ggaaaatatc tctataaagc tctgaaatgc    840
aaggaacctc cttcttctga taggcttgca gctatgcaga tccttttga gatttgccct    900 tgtttttaaat ttggatttat ggcagcaaat ggtgcaatga tcgaggcatt taaaggtgaa    960
aggagagttc atataataga ttttgacata aaccaaggga gtcaatacat aacactgata   1020
caaacactcg ccaaccatca aggtaagcta ccacacttga ggttaacagg ggtcgatgac   1080
cctgagtcag ttcaacgacc tgttggtggc ctgaggatca ttgggcaaag gcttgaaaag   1140
ctagcagaag catataaggt ctcgttcgag tttcatgcag tggcctccaa gacttcactt   1200
gtcaatccat caatgctgaa ctgcaagcct ggggaagcac ttatagttaa ttttgctttc   1260
caactccacc acatgcctga tgagagtgtt tcaacggtaa acgagagaga ccagcttctt   1320
cggatggcta agagcttgaa tccaaaacta gtaactgttg ttgagcaaga tgtgaatact   1380
aacactgccc cttttttccc gagattcacc gaagcttaca actattactc tgctgtgttt   1440
gactctcttg atgcaactct cccacgggag agccaggata gactgaatgt tgagaaacag   1500
tgcctggcaa gggacatagt gaacatagtc gcatgtgagg gagaggaaag gattgagcgg   1560
tatgaagttg cagggaaatg gagagcaagg atgatgatgg ctggcttcac ttcatgttca   1620
atcactccta atgtggttga tatgatccgg aaactcatca aggagtactg cgatagatac   1680
atgttgaagc aggaagtagg tgcgcttcat tttgggtggg aggacaaaag tttgattgtt   1740
gcttcagcat ggaagtaa                                                 1758

<210> SEQ ID NO 102
<211> LENGTH: 1635
<212> TYPE: DNA
<213> ORGANISM: Populus trichocarpa

<400> SEQUENCE: 102
atgaagagag atcatcaaga aaccattggt ggtggtattg gaaacagagc tgaatcttct     60
tcttcatcaa tggaaactgg gaaaggaaaa tcatgggttg aagatgatca agatgcgggt    120
```

```
ggcatggatg aattacttgc tgttttgggt tacaaaatta agtcttcaga tatggctgat      180
gtagctcaaa agcttgaaca actagagatg gttttgggtt ctgaagatgg aatttctcat      240
cttgcttctg atactgttca ctataaccct tcagatctct ctggttgggt tcaaaattca      300
ctccttggac aaccttccac tatcaccccc ttagatttcc ccagtaattc tcaatctaaa      360
gtattcgctg acgactctga atatgatctc agagcaatcc tggagttgc tgcctatcca       420 caacaagaac tcgataagac aatggcagtt tcaggtactt tgtcagagcc acaagacct       480 gtagtcctgg ttgactcaca ggaaactgga gtccgtcttg tccacacact tttggcttgt      540
gcagaggcaa ttcagcaaga aaatcttaaa cttgctgatg cccttgttaa gcatatagga      600
ctacttgcag catctcaaac tggggctatg agaaaagttg caacttactt cgctgaagct      660
ttagctcgtc gaatttacaa gattttccct caagattact gtctcgattc ttcatgttca      720
gatactttag agatgcattt ctacgaaact tgcccttatc tcaagttcgc acatttcact      780
gccaatcaag ccattcttga agctttcgcg aatgcaagtc gagtccacgt tatcgatttt      840
ggtttaaaac agggaatgca atggccggcg ttaatgcaag ctcttgcatt aaggcctggt      900
ggtccgccag cgtttcggtt gacgggatc gggccgccgc agcctgataa cacagatgct       960
ttgcagcaag tggggtggaa gctggcacaa ttggctcaaa ctattggagt agaattcgag     1020
tttcgcggat tcgtagcaaa ctctctggcg gatcttgatg cggagatgct tggcctcctc     1080
cctccagagg tggaggcagt ggctgttaac tcggttttg agctgcatcg cttgttgggt     1140
cggccgggtg gcatcgacaa ggttctcgag tctatcaagg ccatgagacc taaaattgtg     1200
acgattgttg aacaagaagc aaaccacaac ggtccggttt tctagaccg gttcacagag     1260 gccttacatt attactcgag tttgtttgac tctctcgaag gtccggttt gactccaccg      1320 agtcaggacc tggttatgtc cgagctgtac ttagggaggc atatttgtaa tgtggtggca     1380
tgcgaagggg ctgaccgagt tgagcgcac gagacgttgg ctcagtggag aactcggttt      1440
gattcggctg ggtttgaccc ggttcatctt gggtcgaatg cctttaaaca agctagtatg     1500
ttgttggccc tctttgccgg tggtgacggg tataggtgg aggagaataa tggctgtctc      1560
atgcttgggt ggcatacaag gccactaatt gccacctcgg cgtggcagct cgccgctggt     1620
gattcacaac aatga                                                     1635
```

<210> SEQ ID NO 103
<211> LENGTH: 1059
<212> TYPE: DNA
<213> ORGANISM: Populus trichocarpa

<400> SEQUENCE: 103

```
atggaaaaca attgtgtgta tagtgaggaa gatgagcaga tggaattgcc tccgggattt       60
agattccatc caactgatga agagctcata actcactacc tgtctcagaa ggttctggac      120
aactactttt gtgctagagc tattggtgag gtcgatttaa acaagtgtga gccatgggat      180
ttgccttgga gggctaaaat gggtgaaaag gaatggtatt tcttctgtgt tatagaccgg      240
aagtatccca ccggtttaag gacgaatagg gctactgatg ctggttattg gaaagccaca      300
ggcaaagaca aggaaattta cagggctaaa acacttgttg gcatgaagaa gaccttggtt      360
ttctacaaag ggagagcccc caaggagaa aaaccaact gggttatgca tgagtataga       420
ttagagggga aaaccccgt ctataatccc cctaaaacag caaagaatga ttgggtcatc      480
tgtagaattt tgagaagag ttgtggagga aagaaaacac atatttcagg gttggtgagg      540
```

| | |
|---|---|
| ttaagctcgt atggaaatga attaaagcca acaatattgc ctccattgat ggattcttct | 600 |
| caacacaata acgacaagag gactaacata ggtgataagt ctcacgtgac ctgcttctcc | 660 |
| aatccaacgg aggaccagaa accccatgaa accattgctg attgctttaa catttctctt | 720 |
| agagctcctt tgtcttcttc aaacatgtcc ccttcctcag ttctgttttc aaaaccctca | 780 |
| cctccaaact cttctatc ctctcatatt ttaccaaaca tagcaaattt tcaataccca | 840 |
| gattctgtta tgatgccaga acactccatg ttgaggatat tgcttgaaaa ccaaggaccc | 900 |
| ggcatgaacc taaactcaaa acgggagctc tcagaggaca ctggcctcag cactgatatg | 960 |
| tcttcagtgg taaccaacca tgaattggtt catgggtcct ttgaggatcc atcaagttct | 1020 |
| gccggaccag ttgatcttga ttacctttgg aattactga | 1059 |

<210> SEQ ID NO 104
<211> LENGTH: 2463
<212> TYPE: DNA
<213> ORGANISM: Populus trichocarpa

<400> SEQUENCE: 104

| | |
|---|---|
| atgagttttg ggggtttcct tgaaaacact agtcctggtg gtggtggcgc aagaattgtg | 60 |
| gctgatatac tttataacaa taacaacaac atgcccactg gtgcaatagc tcagactcgc | 120 |
| cttgtctctc cttctatcac taaatccatg ttcaactctc ctggactctc tctagcccctt | 180 |
| caacagccaa acatagatgg tcaaggagat ataactagaa tggctgagaa ctttgagaca | 240 |
| agtgtgggta ggagaagcag agaagaggaa catgagagca gatctggtag tgataacatg | 300 |
| gatggtgcgt ctggtgacga tcaagatgca gctgataatc ctccaagaaa aaagagatac | 360 |
| caccgacaca ctccacaaca aatccaagaa cttgaagctt tgtttaagga atgtcctcat | 420 |
| cctgacgaga acaaagatt ggagcttagt agaaggctgt gcttggagac taggcaagtc | 480 |
| aagttctggt ttcaaaatcg tagaacccaa atgaagactc aactggagcg ccatgagaac | 540 |
| tcattactca ggcaagataa cgacaagctt cgagcagaaa acatgtccat aagagatgcc | 600 |
| atgagaaatc catcgtgctc aaactgtggt ggtcctgcga taattggtga tatgtcactt | 660 |
| gaagaacagc attttgaggat tgagaatgct agattaaaag atgaactaga tcgagttgtt | 720 |
| gcacttgcgg gcaagttctt gggtcgcccc atatcttcgt tagcttcttc acttagccct | 780 |
| ccgacgaatt caagcctgga acttgcagtt ggtagtaatg ttttgctgg tttaagcacc | 840 |
| attgctacaa cattgccttt gggacctcat tttgaaggtg ggatttctgg tgcttttgtct | 900 |
| atggtaactc aaactagact agcaacagct ggtgttactg gtattgatag atcagtagag | 960 |
| agatccatgt tcttggagtt ggcttagct gccatggatg aattggtgaa aatggttcag | 1020 |
| acggatgagc ctctttggat cgggagcttt gagggtggta gagaaatatt gaaccatgag | 1080 |
| gggtacttga aaccttcac tccttgcatt ggaatgaagc ctagtggctt tgttagtgag | 1140 |
| gcttctagag agactggtat ggtaatcata aacagtttgg ccttagttga gacactgatg | 1200 |
| gattcgaacc gatgggcaga aatgtttcct tgtatgattg caaggacctc taccactgat | 1260 |
| gtgatagcca gtggaatggg gggaactaga aatggttcac ttcagttgat gcaagccgag | 1320 |
| ctccatgttt tatccccatt ggttccggtg cgtgaggtca attttctccg attttgcaag | 1380 |
| cagcacgcag aggggtttg gctgttgtt gatgtatcca ttgataccat ccgagatact | 1440 |
| tccggtgcac caccgacatt tgtgaactgc aggaggcttc cttctggttg tgtggtgcaa | 1500 |
| gatatgccca atgggtactc caaggttaca tgggttgagc atgcacaata tgatgaaagg | 1560 |
| caaatacacc agctctatcg gccggtgata agctccggca tgggcttcgg tgcccaacga | 1620 |

-continued

```
tggatagcta cccttcaacg tcaatgcgag tgtttggcca tcctcttgtc ctccaatgta    1680
cctagtagag accacacagc gataaactaca agtggtcgcc gaagcatgtt gaagctggcg    1740
caaagaatga ccgataactt ctgtgctggg gtttgtgcct ccacagtgca caaatggaac    1800
aagctgaatg ccggaaatgt tgatgaagat gttaggggtta tgacccgaaa gagtgtcgat    1860
gatcctggtg agccaccagg catagttttg agcgctgcga cctctgtttg gctacctgtt    1920
tctccacaaa ggctctttga tttcctacgc aatgaacgac tcagaagcga gtgggacata    1980
ctctccaacg gtggaccaat gcaggaaatg gcccacattg ctaaaggcca ggatcacggc    2040
aactgtgtct ctctcctacg tgctagcgcc atgaatgcta accagagtag catgctaata    2100
ctgcaagaga catgcataga tgcagcaggc tctcttgtag tgtacgctcc cgttgacact    2160
ccggccatgc acgtagtgat gaacggtggt gattcggctt acgtggcgct tcttccgtca    2220
gggtttgcta tcgtaccgga tgggcctggt tcacgtgacc ccccatcgac taatggcggc    2280
ccgactgcta ataatgtcgg tggccaagag agggtgagtg ggtccctttt gacggtggcc    2340
ttccaaatat tggtgaatag tctacctacg gcgaagctta cagtagaatc tgtggagaca    2400
gtcaacaacc ttatttcatg cactgtccaa aagatcaagg ctgctctcca atgtgaaagc    2460
tga                                                                 2463
```

<210> SEQ ID NO 105
<211> LENGTH: 633
<212> TYPE: DNA
<213> ORGANISM: Populus trichocarpa

<400> SEQUENCE: 105

```
atggcaccca agaagcttaa tggtaatgac aatggttctt tgaagaaagc aagtggtgat      60
catgacaaga aggaaatcca ttataggga gtgaggaaga ggccatgggg gaggtatgct    120
gctgagataa gggatcccgg gaagaaaagc cgggtttggt tggcacgtt tgacacggca    180 gtggaggctg cgagggccta tgataaggcg gcgcgtgagt atcgtggtgc taaggcgaag    240
accaactttc caatagcgga gaaggtggtt gattatgacg atgagaagca gagctctagc    300
cagagcagca ccgttgagtc gtcaagctcc ccggtggttt ctgcggtggc gcgtgatgta    360
actcgccagg ttggtggggt tgtggggatg gggaggtttc cctttgtgtt ccagcagcag    420
ccgccgcatg ttaacgctgt tggtcctgtc tggtttcttg atagtactgt taagcctgag    480
tttgtggctc agcgttttccc tgtccggtat gacccggtgg gtcttgaggg cggggcccat    540
agtgactcgg attcatcatc tgtgattgat tttaagccaa ggagttcaat tcttcatctt    600
gatcttaacc tgcctccacc agctgatgct tga                                 633
```

<210> SEQ ID NO 106
<211> LENGTH: 732
<212> TYPE: DNA
<213> ORGANISM: Populus trichocarpa

<400> SEQUENCE: 106

```
atgtgcacta gaggacattg gaggcctgct gaggatgaga aacttaagga attggttgaa      60
aagtatggtc tcataattg gaacgccatt gccgaaaagc ttcaaggaag atcagggaag    120
agttgtaggt tgagatggtt taatcagctg gatccaagaa tcaatagaag cccgtttaca    180
gaagaggaag aagaaaagact acttgcttcc cacaggattc atgggaatag atgggcaatt    240
attgcaagat ttttccctgg tcgcaccgat aatgcagtga agaatcattg gcatgtcatc    300
```

```
atggcaagaa gatatagaga gaggtctaga cttcatgcaa aaagggctgc tcaaactttg      360
gtaaatgata acaaattatc ctcaaaacaa gatcacatgc acatggattg tgagacgagg      420 aattttt ctt cattttccaa gaaatattgt gaaaaatatg ccaatatcc tatggttact      480 cacagctact taccggcctt ttgcaaagag ttctacaatg aagatccaag tcattgtgaa      540
gatcaaagtc ggccgattga gttttatgat tttctccaag taaacactga ctccaataaa      600
agtgaagtga tagacaatgc aagaagagat gatgaggagg tagatcagca ggaagccttg      660
gaaaataatc agagcaaggc tgatgttcca ttcattgatt ttttctctgt taatggcaaa      720
tcctcatcat aa                                                          732
```

```
<210> SEQ ID NO 107
<211> LENGTH: 988
<212> TYPE: DNA
<213> ORGANISM: Populus trichocarpa

<400> SEQUENCE: 107
atgggcagat ctccttgttg tgagaaagaa cacaccaaca aaggtgcctg gactaaagaa       60
gaagatgaac gtctcattaa ttatatcaaa tctcatggtg aaggttgttg gaggtctctc      120
cctaaggcag ctggtttgct tagatgtggc aaaagttgta gactgagtg gataaactac       180 ctaaggcctg atctcaagag aggaaacttc agtgacgaag aagatgaact catcatcaac      240
cttcacagct tacttggaaa caagtggtct ctcattgctg ctaggctgcc aggaagaact      300
gacaatgaga taaagaatta ttggaatact catatcaaga gaaagctctt tagccgtgga      360
gttgatcctc aaactcaccg tccactcaat tccaccacca cctcctccac cacttccacc      420
accacaaaca gcaccaacaa taaaatagc aacatgggca ccaaaaggat tactaacttt      480
aaacttgaag aacaaaacta tttatttgtt caagcccagc cagagtttat gatgagcaac      540
atagtcaaga aggctagcga ttcaagtatt atcaaggtag gtggcagcag tgactctgct      600
gaagattcca atagtagcag tggcgtgaca gcagaattga aagtgcatcc aaatcataaa      660
ctcaatcttg agctctctat tggtcttcca tgtcaatctc aactttcttc tgtcaatgat      720
cttaatgatt caaagcaagc aaaccaacag catcaagaac aagtagtcac atatcaattg      780
tttgggaccc ctgctactcc cacctccagt gcccctgctg ttgttcatag aacagcatgt      840
ttgtgttctt acaatcgagg gttcaagaac agtcaagcat gtagttgttg taatgccgtg      900
gaaaaatttg taacagctga tagtctttat agattttaca gaccctttgga tgcttgatga      960 tgaccgggga tcagtttgat aaggctag                                         988
```

```
<210> SEQ ID NO 108
<211> LENGTH: 708
<212> TYPE: DNA
<213> ORGANISM: Populus trichocarpa

<400> SEQUENCE: 108
atggaggttt atccataccc atctcgtttt tccatgtctt cattgtgttc ttttggaat        60 tttgttgata aggttaaaga agtttgtaac ttcgttgttt cagctattat tggcaacata      120
ttctctgcga tcttcacctt tttctttgca ttagtgggca ctttgttagg agccatgact      180
ggggcattga taggccaaga aactgaaagt gggtttgttc gaggggctgc agttggagcc      240
atatcagggg ctgttttctc aattgaagta ttcgagtcat ctcttgttct ttggcaatca      300
gatgaatctg ggataggctg tgtccttac ttgattgatt ttatcgcaag ccttcttagt      360
ggacgacttg ttcgtgagcg cattggtcct gctatgttaa gtgcagtaca aagtcagatg      420
```

```
ggtgctgtgg aaacaaattt tgaggagatc ccaaacatct ttgacactgg tggttccaag      480
ggattacctg gagattctct tgagaagatc ccgaagatca gaatcacaag caataacaat      540
gtagatgaat caggagagaa agtctcttgt tcagtttgcc ttcaggactt tcagctggga      600
gagacggtta aagcttgcc tcattgtcat cacatgtttc acctaccttg catagataag       660
tggctactta ggcatgcatc ctgccctctg tgtagaaggg atctgtga                   708
```

<210> SEQ ID NO 109
<211> LENGTH: 882
<212> TYPE: DNA
<213> ORGANISM: Populus trichocarpa

<400> SEQUENCE: 109

```
atgagaatat ctagagcaag atggttcacc ttcttgagga gagtattcca ctaccagaat       60
ggctcaagct ctaatcttgg gtctaatcct ttcaattcta gctcttggat gatgctggag      120
ttcgtagctt tgctccttca aatatgcatt accacgttca ccctggctat ttcgaaggca      180
gagaaccctg tttggcctgt gagaatatgg attattggtt ataatatagg ttgtgtcctt      240
agtctgctgc tgctctatgg tcgttaccgg caacttaacg caactcaagg cgatggtttt      300
ggcctacccg atttggagca acaggggggc agtgaggaat ccagtgtatg caggtactca      360
catttgatga acaagtgccg gacctcactg gaactcttct ttgcgatatg gtttgtgatg      420
ggtaatgttt gggtcttcga ttctcgtttt ggatcttact tccgtgctcc aaaactccat      480
gtgctctgca tctctctgct tgcctggaat gctctcagtt actcgtttcc atttctgttg      540
tttctactgc tatgctgttg tgtgccgctc attagcactg tcattggcta acacatgagc      600
atggggtctg ccgagagagg ggcgtccgat gaccaaatat ccagactacc aagccggagg      660
tacaaagctg tggacaccga ttcggagttt cgcaacagtg ttgattgtga ttcaaccgtt      720
gcaagtgaag atctggaatg ctgtatatgc ctagccaagt ataaagacat agaagaagtt      780
aggcaattgc catgctccca tatgttcac ctcaagtgtg tagatcaatg gcttcgaatt       840
atatcctgct gccctctctg taaacaagaa ctggaaaaat ag                         882
```

<210> SEQ ID NO 110
<211> LENGTH: 966
<212> TYPE: DNA
<213> ORGANISM: Populus trichocarpa

<400> SEQUENCE: 110

```
atggatccca agggctctaa ctcaaaaaac ccacatgagc tacccacttt ctttacccctt      60 acgcacaccc acacttctcc ttctccttct cctcatactc ctccacaacc ccatcatcaa      120
caaccgcaac acctccataa ccaaaaccaa ctacaaccca acatgggtga gaataaagca      180
gcagaaatca aagactttca gattgtagta gctgacaaag aagagcaaaa gaaacagtta      240
gctccaaaaa gaagctcaaa caaagacaga cacacaaaag ttgaaggtag aggtagaagg      300
ataaggatgc cagctctttg tgcagcaaga atctttcaat taacaagaga attgggtcac      360
aaatctgatg gtgagacaat acagtggctt ctacaacaag ctgaaccatc tataattgca      420
gcaactggga ctggtacaat acctgcatca gctttggcag ctgctggtgg tgcaatttca      480
caacaaggag cttctctttc agctggtttg catcaaaaga ttgatgatat aggtgagtcc      540
agtagtagga ggaccagttg ggcaatgtta ggtggcaatt tagggagacc ccatcaagtt      600
acaagtgcag gattatggcc cccagttgga ggttatgggt tccagtcatc atctaatacc      660
```

| | |
|---|---|
| actggtccat caacaacaaa tatagtaagt gaaggtggtg gtggctcgag ttatttgcaa | 720 |
| aaaaatggat tttcagggtt tgacatgcca ggaaacaata ttgggcctat gagtcttact | 780 |
| tcaattttag gtgtgggtag ccagcagtta ccaggattgg agcttgggtt gtcacaagat | 840 |
| gggcatattg gggttttgag cccacaagct ttgagtcaga tttatcagca gatggggcag | 900 |
| gctagggtgc agcagcacca gcagcaaaac ccttctaaag atgattcaca aggatcaggg | 960 |
| cagtaa | 966 |

<210> SEQ ID NO 111
<211> LENGTH: 2079
<212> TYPE: DNA
<213> ORGANISM: Populus trichocarpa

<400> SEQUENCE: 111

| | |
|---|---|
| atgggcgagg aagcagaccc aacaatgaag aagaagaaga aaagggacg tccttctctt | 60 |
| ctagagcttc aaaaacgctc cctcaaacaa caacagctac agcaaacaac ccctatttct | 120 |
| cttaaaaacc ctaatcctct caattccaat tctgccctcc ctaaccgtcg atccgctcgc | 180 |
| cggagctcta attcctatgc accggagtgg attgacggag acgacgacga agacgacgac | 240 |
| gaagacgatg agcgtaaaga gaagaagcat aagctcttgc gcggattgaa ttctcagaaa | 300 |
| aataacaatc agaattccaa ttcgtcgagc ccttcgaatt tgcacggctc tgattcgaat | 360 |
| gctggtggcg gtaatcaaga ggacggaatt agaaggcgca agatcagcgc cgtccgtctt | 420 |
| ggatctgatg atttgggtga aaaggttttg aaagggacag acactattca tgggtcatct | 480 |
| gtggagcctg gtcccactac acctttgcca gacaaaaagt tgttggtctt cattcttgac | 540 |
| agacttcaaa agaaggacac ctatggggtt ttctctgagc cagtggatcc agaagagctt | 600 |
| cctgattact ttgacatcgt tgagaatccc atggattttt ctacagtgag gaaaaagtta | 660 |
| gatgagggag cctacgccca cttggaacaa tttgagaaag atgttctttt gatatgctca | 720 |
| aatgcaatgc agtacaaccc ttccgatact atttacttcc gacaggcaag ggccatgcaa | 780 |
| gagcttgcaa agaaggactt tgagaatctt aggcaagata tgatgatag tgaaccacaa | 840 |
| actaaggttg cgaggagagg gaggccacca gccctaggca agctgaaaaa ggcacttgag | 900 |
| aggtctccaa ttgaccgtgt tggtcctgaa gcttcctcgg atgcaactct tgccaccgga | 960 |
| ggagatcaca ataacttgtc caatggttac aatctcagaa aaagttcttc atacaagtac | 1020 |
| cagcctggtg atgcatttgt ccgggcctct tacagcagtg aaaattattc tacctggtta | 1080 |
| tctgaatggg aaaatgaatt tccagcatct gttgtaaagg ctgtgatgaa gtatggaaag | 1140 |
| aaaccgtttg tgctagatga aacaagcgt gacacctata gcatccatt gggctcccat | 1200 |
| gagccatcca tcttatcgac cttttgaagga gaattaaagc aattagtggt ggtaggttta | 1260 |
| agctctgagc acggttatgc aagaagtctg gctcgatttg ctgctgatct tggccctgtt | 1320 |
| gtttggagaa ttgcttcgaa gaaaattgaa agtgttttgc caacaggact tgagtttggc | 1380 |
| cctgggtggg taggagaaaa taagcaatg gagaagcaaa agattttaaa caaccttgta | 1440 |
| tctgataacc atttaagcag atttcaacct gctgcttctt caagtagaga ggcagcatgg | 1500 |
| aatagagaag gcctgccaga aactgttggc gggttaaatc tcaaaatga ttagctaca | 1560 |
| ctgaacagtg gtgctggtgg gatgaaatcc atgccttctc tccagattca gcagaaacca | 1620 |
| ataattcatc ctgatatgaa tggtttcagt ggaggatttg gatataactc ttcacctcaa | 1680 |
| ccggggatgc cacgaactgt ggcaccgaca ggaaagctca atttggagca gactgcagtg | 1740 |
| ccttcccaaa tgtttggtgt ggttccaact ggcaacagtg ccttcatttc agtgcctggg | 1800 |

```
aatgatttta atacaaataa aggtatgctg tcagaaactt caagtggatt attgcagcct    1860
ggaatttctc cagccgtagg ctccagctct gactctcgta catttggcaa tgtggggttt    1920
ggtggcaaat catcttggca gggattttta ccatatcagc aacaaggtac tgttccattt    1980
ccaccagatc tgaatgttgg attcttggca cctggttcac ctacttcgag tgtgcccatc    2040
ggttcaccac ggcagccaga tttagcattg cagctctga                           2079
```

<210> SEQ ID NO 112
<211> LENGTH: 3342
<212> TYPE: DNA
<213> ORGANISM: Populus trichocarpa

<400> SEQUENCE: 112

```
atgaagtcac cggccaacgg tgccgccgcc gcagtcacca acggtgaagg ggtagagaag      60
aagagcataa accctgagtt atggcaagca tgtgcaggac cactagtgaa cttgccggcg     120
gccggaactc atgtggtcta cttccctcaa gggcatagtg aacaggttgc agcatctttg     180
aagaaggatg tgaatgcgca aattccaaac tacccaaatc ttccctcgaa gctgctatgt     240
ctccttcaca atgtcacctt acatgcggac cctgaaacag atgaagttta tgttcagatg     300
acacttcaac ctgtttcttc ttttgacaag gatgcattat tgaggtcaga tcttgcactg     360
aagtcaaata aaccacagac agagtttttc tgtaaaacat tgacagcaag tgatacaagc     420
actcatggag gtttctccgt gcctcgccgt gcagctgaaa agacattccc gcctcttgat     480
ttctccatgc aaccacctgc tcaagaactt gtagctaggg attttgcatga taatgtttgg    540 actttccggc atatctatcg tggacaacca aagcgtcact tgcttacaac tgggtggagc     600
ttatttgtca gtgggaagag gcttttttgcc ggtgactcag ttttatttat gagagatgaa    660
aagcagcagc ttctattggg catcagaagg gctaacaggc aacctaccaa cttatcatcg     720
tcggtattgt caagtgatag catgcatatt gggatcctag ctgctgcagc ccatgcagca     780
gcaaacaata gcccctttac cgtgtactat aatccaaggg caagtccatc agaatttgtt     840
atccctttag ccaagtatta caaggcagtg tacagcaacc aaatatcact tggcatgcgc     900
ttccgcatga tgttttgaaac tgaagagtca ggaacaagaa ggcatatggg caccattact     960
ggtatcagtg atcttgatgc tgtaagatgg aaaaactcac aatggcgtaa tttgcaggtt    1020
ggttgggatg agtcaactgc tggtgaaaga cgcaatagag tctcgatctg ggagatcgaa    1080
ccagtgactg ctccattttt catatgtcct cctccatttt ttagatctaa gcatccaagg    1140
caaccgggaa tgccagatga tgattccact gattttgata gcctattcaa gaggactatg    1200
ccttggcttg gtgatgatat ctacatgaaa gatccccagg ttctccctgg cctaagccta    1260
gcccagcgaa tgaacatgca gcaaaaccct tcactggcaa actcaatgca gcccaattat    1320
atgcaatcgt tgtcagggtc tgttctgcag aatcttcctg gaggtgatct ttcccgccag    1380
ttaggcttgt catcacctca aatgcctcag ccaaacaact acagttcaa tgcccaaagg     1440 ctgcctcagc aagcacaaca gcttgatcag cttccaaagc tacagtcctt gctcaaccca    1500
ctgggttcca tcatacagtc acagcaacag atgggtgaca tcactcaaca atcgaggcaa    1560
aatatgatgg ctcaaactct accctcaagt caagttcaag cccaacttct gcagcctcaa    1620
actcttgccc agaccaataa cattcttcag caacagccat ctattcaaag ccatcagctt    1680 cttagaaaacc ttccgcaaac cttgcaccag cagcagcaga atcaacagca acatattatg    1740
ggtcagaacc agcagcaaag cctaatgcaa tctcagttgt ctgatcaagt aaaccaacat    1800
```

```
atgcaaatgt ctgacaatca gattcagtct caactgatgc agaagcttca gcagcaacag    1860
caatcagttt cagctcagca atctgctatg catcaggctg gtcaacttgg acagcttcaa    1920
gattcacaaa ggcagctgct ggatgcatcc cagagttttt ctaggtccat gacacccagc    1980
caaatgttgg aaatccctca acaacaccc acttctctcc ctcagccaaa tactattcca     2040
cagcagatga ctaagaataa caaccaaacc aatactcgat tctcacatct gcctcaacag    2100
ctgaaacctc aacaacagca ttctggcatc atgctgttgt cagaaatggc tggtcacatg    2160
ggacttccgc cgagctcaat ggccaatcag ctctccacag ctggtagcag tatattgact    2220
gcagcagctg gaccaggaca gtctggtatc actgatgatg ttccttcctg ttctacttca    2280
ccttccacaa acaattgtcc aaacatagtt caaccaatga tcaacggctg ggcccaccga    2340
agcacagcaa tgggagagga catggctcag tctgccgtga cactctttag ccctagtgca    2400
ttggaaaccg tgtcctctaa tggtaattta gttaaagatc tgctgcagaa atctgaggtt    2460
aagccatcat tgaacatctc caagaatcaa aacccaggat tattttcctc gcaaacatac    2520
ctaaatgggg tagctgccca gatagattat ttggacacat catcttctac aacttctgtt    2580
tgcctatcac aaaatgatgt ccatttgcag cagaataaca attcactgtc atataatccc    2640
caatcagtgt tgttgagaga cgcaagccat gatggtgagc tccagggaga tccgaggaat    2700
aatattttat atgggacaaa cattgatagc caacttgtga tgccaataaa ttctgaccat    2760
ttattaacaa agggcatgat ggggctgggg aaggacttct caaataattt ctcttcagga    2820
ggcatgctta caaattgtga aaattccaaa gatcctcaac aggagctttc atcggcaatt    2880
gtttccaagt catttggagt tccagatatg ccattcaatt caattgactc aacaatcaat    2940
gacagtagct tattgaatag aggttcttgg gctcctccac agcaacagtt cagcgaatg     3000 cgaacatata caaggtgta caagcgtgga gctgtaggaa ggtcaattga cataacgcgg     3060
tattcaggtt atgacgagct taagcaggat ctggctcgta ggtttggtat agagggacag    3120
ttggaagatc aacaaaggat aggctggaaa cttgtttaca ctgatcacga gaatgatgtc    3180
ctgctagtgg gggatgatcc ttgggaagag tttgtgaact gtgtccgctg catcaagatc    3240
ctgtctcctc aagaagtcca acagatgagc ttggatggag attttggcaa ctctgtcctt    3300
cctaatcaag ccggcagtag ttctgataat gtcaatgcat aa                      3342
```

<210> SEQ ID NO 113
<211> LENGTH: 1506
<212> TYPE: DNA
<213> ORGANISM: Populus trichocarpa

<400> SEQUENCE: 113

```
atggtgggtg gtgagaattt atccagaatc acagtatcta aagcttctgg agaagacaca     60
attagcaatg tttcttcttt tggtaaccaa ggcatgccac actctattac agtgccacca    120
ccaaagaaga agcgaaatct ccctggaatg ccagatccag atgcagaagt cgttgcgtta    180
tcaccaaaga ctttagtagc cacaatcaga ttcgtgtgtg agatctgtaa caagggcttt    240
caaagagacc agaacctcca acttcacaga cgaggccata acttaccatg gaagctaaag    300
caacgaacca acaaagagcc aaggaagcgt gtctatgttt gtccagagtc atcttgtgta    360
catcacaacc cagctagagc tcttggtgat cttactggca ttaaaaagca cttctacaga    420
aagcatggtg agaaaaagtg gaagtgtgag agatgttcga agaaatatgc cgtccagtct    480
gattggaaag ctcacttgaa aacttgtggc actaaagagt ataaatgtga ttgtggcact    540
ttgttttcaa ggagggatag ttttgtaaca cacagagcat tttgcgatgc gttagcggag    600
```

```
gagagtgcaa gggcgcaaac cctagcgata atgggaaggg aagggaatgg ttgtgacatc      660
aagcgtgtgg gtgcttcacc accgcctcca ccacttacgc cgtctactag tgtggtgtct      720
ccgggtttat cagttcaaag ctcagaatta gcagaaaatc caattggact ttcaccacca      780
ccaatagcat gtgcctcggc tacaagcaca agctcaacta gctcaaccag taatgtattt      840
gcgactacat ttgcctcttc gacagcaaca ccagctgcta tcccacaaca agcatcagta      900
ccatcctctt tcccaaatct gttttgcggc ttagctcgct ctgattatcc cactactatg      960
ccaacaccta gagcgataga accccatca ctctctcttt caccatcttt ttatctctcc      1020
aacaatactt cgtctctctt cagcacagag caagagcact accattacac accatctccg      1080
caaccagcca tgtctgccac tgcattgctt caaaaagcag cacaaatggg tgcaacgaca      1140
tcaaacccat catttctccg tggtttagga ttacccgtt caactaatca agacagtaat      1200
tgcaataaat gggatgtgaa gccagagaac aacaccactg ttgcagctgg actcggcctt      1260
gggcttccct ccagtgatgt tatgatgggt tcatcttcat tgtttggaaa caaaccagcg      1320
acacttgacc ttctcgggct tggcatggat gctgctagtt ctgctttgct aaattcctat      1380
agtggtggct ttaatgttgg agcagccact gccgcagcat atggtggagg aggagggaga      1440
gggacttctg aagaaacatg ggatggtgtg cctgagagga agccttatgg atctacagga      1500
gcttga                                                                 1506

<210> SEQ ID NO 114
<211> LENGTH: 966
<212> TYPE: DNA
<213> ORGANISM: Populus trichocarpa

<400> SEQUENCE: 114
atggatccca agggctctaa ctcaaaaaac ccacatgagc tacccacttt ctttacccct       60
acgcacaccc acacttctcc ttctccttct cctcatactc ctccacaacc ccatcatcaa      120
caaccgcaac acctccataa ccaaaaccaa ctacaaccca catgggtgaa gaataaagca      180
gcagaaatca aagactttca gattgtagta gctgacaaag aagagcaaaa gaaacagtta      240
gctccaaaaa gaagctcaaa caaagacaga cacacaaaag ttgaaggtag aggtagaagg      300
ataaggatgc cagctctttg tgcagcaaga atctttcaat taacaagaga attgggtcac      360
aaatctgatg gtgagacaat acagtggctt ctacaacaag ctgaaccatc tataattgca      420
gcaactggga ctggtacaat acctgcatca gctttggcag ctgctggtgg tgcaatttca      480
caacaaggag cttctctttc agctggtttg catcaaaaga ttgatgatat aggtgagtcc      540
agtagtagga ggaccagttg ggcaatgtta ggtggcaatt tagggagacc ccatcaagtt      600
acaagtgcag gattatggcc cccagttgga ggttatgggt tccagtcatc atctaatacc      660
actggtccat caacaacaaa tatagtaagt gaaggtggtg gtggctcgag ttatttgcaa      720
aaaaatggat tttcagggtt tgacatgcca ggaaacaata ttgggcctat gagtcttact      780 tcaatttag gtgtgggtag ccagcagtta ccaggattgg agcttgggtt gtcacaagat      840
gggcatattg gggttttgag cccacaagct ttgagtcaga tttatcagca gatggggcag      900
gctagggtgc agcagcacca gcagcaaaac ccttctaaag atgattcaca aggatcaggg      960
cagtaa                                                                 966

<210> SEQ ID NO 115
<211> LENGTH: 690
<212> TYPE: DNA
```

<213> ORGANISM: Populus trichocarpa

<400> SEQUENCE: 115

```
atggaaccat cgtcgtcgtc agcagtagca gcagcaatag tgagtactaa cgccaacatc      60
aacacggatc gaacaagaag gaaaaagaag aagaaatcag tgttgcagca acaccaatca     120
aaacagaacc aaaactcaca gagccacgcc aaatggaaaa cagaagcaca acaacaagtc     180
tactcatcca aactcatcca agccttaagc caagtcaatc tcaacccttc aacttcatca     240
gccccgcgtc aaggtcgagc cgttagagaa gttgctgatc gggctttagc tttcgctgct     300
aaaggtaaaa ccaggtggag ccgagccatt ttaactagcc gcatcaaact caaatttcgg     360
aaacaacaac ataagagaca gagacttgcg tcgtcgtctt cttcttctcc aggatccact     420
accgggagta gcagccggtc gtcgaggaag cataaagtga gtgttttgag gttgaaagcg     480
aagggtttgc cggctgttca aggaaagtt cgtgttcttg gccggttagt tcctggttgc     540
ctgaaacaac cattgcctgt tattttggaa gaagctacag attatattgc tgctttggag     600
atgcaagtta aaaccatgac tgctatagct gagcttcttt ctcgctctac ctccgaagcc     660
agctctactt ctgagccgat gacctcctaa                                      690
```

<210> SEQ ID NO 116
<211> LENGTH: 187
<212> TYPE: PRT
<213> ORGANISM: Populus trichocarpa

<400> SEQUENCE: 116

```
Met Gln Pro Gly Leu Asp Glu Ile Thr Met Thr Ala Trp Lys Asn Leu
1               5                   10                  15
Lys Gln Arg Leu Ser Phe Lys Gly Leu Gly Ser Cys Cys Gly Ser Thr
            20                  25                  30
Ser Trp Ser Ser Arg Ser Ala Thr Pro Thr Met Pro Phe Ile Asp Ile
        35                  40                  45
Glu Gln Glu Glu Glu Glu Pro Ile Met Gln Asn Gln Ala Gln Arg
    50                  55                  60
Gly Gly Gly Ala Ala Ala Ala Ala Pro Gly Ala Gly Met Asn
65                  70                  75                  80
Leu Ala Met Ala Leu Ala Glu Arg Asn Leu Gly Asp Ser Asn Val
                85                  90                  95
Lys Thr Leu Met Ser Leu Ile Glu Glu Thr Asp Gly Val Asp Trp Arg
            100                 105                 110
Lys Lys Asn Asn Ser Asn Asp Lys Ser Arg Arg Asp Lys Glu Gln Glu
        115                 120                 125
Gln Lys Gln Glu Glu Lys Asp Trp Val Cys Cys Val Cys Met Glu
    130                 135                 140
Arg Asn Lys Gly Ala Ala Phe Ile Pro Cys Gly His Thr Phe Cys Arg
145                 150                 155                 160
Val Cys Ser Arg Glu Met Trp Val Asn Arg Gly Cys Cys Pro Ile Cys
                165                 170                 175
Asn Arg Ser Ile Leu Asp Ile Leu Asp Ile Phe
            180                 185
```

<210> SEQ ID NO 117
<211> LENGTH: 214
<212> TYPE: PRT
<213> ORGANISM: Populus trichocarpa

<400> SEQUENCE: 117

```
Met Ala Arg Gly Lys Val Gln Leu Lys Arg Ile Glu Asn Ala Thr Ser
1               5                   10                  15

Arg Gln Val Thr Phe Ser Lys Arg Lys Asn Gly Leu Leu Lys Lys Ala
                20                  25                  30

Tyr Glu Leu Ser Ile Leu Cys Asp Ala Glu Val Ala Val Ile Ile Phe
                35                  40                  45

Ser Gln Lys Gly Thr Leu Phe Lys Phe Ala Ser Ile Asp Gln Ile Gln
    50                  55                  60

Lys Thr Ile Asp Arg Tyr Arg Lys Asn Ala Lys Gln Leu His Thr Asp
65                  70                  75                  80

Arg Ile Asp Val Glu Gln Ser Lys Glu Gln Leu Arg Gln Glu Ser Ala
                85                  90                  95

Asn Met Ala Lys Lys Ile Glu Ile Ile Glu Ile Leu Gln Arg Lys Leu
                100                 105                 110

Leu Gly Gln Asp Leu Asp Ser Cys Ser Pro Glu Glu Leu His Asp Ile
            115                 120                 125

Asp Asn Gln Leu Glu Ile Ser Leu Ser Asn Ile Arg Ala Arg Lys Thr
130                 135                 140

Gln Leu Phe Lys Glu Gln Ile Glu Gln Leu Gln Ala Lys Glu Arg Leu
145                 150                 155                 160

Leu Leu Met Glu Asn Ala Arg Leu Thr Lys Gln Cys Asp Ala Gln Pro
                165                 170                 175

Leu Gln Gln Ser Thr Gln Ser Asn Gln Val Val Ser Tyr Leu Thr Ser
            180                 185                 190

Cys Ser Lys Ser Ser Asp Ile Val Glu Thr Asp Leu Tyr Ile Gly Leu
            195                 200                 205

Pro His Met Arg Cys Leu
            210

<210> SEQ ID NO 118
<211> LENGTH: 584
<212> TYPE: PRT
<213> ORGANISM: Populus trichocarpa

<400> SEQUENCE: 118

Met Ala Tyr Met Cys Ala Asp Ser Gly Asn Leu Met Ala Ile Ala Gln
1               5                   10                  15

Gln Val Ile Lys Gln Lys Gln Gln Glu Gln Gln Gln Gln Gln Gln Ser
                20                  25                  30

His His His His Asn Gln Gln Gln Gln Phe Leu Gly Leu Asn Pro
                35                  40                  45

Phe Ser Leu Asn Pro Trp Pro Thr Asn Ile Met Ser Ala Asn Pro Asn
    50                  55                  60

Leu Gly Tyr Gly Leu Ser Gly Pro Ala Ala Phe Ser Asp Pro Phe Gln
65                  70                  75                  80

Ser Gly Gln Glu Thr Gly Asp Pro Pro Val Phe Ser Phe Ser Asn Met
                85                  90                  95

Glu Gln His His Ser Ser Gly Phe Arg Leu Pro Tyr Phe Thr Gly Ala
                100                 105                 110

Gly Gly Glu Phe Asp Ser Asp Glu Trp Met Asp Ser Leu Met Asn Gly
            115                 120                 125

Gly Asp Ser Thr Asp Ser Ser Asn Leu Pro Ser Gly Cys Asp Ala Trp
130                 135                 140

Gln Asn Ser Thr Asp Phe Gly Met Tyr Thr Ser Asp Pro Phe Asn Thr
```

-continued

```
            145                 150                 155                 160
        Cys Pro Ser Arg Leu Thr Val Gly Cys Ser Pro Pro Ser Asp Leu Asn
                        165                 170                 175
        Gly Val Leu Ser Asn Ser Leu Trp Val Ala Pro Ser Pro Gln Glu
                        180                 185                 190
        Ile Lys Pro Thr Thr Ser Pro Pro Leu Leu Pro Pro Thr Val Lys
                        195                 200                 205
        Asn Glu Thr Val Gly Gly Ser Glu Ile Val Gln Leu Ser Ser Ser
        210                 215                 220
        Pro Val Leu Lys Ala Leu Val Glu Cys Ala Gln Leu Val Glu Ser Lys
        225                 230                 235                 240
        Ala Asp Gln Ala Val Lys Ser Leu Val Lys Cys Lys Asp Leu Val Ser
                        245                 250                 255
        Glu Asn Gly Asp Pro Val Glu Arg Ala Gly Phe Tyr Phe Ala Glu Gly
                        260                 265                 270
        Leu Cys Arg Arg Val Ala Val Gly Glu Leu Asp Val Leu Lys Asn Phe
                        275                 280                 285
        Asp Gln Thr Ser Glu Glu Phe Thr Leu Ser Tyr Lys Ala Leu Asn Asp
                        290                 295                 300
        Ala Cys Pro Tyr Ser Lys Phe Ala His Leu Thr Ala Asn Gln Ala Ile
        305                 310                 315                 320
        Leu Glu Ala Thr Glu Lys Ala Ser Lys Ile His Ile Val Asp Phe Gly
                        325                 330                 335
        Ile Val His Gly Val Gln Trp Ala Ala Leu Leu Gln Ala Leu Ala Thr
                        340                 345                 350
        Arg Ser Ala Gly Lys Pro Val Arg Ile Arg Ile Ser Gly Ile Pro Ala
                        355                 360                 365
        Pro Val Leu Gly Lys Asn Pro Ala Ala Ser Leu Leu Ala Thr Gly Asn
                        370                 375                 380
        Arg Leu Leu Asp Tyr Ala Lys Leu Leu Gly Leu Asn Phe Glu Phe Glu
        385                 390                 395                 400
        Pro Ile Leu Thr Pro Ile Gln Glu Leu Asn Glu Ser Cys Phe Arg Ala
                        405                 410                 415
        Glu Pro Asp Glu Val Leu Ala Val Asn Phe Met Leu Gln Leu Tyr Asn
                        420                 425                 430
        Leu Leu Asp Glu Ser Pro Val Ala Val Glu Thr Ala Leu Lys Met Ala
                        435                 440                 445
        Lys Ser Leu Asn Pro Ile Ile Val Thr Leu Gly Glu Tyr Glu Ala Ser
                        450                 455                 460
        Leu Asn Arg Val Gly Tyr Leu Thr Arg Phe Lys Asn Ala Leu Arg Tyr
        465                 470                 475                 480
        Tyr Thr Ala Val Phe Glu Ser Leu Glu Pro Asn Met Ser Arg Asp Ser
                        485                 490                 495
        Pro Glu Arg Leu Gln Val Glu Arg Leu Leu Gly Arg Glu Phe Leu
                        500                 505                 510
        Val Leu Glu Arg Met Glu Asp Lys Asp Gln Trp Gly Val Leu Met Glu
                        515                 520                 525
        Ser Ser Gly Phe Glu Ser Val Ser Leu Ser His Tyr Ala Met Ser Gln
                        530                 535                 540
        Ala Lys Ile Leu Leu Trp Tyr Cys Asn Tyr Ser Asp Leu Tyr Ser Leu
        545                 550                 555                 560
        Asp Asp Ser Gln Pro Gly Phe Leu Thr Leu Ala Trp Asn Glu Val Pro
                        565                 570                 575
```

```
Leu Leu Thr Val Ser Ser Trp Arg
            580

<210> SEQ ID NO 119
<211> LENGTH: 242
<212> TYPE: PRT
<213> ORGANISM: Populus trichocarpa

<400> SEQUENCE: 119

Met Gly Arg Gly Arg Val Glu Leu Lys Arg Ile Glu Asn Lys Ile Asn
1               5                   10                  15

Arg Gln Val Thr Phe Ala Lys Arg Arg Asn Gly Leu Leu Lys Lys Ala
            20                  25                  30

Tyr Glu Leu Ser Val Leu Cys Asp Ala Glu Val Ala Leu Ile Ile Phe
        35                  40                  45

Ser Asn Arg Gly Lys Leu Tyr Glu Phe Cys Ser Ser Ser Met Leu
    50                  55                  60

Lys Thr Leu Glu Arg Tyr Gln Lys Cys Asn Tyr Gly Ala Pro Glu Pro
65                  70                  75                  80

Asn Val Ser Ala Arg Glu Ala Leu Glu Leu Ser Ser Gln Gln Glu Tyr
                85                  90                  95

Leu Lys Leu Lys Ala Arg Tyr Glu Ala Leu Gln Arg Thr Gln Arg Asn
            100                 105                 110

Leu Leu Gly Glu Glu Leu Gly Pro Leu Ser Ser Lys Glu Leu Glu Ser
        115                 120                 125

Leu Glu Arg Gln Leu Asp Met Ser Leu Lys Gln Ile Arg Ser Thr Arg
    130                 135                 140

Thr Gln Tyr Met Leu Asp Gln Leu His Asp Leu Gln His Lys Glu His
145                 150                 155                 160

Met Leu Thr Ala Ala Asn Lys Ser Leu Lys Glu Arg Leu Met Glu Gly
                165                 170                 175

Tyr Gln Leu Asn Ser Leu Gln Leu Asn Pro Ser Ala Glu Asp Val Glu
            180                 185                 190

Tyr Ala Arg Gln Gln Ala Gln Pro Gln Gly Asp Gly Phe Phe His Ala
        195                 200                 205

Leu Glu Cys Glu Pro Thr Leu Gln Ile Gly Tyr Gln Pro Glu Asn Ile
    210                 215                 220

Thr Met Val Thr Ala Gly Pro Ser Met Thr Thr Tyr Met Pro Gly Trp
225                 230                 235                 240

Leu Ala

<210> SEQ ID NO 120
<211> LENGTH: 585
<212> TYPE: PRT
<213> ORGANISM: Populus trichocarpa

<400> SEQUENCE: 120

Met Ser Leu Val Gly Pro Ala Glu Leu Ser Ala Thr Pro Tyr Gly Asn
1               5                   10                  15

His Lys Leu Tyr Ser Leu Lys Gly Ser Asn Asp Asn Ser Gly Leu Ser
            20                  25                  30

Ala Gln Ile Phe Cys Pro Asp Lys Arg Gln Asn Met Tyr Met Thr Asp
        35                  40                  45

Ser Tyr Ser Ser Glu Ser Tyr Glu Lys Tyr Phe Leu Asp Ser Pro Thr
    50                  55                  60
```

```
Glu Glu Leu Ile Gln Pro Ser Ser Gly Ile Ser Gly Asn Ser Ala
 65                  70                  75                  80

Pro Pro Gln Gly Thr Ser Ser Tyr Gln Leu Arg Lys Asn Leu Gly Pro
             85                  90                  95

Ser Met Ser Pro Gln Asp Asp Pro Tyr Asp Ala Cys Phe Thr Leu Thr
            100                 105                 110

Thr Pro Cys Asp Gly Tyr Gln Phe Asn Ser Glu Ser Asp Tyr Leu Asp
            115                 120                 125

Ile Glu Ser Pro Asp Pro Leu Asn Tyr Asp Glu Tyr Lys Met Lys Leu
            130                 135                 140

Lys Phe Gln Glu Leu Glu Arg Ala Leu Leu Asn Asp Asn Asp Glu Asp
145                 150                 155                 160

Gly Met Phe Gly Asn Ser Gln Ser Met Glu Met Asp Gly Glu Trp Ser
                165                 170                 175

Asp Pro Ile Gln Asn Gly Met Leu His Asp Ser Pro Lys Glu Ser Ser
            180                 185                 190

Ser Ser Asp Ser Ser Leu Ser Ser Ile Ser Ser Asn Lys Glu Val Ser
            195                 200                 205

Gln Leu Ser Pro Arg Thr Pro Arg Arg Leu Leu Phe Glu Cys Ala Asn
210                 215                 220

Ala Ile Ser Glu Gly Asn Ile Glu Lys Ala Ser Thr Leu Ile Asn Glu
225                 230                 235                 240

Leu Arg Gln Leu Val Ser Ile Gln Gly Asp Pro Pro Gln Arg Ile Ala
                245                 250                 255

Ala Tyr Met Val Glu Gly Leu Ala Ala Arg Met Ala Glu Ser Gly Lys
            260                 265                 270

Tyr Leu Tyr Lys Ala Leu Lys Cys Lys Glu Pro Pro Ser Ser Asp Arg
            275                 280                 285

Leu Ala Ala Met Gln Ile Leu Phe Glu Ile Cys Pro Cys Phe Lys Phe
290                 295                 300

Gly Phe Met Ala Ala Asn Gly Ala Met Ile Glu Ala Phe Lys Gly Glu
305                 310                 315                 320

Arg Arg Val His Ile Ile Asp Phe Asp Ile Asn Gln Gly Ser Gln Tyr
                325                 330                 335

Ile Thr Leu Ile Gln Thr Leu Ala Asn His Gln Gly Lys Leu Pro His
            340                 345                 350

Leu Arg Leu Thr Gly Val Asp Asp Pro Glu Ser Val Gln Arg Pro Val
            355                 360                 365

Gly Gly Leu Arg Ile Ile Gly Gln Arg Leu Glu Lys Leu Ala Glu Ala
            370                 375                 380

Tyr Lys Val Ser Phe Glu Phe His Ala Val Ala Ser Lys Thr Ser Leu
385                 390                 395                 400

Val Asn Pro Ser Met Leu Asn Cys Lys Pro Gly Glu Ala Leu Ile Val
                405                 410                 415

Asn Phe Ala Phe Gln Leu His His Met Pro Asp Glu Ser Val Ser Thr
            420                 425                 430

Val Asn Glu Arg Asp Gln Leu Leu Arg Met Ala Lys Ser Leu Asn Pro
            435                 440                 445

Lys Leu Val Thr Val Val Glu Gln Asp Val Asn Thr Asn Thr Ala Pro
            450                 455                 460

Phe Phe Pro Arg Phe Thr Glu Ala Tyr Asn Tyr Tyr Ser Ala Val Phe
465                 470                 475                 480

Asp Ser Leu Asp Ala Thr Leu Pro Arg Glu Ser Gln Asp Arg Leu Asn
```

```
                    485                 490                 495
Val Glu Lys Gln Cys Leu Ala Arg Asp Ile Val Asn Ile Val Ala Cys
            500                 505                 510

Glu Gly Glu Glu Arg Ile Glu Arg Tyr Glu Val Ala Gly Lys Trp Arg
        515                 520                 525

Ala Arg Met Met Met Ala Gly Phe Thr Ser Cys Ser Ile Thr Pro Asn
    530                 535                 540

Val Val Asp Met Ile Arg Lys Leu Ile Lys Glu Tyr Cys Asp Arg Tyr
545                 550                 555                 560

Met Leu Lys Gln Glu Val Gly Ala Leu His Phe Gly Trp Glu Asp Lys
                565                 570                 575

Ser Leu Ile Val Ala Ser Ala Trp Lys
            580                 585

<210> SEQ ID NO 121
<211> LENGTH: 544
<212> TYPE: PRT
<213> ORGANISM: Populus trichocarpa

<400> SEQUENCE: 121

Met Lys Arg Asp His Gln Glu Thr Ile Gly Gly Gly Ile Gly Asn Arg
1               5                   10                  15

Ala Glu Ser Ser Ser Ser Met Glu Thr Gly Lys Gly Lys Ser Trp
            20                  25                  30

Val Glu Asp Asp Gln Asp Ala Gly Gly Met Asp Glu Leu Leu Ala Val
        35                  40                  45

Leu Gly Tyr Lys Ile Lys Ser Ser Asp Met Ala Asp Val Ala Gln Lys
    50                  55                  60

Leu Glu Gln Leu Glu Met Val Leu Gly Ser Glu Asp Gly Ile Ser His
65                  70                  75                  80

Leu Ala Ser Asp Thr Val His Tyr Asn Pro Ser Asp Leu Ser Gly Trp
                85                  90                  95

Val Gln Asn Ser Leu Leu Gly Gln Pro Ser Thr Ile Thr Pro Leu Asp
            100                 105                 110

Phe Pro Ser Asn Ser Gln Ser Lys Val Phe Ala Asp Asp Ser Glu Tyr
        115                 120                 125

Asp Leu Arg Ala Ile Pro Gly Val Ala Ala Tyr Pro Gln Gln Glu Leu
    130                 135                 140

Asp Lys Thr Met Ala Val Ser Gly Thr Leu Ser Glu Pro Thr Arg Pro
145                 150                 155                 160

Val Val Leu Val Asp Ser Gln Glu Thr Gly Val Arg Leu Val His Thr
                165                 170                 175

Leu Leu Ala Cys Ala Glu Ala Ile Gln Gln Glu Asn Leu Lys Leu Ala
            180                 185                 190

Asp Ala Leu Val Lys His Ile Gly Leu Leu Ala Ala Ser Gln Thr Gly
        195                 200                 205

Ala Met Arg Lys Val Ala Thr Tyr Phe Ala Glu Ala Leu Ala Arg Arg
    210                 215                 220

Ile Tyr Lys Ile Phe Pro Gln Asp Tyr Cys Leu Asp Ser Ser Cys Ser
225                 230                 235                 240

Asp Thr Leu Glu Met His Phe Tyr Glu Thr Cys Pro Tyr Leu Lys Phe
                245                 250                 255

Ala His Phe Thr Ala Asn Gln Ala Ile Leu Glu Ala Phe Ala Asn Ala
            260                 265                 270
```

Ser Arg Val His Val Ile Asp Phe Gly Leu Lys Gln Gly Met Gln Trp
            275                 280                 285

Pro Ala Leu Met Gln Ala Leu Ala Leu Arg Pro Gly Gly Pro Pro Ala
        290                 295                 300

Phe Arg Leu Thr Gly Ile Gly Pro Pro Gln Pro Asp Asn Thr Asp Ala
305                 310                 315                 320

Leu Gln Gln Val Gly Trp Lys Leu Ala Gln Leu Ala Gln Thr Ile Gly
                325                 330                 335

Val Glu Phe Glu Phe Arg Gly Phe Val Ala Asn Ser Leu Ala Asp Leu
            340                 345                 350

Asp Ala Glu Met Leu Gly Leu Leu Pro Pro Glu Val Glu Ala Val Ala
        355                 360                 365

Val Asn Ser Val Phe Glu Leu His Arg Leu Leu Gly Arg Pro Gly Gly
    370                 375                 380

Ile Asp Lys Val Leu Glu Ser Ile Lys Ala Met Arg Pro Lys Ile Val
385                 390                 395                 400

Thr Ile Val Glu Gln Ala Asn His Asn Gly Pro Val Phe Leu Asp
                405                 410                 415

Arg Phe Thr Glu Ala Leu His Tyr Tyr Ser Ser Leu Phe Asp Ser Leu
            420                 425                 430

Glu Gly Ser Gly Leu Thr Pro Pro Ser Gln Asp Leu Val Met Ser Glu
        435                 440                 445

Leu Tyr Leu Gly Arg His Ile Cys Asn Val Val Ala Cys Glu Gly Ala
    450                 455                 460

Asp Arg Val Glu Arg His Glu Thr Leu Ala Gln Trp Arg Thr Arg Phe
465                 470                 475                 480

Asp Ser Ala Gly Phe Asp Pro Val His Leu Gly Ser Asn Ala Phe Lys
                485                 490                 495

Gln Ala Ser Met Leu Leu Ala Leu Phe Ala Gly Asp Gly Tyr Arg
            500                 505                 510

Val Glu Glu Asn Asn Gly Cys Leu Met Leu Gly Trp His Thr Arg Pro
        515                 520                 525

Leu Ile Ala Thr Ser Ala Trp Gln Leu Ala Ala Gly Asp Ser Gln Gln
    530                 535                 540

<210> SEQ ID NO 122
<211> LENGTH: 352
<212> TYPE: PRT
<213> ORGANISM: Populus trichocarpa

<400> SEQUENCE: 122

Met Glu Asn Asn Cys Val Tyr Ser Glu Glu Asp Glu Gln Met Glu Leu
1               5                   10                  15

Pro Pro Gly Phe Arg Phe His Pro Thr Asp Glu Glu Leu Ile Thr His
            20                  25                  30

Tyr Leu Ser Gln Lys Val Leu Asp Asn Tyr Phe Cys Ala Arg Ala Ile
        35                  40                  45

Gly Glu Val Asp Leu Asn Lys Cys Glu Pro Trp Asp Leu Pro Trp Arg
    50                  55                  60

Ala Lys Met Gly Glu Lys Glu Trp Tyr Phe Phe Cys Val Ile Asp Arg
65                  70                  75                  80

Lys Tyr Pro Thr Gly Leu Arg Thr Asn Arg Ala Thr Asp Ala Gly Tyr
                85                  90                  95

Trp Lys Ala Thr Gly Lys Asp Lys Glu Ile Tyr Arg Ala Lys Thr Leu
            100                 105                 110

Val Gly Met Lys Lys Thr Leu Val Phe Tyr Lys Gly Arg Ala Pro Lys
            115                 120                 125
Gly Glu Lys Thr Asn Trp Val Met His Glu Tyr Arg Leu Glu Gly Lys
        130                 135                 140
Asn Pro Val Tyr Asn Pro Pro Lys Thr Ala Lys Asn Asp Trp Val Ile
145                 150                 155                 160
Cys Arg Ile Phe Glu Lys Ser Cys Gly Lys Lys Thr His Ile Ser
                165                 170                 175
Gly Leu Val Arg Leu Ser Ser Tyr Gly Asn Glu Leu Lys Pro Thr Ile
                180                 185                 190
Leu Pro Pro Leu Met Asp Ser Ser Gln His Asn Asn Asp Lys Arg Thr
                195                 200                 205
Asn Ile Gly Asp Lys Ser His Val Thr Cys Phe Ser Asn Pro Thr Glu
210                 215                 220
Asp Gln Lys Pro His Glu Thr Ile Ala Asp Cys Phe Asn Ile Ser Leu
225                 230                 235                 240
Arg Ala Pro Leu Ser Ser Ser Asn Met Ser Pro Ser Ser Val Leu Phe
                245                 250                 255
Ser Lys Pro Ser Pro Asn Ser Phe Tyr Ser Ser His Ile Leu Pro
                260                 265                 270
Asn Ile Ala Asn Phe Gln Tyr Pro Asp Ser Val Met Met Pro Glu His
                275                 280                 285
Ser Met Leu Arg Ile Leu Leu Glu Asn Gln Gly Pro Gly Met Asn Leu
                290                 295                 300
Asn Ser Lys Arg Glu Leu Ser Glu Asp Thr Gly Leu Ser Thr Asp Met
305                 310                 315                 320
Ser Ser Val Val Thr Asn His Glu Leu Val His Gly Ser Phe Glu Asp
                325                 330                 335
Pro Ser Ser Ser Ala Gly Pro Val Asp Leu Asp Tyr Leu Trp Asn Tyr
                340                 345                 350

<210> SEQ ID NO 123
<211> LENGTH: 820
<212> TYPE: PRT
<213> ORGANISM: Populus trichocarpa

<400> SEQUENCE: 123

Met Ser Phe Gly Gly Phe Leu Glu Asn Thr Ser Pro Gly Gly Gly Gly
1               5                   10                  15
Ala Arg Ile Val Ala Asp Ile Leu Tyr Asn Asn Asn Asn Met Pro
                20                  25                  30
Thr Gly Ala Ile Ala Gln Thr Arg Leu Val Ser Pro Ser Ile Thr Lys
            35                  40                  45
Ser Met Phe Asn Ser Pro Gly Leu Ser Leu Ala Leu Gln Gln Pro Asn
        50                  55                  60
Ile Asp Gly Gln Gly Asp Ile Thr Arg Met Ala Glu Asn Phe Glu Thr
65                  70                  75                  80
Ser Val Gly Arg Arg Ser Arg Glu Glu His Glu Ser Arg Ser Gly
                85                  90                  95
Ser Asp Asn Met Asp Gly Ala Ser Gly Asp Gln Asp Ala Ala Asp
                100                 105                 110
Asn Pro Pro Arg Lys Lys Arg Tyr His Arg His Thr Pro Gln Gln Ile
                115                 120                 125
Gln Glu Leu Glu Ala Leu Phe Lys Glu Cys Pro His Pro Asp Glu Lys

```
            130                 135                 140
Gln Arg Leu Glu Leu Ser Arg Arg Leu Cys Leu Glu Thr Arg Gln Val
145                 150                 155                 160

Lys Phe Trp Phe Gln Asn Arg Arg Thr Gln Met Lys Thr Gln Leu Glu
                165                 170                 175

Arg His Glu Asn Ser Leu Leu Arg Gln Asp Asn Asp Lys Leu Arg Ala
                180                 185                 190

Glu Asn Met Ser Ile Arg Asp Ala Met Arg Asn Pro Ser Cys Ser Asn
            195                 200                 205

Cys Gly Gly Pro Ala Ile Ile Gly Asp Met Ser Leu Glu Glu Gln His
        210                 215                 220

Leu Arg Ile Glu Asn Ala Arg Leu Lys Asp Glu Leu Asp Arg Val Cys
225                 230                 235                 240

Ala Leu Ala Gly Lys Phe Leu Gly Arg Pro Ile Ser Ser Leu Ala Ser
                245                 250                 255

Ser Leu Ser Pro Pro Thr Asn Ser Ser Leu Glu Leu Ala Val Gly Ser
                260                 265                 270

Asn Gly Phe Ala Gly Leu Ser Thr Ile Ala Thr Thr Leu Pro Leu Gly
            275                 280                 285

Pro His Phe Glu Gly Gly Ile Ser Gly Ala Leu Ser Met Val Thr Gln
        290                 295                 300

Thr Arg Leu Ala Thr Ala Gly Val Thr Gly Ile Asp Arg Ser Val Glu
305                 310                 315                 320

Arg Ser Met Phe Leu Glu Leu Ala Leu Ala Ala Met Asp Glu Leu Val
                325                 330                 335

Lys Met Val Gln Thr Asp Glu Pro Leu Trp Ile Gly Ser Phe Glu Gly
                340                 345                 350

Gly Arg Glu Ile Leu Asn His Glu Gly Tyr Leu Arg Thr Phe Thr Pro
            355                 360                 365

Cys Ile Gly Met Lys Pro Ser Gly Phe Val Ser Glu Ala Ser Arg Glu
        370                 375                 380

Thr Gly Met Val Ile Ile Asn Ser Leu Ala Leu Val Glu Thr Leu Met
385                 390                 395                 400

Asp Ser Asn Arg Trp Ala Glu Met Phe Pro Cys Met Ile Ala Arg Thr
                405                 410                 415

Ser Thr Thr Asp Val Ile Ala Ser Gly Met Gly Gly Thr Arg Asn Gly
                420                 425                 430

Ser Leu Gln Leu Met Gln Ala Glu Leu His Val Leu Ser Pro Leu Val
            435                 440                 445

Pro Val Arg Glu Val Asn Phe Leu Arg Phe Cys Lys Gln His Ala Glu
        450                 455                 460

Gly Val Trp Ala Val Val Asp Val Ser Ile Asp Thr Ile Arg Asp Thr
465                 470                 475                 480

Ser Gly Ala Pro Pro Thr Phe Val Asn Cys Arg Arg Leu Pro Ser Gly
                485                 490                 495

Cys Val Val Gln Asp Met Pro Asn Gly Tyr Ser Lys Val Thr Trp Val
                500                 505                 510

Glu His Ala Gln Tyr Asp Glu Arg Gln Ile His Gln Leu Tyr Arg Pro
            515                 520                 525

Val Ile Ser Ser Gly Met Gly Phe Gly Ala Gln Arg Trp Ile Ala Thr
        530                 535                 540

Leu Gln Arg Gln Cys Glu Cys Leu Ala Ile Leu Leu Ser Ser Asn Val
545                 550                 555                 560
```

Pro Ser Arg Asp His Thr Ala Ile Thr Thr Ser Gly Arg Arg Ser Met
            565                 570                 575

Leu Lys Leu Ala Gln Arg Met Thr Asp Asn Phe Cys Ala Gly Val Cys
            580                 585                 590

Ala Ser Thr Val His Lys Trp Asn Lys Leu Asn Ala Gly Asn Val Asp
            595                 600                 605

Glu Asp Val Arg Val Met Thr Arg Lys Ser Val Asp Asp Pro Gly Glu
        610                 615                 620

Pro Pro Gly Ile Val Leu Ser Ala Ala Thr Ser Val Trp Leu Pro Val
625                 630                 635                 640

Ser Pro Gln Arg Leu Phe Asp Phe Leu Arg Asn Glu Arg Leu Arg Ser
            645                 650                 655

Glu Trp Asp Ile Leu Ser Asn Gly Gly Pro Met Gln Glu Met Ala His
            660                 665                 670

Ile Ala Lys Gly Gln Asp His Gly Asn Cys Val Ser Leu Leu Arg Ala
            675                 680                 685

Ser Ala Met Asn Ala Asn Gln Ser Ser Met Leu Ile Leu Gln Glu Thr
        690                 695                 700

Cys Ile Asp Ala Ala Gly Ser Leu Val Val Tyr Ala Pro Val Asp Thr
705                 710                 715                 720

Pro Ala Met His Val Val Met Asn Gly Gly Asp Ser Ala Tyr Val Ala
            725                 730                 735

Leu Leu Pro Ser Gly Phe Ala Ile Val Pro Asp Gly Pro Gly Ser Arg
            740                 745                 750

Asp Pro Pro Ser Thr Asn Gly Gly Pro Thr Ala Asn Asn Val Gly Gly
            755                 760                 765

Gln Glu Arg Val Ser Gly Ser Leu Leu Thr Val Ala Phe Gln Ile Leu
        770                 775                 780

Val Asn Ser Leu Pro Thr Ala Lys Leu Thr Val Glu Ser Val Glu Thr
785                 790                 795                 800

Val Asn Asn Leu Ile Ser Cys Thr Val Gln Lys Ile Lys Ala Ala Leu
            805                 810                 815

Gln Cys Glu Ser
            820

<210> SEQ ID NO 124
<211> LENGTH: 210
<212> TYPE: PRT
<213> ORGANISM: Populus trichocarpa

<400> SEQUENCE: 124

Met Ala Pro Lys Lys Leu Asn Gly Asn Asp Asn Gly Ser Leu Lys Lys
1               5                   10                  15

Ala Ser Gly Asp His Asp Lys Lys Glu Ile His Tyr Arg Gly Val Arg
            20                  25                  30

Lys Arg Pro Trp Gly Arg Tyr Ala Ala Glu Ile Arg Asp Pro Gly Lys
        35                  40                  45

Lys Ser Arg Val Trp Leu Gly Thr Phe Asp Thr Ala Val Glu Ala Ala
    50                  55                  60

Arg Ala Tyr Asp Lys Ala Ala Arg Glu Tyr Arg Gly Ala Lys Ala Lys
65                  70                  75                  80

Thr Asn Phe Pro Ile Ala Glu Lys Val Val Asp Tyr Asp Asp Glu Lys
                85                  90                  95

Gln Ser Ser Ser Gln Ser Ser Thr Val Glu Ser Ser Ser Ser Pro Val

```
            100                 105                 110
Val Ser Ala Val Ala Arg Asp Val Thr Arg Gln Val Gly Val Val
            115                 120                 125

Gly Met Gly Arg Phe Pro Phe Val Phe Gln Gln Pro Pro His Val
            130                 135                 140

Asn Ala Val Gly Pro Val Trp Phe Leu Asp Ser Thr Val Lys Pro Glu
145                 150                 155                 160

Phe Val Ala Gln Arg Phe Pro Val Arg Tyr Asp Pro Val Gly Leu Glu
                165                 170                 175

Gly Gly Ala His Ser Asp Ser Asp Ser Ser Ser Val Ile Asp Phe Lys
                180                 185                 190

Pro Arg Ser Ser Ile Leu His Leu Asp Leu Asn Leu Pro Pro Pro Ala
                195                 200                 205

Asp Ala
    210

<210> SEQ ID NO 125
<211> LENGTH: 243
<212> TYPE: PRT
<213> ORGANISM: Populus trichocarpa

<400> SEQUENCE: 125

Met Cys Thr Arg Gly His Trp Arg Pro Ala Glu Asp Glu Lys Leu Lys
1               5                   10                  15

Glu Leu Val Glu Lys Tyr Gly Pro His Asn Trp Asn Ala Ile Ala Glu
            20                  25                  30

Lys Leu Gln Gly Arg Ser Gly Lys Ser Cys Arg Leu Arg Trp Phe Asn
        35                  40                  45

Gln Leu Asp Pro Arg Ile Asn Arg Ser Pro Phe Thr Glu Glu Glu Glu
    50                  55                  60

Glu Arg Leu Leu Ala Ser His Arg Ile His Gly Asn Arg Trp Ala Ile
65                  70                  75                  80

Ile Ala Arg Phe Phe Pro Gly Arg Thr Asp Asn Ala Val Lys Asn His
                85                  90                  95

Trp His Val Ile Met Ala Arg Arg Tyr Arg Glu Arg Ser Arg Leu His
            100                 105                 110

Ala Lys Arg Ala Ala Gln Thr Leu Val Asn Asp Asn Lys Leu Ser Ser
        115                 120                 125

Lys Gln Asp His Met His Met Asp Cys Glu Thr Arg Asn Phe Ser Ser
    130                 135                 140

Phe Ser Lys Lys Tyr Cys Glu Lys Tyr Gly Gln Tyr Pro Met Val Thr
145                 150                 155                 160

His Ser Tyr Leu Pro Ala Phe Cys Lys Glu Phe Tyr Asn Glu Asp Pro
                165                 170                 175

Ser His Cys Glu Asp Gln Ser Arg Pro Ile Glu Phe Tyr Asp Phe Leu
            180                 185                 190

Gln Val Asn Thr Asp Ser Asn Lys Ser Glu Val Ile Asp Asn Ala Arg
        195                 200                 205

Arg Asp Asp Glu Glu Val Asp Gln Gln Glu Ala Leu Glu Asn Asn Gln
    210                 215                 220

Ser Lys Ala Asp Val Pro Phe Ile Asp Phe Phe Ser Val Asn Gly Lys
225                 230                 235                 240

Ser Ser Ser
```

-continued

<210> SEQ ID NO 126
<211> LENGTH: 318
<212> TYPE: PRT
<213> ORGANISM: Populus trichocarpa

<400> SEQUENCE: 126

Met Gly Arg Ser Pro Cys Cys Glu Lys Glu His Thr Asn Lys Gly Ala
1               5                   10                  15

Trp Thr Lys Glu Glu Asp Glu Arg Leu Ile Asn Tyr Ile Lys Ser His
            20                  25                  30

Gly Glu Gly Cys Trp Arg Ser Leu Pro Lys Ala Ala Gly Leu Leu Arg
        35                  40                  45

Cys Gly Lys Ser Cys Arg Leu Arg Trp Ile Asn Tyr Leu Arg Pro Asp
    50                  55                  60

Leu Lys Arg Gly Asn Phe Ser Asp Glu Glu Asp Glu Leu Ile Ile Asn
65                  70                  75                  80

Leu His Ser Leu Leu Gly Asn Lys Trp Ser Leu Ile Ala Ala Arg Leu
                85                  90                  95

Pro Gly Arg Thr Asp Asn Glu Ile Lys Asn Tyr Trp Asn Thr His Ile
            100                 105                 110

Lys Arg Lys Leu Phe Ser Arg Gly Val Asp Pro Gln Thr His Arg Pro
        115                 120                 125

Leu Asn Ser Thr Thr Thr Ser Ser Thr Thr Ser Thr Thr Thr Asn Ser
    130                 135                 140

Thr Asn Asn Lys Asn Ser Asn Met Gly Thr Lys Arg Ile Thr Asn Phe
145                 150                 155                 160

Lys Leu Glu Glu Gln Asn Tyr Leu Phe Val Gln Ala Gln Pro Glu Phe
                165                 170                 175

Met Met Ser Asn Ile Val Lys Lys Ala Ser Asp Ser Ser Ile Ile Lys
            180                 185                 190

Val Gly Gly Ser Ser Asp Ser Ala Glu Asp Ser Asn Ser Ser Ser Gly
        195                 200                 205

Val Thr Ala Glu Leu Glu Val His Pro Asn His Lys Leu Asn Leu Glu
    210                 215                 220

Leu Ser Ile Gly Leu Pro Cys Gln Ser Gln Leu Ser Ser Val Asn Asp
225                 230                 235                 240

Leu Asn Asp Ser Lys Gln Ala Asn Gln Gln His Gln Glu Gln Val Val
                245                 250                 255

Thr Tyr Gln Leu Phe Gly Thr Pro Ala Thr Pro Thr Ser Ser Ala Pro
            260                 265                 270

Ala Val Val His Arg Thr Ala Cys Leu Cys Ser Tyr Asn Arg Gly Phe
        275                 280                 285

Lys Asn Ser Gln Ala Cys Ser Cys Cys Asn Ala Val Glu Lys Phe Val
    290                 295                 300

Thr Ala Asp Ser Leu Tyr Arg Phe Tyr Arg Pro Leu Asp Ala
305                 310                 315

<210> SEQ ID NO 127
<211> LENGTH: 235
<212> TYPE: PRT
<213> ORGANISM: Populus trichocarpa

<400> SEQUENCE: 127

Met Glu Val Tyr Pro Tyr Pro Ser Arg Phe Ser Met Ser Ser Leu Cys
1               5                   10                  15

Ser Phe Gly Asn Phe Val Asp Lys Val Lys Glu Val Cys Asn Phe Val

```
            20                  25                  30
Val Ser Ala Ile Ile Gly Asn Ile Phe Ser Ala Ile Phe Thr Phe Phe
        35                  40                  45
Phe Ala Leu Val Gly Thr Leu Leu Gly Ala Met Thr Gly Ala Leu Ile
    50                  55                  60
Gly Gln Glu Thr Glu Ser Gly Phe Val Arg Ala Ala Val Gly Ala
65                  70                  75                  80
Ile Ser Gly Ala Val Phe Ser Ile Glu Val Phe Glu Ser Ser Leu Val
                85                  90                  95
Leu Trp Gln Ser Asp Glu Ser Gly Ile Gly Cys Val Leu Tyr Leu Ile
                100                 105                 110
Asp Val Ile Ala Ser Leu Leu Ser Gly Arg Leu Val Arg Glu Arg Ile
            115                 120                 125
Gly Pro Ala Met Leu Ser Ala Val Gln Ser Gln Met Gly Ala Val Glu
        130                 135                 140
Thr Asn Phe Glu Glu Ile Pro Asn Ile Phe Asp Thr Gly Gly Ser Lys
145                 150                 155                 160
Gly Leu Pro Gly Asp Ser Leu Glu Lys Ile Pro Lys Ile Arg Ile Thr
                165                 170                 175
Ser Asn Asn Val Asp Glu Ser Gly Glu Lys Val Ser Cys Ser Val
                180                 185                 190
Cys Leu Gln Asp Phe Gln Leu Gly Glu Thr Val Arg Ser Leu Pro His
            195                 200                 205
Cys His His Met Phe His Leu Pro Cys Ile Asp Lys Trp Leu Leu Arg
        210                 215                 220
His Ala Ser Cys Pro Leu Cys Arg Arg Asp Leu
225                 230                 235

<210> SEQ ID NO 128
<211> LENGTH: 293
<212> TYPE: PRT
<213> ORGANISM: Populus trichocarpa

<400> SEQUENCE: 128

Met Arg Ile Ser Arg Ala Arg Trp Phe Thr Phe Leu Arg Arg Val Phe
1               5                   10                  15
His Tyr Gln Asn Gly Ser Ser Ser Asn Leu Gly Ser Asn Pro Phe Asn
                20                  25                  30
Ser Ser Ser Trp Met Met Leu Glu Phe Val Ala Leu Leu Leu Gln Ile
            35                  40                  45
Cys Ile Thr Thr Phe Thr Leu Ala Ile Ser Lys Ala Glu Asn Pro Val
    50                  55                  60
Trp Pro Val Arg Ile Trp Ile Ile Gly Tyr Asn Ile Gly Cys Val Leu
65                  70                  75                  80
Ser Leu Leu Leu Leu Tyr Gly Arg Tyr Arg Gln Leu Asn Ala Thr Gln
                85                  90                  95
Gly Asp Gly Phe Gly Leu Pro Asp Leu Glu Gln Gln Gly Gly Ser Glu
                100                 105                 110
Glu Ser Ser Val Cys Arg Tyr Ser His Leu Met Asn Lys Cys Arg Thr
            115                 120                 125
Ser Leu Glu Leu Phe Phe Ala Ile Trp Phe Val Met Gly Asn Val Trp
        130                 135                 140
Val Phe Asp Ser Arg Phe Gly Ser Tyr Phe Arg Ala Pro Lys Leu His
145                 150                 155                 160
```

```
Val Leu Cys Ile Ser Leu Leu Ala Trp Asn Ala Leu Ser Tyr Ser Phe
            165                 170                 175

Pro Phe Leu Leu Phe Leu Leu Cys Cys Val Pro Leu Ile Ser
        180                 185                 190

Thr Val Ile Gly Tyr Asn Met Ser Met Gly Ser Ala Glu Arg Gly Ala
            195                 200                 205

Ser Asp Asp Gln Ile Ser Arg Leu Pro Ser Arg Arg Tyr Lys Ala Val
    210                 215                 220

Asp Thr Asp Ser Glu Phe Arg Asn Ser Val Asp Cys Asp Ser Thr Val
225                 230                 235                 240

Ala Ser Glu Asp Leu Glu Cys Cys Ile Cys Leu Ala Lys Tyr Lys Asp
                245                 250                 255

Ile Glu Glu Val Arg Gln Leu Pro Cys Ser His Met Phe His Leu Lys
            260                 265                 270

Cys Val Asp Gln Trp Leu Arg Ile Ile Ser Cys Cys Pro Leu Cys Lys
        275                 280                 285

Gln Glu Leu Glu Lys
    290

<210> SEQ ID NO 129
<211> LENGTH: 321
<212> TYPE: PRT
<213> ORGANISM: Populus trichocarpa

<400> SEQUENCE: 129

Met Asp Pro Lys Gly Ser Asn Ser Lys Asn Pro His Glu Leu Pro Thr
1               5                   10                  15

Phe Phe Thr Leu Thr His Thr His Thr Ser Pro Ser Pro Ser Pro His
            20                  25                  30

Thr Pro Pro Gln Pro His His Gln Pro Gln His Leu His Asn Gln
        35                  40                  45

Asn Gln Leu Gln Pro Asn Met Gly Glu Asn Lys Ala Ala Glu Ile Lys
    50                  55                  60

Asp Phe Gln Ile Val Val Ala Asp Lys Glu Glu Gln Lys Lys Gln Leu
65                  70                  75                  80

Ala Pro Lys Arg Ser Ser Asn Lys Asp Arg His Thr Lys Val Glu Gly
                85                  90                  95

Arg Gly Arg Arg Ile Arg Met Pro Ala Leu Cys Ala Ala Arg Ile Phe
            100                 105                 110

Gln Leu Thr Arg Glu Leu Gly His Lys Ser Asp Gly Glu Thr Ile Gln
        115                 120                 125

Trp Leu Leu Gln Gln Ala Glu Pro Ser Ile Ile Ala Ala Thr Gly Thr
    130                 135                 140

Gly Thr Ile Pro Ala Ser Ala Leu Ala Ala Ala Gly Gly Ala Ile Ser
145                 150                 155                 160

Gln Gln Gly Ala Ser Leu Ser Ala Gly Leu His Gln Lys Ile Asp Asp
                165                 170                 175

Ile Gly Glu Ser Ser Ser Arg Arg Thr Ser Trp Ala Met Leu Gly Gly
            180                 185                 190

Asn Leu Gly Arg Pro His Gln Val Thr Ser Ala Gly Leu Trp Pro Pro
        195                 200                 205

Val Gly Gly Tyr Gly Phe Gln Ser Ser Ser Asn Thr Thr Gly Pro Ser
    210                 215                 220

Thr Thr Asn Ile Val Ser Glu Gly Gly Gly Ser Ser Tyr Leu Gln
225                 230                 235                 240
```

```
Lys Asn Gly Phe Ser Gly Phe Asp Met Pro Gly Asn Ile Gly Pro
            245                 250                 255

Met Ser Leu Thr Ser Ile Leu Gly Val Gly Ser Gln Gln Leu Pro Gly
        260                 265                 270

Leu Glu Leu Gly Leu Ser Gln Asp Gly His Ile Gly Val Leu Ser Pro
            275                 280                 285

Gln Ala Leu Ser Gln Ile Tyr Gln Gln Met Gly Gln Ala Arg Val Gln
        290                 295                 300

Gln His Gln Gln Gln Asn Pro Ser Lys Asp Asp Ser Gln Gly Ser Gly
305                 310                 315                 320

Gln

<210> SEQ ID NO 130
<211> LENGTH: 692
<212> TYPE: PRT
<213> ORGANISM: Populus trichocarpa

<400> SEQUENCE: 130

Met Gly Glu Glu Ala Asp Pro Thr Met Lys Lys Lys Lys Lys Lys Gly
1               5                   10                  15

Arg Pro Ser Leu Leu Glu Leu Gln Lys Arg Ser Leu Lys Gln Gln Gln
            20                  25                  30

Leu Gln Gln Thr Thr Pro Ile Ser Leu Lys Asn Pro Asn Pro Leu Asn
        35                  40                  45

Ser Asn Ser Ala Leu Pro Asn Arg Arg Ser Ala Arg Arg Ser Ser Asn
    50                  55                  60

Ser Tyr Ala Pro Glu Trp Ile Asp Gly Asp Asp Glu Asp Asp
65                  70                  75                  80

Glu Asp Asp Glu Arg Lys Glu Lys Lys His Lys Leu Leu Arg Gly Leu
                85                  90                  95

Asn Ser Gln Lys Asn Asn Gln Asn Ser Asn Ser Ser Ser Pro Ser
            100                 105                 110

Asn Leu His Gly Ser Asp Ser Asn Ala Gly Gly Gly Asn Gln Glu Asp
        115                 120                 125

Gly Ile Arg Arg Arg Lys Ile Ser Ala Val Arg Leu Gly Ser Asp Asp
    130                 135                 140

Leu Gly Glu Lys Val Leu Lys Gly Thr Asp Thr Ile His Gly Ser Ser
145                 150                 155                 160

Val Glu Pro Gly Pro Thr Thr Pro Leu Pro Asp Lys Lys Leu Leu Val
                165                 170                 175

Phe Ile Leu Asp Arg Leu Gln Lys Lys Asp Thr Tyr Gly Val Phe Ser
            180                 185                 190

Glu Pro Val Asp Pro Glu Glu Leu Pro Asp Tyr Phe Asp Ile Val Glu
        195                 200                 205

Asn Pro Met Asp Phe Ser Thr Val Arg Lys Lys Leu Asp Glu Gly Ala
    210                 215                 220

Tyr Ala His Leu Glu Gln Phe Glu Lys Asp Val Leu Leu Ile Cys Ser
225                 230                 235                 240

Asn Ala Met Gln Tyr Asn Pro Ser Asp Thr Ile Tyr Phe Arg Gln Ala
                245                 250                 255

Arg Ala Met Gln Glu Leu Ala Lys Lys Asp Phe Glu Asn Leu Arg Gln
            260                 265                 270

Asp Ser Asp Asp Ser Glu Pro Gln Thr Lys Val Ala Arg Arg Gly Arg
        275                 280                 285
```

```
Pro Pro Ala Leu Gly Lys Leu Lys Ala Leu Glu Arg Ser Pro Ile
    290                 295                 300

Asp Arg Val Gly Pro Glu Ala Ser Ser Asp Ala Thr Leu Ala Thr Gly
305                 310                 315                 320

Gly Asp His Asn Asn Leu Ser Asn Gly Tyr Asn Leu Arg Lys Ser Ser
                    325                 330                 335

Ser Tyr Lys Tyr Gln Pro Gly Asp Ala Phe Val Arg Ala Ser Tyr Ser
                340                 345                 350

Ser Glu Asn Tyr Ser Thr Trp Leu Ser Glu Trp Asn Glu Phe Pro
                355                 360                 365

Ala Ser Val Val Lys Ala Val Met Lys Tyr Gly Lys Lys Pro Phe Val
    370                 375                 380

Leu Asp Glu Asn Lys Arg Asp Thr Tyr Lys His Pro Leu Gly Ser His
385                 390                 395                 400

Glu Pro Ser Ile Leu Ser Thr Phe Gly Glu Leu Lys Gln Leu Val
                405                 410                 415

Val Val Gly Leu Ser Ser Glu His Gly Tyr Ala Arg Ser Leu Ala Arg
                420                 425                 430

Phe Ala Ala Asp Leu Gly Pro Val Val Trp Arg Ile Ala Ser Lys Lys
                435                 440                 445

Ile Glu Ser Val Leu Pro Thr Gly Leu Glu Phe Gly Pro Gly Trp Val
    450                 455                 460

Gly Glu Asn Lys Ala Met Glu Lys Gln Lys Ile Leu Asn Asn Leu Val
465                 470                 475                 480

Ser Asp Asn His Leu Ser Arg Phe Gln Pro Ala Ala Ser Ser Ser Arg
                485                 490                 495

Glu Ala Ala Trp Asn Arg Glu Gly Leu Pro Glu Thr Val Gly Gly Leu
                500                 505                 510

Asn Pro Gln Asn Glu Leu Ala Thr Leu Asn Ser Gly Ala Gly Gly Met
                515                 520                 525

Lys Ser Met Pro Ser Leu Gln Ile Gln Gln Lys Pro Ile Ile His Pro
530                 535                 540

Asp Met Asn Gly Phe Ser Gly Gly Phe Gly Tyr Asn Ser Ser Pro Gln
545                 550                 555                 560

Pro Gly Met Ala Arg Thr Val Ala Pro Thr Gly Lys Leu Asn Leu Glu
                565                 570                 575

Gln Thr Ala Val Pro Ser Gln Met Phe Gly Val Val Pro Thr Gly Asn
                580                 585                 590

Ser Ala Phe Ile Ser Val Pro Gly Asn Asp Phe Asn Thr Asn Lys Gly
    595                 600                 605

Met Leu Ser Glu Thr Ser Ser Gly Leu Leu Gln Pro Gly Ile Ser Pro
    610                 615                 620

Ala Val Gly Ser Ser Ser Asp Ser Arg Thr Phe Gly Asn Val Gly Phe
625                 630                 635                 640

Gly Gly Lys Ser Ser Trp Gln Gly Phe Leu Pro Tyr Gln Gln Gln Gly
                645                 650                 655

Thr Val Pro Phe Pro Pro Asp Leu Asn Val Gly Phe Leu Ala Pro Gly
                660                 665                 670

Ser Pro Thr Ser Ser Val Pro Ile Gly Ser Pro Arg Gln Pro Asp Leu
                675                 680                 685

Ala Leu Gln Leu
    690
```

<210> SEQ ID NO 131
<211> LENGTH: 1113
<212> TYPE: PRT
<213> ORGANISM: Populus trichocarpa

<400> SEQUENCE: 131

```
Met Lys Ser Pro Ala Asn Gly Ala Ala Ala Val Thr Asn Gly Glu
1               5                   10                  15

Gly Val Glu Lys Lys Ser Ile Asn Pro Glu Leu Trp Gln Ala Cys Ala
                20                  25                  30

Gly Pro Leu Val Asn Leu Pro Ala Ala Gly Thr His Val Val Tyr Phe
            35                  40                  45

Pro Gln Gly His Ser Glu Gln Val Ala Ala Ser Leu Lys Lys Asp Val
50              55                  60

Asn Ala Gln Ile Pro Asn Tyr Pro Asn Leu Pro Ser Lys Leu Leu Cys
65                  70                  75                  80

Leu Leu His Asn Val Thr Leu His Ala Asp Pro Glu Thr Asp Glu Val
                85                  90                  95

Tyr Val Gln Met Thr Leu Gln Pro Val Ser Ser Phe Asp Lys Asp Ala
                100                 105                 110

Leu Leu Arg Ser Asp Leu Ala Leu Lys Ser Asn Lys Pro Gln Thr Glu
            115                 120                 125

Phe Phe Cys Lys Thr Leu Thr Ala Ser Asp Thr Ser Thr His Gly Gly
            130                 135                 140

Phe Ser Val Pro Arg Arg Ala Ala Glu Lys Thr Phe Pro Pro Leu Asp
145                 150                 155                 160

Phe Ser Met Gln Pro Pro Ala Gln Glu Leu Val Ala Arg Asp Leu His
                165                 170                 175

Asp Asn Val Trp Thr Phe Arg His Ile Tyr Arg Gly Gln Pro Lys Arg
            180                 185                 190

His Leu Leu Thr Thr Gly Trp Ser Leu Phe Val Ser Gly Lys Arg Leu
            195                 200                 205

Phe Ala Gly Asp Ser Val Leu Phe Met Arg Asp Glu Lys Gln Gln Leu
    210                 215                 220

Leu Leu Gly Ile Arg Arg Ala Asn Arg Gln Pro Thr Asn Leu Ser Ser
225                 230                 235                 240

Ser Val Leu Ser Ser Asp Ser Met His Ile Gly Ile Leu Ala Ala Ala
                245                 250                 255

Ala His Ala Ala Ala Asn Asn Ser Pro Phe Thr Val Tyr Tyr Asn Pro
            260                 265                 270

Arg Ala Ser Pro Ser Glu Phe Val Ile Pro Leu Ala Lys Tyr Tyr Lys
        275                 280                 285

Ala Val Tyr Ser Asn Gln Ile Ser Leu Gly Met Arg Phe Arg Met Met
    290                 295                 300

Phe Glu Thr Glu Glu Ser Gly Thr Arg Arg His Met Gly Thr Ile Thr
305                 310                 315                 320

Gly Ile Ser Asp Leu Asp Ala Val Arg Trp Lys Asn Ser Gln Trp Arg
                325                 330                 335

Asn Leu Gln Val Gly Trp Asp Glu Ser Thr Ala Gly Glu Arg Arg Asn
            340                 345                 350

Arg Val Ser Ile Trp Glu Ile Glu Pro Val Thr Ala Pro Phe Phe Ile
        355                 360                 365

Cys Pro Pro Pro Phe Phe Arg Ser Lys His Pro Arg Gln Pro Gly Met
    370                 375                 380
```

```
Pro Asp Asp Asp Ser Thr Asp Phe Asp Ser Leu Phe Lys Arg Thr Met
385                 390                 395                 400

Pro Trp Leu Gly Asp Asp Ile Tyr Met Lys Asp Pro Gln Val Leu Pro
            405                 410                 415

Gly Leu Ser Leu Ala Gln Arg Met Asn Met Gln Gln Asn Pro Ser Leu
        420                 425                 430

Ala Asn Ser Met Gln Pro Asn Tyr Met Gln Ser Leu Ser Gly Ser Val
    435                 440                 445

Leu Gln Asn Leu Pro Gly Gly Asp Leu Ser Arg Gln Leu Gly Leu Ser
450                 455                 460

Ser Pro Gln Met Pro Gln Pro Asn Asn Leu Gln Phe Asn Ala Gln Arg
465                 470                 475                 480

Leu Pro Gln Gln Ala Gln Gln Leu Asp Gln Leu Pro Lys Leu Gln Ser
            485                 490                 495

Leu Leu Asn Pro Leu Gly Ser Ile Ile Gln Ser Gln Gln Gln Met Gly
        500                 505                 510

Asp Ile Thr Gln Gln Ser Arg Gln Asn Met Met Ala Gln Thr Leu Pro
    515                 520                 525

Ser Ser Gln Val Gln Ala Gln Leu Leu Gln Pro Gln Thr Leu Ala Gln
530                 535                 540

Thr Asn Asn Ile Leu Gln Gln Pro Ser Ile Gln Ser His Gln Leu
545                 550                 555                 560

Leu Arg Asn Leu Pro Gln Thr Leu His Gln Gln Gln Asn Gln Gln
            565                 570                 575

Gln His Ile Met Gly Gln Asn Gln Gln Ser Leu Met Gln Ser Gln
            580                 585                 590

Leu Ser Asp Gln Val Asn Gln His Met Gln Met Ser Asp Asn Gln Ile
            595                 600                 605

Gln Ser Gln Leu Met Gln Lys Leu Gln Gln Gln Gln Ser Val Ser
610                 615                 620

Ala Gln Gln Ser Ala Met His Gln Ala Gly Gln Leu Gly Gln Leu Gln
625                 630                 635                 640

Asp Ser Gln Arg Gln Leu Leu Asp Ala Ser Gln Ser Phe Ser Arg Ser
            645                 650                 655

Met Thr Pro Ser Gln Met Leu Glu Ile Pro Gln Thr Thr Pro Thr Ser
            660                 665                 670

Leu Pro Gln Pro Asn Thr Ile Pro Gln Gln Met Thr Lys Asn Asn Asn
            675                 680                 685

Gln Thr Asn Thr Arg Phe Ser His Leu Pro Gln Gln Leu Lys Pro Gln
            690                 695                 700

Gln Gln His Ser Gly Ile Met Leu Leu Ser Glu Met Ala Gly His Met
705                 710                 715                 720

Gly Leu Pro Pro Ser Ser Met Ala Asn Gln Leu Ser Thr Ala Gly Ser
            725                 730                 735

Ser Ile Leu Thr Ala Ala Ala Gly Pro Gly Gln Ser Gly Ile Thr Asp
            740                 745                 750

Asp Val Pro Ser Cys Ser Thr Ser Pro Ser Thr Asn Asn Cys Pro Asn
            755                 760                 765

Ile Val Gln Pro Met Ile Asn Gly Trp Ala His Arg Ser Thr Ala Met
            770                 775                 780

Gly Glu Asp Met Ala Gln Ser Ala Val Thr Leu Phe Ser Pro Ser Ala
785                 790                 795                 800
```

```
Leu Glu Thr Val Ser Ser Asn Gly Asn Leu Val Lys Asp Leu Leu Gln
                805                 810                 815

Lys Ser Glu Val Lys Pro Ser Leu Asn Ile Ser Lys Asn Gln Asn Pro
            820                 825                 830

Gly Leu Phe Ser Ser Gln Thr Tyr Leu Asn Gly Val Ala Ala Gln Ile
        835                 840                 845

Asp Tyr Leu Asp Thr Ser Ser Thr Thr Ser Val Cys Leu Ser Gln
    850                 855                 860

Asn Asp Val His Leu Gln Gln Asn Asn Ser Leu Ser Tyr Asn Pro
865                 870                 875                 880

Gln Ser Val Leu Leu Arg Asp Ala Ser His Asp Gly Glu Leu Gln Gly
            885                 890                 895

Asp Pro Arg Asn Asn Ile Leu Tyr Gly Thr Asn Ile Asp Ser Gln Leu
        900                 905                 910

Val Met Pro Ile Asn Ser Asp His Leu Leu Thr Lys Gly Met Met Gly
    915                 920                 925

Leu Gly Lys Asp Phe Ser Asn Asn Phe Ser Ser Gly Gly Met Leu Thr
930                 935                 940

Asn Cys Glu Asn Ser Lys Asp Pro Gln Gln Glu Leu Ser Ser Ala Ile
945                 950                 955                 960

Val Ser Lys Ser Phe Gly Val Pro Asp Met Pro Phe Asn Ser Ile Asp
            965                 970                 975

Ser Thr Ile Asn Asp Ser Ser Leu Leu Asn Arg Gly Ser Trp Ala Pro
        980                 985                 990

Pro Gln Gln Gln Phe Gln Arg Met Arg Thr Tyr Thr Lys Val Tyr Lys
    995                 1000                1005

Arg Gly Ala Val Gly Arg Ser Ile Asp Ile Thr Arg Tyr Ser Gly
    1010                1015                1020

Tyr Asp Glu Leu Lys Gln Asp Leu Ala Arg Arg Phe Gly Ile Glu
    1025                1030                1035

Gly Gln Leu Glu Asp Gln Gln Arg Ile Gly Trp Lys Leu Val Tyr
    1040                1045                1050

Thr Asp His Glu Asn Asp Val Leu Leu Val Gly Asp Asp Pro Trp
    1055                1060                1065

Glu Glu Phe Val Asn Cys Val Arg Cys Ile Lys Ile Leu Ser Pro
    1070                1075                1080

Gln Glu Val Gln Gln Met Ser Leu Asp Gly Asp Phe Gly Asn Ser
    1085                1090                1095

Val Leu Pro Asn Gln Ala Gly Ser Ser Ser Asp Asn Val Asn Ala
    1100                1105                1110

<210> SEQ ID NO 132
<211> LENGTH: 501
<212> TYPE: PRT
<213> ORGANISM: Populus trichocarpa

<400> SEQUENCE: 132

Met Val Gly Gly Glu Asn Leu Ser Arg Ile Thr Val Ser Lys Ala Ser
1               5                   10                  15

Gly Glu Asp Thr Ile Ser Asn Val Ser Ser Phe Gly Asn Gln Gly Met
            20                  25                  30

Pro His Ser Ile Thr Val Pro Pro Lys Lys Lys Arg Asn Leu Pro
        35                  40                  45

Gly Met Pro Asp Pro Asp Ala Glu Val Val Ala Leu Ser Pro Lys Thr
    50                  55                  60
```

-continued

```
Leu Val Ala Thr Ile Arg Phe Val Cys Glu Ile Cys Asn Lys Gly Phe
 65                  70                  75                  80

Gln Arg Asp Gln Asn Leu Gln Leu His Arg Gly His Asn Leu Pro
                 85                  90                  95

Trp Lys Leu Lys Gln Arg Thr Asn Lys Glu Pro Arg Lys Arg Val Tyr
                100                 105                 110

Val Cys Pro Glu Ser Ser Cys Val His His Asn Pro Ala Arg Ala Leu
                115                 120                 125

Gly Asp Leu Thr Gly Ile Lys Lys His Phe Tyr Arg Lys His Gly Glu
130                 135                 140

Lys Lys Trp Lys Cys Glu Arg Cys Ser Lys Lys Tyr Ala Val Gln Ser
145                 150                 155                 160

Asp Trp Lys Ala His Leu Lys Thr Cys Gly Thr Lys Glu Tyr Lys Cys
                165                 170                 175

Asp Cys Gly Thr Leu Phe Ser Arg Arg Asp Ser Phe Val Thr His Arg
                180                 185                 190

Ala Phe Cys Asp Ala Leu Ala Glu Glu Ser Ala Arg Ala Gln Thr Leu
                195                 200                 205

Ala Ile Met Gly Arg Glu Gly Asn Gly Cys Asp Ile Lys Arg Val Gly
210                 215                 220

Ala Ser Pro Pro Pro Pro Leu Thr Pro Ser Thr Ser Val Val Ser
225                 230                 235                 240

Pro Gly Leu Ser Val Gln Ser Ser Glu Leu Ala Glu Asn Pro Ile Gly
                245                 250                 255

Leu Ser Pro Pro Ile Ala Cys Ala Ser Ala Thr Ser Thr Ser Ser
                260                 265                 270

Thr Ser Ser Thr Ser Asn Val Phe Ala Thr Thr Phe Ala Ser Ser Thr
    275                 280                 285

Ala Thr Pro Ala Ala Ile Pro Gln Gln Ala Ser Val Pro Ser Ser Phe
    290                 295                 300

Pro Asn Leu Phe Cys Gly Leu Ala Arg Ser Asp Tyr Pro Thr Thr Met
305                 310                 315                 320

Pro Thr Pro Arg Ala Ile Glu Pro Pro Ser Leu Ser Leu Ser Pro Ser
                325                 330                 335

Phe Tyr Leu Ser Asn Asn Thr Ser Ser Leu Phe Ser Thr Glu Gln Glu
                340                 345                 350

His Tyr His Tyr Thr Pro Ser Pro Gln Pro Ala Met Ser Ala Thr Ala
                355                 360                 365

Leu Leu Gln Lys Ala Ala Gln Met Gly Ala Thr Thr Ser Asn Pro Ser
    370                 375                 380

Phe Leu Arg Gly Leu Gly Leu Pro Arg Ser Thr Asn Gln Asp Ser Asn
385                 390                 395                 400

Cys Asn Lys Trp Asp Val Lys Pro Glu Asn Asn Thr Thr Val Ala Ala
                405                 410                 415

Gly Leu Gly Leu Gly Leu Pro Ser Ser Asp Val Met Met Gly Ser Ser
                420                 425                 430

Ser Leu Phe Gly Asn Lys Pro Ala Thr Leu Asp Leu Leu Gly Leu Gly
                435                 440                 445

Met Asp Ala Ala Ser Ser Ala Leu Leu Asn Ser Tyr Ser Gly Gly Phe
    450                 455                 460

Asn Val Gly Ala Ala Thr Ala Ala Ala Tyr Gly Gly Gly Gly Arg
465                 470                 475                 480
```

```
Gly Thr Ser Glu Glu Thr Trp Asp Gly Val Pro Glu Arg Lys Pro Tyr
                485                 490                 495
Gly Ser Thr Gly Ala
            500

<210> SEQ ID NO 133
<211> LENGTH: 321
<212> TYPE: PRT
<213> ORGANISM: Populus trichocarpa

<400> SEQUENCE: 133

Met Asp Pro Lys Gly Ser Asn Ser Lys Asn Pro His Glu Leu Pro Thr
1               5                   10                  15

Phe Phe Thr Leu Thr His Thr His Thr Ser Pro Ser Pro Ser Pro His
                20                  25                  30

Thr Pro Pro Gln Pro His His Gln Gln Pro Gln His Leu His Asn Gln
            35                  40                  45

Asn Gln Leu Gln Pro Asn Met Gly Glu Asn Lys Ala Ala Glu Ile Lys
    50                  55                  60

Asp Phe Gln Ile Val Val Ala Asp Lys Glu Glu Gln Lys Lys Gln Leu
65                  70                  75                  80

Ala Pro Lys Arg Ser Ser Asn Lys Asp Arg His Thr Lys Val Glu Gly
                85                  90                  95

Arg Gly Arg Arg Ile Arg Met Pro Ala Leu Cys Ala Ala Arg Ile Phe
            100                 105                 110

Gln Leu Thr Arg Glu Leu Gly His Lys Ser Asp Gly Glu Thr Ile Gln
        115                 120                 125

Trp Leu Leu Gln Gln Ala Glu Pro Ser Ile Ile Ala Ala Thr Gly Thr
    130                 135                 140

Gly Thr Ile Pro Ala Ser Ala Leu Ala Ala Ala Gly Gly Ala Ile Ser
145                 150                 155                 160

Gln Gln Gly Ala Ser Leu Ser Ala Gly Leu His Gln Lys Ile Asp Asp
                165                 170                 175

Ile Gly Glu Ser Ser Ser Arg Arg Thr Ser Trp Ala Met Leu Gly Gly
            180                 185                 190

Asn Leu Gly Arg Pro His Gln Val Thr Ser Ala Gly Leu Trp Pro Pro
        195                 200                 205

Val Gly Gly Tyr Gly Phe Gln Ser Ser Ser Asn Thr Thr Gly Pro Ser
    210                 215                 220

Thr Thr Asn Ile Val Ser Glu Gly Gly Gly Ser Ser Tyr Leu Gln
225                 230                 235                 240

Lys Asn Gly Phe Ser Gly Phe Asp Met Pro Gly Asn Asn Ile Gly Pro
                245                 250                 255

Met Ser Leu Thr Ser Ile Leu Gly Val Gly Ser Gln Gln Leu Pro Gly
            260                 265                 270

Leu Glu Leu Gly Leu Ser Gln Asp Gly His Ile Gly Val Leu Ser Pro
        275                 280                 285

Gln Ala Leu Ser Gln Ile Tyr Gln Gln Met Gly Gln Ala Arg Val Gln
    290                 295                 300

Gln His Gln Gln Gln Asn Pro Ser Lys Asp Asp Ser Gly Ser Gly
305                 310                 315                 320

Gln

<210> SEQ ID NO 134
<211> LENGTH: 229
```

<212> TYPE: PRT
<213> ORGANISM: Populus trichocarpa

<400> SEQUENCE: 134

```
Met Glu Pro Ser Ser Ser Ala Val Ala Ala Ile Val Ser Thr
1               5                   10                  15

Asn Ala Asn Ile Asn Thr Asp Arg Thr Arg Lys Lys Lys Lys
            20                  25                  30

Ser Val Leu Gln Gln His Gln Ser Lys Gln Asn Gln Asn Ser Gln Ser
            35                  40                      45

His Ala Lys Trp Lys Thr Glu Ala Gln Gln Val Tyr Ser Lys
        50                  55                  60

Leu Ile Gln Ala Leu Ser Gln Val Asn Leu Asn Pro Ser Thr Ser Ser
65                  70                  75                  80

Ala Pro Arg Gln Gly Arg Ala Val Arg Glu Val Ala Asp Arg Ala Leu
                85                  90                  95

Ala Phe Ala Ala Lys Gly Lys Thr Arg Trp Ser Arg Ala Ile Leu Thr
            100                 105                 110

Ser Arg Ile Lys Leu Lys Phe Arg Lys Gln Gln His Lys Arg Gln Arg
            115                 120                 125

Leu Ala Ser Ser Ser Ser Ser Pro Gly Ser Thr Thr Gly Ser Ser
        130                 135                 140

Ser Arg Ser Ser Arg Lys His Lys Val Ser Val Leu Arg Leu Lys Ala
145                 150                 155                 160

Lys Gly Leu Pro Ala Val Gln Arg Lys Val Arg Val Leu Gly Arg Leu
                165                 170                 175

Val Pro Gly Cys Leu Lys Gln Pro Leu Pro Val Ile Leu Glu Glu Ala
            180                 185                 190

Thr Asp Tyr Ile Ala Ala Leu Glu Met Gln Val Lys Thr Met Thr Ala
        195                 200                 205

Ile Ala Glu Leu Leu Ser Arg Ser Thr Ser Glu Ala Ser Ser Thr Ser
    210                 215                 220

Glu Pro Met Thr Ser
225
```

<210> SEQ ID NO 135
<211> LENGTH: 19
<212> TYPE: DNA
<213> ORGANISM: Artificial
<220> FEATURE:
<223> OTHER INFORMATION: forward cloning primer

<400> SEQUENCE: 135
atgcaaccag gcttggatg                                                19

<210> SEQ ID NO 136
<211> LENGTH: 19
<212> TYPE: DNA
<213> ORGANISM: Artificial
<220> FEATURE:
<223> OTHER INFORMATION: Forward cloning primer

<400> SEQUENCE: 136
atggcgagag gaaaggttc                                                19

<210> SEQ ID NO 137
<211> LENGTH: 25
<212> TYPE: DNA
<213> ORGANISM: Artificial

```
<220> FEATURE:
<223> OTHER INFORMATION: Forward cloning primer

<400> SEQUENCE: 137
atggcatata tgtgtgcaga tagcg                                        25

<210> SEQ ID NO 138
<211> LENGTH: 21
<212> TYPE: DNA
<213> ORGANISM: Artificial
<220> FEATURE:
<223> OTHER INFORMATION: Forward cloning primer

<400> SEQUENCE: 138
atggggagag gtagggttga g                                            21

<210> SEQ ID NO 139
<211> LENGTH: 25
<212> TYPE: DNA
<213> ORGANISM: Artificial
<220> FEATURE:
<223> OTHER INFORMATION: Forward cloning primer

<400> SEQUENCE: 139
atgtctttag ttggacctgc agaac                                        25

<210> SEQ ID NO 140
<211> LENGTH: 28
<212> TYPE: DNA
<213> ORGANISM: Artificial
<220> FEATURE:
<223> OTHER INFORMATION: Forward cloning primer

<400> SEQUENCE: 140
atgaagagag atcatcaaga aaccattg                                     28

<210> SEQ ID NO 141
<211> LENGTH: 27
<212> TYPE: DNA
<213> ORGANISM: Artificial
<220> FEATURE:
<223> OTHER INFORMATION: Forward cloning primer

<400> SEQUENCE: 141
atggaaaaca attgtgtgta tagtgag                                      27

<210> SEQ ID NO 142
<211> LENGTH: 22
<212> TYPE: DNA
<213> ORGANISM: Artificial
<220> FEATURE:
<223> OTHER INFORMATION: Forward cloning primer

<400> SEQUENCE: 142
atgagttttg ggggtttcct tg                                           22

<210> SEQ ID NO 143
<211> LENGTH: 22
<212> TYPE: DNA
<213> ORGANISM: Artificial
<220> FEATURE:
<223> OTHER INFORMATION: Forward cloning primer

<400> SEQUENCE: 143
atggcaccca agaagcttaa tg                                           22
```

<210> SEQ ID NO 144
<211> LENGTH: 26
<212> TYPE: DNA
<213> ORGANISM: Artificial
<220> FEATURE:
<223> OTHER INFORMATION: Forward cloning primer

<400> SEQUENCE: 144
caccatgtgc actagaggac attgga                                              26

<210> SEQ ID NO 145
<211> LENGTH: 22
<212> TYPE: DNA
<213> ORGANISM: Artificial
<220> FEATURE:
<223> OTHER INFORMATION: Forward cloning primer

<400> SEQUENCE: 145
atgggcagat ctccttgttg tg                                                  22

<210> SEQ ID NO 146
<211> LENGTH: 25
<212> TYPE: DNA
<213> ORGANISM: Artificial
<220> FEATURE:
<223> OTHER INFORMATION: Forward cloning primer

<400> SEQUENCE: 146
atggaggttt atccataccc atctc                                               25

<210> SEQ ID NO 147
<211> LENGTH: 27
<212> TYPE: DNA
<213> ORGANISM: Artificial
<220> FEATURE:
<223> OTHER INFORMATION: Forward cloning primer

<400> SEQUENCE: 147
atgagaatat ctagagcaag atggttc                                             27

<210> SEQ ID NO 148
<211> LENGTH: 23
<212> TYPE: DNA
<213> ORGANISM: Artificial
<220> FEATURE:
<223> OTHER INFORMATION: Forward cloning primer

<400> SEQUENCE: 148
atggatccca agggctctaa ctc                                                 23

<210> SEQ ID NO 149
<211> LENGTH: 19
<212> TYPE: DNA
<213> ORGANISM: Artificial
<220> FEATURE:
<223> OTHER INFORMATION: Forward cloning primer

<400> SEQUENCE: 149
atgggcgagg aagcagacc                                                      19

<210> SEQ ID NO 150
<211> LENGTH: 19
<212> TYPE: DNA
<213> ORGANISM: Artificial
<220> FEATURE:
<223> OTHER INFORMATION: Forward cloning primer

<400> SEQUENCE: 150
atgaagtcac cggccaacg                                                    19

<210> SEQ ID NO 151
<211> LENGTH: 23
<212> TYPE: DNA
<213> ORGANISM: Artificial
<220> FEATURE:
<223> OTHER INFORMATION: Forward cloning primer

<400> SEQUENCE: 151
atggtgggtg gtgagaattt atc                                               23

<210> SEQ ID NO 152
<211> LENGTH: 21
<212> TYPE: DNA
<213> ORGANISM: Artificial
<220> FEATURE:
<223> OTHER INFORMATION: Forward cloning primer

<400> SEQUENCE: 152
atggatccca agggctctaa c                                                 21

<210> SEQ ID NO 153
<211> LENGTH: 20
<212> TYPE: DNA
<213> ORGANISM: Artificial
<220> FEATURE:
<223> OTHER INFORMATION: Forward cloning primer

<400> SEQUENCE: 153
atggaaccat cgtcgtcagc                                                   20

<210> SEQ ID NO 154
<211> LENGTH: 22
<212> TYPE: DNA
<213> ORGANISM: Artificial
<220> FEATURE:
<223> OTHER INFORMATION: Reverse cloning primer

<400> SEQUENCE: 154
taaatgcagt aaatgatgga gc                                                22

<210> SEQ ID NO 155
<211> LENGTH: 20
<212> TYPE: DNA
<213> ORGANISM: Artificial
<220> FEATURE:
<223> OTHER INFORMATION: Reverse cloning primer

<400> SEQUENCE: 155
gcacgagaaa aactacaacc                                                   20

<210> SEQ ID NO 156
<211> LENGTH: 24
<212> TYPE: DNA
<213> ORGANISM: Artificial
<220> FEATURE:
<223> OTHER INFORMATION: Reverse cloning primer

<400> SEQUENCE: 156
ttatcgccat gacaaaactg tgag                                              24

<210> SEQ ID NO 157

```
<211> LENGTH: 23
<212> TYPE: DNA
<213> ORGANISM: Artificial
<220> FEATURE:
<223> OTHER INFORMATION: Reverse cloning primer

<400> SEQUENCE: 157
cattacttgc actgttccta cgg                                              23

<210> SEQ ID NO 158
<211> LENGTH: 29
<212> TYPE: DNA
<213> ORGANISM: Artificial
<220> FEATURE:
<223> OTHER INFORMATION: Reverse cloning primer

<400> SEQUENCE: 158
gtaatcaaat agtagctgtt acttccatg                                        29

<210> SEQ ID NO 159
<211> LENGTH: 23
<212> TYPE: DNA
<213> ORGANISM: Artificial
<220> FEATURE:
<223> OTHER INFORMATION: Reverse cloning primer

<400> SEQUENCE: 159
gtcattgttg tgaatcacca gcg                                              23

<210> SEQ ID NO 160
<211> LENGTH: 28
<212> TYPE: DNA
<213> ORGANISM: Artificial
<220> FEATURE:
<223> OTHER INFORMATION: Reverse cloning primer

<400> SEQUENCE: 160
aagttcagta attccaaagg taatcaag                                         28

<210> SEQ ID NO 161
<211> LENGTH: 24
<212> TYPE: DNA
<213> ORGANISM: Artificial
<220> FEATURE:
<223> OTHER INFORMATION: Reverse cloning primer

<400> SEQUENCE: 161
gcataatcag ctttcacatt ggag                                             24

<210> SEQ ID NO 162
<211> LENGTH: 19
<212> TYPE: DNA
<213> ORGANISM: Artificial
<220> FEATURE:
<223> OTHER INFORMATION: Reverse cloning primer

<400> SEQUENCE: 162
ccatcaagca tcggctggc                                                   19

<210> SEQ ID NO 163
<211> LENGTH: 29
<212> TYPE: DNA
<213> ORGANISM: Artificial
<220> FEATURE:
<223> OTHER INFORMATION: Reverse cloning primer

<400> SEQUENCE: 163
```

```
gttgtagtat ataatacaag actactgag                                    29
```

<210> SEQ ID NO 164
<211> LENGTH: 21
<212> TYPE: DNA
<213> ORGANISM: Artificial
<220> FEATURE:
<223> OTHER INFORMATION: Reverse cloning primer

<400> SEQUENCE: 164

```
cctggtggtc atcaagcatc c                                            21
```

<210> SEQ ID NO 165
<211> LENGTH: 24
<212> TYPE: DNA
<213> ORGANISM: Artificial
<220> FEATURE:
<223> OTHER INFORMATION: Reverse cloning primer

<400> SEQUENCE: 165

```
tcacagatcc cttctacaca gagg                                         24
```

<210> SEQ ID NO 166
<211> LENGTH: 29
<212> TYPE: DNA
<213> ORGANISM: Artificial
<220> FEATURE:
<223> OTHER INFORMATION: Reverse cloning primer

<400> SEQUENCE: 166

```
ctattttcc agttcttgtt tacagagag                                     29
```

<210> SEQ ID NO 167
<211> LENGTH: 24
<212> TYPE: DNA
<213> ORGANISM: Artificial
<220> FEATURE:
<223> OTHER INFORMATION: Reverse cloning primer

<400> SEQUENCE: 167

```
ttactgccct gatccttgtg aatc                                         24
```

<210> SEQ ID NO 168
<211> LENGTH: 23
<212> TYPE: DNA
<213> ORGANISM: Artificial
<220> FEATURE:
<223> OTHER INFORMATION: Reverse cloning primer

<400> SEQUENCE: 168

```
tcagagctgc aatgctaaat ctg                                          23
```

<210> SEQ ID NO 169
<211> LENGTH: 29
<212> TYPE: DNA
<213> ORGANISM: Artificial
<220> FEATURE:
<223> OTHER INFORMATION: Reerse cloning primer

<400> SEQUENCE: 169

```
ttatgcattg acattatcag aactactgc                                    29
```

<210> SEQ ID NO 170
<211> LENGTH: 25
<212> TYPE: DNA

<210> SEQ ID NO 170
<211> LENGTH: 25
<212> TYPE: DNA
<213> ORGANISM: Artificial
<220> FEATURE:
<223> OTHER INFORMATION: Reverse cloning primer

<400> SEQUENCE: 170
tcaagctcct gtagatccat aaggc                                           25

<210> SEQ ID NO 171
<211> LENGTH: 24
<212> TYPE: DNA
<213> ORGANISM: Artificial
<220> FEATURE:
<223> OTHER INFORMATION: Reverse cloning primer

<400> SEQUENCE: 171
ttactgccct gatccttgtg aatc                                            24

<210> SEQ ID NO 172
<211> LENGTH: 23
<212> TYPE: DNA
<213> ORGANISM: Artificial
<220> FEATURE:
<223> OTHER INFORMATION: Reverse cloning primer

<400> SEQUENCE: 172
ttaggaggtc atcggctcag aag                                             23

<210> SEQ ID NO 173
<211> LENGTH: 561
<212> TYPE: DNA
<213> ORGANISM: Populus tremula x tremuloid

<400> SEQUENCE: 173
atgcaaccag gcttggatga gatcacaatg acggggtgga agaatctgaa gcaacggctg      60
tcattcaagg gcctgggtag ttgctgcggg agcacaagct ggatttccag aagtaccacc     120
caaaccatgc cctttatcga tatagaggaa gaagaagagg aagagaccac catgcaaaac     180
caagctcaaa gaggaggagg aggaggagca gcagcagcgc caggtgctgg gatgaatctg     240
gcaatggcat tagctgctga gcgcgattta ggggattcaa atgtcaagac attgatgagt     300
ttgatcgaag aaacggacgg tgttgattgg aggaagaaga ataacagtaa taacaaaagc     360
aggagggaca aggaacagga acagaagcag gaagaagaga aggattgggt atgctgcgtg     420
tgcatggaga gaaataaagg agcagctttt attccatgtg gacacacctt ttgtagggtt     480
tgttcaagag aaatgtgggt taatcgaggg tgctgtcctg tctgcaaccg ttccattctc     540
gacatccttg atatcttcta g                                              561

<210> SEQ ID NO 174
<211> LENGTH: 660
<212> TYPE: DNA
<213> ORGANISM: Populus tremula x tremuloides

<400> SEQUENCE: 174
atggcgagag gaaaggttca gctgaaaagg atagagaatg caactagcag gcaagtgacc      60
ttctccaaga gaaaaaatgg gttattgaag aaagcttatg agctatcaat tctgtgcgat     120
gctgaagttg cagtgatcat attttcacag aaaggaacac tctttaagtt tgcaagcact     180
gatcagatac aaaagacgat tgaccggtac cgtaaaaatg caaagcaatt gcacactgac     240
aggattgacg tggaacaata ttctaaggag caattaagac aagaatcaga aaacatggcc     300
aagaagattg agataatcga gattttgcaa cgaaagcttt tagggcaaga tttagattca     360

```
tgctctcccg aagagctcca tgacattggc aatcagcttg agatcagttt aagcaatatc    420
agggctagaa agactcagtt attcaaggag cagatagaac agctgaaagc aaaggaaaga    480
ttgttgttaa tggagaatgc aaggttgact aaacagcgcg atgcacagcc attgcagcaa    540
tcaactcaat cgaaccaagt ggtgtcatac ttgagctcat gtagcaagag ttcagatatc    600
gtggagactg atctgtacat tggacagcca cagatgcgct ggttgtagtt tttctcgtgc    660
```

<210> SEQ ID NO 175
<211> LENGTH: 916
<212> TYPE: DNA
<213> ORGANISM: Populus tremula x tremuloides

<400> SEQUENCE: 175

```
atggggagag gtagggttga gttgaagaga attgagaaca agatcaacag gcaagtaaca     60
tttgcaaaga gaaggaatgg acttttgaag aaagcctatg agctttccgt tctttgtgat    120
gcagaggttg ctctcatcat cttctccaat agaggaaagc tgtacgagtt ttgcagtagt    180
tcaagcatgc tcaaaactct tgagaggtac cagaagtgca attatggagc accagagcca    240
aatgtgtctg caagggaggc cctggaactg agtagtcagc aggaatatct gaagcttaaa    300
gcacgttatg aagccctgca agaacccaa aggaatcttt gggagaaga acttggccct    360 ctaagcagca aagagctaga atcacttgaa aggcagcttg atatgtcatt gaagcagatc    420
agatcaacaa ggacccaata catgctggat cagctcaatg acctacagca taaggagcac    480
atgctgactg cagctaataa gtccctgaaa gaaaggttga tggaaggcta ccaattaaat    540
tcactccagt tgaatccaag tgcagaagat gtggagtacg ctagacaaca agcccaaccc    600
cagggtgatg ggttttttca tgctttggag tgtgaaccta cactacaaat tgggtatcag    660
ccagaaaata taacaatggt cactgctggc ccaagtatga ctacttacat gccaggttgg    720
ttagcatgat aagaagacta gctatggttc tcactctcag ccatgcatgg tattcctttc    780
ctcaacatga tggttcccat atttgatcag caaatttgtg ttttgtcttg tatgttattg    840
atgaaacagt cttcgtttag cacgtaggtg gtctatatca taattctact gcaccgtagg    900
aacagtgcaa gtaatg                                                    916
```

<210> SEQ ID NO 176
<211> LENGTH: 636
<212> TYPE: DNA
<213> ORGANISM: Populus tremula x tremuloides

<400> SEQUENCE: 176

```
atggcaccca agaagcttaa tggtaatgat gacaatggtt ccttgaagaa agcaagtggt     60
gatcatgata agaaggaaat ccattatagg ggagtgagga gaggccatg ggggaggtat    120 gctgctgaga taagggatcc cgggaagaaa agccgggttt ggttgggcac gtttgacacg    180
gcagtggagc tgcaagggc ctatgataag cggcgcgtg agtatcgtgg tgccaaggcg    240
aaaaccaact ttccattagc ggagaaggtg gttgattatg acgatgagaa gcagagctct    300
agccagagca gcaccgttga gtcgtcaagc tccccggtgg tttctgcggt ggcgcgtgat    360
gtaactcgcc aggttggtgg ggttttgggg atggggaggt ttcccttcgt gttccagcag    420
cagcagccga atgtaaacgc tgttggtcct gtctggtttc ttgatggtgt taagcctcag    480
tttgtggctc agcgtttccc tgtacggttt gaccggtgg gtctcgaggg cggggcccac    540
agtgactcgg attcatcatc tgtgattgat tttaagccaa ggagttcaat tcttgatttt    600
```

```
gatcttaacc tgcctccgcc agccgatgct tgatgg                              636
```

<210> SEQ ID NO 177
<211> LENGTH: 827
<212> TYPE: DNA
<213> ORGANISM: Populus tremula x tremuloides

<400> SEQUENCE: 177

```
atgtgcacta gaggacattg gaggcctgct gaggatgagg aacttaagga attggttgaa     60
aagtatggtc ctcataattg gaacgccatt gccgaaaagc ttcaaggaag atcagggaag    120
agttgtaggt tgagatggtt taatcagctg gatccaagaa tcaatagaag cccgtttaca   180
gaagaggaag aagaaagact acttgcttcc cacaggattc atgggaatag atgggcaatt   240
attgcaagat ttttccctgg tcgcaccgat aatgcagtga agaatcattg gcatgtcatc    300
atggcaagaa gatatagaga gaggtctaga cttcatgcaa aaagggctgc tcaaactttg   360
gtaaatgata caaattatc ctcaaaacaa gatcacatgc acattgattg cgagacgagg    420
aacttttctt catttgccaa gaaatattgt gaaaaatatg ccactatcc tatggttact    480
cacagctact taccggcctt tggcaaagag ttctacaatg cagatccaag tcattgtgaa    540
gatcaaagtc ggccgattga gttttatgat tttctccaag taaacactga ctccaacaaa    600
agtgaagtga tagacaatgc aagaagagat gacgaggagg tagatcagca ggaagccatg    660
gaaaatgatc agagcaaggg tgatgttcca ttcattgatt ttttctctgt taatggcaaa    720
tcctcatcat aacacatgca gcttggtggt gtgtcaaacg agggaccaac aaatgcatag    780
taagcataca actaattact cagtagtctt gtattatata ctacaac                 827
```

<210> SEQ ID NO 178
<211> LENGTH: 957
<212> TYPE: DNA
<213> ORGANISM: Populus tremula x tremuloides

<400> SEQUENCE: 178

```
atggatccca agggctctaa ctcaaaaaac ccacatgagt tagccacttt cttgacccac     60
acccacccctt ctcctcctca tcctcctcct cctccacaac cccatcttca acaaccacaa   120
caactccata gccaaaacca caacaaccc aacatgggag acaacaaacc agcagaaatc    180
aaagactttc agattgtagt agctgacaaa gaagagcaaa agaaacagtt agcaccaaag    240
agaagctcaa acaaagacag acacacaaaa gttgaaggta gaggtagaag gataaggatg   300
ccagctcttt gtgcagcgag aatctttcaa ttgacaagag aattgggtca caaatctgat   360
ggagagacaa tacagtggct tctacaacaa gctgaaccat ctataattgc agcaactggg   420
actggtacta tacctgcatc agcttttagca gctgctggcg gtgcaatttc acaacaagga   480
gcttctcttt ctgctggttt gcatcaaaag atcgatgatt taggtgggtc cagtagtagt   540
agggccagtt gggcaatgtt aggtggcaat ttagggagac cccatcatgt taccactgca   600
ggattatggc cccagttgg aggttatggg ttccagtcat catctagtac cactggtcca   660
tcaacaacaa atatagtaag tgaaggtggt ggtggttcga gttatttgca aaaaaatgga   720
ttttcagggt ttgacttgcc aggaaacaat attgggccta tgagttttac ttcaattttta   780
ggtgtgggta gccagcagtt accaggattg gagcttgggt tgtcacaaga tgggcatatt   840
ggggttttga gcccacaagc tttgagtcag atttatcagc aggtggggca ggctagggtg    900
cagcagcacc agcagcaaaa tccttctaaa gatgattcac aaggatcagg gcagtaa       957
```

```
<210> SEQ ID NO 179
<211> LENGTH: 681
<212> TYPE: DNA
<213> ORGANISM: Populus tremula x tremuloides

<400> SEQUENCE: 179
atggaaccat cgtcgtcagc agcagcagca atagtgagca ctaacgccaa catcaacacg      60
gatcgaacaa gaaggaaaaa gaagaagaaa tcagtgttgc agcaacacca atcaaaacag     120
aaccaaaact cacagagcca cgccaaatgg aaaacagaag cacaacaaca agtctactca     180
tccaaactca tccaagcctt aagccaagtc aatctcaacc cttcaacttc atcagccccg     240
cgtaaaggtc gagccgttag agaagtggct gatcgagctt tagctttcgc tgctaaaggt     300
aaaaccaggt ggagccgagc cattttaact agccgcatca aactcaaatt tcggaaacaa     360
cataagagac agagacttgc gtcgtcgtcg tcttcttctc caggatccac taccgggagt     420
ggcagccggt cgtcgaggaa gcataaagtg agtgttttga ggttgaaagc gaagggtttg     480
ccggctgttc aaaggaaagt tcgtgttctt gggcggttag ttcctggttg ccggaaacaa     540
ccattgcctg ttattttgga agaagctaca gattatattg ctgctttgga gatgcaagtt     600
aaaaccatga ctgctatagc tgagcttctt tctcgctcta cctccgaagc cagctctact     660
tctgagccga tgacctccta a                                               681

<210> SEQ ID NO 180
<211> LENGTH: 447
<212> TYPE: DNA
<213> ORGANISM: Populus tremula x tremuloides

<400> SEQUENCE: 180
atggcatata tgtgtgcaga tagcggaaat ctaatggcaa tagcccaaca agttattaag      60
caaaaacaac aacaagaaca acagcagcaa caaagccacc accaccacca taaccaacag     120
caacaatttc ttggcctaaa cccatttttct ttaaatcctt ggccgactaa tataatgtct     180
gctaacccaa acttgggtta cgggctctcg ggtccggctg cttttctctga cccttttcag     240 agtggacaag aaacaggtga cccacctgtg tttagtttct cgaacatgga gcagcaccac     300
tcaagcgggt ttcggcttcc ttattttact ggagctggtg gtgagtttga ctcggatgag     360
tggatggaca gtttaatgaa cggtggagat tcaacggata gttctaatct tccttctggt     420
tgtgacgcgt ggcaaaacag tactgat                                         447

<210> SEQ ID NO 181
<211> LENGTH: 473
<212> TYPE: DNA
<213> ORGANISM: Populus tremula x tremuloides

<400> SEQUENCE: 181
atgtctttag ttggacctgc agaactctct gccagagcat acggaaataa taagctgtac      60
tcactgaaag ggagcaatga caactctggt ttgtctgccc aaatattcgg gcctgataaa     120
cggcagaaca tgtatatgac cgattcttac tcttgtgaga gttatgagaa gttcttcctt     180
gattccccaa cagaagaaat aatacaacca tcaagttctg acatttcagg gaactcagct     240
catccacaag gggcatcttc ctaccagcca agaaagagtt caggttcaac catgttccct     300
caagatccct acaatgcttc tttcaatttg accacaccct gcgatggcta tccattcatt     360
tccgagtcag attacttgga cattgagagc ccagatccac taaactatga tgaatataag     420
atgaaattaa agcttcagga acttgagaga gcgcttctaa atgataatga tga            473
```

<210> SEQ ID NO 182
<211> LENGTH: 219
<212> TYPE: DNA
<213> ORGANISM: Populus tremula x tremuloides

<400> SEQUENCE: 182

| | | |
|---|---|---|
| atgaagagag atcatcaaga aaccattggt ggtggtattg gaaacagagg tgaatcttct | 60 |
| tcttcatcaa tggaaactgg gaaaggaaaa tcatgggttg aagatgatca agatgcgggt | 120 |
| ggcatggatg aattacttgc tgttttgggt tacaaaatca agtcttcaga tatggctgat | 180 |
| gtagctcaaa agcttgaaca actaaagatg gctttgggt | 219 |

<210> SEQ ID NO 183
<211> LENGTH: 320
<212> TYPE: DNA
<213> ORGANISM: Populus tremula x tremuloides

<400> SEQUENCE: 183

| | | |
|---|---|---|
| atggaaaaca attgtgtgta tagcgaggaa gatgagcaga tggaattgcc tccgggattt | 60 |
| agattccatc caactgatga agagctcata actcactacc tgtctcagaa ggttcttgac | 120 |
| aactacttct gtgctagagc tattggcgag gtcgatttaa acaagtgtga gccatgggat | 180 |
| ttgccttgga gggctaaaat gggtgaaaag gaatggtatt tcttctgtgt tatagaccgg | 240 |
| aagtatccca ccggtttaag gacgaacagg gctactgatg ctggttactg gaaagccaca | 300 |
| ggcaaagaca aggaaattta | 320 |

<210> SEQ ID NO 184
<211> LENGTH: 440
<212> TYPE: DNA
<213> ORGANISM: Populus tremula x tremuloides

<400> SEQUENCE: 184

| | | |
|---|---|---|
| atgagttttg ggggttttcct tgaaaacact agtcctggtg gtggtggcgc aagaattgtg | 60 |
| gctgatatac cttataacat taacaacaac atgcccactg gtgcaatagc tcatactcgc | 120 |
| cttgtctctc cttctctcac taaatccatg ttcaactctc ctggactctc tctagccctt | 180 |
| ccaaacataa atggtcaagg agatataact aaaatggccg agaactttga dcaagtgtg | 240 |
| ggtaggagaa gcaaagaaga ggagcatgag agcagatctg gtagtgataa catggatggt | 300 |
| gcgtctggtg acgatcaaga tgcagctgaa atcctccaa gaaaaagag ataccaccga | 360 |
| cacactccac aacaaatcca agaacttgaa gctttgttta aggaatgtcc tcatcctgac | 420 |
| gagaaacaaa gattggagct | 440 |

<210> SEQ ID NO 185
<211> LENGTH: 283
<212> TYPE: DNA
<213> ORGANISM: Populus tremula x tremuloides

<400> SEQUENCE: 185

| | | |
|---|---|---|
| atgggcagat ctccttgttg tgagaaagaa cacaccaaca aggagcgtg gactaaggaa | 60 |
| gaagatgaac gtctcattaa ttatatcaaa tctcatggtg aaggttgttg gaggtctctc | 120 |
| cctaaggcag ctggtttgct tcgatgtggc aaaagttgta gactgaggtg gataaactac | 180 |
| ctgaggcctg atctcaagag aggaaacttc agtgacgagg aagatgaact catcatcaac | 240 |
| ctacacagct tacttggaaa caagtggtct ctcattgctg cta | 283 |

<210> SEQ ID NO 186
<211> LENGTH: 379
<212> TYPE: DNA
<213> ORGANISM: Populus tremula x tremuloides

<400> SEQUENCE: 186

| | | |
|---|---|---|
| atggaggttt atccataccc atctcgtttt tccatgtctt cattgtgttc ttttgggaat | 60 |
| tttgttgata aggttaaaga agtttgtaac ttcgttgttt cagctattat tggcaacata | 120 |
| ttctctgcga tcttcacctt tttctttgca ttagtgggca ctttgttagg agccatgact | 180 |
| ggggcattga taggccaaga aactgaaagt gggtttgttc gggggctgc agttggagcc | 240 |
| atatcaggag ctgttttctc aattgaagta ttcgagtcat ctcttgttct ttggcaatca | 300 |
| gatgaatctg ggataggctg tgtcctttac ttgattgatg ttatcgcaag ccttcttagt | 360 |
| ggacgacttg ttcgtgagc | 379 |

<210> SEQ ID NO 187
<211> LENGTH: 266
<212> TYPE: DNA
<213> ORGANISM: Populus tremula x tremuloides

<400> SEQUENCE: 187

| | | |
|---|---|---|
| atgagaatat ctagagcaag atggttcacc ttcttgagaa gagtattcca ctaccagaat | 60 |
| ggctcaaggt ctaatcttgg gtctaatcct tcaactcca gcacttggat gatgctggag | 120 |
| tttgtagctt tggtcattca aataagtatt accatgttca ccctggctat ttccaaggca | 180 |
| gagaagccag tttggccagt gagaaatatgg attattggct ataatattgg ttgtgtcctt | 240 |
| agtctgctgc tgctctatgg gcgata | 266 |

<210> SEQ ID NO 188
<211> LENGTH: 255
<212> TYPE: DNA
<213> ORGANISM: Populus tremula x tremuloides

<400> SEQUENCE: 188

| | | |
|---|---|---|
| atgggcgagg aagcagaccc aacaatgaag aagaagaaga aaaagggacg tccttctctt | 60 |
| ctagagcttc aaaaacgctc catcaaacaa caacagcttc agcaaacaac ccctatttct | 120 |
| cttaaaaacc ctaatcctct caactccaat tctgtcctcc ctaaccgtcg atccgctcgc | 180 |
| cggagctcta attcctatgc accggagtgg attgacggag acgacgaaga agatgacgac | 240 |
| gaagacgatg agcgt | 255 |

<210> SEQ ID NO 189
<211> LENGTH: 273
<212> TYPE: DNA
<213> ORGANISM: Populus tremula x tremuloides

<400> SEQUENCE: 189

| | | |
|---|---|---|
| atgaagtcac cggcaaccgg tgccggagga accgcggcaa cctccacagc taccaacggt | 60 |
| gaaggggcag agaagaagag cataaaccct gagttatggc aagcatgtgc aggaccgcta | 120 |
| gtgaacttgc cggcggccgg aactcatgtt gtctacttcc ctcaagggca tagtgaacag | 180 |
| gtagcagcat ctttgaagaa ggacgtgaat gcgcaaattc caaactaccc aaatcttcca | 240 |
| tcgaagcttc tatgtctcct tcacaatgtc acc | 273 |

<210> SEQ ID NO 190
<211> LENGTH: 456
<212> TYPE: DNA

<213> ORGANISM: Populus tremula x tremuloides

<400> SEQUENCE: 190

| | |
|---|---|
| atggtgggtg gtgagaattt atccagaatg acagtatcta aagcttctgg agaagacaca | 60 |
| attagcaatg tttcttcttt gggtaaccaa ggcatgccac acactattac agtgccacca | 120 |
| ccaaagaaga agcgaaatct ccctggaatg ccagatccag atgcagaagt cgttgcgtta | 180 |
| tcgccaaaga ctttagtagc cacaatcaga ttcgtgtgtg agatctgtaa caagggcttt | 240 |
| caaagagacc agaacctcca acttcacaga cgaggccata acttaccatg gaagctaaag | 300 |
| caacgaacca caaagagcc aaggaagcgt gtctatgttt gtccagagtc atcttgtgta | 360 |
| catcacaacc cagctagagc tcttggtgat cttactggca ttaaaaagca cttctacaga | 420 |
| aagcatggtg agaaaaagtg gaagtgtgag agatgt | 456 |

<210> SEQ ID NO 191
<211> LENGTH: 407
<212> TYPE: DNA
<213> ORGANISM: Populus tremula x tremuloides

<400> SEQUENCE: 191

| | |
|---|---|
| atggatccca agggctctaa ctcaaaaaac ccacatgagt tacccacttt cttgacccac | 60 |
| acccacccctt ctcctcctca tcctcctcct cctccacaac cccatcttca acaaccacaa | 120 |
| caactccata gccaaaacca acaacaaccc aacatgggag acaacaaacc agcagaaatc | 180 |
| aaagactttc agattgtagt agctgacaaa gaagagcaaa agaaacagtt agcaccaaag | 240 |
| agaagctcaa acaagacag acacacaaaa gttgaaggta gaggtagaag gataaggatg | 300 |
| ccagctcttt gtgcagcgag aatctttcaa ttgacaagag aattgggtca caaatctgat | 360 |
| ggagagacaa tacagtggct tctacaacaa gctgaaccat ctataat | 407 |

<210> SEQ ID NO 192
<211> LENGTH: 482
<212> TYPE: DNA
<213> ORGANISM: Populus tremula x tremuloides

<400> SEQUENCE: 192

| | |
|---|---|
| ttatcgccat gacaaaactg tgagtagtgg cacctcattc caagctaaag ttaagaaccc | 60 |
| aggctgagaa tcatcaagag aatacaaatc actgtaattg caataccata agagtatctt | 120 |
| agcctgactc attgcataat ggctaagcga aaccgattca aaacctgaac tttccattaa | 180 |
| aactccccat tgatctttat cctccatcct ttcccttctc attccaggct cctctggccc | 240 |
| tacaacacta gaaattctct gacccaataa caacctctca acttgaagcc tctctggtga | 300 |
| gtctctactc aagttaggct caagaggctc aaaaacagca gtgtagtatc tcaaagcatt | 360 |
| cttaaaccga gtcaagtacc caacccggtt caaactagct tcatattcac caagagtgac | 420 |
| aattatcggg ttcaacgatt tagccatctt taaagcagtt tctacagcaa ctggagactc | 480 |
| at | 482 |

<210> SEQ ID NO 193
<211> LENGTH: 401
<212> TYPE: DNA
<213> ORGANISM: Populus tremula x tremuloides

<400> SEQUENCE: 193

| | |
|---|---|
| gtaatcaaat agtagctgtt acttccaagc tgaagcaaca atcaaacttt tgtcctccca | 60 |
| cccaaaatga agggcaccta cttcctgctt caacatgtat ctatcgcagt actccttaat | 120 |

```
gagtttccgg atcatatcca ccacattagg agtgattgaa catgaagtga agccagccat    180
catcatcctt gctctccatt tccctgcaac ttcataccgc tcaatccttt cctctccctc    240
acatgcgact atgttcacta tgtcccttgc caggcactgt ttctcaacat tcagtctatc    300
ctggctctcc cgtgggagag ttgcatcaag agagtcaaac acagcagagt aatagttgta    360
agcttcggta aatctcggga aaaaggggc agtattagta t                         401
```

<210> SEQ ID NO 194
<211> LENGTH: 373
<212> TYPE: DNA
<213> ORGANISM: Populus tremula x tremuloides

<400> SEQUENCE: 194

```
gtcattgttg tgaatcacca gcggcgagct gccacgccga ggtggcaatt agtggccttg     60
tatgccaccc aagcatgaga cagccattat tctcctccac cctatacccg tcaccaccgg    120
caaagagggc caacaacata ctagcttgtt taaaggcatt cgacccaaga tgaacgggt     180 caaacccagc cgaatcaaac cgagttctcc actgagccaa cgtctcgtgt cgctcaactc    240
ggtcagcccc ttcgcatgcc accacattac aaatatgcct ccctaagtac agctcggaca    300
tagccaggtc ctgactcggt ggagtcaaac cggaccctte gagagagtca aacaaagtcg    360
agtaataatg taa                                                       373
```

<210> SEQ ID NO 195
<211> LENGTH: 438
<212> TYPE: DNA
<213> ORGANISM: Populus tremula x tremuloides

<400> SEQUENCE: 195

```
aagttcagta attccaaagg taatcaagat caactggtcc ggcagagctt gatggatcct     60
caaaggacct atgaaccaat tcatggttgg ttaccactga agacatatca gtgctgaggc    120
cagtgtcctc tgaaagctcc cgttttgagt ataggttcat gccgggtcca tggttttcaa    180
gcaatatcct caacatggag tgttctggca tcataacaga atctgggtat tgaaaacttg    240
ctatgtttgg taaaatttga gaggaatata agagtttgg aggtgagggt tttgaaaaca    300
gaactgagga aggggacatg tttgaagaag acaaaggagc tccaagagaa atgttaaagc    360
aatcagcaat gatttcatgg ggtttctggt cctccgttgg tttggagaag caggtcacgt    420
gagacttatc acctatgt                                                  438
```

<210> SEQ ID NO 196
<211> LENGTH: 413
<212> TYPE: DNA
<213> ORGANISM: Populus tremula x tremuloides

<400> SEQUENCE: 196

```
gcataatcag ctttcacatt ggagagcagc cttgatcttt tggacagtgc atgaaataag     60
gttgttgact gtctccacag attctactgt gagcttcgcc gtagggagac tattcaccag    120
tatttggaag gccaccgtca aaagggaccc acttaccctc tcttggccac cgacattatt    180
agcagtctgg acgccattgg tcgttggggg gccacgtgaa ccaggcccat ccggtacgat    240
agcgaaccct gacggaagaa gcgccacgta agccgaatca ccgccgttca tcactacgtg    300
catgccggga gtgtcaacgg gagcgtacac tacaagagag cctgctgcat ctatgcatgt    360
ctcttgcagt attagcatgc tactctggtt agcattcatg gcgctagcac gta            413
```

<210> SEQ ID NO 197
<211> LENGTH: 384
<212> TYPE: DNA
<213> ORGANISM: Populus tremula x tremuloides

<400> SEQUENCE: 197

| | |
|---|---|
| cctggtggtc atcaagcatc caaaggtctg taaaatctat aaagactatc agctgttaca | 60 |
| aattttttcca cggcattaca gcaactacat gcttgactgt tcttgaaccc tcgattgtaa | 120 |
| gaacacaaac atgctgttct atgaacaaca gcaggggcac tggaagtagg agtagctgag | 180 |
| gtcccaaaca attgatatgt gactacttgt tcttgatgct gttggtttgc ttgctttgaa | 240 |
| tcattaagat cattgataga agatagttga gattgacatg gaaggccaat agagagctca | 300 |
| agattgagtt tgtgatttgg atacacttct aattctgctg tcacgccact gctactattg | 360 |
| gaatcttcag cagagtcact gctg | 384 |

<210> SEQ ID NO 198
<211> LENGTH: 176
<212> TYPE: DNA
<213> ORGANISM: Populus tremula x tremuloides

<400> SEQUENCE: 198

| | |
|---|---|
| tcacagatcc cttctacaca gagggcagga tgcatgccta agtagccact tatctatgca | 60 |
| aggtaggtga acatgtgat gacaatgagg caagcttctg accgtctctc ccagctgaaa | 120 |
| gtcctgaagg caaactgaac aagagacttt ctctcctgat tcatctacat tgttat | 176 |

<210> SEQ ID NO 199
<211> LENGTH: 169
<212> TYPE: DNA
<213> ORGANISM: Populus tremula x tremuloides

<400> SEQUENCE: 199

| | |
|---|---|
| ctattttttcc agttcttgtt tacagagagg gcagcaggat ataattcgaa gccattgatc | 60 |
| tacacacttg aggtggaaca tatgggaaca tggcaatttc ctaacttctt ctttgtctttt | 120 |
| gtacttggct aggcagatac aacattccag atcttcactt gcaatggtt | 169 |

<210> SEQ ID NO 200
<211> LENGTH: 255
<212> TYPE: DNA
<213> ORGANISM: Populus tremula x tremuloides

<400> SEQUENCE: 200

| | |
|---|---|
| tcagagctgc aatgctaaat ctggctgccg tggtgaaccg atgggcacac tcgaagtagg | 60 |
| tgaaccaggt gccaagaatc caacattcag atctggtgga atggaacag taccttgttg | 120 |
| ctgatatggt aaaaatccct gccaagatga tttgccacca acccacat tgccaaatgt | 180 |
| acgagagtca gagctggagc ctacggctgg agaaattcca ggctgcaata atccacttga | 240 |
| agtttctgac agcat | 255 |

<210> SEQ ID NO 201
<211> LENGTH: 322
<212> TYPE: DNA
<213> ORGANISM: Populus tremula x tremuloides

<400> SEQUENCE: 201

| | |
|---|---|
| ttatgcattg acattatcag aactactgcc ggcttgatta ggaaggacag agttgccaaa | 60 |
| atctccatcc aagctcatct gttggacttc ttgaggagac aggatcttga tgcagcggac | 120 |

```
acagttcaca aactcttccc aagggtcatc ccccactagc aggacatcat tctcgtgatc    180
agtgtaaaca agtttccagc ctatcctttg ttgattttcc aactgtccct ctataccaaa    240
actacgagcc agatcctgct taagctcgtc ataacctgaa taccgtgtta tgtcaattga    300
acttcctaca gctccacgtt tg                                             322

<210> SEQ ID NO 202
<211> LENGTH: 433
<212> TYPE: DNA
<213> ORGANISM: Populus tremula x tremuloides

<400> SEQUENCE: 202
tcaagctcct gtagatccat aaggcttcct ctcaggcaca ccgtcccatg tttcttcaga     60
agtccctctc cctcctcctc caccatatgc tgcggcagtg gctgctccaa catgaaagcc    120
accactatag gaatttagca aagcagaact agcagcatcc atgccaagcc caagaaggtc    180
aagtgtcgtt ggtttgtttc caaacaatga agatgaaccc atcataacat cactggaggg    240
aagcccaagg cctagtccag ctgcgacagt ggtgttgttc tccggcttca catcccattt    300
attgcagtta ctgtcttgat tagttgaacg gggcaatcct aaaccacgga gaaatgatgg    360
gtttgatgtc gttgcaccca tttgtgctgc tttttgaagc aatgcagtgg cagacatggc    420
tggttgcgga gat                                                       433

<210> SEQ ID NO 203
<211> LENGTH: 360
<212> TYPE: DNA
<213> ORGANISM: Populus tremula x tremuloides

<400> SEQUENCE: 203
ttactgccct gatccttgtg aatcatcttt agaaggattt tgttgctggt gctgctgctg     60
gtgcactcta gcatgcccca tctgctgata aatctgattc aaagcttgtg gactcaaaac    120
cccaatatgg ccgtcctgtg acaacccaag ttccaatcct ggtaactgct gggtaccccc    180
acctaaaatt gaagtaaaac tcataggccc catgttgtta ctcggcaagt caaaccctgg    240
aaacccaagt ttttgcaaat aacttgaacc accagcagca gcagcttcag tccctatatt    300
tgttgttgat ggaccagtgg aattagatga tgactggaac ccataacctc caactggggg    360
```